(12) United States Patent
Tanaka et al.

(10) Patent No.: US 7,691,882 B2
(45) Date of Patent: Apr. 6, 2010

(54) HETEROCYCLES SUBSTITUTED PYRIDINE DERIVATIVES AND ANTIFUNGAL AGENT CONTAINING THEREOF

(75) Inventors: Keigo Tanaka, Tsukuba (JP); Satoshi Inoue, Tsukuba (JP); Norio Murai, Tsukuba (JP); Masayuki Matsukura, Tsukuba (JP); Kazutaka Nakamoto, Tsukuba (JP); Shuji Shirotori, Tsukuba (JP); Shinya Abe, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 408 days.

(21) Appl. No.: 11/589,128

(22) Filed: Oct. 30, 2006

(65) Prior Publication Data
US 2007/0105904 A1 May 10, 2007

Related U.S. Application Data

(60) Provisional application No. 60/731,267, filed on Oct. 31, 2005, provisional application No. 60/753,391, filed on Dec. 27, 2005.

(30) Foreign Application Priority Data

Oct. 31, 2005 (JP) ............................. 2005-317680
Dec. 27, 2005 (JP) ............................. 2005-374395

(51) Int. Cl.
*A61K 31/443* (2006.01)
*C07D 413/14* (2006.01)

(52) U.S. Cl. .................................... 514/333; 546/256
(58) Field of Classification Search ................ 546/256; 514/333
See application file for complete search history.

(56) References Cited

U.S. PATENT DOCUMENTS

| | | | |
|---|---|---|---|
| 4,576,956 A | 3/1986 | Makisumi et al. |
| 4,720,493 A | 1/1988 | Kawakita et al. |
| 4,785,010 A | 11/1988 | Zoller et al. |
| 5,034,393 A | 7/1991 | Hackler et al. |
| 5,296,484 A | 3/1994 | Coghlan et al. |
| 5,350,749 A | 9/1994 | Hackler et al. |
| 5,710,171 A | 1/1998 | Dinsmore et al. |
| 5,747,518 A | 5/1998 | Yoshikawa et al. |
| 5,852,042 A | 12/1998 | Jakobi et al. |
| 5,945,431 A | 8/1999 | Jin et al. |
| 6,022,884 A | 2/2000 | Mantlo et al. |
| 6,080,767 A | 6/2000 | Klein et al. |
| 6,313,127 B1 | 11/2001 | Waterson et al. |
| 6,380,218 B1 | 4/2002 | Marfat et al. |
| 6,414,013 B1 | 7/2002 | Fancelli et al. |
| 6,596,718 B1 | 7/2003 | Flohr et al. |
| 6,630,495 B1 | 10/2003 | Cooke et al. |
| 2003/0045554 A1 | 3/2003 | Sankaranarayanan |
| 2003/0114491 A1 | 6/2003 | Kim et al. |
| 2004/0038239 A1 | 2/2004 | Tsukahara et al. |
| 2004/0044040 A1 | 3/2004 | Neubert et al. |
| 2004/0152730 A1 | 8/2004 | Farina et al. |
| 2005/0119229 A1 | 6/2005 | Ammermann et al. |
| 2006/0264419 A1 | 11/2006 | Schiemann et al. |
| 2006/0270637 A1 | 11/2006 | Gravestock et al. |
| 2007/0105904 A1 | 5/2007 | Tanaka et al. |

(Continued)

FOREIGN PATENT DOCUMENTS

DE 19727117 A1 1/1999

(Continued)

OTHER PUBLICATIONS

AKos Screening Library, Feb. 7, 2006. CAS Registry No. 434304-24-2.

(Continued)

*Primary Examiner*—Patricia L Morris
(74) *Attorney, Agent, or Firm*—Birch, Stewart, Kolasch & Birch, LLP

(57) ABSTRACT

An object of the present invention is to provide an antifungal agent which has excellent antifungal effects and is superior in terms of its physical properties, safety and metabolic stability. According to the present invention, there is disclosed a compound represented by the following formula (I), or a salt thereof:

(I)

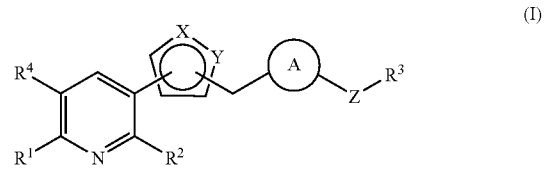

wherein $R^1$ represents a hydrogen atom, a halogen atom, an amino group, a $C_{1-6}$ alkyl group, a $C_{1-6}$ alkoxy group or a $C_{1-6}$ alkoxy $C_{1-6}$ alkyl group; $R^2$ represents a hydrogen atom, a $C_{1-6}$ alkyl group, an amino group or a di $C_{1-6}$ alkylamino group; one of X and Y is a nitrogen atom while the other is a nitrogen atom or an oxygen atom; ring A represents a 5- or 6-member heteroaryl ring or a benzene ring which may have a halogen atom, or 1 or 2 $C_{1-6}$ alkyl groups; Z represents a single bond, a methylene group, an ethylene group, an oxygen atom, a sulfur atom, —$CH_2O$—, —$OCH_2$—, —NH—, —$CH_2NH$—, —$NHCH_2$—, —$CH_2S$—, or —$SCH_2$—; $R^3$ represents a hydrogen atom, a halogen atom, a $C_{1-6}$ alkyl group, a $C_{3-8}$ cycloalkyl group, a $C_{6-10}$ aryl group, a 5- or 6-member heteroaryl group, or 5- or 6-member non-aromatic heterocyclic group which may have 1 or 2 substituents; and $R^4$ represents a hydrogen atom or a halogen atom.

18 Claims, No Drawings

U.S. PATENT DOCUMENTS

| | | |
|---|---|---|
| 2007/0105943 A1 | 5/2007 | Nakamoto et al. |
| 2007/0167493 A1 | 7/2007 | Sankaranarayanan |

FOREIGN PATENT DOCUMENTS

| | | | |
|---|---|---|---|
| EP | 0 124 067 A1 | 11/1984 | |
| EP | 0 124 154 A2 | 11/1984 | |
| EP | 0274867 A2 | 7/1988 | |
| EP | 0 326 328 A2 | 8/1989 | |
| EP | 0 414 386 A1 | 2/1991 | |
| EP | 0533130 A1 | 3/1993 | |
| EP | 0976744 A1 | 2/2000 | |
| EP | 1 216 980 A1 | 6/2002 | |
| EP | 1217000 A1 | 6/2002 | |
| EP | 1 229 034 A1 | 8/2002 | |
| EP | 1275301 A1 | 1/2003 | |
| EP | 1275653 A1 | 1/2003 | |
| EP | 1 782 811 A1 | 5/2007 | |
| JP | 54-2325 A | 1/1979 | |
| JP | 59-073575 | 4/1984 | |
| JP | 59-206353 A | 11/1984 | |
| JP | 61-148178 A | 7/1986 | |
| JP | 64-3162 A | 1/1989 | |
| JP | 1-246264 A | 10/1989 | |
| JP | 3-66689 A | 3/1991 | |
| JP | 3-161470 A | 7/1991 | |
| JP | 7-25853 A | 1/1995 | |
| JP | 10-505600 A | 6/1998 | |
| JP | 2000-504336 A | 4/2000 | |
| JP | 2000-178243 A | 6/2000 | |
| JP | 2001-522834 A | 11/2001 | |
| JP | 2002-275159 A | 9/2002 | |
| JP | 2002-284766 A | 10/2002 | |
| JP | 2003-506466 A | 2/2003 | |
| JP | 2004-529151 A | 9/2004 | |
| JP | 2005-033079 A | 2/2005 | |
| JP | 2005-526751 A | 9/2005 | |
| JP | 2006-519247 A | 8/2006 | |
| WO | WO-86/03203 A1 | 6/1986 | |
| WO | WO-93/12084 A1 | 6/1993 | |
| WO | WO-96/09294 A1 | 3/1996 | |
| WO | WO-97/27852 A1 | 8/1997 | |
| WO | WO-97/28128 A1 | 8/1997 | |
| WO | WO-98/25883 A1 | 6/1998 | |
| WO | WO-98/50029 A1 | 11/1998 | |
| WO | WO-99/24404 A1 | 5/1999 | |
| WO | WO-99/48492 A1 | 9/1999 | |
| WO | WO-99/50247 A1 | 10/1999 | |
| WO | WO-00/07991 A1 | 2/2000 | |
| WO | WO-00/51998 A1 | 9/2000 | |
| WO | WO-00/62778 A1 | 10/2000 | |
| WO | WO-00/73283 A1 | 12/2000 | |
| WO | WO-01/11966 A1 | 2/2001 | |
| WO | WO-01/21584 A1 | 3/2001 | |
| WO | WO-01/25181 A1 | 4/2001 | |
| WO | WO-01/27096 A1 | 4/2001 | |
| WO | WO-01/51456 A2 | 7/2001 | |
| WO | WO-01/53274 A1 | 7/2001 | |
| WO | WO-01/74779 A1 | 10/2001 | |
| WO | WO-02/00651 A2 | 1/2002 | |
| WO | WO-02/04626 A1 | 1/2002 | |
| WO | WO-02/06275 A1 | 1/2002 | |
| WO | WO-02/22583 A2 | 3/2002 | |
| WO | WO-02/060875 A1 | 8/2002 | |
| WO | WO-02/060896 A1 | 8/2002 | |
| WO | WO-02/060898 A1 | 8/2002 | |
| WO | WO-02/083645 A1 | 10/2002 | |
| WO | WO-02/085897 A1 | 10/2002 | |
| WO | WO-03/027095 A1 | 4/2003 | |
| WO | WO-03/031435 A1 | 4/2003 | |
| WO | WO-03/045385 A1 | 6/2003 | |
| WO | WO-03/059903 A2 | 7/2003 | |
| WO | WO-03/068232 A1 | 8/2003 | |
| WO | WO-03/068235 A1 | 8/2003 | |
| WO | WO-04/000813 A1 | 12/2003 | |
| WO | WO-2004/014370 A2 | 2/2004 | |
| WO | WO-2004/029027 A1 | 4/2004 | |
| WO | WO-2004/033432 A1 | 4/2004 | |
| WO | WO-2004/048567 A2 | 6/2004 | |
| WO | WO-2004/052280 A2 | 6/2004 | |
| WO | WO-2004/089931 A1 | 10/2004 | |
| WO | WO-2005/033079 A1 | 4/2005 | |
| WO | WO-2006/016548 A1 | 2/2006 | |
| WO | WO-2006/106711 A1 | 10/2006 | |
| WO | WO-2007/052615 A1 | 5/2007 | |
| WO | WO-2009/081970 A1 | 7/2009 | |
| WO | WO-2009/084621 A1 | 7/2009 | |

OTHER PUBLICATIONS

Aurora Screening Library, Jan. 1, 2007, CAS Registry No. (RN): 431922-54-2.

Interchim Intermediate, Jul. 9, 2007, CAS Registry No. (RN): 438574-99-3.

Ambinter Stock Screening, Jan. 1, 2007, CAS Registry No. (RN): 764713-41-9.

Ikizler. et al, "Antimicrobial activities of some 4H-1,2,4- triazoles" Indian Journal of Pharmaceutical Sciences, 1999, vol. 61, No. 5, p. 271-274.

Satyanarayana, et al., "Studies on the synthesis and biological activity of 3- arylaminomethyl-5-(3-pyridyl)-1, 3, 4-oxadiazole-2-thione derivatives" Bolletino Chimico Farmaceutico, 2001, vol. 140, No. 4, p. 228-232.

Gardner et al., Nature, vol. 419, pp. 498-511, (2002).

Naik et al., J. of Biological Chemistry, vol. 278, No. 3, pp. 2036-2042, (2003).

Shinkai et al., J. Med. Chem., vol. 31, pp. 2092-2097, (1988).

Ohshima et al., J. Med. Chem., vol. 35, pp. 3402-3413, (1992).

Okawa et al., Synthesis, No. 10., pp. 1467-1475 (1998).

Chan, L., et al., Database Crossfire Beilstein: Beilstein Institute Zur Foerderung Der Chemischen Wissenschaften; XP-002512523; Database accession No. 8422493 (1999).

Okawa T., et al., "Pyrido [2, 3-d] pyrimidine derivatives. Synthesis via intermolecular aza-Wittig reaction/heterocyclization and the crystal structure", Database CA [Online] Chemical Abstract Service; XP002512524; Database accession No. 677971 (1998).

Kajino M., et al., "Preparation and formulation of quinazoline derivatives as allergy inhibitors", Database CA [Online], Chemical Abstract Service; XP002512525 Database accession No. 216905 (1999).

Piechaczek J., et al., "Monoamine oxidase inhibitors. VII. Derivatives of quinolinecarboxylic acids", Database CA [Online], Chemical Abstract Service; XP002512526 Database accession No. 75701 (1966).

Modena T., et al., "Plant growth regulating activities of 2-[2-(arylamino)-2-oxoethyl] benzoic acids", Database CA [Online], Chemical Abstract Service; XP002512527 Database accession No. 597690 (1993).

Chang, K. Y. et al., "Synthesis and Structure-Activity Relationships of Quaternary Ammonium Cephalosporins with 3-Pyrazolylpyridinium Derivatives," Bioorganic & Medicinal Chemistry Letters (2000) vol. 10, No. 11, pp. 1211-1214.

Plate, R. et al., "Synthesis and Muscarinic Activities of 3-(Pyrazolyl)-1,2,5,6- tetrahydropyridine Derivatives," Bioorganic & Medicinal Chemistry Letters (1996) vol. 10, No. 2, pp. 227-237.

Vrzheschch, P. V. et al., "Supercooperativity in platelet aggregation: Substituted pyridyl isoxazoles, a new class of supercooperative platelet aggregation inhibitors," FEBS Letters (1994) vol. 351, No. 2, pp. 168-180.

Lukevics, E. et al., "Synthesis and cytotoxicity of silyl- and carbonyl-substituted isoxazoles," Chemistry of Heterocyclic Compounds (2000) vol. 36, No. 10, pp. 1226-1231.

Guillory, J. Keith, "Generation of Polymorphs, Hydrates, Solvates, and Amorphous Solids," *Polymorphism in Pharmaceutical Solids*, ed. Harry G. Brittain, Marcel Dekker, Inc., New York, 1999, pp. 183-226.

Tanaka et al., "An Effective Lewis Acid-Mediated 1,3-Dipolar Cycloaddition of Nitrile Oxide Using Acetylene: Synthesis of a (2-Aminopyridin-3-yl) isoxazole Derivative and Its Application to Novel Antifungal Agents," pp. 1-8.

Vippagunta et al., "Crystalline Solids," *Advanced Drug Delivery Reviews*, vol. 48, 2001, pp. 3-26.

Office Action from co-pending U.S. Appl. No. 10/573,890, mailed Jul. 29, 2009.

HETEROCYCLES SUBSTITUTED PYRIDINE DERIVATIVES AND ANTIFUNGAL AGENT CONTAINING THEREOF

CROSS REFERENCES TO RELATED APPLICATIONS

This application claims priorities of U.S. Provisional Application Ser. No. 60/731,267, filed Oct. 31, 2005, Japanese Patent Application No. 2005-317680, filed Oct. 31, 2005, U.S. Provisional Application Ser. No. 60/753,391, filed Dec. 27, 2005, and Japanese Patent Application No. 2005-374395, filed in Dec. 27, 2005, the disclosures of which are hereby incorporated by reference in entireties.

FIELD OF THE INVENTION

The present invention relates to heterocyclic substituted pyridine derivatives and to antifungal agents comprising the same.

DESCRIPTION OF THE RELATED ART

In recent years, managements of opportunistic infections have become more and more significant more than ever because of an increase in the number of elderly people and immunocompromised patients as a result of advanced chemotherapies or the like. As demonstrated by the fact that opportunistic infections are occurring one after another by different avirulent pathogen, it is shown that the problem of infectious disease will not ends as long as there are underlying diseases that diminish the immune functions of patients. Consequently, new strategies for infectious diseases control, including the problem of drug-resistant pathogen, will be one of the important issues in the soon-to-come aged society.

In the field of antifungal agents, heretofore, for instance, amphotericine B which is based on a polyene skeleton, fluconazole, itraconazole and voriconazole which are based on an azole skeleton, or the like, have been developed for the treatment of deep seated mycoses. Most of pre-existing drugs already available commercially have similar mechanism of action, and currently, the appearance of azole-resistant fungi or the like has been problems.

In recent years, as a 1,3-β-glucan synthetase inhibitor with a novel mechanism, naturally occurring compound-derived cyclic hexapeptides caspofungin and micafungin or the like, have been developed; however, from the fact that these agents only exist in injectable form, they are not yet sufficient practically as antifungal agents.

Since there have been the situations that the pre-existing antifungal agents are insufficient for treatment of the deep seated mycoses, there is a demand and need for development of agents which are based on a novel mechanism and are of high safety.

As the related art relevant to antifungal agents based on such a novel mechanism, Patent Documents 1 and 2 describe pyridine derivatives which demonstrates effects against the onset, progress, and persistence of infections by inhibiting the expression of cell wall proteins, inhibiting the cell wall assembly and also adhesion onto cells, and preventing pathogens from showing pathogenicity, with the process which transports GPI (Glycosylphosphatidylinositol)-anchored proteins to the cell wall being inhibited.

However, groups of the compounds disclosed in Patent Document 1 have 2-benzyl pyridine moieties as the common structure, clearly differing structurally from compounds according to the present invention. In addition, the groups of the compounds disclosed in Patent Document 1 bear the problem that, although these compounds demonstrate activities in vitro, they are easily metabolized inside the body. The group of compounds disclosed in Patent Document 2 exhibits excellent antifungal activity, but the group of representative compounds has the structure represented by the following formula:

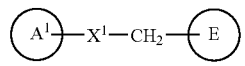

$A^1$=optionally substituted 3-pyridyl or quinolyl, etc.

$X^1$=—C(=O)—NH, —NH—C(=O)—, etc.

E=furyl, thienyl, pyrrolyl, phenyl, pyridyl, tetrazolyl, thiazolyl, or pyrazolyl Looking only at those having pyridine ring skeletons, this group differs structurally from the compounds according to the present invention in that the common structure has a single ring bound via an amidemethylene linker at the pyridine ring 3-position.

Patent Documents 3 to 5 also provide examples of related art with structures similar to the compounds according to the present invention. Patent Documents 3 and 4 describe pyridine derivatives substituted by a pyrazole ring, which are used as glycine transporter inhibitors or 5-HT receptor ligands, while Patent Document 5 describes 5-member heterocyclic substituted pyridine derivatives which are used as an AGE disruptor and inhibitor.

However, Patent Documents 3 to 5 do not disclose the compounds according to the present invention, and the antifungal effects of the compounds disclosed in Patent Documents 3 to 5 against Candida, Aspergillus, Cryptococcus and the like which are common fungi in human fungal disease are not disclosed.

[Patent Document 1] International Publication WO 02/04626 pamphlet

[Patent Document 2] International Publication WO 05/033079 pamphlet

[Patent Document 3] International Publication WO 03/031435 pamphlet

[Patent Document 4] International Publication WO 04/089931 pamphlet

[Patent Document 5] International Publication WO 02/085897 pamphlet

BRIEF SUMMARY OF THE INVENTION

It is an object of the present invention to provide an antifungal agent which has excellent antifungal action not found in the antifungal agents in the prior art, and which is also excellent in terms of property, safety and metabolic stability.

As a result of exhaustive research conducted in view of the above circumstances, the present inventors have succeeded in synthesizing novel pyridine derivatives (hereinafter, the compounds of the present invention) represented by the following formula (I):

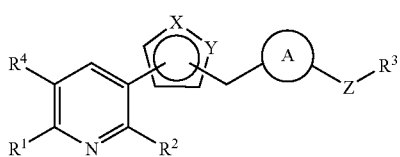

(I)

and having a chemical structure in which a pyridine ring and a 5- or 6-member heteroaryl ring or benzene ring are joined with a 5-member heteroaryl methyl group as a linker, and have perfected the present invention upon discovering that these compounds have excellent antifungal action.

That is, the present invention provides:

[1] a compound represented by the following formula (I), or a salt thereof:

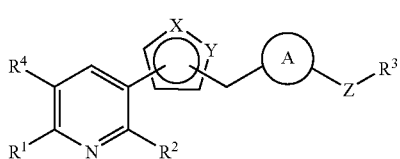

(I)

wherein $R^1$ represents a hydrogen atom, a halogen atom, an amino group, $R^{11}$—NH— (wherein $R^{11}$ represents a $C_{1-6}$ alkyl group, a hydroxy $C_{1-6}$ alkyl group, a $C_{1-6}$ alkoxy $C_{1-6}$ alkyl group, or a $C_{1-6}$ alkoxycarbonyl $C_{1-6}$ alkyl group), $R^{12}$—(CO)—NH— (wherein $R^{12}$ represents a $C_{1-6}$ alkyl group or a $C_{1-6}$ alkoxy $C_{1-6}$ alkyl group), a $C_{1-6}$ alkyl group, a hydroxy $C_{1-6}$ alkyl group, a cyano $C_{1-6}$ alkyl group, a $C_{1-6}$ alkoxy group or a $C_{1-6}$ alkoxy $C_{1-6}$ alkyl group;

$R^2$ represents a hydrogen atom, a $C_{1-6}$ alkyl group, an amino group or a di $C_{1-6}$ alkylamino group;

one of X and Y is a nitrogen atom while the other is a nitrogen atom or an oxygen atom;

ring A represents a 5- or 6-member heteroaryl ring or a benzene ring which may have 1 or 2 halogen atoms, or 1 or 2 $C_{1-6}$ alkyl groups;

Z represents a single bond, a methylene group, an ethylene group, an oxygen atom, a sulfur atom, —CH$_2$O—, —OCH$_2$—, —NH—, —CH$_2$NH—, —NHCH$_2$—, —CH$_2$S—, or —SCH$_2$—;

$R^3$ represents a hydrogen atom, a halogen atom, a $C_{1-6}$ alkyl group, a $C_{3-8}$ cycloalkyl group, a $C_{6-10}$ aryl group, a 5- or 6-member heteroaryl group, or 5- or 6-member non-aromatic heterocyclic group which may have 1 or 2 substituents selected from substituent group α: and

[Substituent Group α]

substituent group α represents the group consisting of a halogen atom, a cyano group, a $C_{1-6}$ alkyl group, a $C_{1-6}$ alkoxy group, a $C_{1-6}$ alkoxycarbonyl group, a $C_{3-8}$ cycloalkyl group, a $C_{2-6}$ alkenyl group and a $C_{2-6}$ alkynyl group $R^4$ represents a hydrogen atom or a halogen atom;

excluding compounds where all of $R^1$, $R^2$, and $R^4$ represent the hydrogen atom at the same time when Z represents the single bond or $R^3$ represents the hydrogen atom;

[2] a compound represented by the following formula (I'), or a salt thereof:

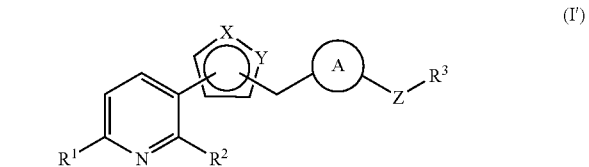

(I')

wherein $R^1$ represents a hydrogen atom, a halogen atom, an amino group, a $C_{1-6}$ alkyl group, a $C_{1-6}$ alkoxy group or a $C_{1-6}$ alkoxy $C_{1-6}$ alkyl group;

$R^2$ represents a hydrogen atom or an amino group;

one of X and Y is a nitrogen atom while the other is a nitrogen atom or an oxygen atom;

ring A represents a 5- or 6-member heteroaryl ring or a benzene ring;

Z represents a methylene group, an oxygen atom, —CH$_2$O—, —OCH$_2$—, —NH—, —NHCH$_2$— or —CH$_2$NH—;

and $R^3$ represents a $C_{1-6}$ alkyl group, a $C_{3-8}$ cycloalkyl group, a $C_{6-10}$ aryl group or a 5- or 6-member heteroaryl group which may have 1 or 2 substituents selected from substituent group α:

[Substituent Group α]

substituent group α represents the group consisting of a halogen atom, a $C_{1-6}$ alkyl group, a $C_{1-6}$ alkoxy group, a $C_{3-8}$ cycloalkyl group, a $C_{2-6}$ alkenyl group and a $C_{2-6}$ alkynyl group;

[3] the compound according to item [1] or [2], or the salt thereof, wherein a partial structure represented by formula (II):

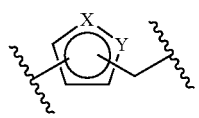

(II)

in the compound represented by the formula (I) or the formula (I'):

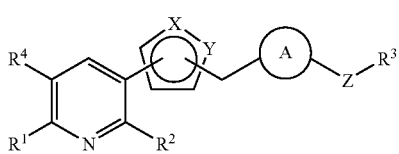

(I)

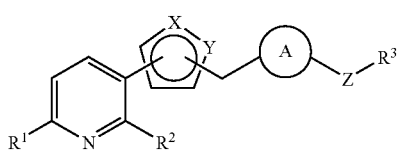

(I')

is a partial structure selected from the group consisting of:

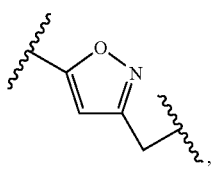
(III)

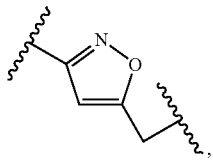
(IV)

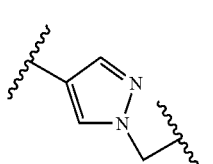
(V)
and

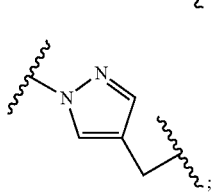
(VI)
;

[4] the compound according to item [1] or [2], or the salt thereof, wherein one of X and Y is a nitrogen atom and the other is an oxygen atom;

[5] the compound according to item [4] or the salt thereof, wherein a partial structure represented by the formula (II):

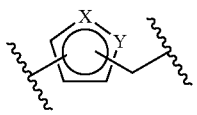
(II)

in the compound represented by the formula (I) or the formula (I'):

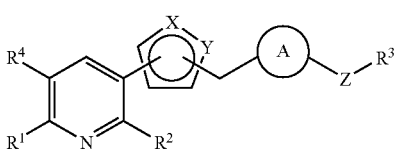
(I)

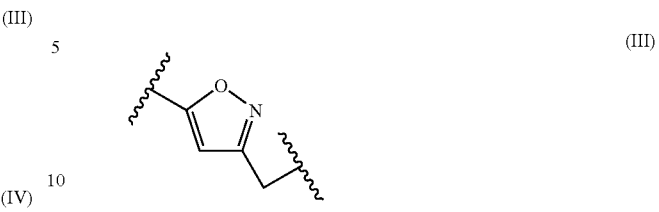
(I')

is a partial structure represented by the following formula (III):

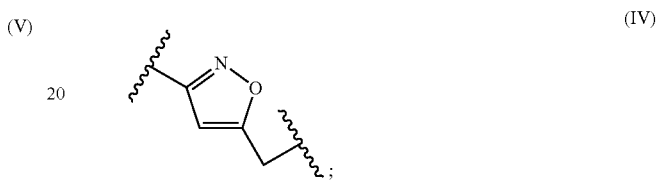
(III)

or a partial structure represented by the following formula (IV):

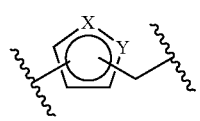
(IV)
;

[6] the compound according to item [1] or [2], or the salt thereof, wherein X and Y are both nitrogen atoms;

[7] the compound according to item [6] or the salt thereof, wherein a partial structure represented by the formula (II):

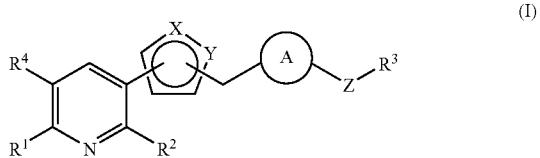
(II)

in the compound represented by the formula (I) or the formula (I'):

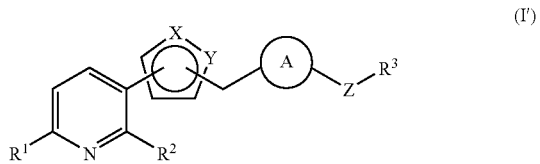
(I)

(I')

is a partial structure represented by the following formula (V):

(V)

or a partial structure represented by the following formula (VI):

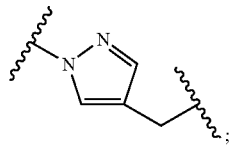

(VI)

[8] the compound according to any one of items [1] to [7] or the salt thereof, wherein $R^2$ represents an amino group;

[9] the compound according to item [8] or the salt thereof, wherein $R^1$ represents a hydrogen atom, an amino group or a $C_{1-6}$ alkoxy $C_{1-6}$ alkyl group;

[10] the compound according to any one of items [1] to [7] or the salt thereof, wherein $R^1$ represents an amino group and $R^2$ represents a hydrogen atom;

[11] the compound according to any one of items [1] to [10] or the salt thereof, wherein the ring A represents a pyridine ring, a benzene ring, a furan ring, a thiophene ring or a pyrrole ring;

[12] the compound according to item [11] or a salt thereof, wherein ring A represents a pyridine ring or a benzene ring;

[13] the compound according to any one of items [1] to [12] or the salt thereof, wherein Z represents an oxygen atom, —$CH_2O$— or —$OCH_2$—;

[14] a pharmaceutical composition comprising the compound according to any one of items [1] to [13] or the salt thereof.

[15] a medicament comprising the compound according to any one of items [1] to [13] or the salt thereof;

[16] an antifungal agent comprising the compound according to any one of items [1] to [13] or the salt thereof, as an active ingredient;

[17] a method for preventing and/or treating a fungal infection comprising administering a pharmacologically effective dose of the compound according to any one of items [1] to [13] or the salt thereof;

[18] a use of the compound according to any one of items [1] to [13] or the salt thereof for manufacturing an antifungal agent.

ADVANTAGEOUS EFFECTS OF THE INVENTION

The compound (I) of the present invention or a salt thereof 1) acts against the onset, development and persistence of infections by inhibiting fungal GPI biosynthesis, thereby inhibiting expression of cell wall proteins and blocking cell wall assembly while preventing the fungus from attaching to cells so that the pathogen cannot become pathogenic, and 2) is superior in terms of physical properties, safety and metabolic stability, and is extremely useful as a preventive or therapeutic agent for fungal infections.

DETAILED DESCRIPTION OF THE INVENTION

The present invention is explained below in more detail by reference to the symbols and the terms used herein being defined and the following examples.

Herein, a structural formula of a compound sometimes represents a certain isomer for convenience of description. However, compounds according to the present invention may include all possible isomers, such as structurally possible geometric isomers, optical isomers generated due to the presence of asymmetric carbons, stereoisomers, tautomers, and mixtures of isomers, and are not limited to formulae being used for the convenience of description, and may be either one of two isomers or a mixture of both isomers. Thus, the compounds according to the present invention may be either optically active compounds having an asymmetric carbon atom in their molecules or their racemates, and are not restricted to either of them but include both. Furthermore, the compounds according to the present invention may exhibit crystalline polymorphism, but likewise are not restricted to any one of these, but may be in any one of these crystal forms or exist as a mixture of two or more crystal forms. The compounds according to the present invention also include both anhydrous and solvates such as hydrated forms.

The term "$C_{1-6}$ alkyl group" used in the present specification refers to a straight-chain or branched-chain alkyl group with 1 to 6 carbon atoms which is a monovalent group induced by removal of any one hydrogen atom from an aliphatic hydrocarbon with 1 to 6 carbon atoms. Specifically, examples of "$C_{1-6}$ alkyl group" includes a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a neopentyl group, a 1-methylbutyl group, a 2-methylbutyl group, a 1,1-dimethylpropyl group, a 1,2-dimethylpropyl group, a n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2,-trimethylpropyl group, a 1,2,2-trimethylpropyl group, a 1-ethyl-1-methylpropyl group, a 1-ethyl-2-methylpropyl group or the like, preferably a methyl group, an ethyl group, a n-propyl group, an isopropyl group, a n-butyl group, an isobutyl group, a sec-butyl group or a tert-butyl group or the like.

The term "$C_{2-6}$ alkenyl group" used in the present specification refers to a straight-chain or branched-chain alkenyl group with 2 to 6 carbon atoms which may contain 1 or 2 double bonds. Specifically, examples of "$C_{2-6}$ alkenyl group" include an ethenyl group, a 1-propenyl group, a 2-propenyl group, a 1-butenyl group, a 2-butenyl group, a 3-butenyl group, a 2-methyl-1-propenyl group, a pentenyl group, a 3-methyl-2-butenyl group, a hexenyl group, a hexanedienyl group or the like, preferably an ethenyl group, a 1-propenyl group, a 2-propenyl group, a 1-butenyl group, a 2-butenyl group, a 3-butenyl group, a 2-methyl-1-propenyl group, a 3-methyl-2-butenyl group or the like.

The term "$C_{2-6}$ alkynyl group" used in the present specification refers to a straight-chain or branched-chain alkynyl chain with 2 to 6 carbon atoms which may contain 1 or 2 triple bonds. Specifically, examples of "$C_{2-6}$ alkynyl group" include an ethynyl group, a 1-propynyl group, a 2-propynyl group, a 1-butynyl group, a 2-butynyl group, a 3-butynyl group, a pentynyl group, a hexynyl group, a hexanediynyl group or the like, preferably an ethynyl group, a 1-propynyl group, a 2-propynyl group, a 1-butynyl group, a 2-butynyl group, a 3-butynyl group or the like.

The term "$C_{3-8}$ cycloalkyl group" used in the present specification refers to a cyclic aliphatic hydrocarbon group with 3 to 8 carbon atoms. Specifically, examples of "$C_{3-8}$ cycloalkyl group" include a cyclopropyl group, a cyclobutyl group, a cyclopentyl group, a cyclohexyl group, a cycloheptyl group, a cyclooctyl group or the like, preferably a cyclopropyl group, a cyclobutyl group, a cyclopentyl group, a cyclohexyl group or the like.

The term "$C_{1-6}$ alkoxy group" used in the present specification refers to a group in which an oxygen atom is bonded to terminus of the "$C_{1-6}$ alkyl group" defined above. Specifically, examples of "$C_{1-6}$ alkoxy group" include a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a neopentyloxy group, a 1-methylbutoxy group, a 2-methylbutoxy group, a 1,1-dimethylpropoxy group, a 1,2-dimethylpropoxy group, a n-hexyloxy group, an isohexyloxy group, a 1-methylpentyloxy group, a 2-methylpentyloxy group, a 3-methylpentyloxy group, a 1,1-dimethylbutoxy group, a 1,2-dimethylbutoxy group, a 2,2-dimethylbutoxy group, a 1,3-dimethylbutoxy group, a 2,3-dimethylbutoxy group, a 3,3-dimethylbutoxy group, a 1-ethylbutoxy group, a 2-ethylbutoxy group, a 1,1,2-trimethylpropoxy group, a 1,2,2-trimethylpropoxy group, a 1-ethyl-1-methylpropxy group, a 1-ethyl-2-methylpropoxy group or the like, preferably a methoxy group, an ethoxy group, a n-propoxy group, an isopropoxy group, a n-butoxy group, an isobutoxy group, a sec-butoxy group, a tert-butoxy group or the like.

The term "hydroxyl $C_{1-6}$ alkyl group" used in the present specification refers to a group in which any of the hydrogen atoms in a "$C_{1-6}$ alkyl group" as defined above has been replaced by a hydroxyl group. Specifically, examples of "hydroxyl $C_{1-6}$ alkyl group" include a hydroxymethyl group, a 1-hydroxyethyl group, a 2-hydroxyethyl group, a 1-hydroxy-n-propyl group, a 2-hydroxy-n-propyl group, a 3-hydroxy-n-propyl group, a 1-hydroxy-isopropyl group, a 2-hydroxy-isopropyl group, a 3-hydroxy-isopropyl group, a 1-hydroxy-tert-butyl group or the like, preferably a hydroxymethyl group, a 1-hydroxyethyl group, a 2-hydroxyethyl group or the like.

The term "$C_{1-6}$ alkoxycarbonyl group" used in the present specification refers to a group in which a carbonyl group is bonded to terminus of the "$C_{1-6}$ alkoxy group" defined above. Specifically, examples of "$C_{1-6}$ alkoxycarbonyl group" include a methoxycarbonyl group, an ethoxycarbonyl group, a n-propoxycarbonyl group, an isopropoxycarbonyl group or the like.

The term "$C_{1-6}$ alkoxycarbonyl $C_{1-6}$ alkyl group" used in the present specification refers to a group in which the "$C_{1-6}$ alkyl group" defined above is bonded to terminus of the "$C_{1-6}$ alkoxycarbonyl group" defined above. Specifically, examples of the "$C_{1-6}$ alkoxycarbonyl $C_{1-6}$ alkyl group" include a methoxycarbonyl methyl group, a methoxycarbonyl ethyl group, an ethoxycarbonyl methyl group, an ethoxycarbonyl ethyl group or the like.

The term "$C_{6-10}$ aryl group" used in the present specification refers to an aromatic hydrocarbon cyclic group with 6 to 10 carbon atoms. Specifically, examples of "$C_{6-10}$ aryl group" include a phenyl group, a 1-naphthyl group, a 2-naphthyl group, an indenyl group, an azulenyl group, a heptalenyl group or the like, preferably a phenyl group, a 1-naphthyl group, 2-naphthyl group or the like.

The term "$C_{1-6}$ alkoxy $C_{1-6}$ alkyl group" used in the present specification refers to a group in which any of the hydrogen atoms in a "$C_{1-6}$ alkyl group" as defined above has been replaced by a "$C_{1-6}$ alkoxy group" as defined above. Specifically, examples of "$C_{1-6}$ alkoxy $C_{1-6}$ alkyl group" include a methoxymethyl group, an ethoxymethyl group, a n-propoxymethyl group, a methoxyethyl group, an ethoxyethyl group or the like.

The term "halogen atom" used in the present specification refers a fluorine atom, a chlorine atom, a bromine atom or an iodine atom.

The term "hetero atom" used in the present specification refers to a nitrogen atom, a sulfur atom or an oxygen atom.

The term "5- or 6-member heteroaryl ring" used in the present specification refers to an aromatic ring in which the number of atoms making up the ring is 5 or 6, and 1 or more hetero atoms are included in the atoms making up the ring. Specifically, examples of "5- or 6-member heteroaryl ring" include a furan ring, a thiophene ring, a pyrrole ring, a pyridine ring, a pyrazine ring, a pyridazine ring, a pyrimidine ring, a triazole ring (a 1,2,3-triazole ring, a 1,2,4-triazole ring, etc.), a tetrazole ring (a 1H-tetrazole ring, a 2H-tetrazole ring, etc.), a thiazole ring, a pyrazole ring, an oxazole ring, an isoxazole ring, an isothiazole ring, an oxadiazole ring, a thiadiazole ring or the like.

The term "5- or 6-member heteroaryl group" used in the present specification refers to a monovalent group induced by removing 1 hydrogen atom from any position in an aromatic ring in which the number of atoms making up the ring is 5 or 6 and 1 or more hetero atoms are included in the atoms making up the ring. Specifically, examples of "5- or 6-member heteroaryl group" include a furyl group (a 2-furyl group or a 3-furyl group, etc.), a thienyl group (a 2-thienyl group or a 3-thienyl group, etc.), a pyrrolyl group (a 1-pyrrolyl group, a 2-pyrrolyl group or a 3-pyrrolyl group, etc.), a pyridyl group (a 2-pyridyl group, a 3-pyridyl group, a 4-pyridyl group, etc.), a pyrazinyl group, a pyridazinyl group (a 3-pyridazinyl group or a 4-pyridazinyl group, etc.), a pyrimidinyl group (a 2-pyrimidinyl group, a 4-pyrimidinyl group or a 5-pyrimidinyl group, etc.), a triazolyl group (a 1,2,3-triazolyl group or a 1,2,4-triazolyl group, etc.), a tetrazolyl group (a 1H-tetrazolyl group or a 2H-tetrazolyl group, etc.), a thiazolyl group (a 2-thiazolyl group, a 4-thiazolyl group or a 5-thiazolyl group, etc.), a pyrazolyl group (a 3-pyrazolyl group or a 4-pyrazolyl group, etc.), an oxazolyl group (a 2-oxazolyl group, a 4-oxazolyl group or a 5-oxazolyl group, etc.), an isoxazolyl group (a 3-isoxazolyl group, a 4-isoxazolyl group or a 5-isoxazolyl group, etc.), an isothiazolyl group (a 3-isothiazolyl group, a 4-isothiazolyl group or a 5-isothiazolyl group, etc.), an oxadiazolyl group, a thiadiazolyl group or the like.

The term "5- or 6-member non-aromatic heterocyclic group" used in the present specification refers to a monovalent group induced by removing 1 hydrogen atom from any position in a non-aromatic ring in which the number of atoms making up the ring is 5 or 6 and 1 or more hetero atoms are included in the atoms making up the ring. Specifically, examples of "5- or 6-member non-aromatic heterocyclic group" include a pyrrolidinyl group, a piperadinyl group, a piperidinyl group, a morpholinyl group, a tetrahydrofuryl group, a tetrahydropyranyl group or the like.

The term "di $C_{1-6}$ alkylamino group" used in the present specification refers to a group in which 2 hydrogen atoms of the amino group are replaced with the "$C_{1-6}$ alkyl groups" defined above being the same as or different from each other.

Specifically, examples of the term "di $C_{1-6}$ alkylamino group" include a N,N-dimethylamino group, a N,N-diethylamino group, a N,N-di-n-propylamino group, a N,N-di-isopropylamino group, a N,N-di-n-butylamino group, a N,N-isobutylamino group, a N,N-di-sec-butylamino group, a N,N-di-tert-butylamino group, a N-ethyl-N-methylamino group, a N-n-propylamino-N-methylamino group, a N-isopropyl-N-methylamino group, a N-n-butyl-N-methylamino group, a N-isobutyl-N-methylamino group, a N-sec-butyl-N-methylamino group, a N-tert-butyl-N-methlamino group or the like, preferably a N,N-dimethylamino group, a N,N-diethylamino group, N-ethyl-N-methylamino group or the like.

The term "may have 1 or 2 substituents" used in the specification means that there may be 1 or 2 substituents in any combination in sites capable of substituting.

$R^1$ preferably represents a hydrogen atom, a halogen atom, an amino group, a $C_{1-6}$ alkyl group, a $C_{1-6}$ alkoxy group, a $C_{1-6}$ alkylamino group, a hydroxyl $C_{1-6}$ alkylamino group, or a $C_{1-6}$ alkoxy $C_{1-6}$ alkyl group, and more preferably a hydrogen atom, an amino group or a $C_{1-6}$ alkoxy $C_{1-6}$ alkyl group, with a methoxymethyl group being preferred as the $C_{1-6}$ alkoxy $C_{1-6}$ alkyl group.

$R^2$ represents a hydrogen atom, an amino group or di $C_{1-6}$ alkylamino group, with a hydrogen atom or an amino group being preferred.

One of X and Y is a nitrogen atom while the other is a nitrogen atom or an oxygen atom.

The partial structure which contains X and Y and which is represented by formula (II) below:

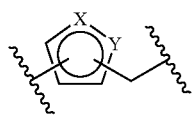
(II)

has a structure such as those shown below, preferably with the left side bound to the 3-position of a pyridine ring via a single bond, and the right side bound to an A ring via a methylene group:

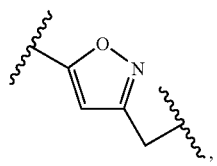
(III)

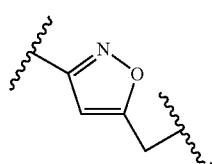
(IV)

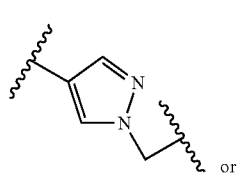
(V)
or

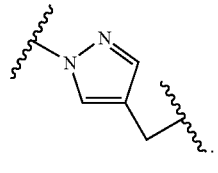
(VI)

In the case of the partial structure of formula (III), for example, the structure of the compound of the present invention is shown by the following formula:

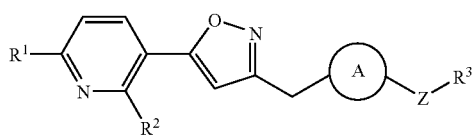

It is preferable that one of X and Y be a nitrogen atom and the other be an oxygen atom, or that both X and Y be nitrogen atoms, and when one of X and Y is a nitrogen atom and the other is an oxygen atom, the partial structure which contains X and Y, and which is represented by the following formula (II):

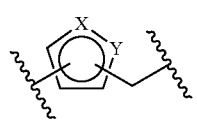
(II)

has a structure such as that shown by formulae (III) or (IV) below, preferably with the left end bound to the 3-position of a pyridine ring via a single bond and the right end linked to an A ring via a methylene group:

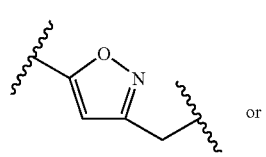
(III)

or

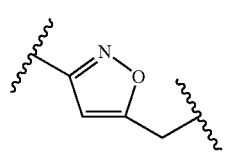
(IV)

while if X and Y are both nitrogen atoms, the partial structure which contains X and Y, and which is represented by the following formula (II):

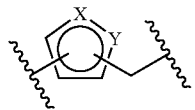

(II)

has a structure such as that shown by formula (V) or (VI) below, preferably with the left end bound to the 3-position of a pyridine ring via a single bond and the right end bound to an A ring via a methylene group:

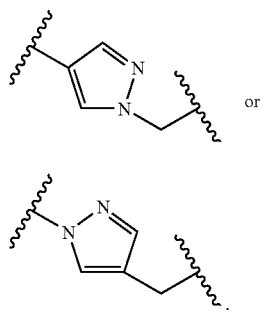

(V)

or (VI)

A ring A represents a 5- or 6-member heteroaryl ring or a benzene ring which may have a halogen atom or 1 or 2 $C_{1-6}$ alkyl groups, and preferably represents a pyridine ring, a benzene ring, a furan ring, a thiophene ring or a pyrrole ring, or more preferably a pyridine ring, a benzene ring or a thiophene ring, still more preferably a pyridine ring or a benzene ring.

Z preferably represents a single bond, a methylene group, an ethylene group, an oxygen atom, a sulfur atom, —$CH_2O$—, —$OCH_2$—, —NH—, —$NHCH_2$—, —$CH_2NH$—, —$CH_2$—S—, or —$SCH_2$—. Of these a methylene group, an oxygen atom, —$CH_2O$— or —$OCH_2$— is preferred, and an oxygen atom, —$CH_2O$— or —$OCH_2$— is especially preferred.

$R^3$ represents a hydrogen atom, halogen atom, a $C_{1-6}$ alkyl group, a $C_{3-8}$ cycloalkyl group, a $C_{6-10}$ aryl group or a 5- or 6-member ring heteroaryl group which may have 1 or 2 substituents each selected from substituent group α:

[Substituent Group α]

a halogen atom, a cyano group, a $C_{1-6}$ alkyl group, a $C_{1-6}$ alkoxy group, $C_{1-6}$ alkoxycarbonyl group, a $C_{3-8}$ cycloalkyl group, a $C_{2-6}$ alkenyl group and a $C_{2-6}$ alkynyl group.

Examples of preferable groups as $R^3$ include a n-butyl group, a cyclopropyl group, a phenyl group, a fluorophenyl group, a furyl group, a chlorofuryl group, a methylfuryl group, a thienyl group, a bromothienyl group, a methylthienyl group, a pyridyl group and a methylpyridyl group, more preferably a n-butyl group, a cyclopropyl group, a phenyl group, a fluorophenyl group, a pyridyl group or a methylpyridyl group.

Z and $R^3$ may constitute the substituent of ring A in any combination. Preferable examples of $R^3$—Z— as the substituent of ring A constituted in this way include a phenoxy group, a benzyloxy group, a 2-fluoro-benzyloxy group, a 3-fluoro-benzyloxy group, a 4-fluoro-benzyloxy group, a pyridin-2-yloxymethyl group, a 6-methyl-pyridin-2-yloxymethyl group, a pyridin-2-ylmethoxy, a 6-methyl-pyridin-2-ylmethoxy group, a 4-methyl-pyridin-2-ylmethoxy group, a butoxymethyl group and a cyclopropylmethoxy group and the like.

Preferable examples of the compounds of the present invention include the following compounds:

3-(3-(4-benzyloxy-benzyl)-isoxazol-5-yl)-pyridin-2-ylamine;
3-(3-(4-pyridin-2-yloxymethyl)-benzyl)-isoxazol-5-yl)-pyridin-2-ylamine;
3-(3-(4-(pyridin-2-ylmethoxy)-benzyl)-isoxazol-5-yl)-pyridin-2-ylamine;
3-(3-(4-(4-methyl-pyridin-2-ylmethoxy)-benzyl)-isoxazol-5-yl)-pyridin-2-ylamine;
3-(3-(6-benzyloxy-pyridin-3-ylmethyl)-isoxazol-5-yl)-pyridin-2-ylamine;
3-(3-(4-benzyloxy-benzyl)-isoxazol-5-yl)-pyridin-2,6-diamine;
3-(3-(4-pyridin-2-yloxymethyl)-benzyl)-isoxazol-5-yl)-pyridine-2,6-diamine;
3-(3-(4-(6-methyl-pyridin-2-yloxymethyl)-benzyl)-isoxazol-5-yl)-pyridin-2,6-diamine;
3-(3-(4-butoxymethyl-benzyl)-isoxazol-5-yl)-pyridin-2,6-diamine;
3-(3-(4-phenoxy-benzyl)-isoxazol-5-yl)-pyridin-2,6-diamine;
3-(3-(4-(4-methyl-pyridin-2-ylmethoxy)-benzyl)-isoxazol-5-yl)-pyridin-2,6-diamine;
3-(3-(6-benzyloxy-pyridin-3-ylmethyl)-isoxazol-5-yl)-pyridin-2,6-diamine;
6-methoxymethyl-3-(3-(4-pyridin-2-yloxymethyl)-benzyl)-isoxazol-5-yl)-pyridin-2-ylamine;
3-(5-(4-benzyloxy-benzyl)-isoxazol-3-yl)-pyridin-2-ylamine;
3-(5-(4-(pyridin-2-yloxymethyl)-benzyl)-isoxazol-3-yl)-pyridin-2-ylamine;
3-(1-(4-benzyloxy-benzyl)-1H-pyrazol-4-yl)-pyridin-2-ylamine;
3-(1-(4-(pyridin-2-yloxymethyl)-benzyl)-1H-pyrazol-4-yl)-pyridin-2-ylamine;
3-(1-(4-butoxymethyl-benzyl)-1H-pyrazol-4-yl)-pyridin-2-ylamine;
3-(1-(4-benzyloxy-benzyl)-1H-pyrazol-4-yl)-pyridin-2,6-diamine;
3-(1-(4-(pyridin-2-yloxymethyl)-benzyl)-1H-pyrazol-4-yl)-pyridin-2,6-diamine;
3-(1-(4-butoxymethyl-benzyl)-1H-pyrazol-4-yl)-pyridin-2,6-diamine;
3-(3-(6-phenoxy-pyridin-3-ylmethyl)-isoxazol-5-yl)-pyridin-2,6-diamine;
3-(3-(4-(5-fluoro-pyridin-2-ylmethoxy)-benzyl)-isoxazol-5-yl)-pyridin-2-ylamine;
3-(3-(4-(4-methyl-pyridin-2-yloxymethyl)-benzyl)-isoxazol-5-yl)-pyridin-2-ylamine;
3-(3-(4-(6-fluoro-pyridin-2-ylmethoxy)-benzyl)-isoxazol-5-yl)-pyridin-2-ylamine;
3-(3-(4-(4-chloro-pyridin-2-ylmethoxy)-benzyl)-isoxazol-5-yl)-pyridin-2-ylamine;
3-(3-(4-(6-chloro-pyridin-2-ylmethoxy)-benzyl)-isoxazol-5-yl)-pyridin-2-ylamine;
3-(3-(6-phenoxymethyl-pyridin-3-ylmethyl)-isoxazol-5-yl)-pyridin-2-ylamine;
3-(3-(4-(6-fluoro-pyridin-2-yloxymethyl)-benzyl)-isoxazol-5-yl)-pyridin-2-ylamine;

3-(3-(6-(4-fluoro-benzyloxy)-pyridin-3-ylmethyl)-isoxazol-5-yl)-pyridin-2-ylamine;
3-(3-(4-(5-chloro-furan-2-ylmethyl)-benzyl)-isoxazol-5-yl)-pyridin-2-ylamine;
3-(3-(4-phenylaminomethyl-benzyl)-isoxazol-5-yl)-pyridin-2-ylamine;
3-(3-(4-(4-methyl-pyridin-2-yloxymethyl)-benzyl)-isoxazol-5-yl)-pyridin-2,6-diamine;
3-(3-(4-(6-fluoro-pyridin-2-ylmethoxy)-benzyl)-isoxazol-5-yl)-pyridin-2,6-diamine;
3-(3-(4-(5-methyl-furan-2-ylmethyl)-benzyl)-isoxazol-5-yl)-pyridin-2,6-diamine;
3-(3-(4-(4-chloro-pyridin-2-ylmethoxy)-benzyl)-isoxazol-5-yl)-pyridin-2,6-diamine;
3-(3-(4-(6-chloro-pyridin-2-ylmethoxy)-benzyl)-isoxazol-5-yl)-pyridin-2,6-diamine;
3-(3-(6-phenoxymethyl-pyridin-3-ylmethyl)-isoxazol-5-yl)-pyridin-2,6-diamine;
3-(3-(4-(5-fluoro-pyridin-2-ylmethoxy)-benzyl)-isoxazol-5-yl)-pyridin-2,6-diamine;
3-(3-(4-(6-fluoro-pyridin-2-ylmethoxy)-benzyl)-isoxazol-5-yl)-pyridin-2,6-diamine;
3-(3-(1-benzyl-1H-pyrrol-3-ylmethyl)-isoxazol-5-yl)-pyridin-2,6-diamine;
3-(3-(6-(4-fluoro-benzyloxy)-pyridin-3-ylmethyl)-isoxazol-5-yl)-pyridin-2,6-diamine;
3-(3-(4-(5-chloro-furan-2-ylmethyl)-benzyl)-isoxazol-5-yl)-pyridin-2,6-diamine;
3-(3-(6-(3-fluoro-phenoxy)pyridin-3-ylmethyl)-isoxazol-5-yl)-pyridin-2,6-diamine;
3-(3-(4-phenylaminomethyl-benzyl)-isoxazol-5-yl)-pyridin-2,6-diamine;
3-(3-(6-(4-fluoro-phenoxy)-pyridin-3-ylmethyl)-isoxazol-5-yl)-pyridin-2,6-diamine;
3-(3-(4-(thiazol-2-ylmethoxy)-benzyl)-isoxazol-5-yl)-pyridin-2,6-diamine;
3-(3-(5-(4-fluoro-phenoxy-thiophen-2-ylmethyl)-isoxazol-5-yl)-pyridin-2,6-diamine;
6-methoxymethyl-3-(3-(4-(pyridin-2-ylmethoxy)-benzyl)-isoxazol-5-yl)-pyridin-2-ylamine;
6-methyl-3-(3-(4-pyridin-2-yloxymethyl)-benzyl)-isoxazol-5-yl)-pyridin-2-ylamine;
5-(3-(4-pyridin-2-yloxymethyl)-benzyl)-isoxazol-5-yl)-pyridin-2-ylamine;
3-(1-(4-(pyridin-2-ylmethoxy)-benzyl)-1H-pyrazol-4-yl)-pyridin-2-ylamine; and
3-(3-(4-(pyridin-2-yloxymethyl)-benzyl)-isoxazol-5-yl)-pyridine.

Examples of the term "salt" used in the present specification include a salt with an inorganic acid, a salt with an organic acid, a salt with an inorganic base, a salt with an organic base, a salt with an acidic or basic amino acid or the like. Among these salts, it is preferable that a salt used herein be a pharmaceutically acceptable.

Preferable examples of the salt with the inorganic acid include salts with hydrochloric acid, hydrobromic acid, sulfuric acid, nitric acid, phosphoric acid or the like. Preferable examples of the salt with the organic acid include salts with acetic acid, succinic acid, fumaric acid, maleic acid, tartaric acid, citric acid, lactic acid, stearic acid, benzoic acid, methanesulfonic acid, ethanesulfonic acid, p-toluenesulfonic acid or the like.

Preferable examples of the salt with the acidic amino acid include salts with aspartic acid, glutamic acid or the like. Preferable examples of the salt with the basic amino acid include salts with arginine, lysine, ornithine or the like.

The term "antifungal agent" used in the present specification refers to a preventive agent or a therapeutic agent for fungal infection.

The compounds according to the present invention, or salts or hydrates thereof, can be formulated into tablets, powders, fine granules, granules, coated tablets, capsulates, syrups, troches, inhalants, suppositories, injections, ointments, eye ointments, tapes, eye drops, nose drops, ear drops, cataplasms, lotions or the like, by the conventional methods.

Such formulation can be achieved by using typical diluents, binders, lubricants, colorants, flavorants, and, as necessary, stabilizers, emulsifiers, absorbefacients, surfactants, pH modulators, preservatives, antioxidants or the like, and materials commonly used as ingredients of pharmaceutical preparations according to the conventional methods. For example, an oral preparation can be produced by combining a compound of the present invention or a pharmaceutically acceptable salt thereof with a diluent, and if required, a binder, a disintegrating agent, a lubricant, a colorant, a flavorant or the like, and formulating the mixture into powders, fine granules, granules, tablets, coated tablets, capsules or the like according to the conventional methods.

Examples of the materials include animal and vegetable oils such as soy bean oil, beef tallow, and synthetic glyceride; hydrocarbons such as liquid paraffin, squalane, and solid paraffin; ester oils such as octyldodecyl myristate and isopropyl myristate; higher alcohols such as cetostearyl alcohol and behenyl alcohol; silicone resins; silicone oils; surfactants such as polyoxyethylene fatty acids ester, sorbitan fatty acid ester, polyoxyethylene sorbitan fatty acid ester, polyoxyethylene hydrogenated castor oil, and polyoxyethylene polyoxypropylene block co-polymer; water-soluble polymers such as hydroxyethyl cellulose, polyacrylic acid, carboxyvinyl polymer, polyethylene glycol, polyvinylpyrrolidone, and methyl cellulose; lower alcohols such as ethanol and isopropanol; polyhydric alcohols such as glycerol, propylene glycol, dipropylene glycol, and sorbitol; sugars such as glucose and sucrose; inorganic powder such as anhydrous silicic acid, magnesium aluminum silicate, and aluminum silicate; and pure water. Examples of the diluents include lactose, corn starch, white sugar, glucose, mannitol, sorbitol, crystalline cellulose, silicon dioxide or the like. Examples of the binders include polyvinyl alcohol, polyvinyl ether, methylcellulose, ethylcellulose, gum Arabic, tragacanth, gelatin, shellac, hydroxypropyl methylcellulose, hydroxypropyl cellulose, polyvinylpyrrolidone, polypropylene glycol-polyoxyethylene block co-polymer, and meglumine or the like. Examples of disintegrating agents include starch, agar, gelatin powder, crystalline cellulose, calcium carbonate, sodium hydrogencarbonate, calcium citrate, dextrin, pectin, calcium carboxymethyl cellulose or the like. Examples of lubricants include magnesium stearate, talc, polyethylene glycol, silica, hydrogenated vegetable oil or the like. Examples of colorants include those pharmaceutically acceptable. Examples of flavorants include cocoa powder, peppermint camphor, aromatic powder peppermint oil, Borneo camphor, cinnamon powder or the like. Tablets and granules may be coated with sugar, or if required, other appropriate coatings can be made. Solutions, such as syrups or injectable preparations, to be administered can be formulated by combining a compound according to the present invention or a pharmaceutically acceptable salt thereof with a pH modulator, a solubilizing agent, an isotonizing agent or the like, and if required, with an auxiliary solubilizing agent, a stabilizer or the like, according to the conventional methods. Methods for manufacturing external preparations are not limited and such preparations can be manufactured by the conventional methods. Specifically, various materials typically used for manufacturing pharmaceuticals, quasi drugs, cosmetics or the like can be used as base materials for the external formulation. More specifically, examples of base materials to be used include animal and vegetable oils, minerals oils, ester oils, wax, higher alcohols, fatty acids, silicone oil, surfactants, phospholipids, alcohols, polyhydric alcohols, water-soluble polymers, clay minerals, pure water or the like. Furthermore, external preparations of the present invention can contain, as required, pH modulators, antioxidants, chelating agents, antibacterial/antifungal agents, colorants, odoriferous substances or the like. But this does not limit the type of base materials that are to be used in the external preparations of the present invention. If required, the preparation may contain differentiation inducers, blood flow improving agents, antimicrobial agents, antiphlogistics, cell activators, vitamins, amino acids, humectants, keratolytic agents or the like. The amount of the base materials listed above is adjusted within a concentration range used for producing typical external preparations.

When administering the compound of the present invention or a salt thereof, the forms of the compounds are not limited in particular, and the compound can be given orally or parenterally by the conventional method. For instance, the compound can be administered as a dosage form such as tablets, powders, granules, capsules, syrups, troches, inhalants, suppositories, injections, ointments, eye ointments, tapes, eye drops, nasal drops, ear drops, cataplasms and lotions.

Dose of a medicament according to the present invention can be selected appropriately according to symptom severity, age, sex, body weight, forms of administration, type of salts, specific type of disease or the like.

The does varies remarkably depending on the patient's disease, symptom severity, age and sex, drug susceptibility or the like. An oral preparation according to the present invention can be generally administered once or several time at a dose of from 1 to 10000 mg/adult/day, preferably from 10 to 2000 mg/adult/day. An injection according to the present invention can be generally administered at a dose of from 0.1 to 10000 mg/adult/day, preferably from 1 to 2000 mg/adult/day.

General Synthesis Methods

The method for manufacturing the compounds represented by formula (I) according to the present invention (hereinafter referred to as compounds (I)) is discussed here. The compounds according to the present invention can be synthesized by ordinary organic synthesis methods, but for example, among the compounds (I), the compounds represented by formula (1a), formula (2a), formula (3a), formula (4a), formula (5a), formula (6a-1), formula (6a-3), formula (7), formula (8a), formula (9a) and formula (10a) (hereinafter referred to as compound (1a), compound (2a), compound (3a), compound (4a), compound (5a), compound (6a-1), compound (6a-3), compound (7a), compound (8a), compound (9a) and compound (10a), respectively) can be synthesized by the methods given [Manufacturing Method 1] to [Manufacturing Method 10] below and the like.

Manufacturing Method 1

Typical Method for Manufacturing Compound (1a)

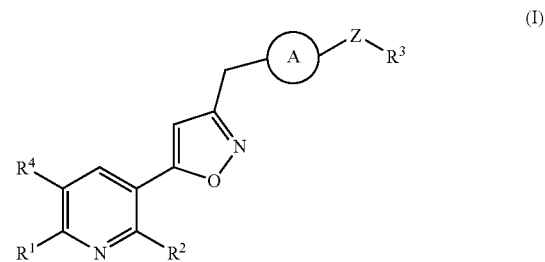

(wherein ring A, $R^1$, $R^2$, $R^3$, and $R^4$ and Z are defined as above.)

Manufacturing Method 1-1

Method for Manufacturing Compound (1a)

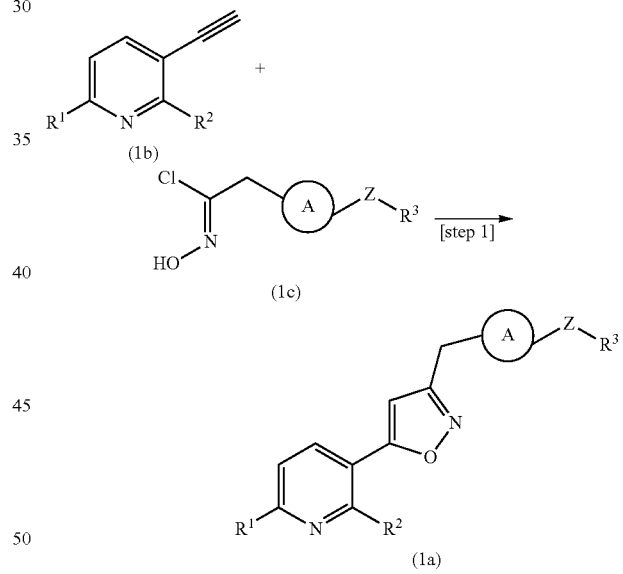

(wherein the ring A, $R^1$, $R^2$, $R^3$, and Z have the same meanings as defined above.)

Compound (1b) which is a commercially available product can be used as is or compound (1b) can also be manufactured from a commercially available product by the well known methods. In addition, compound (1b) can be manufactured by the methods described in the Manufacturing Examples in the Examples or according to [Manufacturing Method 1-2-1] or the like.

Compound (1c) can be manufactured by the well known methods from a commercial available product. Compound (1c) can also be manufactured by the methods described in the Manufacturing Examples in the Examples or according to [Manufacturing Method 1-3-1] and the like.

[Step 1]

This step is a step wherein compound (1a) is obtained by reacting compound (1b) and compound (1c) in the presence of a base. There are no particular limitations on the solvent used in this reaction as long as it dissolves the starting materials to a certain extent without impeding the reaction. Examples of the solvents used in this reaction include ether solvents such as tetrahydrofuran and diethyl ether; aromatic hydrocarbon solvents such as benzene and toluene; amide solvents such as N,N-dimethylformamide and N-methylpyrrolidinone; alcohol solvents such as methanol and ethanol; and water, methylene chloride, chloroform, ethyl acetate, dimethyl sulfoxide, mixed solvents of the foregoing and the like. Examples of the base used in this reaction include triethylamine, N,N-diisopropylethylamine, sodium hydrogencarbonate, potassium carbonate and the like. Compound (1c) can be used in the amount of 1 to 3 equivalents, preferably 1 to 2 equivalents, based on compound (1b). The base can be used in the amount of 1 to 3 equivalents based on compound (1c). The reaction temperature is from room temperature to reflux temperature, and the reaction time is from 10 minutes to 24 hours.

Manufacturing Method 1-2-1

Method 1 for Manufacturing Compound (1b)

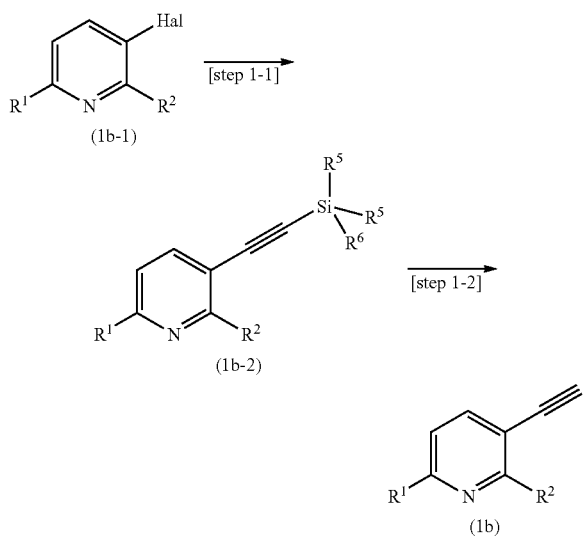

(wherein $R^1$ and $R^2$ are defined as above, Hal represents a halogen atom, and $R^5$ and $R^6$ represent each independently $C_{1-6}$ alkyl groups.)

Compound (1b-1) which is a commercially available product can be used as is, or compound (1b-1) can also be manufactured from commercially available products by the well known methods.

[Step 1-1]

This step is a step wherein compound (1b-2) is obtained by reacting compound (1b-1) with an ethynyl silane derivative. Compound (1b-2) can be obtained by reacting compound (1b-1) with an ethynyl silane derivative in the presence of a palladium catalyst, a base and a copper catalyst. A phosphine ligand may also be added to obtain good results. There are no particular limitations on the solvent used in this reaction as long as it can dissolve the starting materials to a certain extent without impeding the reaction. Examples of the solvents used in this reaction include ether solvents such as tetrahydrofuran and 1,4-dioxane; amide solvents such as N,N-dimethylformamide and N-methylpyrrolidinone; and acetonitrile, dimethyl sulfoxide, mixed solvents of the foregoing and the like. Examples of the ethynyl silane derivative include trimethylsilylacetylene, triethylsilylacetylene, triisopropylsilylacetylene, t-butyldimethylsilylacetylene and the like. Examples of the palladium catalysts include palladium (II) acetate, tetrakis(triphenylphosphine)palladium (0), dichlorobis(triphenylphosphine)palladium (II), dichlorobis(tri-o-tolylphosphine)palladium (II), bis(tri-t-butylphosphine)palladium (0), or tris(dibenzylideneacetone)dipalladium (0) and the like. Examples of the base include triethylamine, N,N-diisopropylethylamine, pyridine and the like. Examples of the phosphine ligand include triphenylphosphine, tri-o-tolylphosphine, tri-t-butylphosphine and the like. A copper catalyst can be added in this reaction. Examples of the copper catalyst include copper, copper (I) iodide, copper (I) bromide, copper (I) chloride and the like. The ethynyl silane derivative is used in the amount of 1 to 5 equivalents based on compound (1b-1). The palladium catalyst is used in the amount of 0.01 to 0.3 equivalents based on compound (1b-1). The base is used in the amount of 2 to 5 equivalents based on compound (1b-1). The phosphine ligand is used in the amount of 0.01 to 1.2 equivalents based on compound (1b-1). The copper catalyst is used in the amount of 0.001 to 0.3 equivalents based on compound (1b-1). The reaction temperature is from room temperature to reflux temperature, and the reaction time is from 30 minutes to 24 hours.

[Step 1-2]

This step is a step wherein compound (1b) is obtained by reacting compound (1b-2) with a base. There are no particular limitations on the solvent used in this reaction as long as it dissolves the starting materials to a certain extent without impeding the reaction. Examples of the solvents in this step include ether solvents such as tetrahydrofuran and diethyl ether; alcohol solvents such as methanol and ethanol; amide solvents such as N,N-dimethylformamide and N-methylpyrrolidinone; and acetonitrile, dimethyl sulfoxide, water, mixed solvents of the foregoing and the like. Examples of the base include potassium carbonate, sodium hydroxide, tetrabutylammonium fluoride, potassium fluoride, cesium fluoride and the like. The base is used in the amount of 0.05 to 10 equivalents based on compound (1b-2). The reaction temperature is from 0° C. to reflux temperature, and the reaction time is from 5 minutes to 24 hours.

Manufacturing Method 1-2-2

Method 2 for Manufacturing Compound (1b)

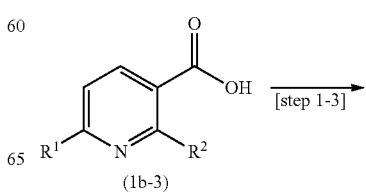

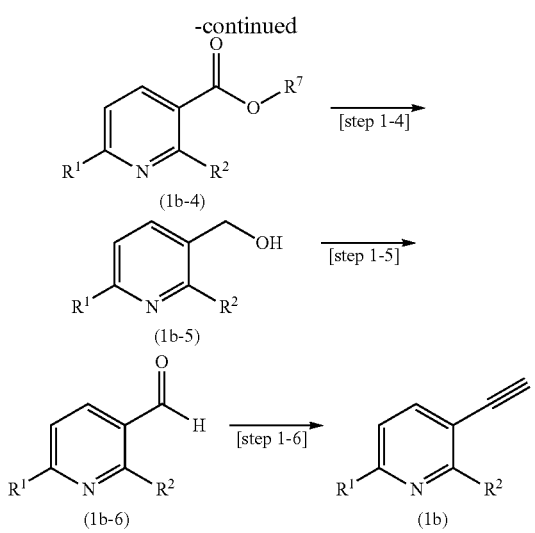

(wherein R¹ and R² are defined as above, and R⁷ represents a $C_{1-6}$ alkyl group.)

Compound (1b-3) which is a commercially available product can be used as is, or compound (1b-3) can also be manufactured from commercially available products by the well known methods.

[Step 1-3]

This step is a step wherein compound (1b-4) is obtained by esterifying compound (1b-3) in the presence of an acid. The solvent used in this reaction is preferably an alcohol solvent such as methanol, ethanol and the like. Examples of the acids include sulfuric acid, hydrochloric acid, hydrobromic acid and the like. The acid can be used in the amount from a catalytic amount to a solvent amount based on compound (1b-3). The reaction temperature is from room temperature to reflux temperature, and the reaction time is from 1 hour to 72 hours.

Compound (1b-4) can also be obtained from compound (1b-4) by the methods described as Alternative Methods (1), (2) and (3) below.

Alternative Method (1): Compound (1b-4) can be converted into a methyl ester derivative using diazomethane or trimethylsilyl diazomethane. There are no particular limitations on the solvent used in this reaction as long as it dissolves the starting materials to a certain extent without impeding the reaction. Examples of the solvent used in this reaction include ether solvents such as tetrahydrofuran and diethyl ether; aromatic hydrocarbon solvents such as benzene and toluene; alcohol solvents such as methanol and ethanol; and methylene chloride, hexane, mixed solvents of the foregoing and the like. The diazomethane or trimethylsilyl diazomethane is used in the amount of 1 to 2 equivalents based on compound (1b-3). The reaction temperature is from 0° C. to room temperature, and the reaction time is from 10 minutes to 24 hours.

Alternative Method (2): Compound (1b-3) can be converted into compound (1b-4) using an alkylating agent in the presence of a base. There are no particular limitations on the solvent used in this reaction as long as it dissolves the starting materials to a certain extent without impeding the reaction. Examples of the solvents used in this reaction include ether solvents such as tetrahydrofuran and diethyl ether; aromatic hydrocarbon solvents such as benzene and toluene; amide solvents such as N,N-dimethylformamide and N-methylpyrrolidinone; alcohol solvents such as methanol and ethanol; and water, acetone, acetonitrile, dimethyl sulfoxide, mixed solvents of the foregoing and the like. A phase-transfer catalyst such as tetrabutylammonium bromide can also be added to this reaction. Examples of the base used in this reaction include potassium hydroxide, sodium hydroxide, lithium hydroxide, potassium carbonate, cesium carbonate, cesium fluoride and the like. Examples of the alkylating agents include iodomethane, iodoethane, dimethylsulfate and the like. The base is used in the amount of 1 to 1.5 equivalents based on compound (1b-3). The alkylating agent is used in the amount of 1 to 2 equivalents based on compound (1b-3). The reaction temperature is from 0° C. to reflux temperature, and the reaction time is from 1 hour to 72 hours.

Alternative Method (3): Compound (1b-3) can be converted into an acid chloride using a halogenating agent, and then converted into compound (1b-4) by addition of alcohol. There are no particular limitations on the solvent used in this reaction as long as it dissolves the starting materials to a certain extent without impeding the reaction. Examples of the solvents used in this reaction include aromatic hydrocarbon solvents such as benzene and toluene; amide solvents such as N,N-dimethylformamide and N-methylpyrrolidinone; and acetonitrile, methylene chloride, 1,2-dichloroethane, mixed solvents of the foregoing and the like. The halogenating agent can also be used as the solvent. A catalytic amount of pyridine or a phase-transfer catalyst such as benzyltriethylammonium chloride can also be added to this reaction. Examples of the halogenating agents include thionyl chloride, phosphorus pentachloride and the like. Examples of the alcohols include methanol, ethanol and the like. The halogenating agent is used in the amount of 1 to 20 equivalents based on compound (1b-3). The alcohol is used in the amount of 1 to 20 equivalents based on compound (1b-3). The reaction temperature during conversion to an acid chloride is from 0° C. to reflux temperature, with a reaction time being from 10 minutes to 48 hours. The reaction temperature for reacting the alcohol is from 0° C. to reflux temperature, with a reaction time being from 10 minutes to 48 hours. The alcohol can be used as the solvent in this reaction. In this case, compound (1b-4) can be obtained by adding the halogenating agent to a mixture of the solvent and compound (1b-3). The reaction temperature is from 0° C. to room temperature, and the reaction time is from 10 minutes to 24 hours.

[Step 1-4]

This step is a step wherein compound (1b-5) is obtained by reduction of compound (1b-4). There are no particular limitations on the solvent used in this reaction as long as it dissolves the starting materials to a certain extent without impeding the reaction, but tetrahydrofuran is preferred. Examples of the reducing agent in this reaction include lithium aluminum hydride, lithium aluminum hydride-aluminum chloride (aluminum chloride in the amount of 1 to 1.5 equivalents based on lithium aluminum hydride), lithium borohydride and the like. The reducing agent is used in the amount of 0.5 to 4 equivalents based on compound (1b-4). The reaction temperature is from 0° C. to reflux temperature, and the reaction time is from 10 minutes to 48 hours.

[Step 1-5]

This step is a step wherein compound (1b-6) is obtained by oxidation of compound (1b-5). There are no particular limitations on the solvent used in this reaction as long as it dissolves the starting materials to a certain extent without impeding the reaction. Examples of the solvents used in this reaction include ether solvents such as tetrahydrofuran and diethyl ether; aromatic hydrocarbon solvents such as benzene and toluene; alcohol solvents such as methanol and ethanol; and methylene chloride, acetone, hexane, mixed solvents of the foregoing and the like. Examples of oxidizing agent used in this reaction include manganese dioxide, pyridinium chlorochromate, pyridinium dichromate, dimethyl sulfoxide-activator, tetrapropylammonium perruthenate, dichlorotris (triphenylphosphine)ruthenium (II), 1,1,1-tris(acetyloxy)-1,1-dihydro-1,2-benziodoxol-3-(1H)-on (Dess-Martin Periodinane) and the like. The oxidizing agent is used in the amount of from the catalytic amount to 20 equivalents based on compound (1b-5). When oxidizing with dimethyl sulfoxide-activator, examples of the activator include acid anhydrides such as acetic anhydride and trifluoroacetic anhydride; acid chlorides such as oxalyl chloride and thionyl chloride; and chlorine, N-chlorosuccinimide and the like. The dimethyl sulfoxide is used in the amount of 1 to 20 equivalents based on the activator. When using tetrapropyl ammonium perruthenate or dichlorotris(triphenylphosphine)ruthenium (II) in a catalytic amount, an oxidizing agent such as N-methylmorpholine-N-oxide or bis(trimethylsilyl)peroxide can be used at the same time. The reaction temperature is from −78° C. to reflux temperature, and the reaction time is from 10 minutes to 72 hours.

[Step 1-6]

This step is a step wherein compound (1b) is obtained from compound (1b-6) in the presence of a base using a diazo compound. Examples of the diazo compound used in this reaction include trimethylsilyl diazomethane, (1-diazo-2-oxopropyl)-phosphoric acid dimethyl ester, diazomethyl phosphoric acid dimethyl ester and the like. There are no particular limitations on the solvent used in this reaction as long as it dissolves the starting materials to a certain extent without impeding the reaction. Examples of the solvents used in this reaction include ether solvents such as tetrahydrofuran and diethyl ether; aromatic hydrocarbon solvents such as benzene and toluene; alcohol solvents such as methanol and ethanol; and methylene chloride, hexane, mixed solvents of the foregoing and the like. When using trimethylsilyl diazomethane as the diazo compound, n-butyl lithium and lithium diisopropylamide can be used as the base. When using a phosphoric acid ester derivative such as (1-diazo-2-oxopropyl)-phosphoric acid dimethyl ester and diazomethyl phosphoric acid dimethyl ester as the diazo compound, potassium carbonate, potassium t-butoxide and the like can be used as the base. The diazo compound is used in the amount of 1 to 1.5 equivalents based on compound (1b-6). The base is used in the amount of 1 to 2 equivalents based on compound (1b-6). The reaction temperature is from −78° C. to room temperature, and the reaction time is from 10 minutes to 24 hours.

Compound (1b) can also be obtained from compound (1b-6) by the methods given below as Alternative Methods (1).

Alternative Method (1): Compound (1b-6) can be converted into a dihaloalkene in the presence of a base, and then reacted with a base to obtain compound (1b).

Dihaloalkene synthesis: There are no particular limitations on the solvent used in this reaction as long as it dissolves the starting materials to a certain extent without impeding the reaction. Examples of the solvent used in this synthesis include ether solvents such as tetrahydrofuran and diethyl ether; aromatic hydrocarbon solvents such as benzene and toluene; and hexane, mixed solvents of the foregoing and the like. Examples of the reagent for converting compound (1b-6) into dihaloalkene include (dichloromethyl)-phosphoric acid dimethyl ester, dibromomethyl triphenyl phosphonium bromide (*Tetrahedron Letters*, Vol. 40, No. 49, 8575-8578) and the like. Examples of the base in this reaction include lithium diisopropylamide, potassium t-butoxide and the like. The reagent for converting into dihaloalkene is used in the amount of 1 to 1.5 equivalents based on compound (1b-6). The base is used in the amount of 1 to 2 equivalents based on compound (1b-6). The reaction temperature is from −78° C. to room temperature, and the reaction time is from 10 minutes to 24 hours.

As another synthetic method of dihaloalkene, following alternative method using carbon tetrabromide can be applied. Compound (1b-6) is converted into dihaloalkene by reacting carbon tetrabromide and triphenylphosphine. Zinc can also be added in this reaction. There are no particular limitations on the solvent used in this reaction as long as it dissolves the starting materials to a certain extent without impeding the reaction. Preferable examples of the solvent used in this synthesis include tetrahydrofuran and methylene chloride. The carbon tetrabromide is used in the amount of 1 to 2 equivalents based on compound (1b-6). The triphenylphosphine is used in the amount of 2 to 4 equivalents based on compound (1b-6). The zinc is used in the amount of 1 equivalent based on the carbon tetrabromide. The reaction temperature is from 0° C. to room temperature, and the reaction time is from 10 minutes to 12 hours.

Synthesis of compound (1b) from dihaloalkene: There are no particular limitations on the solvent used in this reaction as long as it dissolves the starting materials to a certain extent without impeding the reaction. Examples of the solvent used in this synthesis include ether solvents such as tetrahydrofuran and diethyl ether; aromatic hydrocarbon solvents such as benzene and toluene; and hexane, mixed solvents of the foregoing and the like. Examples of the base used in this reaction include n-butyl lithium, t-butyl lithium, potassium t-butoxide and the like. The base is used in the amount of 2 to 3 equivalents based on the dihaloalkene. The reaction temperature is from −78° C. to room temperature, and the reaction time is from 10 minutes to 24 hours.

Manufacturing Method 1-2-3

Method for Manufacturing Compound (1b-3)

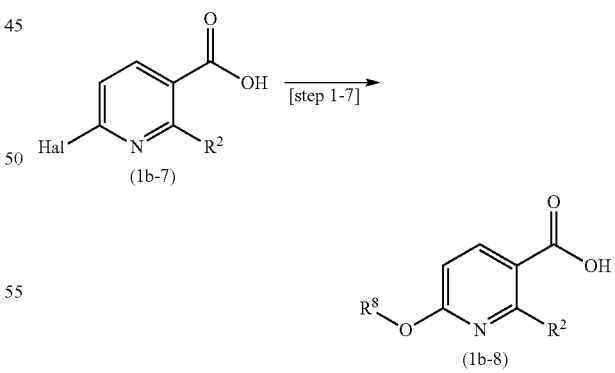

(wherein $R^2$ and Hal are defined as above, and $R^8$ represents a $C_{1-6}$ alkyl.)

Compound (1b-7) which is a commercially available product can be used as is, or compound (1b-7) can also be manufactured by from a commercially available product with the well known methods, for example, WO 2005/033079 A1, pp 85-86, etc.

[Step 1-7]

This step is a step wherein compound (1b-8) is obtained by reacting compound (1b-7) with an alcohol in the presence of a base. This step is carried out according to the procedures of [Step 1-39] given below or the method disclosed in Journal of Medicinal Chemistry, Vol. 46, No. 5, pp 702-705 or the like. There are no particular limitations on the solvent used in this reaction as long as it dissolves the starting materials to a certain extent without impeding the reaction. Examples of the solvents in this step include ether solvents such as tetrahydrofuran and diethyl ether; aromatic hydrocarbon solvents such as benzene and toluene; amide solvents such as N,N-dimethylformamide and N-methylpyrrolidinone; alcohol solvents such as methanol and ethanol; and dimethyl sulfoxide, mixed solvents of the foregoing and the like. Examples of the base in this step include sodium hydride, potassium t-butoxide, potassium hexamethyldisilazide and the like. A copper catalyst can be added in this reaction. Examples of the copper catalyst include copper, copper (I) iodide, copper (I) bromide, copper (I) chloride and the like. The base can be used in the amount of 1 to 20 equivalents based on compound (1b-7). The alcohol can be used in the amount of 1 to 20 equivalents based on compound (1b-7). The copper catalyst can be used in the amount of 0.01 to 0.3 equivalents based on compound (1b-7). The reaction temperature is from 0° C. to reflux temperature, and the reaction time is from 30 minutes to 48 hours.

Manufacturing Method 1-2-4

Method 1 for Manufacturing Compound (1b-4)

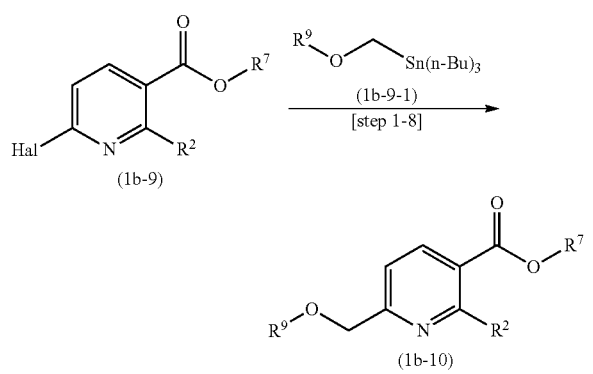

(wherein $R^2$, $R^7$ and Hal are defined as above and $R^9$ represents a $C_{1-6}$ alkyl group.)

Compound (1b-9) which is a commercially available product can be used as is, or compound (1b-9) can also be manufactured from commercially available products by the well known methods. Compound (1b-9-1) which is a commercially available product can be used as is, or compound (1b-9-1) can also be manufactured from commercially available products by the well known methods (for example, WO 2005/033079 A1, pp 85-86, etc.).

[Step 1-8]

This step is a step wherein compound (1b-10) is obtained by reacting compound (1b-9) with compound (1b-9-1) in the presence of a palladium catalyst. A phosphine ligand may also be added to obtain good results. There are no particular limitations on the solvent used in this reaction as long as it dissolves the starting materials to a certain extent without impeding the reaction. Examples of the solvents in this step include ether solvents such as 1,4-dioxane and tetrahydrofuran; aromatic hydrocarbon solvents such as toluene and xylene; amide solvents such as N,N-dimethylformamide and N-methylpyrrolidinone; and dimethyl sulfoxide, mixed solvents of the foregoing and the like. Examples of the palladium catalyst include palladium (II) acetate, tris(dibenzylideneacetone)dipalladium (0), dichlorobis(triphenylphosphine)palladium (II), dichlorobis(tri-o-tolylphosphine)palladium (II), bis(tri-t-butylphosphine)palladium (0), tetrakis(triphenylphosphine)palladium (0), 1,1'-bis(diphenylphosphinoferrocene)dichloropalladium (II) and the like. Examples of the phosphine ligand include triphenylphosphine, tri-o-tolylphosphine, tri-t-butylphosphine, diphenylphosphinoferrocene and the like. Compound (1b-9-1) is used in the amount of 1 to 3 equivalents based on compound (1b-9). The palladium catalyst is used in the amount of 0.01 to 0.3 equivalents based on compound (1b-9). The phosphine ligand is used in the amount of 0.01 to 1.2 equivalents based on compound (1b-9). The reaction temperature is from room temperature to reflux temperature, and the reaction time is from 10 minutes to 24 hours.

Manufacturing Method 1-2-5

Method 2 for Manufacturing Compound (1b-4)

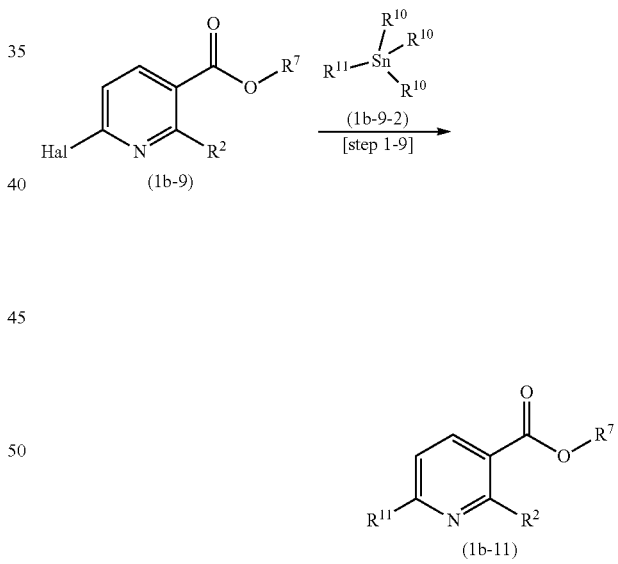

(wherein Hal, $R^2$ and $R^7$ are defined as above, $R^{10}$ and $R^{11}$ each independently represents $C_{1-6}$ alkyl groups.)

Compound (1b-9) and compound (1b-9-2) which are commercially available products can be used as is or may be obtained from commercially available products by the known methods

[Step 1-9]

This step is a step wherein compound (1b-11) is obtained by alkylating compound (1b-9) through a reaction with compound (1b-9-2) in the presence of a palladium catalyst. Compound (1b-11) can be manufactured according to the method similar to those of [Step 1-8].

Manufacturing Method 1-2-6

Method for Manufacturing Compound (1b-5)

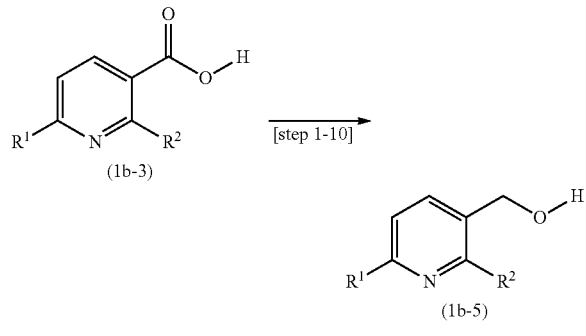

(wherein $R^1$ and $R^2$ are defined as above.)

Compound (1b-3) which is a commercially available product can be used as is or may be obtained from commercially available products by the known methods.

[Step 1-10]

This step is a step wherein compound (1b-5) is obtained by reducing compound (1b-3). Compound (1b-5) can be manufactured according to methods similar to those of [Step 1-4].

Manufacturing Method 1-2-7

Method for Manufacturing Halogen-Modified Product of Pyridine Ring

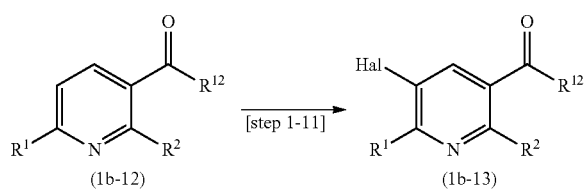

(wherein $R^1$, $R^2$ and Hal is defined as above; $R^{12}$ represents a hydrogen atom, a hydroxy group, or $OR^7$ ($R^7$ is defined as above).)

Compound (1b-12) which is a commercially available product can used as is or may be obtained from commercially available products by the known methods.

[Step 1-11]

This step is a step wherein compound (1b-13) is obtained by substituting a halogen atom for a hydrogen atom on the pyridine ring of compound (1b-12). This step can be carried out according to, for instance, European Journal of Medicinal Chemistry, Vol. 12, No. 6, 531-536, or, Journal of Organic Chemistry, Vol. 49, No. 26, 5237-5243, or the like. There are no particular limitations on the solvent used in this reaction as long as it dissolves the starting materials to a certain extent without impeding the reaction. Examples of the solvent include halogen solvents such as chloroform and dichloromethane; ether solvents such as tetrahydrofuran and diethyl ether; amide solvents such as N,N-dimethylformamide and N-methylpyrrolidinone; acid solvents such as acetic acid and hydrochloric acid aqueous solution; dimethyl sulfoxide; acetonitrile; mixed solvents of the foregoing, or the like. Examples of halogenation reagent include N-chlorosuccinimide, N-bromosuccinimide, chlorine and bromine. The halogenation reagent is used in the amount of 1.0 to 1.5 equivalents based on compound (1b-12). The reaction temperature is from room temperature to 50° C., and the reaction time is from 5 minutes to 24 hours.

Manufacturing Method 1-2-8

Method for Manufacturing Compound (1b-6)

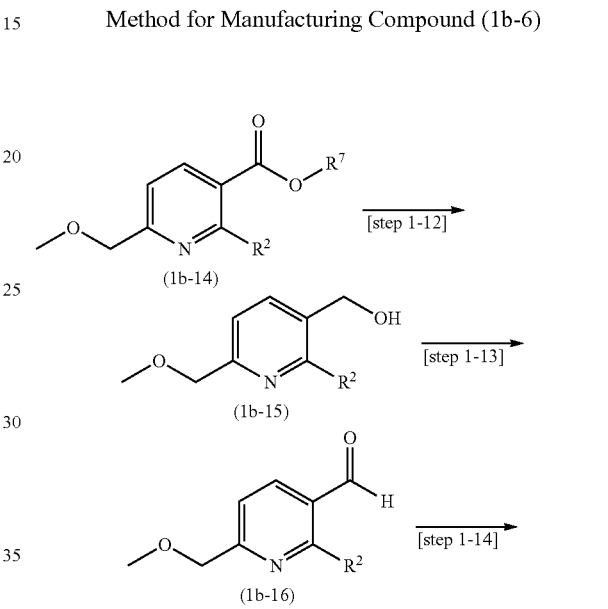

(wherein $R^2$ and $R^7$ is defined as above.)

Compound (1b-14) can be manufactured according to the methods described in [Manufacturing Method 1-2-4] given above.

[Step 1-12]

This step is a step wherein compound (1b-15) is obtained by reducing compound (1b-14). Compound (1b-15) can be manufactured according to the methods similar to those of [Step 1-4].

[Step 1-13]

This step is a step wherein compound (1b-16) is obtained by oxidizing compound (1b-15). Compound (1b-16) can be manufactured according to the methods similar to those of [Step 1-5].

[Step 1-14]

This step is a step wherein compound (1b-17) is obtained by reacting compound (1b-16) with boron tribromide. There are no particular limitations on the solvent used in this reaction as long as it dissolves the starting materials to a certain extent without impeding the reaction. Examples of the solvent include halogenated hydrocarbon solvents such as methylene chloride; aromatic hydrocarbon solvents such as benzene and toluene; mixed solvents of the foregoing, or the like. Boron tribromide can be used in the amount of 1 to 5 equivalents based on compound (1b-16), preferably 3 equivalents. The reaction temperature is from −20° C. to room temperature, and preferably 0° C. The reaction time is 10 minutes to 24 hours.

Manufacturing Method 1-3-1

Method 1 for Manufacturing Compound (1c)

isopropyl magnesium chloride. A catalytic amount of iodine, dibromoethane and the like can be added when preparing the Grignard reagents using metal magnesium. The temperature for preparing the organolithium compound is from −78° C. to room temperature, preferably from −78° C. to −40° C., the base is used in the amount of 1 to 1.5 equivalents based on compound (1c-1), and the reaction time is from 30 minutes to 24 hours. The temperature for preparing the Grignard reagents using metal magnesium is from room temperature to reflux temperature of the solvent, the metal magnesium is used in the amount of 1 to 2 equivalents based on compound (1c-1), and the reaction time is from 30 minutes to 24 hours.

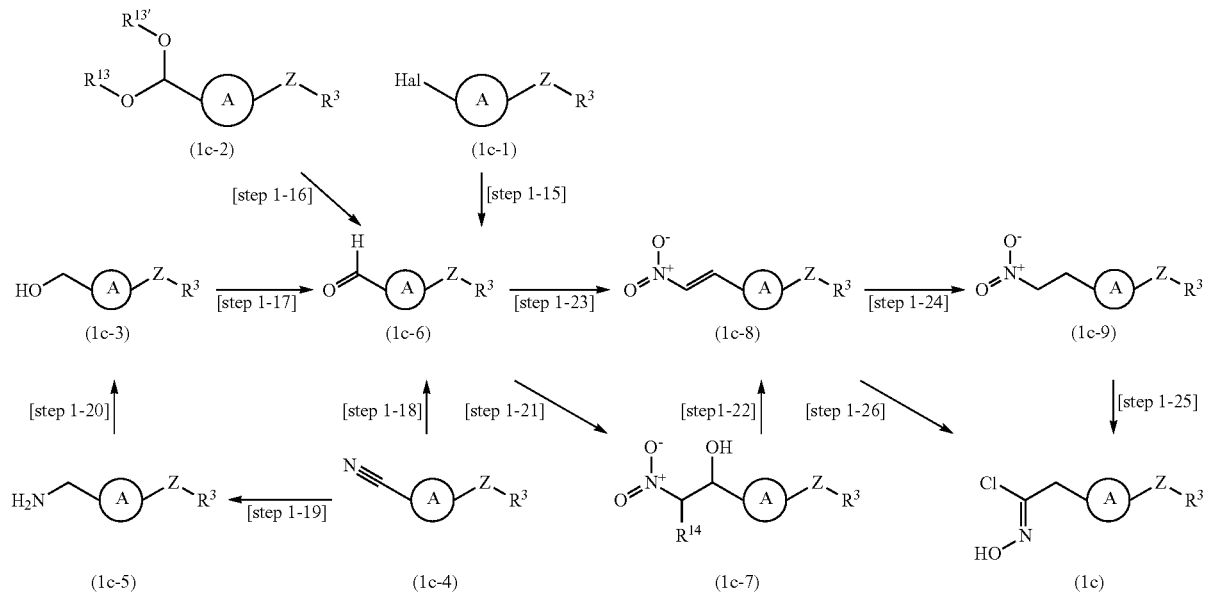

(wherein ring A, $R^3$, Z and Hal are defined as above, $R^{13}$ and $R^{13'}$ represent $C_{1-6}$ alkyl groups or crosslinked —$(CH_2)_n$—, n is 2 or 3, and $R^{14}$ represents a hydrogen atom, a sodium atom, a potassium atom and a lithium atom.)

Each compound in the above reaction scheme which is commercially available products can be used as is, or each compound can also be manufactured from commercially available products by the well known methods. In addition, each compound can be manufactured by the methods described in the manufacturing examples in the examples and by the methods described in [Manufacturing Method 1-3-1] to [Manufacturing Method 1-3-23].

[Step 1-15]

This step is a step wherein compound (1c-6) is obtained by reacting a formylation reagent with an organometallic compound obtained by substituting a metal atom for the halogen atom in compound (1c-1). There are no particular limitations on the solvent used in this reaction as long as it dissolves the starting materials to a certain extent without impeding the reaction. Preferable examples of the solvents used in this reaction include ether solvents such as tetrahydrofuran and diethyl ether. Examples of the organometallic compound include organolithium compounds obtained using a base such as n-butyl lithium, s-butyl lithium, t-butyl lithium and lithium diisopropylamide, or Grignard reagents obtained using a base such as metal magnesium, ethyl magnesium bromide and The temperature for preparing the Grignard reagents using ethyl magnesium bromide or isopropyl magnesium chloride is from −60° C. to reflux temperature, the ethyl magnesium bromide or isopropyl magnesium bromide is used in the amount of 1 to 1.6 equivalents based on compound (1c-1), and the reaction time is from 5 minutes to 12 hours. Examples of the formylation agents include dimethylformamide, N-formylpiperidine, N-formylmorpholine, N-methylformanilide and the like. The formylation reagent can be used in the amount of 1 to 20 equivalents, preferably 1 to 2 equivalents, based on the organometallic compound. The temperature for reacting the organometallic compound and formylation reagent is from −78° C. to room temperature in the case of the organolithium compounds, with a reaction time being from 5 minutes to 6 hours, while in the case of the Grignard reagents the reaction temperature is from −78° C. to reflux temperature of the solvent, with a reaction time being from 5 minutes to 24 hours.

[Step 1-16]

This step is a step wherein compound (1c-6) is obtained by reacting an acid to the acetal of compound (1c-2), so as to deprotect the acetal. There are no particular limitations on the solvent used in this reaction as long as it dissolves the starting materials to a certain extent without impeding the reaction. Examples of the solvent used in this reaction include ether solvents such as tetrahydrofuran and diethyl ether; aromatic hydrocarbon solvents such as benzene and toluene; amide solvents such as N,N-dimethylformamide and N-methylpyrrolidinone; alcohol solvents such as methanol and ethanol; dimethyl sulfoxide and water, mixed solvents of the foregoing and the like. Examples of the acid in this reaction include inorganic acids such as hydrochloric acid, sulfuric acid, and hydrobromic acid; organic acids such as citric acid, trifluoroacetic acid, p-toluenesulfonic acid and the like. The acid can be used in the amount of from a catalytic amount to an excess amount based on compound (1c-2). The reaction temperature is from 0° C. to the reflux temperature of the solvent, and the reaction time is from 5 minutes to 24 hours.

[Step 1-17]

This step is a step wherein compound (1c-6) is obtained by oxidation of compound (1c-3). Compound (1c-6) can be manufactured according to the methods similar to those of [Step 1-5].

[Step 1-18]

This step is a step wherein compound (1c-6) is obtained by reduction of compound (1c-4). Compound (1c-6) can be obtained by means of the reduction reaction using a reducing agent such as diisobutylaluminum hydride, sodium triethoxyaluminum hydride, lithium triethoxyaluminum hydride and the like. There are no particular limitations on the solvent used, but in the case of a reducing reaction using a reducing agent, hydrocarbons such as toluene and ethers such as tetrahydrofuran can be used. The reducing agent is used in the amount of 1 to 2 equivalents based on compound (1c-4). The reaction temperature is from −78° C. to room temperature, and the reaction time is from 10 minutes to 24 hours.

[Step 1-19]

This step is a step wherein compound (1c-5) is obtained by reduction of compound (1c-4). Compound (1c-5) can be obtained either by the reduction reaction using a reducing agent such as lithium aluminum hydride or diisobutylaluminum hydride, or by catalytic hydrogenation using a Raney nickel, palladium-carbon or other catalyst in a hydrogen atmosphere. There are no particular limitations on the solvent used, but in the case of a reducing reaction using a reducing agent, ethers such as tetrahydrofuran and diethyl ether, or hydrocarbons such as toluene can be used preferably, while in the case of catalytic hydrogenation, alcohols such as methanol, ethanol, propanol and the like can be used preferably. The reducing agent is used in the amount of 1 to 10 equivalents based on compound (1c-4). There are no particular limitations on the reaction temperature, but in the case of the reducing reaction using a reducing agent, the reaction temperature is from −78° C. to a reflux temperature of the solvent used, while in the case of the catalytic hydrogenation, the reaction temperature is from room temperature to a reflux temperature of the solvent used. The reaction time is from 10 minutes to 24 hours. The atmospheric pressure in the case of catalytic hydrogenation is from 1 to 4 atms. An amount of catalyst from a catalytic amount to excess may be used in catalytic hydrogenation.

[Step 1-20]

This step is a step wherein compound (1c-3) is obtained by converting the amino groups of compound (1c-5) into acetoxy groups by reacting with sodium nitrite and acetic acid, followed by hydrolysis using a base.

Acetoxylation reaction: Preferable example of the solvent used in this reaction includes a mixed solvent of acetic acid and water. More preferably, the ratio of acetic acid to water is from 1:5 to 5:1. Sodium nitrite is used in the amount of 1 to 20 equivalents based on compound (1c-5). The reaction temperature is from 0° C. to room temperature, and the reaction time is from 1 hour to 12 hours.

Hydrolysis reaction: There are no particular limitations on the solvent used in this reaction as long as it dissolves the starting materials to a certain extent without impeding the reaction. Examples of the solvent in this reaction include alcohol solvents such as methanol and ethanol; ether solvents such as tetrahydrofuran; amide solvents such as N,N-dimethylformamide and N-methylpyrrolidinone; and water, dimethyl sulfoxide, mixed solvents of the foregoing and the like. Examples of the base include sodium hydroxide, potassium hydroxide, potassium carbonate and the like. The reaction temperature is from 0° C. to 60° C., preferably from 20° C. to 40° C., and the reaction time is from 30 minutes to 12 hours.

Compound (1c-3) can also be obtained from compound (1c-5) by the method described as Alternative Method (1) below.

Alternative Method (1): This step is a step wherein compound (1c-3) is obtained by heating compound (1c-5) in the presence of a strong base. Preferable example of the solvent in this step includes diethylene glycol, and preferable example of the base includes potassium hydroxide. The potassium hydroxide is used in the amount of 5 to 30 equivalents based on compound (1c-5), the reaction temperature is from 150° C. to 230° C., and the reaction time is from 1 hour to 12 hours. Note that during the reaction, an inactive gas is preferably substituted inside the reaction container.

[Step 1-21]

This step is a step wherein compound (1c-7) is obtained by reacting compound (1c-6) with nitromethane in the presence of a base. There are no particular limitations on the solvent used in this reaction as long as it dissolves the starting materials to a certain extent without impeding the reaction. Examples of the solvents used in this reaction include alcohol solvents such as methanol and ethanol; ether solvents such as tetrahydrofuran and diethyl ether; and the like. Examples of the base in this reaction include sodium methoxide, sodium ethoxide, n-butyl lithium, lithium diisopropylamide, sodium hydroxide, potassium hydroxide, potassium carbonate, potassium t-butoxide or the like. The nitromethane can be used in the amount of 1 to 20 equivalents based on compound (1c-6). The base is used in the amount of 1 to 2 equivalents based on compound (1c-6). The reaction temperature is from −78° C. to reflux temperature, and the reaction time is from 5 minutes to 48 hours.

[Step 1-22]

This step is a step wherein compound (1c-8) is obtained by esterifying the hydroxyl groups of compound (1c-7) in the presence of a base, followed by elimination in situ. There are no particular limitations on the solvent used in this reaction as long as it dissolves the starting materials to a certain extent without impeding the reaction. Examples of the solvents used in this reaction include ether solvents such as tetrahydrofuran and diethyl ether; amide solvents such as N,N-dimethylformamide and N-methylpyrrolidinone; and methylene chloride, dimethyl sulfoxide, mixed solvents of the foregoing and the like. Examples of the base in this reaction include triethylamine, N,N-diisopropylethylamine and the like. Examples of the esterification agents include acetic anhydride, methanesulfonyl chloride, p-toluenesulfonyl chloride and the like. The base is used in the amount of 1.0 to 4.0 equivalents based on compound (1c-7). The esterification agent is used in the amount of 1.0 to 2.0 equivalents based on compound (1c-7). The reaction temperature is from room temperature to reflux temperature, and the reaction time is from 30 minutes to 24 hours.

Compound (1c-8) can also be obtained from compound (1c-7) by the method described below as Alternative Method (1).

Alternative Method (1): Compound (1c-8) can be obtained by dehydrating compound (1c-7) in an acetic acid solvent in the presence of an acetic acid salt. Acetic acid is used as the solvent in this reaction, but a mixed solvent of acetic acid and methanol, tetrahydrofuran and the like can also be used. Examples of acetic acid salt include ammonium acetate, ethylene diamine diacetic acid salt and the like. The acetic acid salt is used in the amount of 1 to 20 equivalents based on compound (1c-7). The reaction temperature is from room temperature to reflux temperature, and the reaction time is from 30 minutes to 72 hours.

[Step 1-23]

This step is a step wherein compound (1c-8) is obtained by reacting compound (1c-6) with nitromethane in the presence of a base, and then dehydrating by addition of an acid to the reaction system. There are no particular limitations on the solvent used in this reaction as long as it dissolves the starting materials to a certain extent without impeding the reaction. Examples of the solvent used in this reaction include water; alcohol solvents such as methanol and ethanol; ether solvents such as tetrahydrofuran and diethyl ether; mixed solvents of the foregoing and the like. Examples of the base used in this reaction include sodium methoxide, sodium ethoxide, n-butyl lithium, lithium diisopropylamide, sodium hydroxide, potassium hydroxide, potassium carbonate, potassium t-butoxide and the like. Examples of the acid used in this reaction include hydrochloric acid, sulfuric acid, acetic acid and the like. The nitromethane is used in the amount of 1 to 20 equivalents based on compound (1c-6). The base is used in the amount of 1 to 2 equivalents based on compound (1c-6). The acid can be added in an excess amount. The reaction temperature for the reaction with nitromethane is from −78° C. to reflux temperature, with a reaction time being from 5 minutes to 48 hours. The reaction temperature for the dehydration reaction is from room temperature to reflux temperature, with a reaction time being from 5 minutes to 48 hours.

Compound (1c-8) can also be obtained from compound (1c-6) by the method given below as Alternative Method (1).

Alternative Method (1): Compound (1c-8) can be obtained by reacting compound (1c-6) with nitromethane in the presence of an acetic acid salt. Acetic acid is used as the solvent in this reaction, but a mixed solvent of acetic acid and methanol, tetrahydrofuran and the like can also be used. Examples of the acetic acid salt used in this reaction include ammonium acetate, ethylenediamine diacetic acid salt and the like. Nitromethane is used in the amount of 1 to 10 equivalents based on compound (1c-6). The acetic acid salt is used in the amount of 1 to 20 equivalents based on compound (1c-6). The reaction temperature is from room temperature to reflux temperature, and the reaction time is from 30 minutes to 72 hours.

[Step 1-24]

This step is a step wherein compound (1c-9) is obtained by reduction of compound (1c-8). In order to obtain good results, an acid such as acetic acid or hydrochloric acid can be added. There are no particular limitations on the solvent used in this reaction as long as it dissolves the starting materials to a certain extent without impeding the reaction. Examples of the solvents used in this reaction include alcohol solvents such as methanol and ethanol; ether solvents such as tetrahydrofuran; and dimethyl sulfoxide and the like. Examples of the reducing agent used in this reaction include sodium borohydride, lithium borohydride and the like. The reducing agent is used in the amount of 0.5 to 3 equivalents based on compound (1c-8). The reaction temperature is from −20° C. to 80° C., and the reaction time is from 10 minutes to 12 hours. In the case of adding the acid, the acid can be added in the amount of 1 equivalent to the solvent amount based on the reducing agent.

[Step 1-25]

This step is a step wherein compound (1c) is obtained by anionization of the nitroethyl moiety in compound (1c-9) using a base, followed by adding titanium (IV) chloride.

Anionization reaction of compound (1c-9): There are no particular limitations on the solvent used in this reaction as long as it dissolves the starting materials to a certain extent without impeding the reaction. Examples of the solvents used in this reaction include alcohol solvents such as methanol and ethanol; ether solvents such as tetrahydrofuran; and the like. Examples of the base used in this reaction include lithium methoxide, sodium methoxide, potassium t-butoxide, n-butyl lithium and the like. The base is used in the amount of 1 to 2 equivalents based on compound (1c-9). The reaction temperature is from −78° C. to room temperature, and the reaction time is from 5 minutes to 1 hour.

Reaction with titanium (IV) chloride: There are no particular limitations on the solvents used in this reaction as long as it dissolves the starting materials to a certain extent without impeding the reaction. Examples of the solvents used in this reaction include ether solvents such as tetrahydrofuran; and methylene chloride, 1,2-dichloroethane, mixed solvents of the foregoing and the like. The titanium (IV) chloride is used in the amount of 1 to 3 equivalents based on compound (1c-9). The reaction temperature is from −10° C. to room temperature, and the reaction time is from 10 minutes to 12 hours.

[Step 1-26]

This step is a step wherein compound (1c) is obtained by reacting compound (1c-8) with titanium (IV) chloride in the presence of triethylsilane. There are no particular limitations on the solvent used in this reaction as long as it dissolves the starting materials to a certain extent without impeding the reaction. Examples of the solvents used in this reaction include ether solvents such as tetrahydrofuran; and methylene chloride, 1,2-dichloroethane, mixed solvents of the foregoing and the like. The triethylsilane is used in the amount of 1 to 3 equivalents based on compound (1c-8). The titanium (IV) chloride is used in the amount of 1 to 3 equivalents based on compound (1c-8). The reaction temperature is from −20° C. to room temperature, and the reaction time is from 10 minutes to 12 hours.

Manufacturing Method 1-3-2

Method 2 for Manufacturing Compound (1c)

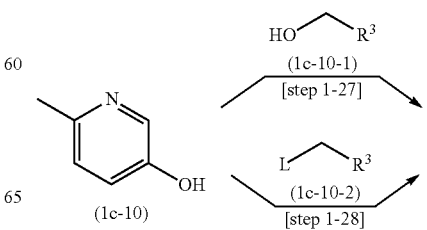

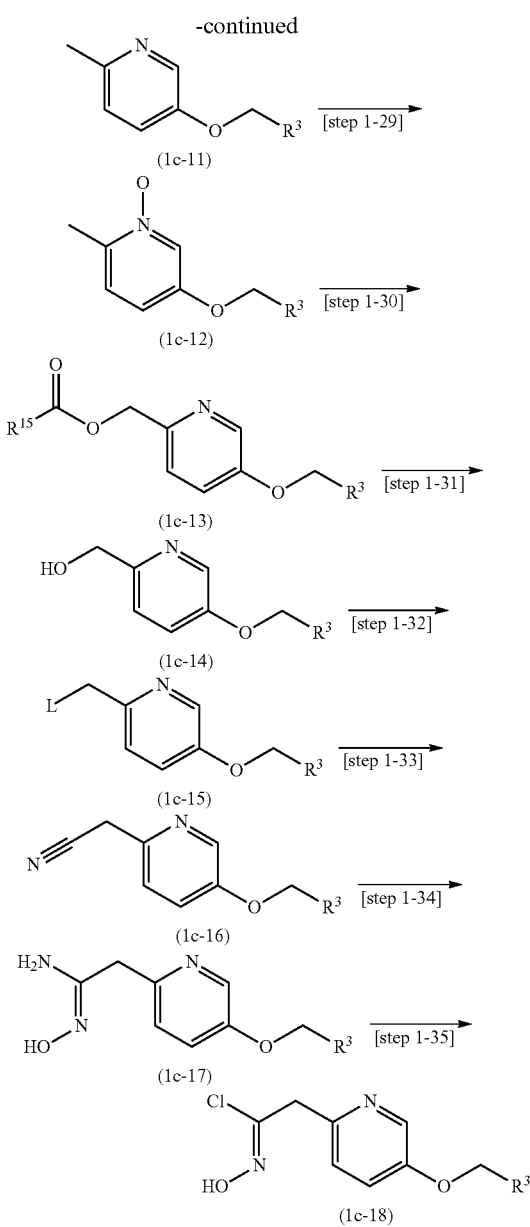

(wherein R³ is defined as above; in the formula, R¹⁵ represents a $C_{1-6}$ alkyl group which may be substituted with a halogen or the like; L represents a leaving group such as a halogen atom, a p-toluenesulfonyl group and a trifluoromethanesulfonyl group.)

Compound (1c-10), compound (1c-10-1) and compound (1c-10-2) which are commercially available products can be used as is or they can also be manufactured from commercially available products by the known methods.

[Step 1-27]

This step is a step wherein compound (1c-11) is obtained by reacting compound (1c-10) with an organophosphorous compound, an azo reagent and compound (1c-10-1). There are no particular limitations on the solvent used in this reaction as long as it dissolves the starting materials to a certain extent without impeding the reaction. Examples of the solvents used in this reaction include ether solvents such as tetrahydrofuran and diethyl ether; aromatic hydrocarbon solvents such as benzene and toluene; amide solvents such as N,N-dimethylformamide and N-methylpyrrolidinone; ethyl acetate; acetonitrile; methylene chloride; mixed solvents of the foregoing and the like. Examples of the organophosphorous compound include triphenyl phosphine, tri-n-butyl phosphine and the like. Examples of the azo compound include ester derivatives such as diethyl azodicarboxylate and diisopropyl azodicarboxylate, and amide derivatives such as 1,1'-(azodicarbonyl)dipiperidine. Compound (1c-10-1) is used in the amount of 1 to 1.5 equivalents based on compound (1c-10). The organophosphorous compound is used in the amount of 1 to 3 equivalents based on compound (1c-10). The azo reagent is used in the amount of 1 to 3 equivalents based on compound (1c-10). The reaction temperature is from 0° C. to reflux temperature, and the reaction time is from 5 minutes to 24 hours.

[Step 1-28]

This step is a step wherein compound (1c-11) is obtained by reacting compound (1c-10) with compound (1c-10-2), in the presence of a base. There are no particular limitations on the solvent used in this reaction as long as it dissolves the starting materials to a certain extent without impeding the reaction. Examples of the solvents used in this reaction include ether solvents such as tetrahydrofuran, diethyl ether or the like; aromatic hydrocarbon solvents such as benzene, toluene or the like; amide solvents such as N,N-dimethylformamide, N-methylpyrrolidinone or the like; alcohol solvents such as methanol, ethanol or the like; dimethyl sulfoxide; mixed solvents of the foregoing and the like. Examples of the base include sodium hydride, potassium t-butoxide, sodium ethoxide, sodium methoxide, N,N-diisopropylethylamine, triethylamine, potassium hydroxide, sodium hydroxide, potassium carbonate, sodium carbonate and the like. The base is used in the amount of 1 to 5 equivalents based on compound (1c-10-2). Compound (1c-10-2) is used in the amount of 1 to 20 equivalents based on compound (1c-10). The reaction temperature is from 0° C. to reflux temperature, and the reaction time is from 5 minutes to 6 hours.

[Step 1-29]

This step is a step wherein compound (1c-12) is obtained by reacting compound (1c-11) with peroxide. Examples of the peroxide used in this reaction include m-chloroperbenzoic acid, hydrogen peroxide, dimethyldioxirane, benzoyl peroxide, peracetic acid or the like. There are no particular limitations on the solvent used in this reaction as long as it dissolves the starting materials to a certain extent without impeding the reaction. Examples of the solvent include halogen solvents such as chloroform and methylene chloride; alcohol solvents such as methanol and ethanol; amide solvents such as N,N-dimethylformamide and N-methylpyrrolidinone; aromatic hydrocarbon solvents such as benzene and toluene, diethyl ether; acetone; acetonitrile; acetic acid; water or the like. Peroxide is used in the amount of 1 to 5 equivalents based on compound (1c-11). The reaction temperature is from −40° C. to reflux temperature, and the reaction time is from 1 minute to 48 hours.

[Step 1-30]

This step is a step wherein compound (1c-13) is obtained by reacting compound (1c-12) with an acid anhydride. Examples of the acid anhydride used in this reaction include acetic anhydride, trifluoroacetic acid anhydride, or the like. There are no particular limitations on the solvent used in this reaction as long as it dissolves the starting materials to a certain extent without impeding the reaction. Examples of the solvent include halogen solvents such as chloroform and methylene chloride; aromatic hydrocarbon solvents such as benzene and toluene; acetic acid, trifluoroacetic acid or the like. Acid anhydride can also be used as the solvent. Acid anhydride is used in the amount of 1 equivalent to excess based on compound (1c-12). The reaction temperature is from 0° C. to reflux temperature, and the reaction time is from 10 minutes to 24 hours.

[Step 1-31]

This step is a step wherein compound (1c-14) is obtained by hydrolyzing compound (1c-13). Compound (1c-14) can be obtained by hydrolyzing compound (1c-13), for instance, in the presence of an acid such as sulfuric acid, or, for instance, in the presence of an alkali such as sodium hydroxide, potassium hydroxide, sodium methoxide, potassium carbonate or sodium carbonate. There are no particular limitations on the solvent used in this reaction as long as it dissolves the starting materials to a certain extent without impeding the reaction. Examples of the solvent include ether solvents such as 1,4-dioxane and tetrahydrofuran; alcohol solvents such as methanol and ethanol; halogen solvents such as methylene chloride and chloroform; aromatic hydrocarbon solvents such as benzene and toluene; amide solvents such as N,N-dimethylformamide and N-methylpyrrolidinone; dimethyl sulfoxide, acetonitrile, water, mixed solvents of the foregoing or the like. The acid or the base is used in the amount of 1 equivalent to excess based on compound (1c-13). The reaction temperature is from 0° C. to reflux temperature, and the reaction time is from 10 minutes to 24 hours.

[Step 1-32]

This step is a step wherein compound (1c-15) is obtained by converting the hydroxyl group of compound (1c-14) to a leaving group.

When L is a methanesulfonyloxy group, p-toluenesulfonyloxy group or other sulfuric acid ester; compound (1c-15) can be obtained by reacting compound (1c-14) with sulfonyl chloride under basic conditions. There are no particular limitations on the solvent used in this reaction as long as it dissolves the starting materials to a certain extent without impeding the reaction. Examples of the solvent include ether solvents such as 1,4-dioxane and tetrahydrofuran; aromatic hydrocarbon solvents such as benzene and toluene; amide solvents such as N,N-dimethylformamide and N-methylpyrrolidinone; and dimethyl sulfoxide, methylene chloride, mixed solvents of the foregoing and the like. Examples of the base include triethylamine, N,N-diisopropylethylamine and the like. Examples of the sulfonyl chloride include methanesulfonyl chloride, p-toluenesulfonyl chloride and the like. The base is used in the amount of 1 to 3 equivalents based on compound (1c-14). The sulfonyl chloride is used in the amount of 1 to 2 equivalents based on compound (1c-14). The reaction temperature is from 0° C. to room temperature, and the reaction time is from 10 minutes to 24 hours.

When L is a chlorine atom or a bromine atom; compound (1c-15) can be obtained by halogenating compound (1c-14) with tetrachloromethane or tetrabromomethane in the presence of triphenylphosphine. There are no particular limitations on the solvent used in this reaction as long as it dissolves the starting materials to a certain extent without impeding the reaction. Examples of the solvent include ether solvents such as tetrahydrofuran; amide solvents such as N,N-dimethylformamide and N-methylpyrrolidinone; and methylene chloride, mixed solvents of the foregoing and the like. The tetrachloromethane or tetrabromomethane can also be used as the solvent. The triphenylphosphine is used in the amount of 1 to 2 equivalents based on compound (1c-14). The tetrachloromethane or tetrabromomethane is used in the amount of 1 equivalent to the solvent amount based on compound (1c-14). The reaction temperature is from 0° C. to reflux temperature, and the reaction time is from 10 minutes to 12 hours.

Compound (1c-15) can also be obtained from compound (1c-14) according to the methods described below as Alternative Methods (1), (2) and (3).

Alternative Method (1): Compound (1c-14) can be converted into compound (1c-15) under acidic conditions. There are no particular limitations on the solvent used in this reaction as long as it dissolves the starting materials to a certain extent without impeding the reaction. Examples of the solvent include ether solvents such as diethyl ether; water, ethyl acetate, mixed solvents of the foregoing and the like. In this reaction, a phase-transfer agent such as tetrabutylammonium bromide can be used in the amount of 0.01 to 2 equivalents based on compound (1c-14). Examples of the acid include hydrochloric acid, hydrobromic acid and the like. Sulfuric acid can also be added to obtain good results. The reaction temperature is from 0° C. to room temperature, and the reaction time is from 10 minutes to 12 hours.

Alternative Method (2): Compound (1c-15) can be obtained by reacting compound (1c-14) with thionyl chloride. There are no particular limitations on the solvent used in this reaction as long as it dissolves the starting materials to a certain extent without impeding the reaction. Examples of the solvent include aromatic hydrocarbon solvents such as benzene and toluene; and acetonitrile, chloroform, methylene chloride and the like, and the thionyl chloride can also be used as the solvent. Pyridine can also be added to the reaction in a catalytic amount to improve the yield. The thionyl chloride is used in the amount of 1 equivalent to the solvent amount based on compound (1c-14). The reaction temperature is from 0° C. to reflux temperature, and the reaction time is from 10 minutes to 12 hours.

Alternative Method (3): Compound (1c-15) can be obtained by reacting compound (1c-14) with phosphorus halide. There are no particular limitations on the solvent used in this reaction as long as it dissolves the starting materials to a certain extent without impeding the reaction. Examples of the solvent include ether solvents such as diethyl ether; N,N-dimethylformamide, acetonitrile, chloroform and the like. Examples of the phosphorus halide include phosphorus oxychloride, phosphorus trichloride, phosphorus tribromide and the like. The phosphorus halide is used in the amount of 0.33 to 3 equivalents based on compound (1c-14). The reaction temperature is from 0° C. to reflux temperature, and the reaction time is from 10 minutes to 12 hours.

[Step 1-33]

This step is a step wherein compound (1c-16) is obtained by converting the leaving group of compound (1c-15) to a cyano group. To obtain good results, an inorganic salt such as sodium iodide or the like may also be added in the amount of 1 to 2 equivalents based on compound (1c-15). Examples of the cyanization agent used in this reaction include sodium cyanide, potassium cyanide, lithium cyanide or the like. There are no particular limitations on the solvent used in this reaction as long as it dissolves the starting materials to a certain extent without impeding the reaction. Examples of the solvent include alcohol solvents such as methanol and ethanol; ether solvents such as 1,4-dioxane and tetrahydrofuran; amide solvents such as N,N-dimethylformamide and N-methylpyrrolidinone; dimethyl sulfoxide; acetonitrile; acetone; water; mixed solvents of the foregoing or the like. The cyanidation agent is used in the amount of 1 to 5 equivalents based on compound (1c-15). The reaction temperature is from room temperature to reflux temperature, and the reaction time is from 30 minutes to 48 hours.

[Step 1-34]

This step is a step wherein compound (1c-17) is obtained by reacting compound (1c-16) with hydroxylammonium chloride. Examples of the base used in this reaction include pyridine, sodium acetate, potassium acetate, sodium bicarbonate, sodium carbonate, sodium hydroxide, potassium hydroxide or the like. There are no particular limitations on the solvent used in this reaction as long as it dissolves the starting materials to a certain extent without impeding the reaction. Examples of the solvent include halogenated hydrocarbons such as dichloromethane and chloroform; sulfoxides such as dimethyl sulfoxide; ethers such as tetrahydrofuran and 1,4-dioxane; alcohols such as methanol and ethanol; amides such as N-methylpyrrolidinone, N,N-dimethylformamide and N,N-dimethylacetamide; pyridine; water, mixed solvents of the foregoing, or the like. Hydroxylammonium chloride is used in the amount of 1 to 5 equivalents based on compound (1c-16). The base is used in the amount of 1 equivalent to excess based on compound (1c-16). The reaction temperature is from 0° C. to reflux temperature, and the reaction time is from minutes to 48 hours.

[Step 1-35]

This step is a step wherein compound (1c-18) is obtained by reacting compound (1c-17) with sodium nitrite and a chlorine source. Examples of the chlorine source used in this reaction include hydrochloric acid, copper chloride or the like. There are no particular limitations on the solvent used in this reaction as long as it dissolves the starting materials to a certain extent without impeding the reaction. Examples of the solvent include ether solvents such as 1,4-dioxane and tetrahydrofuran; amide solvents such as N,N-dimethylformamide and N-methylpyrrolidinone; dimethyl sulfoxide; acetonitrile; acetone; hydrochloric acid aqueous solution; water; mixed solvents of the foregoing, or the like. Sodium nitrite can be used in the amount of 1 to 10 equivalents based on compound (1c-17). The chlorine source can be used in the amount of 1 equivalent to excess based on compound (1c-17). The reaction temperature is from −40° C. to reflux temperature, and the reaction time is from 1 minute to 24 hours.

Manufacturing Method 1-3-3

Method 1 for Manufacturing Compound (1c-1)

able products can be used as is, or they can be obtained from commercially available products by the well known methods.

[Step 1-36]

This step is a step wherein compound (1c-21) is obtained by reacting compound (1c-19) with compound (1c-19-1) in the presence of a base. Compound (1c-21) can be manufactured according to the methods similar to those of [Step 1-28].

[Step 1-37]

This step is a step wherein compound (1c-21) is obtained by reacting compound (1c-20) with an organophosphorous compound, an azo reagent and compound (1c-19-1). Compound (1c-21) can be manufactured according to the methods similar to those of [Step 1-27].

[Step 1-38]

This step is a step wherein compound (1c-21) is obtained by reacting compound (1c-20) with compound (1c-20-1) in the presence of a base. A catalytic amount of sodium iodide, potassium iodide or tetrabutylammonium iodide can be added to obtain good results, and a copper catalyst can also be added in order to obtain good results. There are no particular limitations on the solvent used in this reaction as long as it dissolves the starting materials to a certain extent without impeding the reaction. Examples of the solvents used in this reaction include ether solvents such as tetrahydrofuran and diethyl ether; aromatic hydrocarbon solvents such as benzene and toluene; amide solvents such as N,N-dimethylformamide and N-methylpyrrolidinone; alcohol solvents such as methanol and ethanol; and dimethyl sulfoxide, mixed solvents of the foregoing and the like. Examples of the base include sodium hydride, potassium t-butoxide, sodium ethoxide, sodium methoxide, N,N-diisopropylethylamine, triethylamine, potassium hydroxide, sodium hydroxide, potassium carbonate, sodium carbonate and the like. Examples of the copper catalysts include copper, copper (I) iodide, copper (I) bromide, copper (I) chloride and the like. Compound (1c-20-1) is used in the amount of 1 to 5 equivalents based on compound (1c-20). The base is used in the amount of 1 to 5 equivalents based on compound (1c-20). The copper catalyst can be used in the amount of 0.01 to 0.3 equivalents based on compound (1b-20). The reaction temperature is from 0° C. to reflux temperature, and the reaction time is from 5 minutes to 48 hours.

Manufacturing Method 1-3-4

Method 2 for Manufacturing Compound (1c-1)

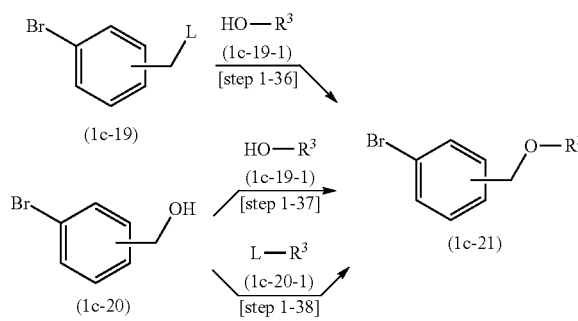

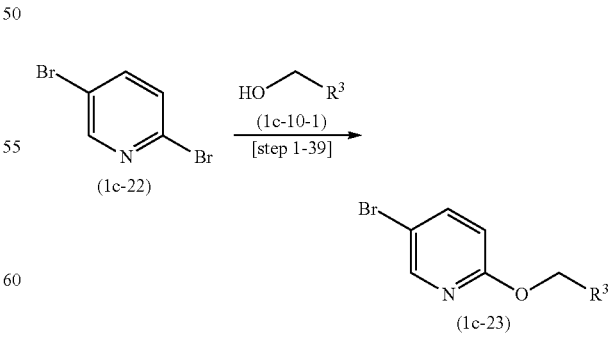

(wherein $R^3$ and L are defined as above.)

Compound (1c-19), compound (1c-20), compound (1c-19-1) and compound (1c-20-1) which are commercially avail- (wherein $R^3$ is defined as above.)

Compound (1c-22) and Compound (1c-10-1) may be commercially available products or can also be manufactured from the commercially available products by the well known methods.

[Step 1-39]

This step is a step wherein compound (1c-23) is obtained by reacting compound (1c-22) with compound (1c-10-1) in the presence of a base. A copper catalyst can also be added in this reaction. There are no particular limitations on the solvent used in this reaction as long as it dissolves the starting materials to a certain extent without impeding the reaction. Examples of the solvents used in this reaction include ether solvents such as tetrahydrofuran and diethyl ether; aromatic hydrocarbon solvents such as benzene and toluene; amide solvents such as N,N-dimethylformamide and N-methylpyrrolidinone; alcohol solvents such as methanol and ethanol; and dimethyl sulfoxide, mixed solvents of the foregoing and the like. Examples of the base include sodium hydride, potassium t-butoxide, sodium ethoxide, sodium methoxide, potassium hydroxide, sodium hydroxide and the like. Examples of the copper catalyst include copper, copper (I) iodide, copper (I) bromide, copper (I) chloride and the like. The base is used in the amount of 1 to 5 equivalents based on compound (1c-10-1). Compound (1c-10-1) is used in the amount of 1.0 to 3.0 equivalents based on compound (1c-22). The copper catalyst can be used in the amount of 0.01 to 1 equivalents based on compound (1c-10-1). The reaction temperature is from room temperature to reflux temperature, and the reaction time is from 10 minutes to 48 hours.

Manufacturing Method 1-3-5

Method 3 for Manufacturing Compound (1c-1), (1c-2) and (1c-6)

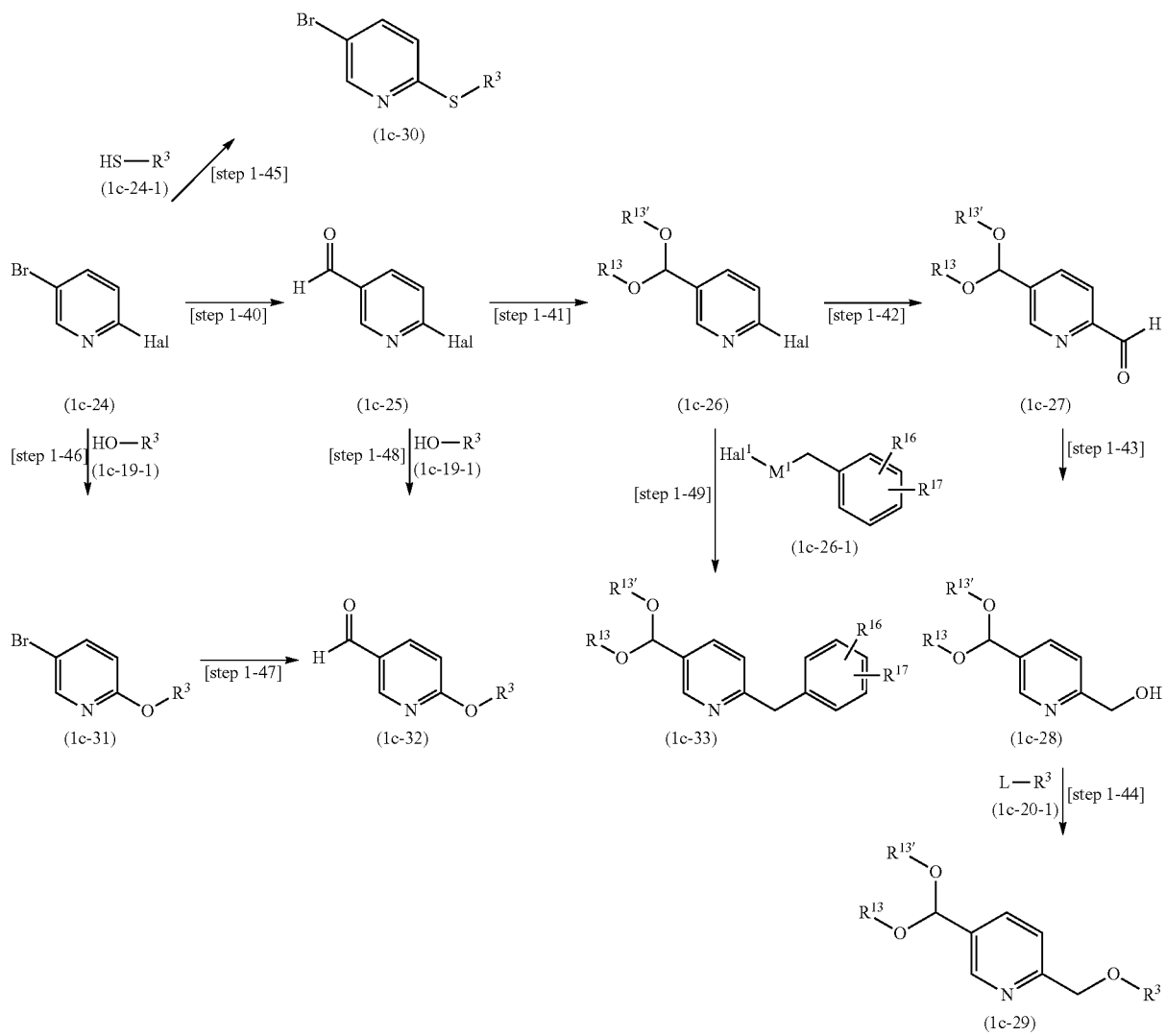

(wherein Hal, L, $R^3$, $R^{13}$ and $R^{13'}$ is defined as above; in addition, $R^{16}$ and $R^{17}$ represent a halogen group, a $C_{1-6}$ alkyl group and a $C_{1-6}$ alkoxy group; $Hal^1$ represents a chlorine atom and a bromine atom; $M^1$ represents a magnesium atom and a zinc atom.)

Compound (1c-24), compound (1c-25), compound (1c-19-1), compound (1c-20-1), compound (1c-24-1) and compound (1c-26-1) which are commercially available products can be used as is, or they can be manufactured from commercially available products by the known methods.

[Step 1-40]

This is a step wherein compound (1c-25) is obtained by converting compound (1c-24) into an organometallic compound by substituting a metal atom for a halogen atom of compound (1c-24), and then applying a formylating reagent. There are no particular limitations on the solvent used in this step as long as it dissolves the starting materials to a certain extent without impeding the reaction, but diethyl ether is desirable. Examples of the organometallic compounds include organolithium compounds obtained by applying a base such as n-butyl lithium, s-butyl lithium, t-butyl lithium or the like. The temperature at which the organolithium compound is to be prepared is from −100° C. to room temperature, and preferably from −78° C. to −40° C. The base can be used in the amount of 1 to 1.2 equivalents based on compound (1c-24), and the reaction time is from 10 minutes to 24 hours. Examples of the formylating reagent include N,N-dimethylformamide, N-formylpiperidine, N-formylmorpholine, N-methylformanilide or the like. The formylating reagent can be used in the amount of 1 to 20 equivalents based on compound (1c-24), and preferably 1 to 2 equivalents. The temperature for reacting the organometallic compound and the formylating reagent is from −78° C. to room temperature, and the reaction time is from 5 minutes to 24 hours.

[Step 1-41]

This step is a step wherein compound (1c-26) is obtained by protecting the formyl group of compound (1c-25) with an acetal, in the presence of an alcohol and an acid catalyst. Preferable examples of alcohol used in this reaction include methanol, ethanol, ethylene glycol, propylene glycol or the like. Examples of the acid caltalyst include hydrochloric acid, sulfuric acid, p-toluenesulfonic acid, acetic acid, ammonium chloride or the like. There are no particular limitations on the solvent used in this step as long as it dissolves the starting materials to a certain extent without impeding the reaction. Examples of the solvent include alcohol solvents such as methanol, ethanol and ethylene glycol; aromatic hydrocarbon solvents such as benzene and toluene; halogenated hydrocarbon solvents such as dichloromethane and chloroform, or the like. The alcohol is used in the amount of 1 equivalent to the solvent amount based on compound (1c-25). The acid catalyst is used in the amount of 0.05 equivalents to excess based on compound (1c-25). The reaction temperature is from room temperature to reflux temperature, and the reaction time is from 10 minutes to 24 hours.

[Step 1-42]

This step is a step wherein compound (1c-27) is obtained by converting compound (1c-26) into an organometallic compound by substituting a metal atom for a halogen atom of compound (1c-26), and then applying a formylation reagent. Compound (1c-27) can be manufactured according to the methods similar to those of [Step 1-15].

[Step 1-43]

This step is a step wherein compound (1c-28) is obtained by reducing compound (1c-27). Examples of the reducing agent used in this reaction include sodium borohydride, lithium borohydride, lithium aluminumhydride, or the like. There are no particular limitations on the solvent used in this reaction as long as it dissolves the starting materials to a certain extent without impeding the reaction. Examples of the solvent include alcohol solvents such as methanol and ethanol; ether solvents such as diethyl ether and tetrahydrofuran; aromatic hydrocarbon solvents such as benzene and toluene; halogenated hydrocarbon solvents such as dichloromethane and chloroform; water, mixed solvents of the foregoing, or the like. Preferably alcohol solvents are desirable when using a reducing agent such as sodium borohydride; ether solvents are desirable when using a reducing agent such as lithium aluminumhydride. The reducing agent is used in the amount of 0.25 to 4 equivalents based on compound (1c-27). The reaction temperature is from 0° C. to reflux temperature, and the reaction time is from 5 minutes to 24 hours.

[Step 1-44]

This step is a step wherein compound (1c-29) is obtained by reacting compound (1c-28) and compound (1c-20-1), in the presence of a base. Compound (1c-29) can be obtained according to the methods similar to those of [Step 1-38].

[Step 1-45]

This step is a step wherein compound (1c-30) is obtained by reacting compound (1c-24) and compound (1c-24-1), in the presence of a base. Compound (1c-30) can be manufactured according to the methods similar to those of [Step 1-39].

[Step 1-46]

This step is a step wherein compound (1c-31) is obtained by reacting compound (1c-24) and compound (1c-19-1), in the presence of a base. Compound (1c-31) can be manufactured according to the methods similar to those of [Step 1-39].

[Step 1-47]

This step is a step wherein compound (1c-32) is obtained by converting compound (1c-31) into an organometallic compound by substituting a metal atom for a halogen atom of compound (1c-31), and then reacting with a formylating agent. Compound (1c-32) can be manufactured according to the methods similar to those of [Step 1-15].

[Step 1-48]

This step is a step wherein compound (1c-32) is obtained by reacting compound (1c-25) and compound (1c-19-1), in the presence of a base. Compound (1c-32) can be manufactured according to the methods similar to those of [Step 1-39].

[Step 1-49]

This step is a step wherein compound (1c-33) is obtained by reacting compound (1c-26) and compound (1c-26-1), in the presence of a nickel catalyst. There are no particular limitations on the solvent used in this reaction as long as it dissolves the starting materials to a certain extent without impeding the reaction. Preferable examples of the solvent include ether solvents such as tetrahydrofuran, dioxane and diethyl ether. Examples of the nickel catalyst include 1,3-bis(diphenylphosphino)propane nickel (II) chloride, bis(triphenylphosphine)nickel (II) chloride, 1,2-bis(diphenylphosphino)ethane nickel (II) chloride, 1,1'-bis(diphenylphosphino)ferrocene nickel (II) chloride or the like. Compound (1c-26-1) is used in the amount of 1 to 2 equivalents based on compound (1c-26), and the nickel catalyst is used in the amount of 0.02 to 0.2 equivalents based on compound (1c-26). The reaction temperature is from −10° C. to 80° C., and the reaction time is from 30 minutes to 12 hours.

In addition, when $M^1$ is a zinc atom, compound (1c-26-1) can be prepared in situ and used in the reaction, as describe below. The reaction in [Step 1-49] can be carried out by synthesizing compound (1c-26-1) in situ using benzyl halide and activated zinc. In this case, the activated zinc is used in the amount of 1 to 1.3 equivalents based on benzyl halide. The reaction temperature for obtaining compound (1c-26-1) is from −10° C. to room temperature, preferably from −5° C. to 10° C., and the reaction time is from 1 hour to 10 hours.

Manufacturing Method 1-3-6

Method 1 for Manufacturing Compound (1c-2)

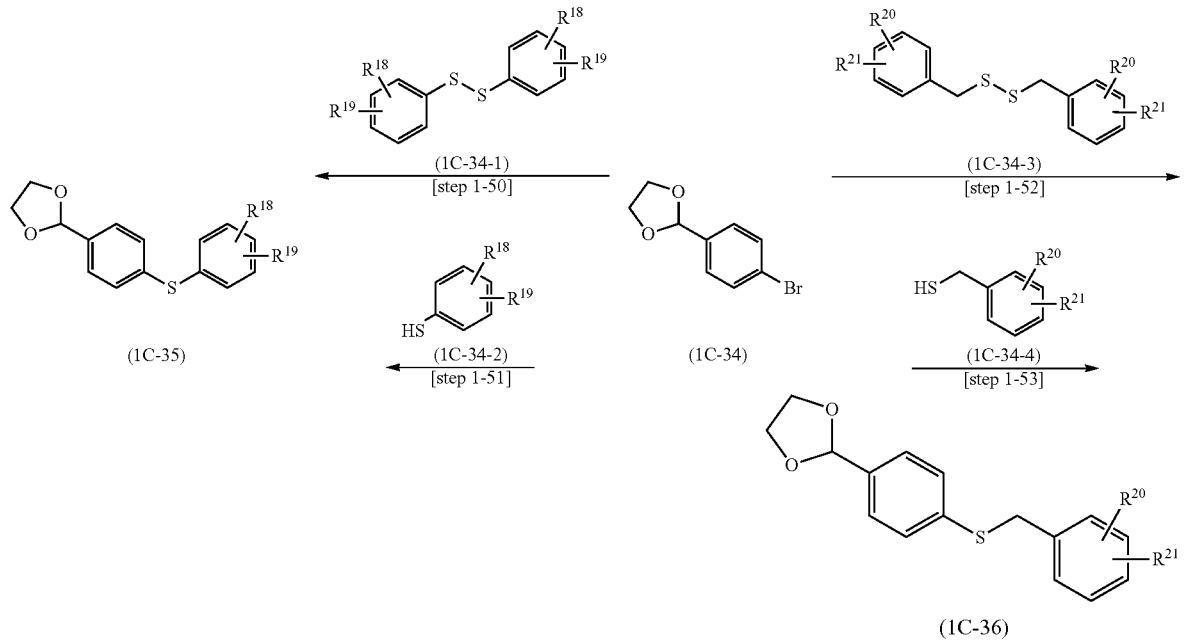

(wherein $R^{18}$, $R^{19}$, $R^{20}$ and $R^{21}$ represent a halogen, a $C_{1-6}$ alkyl group and a $C_{1-6}$ alkoxy group.)

Compound (1c-34), compound (1c-34-1), compound (1c-34-2), compound (1c-34-3) and compound (1c-34-4) which are commercially available products can be used as is, or they can also be manufactured from commercially available products by the known methods.

[Step 1-50]

This step is a step wherein compound (1c-35) is obtained by converting compound (1c-34) into an organometallic compound by substituting a metal atom for a halogen atom of compound (1c-34), and then reacting with compound (1c-34-1). There are no particular limitations on the solvent used in this reaction as long as it dissolves the starting materials to a certain extent without impeding the reaction. Preferable examples of the solvent include ether solvents such as tetrahydrofuran and diethyl ether. Examples of the organometallic compound include organolithium compounds obtained by applying a base such as n-butyl lithium, s-butyl lithium, t-butyl lithium, lithium diisopropyl amide, or the like. The temperature at which the organolithium compound is to be prepared is from −78° C. to room temperature, preferably from −78° C. to −40° C. The base is used in the amount of 1 to 1.5 equivalents based on compound (1c-34). The reaction time is from 30 minutes to 24 hours. Compound (1c-34-1) is used in the amount of 1 to 2 equivalents based on compound (1c-34). The temperature for reacting the organometallic compound and compound (1c-34-1) is from −78° C. to room temperature, and the reaction time is from 5 minutes to 12 hours.

[Step 1-51]

This step is a step wherein compound (1c-35) is obtained by reacting compound (1c-34) and compound (1c-34-2), in the presence of a base. There are no particular limitations on the solvent used in this reaction as long as it dissolves the starting materials to a certain extent without impeding the reaction. Examples of the solvent include ether solvents such as tetrahydrofuran and diethyl ether; aromatic hydrocarbon solvents such as benzene and toluene; amide solvents such as N,N-dimethylformamide and N-methylpyrrolidinone; alcohol solvents such as methanol and ethanol; dimethyl sulfoxide, mixed solvents of the forgoing, or the like. Examples of the base include sodium hydride, potassium t-butoxide, sodium ethoxide, sodium methoxide, potassium hydroxide, sodium hydroxide or the like. The base is used in the amount of 1 to 5 equivalents based on compound (1c-34). Compound (1c-34-2) is used in the amount of 1 to 2 equivalents based on compound (1c-34). The reaction temperature is from room temperature to reflux temperature, and the reaction time is from 5 minutes to 24 hours.

[Step 1-52]

This step is a step wherein compound (1c-36) is obtained by converting compound (1c-34) into an organometallic compound by substituting a metal atom for a halogen atom of compound (1c-34), and then reacting compound (1c-34-3). Compound (1c-36) can be manufactured according to the methods similar to those of [Step 1-50].

[Step 1-53]

This step is a step wherein compound (1c-36) is obtained by reacting compound (1c-34) and compound (1c-34-4) in the presence of a base. Compound (1c-36) can be manufactured according to the methods similar to those of [Step 1-51].

Manufacturing Method 1-3-7

Method 2 for Manufacturing Compound (1c-2)

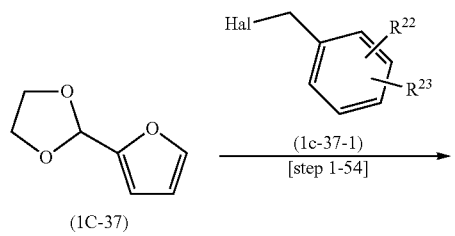

(wherein Hal is defined as above; $R^{22}$ and $R^{23}$ represent a halogen atom, a $C_{1-6}$ alkyl group and a $C_{1-6}$ alkoxy group.)

Compound (1c-37) and compound (1c-37-1) which are commercially available products can be used as is, or they can be manufactured from commercially available products by the known methods.

[Step 1-54]

This step is a step wherein compound (1c-38) is obtained by converting compound (1c-37) into an organometallic compound by substituting a metal atom for the hydrogen atom at position 5 of compound (1c-37), and then reacting with compound (1c-37-1). There are no particular limitations on the solvent used in this reaction as long as it dissolves the starting materials to a certain extent without impeding the reaction. Preferable examples of the solvent include ether solvents such as tetrahydrofuran and diethyl ether. Examples of the organometallic compound include organolithium compounds obtained by applying a base such as n-butyl lithium, s-butyl lithium, t-butyl lithium, lithium diisopropyl amide or the like. The temperature at which the organolithium compound is to be prepared is from −78° C. to room temperature, preferably from −78° C. to −40° C. The base is used in the amount of 1 to 1.5 equivalents based on compound (1c-37). The reaction time is from 30 minutes to 24 hours. Compound (1c-37-1) is used in the amount of 1 to 2 equivalents based on compound (1c-37). The temperature for reacting the organometallic compound and compound (1c-37-1) is from −78° C. to room temperature. The reaction time is from 5 minutes to 12 hours.

Manufacturing Method 1-3-8

Method 1 for Manufacturing Compound (1c-3)

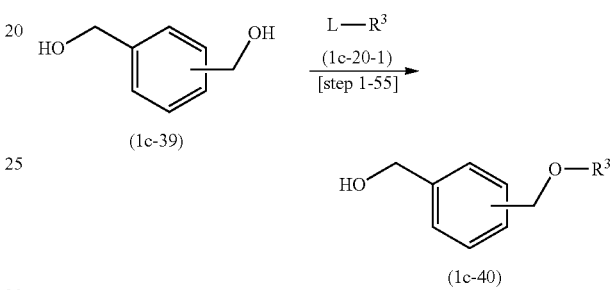

(wherein $R^3$ and L are defined as above.)

Compound (1c-39) and Compound (1c-20-1) may be commercially available products or can also be manufactured from the commercially available products by the well known methods.

[Step 1-55]

This step is a step wherein compound (1c-40) is obtained by reacting compound (1c-39) with compound (1c-20-1). Compound (1c-20-1) is used in the amount of 0.2 to 1.0 equivalents based on compound (1c-39). Compound (1c-40) can be manufactured according to the methods similar to those of [Step 1-38].

Manufacturing Method 1-3-9

Method 2 for Manufacturing Compound (1c-3)

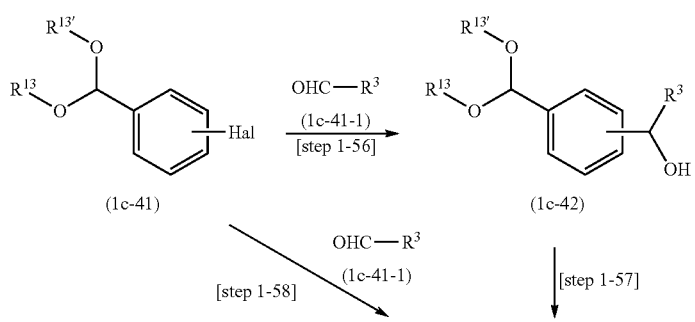

-continued

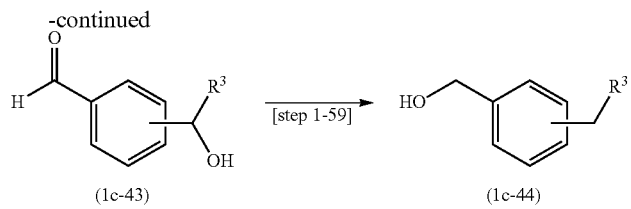

(wherein $R^3$, $R^{13}$, $R^{13'}$ and Hal are defined as above.)

Compound (1c-41) and compound (1c-41-1) may be commercially available products or can also be manufactured from the commercially available products by the well known methods.

[Step 1-56]

This step is a step wherein the halogen atom in compound (1c-41) is replaced with a metal atom to obtain an organometallic compound, which is then reacted with compound (1c-41-1) to obtain compound (1c-42). There are no particular limitations on the solvent used in this reaction as long as it dissolves the starting materials to a certain extent without impeding the reaction. Examples of the solvents used in this reaction include ether solvents such as tetrahydrofuran and diethyl ether; aromatic hydrocarbon solvents such as benzene and toluene; mixed solvents of the foregoing and the like. Examples of the reagent for converting compound (1c-41) into an organometallic compound include n-butyl lithium, s-butyl lithium, ethyl magnesium bromide, ethyl magnesium chloride, isopropyl magnesium chloride, magnesium, zinc and the like. The reagent for converting compound (1c-41) into an organometallic compound is used in the amount of 1 to 3 equivalents based on compound (1c-41). Compound (1c-41-1) is used in the amount of 1 to 2 equivalents based on compound (1c-41). The reaction temperature in the reaction for converting compound (1c-41) into an organometallic compound is from −78° C. to reflux temperature, with a reaction time being from 10 minutes to 12 hours. The reaction temperature in the reaction of adding compound (1c-41-1) is from −78° C. to room temperature, with a reaction time being from 10 minutes to 6 hours.

[Step 1-57]

This step is a step wherein compound (1c-43) is obtained by deprotecting the acetal of compound (1c-42). Compound (1c-43) is manufactured according to the methods similar to those of [Step 1-16].

[Step 1-58]

This step is a step wherein compound (1c-43) is obtained by reacting compound (1c-41) with compound (1c-41-1). In this step, compound (1c-42) is obtained according to the methods similar to those of [Step 1-56], after which an acid is added in the reaction system or at the work-up stage to obtain compound (1c-43). Examples of the acids used in this reaction include inorganic acids such as hydrochloric acid, sulfuric acid and hydrobromic acid; organic acids such as citric acid, trifluoroacetic acid and p-toluenesulfonic acid; acidic silica gels and the like. The acid can be used in the amounts of from the catalytic amount to the solvent amount based on Compound (1c-41). The reaction temperature is from 0° C. to the reflux temperature of the solvent, and the reaction time is from 5 minutes to 24 hours.

[Step 1-59]

This step is a step wherein compound (1c-44) is obtained by reducing compound (1c-43). There are no particular limitations on the solvent used in this reaction as long as it dissolves the starting materials to a certain extent without impeding the reaction. Examples of the solvents used in this reaction include ether solvents such as tetrahydrofuran and diethyl ether; aromatic hydrocarbon solvents such as benzene and toluene; and the like. Examples of the reducing agent include lithium aluminum hydride-aluminum chloride and the like. The lithium aluminum hydride is used in the amount of 2 to 6 equivalents based on compound (1c-43). The aluminum chloride is used in the amount of 2 to 9 equivalents based on compound (1c-43). The reaction temperature is from 0° C. to reflux temperature, and the reaction time is from 10 minutes to 48 hours.

Manufacturing Method 1-3-10

Method 3 for Manufacturing Compound (1c-3)

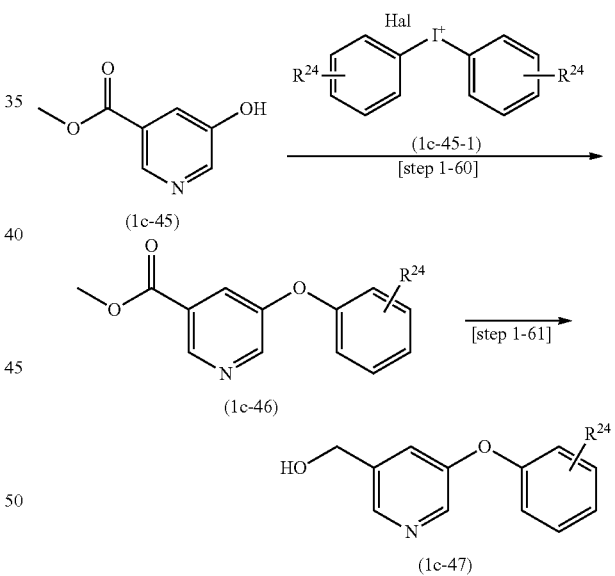

(wherein Hal is defined as above; $R^{24}$ represents a hydrogen atom, a halogen, a $C_{1-6}$ alkyl group and a $C_{1-6}$ alkoxy group, or the like.)

Compound (1c-45) and compound (1c-45-1) which are commercially available products can be used as is or they can also be manufactured from commercially available products by the known methods.

[Step 1-60]

This step is a step wherein compound (1c-46) is obtained by reacting compound (1c-45) and compound (1c-45-1). Compound (1c-46) can be obtained by reacting compound (1c-45) and compound (1c-45-1), for instance, in a solvent such as tetrahydrofuran, N,N-dimethylformamide or dimethyl sulfoxide, for instance, in the presence of a base such as potassium t-butoxide. Compound (1c-45-1) is used in the amount of 1 to 1.5 equivalents based on compound (1c-45). The base is used in the amount of 1 to 1.5 equivalents based on compound (1c-45). The reaction temperature is from room temperature to reflux temperature. The reaction time is from 30 minutes to 24 hours.

[Step 1-61]

This step is a step wherein compound (1c-47) is obtained by reducing the compound (1c-46). Compound (1c-47) can be manufactured according to the methods similar to those of [Step 1-4].

Manufacturing Method 1-3-11

Method 4 for Manufacturing Compound (1c-3)

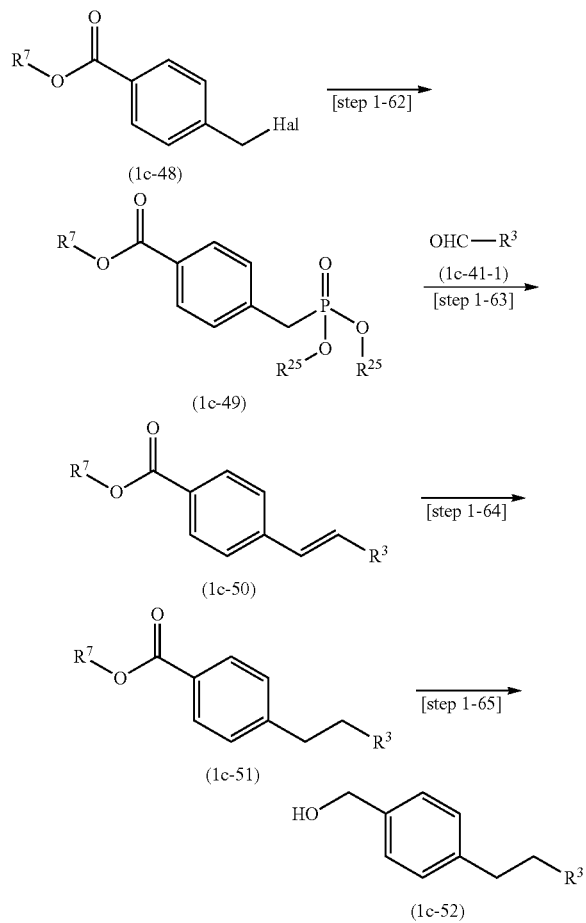

(wherein $R^3$, $R^7$ and Hal are defined as above; in addition, $R^{25}$ represents a $C_{1-6}$ alkyl group.)

Compound (1c-48) and compound (1c-41-1) which are commercially available products can be used as is, or they can be manufactured from commercially products by the known methods.

[Step 1-62]

This step is a step wherein compound (1c-49) is obtained by substituting a phosphorus atom for a halogen atom of compound (1c-48). This reaction is carried out by mixing compound (1c-48) and trialkylphosphite in a solvent or in the absence of solvent, and heating. There are no particular limitations on the solvent used in this reaction as long as it dissolves the starting materials to a certain extent without impeding the reaction. Examples of the solvent include aromatic hydrocarbon solvents such as toluene and xylene or mixed solvents of the foregoing. The trialkylphosphite is added in the amount of 1 to 1.2 equivalents based on compound (1c-48). The reaction temperature is from 100° C. to 150° C., and the reaction time is from 30 minutes to 2 hours.

[Step 1-63]

This step is a step wherein compound (1c-50) is obtained by adding a base to compound (1c-49) and then reacting with compound (1c-41-1). There are no particular limitations on the solvent used in this reaction as long as it dissolves the starting materials to a certain extent without impeding the reaction. Examples of the solvent include ether solvents such as tetrahydrofuran and 1,4-dioxane; amide solvents such as N,N-dimethylformamide and N-methylpyrrolidinone; or mixed solvents of the foregoing. Examples of the base include metal hydrides such as sodium hydride and potassium hydride; metal alcoholates such as sodium methoxide and potassium t-butoxide. Compound (1c-41-1) is added in the amounts of 1 to 2 equivalents based on compound (1c-49). The reaction temperature is from room temperature to 80° C., and the reaction time is from 30 minutes to 12 hours.

[Step 1-64]

This step is a step wherein a double bond of compound (1c-50) is hydrogenated, leading to compound (1c-51). This step is a reaction whereby hydrogen addition is carried with compound (1c-50) in a solvent, under a hydrogen atmosphere, and using a metal catalyst. There are no particular limitations on the solvent used in this reaction as long as it dissolves the starting materials to a certain extent without impeding the reaction. Examples of the solvent include ether solvents such as tetrahydrofuran and 1,4-dioxane; alcohol solvents such as methanol and ethanol; ester solvents such as ethyl acetate or mixed solvents of the foregoing. Examples of the metal catalyst include palladium (II) oxide, palladium hydroxide, platinum (IV) oxide, Raney nickel or the like. The metal catalyst is used in a catalytic amount to excess based on compound (1c-50). The reaction temperature is from room temperature to 80° C., the reaction time is from 5 minutes to 24 hours. The reaction pressure is from 1 atmosphere to 4 atmospheres.

[Step 1-65]

This step is a step wherein alcohol product (1c-52) is obtained by reducing the ester group of compound (1c-51). There are no particular limitations on the solvent used in this reaction as long as it dissolves the starting materials to a certain extent without impeding the reaction. Examples of the solvent include ether solvents such as ether and tetrahydrofuran; aromatic hydrocarbon solvents such as toluene and xylene; or mixed solvents of the foregoing. Examples of the reducing agent include sodium borohydride, lithium aluminum hydride, diisobutylaluminum hydride, or the like. The reducing agent is added in the amount of 0.5 to 2 equivalents of compound (1c-51). The reaction temperature is from −20° C. to reflux temperature of the solvent, and the reaction time is from 10 minutes to 24 hours.

Manufacturing Method 1-3-12

Method 5 for Manufacturing Compound (1c-3)

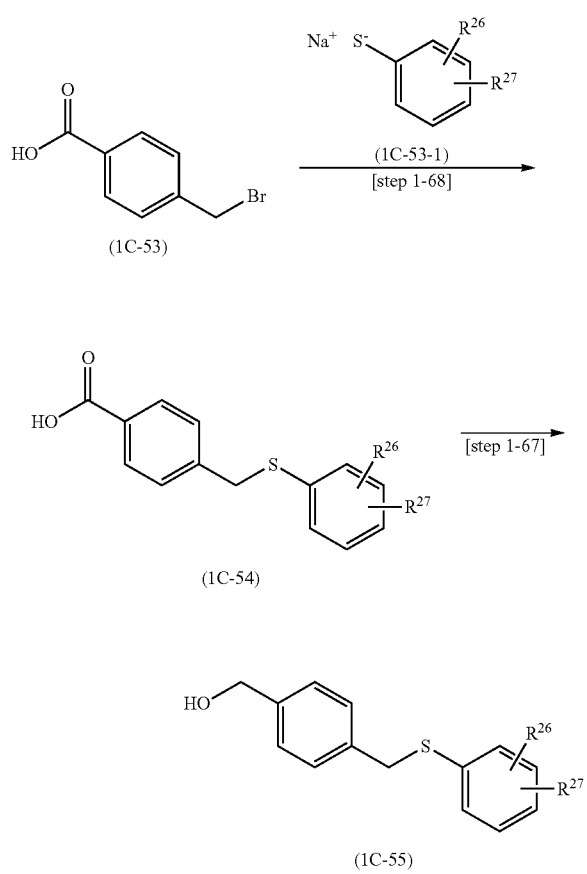

(wherein $R^{26}$ and $R^{27}$ represent a halogen atom, a $C_{1-6}$ alkyl group and a $C_{1-6}$ alkoxy group.)

Compound (1c-53) and compound (1c-53-1) which are commercially available products can be used as is, or they may be manufactured from commercially available products by the known methods.

[Step 1-66]

This step is a step wherein compound (1c-54) is obtained by reacting compound (1c-53) and compound (1c-53-1). There are no particular limitations on the solvent used in this reaction as long as it dissolves the starting materials to a certain extent without impeding the reaction. Examples of the solvent include alcohol solvents such as ethanol and methanol, or the like. Compound (1c-53-1) is used in the amount of 1 to 2 equivalents based on compound (1c-53). The reaction temperature is the reflux temperature, and the reaction time is from 30 minutes to 12 hours.

[Step 1-67]

This step is a step wherein compound (1c-55) is obtained by reducing compound (1c-54). Compound (1c-55) can be manufactured according to the methods similar to those of [Step 1-4].

Manufacturing Method 1-3-13

Method 1 for Manufacturing Compound (1c-4)

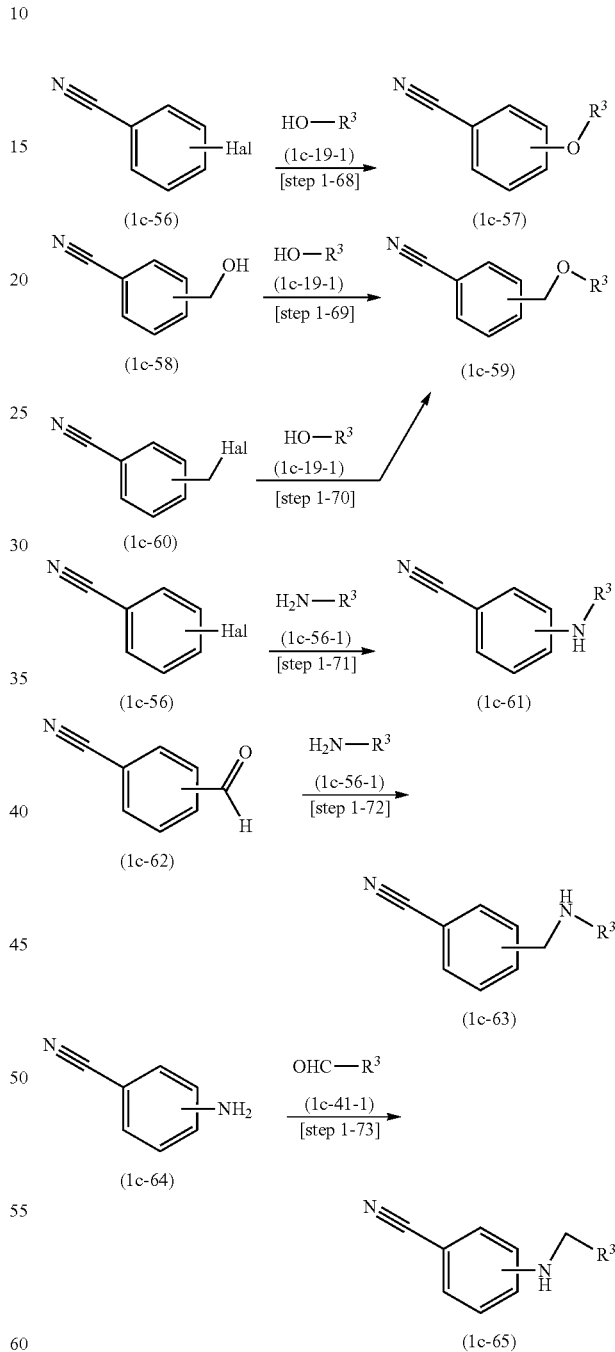

(wherein $R^3$ and Hal are defined as above.)

Compound (1c-56), compound (1c-58), compound (1c-60), compound (1c-62), compound (1c-64), compound (1c-19-1), compound (1c-41-1) and compound (1c-56-1) which are commercially available products can be used as is, or they can also be manufactured from the commercially available products by the well known methods.

[Step 1-68]

This step is a step wherein compound (1c-57) is obtained by reacting compound (1c-56) with compound (1c-19-1) in the presence of a base. There are no particular limitations on the solvent used in this reaction as long as it dissolves the starting materials to a certain extent without impeding the reaction. Examples of the solvent used in this reaction include ether solvents such as tetrahydrofuran; amide solvents such as N,N-dimethylformamide and N-methylpyrrolidinone; alcohol solvents such as methanol and ethanol; and dimethyl sulfoxide, mixed solvents of the foregoing and the like. Examples of the base include sodium hydride, potassium t-butoxide, sodium ethoxide, sodium methoxide, N,N-diisopropylethylamine, triethylamine, potassium hydroxide, sodium hydroxide, potassium carbonate, sodium carbonate and the like. The base is used in the amount of 1 to 5 equivalents based on compound (1c-19-1). Compound (1c-19-1) is used in the amount of 1 equivalent to the solvent amount based on compound (1c-56). The reaction temperature is from room temperature to reflux temperature, and the reaction time is from 30 minutes to 48 hours.

[Step 1-69]

This step is a step wherein compound (1c-59) is obtained by reacting compound (1c-58) with compound (1c-19-1). Compound (1c-59) can be manufactured according to the methods similar to those of [Step 1-37].

[Step 1-70]

This step is a step wherein compound (1c-59) is obtained by reacting compound (1c-60) with compound (1c-19-1). Compound (1c-59) can be obtained according to the methods similar to those of [Step 1-36].

[Step 1-71]

This step is a step wherein compound (1c-61) is obtained by reacting compound (1c-56) with compound (1c-56-1) in the presence of a palladium catalyst. A phosphine ligand can also be added to the reaction system to obtain good results. There are no particular limitations on the solvent used in this reaction as long as it dissolves the starting materials to a certain extent without impeding the reaction. Examples of the solvent in this reaction include ether solvents such as 1,4-dioxane and tetrahydrofuran; alcohol solvents such as methanol and ethanol; aromatic hydrocarbons solvent such as toluene and xylene; amide solvents such as N,N-dimethylformamide and N-methylpyrrolidinone; and dimethyl sulfoxide, mixed solvents of the foregoing and the like. Examples of palladium catalyst include palladium (II) acetate, tris(dibenzylidenacetone)dipalladium (0), dichlorobis(triphenylphosphine)palladium (II), dichlorobis(tri-o-tolylphosphine)palladium (II), bis(tri-t-butylphosphine)palladium (0), tetrakis(triphenylphosphine)palladium (0), palladium (0) pentadienone and the like. Examples of the phosphine ligand include triphenylphosphine, tri-o-tolylphosphine, tri-t-butylphosphine, diphenylphosphinoferrocene, 2-dicyclohexylphosphinobiphenyl, 2-di-t-butylphosphinobiphenyl, 2,2'-bis(diphenylphosphino)-1,1'-binaphthyl (BINAP) and the like. Examples of the base include sodium t-butoxide, cesium carbonate, potassium carbonate, potassium phosphate and the like. Compound (1c-56-1) is used in the amount of 1 equivalent to excess based on compound (1c-56). The palladium catalyst is used in the amount of 0.01 to 0.3 equivalents based on compound (1c-56). The phosphine ligand is used in the amount of 0.01 to 1.2 equivalents based on compound (1c-56). The base is used in the amount of 1 to 4 equivalents based on compound (1c-56). The reaction temperature is from room temperature to reflux temperature, and the reaction time is from 30 minutes to 72 hours.

[Step 1-72]

This step is a step wherein compound (1c-63) is obtained by a reductive amination in which compound (1c-62) is reacted with compound (1c-56-1). Acetic acid can also be added to promote the reaction. There are no particular limitations on the solvent used in this reaction as long as it dissolves the starting materials to a certain extent without impeding the reaction. Examples of the solvent in this reaction include ether solvents such as 1,4-dioxane and tetrahydrofuran; alcohol solvents such as methanol and ethanol; and methylene chloride, mixed solvents of the foregoing an the like. Examples of the reducing agent include lithium aluminum hydride, sodium borohydride, sodium cyanoborohydride, sodium triacetoxyborohydride, 2-picoline-borane and the like. Compound (1c-56-1) is used in the amount of 1 to 2 equivalents based on compound (1c-62). The reducing agent is used in the amount of 0.5 to 2 equivalents based on compound (1c-62). The reaction temperature is from room temperature to reflux temperature, and the reaction time is from 10 minutes to 24 hours.

[Step 1-73]

This step is a step wherein compound (1c-65) is obtained by a reductive amination in which compound (1c-64) is reacted with compound (1c-41-1). Compound (1c-65) can be manufactured according to the methods similar to those of [Step 1-72].

Manufacturing Method 1-3-14

Method 2 for Manufacturing Compound (1c-4)

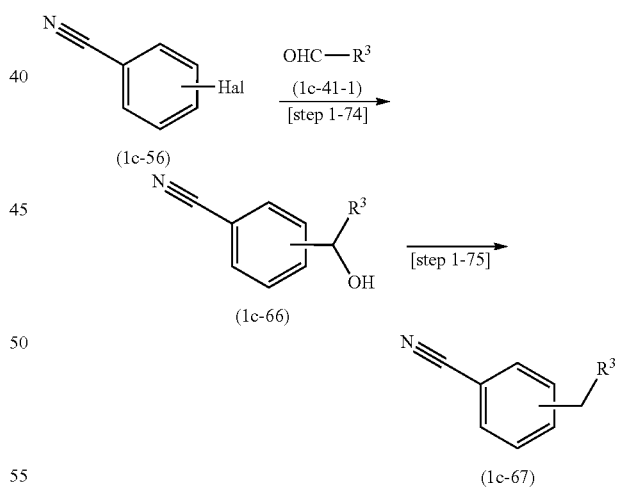

(wherein R³ and Hal are defined as above.)

Compound (1c-56) and compound (1c-41-1) which are commercially available products can be used as is, or compound (1c-56) and compound (1c-41-1) can also be manufactured from commercially available products by the well known methods.

[Step 1-74]

This step is a step wherein compound (1c-66) is obtained by reacting compound (1c-56) with compound (1c-41-1).

Compound (1c-66) can be manufactured according to the methods similar to those of [Step 1-56].

[Step 1-75]

This step is a step wherein compound (1c-67) is obtained by reducing compound (1c-66) with iodotrimethylsilane. There are no particular limitations on the solvent used in this reaction as long as it dissolves the starting materials to a certain extent without impeding the reaction. Examples of the solvent include ether solvents such as tetrahydrofuran; and acetonitrile, methylene chloride and the like, preferably methylene chloride and acetonitrile. The iodotrimethylsilane is used in the amount of 2 to 10 equivalents based on compound (1c-66), the reaction temperature is from 0° C. to 60° C., and the reaction time is from 5 minutes to 6 hours. The iodotrimethylsilane used in the reaction may be a commercially available product, or may be prepared at the time of use by reacting sodium iodide and chlorotrimethylsilane in acetonitrile at room temperature.

Manufacturing Method 1-3-15

Method 3 for Manufacturing Compound (1c-4)

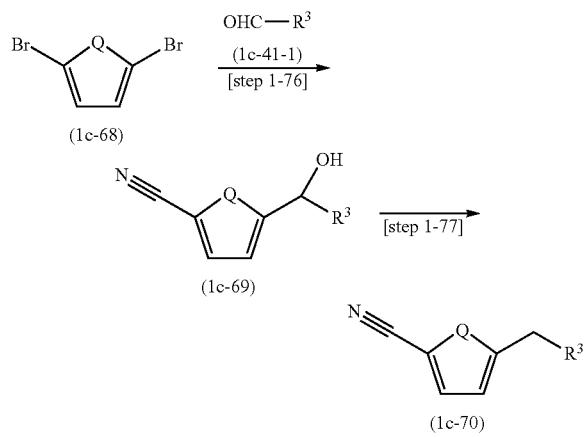

(wherein $R^3$ is defined as above, and Q represents a sulfur atom and oxygen atom.)

Compound (1c-68) and compound (1c-41-1) which are commercially available products can be used as is, or they can also be manufactured from the commercially available products by the well known methods.

[Step 1-76]

This step is a step wherein one of the bromide atoms in compound (1c-68) is anionized using an organometallic reagent, which is reacted with compound (1c-41-1), then the other bromide atom in compound (1c-68) is anionized by adding the further organometallic reagent in the same container, which is then reacted with a cyanization reagent to obtain compound (1c-69). There are no particular limitations on the solvent used in this reaction as long as it dissolves the starting materials to a certain extent without impeding the reaction. Examples of the solvent include ether solvents such as tetrahydrofuran and diethyl ether; aromatic hydrocarbon solvents such as benzene and toluene; mixed solvents of the foregoing and the like. Examples of the organometallic reagent include n-butyl lithium, s-butyl lithium and the like. Preferable examples of the cyanization reagent include p-toluenesulfonyl cyanide. The organometallic reagent is used in the total amount of 2 to 3 equivalents based on compound (1c-68). Compound (1c-41-1) is used in the amount of 1 to 1.5 equivalents based on compound (1c-68). The cyanization reagent is used in the amount of 1 to 1.5 equivalents based on compound (1c-68). The reaction temperature is from −78° C. to room temperature, and the reaction time is from 10 minutes to 24 hours.

[Step 1-77]

This step is a step wherein compound (1c-70) is obtained by reducing compound (1c-69). Compound (1c-70) can be manufactured according to the methods similar to those of [Step 1-75].

Manufacturing Method 1-3-16

Method 1 for Manufacturing Compound (1c-5)

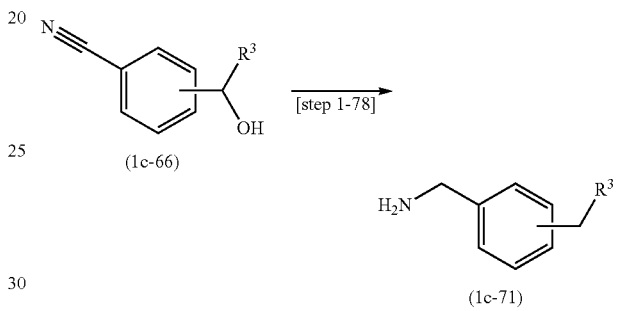

(wherein $R^3$ is defined as above.)

Compound (1c-66) can be manufactured from a commercially available product by the well known methods, or compound (1c-66) can be manufactured according to the methods similar to those of [Step 1-74].

[Step 1-78]

This step is a step wherein compound (1c-71) is obtained by reducing compound (1c-66). There are no particular limitations on the solvent used in this reaction as long as it dissolves the starting materials to a certain extent without impeding the reaction. Examples of the solvent include ether solvents such as tetrahydrofuran and diethyl ether; aromatic hydrocarbon solvents such as benzene and toluene and the like. Examples of the reducing agent include lithium aluminum hydride-aluminum chloride. The lithium aluminum hydride is used in the amount of 3 to 8 equivalents based on compound (1c-66). The aluminum chloride is used in the amount of 3 to 10 equivalents based on compound (1c-66). The reaction temperature is from 0° C. to reflux temperature, and the reaction time is from 10 minutes to 48 hours.

Manufacturing Method 1-3-17

Method 2 of Manufacturing Compound (1c-5)

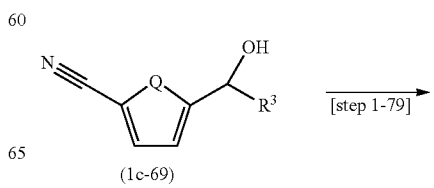

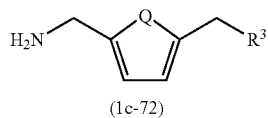

(1c-72)

(wherein $R^3$ and Q are defined as above.)

Compound (1c-69) can be manufactured from commercially available products by the well known methods, or compound (1c-69) can be manufactured according to the methods similar to those of [Step 1-76].

[Step 1-79]

This step is a step wherein compound (1c-72) is obtained by reducing compound (1c-69). Compound (1c-72) can be manufactured according to the methods similar to those of [Step 1-78].

Manufacturing Method 1-3-18

Method 1 for Manufacturing Compound (1c-6)

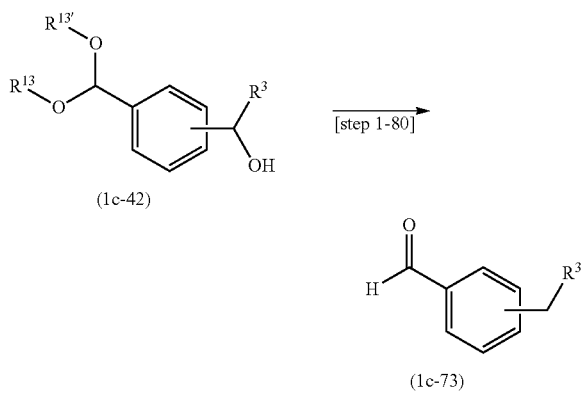

(wherein $R^3$, $R^{13}$ and $R^{13'}$ are defined as above.)

Compound (1c-42) can be manufactured from commercially available products by the well known methods, or compound (1c-42) can be manufactured according to the methods similar to those of [Step 1-56].

[Step 1-80]

This step is a step wherein compound (1c-73) is obtained by simultaneous reduction and acetal deprotection of compound (1c-42) using iodotrimethylsilane. There are no particular limitations on the solvent used in this reaction as long as it dissolves the starting materials to a certain extent without impeding the reaction. Examples of the solvent include ether solvents such as tetrahydrofuran; acetonitrile, methylene chloride and the like, and preferably methylene chloride or acetonitrile. The iodotrimethylsilane is used in the amount of 2 to 10 equivalents based on compound (1c-42). The reaction temperature is from 0° C. to 60° C., and the reaction time is from 5 minutes to 6 hours. The iodotrimethylsilane used in the reaction may be a commercial product, or may be prepared at the time of use by reacting sodium iodide and chlorotrimethylsilane in acetonitrile at room temperature.

Manufacturing Method 1-3-19

Method 2 for Manufacturing Compound (1c-6)

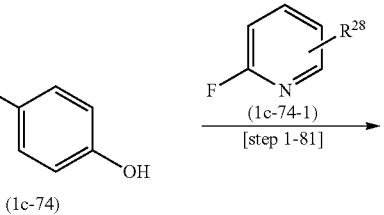

(1c-74)

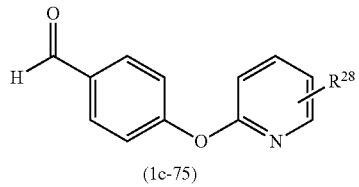

(1c-75)

(wherein $R^{28}$ represent a halogen or a $C_{1-6}$ alkyl group.)

Compound (1c-74) and compound (1c-74-1) which are commercially available products can be used as is, or they may be manufactured from commercially available products by the known methods.

[Step 1-81]

This step is a step wherein compound (1c-75) is obtained by reacting compound (1c-74) and compound (1c-74-1), in the presence of a base. There are no particular limitations on the solvent used in this reaction as long as it dissolves the starting materials to a certain extent without impeding the reaction. Examples of the solvent include ether solvents such as tetrahydrofuran and 1,4-dioxane; aromatic hydrocarbon solvents such as benzene and toluene; amide solvents such as N,N-dimethylformamide and N-methylpyrrolidinone, dimethyl sulfoxide, mixed solvents of the foregoing, or the like. Examples of the base include sodium hydride, potassium t-butoxide, sodium hydroxide, potassium hydroxide, sodium bicarbonate, potassium carbonate or the like. Compound (1c-74) is used in the amount of 0.5 to 2 equivalents based on compound (1c-74-1). The base is used in the amount of 0.5 to 5 equivalents based on compound (1c-74-1). The reaction temperature is from 100° C. to 170° C., and the reaction time is from 30 minutes to 12 hours.

Manufacturing Method 1-3-20

Method 3 for Manufacturing Compound (1c-6)

[Step 1-84]

This step is a step wherein compound (1c-78) is obtained by reacting compound (1c-79) and compound (1c-76-1), in equivalents based on compound (1c-76). The reaction temperature is from room temperature to 80° C., and the reaction time is from 30 minutes to 72 hours.

[Step 1-83]

This step is a step wherein compound (1c-78) is obtained by reducing the cyano group of compound (1c-77). Compound (1c-78) can be manufactured according to the methods similar to those of [Step 1-18]. the presence of a base. Com

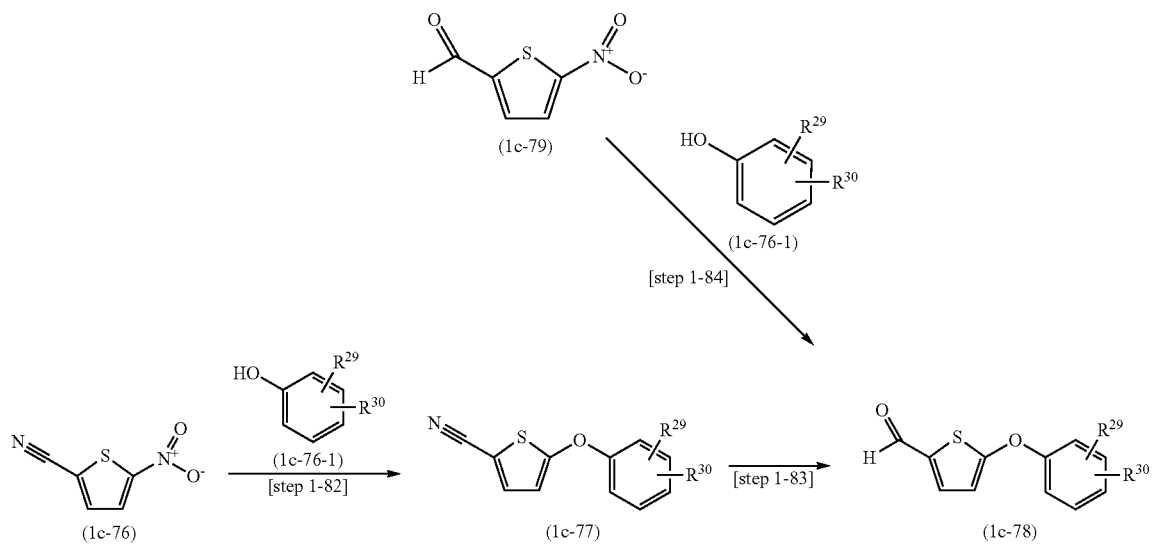

(wherein $R^{29}$ and $R^{30}$ represent a halogen, a $C_{1-6}$ alkyl group and a $C_{1-6}$ alkoxy group.)

Compound (1c-76), compound (1c-79) and compound (1c-76-1) which are commercially available products can be used as is, or they may be manufactured from commercially available products by the known methods.

[Step 1-82]

This step is a step wherein compound (1c-77) is obtained by reacting compound (1c-76) and compound (1c-76-1), in the presence of a bas. There are no particular limitations on the solvent used in this reaction as long as it dissolves the starting materials to a certain extent without impeding the reaction. Examples of the solvent include ether solvents such as tetrahydrofuran and 1,4-dioxane; aromatic hydrocarbon solvents such as benzene and toluene; amide solvents such as N,N-dimethylformamide and N-methylpyrrolidinone; dimethyl sulfoxide, mixed solvents of the foregoing, or the like. Examples of the base include sodium hydride, potassium t-butoxide, sodium hydroxide, potassium hydroxide, sodium bicarbonate, potassium carbonate, or the like. Compound (1c-76-1) is used in the amount of 1 to 2 equivalents based on compound (1c-76). The base is used in the amount of 2 to 3 pound (1c-78) can be obtained according to the methods similar to those of [Step 1-82].

Manufacturing Method 1-3-21

Method 4 for Manufacturing Compound (1c-6)

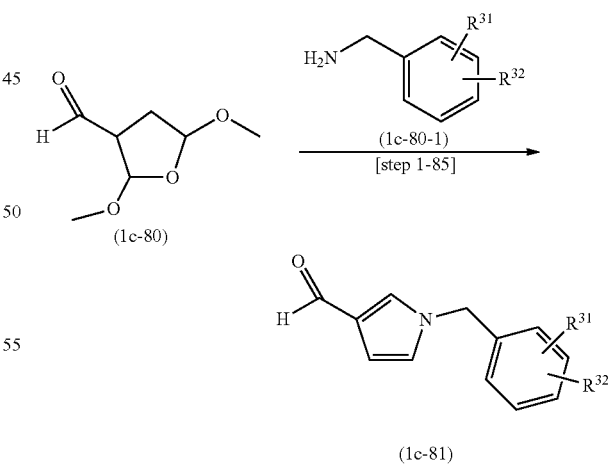

(wherein $R^{31}$ and $R^{32}$ represent a halogen, a $C_{1-6}$ alkyl group and a $C_{1-6}$ alkoxy group.)

Compound (1c-80) and compound (1c-80-1) which are commercially available products can be used as is, or they may be manufactured from commercially available products by the known methods.

[Step 1-85]

This step is a step wherein compound (1c-81) is obtained by reacting compound (1c-80) and compound (1c-80-1). Examples of the solvent include acetic acid, or the like. Compound (1c-80-1) is used in the amount of 1 equivalent based on compound (1c-80). The reaction temperature is from 50° C. to 110° C., and the reaction time is from 5 minutes to 1 hours.

Manufacturing Method 1-3-22

Method 5 for Manufacturing Compound (1c-6)

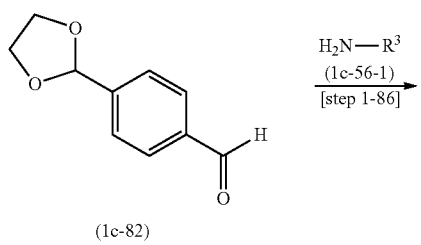

(wherein $R^3$ is defined as above.)

Compound (1c-82) and compound (1c-56-1) which are commercially available products can be used as is, or they may be manufactured from commercially available products by the known methods.

[Step 1-86]

This step is a step wherein compound (1c-83) is obtained by carrying out a reductive amination of compound (1c-82) and compound (1c-56-1). Compound (1c-83) can be manufactured according to the methods similar to those of [Step 1-72].

[Step 1-87]

This step is a step wherein compound (1c-84) is obtained by deprotecting of acetal in compound (1c-83) by adding an acid. Compound (1c-84) can be manufactured according to the methods similar to those of [Step 1-16].

Manufacturing Method 1-3-23

Method 6 for Manufacturing Compound (1c-6)

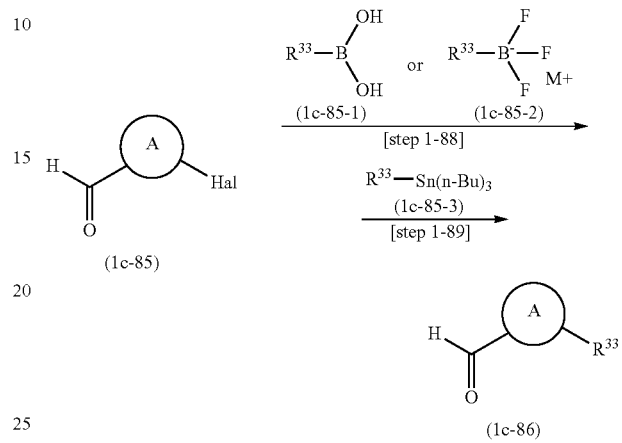

(wherein ring A and Hal are defined as above; $R^{33}$ represents a $C_{1-6}$ alkyl group, a $C_{3-8}$ cycloalkyl group, a $C_{6-10}$ aryl group, or a 5- or 6-membered ring heteroaryl group, which may have 1 or 2 substituents selected from the substituent group $\alpha^1$, respectively; $M^+$ represents a potassium cation and a sodium cation.

[Substituent Group $\alpha^1$]

a cyano group, a $C_{1-6}$ alkyl group, a $C_{1-6}$ alkoxy group, a $C_{1-6}$ alkoxycarbonyl group and a $C_{3-8}$ cycloalkyl group)

Compound (1c-85), compound (1c-85-1), compound (1c-85-2) and compound (1c-85-3) which are commercially available products can be used as is, or they may also be manufactured from commercially available products by the known methods.

[Step 1-88]

This step is a step wherein compound (1c-86) is obtained by reacting compound (1c-85) and compound (1c-85-1) or compound (1c-85-2), in the presence of a palladium catalyst and a base. An inorganic salt such as lithium chloride; an ammonium salt such as tetrabutylammonium chloride; or a phosphine ligand can also be added to obtain good results. This reaction can be carried out under an inert gas atmosphere, such as nitrogen gas and argon gas. There are no particular limitations on the solvent used in this reaction as long as it dissolves the starting materials to a certain extent without impeding the reaction. Examples of the solvent include ether solvents such as 1,4-dioxane and tetrahydrofuran; aromatic hydrocarbon solvents such as toluene and xylene; amide solvents such as N,N-dimethylformamide and N-methylpyrrolidinone; dimethyl sulfoxide, water, mixed solvents of the foregoing, and the like. Examples of the palladium catalyst include palladium (II) acetate, tetrakis(triphenylphosphine)palladium (0), dichlorobis(triphenylphosphine)palladium (II), tris(dibenzylidene acetone)dipalladium (0), palladium carbon, bis(tri-t-butyl phosphine)palladium (0), 1,1'-bis(diphenyl phosphinoferrocene)dichloro palladium (II), or the like. Examples of the phosphine ligand include triphenylphosphine, tri-o-tolylphosphine, tri-t-butylphosphine, tricyclohexyl phosphine, diphenylphosphinoferrocene, 2-dicyclohexylphosphino-2',6'-dimethoxybiphenyl, 2-dicyclohexylphosphino-2',4',6'-triisopropylbiphenyl, 2-di-t-butylphosphino-2',4',6'-triisopropylbiphenyl, 2-di-t-butylphosphinobiphenyl, 2-dicyclohexylphosphinobiphenyl, 2-dicyclohexylphosphino-2'-(N,N-dimethylamino)biphenyl, 2-di-t-butylphosphino-2'-(N,N-dimethylamino)biphenyl, 2,2'-bis(diphenylphosphino)-1,1'-binaphthyl, 1,2-bis(diphenylphosphino)ethane, 1,3-bis(diphenylphosphino)propane, 1,4-bis(diphenylphosphino)butane, or the like. Examples of the base include potassium carbonate, sodium carbonate, cesium carbonate, potassium fluoride, cesium fluoride, potassium phosphate, sodium hydroxide, barium hydroxide, potassium hydroxide, or the like. Compound (1c-85-1) or compound (1c-85-2) is used in the amount of 1 to 3 equivalents based on compound (1c-85). The palladium catalyst is used in the amount of 0.01 to 0.25 equivalents based on compound (1c-85). The phosphine ligand is used in the amount of 0.01 to rocene, or the like. Examples of the copper reagent include copper (I) iodide, copper (I) bromide, copper (I) chloride, or the like. Compound (1c-85-3) is used in the amount of 1 to 3 equivalents based on compound (1c-85). The palladium catalyst is used in the amount of 0.01 to 0.25 equivalents based on compound (1c-85). The phosphine ligand is used in the amount of 0.01 to 1 equivalent based on compound (1c-85). The copper reagent is used in the amount of 0.1 to 3 equivalents based on compound (1c-85). Inorganic salt such as lithium chloride, or ammonium salt such as tetrabutylammonium chloride, are used in the amount of 0.5 to 2 equivalents. The reaction temperature is from room temperature to reflux temperature, and the reaction time is from 10 minutes to 72 hours.

Manufacturing Method 1-3-24

Method for Manufacturing Compound (1c-85-2)

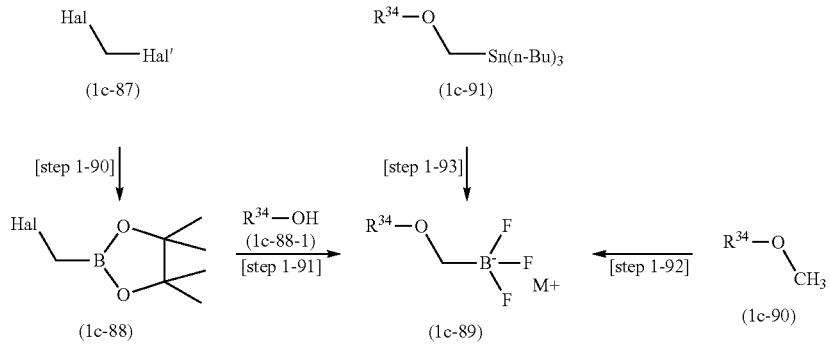

1 equivalent based on compound (1c-85). Inorganic salts such as lithium chloride, or ammonium salts such as tetrabutylammonium chloride, are used in the amount of 0.5 to 2 equivalents. The reaction temperature is from room temperature to reflux temperature, and the reaction time is from 10 minutes to 72 hours.

[Step 1-89]

This step is a step wherein compound (1c-86) is obtained by reacting compound (1c-85) with compound (1c-85-3), under a palladium catalyst. An inorganic salt such as lithium chloride, an ammonium salt such as tetrabutylammonium chloride, a phosphine ligand, or a copper reagent can also be added to obtain good results. This reaction can be carried out under an inert gas atmosphere, such as nitrogen gas and argon gas. There are no particular limitations on the solvent used in this reaction as long as it dissolves the starting materials to a certain extent without impeding the reaction. Examples of the solvent include ether solvents such as 1,4-dioxane and tetrahydrofuran; aromatic hydrocarbon solvents such as toluene and xylene; amide solvents such as N,N-dimethyl formamide and N-methyl pyrrolidinone; dimethyl sulfoxide, mixed solvents of the foregoing, or the like. Examples of the palladium catalyst include palladium (II) acetate, tris (dibenzylideneacetone)dipalladium (0), dichlorobis(triphenylphosphine)palladium (II), dichlorobis(tri-o-tolylphosphine)palladium (II), bis(tri-t-butylphosphine)palladium (0), tetrakis(triphenylphosphine)palladium (0), 1,1'-bis(diphenylphosphinoferrocene)dichloro palladium (II), or the like. Examples of the phosphine ligand include triphenylphosphine, tri-o-tolylphosphine, tri-t-butylphosphine, diphenylphosphinofer- (wherein Hal and Hal' each independently represents a halogen atom; $R^{34}$ represents a $C_{1-6}$ alkyl group, a $C_{1-6}$ alkoxy$C_{1-6}$ alkyl group, a $C_{3-8}$ cycloalkyl$C_{1-6}$ alkyl group or a $C_{3-8}$ cycloalkyl group; $M^+$ represents a potassium cation and a sodium cation.)

Compound (1c-87), compound (1c-88-1), compound (1c-90) and compound (1c-91) which are commercially available products can be used as is, or they may be manufactured from commercially available products by the known methods. Compound (1c-91) which a commercially available product can be used as is, or may be manufactured from commercially available products by the known methods (for instance, WO2005/033079 A1, pages 82-84, and the like).

[Step 1-90]

This step is a step wherein compound (1c-88) is manufactured by reacting an organometallic reagent and compound (1c-87) to generate an anionized compound, which is reacted with boric acid ester, then neutralizing the reaction mixture by the addition of an acid, and finally by reacting with a diol such as pinacol. This reaction can also be carried out by adding an organometallic reagent to a mixture of compound (1c-87) and boric acid ester, in which the generation of anion from compound (1c-87) and reacting with boric acid ester are occurred simultaneously. This reaction can also be carried out under an inert gas stream or atmosphere, such as nitrogen or argon. Examples of compound (1c-87) include chloroiodomethane, dibromo methane, bromoiodomethane, or the like, and preferably, chloroiodomethane and dibromo methane. There are no particular limitations on the solvent used in this reaction as long as it dissolves the starting materials to a certain extent without impeding the reaction. Examples of the solvent include ether solvents such as tetrahydrofuran, 1,2-dimethoxyethane, methyl-t-butyl ether, cyclopentyl methyl ether, diethyl ether, diisopropyl ether, dibutyl ether and dicyclopentyl ether; aromatic hydrocarbon solvents such as benzene and toluene; aliphatic hydrocarbon solvents such as heptane and hexane, mixed solvents of the foregoing, or the like, and preferably tetrahydrofuran. Examples of the boric acid ester include trimethyl borate, triisopropyl borate or the like, and preferably triisopropyl borate. Examples of the organometallic reagent include n-butyl lithium, s-butyl lithium and the like, and preferably n-butyl lithium. Examples of the acid include methanesulfonic acid, p-toluenesulfonic acid, hydrochloric acid-ethyl acetate solution, hydrochloric acid-methanol solution, or the like, and preferably methanesulfonic acid and hydrochloric acid-ethyl acetate solution. Boric acid ester can be used in the amount of 0.8 to 1.2 equivalents based on compound (1c-87), and preferably 0.9 to 1 equivalents. The organometallic reagent can be used in the amount of 0.8 to 1.2 equivalents based on compound (1c-87), and preferably 0.8 to 1 equivalents. A mixture of the anionized compound prepared at −78° C. from compound (1c-87) and boric acid ester is stirred for 1 to 3 hours at the temperature mentioned below. This mixture is neutralized at the temperature mentioned below, then pinacol is added and stirred for 10 to 60 minutes at the temperature mentioned below.

[Reaction Temperature During the Reaction of Anionized Compound and Boric Acid Ester]

The mixture of anionized compound and boric acid ester is stirred at 0° C. to room temperature, and more preferably at room temperature.

[Reaction Temperature During Neutralization Reaction and Reaction with Diol]

The temperature during the neutralization reaction and the addition of the diol is from −20° C. to room temperature, and more preferably 0° C. The temperature after the addition of the diol is from 0° C. to room temperature, and more preferably from room temperature

[Step 1-91]

This step is a step wherein anionized compound, generated by reacting compound (1c-88-1) with a base, is reacted with compound (1c-88), followed by reacting with a hydrogen fluoride salt (potassium hydrogen fluoride or sodium hydrogen fluoride) to obtain compound (1c-89). This step can also be carried out by adding a catalytic amount of iodine compound such as potassium iodide and tetrabutylammonium iodide. This reaction can also be carried out under an inert gas stream or atmosphere, such as nitrogen or argon. There are no particular limitations on the solvent used in this reaction as long as it dissolves the starting materials to a certain extent without impeding the reaction. Examples of the solvent include ether solvents such as tetrahydrofuran, 1,2-dimethoxyethane, methyl-t-butyl ether, cyclopentyl methyl ether, diethyl ether, diisopropyl ether, dibutyl ether and dicyclopentyl ether; aromatic hydrocarbon solvents such as benzene and toluene; amide solvents such as N,N-dimethylformamide and N-methylpyrrolidinone; dimethyl sulfoxide, mixed solvents of the foregoing, or the like, and preferably tetrahydrofuran or N,N-dimethylformamide. Examples of the base include sodium hydride, potassium bis(trimethylsilyl)amide, potassium hydride, and preferably sodium hydride and potassium bis(trimethylsilyl)amide. Compound (1c-88-1) can be used in the amount of 1 to 5 equivalents based on compound (1c-88), and preferably 2 to 3 equivalents. The above-mentioned base can be used in the amount of 1 to 5 equivalents based on compound (1c-88), and preferably 2 to 3 equivalents. The above-mentioned hydrogen fluoride salt can be used in the amount of 2 to 8 equivalents based on compound (1c-88), and preferably 3 to 5 equivalents.

The reaction time for aniozation reaction of compound (1c-88-1) is, preferably from 30 to 60 minutes for stirring for at the temperature mentioned below, and after adding compound (1c-88) to the mixture, the reaction time is from 1 to 12 hours for stirring at the temperature mentioned below. After adding hydrogen fluoride salt to the reaction mixture, the reaction time is from 10 to 120 minutes for stirring at the temperature mentioned below.

[Reaction Temperature During Anionization Reaction]

The temperature during addition of the base is from 0° C. to room temperature, more preferably 0° C. The temperature after addition of the base is from 0° C. to 70° C., more preferably from room temperature to 50° C.

[Reaction Temperature During Reaction of Anionized Compound and Compound (1c-88)]

The temperature during addition of compound (1c-88) is from 0° C. to room temperature, and more preferably 0° C. The temperature after addition of compound (1c-88) is from room temperature to 100° C., more preferably from room temperature to 70° C.

[Reaction Temperature During Addition of Hydrogen Fluoride Salt]

The temperature during addition of the reagent is from 0° C. to room temperature, and more preferably 0° C. The temperature after addition of the reagent is from 0° C. to room temperature, and more preferably room temperature.

[Step 1-92]

This step is a step wherein anionized compound generated by reacting an organometallic reagent and compound (1c-90) is reacted with boric acid ester, followed by reacting with a hydrogen fluoride salt (potassium hydrogen fluoride or sodium hydrogen fluoride, or the like) to obtain compound (1c-89). In this step, the reaction can be carried out in a solvent or using a large amount of compound (1c-90) as the solvent. In addition, this step can be carried out in the presence of a base. This step can be carried out according to the general methods, for instance, $5^{th}$ Edition of Jikkenka-gakukoza 18 (pages 20 to 23), Tetrahedron Letters, Vol. 24, No. 31, pp. 3165-3168, and the like. This reaction can also be carried out under an inert gas stream or atmosphere, such as nitrogen or argon. There are no particular limitations on the solvent used in this reaction as long as it dissolves the starting materials to a certain extent without impeding the reaction. Examples of the solvent include aliphatic hydrocarbon solvents such as heptane and hexane, or the like. Preferably, compound (1c-90) is used in large amount as a solvent. Examples of the organometallic reagent include t-butyl lithium, sec-butyl lithium, or the like, preferably sec-butyl lithium. Examples of the base include potassium t-butoxide, potassium sec-butoxide, potassium methoxide, or the like, preferably potassium t-butoxide. An organometallic reagent is added to a mixture of compound (1c-90) and solvent at −75 to −60° C. (preferably −75 to −70° C.), then the mixture is stirred for 5 to 30 minutes (preferably 5 to 10 minutes) at −20 to 0° C. (preferably −10 to −5° C.). Then, boric acid ester is added to the mixture at −75 to −70° C., the mixture is then stirred for 10 to 60 minutes (preferably 10 to 30 minutes) at 10° C. to room temperature (preferably room temperature). Hydrogen fluoride salt is added to the mixture at 0 to 5° C., water is then added at the same temperature, the reaction mixture is warmed to room temperature, to obtain compound (1c-89). Preferably, compound (1c-90) is used in solvent amount based on the organometallic reagent. The base can be used in the amount of preferably 0.6 to 1 equivalents based on the organometallic reagent. The boric acid ester can be used in the amount of 1 to 2 equivalents based on the organometallic reagent, and preferably 1 to 1.8 equivalents. The above-mentioned hydrogen fluoride salt can be used in the amount of 3 to 10 equivalents based on the above-mentioned boric acid ester compound, and preferably 3 to 5 equivalents.

[Step 1-93]

This step is a step wherein anionized compound, generated by reacting a organometallic reagent with compound (1c-91), reacted with a boric acid ester (triisopropyl borate, trimethyl borate, 2-isopropoxy-4,4,5,5-tetramethyl-1,3,2-dioxaborolane, or the like), followed by reacting with a hydrogen fluoride salt (potassium hydrogen fluoride or sodium hydrogen fluoride, or the like) to obtain compound (1c-89). This reaction can also be carried out under an inert gas stream or atmosphere, such as nitrogen or argon. There are no particular limitations on the solvent used in this reaction as long as it dissolves the starting materials to a certain extent without impeding the reaction. Examples of the solvent include ether solvents such as tetrahydrofuran, 1,2-dimethoxyethane, methyl t-butyl ether, cyclopentyl methyl ether, diethyl ether, diisopropyl ether, dibutyl ether and dicyclopentyl ether; aromatic hydrocarbon solvents such as benzene and toluene; aliphatic hydrocarbon solvents such as heptane and hexane, mixed solvents of the foregoing, and the like, and preferably tetrahydrofuran. Examples of the above-mentioned organometallic reagent include n-butyl lithium, sec-butyl lithium, methyl lithium or the like, preferably n-butyl lithium. Compound (1c-89) can be obtained by the two methods described below. If it is difficult to carry out the reaction (i), such as the anion generated by reacting organometallic reagent and compound (1c-91) is unstable, reaction (ii) is preferred.

(i) In a solvent, an organometallic reagent and compound (1c-91) are stirred for 30 to 120 minutes (preferably 30 to 60 minutes) at −75 to −60° C. (preferably −75 to −70° C.). Then, boric acid ester is added to the mixture at −75 to −70° C., whereafter the mixture is stirred for 10 to 120 minutes (preferably 20 to 80 minutes) at 0° C. to room temperature (preferably 0 to 5° C.). A hydrogen fluoride salt is added to the mixture at 0 to 5° C., water is then added at the same temperature, and the reaction mixture is warmed to room temperature, to obtain compound (1c-89).

(ii) In a solvent, an organometallic reagent is added to a mixture of a boric acid ester and compound (1c-89) at −75 to −60° C. (preferably −75 to −70° C.), and stirred for 10 to 120 minutes (preferably 20 to 60 minutes) at −75 to 5° C. (preferably 0 to 5° C.). Hydrogen fluoride salt is added to the mixture at 0 to 5° C., whereafter water is added at the same temperature, and the reaction mixture is warmed to room temperature, to obtain compound (1c-89).

The organometallic reagent can be used in the amount of 0.8 to 1.2 equivalents based on compound (1c-91), and preferably 1 equivalent. The boric acid ester can be used in the amount of 1 to 2 equivalents based on compound (1c-91), and preferably 1 to 1.2 equivalents. The hydrogen fluoride salt can be used in the amount of 3 to 10 equivalents based on compound (1c-91), and preferably 3 to 5 equivalents.

Manufacturing Method 2

Typical Method for Manufacturing Compound (2a)

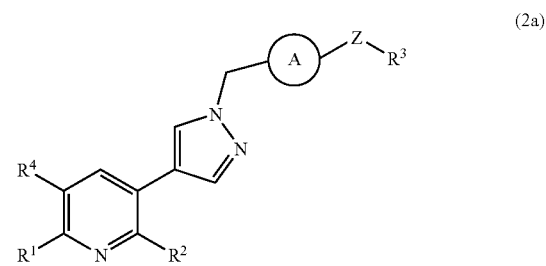

(2a)

(wherein ring A, $R^1$, $R^2$, $R^3$, $R^4$ and Z are defined as above.)

Manufacturing Method 2-1-1

Method 1 for Manufacturing Compound (2a)

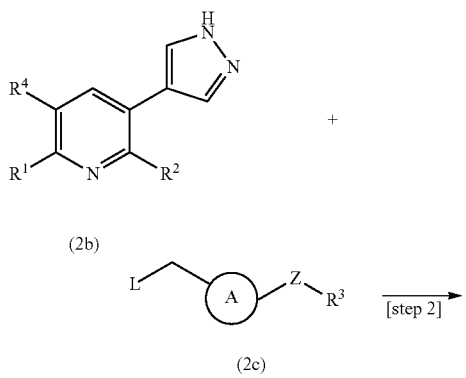

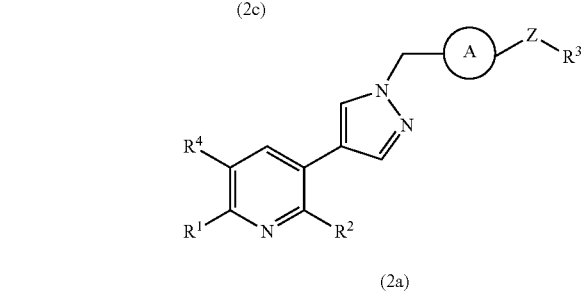

(2a)

(wherein ring A, $R^1$, $R^2$, $R^3$, $R^4$ and Z are defined as above.)

Compound (2b) can be manufactured from commercially available products by the well known methods, or can also be manufactured according to the methods described in the Manufacturing Examples in the Examples, [Manufacturing Method 2-2-1] given below or the like.

Compound (2c) which is a commercially available product can be used as is, or compound (2c) can also be manufactured from commercially available products by the well known methods. Compound (2c) can further be manufactured according to the methods described in the Manufacturing Examples in the Examples, [Manufacturing Method 2-3] given below or the like.

[Step 2]

This step is a step wherein compound (2a) is manufactured by reacting compound (2b) and compound (2c) in the presence of a base. There are no particular limitations on the solvent used in this reaction as long as it dissolves the starting materials to a certain extent without impeding the reaction. Examples of the solvent include ether solvents such as tetrahydrofuran and diethyl ether; aromatic hydrocarbon solvents such as benzene and toluene; amide solvents such as N,N-dimethylformamide and N-methylpyrrolidinone; alcohol solvents such as methanol and ethanol; and dimethyl sulfoxide, mixed solvents of the foregoing and like. Examples of the base include sodium hydride, potassium t-butoxide, sodium ethoxide, triethylamine, sodium hydroxide, potassium hydroxide and the like. Compound (2c) is used in the amount of 1 to 5 equivalents based on compound (2b). The base is used in the amount of 1 to 5 equivalents based on compound (2b). The reaction temperature is from 0° C. to reflux temperature, and the reaction time is from 10 minutes to 24 hours.

Manufacturing Method 2-1-2

Method 2 for Manufacturing Compound (2a)

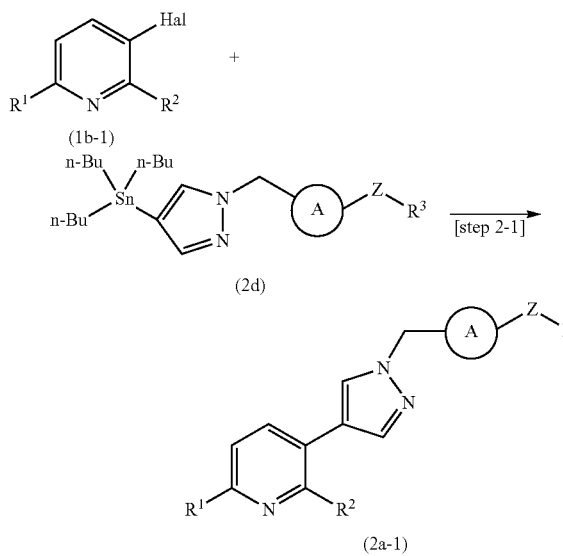

(wherein ring A, $R^1$, $R^2$, $R^3$, Hal and Z are defined as above.)

Compound (1b-1) which is a commercially available product can be used as is, or compound (1b-1) can also be manufactured from commercially available products by the well known methods. Compound (2d) can be manufactured from commercially available products by the well known methods, or can be manufactured according to the methods described in the Manufacturing Examples in the Examples, [Manufacturing Method 2-4] given below or the like.

[Step 2-1]

This step is a step wherein compound (2a-1) is obtained by reacting compound (1b-1) with compound (2d) in the presence of a palladium catalyst. Inorganic salts such as lithium chloride, ammonium salts such as tetrabutylammonium chloride, phosphine ligands, or copper reagents can be added to obtain good results. There are no particular limitations on the solvent used in this reaction as long as it dissolves the starting materials to a certain extent without impeding the reaction. Examples of the solvent include ether solvents such as 1,4-dioxane and tetrahydrofuran; aromatic hydrocarbon solvents such as toluene and xylene, amide solvents such as N,N-dimethylformamide and N-methylpyrrolidinone; dimethyl sulfoxide, mixed solvents of the foregoing and the like. Examples of the palladium catalyst include palladium (II) acetate, tris(dibenzylidenacetone)dipalladium (0), dichlorobis(triphenylphosphine)palladium (II), dichlorobis(tri-o-tolylphosphine)palladium (II), bis(tri-t-butylphosphine)palladium (0), tetrakis(triphenylphosphine)palladium (0) and the like. Examples of the phosphine ligand include triphenylphosphine, tri-o-tolylphosphine, tri-t-butylphosphine and the like. Examples of the copper reagent include copper (I) iodide, copper (I) bromide, copper (I) chloride and the like. Compound (2d) is used in the amount of 1 to 3 equivalents based on compound (1b-1). The palladium catalyst is used in the amount of 0.01 to 0.3 equivalents based on compound (1b-1). The phosphine ligand is used in the amount of 0.01 to 1.2 equivalents based on compound (1b-1). The copper reagent is used in the amount of 0.1 to 3 equivalents based on compound (1b-1). The inorganic salts such as lithium chloride or ammonium salts such as tetrabutylammonium chloride are used in the amount of 1 to 3 equivalents based on compound (1b-1). The reaction temperature is from room temperature to reflux temperature, and the reaction time is from 10 minutes to 48 hours.

Manufacturing Method 2-1-3

Method 3 for Manufacturing Compound (2a)

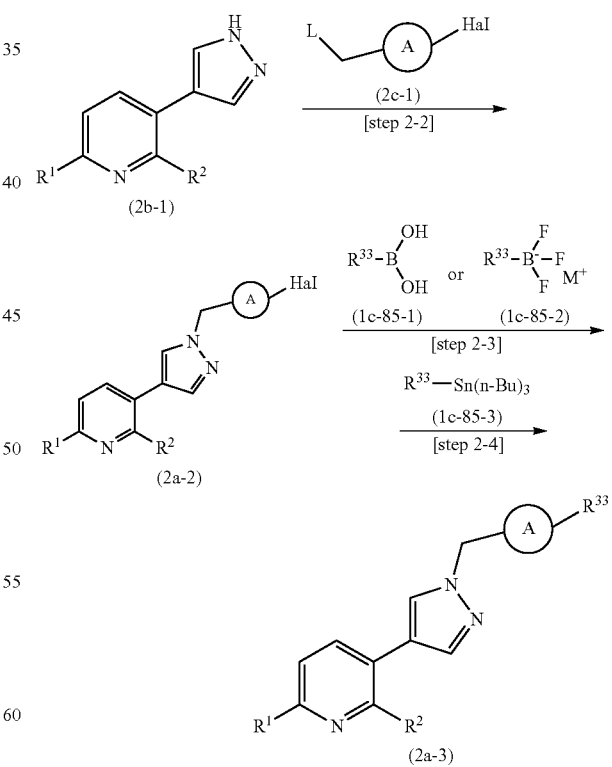

(wherein ring A, Hal, L, $R^1$, $R^2$ and $R^{33}$ are defined as above.)

Compound (2b-1) can be manufactured from commercially available products by the known methods, and can also be manufactured according to the methods described in the Manufacturing Example in Examples or [Manufacturing Method 2-2-1], and the like. Compound (2c-1) which is a commercially available product can be used as is, or may also be manufactured from commercially available products by the known methods. Compounds (1c-85-1), (1c-85-2) and (1c-85-3) which are commercially available products can be used as is, or may also be manufactured from commercially available products by the known methods.

[Step 2-2]

This step is a step wherein compound (2a-2) is obtained by reacting compound (2b-1) and compound (2c-1), in the presence of a base. Compound (2a-2) can be manufactured according to the methods similar to those of [Step 2].

[Step 2-3]

This step is a step wherein compound (2a-3) is obtained by reacting compound (1c-85-1) or compound (1c-85-2) and compound (2a-2), in the presence of a palladium catalyst and a base. Compound (2a-3) can be manufactured according to the methods similar to those of [Step 1-88].

[Step 2-4]

This step is a step wherein compound (2a-3) is obtained by reacting compound (1c-85-3) and compound (2a-2), in the presence of a palladium catalyst. Compound (2a-3) can be manufactured according to the methods similar to those of [Step 1-89].

Manufacturing Method 2-2-1

Method 1 for Manufacturing Compound (2b)

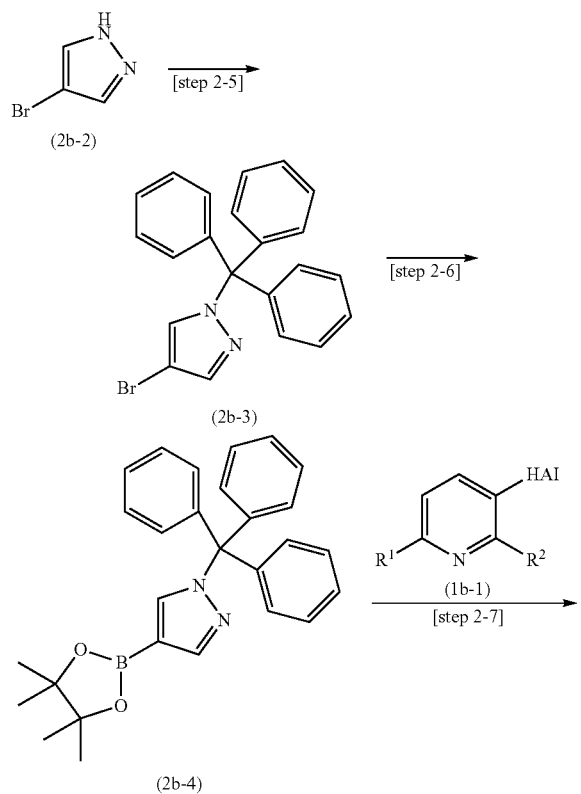

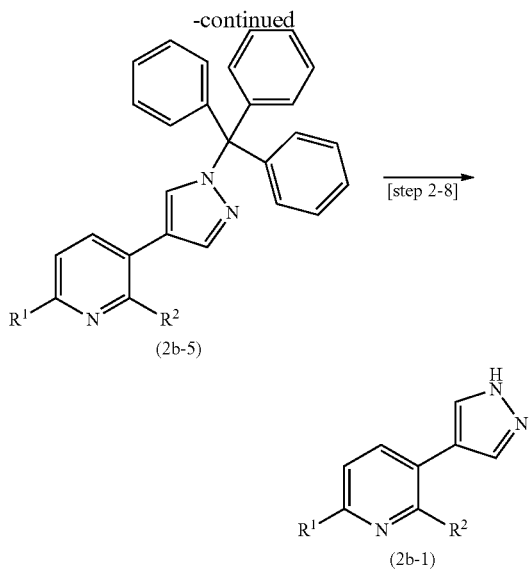

(wherein $R^1$, $R^2$ and Hal are defined as above.)

A commercially available product can be used as is for compound (2b-2). Compound (1b-1) which is a commercially available product can be used as is or compound (1b-1) can also be manufactured from commercially available products by the well known methods.

[Step 2-5]

This step is a step wherein compound (2b-3) is obtained by reacting compound (2b-2) with chlorotriphenylmethane in the presence of a base. There are no particular limitations on the solvent used in this reaction as long as it dissolves the starting materials to a certain extent without impeding the reaction. Examples of the solvent include ether solvents such as tetrahydrofuran and diethyl ether; amide solvents such as N,N-dimethylformamide and N-methylpyrrolidinone; and dimethyl sulfoxide, mixed solvents of the foregoing and the like. Examples of the base include triethylamine, sodium hydride, potassium t-butoxide, potassium carbonate, sodium hydroxide and the like. The base is used in the amount of 1 to 4 equivalents based on compound (2b-2). The chlorotriphenylmethane is used in the amount of 1 to 4 equivalents based on compound (2b-2). The reaction temperature is from room temperature to reflux temperature, and the reaction time is from 1 hour to 24 hours.

[Step 2-6]

This step is a step wherein compound (2b-4) is obtained by reacting compound (2b-3) with a boronic acid derivative in the presence of a palladium catalyst and a base. A phosphine ligand may also be added to obtain good results. There are no particular limitations on the solvent used in this reaction as long as it dissolves the starting materials to a certain extent without impeding the reaction. Examples of the solvent include ether solvents such as 1,4-dioxane and tetrahydrofuran; aromatic hydrocarbon solvents such as benzene and toluene; amide solvents such as N,N-dimethylformamide and N-methylpyrrolidinone; and dimethyl sulfoxide, mixed solvents of the foregoing and the like. Examples of the palladium catalyst include palladium (II) acetate, tris(dibenzylidenacetone)dipalladium (0), dichlorobis(triphenylphosphine)palladium (II), bis(tri-t-butylphosphine)palladium (0), tetrakis(triphenylphosphine)palladium (0), 1,1'-bis(diphenylphosphinoferrocene)dichloropalladium (II) and the like, preferably 1,1'-bis(diphenylphosphinoferrocene)dichloropalladium (II). Examples of the base include potassium acetate, triethylamine, N,N-diisopropylethylamine, potassium phenoxide, potassium carbonate and the like, preferably potassium acetate. Examples of the boronic acid derivative include bis(pinacolate)diboron, 4,4,5,5,-tetramethyl-[1,3,2]-dioxaborolane and the like. Examples of the phosphine ligand include triphenylphosphine, tri-t-butylphosphine, tricyclohexylphosphine, diphenylphosphinoferrocene, 2-dicyclohexylphosphinobiphenyl and the like. The palladium catalyst is used in the amount of 0.01 to 0.3 equivalents based on compound (2b-3). The base is used in the amount of 1 to 10 equivalents based on compound (2b-3). The boronic acid derivative is used in the amount of 1 to 3.0 equivalents based on compound (2b-3). The phosphine ligand is used in the amount of 0.01 to 1.2 equivalents based on compound (2b-3). The reaction temperature is from room temperature to reflux temperature, and the reaction time is from 10 minutes to 24 hours.

Compound (2b-4) can also be obtained from compound (2b-3) according to the method given below as Alternative Method (1).

Alternative Method (1): Compound (2b-4) can be obtained by first anionizing the bromine atom of compound (2b-3) using an organometallic reagent, and then reacting with a boronic acid ester. There are no particular limitations on the solvent used in this reaction as long as it dissolves the starting materials to a certain extent without impeding the reaction. Examples of the solvent include ether solvents such as tetrahydrofuran and diethyl ether; aromatic hydrocarbon solvents such as benzene and toluene; and hexane, mixed solvents of the foregoing and the like. Examples of the organometallic reagent include n-butyl lithium, s-butyl lithium, t-butyl lithium and the like. Examples of the boronic acid ester include 2-methoxy-4,4,5,5-tetramethyl-[1,3,2]-dioxaborolane, trimethyl borate, triisopropyl borate and the like. (1-Triphenylmethyl)-pyrazol-4-yl boronic acid, which is produced in the case of using trimethyl borate or triisopropyl borate as the boronic acid ester, can be converted into a boronic acid pinacol ester in accordance with the literature (Journal of Heterocyclic Chemistry, Vol. 41, No. 6, 931 to 939, so as to obtain compound (2b-4). The organometallic reagent is used in the amount of 1 to 1.5 equivalents based on compound (2b-3). The boronic acid ester is used in the amount of 1 to 1.5 equivalents based on compound (2b-3). The reaction temperature for the anionization reaction is from −90° C. to −60° C., and the reaction time is from 10 minutes to 24 hours. The temperature for the reaction with the boronic acid ester is from −78° C. to 0° C., with a reaction time being from 10 minutes to 12 hours.

Note that (1-triphenylmethyl)-pyrazol-4-yl boronic acid, which is produced in the case of using trimethyl borate or triisopropyl borate as the boronic acid ester in this reaction, can be used in place of compound (2b-4) as the substrate in [Step 2-7].

[Step 2-7]

This step is a step wherein compound (2b-5) is obtained by reacting compound (2b-4) with compound (1b-1) in the presence of a palladium catalyst and a base. A phosphine ligand can be added to obtain good results. A quaternary ammonium salt such as tetrabutylammonium bromide, tetrabutylammonium chloride and the like can also be added in the amount of 0.1 to 2 equivalents based on compound (2b-4). There are no particular limitations on the solvent used in this reaction as long as it dissolves the starting materials to a certain extent without impeding the reaction. Examples of the solvent include ether solvents such as 1,4-dioxane and tetrahydrofuran; aromatic hydrocarbon solvents such as benzene and toluene; amide solvents such as N,N-dimethylformamide and N-methylpyrrolidinone; alcohol solvents such as methanol and ethanol; and dimethyl sulfoxide, water, mixed solvents of the foregoing and the like. Examples of the palladium catalyst include palladium (II) acetate, tris(dibenzylidenacetone)dipalladium (0), dichlorobis(triphenylphosphine)palladium (II), bis(tri-t-butylphosphine)palladium (0), tetrakis(triphenylphosphine)palladium (0), 1,1'-bis(diphenylphosphinoferrocene)dichloropalladium (II) and the like. Examples of the base include sodium carbonate, potassium carbonate, cesium carbonate, cesium fluoride, potassium phosphate, sodium hydroxide, potassium hydroxide and the like. Examples of the phosphine ligand include triphenylphosphine, tri-t-butylphosphine, tricyclohexylphosphine, diphenylphosphinoferrocene, 2-dicyclohexylphosphinobiphenyl and the like. The palladium catalyst is used in the amount of 0.01 to 0.3 equivalents based on compound (2b-4). The base is used in the amount of 1.5 to 10 equivalents based on compound (2b-4). Compound (1b-1) is used in the amount of 1.0 to 3.0 equivalents based on compound (2b-4). The phosphine ligand is used in the amount of 0.01 to 1.2 equivalents based on compound (2b-4). The reaction temperature is from room temperature to reflux temperature, and the reaction time is from 10 minutes to 24 hours.

[Step 2-8]

This step is a step wherein compound (2b-1) is obtained by deprotecting the triphenylmethyl group of compound (2b-5) under acidic conditions. There are no particular limitations on the solvent used in this reaction as long as it dissolves the starting materials to a certain extent without impeding the reaction. Example of the solvent include ether solvents such as 1,4-dioxane and tetrahydrofuran; aromatic hydrocarbon solvents such as benzene and toluene, alcohol solvents such as methanol and ethanol; methylene chloride, water, mixed solvents of the foregoing and the like. Examples of the acid include hydrochloric acid, sulfuric acid, hydrobromic acid, trifluoroacetic acid, formic acid and the like. The acid is used in the amounts of from 2 equivalents to the solvent amount based on compound (2b-5). The reaction temperature is from 0° C. to reflux temperature, and the reaction time is from 10 minutes to 24 hours.

Manufacturing Method 2-2-2

Method 2 for Manufacturing Compound (2b)

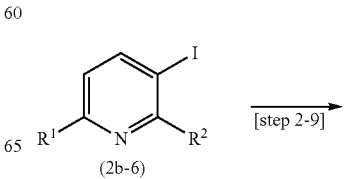

-continued

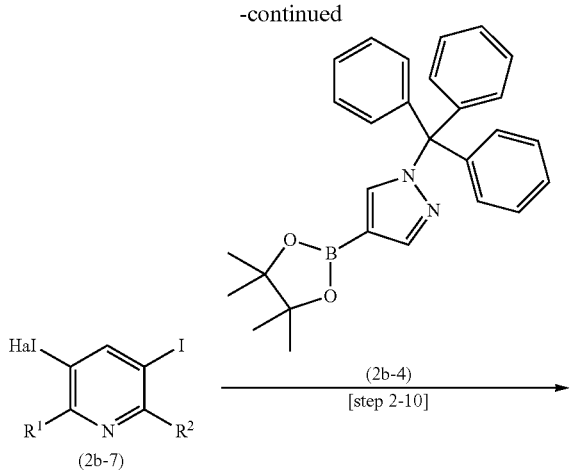

(wherein $R^1$, $R^2$ and Hal are defined as above.)

Compound (2b-6) which is a commercially available product can be used as is, or may be manufactured from commercially available products by the known methods. Compound (2b-4) can be manufactured according to the methods described in [Manufacturing Method 2-2-1].

[Step 2-9]

This step is a step wherein compound (2b-7) is obtained by substituting a halogen atom for a hydrogen atom on the pyridine ring of compound (2b-6). Compound (2b-7) can be manufactured according to the methods similar to those of [Step 1-11].

[Step 2-10]

This step is a step wherein compound (2b-8) is obtained by reacting compound (2b-7) with compound (2b-4), in the presence of a palladium catalyst and a base. Compound (2b-8) can be manufactured according to the methods similar to those of [Step 2-7]. With the proviso that compound (2b-4) is used in the amount of 1 to 1.2 equivalents based on compound (2b-7).

[Step 2-11]

This step is a step wherein compound (2b-9) is obtained by deprotecting the triphenyl methyl group of compound (2b-8)

under acidic conditions. Compound (2b-9) can be manufactured according to the methods similar to those of [Step 2-8].

Manufacturing Method 2-3

Method for Manufacturing Compound (2c)

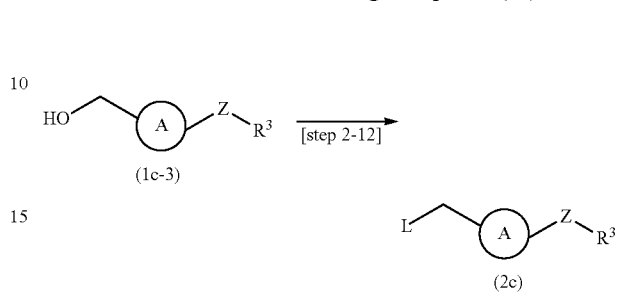

(wherein ring A, L, $R^3$ and Z are defined as above.)

Compound (1c-3) which is a commercially available product can be used as is, or compound (1c-3) can also be manufactured from commercially available products by the well known methods. Compound (1c-3) can further be manufactured according to the methods described in the Manufacturing Examples in the Examples, [Manufacturing Method 1-3-1] given above or the like.

[Step 2-12]

This step is a step wherein compound (2c) is obtained by converting the hydroxyl group of compound (1c-3) into a leaving group. Compound (2c) can be manufactured according to the methods similar to those of [Step 1-32].

Manufacturing Method 2-4

Method for Manufacturing Compound (2d)

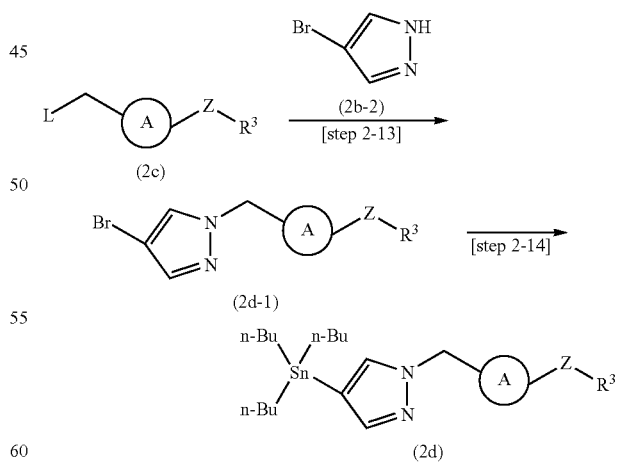

(wherein ring A, L, $R^3$ and Z are defined as above.)

Compound (2c) which is a commercially available product can be used as is, or compound (2c) can also be manufactured from commercially available products by the well known methods. Compound (2c) can further be manufactured according to the methods described in the Manufacturing Examples in the Examples, [Manufacturing Method 2-3] given above or the like. A commercial product may be used as is for compound (2b-2).

[Step 2-13]

This step is a step wherein compound (2d-1) is obtained by reacting compound (2c) with compound (2b-2). Compound (2d-1) can be manufactured according to the methods similar to those of [Step 2].

[Step 2-14]

This step is a step wherein compound (2d) is obtained by reacting compound (2d-1) with hexa(n-butyl)ditin in the presence of a palladium catalyst. A phosphine ligand can be added into this reaction in order to obtain good results. There are no particular limitations on the solvent used in this reaction as long as it dissolves the starting materials to a certain extent without impeding the reaction. Examples of the solvent include ether solvents such as 1,4-dioxane and tetrahydrofuran; aromatic hydrocarbon solvents such as toluene and xylene; amide solvents such as N,N-dimethylformamide and N-methylpyrrolidinone; dimethyl sulfoxide, mixed solvents of the foregoing and the like. Examples of the palladium catalyst include palladium (II) acetate, tris(dibenzylidenacetone)dipalladium (0), dichlorobis(triphenylphosphine)palladium (II), dichlorobis(tri-o-tolylphosphine)palladium (II), tetrakis(triphenylphosphine)palladium (0) and the like. Examples of the phosphine ligand include triphenylphosphine, tri-o-tolylphosphine and the like. The hexa(n-butyl) ditin is used in the amount of 1 to 10 equivalents, preferably 3 to 5 equivalents, based on compound (2d-1). The palladium catalyst is used in the amount of 0.01 to 0.3 equivalents based on compound (2d-1). The phosphine ligand is used in the amount of 0.01 to 1.2 equivalents based on compound (2d-1). The reaction temperature is from room temperature to reflux temperature, and the reaction time is from 10 minutes to 48 hours.

Compound (2d) can also be obtained from compound (2d-1) according to the method given below as Alternative Method (1).

Alternative Method (1): Compound (2d) can be obtained by first anionizing the bromine atom of compound (2d-1) using an organometallic reagent, and then reacting with tri(n-butyl) tin chloride. There are no particular limitations on the solvent used in this reaction as long as it dissolves the starting materials to a certain extent without impeding the reaction. Examples of the solvent include ether solvents such as tetrahydrofuran and diethyl ether; aromatic hydrocarbon solvents such as benzene and toluene; hexane, mixed solvents of the foregoing and the like. Examples of the organometallic reagent include n-butyl lithium, s-butyl lithium, t-butyl lithium and the like. The organometallic reagent is used in the amount of 1 to 1.5 equivalents based on compound (2d-1). The tri(n-butyl)tin chloride is used in the amount of 1 to 1.5 equivalents based on compound (2d-1). The reaction temperature for the anionization reaction is from −90° C. to −60° C., with a reaction time being from 10 minutes to 24 hours.

The temperature for the reaction with the tri(n-butyl)tin chloride is from −78° C. to 0° C., with a reaction time being from 10 minutes to 12 hours.

Manufacturing Method 3

Typical Method for Manufacturing Compound (3a)

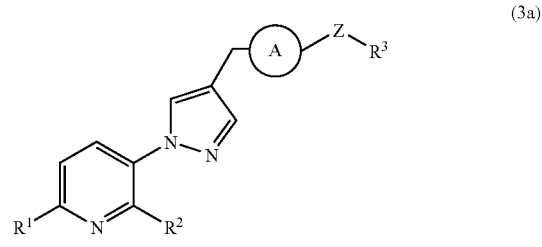

(3a)

(wherein ring A, R$^1$, R$^2$, R$^3$ and Z are defined as above.)

Manufacturing Method 3-1

Method for Manufacturing Compound (3a)

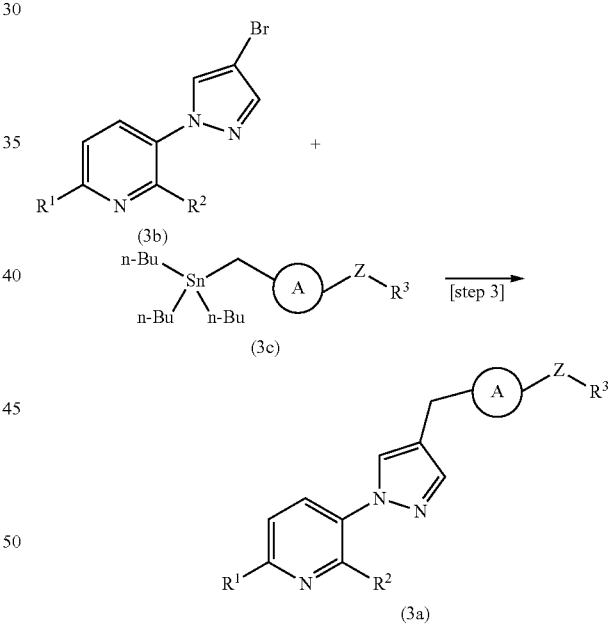

(wherein ring A, R$^1$, R$^2$, R$^3$ and Z are defined as above.)

Compound (3b) can be manufactured from commercially available products by the well known methods, or compound (3b) can also be manufactured according to the methods given in the Manufacturing Examples in the Examples, [Manufacturing Method 3-2] given below or the like.

Compound (3c) can be manufactured from a commercially available product by the well known methods, or compound (3c) can also be manufactured according to the methods given in the Manufacturing Examples in the Examples, [Manufacturing Method 3-3] given below or the like.

[Step 3]

This step is a step wherein compound (3a) is obtained by reacting compound (3b) with compound (3c). Compound (3a) can be manufactured according to the methods similar to those of [Step 1-8].

Manufacturing Method 3-2

Method for Manufacturing Compound (3b)

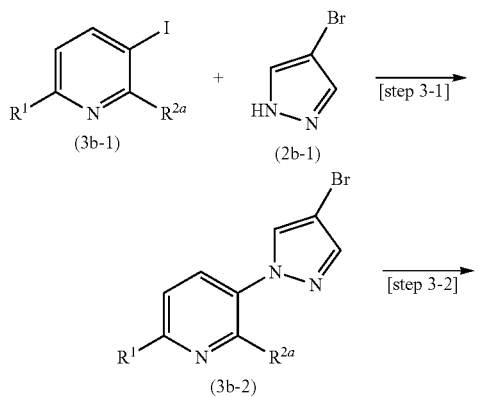

(wherein $R^1$ and $R^2$ are defined as above, and $R^{2a}$ represents a hydrogen atom and $-NHR^{2b}$. $R^{2b}$ represents a protective group such as t-butoxycarbonyl, t-butylcarbonyl and the like.)

Compound (3b-1) which is a commercially available product can be used as is, or compound (3b-1) can also be manufactured from commercially available products by the well known methods. A commercial product can be used as is for compound (2b-1).

[Step 3-1]

This step is a step wherein compound (3b-2) is obtained by reacting compound (3b-1) with compound (2b-1) in the presence of a base and a copper catalyst. A copper ligand can also be added to improve the yield. There are no particular limitations on the solvent used in this reaction as long as it dissolves the starting materials to a certain extent without impeding the reaction. Examples of the solvent include ether solvents such as 1,4-dioxane and tetrahydrofuran; aromatic hydrocarbon solvents such as benzene, toluene and xylene; amide solvents such as N,N-dimethylformamide and N-methylpyrrolidinone; and dimethyl sulfoxide, mixed solvents of the foregoing and the like. Examples of the base used in this reaction include potassium carbonate, cesium carbonate, potassium phosphate, potassium t-butoxide, sodium t-butoxide and the like. Examples of the copper catalyst include copper (I) iodide, copper (I) bromide, copper (I) chloride and the like. Examples of the copper ligand include 1,2-cyclohexanediamine, N,N-dimethyl-cyclohexane-1,2-diamine, 1,10-phenanthroline and the like. Compound (2b-1) is used in the amounts of from 1 to 5 equivalents based on compound (3b-1). The base is used in the amount of 1 to 5 equivalents based on compound (3b-1). The copper catalyst is used in the amount of 0.01 to 0.3 equivalents based on compound (3b-1). The copper ligand is used in the amount of 1 to 3 equivalents based on the copper catalyst. The reaction temperature is from 50° C. to reflux temperature, and the reaction time is from 30 minutes to 48 hours.

[Step 3-2]

This step is a step wherein compound (3b) is obtained by reacting acid with compound (3b-2), so as to deprotect an amine moiety. There are no particular limitations on the solvent used in this reaction as long as it dissolves the starting materials to a certain extent without impeding the reaction. Examples of the solvent include alcohol solvents such as methanol and ethanol; and water, mixed solvents of the foregoing and the like. Examples of the acid include inorganic acids such as hydrochloric acid, sulfuric acid, and hydrobromic acid; organic acids such as trifluoroacetic acid, p-toluenesulfonic acid; and the like. The acid is used in the amounts of from 2 equivalents to the solvent amount based on compound (3b-2). The reaction temperature is from room temperature to reflux temperature, and the reaction time is from 30 minutes to 72 hours.

Manufacturing Method 3-3

Method for Manufacturing Compound (3c)

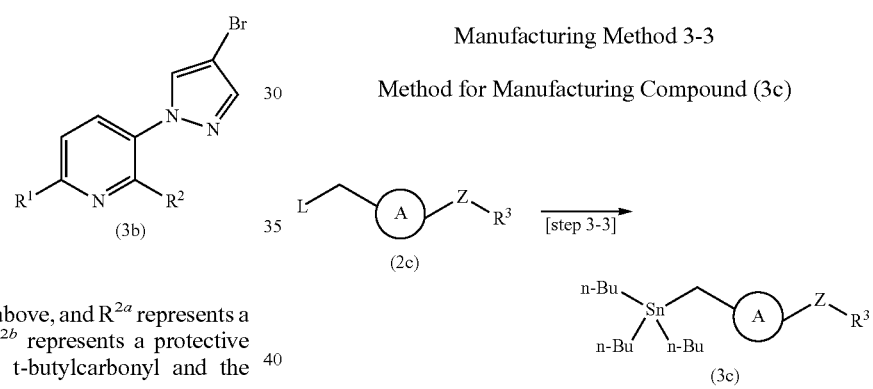

(wherein ring A, L, $R^3$ and Z are defined as above.)

Compound (2c) can be manufactured from commercially available products by the well known methods, or compound (2c) can also be manufactured according to the methods described in the Manufacturing Examples in the Examples, [Manufacturing Method 2-3] given above or the like.

[Step 3-3]

This step is a step wherein compound (3c) is obtained by reacting compound (2c) with tributyltin-anions. There are no particular limitations on the solvent used in this reaction as long as it dissolves the starting materials to a certain extent without impeding the reaction. Examples of the solvent include ether solvents such as tetrahydrofuran and diethyl ester; aromatic hydrocarbon solvents such as benzene, toluene and xylene; mixed solvents of the foregoing and the like. The tributyltin-anions used in the reaction can be synthesized by reacting an organometallic reagent with tributyltin hydride. Examples of the organometallic reagent include lithium diisopropylamide, isopropyl magnesium chloride, methyl magnesium iodide and the like. The tributyltin hydride is used in the amount of 1 to 2 equivalents based on compound (2c). The organometallic reagent is used in the amount of 1 to 1.5 equivalents based on tributyltin hydride.

The reaction temperature is from −78° C. to room temperature, and the reaction time is from 10 minutes to 12 hours.

Manufacturing Method 4

Typical Method for Manufacturing Compound (4a)

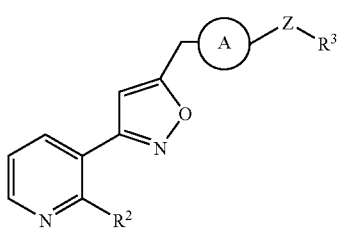

(4a)

(wherein ring A, $R^2$, $R^3$ and Z are defined as above.)

Manufacturing Method 4-1

Method for Manufacturing Compound (4a)

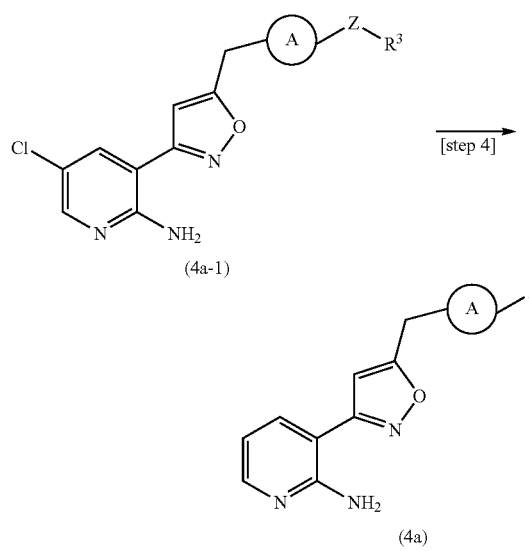

(wherein ring A, $R^3$ and Z are defined as above.)

Compound (4a-1) can be manufactured from commercially available products by the well known method, or compound (4a-1) can be manufactured according to the methods described in the Manufacturing Examples in the Examples, [Manufacturing Method 4-2] given below or the like.

[Step 4]

This step is a step wherein compound (4a) is obtained by substituting a hydrogen atom for a chlorine atom of compound (4a-1). Compound (4a) can be obtained by reacting compound (4a-1) in the presence of a palladium catalyst, a base and a hydrogen source. A phosphine ligand can also be added to obtain good results. There are no particular limitations on the solvent used in this reaction as long as it dissolves the starting materials to a certain extent without impeding the reaction. Examples of the solvent include ether solvents such as 1,4-dioxane and tetrahydrofuran; aromatic hydrocarbon solvents such as toluene and xylene; amide solvents such as N,N-dimethylformamide and N-methylpyrrolidinone; and dimethyl sulfoxide, mixed solvents of the foregoing and the like. Examples of the palladium catalyst include bis(tri-t-butylphosphine)palladium (0), palladium (II) acetate, tetrakis(triphenylphosphine)palladium (0), dichlorobis(triphenylphosphine)palladium (II), tris(dibenzylidenacetone)dipalladium (0) and the like. Examples of the base include triethylamine, N,N-diisopropylethylamine and the like. Examples of the hydrogen source include formic acid, potassium formate, sodium formate, lithium formate, ammonium formate and the like. Examples of the phosphine ligand include triphenylphosphine, tri-o-tolylphosphine, tri-t-butylphosphine and the like. The palladium catalyst is used in the amount of 0.01 to 0.3 equivalents based on compound (4a-1). The base is used in the amount of 2 to 5 equivalents based on compound (4a-1). The hydrogen source is used in the amount of 1 to 5 equivalents based on compound (4a-1). The phosphine ligand is used in the amount of 0.01 to 1.2 equivalents based on compound (4a-1). The reaction temperature is from room temperature to reflux temperature, and the reaction time is from 30 minutes to 24 hours.

Manufacturing Method 4-2

Method for Manufacturing Compound (4a-1)

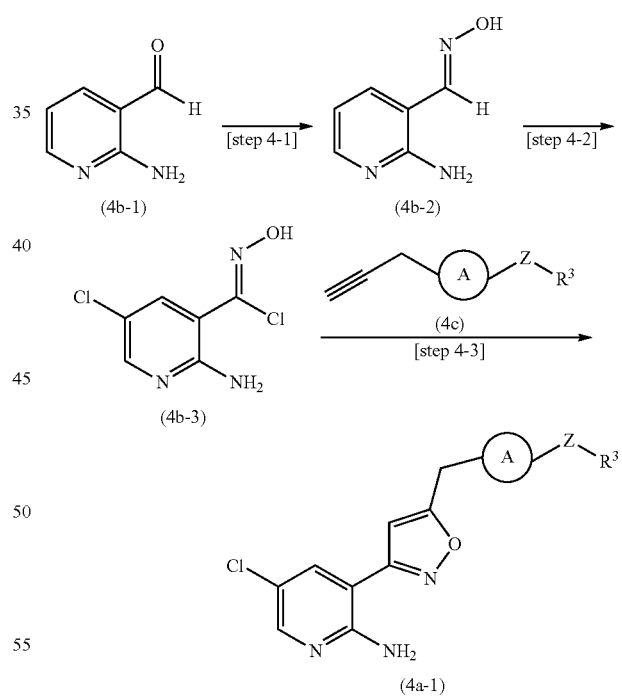

(wherein ring A, $R^3$ and Z are as defined above.)

Compound (4b-1) which is a commercially available product can be used as is. Compound (4c) can be manufactured from commercially available products by the well known methods, or compound (4c) can also be manufactured according to the methods described in the Manufacturing Examples in the Examples, [Manufacturing Method 4-3] given below or the like.

[Step 4-1]

This step is a step wherein compound (4b-2) is obtained by reacting compound (4b-1) with hydroxylamine or hydroxylamine hydrochloride in the presence of a base. There are no particular limitations on the solvent used in this reaction as long as it dissolves the starting materials to a certain extent without impeding the reaction. Examples of the solvent include alcohol solvents such as methanol and ethanol; and methylene chloride, water and the like. The base can also be used as the solvent. Examples of the base include pyridine, sodium hydroxide, potassium hydroxide, sodium acetate, sodium carbonate, sodium hydrogen carbonate and the like. Hydroxylamine or hydroxylamine hydrochloride is used in the amounts of from 1 to 10 equivalents based on compound (4b-1). The base is used in the amount of 1 equivalent to the solvent amount based on compound (4b-1). The reaction temperature is from 0° C. to reflux temperature, and the reaction time is from 10 minutes to 24 hours.

[Step 4-2]

This step is a step wherein compound (4b-3) is obtained by reacting compound (4b-2) with a chlorinating agent. There are no particular limitations on the solvent used in this reaction as long as it dissolves the starting materials to a certain extent without impeding the reaction. Examples of the solvent include ether solvents such as 1,4-dioxane and tetrahydrofuran; alcohol solvents such as methanol and ethanol, amide solvents such as N,N-dimethylformamide and N-methylpyrrolidinone; and dimethyl sulfoxide, methylene chlorine, water, mixed solvents of the foregoing and the like. Examples of the chlorinating agent include N-chlorosuccinimide, sodium hypochlorite, chlorine and the like. The chlorinating agent is used in the amount of 2 to 5 equivalents based on compound (4b-2). The reaction temperature is from 0° C. to room temperature, and the reaction time is from 10 minutes to 24 hours.

[Step 4-3]

This step is a step wherein compound (4a-1) is obtained by reacting compound (4b-3) with compound (4c). Compound (4a-1) can be manufactured according to the methods similar to those of [Step 1].

Manufacturing Method 4-3

Method for Manufacturing Compound (4c)

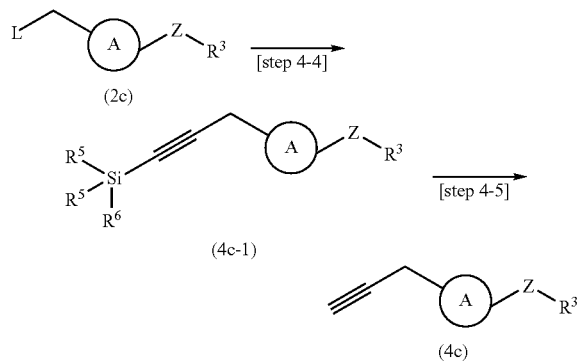

(wherein ring A, $R^3$, $R^5$, $R^6$, L and Z are defined as above.)

Compound (2c) can be manufactured from commercially available products by the well known methods, or compound (2c) can also be manufactured according to the methods described in the Manufacturing Examples in the Examples, [Manufacturing Method 2-3] given below or the like.

[Step 4-4]

This step is a step wherein compound (4c-1) is obtained by reacting compound (2c) with an ethynylsilane derivative. Compound (4c-1) can be obtained by reacting compound (2c) with an ethynyl Grignard reagent obtained by reacting an ethynyl silane derivative with a Grignard reagent. A copper reagent such as copper (I) bromide, copper (I) iodide and the like can also be added to obtain good results. Examples of the ethynylsilane derivative include trimethylsilyl acetylene, triethylsilyl acetylene, triisopropylsilyl acetylene, t-butyldimethylsilyl acetylene and the like. An alkyl magnesium halide such as ethyl magnesium bromide and isopropyl magnesium chloride can be used as the Grignard reagent. The ethynylsilane derivative can be used in the amount of 1 to 3 equivalents based on compound (2c). The Grignard reagent can be used in the amount of 1 to 3 equivalents based on compound (2c). The copper reagent can be used in the amount of 0.1 to 3 equivalents based on compound (2c). The reaction temperature is from room temperature to reflux temperature, and the reaction time is from 1 hour to 72 hours.

[Step 4-5]

This step is a step wherein compound (4c) is obtained by deprotecting the trimethylsilyl group of compound (4c-1). Compound (4c) can be manufactured according to the methods similar to those of [Step 1-2].

Manufacturing Method 5

Typical Method for Manufacturing Compound (5a)

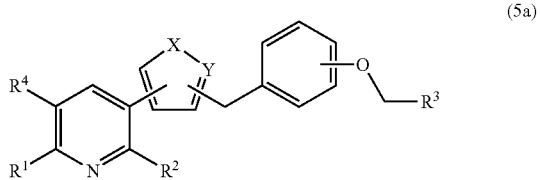

(wherein $R^1$, $R^2$, $R^3$, $R^4$, X and Y are defined as above.)

Manufacturing Method 5-1

Method for Manufacturing Compound (5a)

Examples of the solvent include ether solvents such as tetrahydrofuran and diethyl ether, aromatic hydrocarbon solvents such as benzene and toluene, amide solvents such as Compound (5a) can also be obtained from compound (5a-1) according to the method described below as Alternative Method (1).

Alternative Method (1): Compound (5a) can be obtained by reacting compound (5a-1) with compound (1c-10-2) in the presence of a base. There are no particular limitations on the solvent used in this reaction as long as it dissolves the starting materials to a certain extent without impeding the reaction. N,N-dimethylformamide and N-methylpyrrolidinone; and dimethyl sulfoxide, mixed solvents of the foregoing and the like. Examples of the base include sodium hydride, potassium carbonate, sodium carbonate, cesium carbonate, potassium hydroxide, sodium hydroxide and the like. A catalytic amount of sodium iodide or potassium iodide or tetrabutylammonium iodide can also be added to obtain good results. The base is added in the amount of 1 to 1.5 equivalents based on compound (5a-1). The reaction temperature is from room temperature to reflux temperature, and the reaction time is from 10 minutes to 48 hours.

[Step 5-2]

This step is a step wherein compound (5a) is obtained by reacting compound (5a-1) with compound (1c-10-1). Com-

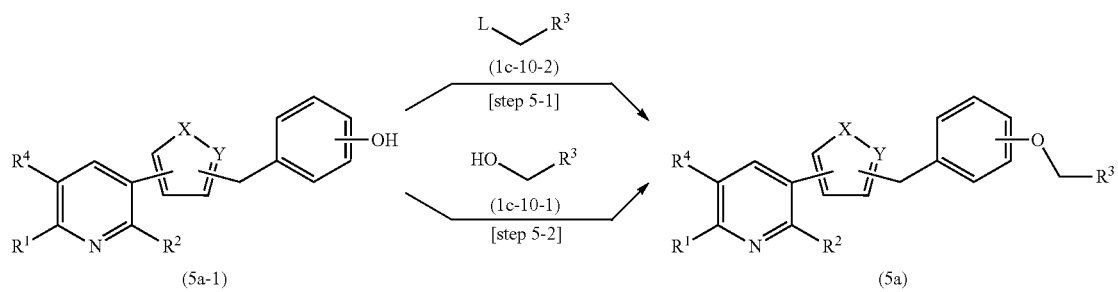

(wherein $R^1$, $R^2$, $R^3$, $R^4$, X and Y are defined as above.)

Compound (5a-1) can be manufactured according to the method described in the Manufacturing Examples in the Examples, [Manufacturing Method 5-2] given below or the like. Compound (1c-10-1) and compound (1c-10-2) which are commercially available products can be used as is, or they can also be manufactured from commercially available products by the well known methods.

[Step 5-1]

This step is a step wherein compound (5a) is obtained by adding 1 equivalent of base to compound (5a-1) to obtain phenoxide ions, followed by reacting with compound (1c-10-2).

Phenoxide ion production: Phenoxide ions can be obtained by adding 1 equivalent of a base to compound (5a-1) in a solvent such as tetrahydrofuran or methanol. Examples of the base include potassium hydroxide, sodium hydroxide, potassium carbonate, sodium carbonate, potassium t-butoxide and the like, preferably sodium hydroxide. The solvent is preferably concentrated for use in the following reaction. The reaction temperature is room temperature, and the reaction time is from 5 minutes to 1 hour.

Reaction of phenoxide ions with compound (1c-10-2): The phenoxide ions and compound (1c-10-2) are reacted in a solvent to obtain compound (5a). There are no particular limitations on the solvent used in this reaction as long as it dissolves the starting materials to a certain extent without impeding the reaction. Example of the solvent include amide solvents such as N,N-dimethylformamide, N-methylpyrrolidinone and hexamethylphosphoramide; and dimethyl sulfoxide, mixed solvents of the foregoing and the like. Compound (1c-10-2) is used in the amount of 1 to 3 equivalents based on compound (5a-1). The reaction temperature is from room pound (5a) can be manufactured according to the methods similar to those of [Step 1-37].

Manufacturing Method 5-2

Method for Manufacturing Compound (5a-1)

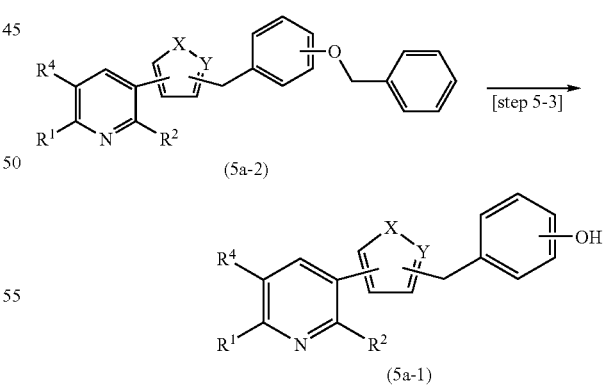

(wherein $R^1$, $R^2$, $R^4$, X and Y are defined as above.)

Compound (5a-2) can be manufactured according to the methods described in the Manufacturing Examples in the Examples, [Manufacturing Method 1], [Manufacturing Method 2], [Manufacturing Method 3] and [Manufacturing Method 4] which are given above or the like.

[Step 5-3]

This step is a step wherein compound (5a-1) is obtained by reacting acid with compound (5b-2). An additive such as thioanisole may be added in the reaction system to obtain better results. There are no particular limitations on the solvent used in this reaction as long as it dissolves the starting materials to a certain extent without impeding the reaction. Examples of the solvent include ether solvents such as diethyl ether and tetrahydrofuran; and methylene chloride, trifluoroacetic acid and the like. Examples of the acid include organic acids such as trifluoroacetic acid and methanesulfonic acid; inorganic acids such as sulfuric acid; Lewis acids such as boron trifluoride diethyl etherate; and the like. Examples of the additives include thioanisole, ethanethiol, dl-methionine and the like. The acid is used in the amount of 1 equivalent to the solvent amount based on compound (5a-2). The additive is used in the amount of 1 to 5 equivalents based on compound (5a-2). The reaction temperature is from 0° C. to reflux temperature, and the reaction time is from 10 minutes to 72 hours.

Compound (5a-1) can also be obtained from compound (5a-2) according to the method described below as Alternative Method (1).

Alternative Method (1): Compound (5a-1) can be obtained by reacting compound (5a-2) with boron tribromide or boron trichloride. There are no particular limitations on the solvent used in this reaction as long as it dissolves the starting materials to a certain extent without impeding the reaction, but methylene chloride is preferably used. The boron tribromide or boron trichloride is used in the amount of 1 to 5 equivalents based on compound (5a-2). The reaction temperature is from −78° C. to room temperature, and the reaction time is from 30 minutes to 24 hours.

Manufacturing Method 6-1

Method 1 for Manufacturing Halogen-Modified Product of Compound (1a)

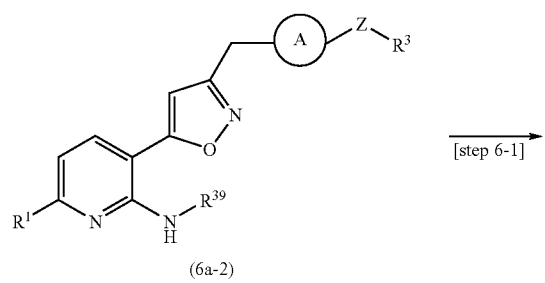

(6a-2)

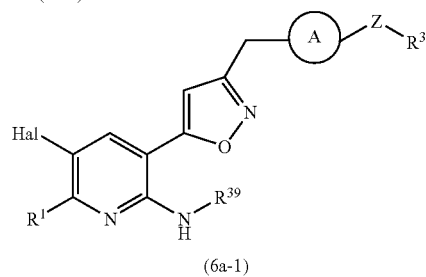

(6a-1)

(wherein ring A, Z, Hal, $R^1$ and $R^3$ are defined as above; $R^{39}$ represents a hydrogen atom or a $C_{1-6}$ alkyl group.)

Compound (6a-2) can be manufactured according to the methods described in [Manufacturing Method 1].

[Step 6-1]

This step is a step wherein compound (6a-1) is obtained by substituting a halogen atom for a hydrogen atom on the pyridine ring of compound (6a-2). Compound (6a-1) can be manufactured according to the methods similar to those of [Step 1-1].

Manufacturing Method 6-2

Method 2 for Manufacturing Halogen-Modified Product of Compound (1a)

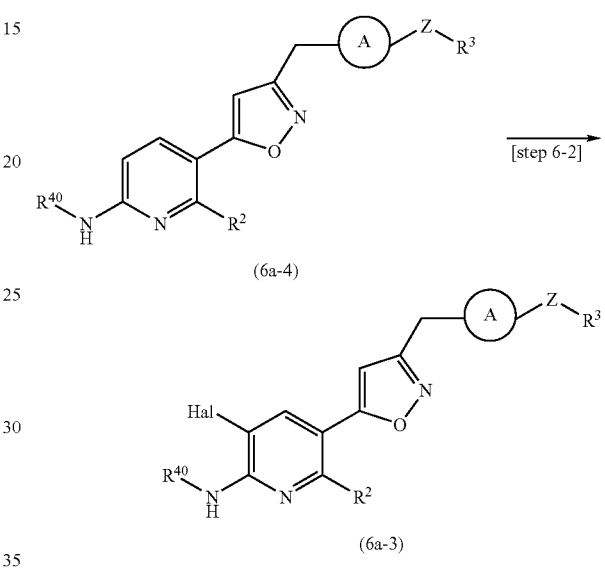

(wherein ring A, Z, Hal, $R^2$ and $R^3$ are defined as above; $R^{40}$ represents a hydrogen atom or a $C_{1-6}$ alkyl group.)

Compound (6a-4) can be manufactured according to the methods described in [Manufacturing Method 1].

[Step 6-2]

This step is a step wherein compound (6a-3) is obtained by substituting a halogen atom for a hydrogen atom on the pyridine ring of compound (6a-4). Compound (6a-3) can be manufactured according to the methods similar to those of [Step 1-11].

Manufacturing Method 7

Method 3 for Manufacturing Halogen-Modified Product of Compound (1a)

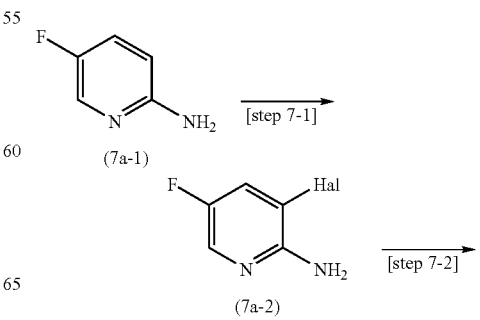

-continued

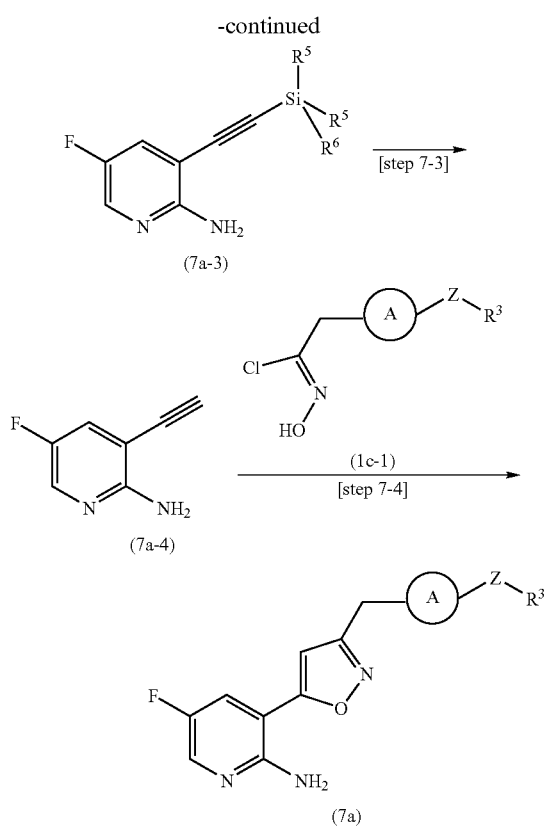

(wherein ring A, Hal, $R^3$, $R^5$, $R^6$ and Z is defined as above.)

Compound (7a-1) which is a commercially available can be used as is. Compound (1c-1) can be manufactured from commercially available products by the known methods, and can be manufactured according to the methods described in Manufacturing Example of Example or [Manufacturing Method 1-3-1], and the like.

[Step 7-1]

This step is a step wherein compound (7a-2) is obtained by substituting a halogen atom for a hydrogen atom on the pyridine ring of compound (7a-1). Compound (7a-2) can be manufactured according to the methods similar to those of [Step 1-11].

[Step 7-2]

This step is a step wherein compound (7a-3) is obtained by reacting compound (7a-2) and an ethinylsilane derivative. Compound (7a-3) can be manufactured according to the methods similar to those of [Step 1-1].

[Step 7-3]

This step is a step wherein compound (7a-4) is obtained by reacting compound (7a-3) with a base. Compound (7a-4) can be manufactured according to the methods similar to those of [Step 1-2].

[Step 7-4]

This step is a step wherein compound (7a) is obtained by reacting compound (7a-4) and compound (1c-1), in the presence of a base. Compound (7a) can be manufactured according to the methods similar to those of [Step 1].

Manufacturing Method 8

Method 1 for Manufacturing Amino Group-Modified Product of Compound (1a)

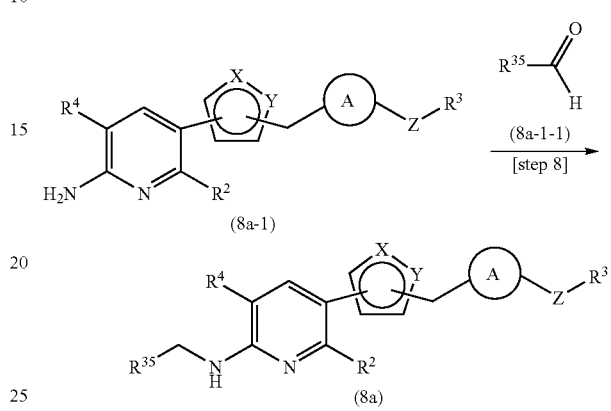

(wherein ring A, $R^2$, $R^3$, $R^4$, X, Y and Z are defined as above; $R^{35}$ represents a hydrogen atom, a $C_{1-5}$ alkyl group, a hydroxy $C_{1-5}$ alkyl group, a $C_{1-6}$ alkoxy carbonyl group or a $C_{1-6}$ alkoxy $C_{1-5}$ alkyl group.)

Compound (8a-1-1) which is a commercially available product can be used as is, or may also be manufactured from commercially available products by the known methods. Compound (8a-1) can be manufactured according to the methods described in [Manufacturing Method 1], or the like.

[Step 8]

This step is a step wherein compound (8a) is obtained by reacting compound (8a-1) and compound (8a-1-1) in the presence of a reducing agent. This step can be carried out by adding an acid such as acetic acid or hydrochloric acid in catalytic amount to solvent amount. There are no particular limitations on the solvent used in this reaction as long as it dissolves the starting materials to a certain extent without impeding the reaction. Examples of the solvent include ether solvents such as tetrahydrofuran and diethyl ether; aromatic hydrocarbon solvents such as benzene and toluene; amide solvents such as N,N-dimethylformamide and N-methylpyrrolidinone; alcohol solvents such as methanol and ethanol; halogenated hydrocarbon solvents such as methylene chloride and chloroform, 1,2-dichloroethane; water, acetic acid, mixed solvents of the foregoing, or the like, preferably a mixed solvent of N,N-dimethylformamide and acetic acid. Examples of the reducing agent used in this reaction include α-picoline borane, pyridine-borane, sodium cyanoborohydride, sodium triacetoxyborohydride and the like, preferably α-picoline borane. Compound (8a-1-1) can be used in the amount of 1 to 5 equivalents based on compound (8a-1), preferably 1 to 1.5 equivalents. The reducing agent can be used in the amount of 0.5 to 5 equivalents based on compound (8a-1), preferably 1 to 1.5 equivalents. The reaction temperature is from 0° C. to reflux temperature, and the reaction time is from 10 minutes to 48 hours.

Manufacturing Method 9

Method 2 for Manufacturing Amino Group-Modified Product of Compound (1a)

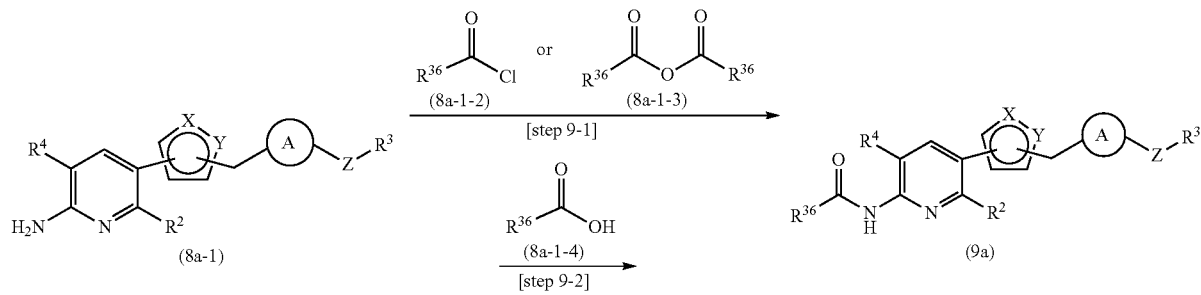

(wherein ring A, $R^2$, $R^3$, $R^4$, X, Y and Z are defined as above; $R^{36}$ represents a $C_{1-6}$ alkyl group or a $C_{1-6}$ alkoxyalkyl group.)

Compound (8a-1-2), compound (8a-1-3) and compound (8a-1-4) which are commercially available products can be used as is, or they may also be manufactured from commercially available products by the known methods. Compound (8a-1) can be manufactured according to the methods described in [Manufacturing Method 1], or the like.

[Step 9-1]

This step is a step wherein compound (9a) is obtained by reacting compound (8a-1-2) or compound (8a-1-3) with compound (8a-1), in the presence of a base. There are no particular limitations on the solvent used in this reaction as long as it dissolves the starting materials to a certain extent without impeding the reaction. Examples of the solvent include ether solvents such as tetrahydrofuran and diethyl ether; aromatic hydrocarbon solvents such as benzene and toluene; amide solvents such as N,N-dimethylformamide and N-methylpyrrolidinone; halogenated hydrocarbon solvents such as methylene chloride and chloroform, mixed solvents of the foregoing, or the like. Examples of the base include triethylamine, pyridine, potassium carbonate, or the like. A catalytic amount of 4-dimethylaminopyridine can also be added in order to accelerate the reaction. Compound (8a-1-2) or compound (8a-1-3) can be used in the amount of 1 to 5 equivalents based on compound (8a-1), preferably 1 to 1.5 equivalents. The base can be used in the amount of 0.5 equivalents to solvent amount based on compound (8a-1), preferably 1 to 1.5 equivalents. The reaction temperature is from 0° C. to reflux temperature, and the reaction time is from 10 minutes to 48 hours.

[Step 9-2]

This step is a step wherein compound (9a) is obtained by reacting compound (8a-1) and compound (8a-1-4), in the presence of a condensing reagent. There are no particular limitations on the solvent used in this reaction as long as it dissolves the starting materials to a certain extent without impeding the reaction. Examples of the solvent include halogenated hydrocarbon solvents such as methylene chloride and chloroform; ether solvents such as tetrahydrofuran and 1,4-dioxane; amide solvents such as N,N-dimethylformamide and N-methylpyrrolidinone; sulfoxide solvents such as dimethyl sulfoxide; ester solvents such as ethyl acetate, mixed solvents of the foregoing, or the like. Examples of the condensing reagent include Bop (1H-1,2,3-benzotriazole-1-yloxy(tri(dimethylamino))phosphonium hexafluorophosphate), WSC (1-ethyl-3-(3-dimethylaminopropyl)carbodiimide hydrochloride), DCC (N,N-dicyclohexylcarbodiimide), or the like. A catalytic amount of 4-dimethylaminopyridine can also be added to accelerate the reaction. In addition, this step can also be carried out by adding a base such as triethylamine in the amount of 1 to 5 equivalents. Compound (8a-1-4) can be used in the amount of 1 to 3 equivalents based on compound (8a-1), preferably 1 to 1.5 equivalents. The condensing reagent can be used in the amount of 1 to 3 equivalents based on compound (8a-1), preferably 1 to 1.5 equivalents. The reaction temperature is from 0° C. to reflux temperature, and the reaction time is from 10 minutes to 48 hours.

Manufacturing Method 10

Method 2 for Manufacturing Amino Group-Modified Product of Compound (1a)

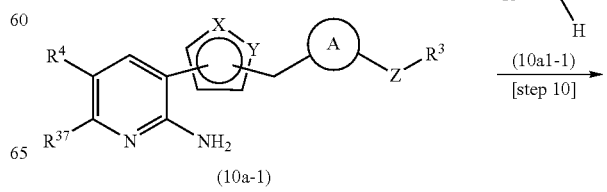

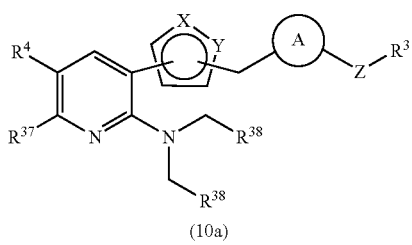

(wherein ring A, $R^3$, $R^4$, X, Y and Z are defined as above; $R^{37}$ represents a hydrogen atom, a halogen atom, $R^{12}$—(CO)—NH— ($R^{12}$ is a $C_{1-6}$ alkyl group or a $C_{1-6}$ alkoxy $C_{1-6}$ alkyl group), a $C_{1-6}$ alkyl group, a hydroxy $C_{1-6}$ alkyl group, a cyano $C_{1-6}$ alkyl group, a $C_{1-6}$ alkoxy group or a $C_{1-6}$ alkoxy $C_{1-6}$ alkyl group; $R^{38}$ represents a hydrogen atom and a $C_{1-5}$ alkyl group.)

Compound (10a-1-1) which is be a commercially available product can be used as is, or may also be manufactured from the commercially available products by the known methods. Compound (10a-1) can be manufactured according to the methods described in [Manufacturing Method 1], or the like.

[Step 10]

This step is a step wherein compound (10a) is obtained by reacting compound (10a-1) and compound (10a-1-1) in the presence of a reducing agent. Compound (10a) can be manufactured according to the methods similar to those of [Step 8].

EXAMPLES

The compounds according to the present invention can be manufactured, for example, according to the methods described in the following manufacturing examples and examples. These are only examples, however, and the compounds according to the present invention are in no way limited to the following specific examples.

Example 1

3-(3-(4-Benzyloxy-benzyl)-isoxazol-5-yl)-pyridin-2-ylamine

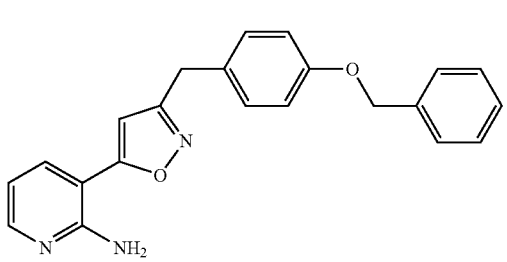

To a mixture of 4-benzyloxy-phenyl-acetohydroximoyl chloride (1.2 g, 4.4 mmol) described in Manufacturing Example 1-1-3 and tetrahydrofuran (34 mL) were added 3-Ethynyl-pyridin-2-ylamine (260 mg, 2.2 mmol) described in Manufacturing Example 1-2-3 and triethylamine (3.0 mL, 22 mmol) at 0° C., which was stirred for 1 hour at room temperature. To the reaction mixture was added water at room temperature, which was then extracted with ethyl acetate-tetrahydrofuran (2:1). The organic layer was washed with saturated aqueous sodium chloride, and the solvent was evaporated under a reduced pressure. The residue was purified by NH silica gel column chromatography (ethyl acetate:heptane=1:3) to obtain the title compound (240 mg, 15%).

$^1$H-NMR Spectrum (CDCl$_3$) δ (ppm): 4.00 (2H, s), 5.05 (2H, s), 5.41 (2H, s), 6.24 (1H, s), 6.71 (1H, dd, J=4.9, 7.6 Hz), 6.93-6.97 (2H, m), 7.18-7.22 (2H, m), 7.31-7.44 (5H, m), 7.70 (1H, dd, J=1.7, 7.6 Hz), 8.13 (1H, dd, J=1.8, 4.9 Hz).

The starting material, 4-benzyloxy-phenyl-acetohydroximoyl chloride, was synthesized as follows.

Manufacturing Example 1-1-1

1-Benzyloxy-4-((E)-2-nitro-vinyl)-benzene

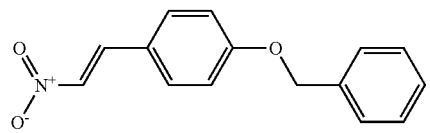

To a mixture of 4-benzyloxybenzaldehyde (1.0 g, 4.7 mmol) and sodium methoxide (28% methanol solution, 150 μL, 0.74 mmol) and methanol (10 mL) were added nitromethane (330 μL, 6.1 mmol) and sodium methoxide (28% methanol solution, 1.0 mL, 4.9 mmol) at 0° C., which was stirred for 10 minutes at room temperature. The reaction mixture was cooled to 0° C., and 5 N aqueous hydrochloric acid solution (20 mL) was added thereto at the same temperature. The reaction mixture was then stirred for 15 minutes at room temperature. The precipitated solids were filtered to obtain the title compound (1.2 g, 100%).

$^1$H-NMR Spectrum (DMSO-d$_6$) δ (ppm): 5.20 (2H, s), 7.10-7.14 (2H, m), 7.32-7.48 (5H, m), 7.82-7.85 (2H, m), 8.12 (2H, dd, J=13.5, 18.2 Hz).

Manufacturing Example 1-1-2

1-Benzyloxy-4-(2-nitro-ethyl)-benzene

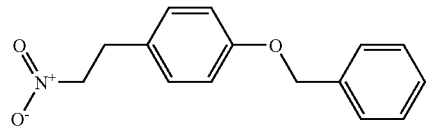

To a mixture of 1-benzyloxy-4-((E)-2-nitro-vinyl)-benzene (1.0 g, 3.9 mmol) described in Manufacturing Example 1-1-1, acetic acid (1 mL) and dimethyl sulfoxide (17 mL) was added sodium borohydride (250 mg, 6.3 mmol) at room temperature while cooling appropriately, and the reaction mixture was stirred for 40 minutes at room temperature. Water was added to the reaction mixture. The reaction mixture was partitioned into ethyl acetate and water. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=1:3) to obtain the title compound (710 mg, 70%).

$^1$H-NMR Spectrum (CDCl$_3$) δ (ppm): 3.26 (2H, t, J=7.2 Hz), 4.56 (2H, t, J=7.2 Hz), 5.04 (2H, s), 6.92 (2H, d, J=8.4 Hz), 7.11 (2H, d, J=8.8 Hz), 7.30-7.42 (5H, m).

Manufacturing Example 1-1-3

4-Benzyloxy-phenyl-acetohydroximoyl chloride

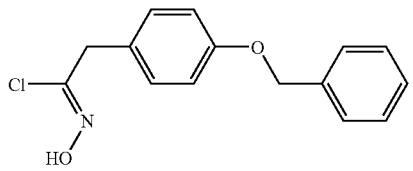

To a mixture of 1-benzyloxy-4-(2-nitro-ethyl)-benzene (340 mg, 1.3 mmol) described in Manufacturing Example 1-1-2 and methanol (5 mL) was added lithium methoxide (100 mg, 2.6 mmol) at room temperature, which was stirred for 15 minutes at room temperature. The reaction mixture was concentrated under a reduced pressure. Methylene chloride (4 mL) and tetrahydrofuran (2 mL) were added to the residue. Titanium (IV) chloride was added at −78° C. to the reaction mixture, which was then stirred for 50 minutes at 0° C. The reaction mixture was cooled to −78° C., and after adding water (5 mL), the reaction mixture was gradually warmed to room temperature. The reaction mixture was partitioned into ethyl acetate and water. The organic layer was washed with saturated aqueous sodium chloride, and the solvent was evaporated under a reduced pressure. The residue was purified by neutral silica gel column chromatography (ethyl acetate:heptane=1:3) to obtain the title compound (310 mg, 84%).

$^1$H-NMR Spectrum (CDCl$_3$) δ (ppm): 3.83 (2H, s), 5.07 (2H, s), 6.94-6.98 (2H, m), 7.17-7.21 (2H, m), 7.32-7.44 (5H, m).

The starting material, 3-ethynyl-pyridin-2-ylamine, was synthesized as follows.

Manufacturing Example 1-2-1

3-Iodopyridin-2-ylamine

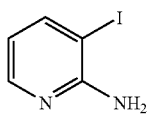

A mixture of N-(3-Iodopyridin-2-yl)-2,2-dimethyl-propionamide (66.2 g, 218 mmol) described in Manufacturing Example 39-1-2, 5 N aqueous sodium hydroxide solution (200 mL) and methanol (200 mL) was stirred under reflux for 1 hour and 20 minutes. The reaction solution was allowed to room temperature and partitioned into water and ethyl acetate. The aqueous layer was extracted with ethyl acetate three times. The organic layers were combined, washed with saturated aqueous sodium chloride, and dried over anhydrous sodium sulfate. The sodium sulfate was removed by filtration, and the solvent was concentrated under a reduced pressure to obtain the title compound (41.2 g, 85.9%).

$^1$H-NMR Spectrum (DMSO-d$_6$) δ (ppm): 6.00 (2H, brs), 6.32 (1H, dd, J=4.8 Hz, 7.2 Hz), 7.87 (1H, d, J=7.2 Hz), 7.92 (1H, d, J=4.8 Hz).

Manufacturing Example 1-2-2

3-Trimethylsilanylethynyl-pyridin-2-ylamine

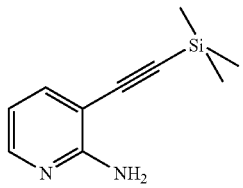

To a mixture of 3-iodopyridin-2-ylamine (40.2 g, 183 mmol) described in Manufacturing Example 1-2-1, trimethylsilylacetylene (51.7 mL, 366 mmol), copper (I) iodide (3.49 g, 18.3 mmol), N,N-diisopropylethylamine (63.7 mL, 366 mmol) and N-methylpyrrolidinone (200 mL) was added tetrakis(triphenylphosphine)palladium (0) (10.6 g, 9.15 mmol) under nitrogen atmosphere, which was stirred for 3 hours and 10 minutes at room temperature. Water was added to the reaction solution, which was then extracted with ethyl acetate 4 times. The solvent was concentrated under a reduced pressure. The residue was purified by NH silica gel chromatography (heptane:ethyl acetate=4:1). The resulting solution was concentrated under a reduced pressure, and the residue was purified by silica gel chromatography (heptane:ethyl acetate=2:1 then 1:1) to obtain the title compound (28.1 g, 80.7%).

$^1$H-NMR Spectrum (DMSO-d$_6$) δ (ppm): 0.25 (9H, s), 6.09 (2H, brs), 6.51-6.57 (1H, m), 7.50-7.55 (1H, m), 7.95-7.99 (1H, m).

Manufacturing Example 1-2-3

3-Ethynyl-pyridin-2-ylamine

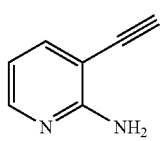

To a solution of 3-trimethylsilanylethynyl-pyridin-2-ylamine (28.1 g, 148 mmoL) described in Manufacturing Example 1-2-2 in tetrahydrofuran (300 mL) was added tetrabutylammonium fluoride (1 M tetrahydrofuran solution, 20 mL, 20 mmol), which was stirred for 15 minutes at room temperature. Water was added to the reaction solution, which was then extracted with ethyl acetate 4 times. The organic layer was dried over anhydrous sodium sulfate, and the solvent was evaporated under a reduced pressure. The residue was purified by silica gel chromatography (heptane:ethyl acetate=1:1 then 1:2) to obtain the title compound (16.4 g, 93.7%).

$^1$H-NMR Spectrum (DMSO-d$_6$) δ (ppm): 4.43 (1H, s), 6.14 (2H, brs), 6.53 (1H, dd, J=4.8 Hz, 7.2 Hz), 7.53 (1H, d, J=7.2 Hz), 7.96 (1H, d, J=4.8 Hz).

Manufacturing Example 1-3-1

3-Trimethylsilanylethynyl-pyridin-2-ylamine (Alternative Method)

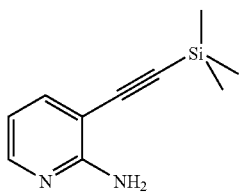

To a solution of 2-amino-3-bromopyridine (5.72 g, 33.1 mmol) in N-methylpyrrolidinone (120 mL) were added trimethylsilyl acetylene (9.36 mL, 66.2 mmol), tetrakis(triphenylphosphine)palladium (0) (1.91 g, 1.66 mmol), copper (I) iodide (630 mg, 3.31 mmol) and N,N-diisopropylethylamine (11.5 mL, 66.2 mmol) at room temperature, which was stirred under nitrogen atmosphere for 6 hours at 70° C. Water was added to the reaction solution, which was then extracted with ethyl acetate. The organic layer was washed with water and saturated aqueous sodium chloride, and dried over anhydrous magnesium sulfate, and the solvent was evaporated under a reduced pressure. The residue was purified by silica gel column chromatography (heptane:ethyl acetate=2:1) to obtain the title compound (5.94 g, 94%).

$^1$H-NMR Spectrum (DMSO-d$_6$) δ (ppm): 0.23 (9H, s), 6.07 (2H, brs), 6.51 (1H, dd, J=4.9, 7.5 Hz), 7.49 (1H, dd, J=1.8, 7.5 Hz), 7.94 (1H, dd, J=1.8, 4.9 Hz).

Example 2

3-(3-(4-(Pyridin-2-yloxymethyl)-benzyl)-isoxazol-5-yl)-pyridin-2-ylamine

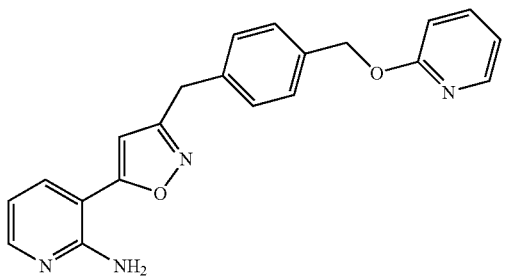

To a solution of (4-(pyridin-2-yloxymethyl)-phenyl)-acetohydroximoyl chloride (510 mg, 1.84 mmol) described in Manufacturing Example 2-1-5 and 3-ethynyl-pyridin-2-ylamine (150 mg, 1.27 mmol) described in Manufacturing Example 1-2-3 in tetrahydrofuran (5 mL) was added triethylamine (708 μL, 5.08 mmol) at room temperature, which was stirred for 95 minutes at room temperature. Water was added at room temperature to the reaction solution, which was then extracted with ethyl acetate. The organic layer was washed with saturated aqueous sodium chloride, and dried over anhydrous magnesium sulfate, and the solvent was evaporated under a reduced pressure. The residue was purified by NH silica gel column chromatography (heptane:ethyl acetate=2:1) to obtain the title compound (120 mg, 26%).

$^1$H-NMR Spectrum (CDCl$_3$) δ (ppm): 4.08 (2H, s), 5.37 (2H, s), 6.33 (1H, s), 6.45 (2H, brs), 6.79-6.82 (2H, m), 6.88-6.91 (1H, m), 7.30 (2H, d, J=8.1 Hz), 7.45 (2H, d, J=8.1 Hz), 7.57-7.61 (1H, m), 7.85 (1H, d, J=7.3 Hz), 8.03 (1H, d, J=5.5 Hz), 8.17 (1H, m).

The starting material; (4-(pyridin-2-yloxymethyl)-phenyl)-acetohydroximoyl chloride, was synthesized as follows.

Manufacturing Example 2-1-1

(4-(Pyridin-2-yloxymethyl)-phenyl)methanol

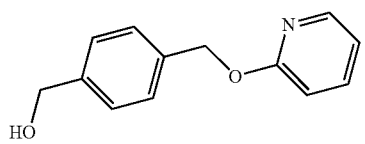

To a mixture of 1,4-benzenedimethanol (5.5 g, 40 mmol), 2-fluoropyridine (1.3 g, 13 mmol) and N,N-dimethylformamide (15 mL) was added sodium hydride (1.4 g, 40 mmol, 66% in oil) at 0° C., which was stirred for 20 minutes at room temperature and for 1 hour at 70° C. Water was added to the reaction mixture, which was then extracted with ethyl acetate. The organic layer was washed with saturated aqueous sodium chloride, and the solvent was evaporated under a reduced pressure. The residue was purified by NH silica gel column chromatography (ethyl acetate:heptane=1:1) to obtain the title compound (1.9 g, 66%).

$^1$H-NMR Spectrum (CDCl$_3$) δ (ppm): 4.71 (2H, s), 5.38 (2H, s), 6.81 (1H, td, J=0.9, 8.4 Hz), 6.89 (1H, ddd, J=0.9, 5.1, 7.1 Hz), 7.37-7.47 (4H, m), 7.59 (1H, ddd, J=2.0, 7.1, 8.3 Hz), 8.17 (1H, ddd, J=0.7, 2.0, 5.1 Hz).

Manufacturing Example 2-1-2

4-(Pyridin-2-yloxymethyl)-benzaldehyde

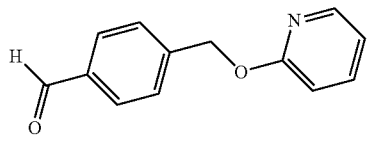

To a mixture of (4-(pyridin-2-yloxymethyl)-phenyl)methanol (1.9 g, 8.6 mmol) described in Manufacturing Example 2-1-1 and methylene chloride (30 mL) was added manganese dioxide (15 g, 17 mmol) at room temperature, which was stirred overnight at that temperature. The reaction mixture was filtered through a Celite pad, and the solvent was evaporated under a reduced pressure. The residue was purified by silica gel column chromatography (ethyl acetate:heptane=1:4) to obtain the title compound (770 mg, 42%).

$^1$H-NMR Spectrum (CDCl$_3$) δ (ppm): 5.48 (2H, s), 6.85 (1H, d, J=8.2 Hz), 6.90-6.93 (1H, m), 7.60-7.64 (3H, m), 7.89 (2H, d, J=8.1 Hz), 8.16 (1H, dd, J=1.3, 4.9 Hz), 10.0 (1H, s).

Manufacturing Example 2-1-3

2-(4-((E)-2-Nitro-vinyl)-benzyloxy)-pyridine

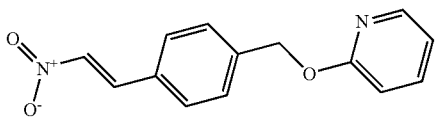

A mixture of 4-(pyridin-2-yloxymethyl)-benzaldehyde (23.4 g, 110 mmol) described in Manufacturing Example 2-1-2, nitromethane (33.6 g, 550 mmol), ammonium acetate (17.0 g, 220 mmol) and acetic acid (200 mL) was stirred for 1 hour and 45 minutes at 100° C. The reaction solution was stirred on an ice bath while adding a small amount of water, and the precipitated solids were filtered to obtain the title compound (21.0 g, 74.5%).

$^1$H-NMR Spectrum (DMSO-d$_6$) δ (ppm): 5.41 (2H, s), 6.91 (1H, dd, J=0.8, 8.4 Hz), 6.99-7.10 (1H, m), 7.53 (2H, d, J=8.0 Hz), 7.72-7.79 (1H, m), 7.86 (2H, d, J=8.0 Hz), 8.13 (1H, d, J=10 Hz), 8.15-8.20 (1H, m), 8.23 (1H, d, J=10 Hz).

Manufacturing Example 2-1-4

2-(4-(2-Nitro-ethyl)-benzyloxy)-pyridine

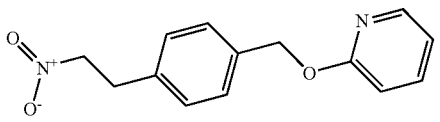

To a solution of 2-(4-((E)-2-nitro-vinyl)-benzyloxy)-pyridine (21.0 g, 81.9 mmol) described in Manufacturing Example 2-1-3, acetic acid (21 mL) in dimethyl sulfoxide (200 mL) was added sodium borohydride (4.96 g, 131 mmol) at room temperature while cooling appropriately. After addition of sodium borohydride, the cooling bath was removed, followed by stirring for 15 minutes at room temperature. The reaction solution was partitioned into water and ethyl acetate. The ethyl acetate layer was washed with water twice and with saturated aqueous sodium chloride once, and dried over anhydrous magnesium sulfate, and the solvent was evaporated under a reduced pressure. The residue was purified by NH silica gel column chromatography (ethyl acetate:heptane=1:3) to obtain the title compound (16.3 g, 77.1%).

$^1$H-NMR Spectrum (DMSO-d$_6$) δ (ppm): 3.23 (2H, t, J=6.8 Hz), 4.85 (2H, t, J=6.8 Hz), 5.32 (2H, s), 6.82-6.88 (1H, m), 6.96-7.01 (1H, m), 7.28 (2H, d, J=8.0 Hz), 7.38 (2H, d, J=8.0 Hz), 7.69-7.74 (1H, m), 8.15-8.19 (1H, m).

Manufacturing Example 2-1-5

4-(Pyridin-2-yloxymethyl)-phenyl-acetohydroximoyl chloride

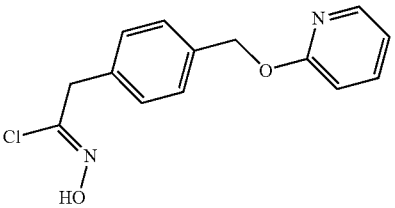

Lithium wire (323 mg, 46.6 mmol) was added to and dissolved in methanol (75 mL). To the mixture solution was added 2-(4-(2-nitro-ethyl)-benzyloxy)-pyridine (6.0 g, 23.3 mmol) described in Manufacturing Example 2-1-4. The reaction solution was concentrated under a reduced pressure. Toluene was added to the residue, and the solvent was concentrated under a reduced pressure. A solution of the resulting residue in methylene chloride (90 mL) and tetrahydrofuran (45 mL) was cooled to −78° C., and titanium (IV) chloride (8.15 mL, 74.4 mmol) was added while stirring. Immediately after addition of the titanium (IV) chloride, the reaction mixture was stirred for 10 minutes at 0° C. and 30 minutes at room temperature. The reaction solution was poured into an ice water and extracted with ethyl acetate. The organic layer was dried over anhydrous magnesium sulfate, and the magnesium sulfate was removed by filtration. The filtrate was passed through a glass filter covered with neutral silica gel, washed with ethyl acetate. The resulting eluate was concentrated under a reduced pressure. A small amount of ethyl acetate was added to the residue, and the precipitated solids were filtered out to obtain the title compound (1.86 g, 28.8%).

$^1$H-NMR Spectrum (DMSO-d$_6$) δ (ppm): 3.82 (2H, s), 5.33 (2H, s), 6.84-6.89 (1H, m), 1.97-7.01 (1H, m), 7.25 (2H, d, J=8.4 Hz), 7.41 (2H, d, J=8.4 Hz), 7.70-7.76 (1H, m), 8.15-8.18 (1H, m), 11.7 (1H, s).

Example 3

3-(3-(4-(6-Methyl-pyridin-2-yloxymethyl)-benzyl)-isoxazol-5-yl)-pyridin-2-ylamine

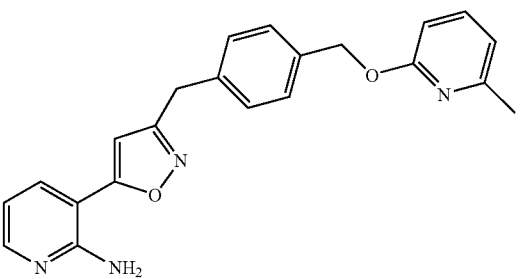

To a solution of 3-ethynyl-pyridin-2-ylamine (30 mg, 0.25 mmol) described in Manufacturing Example 1-2-3 in anhydrous tetrahydrofuran (5 mL) was added (4-(6-methyl-pyridin-2-yloxymethyl)-phenyl)-acetohydroximoyl chloride (222 mg, 0.76 mmol) described in Manufacturing Example 3-1-5 at room temperature. Triethylamine (142 μL, 1.0 mmol) was added dropwise to the reaction solution, and stirred overnight at room temperature. The reaction mixture was partitioned into water and ethyl acetate. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=1:3 then 1:1) to obtain the title compound (10.5 mg, 11%).

$^1$H-NMR Spectrum (DMSO-$d_6$) δ (ppm): 2.39 (3H, s), 4.04 (2H, s), 5.29 (2H, s), 6.26 (2H, brs), 6.61-6.64 (1H, m), 6.68-6.71 (1H, m), 6.81 (1H, s), 6.83 (1H, d, J=7.2 Hz), 7.33 (2H, d, J=8.0 Hz), 7.42 (2H, d, J=8.0 Hz), 7.57-7.61 (1H, dd, J=7.2, 8.4 Hz), 7.87 (1H, dd, J=2.0, 7.6 Hz), 8.08 (1H, dd, J=2.4, 5.0 Hz).

The starting material, (4-(6-methyl-pyridin-2-yloxymethyl)-benzene)-acetohydroximoyl chloride, was synthesized as follows.

Manufacturing Example 3-1-1

2-(4-Bromo-benzyloxy)-6-methyl-pyridine

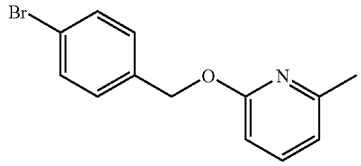

To a solution of (4-bromo-phenyl)-methanol (4.54 g, 24.3 mmol) in N,N-dimethylformamide (50 mL) was added sodium hydride (999 mg, 25 mmol, 60% in oil) under nitrogen atmosphere on an ice bath (0° C.), which was stirred for 30 minutes at room temperature. 2-Fluoro-6-methylpyridine (1.8 g, 16.2 mmol) was then added to the reaction mixture on an ice bath (0° C.), and stirred for 5 hours at room temperature. The reaction mixture was partitioned into water and ethyl acetate on the ice bath (0° C.). The organic layer was washed with water and saturated aqueous sodium chloride, and dried over anhydrous magnesium sulfate, and the solvent was evaporated under a reduced pressure. The residue was purified by silica gel column chromatography (ethyl acetate:heptane=1:15) to obtain the title compound (3.65 g, 81%).

$^1$H-NMR Spectrum (CDCl$_3$) δ (ppm): 2.44 (3H, s), 5.32 (2H, s), 6.57-6.59 (1H, m), 6.71-6.74 (1H, m), 7.26-7.35 (2H, m), 7.44-7.49 (3H m).

Manufacturing Example 3-1-2

4-(6-Methyl-pyridin-2-yloxymethyl)-benzaldehyde

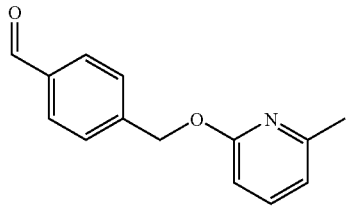

To a solution of 2-(4-bromo-benzyloxy)-6-methyl-pyridine (7.30 g, 26.2 mmol) described in Manufacturing Example 3-1-1 in anhydrous tetrahydrofuran (200 mL) was added dropwise n-butyl lithium (2.67 M n-hexane solution, 11.8 mL, 31.4 mmol) on a dry ice-ethanol bath (−78° C.), which was stirred for 30 minutes at −78° C. N,N-dimethylformamide (4.04 mL, 52.4 mmol) was added to this mixture at −78° C., and stirred for 5 minutes. Water and ethyl acetate were added to the reaction mixture, which was stirred for 10 minutes at room temperature, and the organic layer was then separated. This organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=1:3) to obtain the title compound (4.19 g, 70%).

$^1$H-NMR Spectrum (CDCl$_3$) δ (ppm): 2.44 (3H, s), 5.46 (2H, s), 6.12-6.64 (1H, m), 6.74-6.75 (1H, m), 7.44-7.50 (1H, m), 7.62 (2H, d, J=8.0 Hz), 7.88 (2H, d, J=8.0 Hz), 10.0 (1H, s).

Manufacturing Example 3-1-3

2-Methyl-6-(4-((E)-2-nitro-vinyl)-benzyloxy)-pyridine

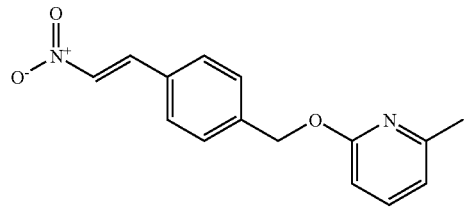

To a solution of 4-(6-methyl-pyridin-2-yloxymethyl)-benzaldehyde (4.19 g, 18.5 mmol) described in Manufacturing Example 3-1-2 in acetic acid (30 mL) were added nitromethane (5.65 g, 92.6 mmol) and ammonium acetate (2.85 g, 37.0 mmol) under nitrogen atmosphere, which was stirred for 3 hours at 110° C. The reaction mixture was partitioned into water and ethyl acetate. The organic layer was washed with water and saturated aqueous sodium chloride, and dried over anhydrous magnesium sulfate, and the solvent was evaporated under a reduced pressure to obtain the title compound (5.50 g) as a crude product.

$^1$H-NMR Spectrum (CDCl$_3$) δ (ppm): 2.45 (3H, s), 5.43 (2H, s), 6.05-6.28 (1H, m), 6.74-6.76 (1H, m), 7.47-7.51 (1H, m), 7.55 (4H, s), 7.59 (1H, d, J=13.6 Hz), 8.01 (1H, d, J=13.6 Hz).

Manufacturing Example 3-1-4

2-Methyl-6-(4-(2-nitro-ethyl)-benzyloxy)pyridine

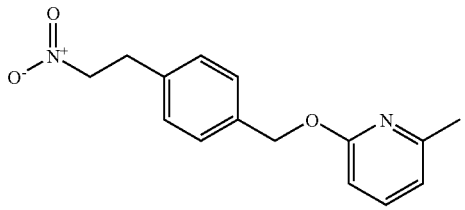

To a solution of 2-methyl-6-(4-((E)-2-nitro-vinyl)-benzyloxy)-pyridine (5.00 g, 18.5 mmol) described in Manufacturing Example 3-1-3 and acetic acid (5 mL) in dimethyl sulfoxide (50 mL) was added sodium borohydride (1.2 g, 29.6 mmol) under nitrogen atmosphere at room temperature while cooling appropriately, which was stirred for 10 minutes at room temperature. Water was then added dropwise. The mixture was partitioned into water and ethyl acetate. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=1:5 then 1:2) to obtain the title compound (2.8 g, 56%).

$^1$H-NMR Spectrum (DMSO-$d_6$) δ (ppm): 2.39 (3H, s), 3.22 (2H, t, J=6.8 Hz), 4.85 (2H, t, J=6.8 Hz), 5.28 (2H, s), 6.64 (1H, d, J=8.0 Hz), 7.84 (1H, d, J=8.0 Hz), 7.28 (2H, d, J=7.6 Hz), 7.39 (2H, d, J=7.6 Hz), 7.59 (1H, t, J=8.0 Hz).

Manufacturing Example 3-1-5

4-(6-Methyl-pyridin-2-yloxymethyl)-phenyl)-acetohydroximoyl chloride

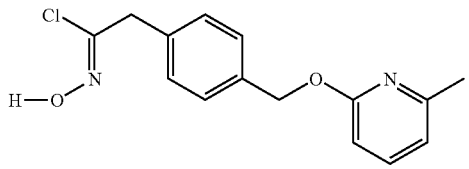

To a solution of 2-methyl-6-(4-(2-nitro-ethyl)-benzyloxy)pyridine (500 mg, 1.84 mmol) described in Manufacturing Example 3-1-4 in methanol (10 mL) was added lithium methoxide (140 mg, 3.68 mmol) under nitrogen atmosphere at room temperature, which was stirred for 30 minutes at room temperature. The reaction mixture was concentrated under a reduced pressure. Anhydrous methylene chloride (10 mL) and anhydrous tetrahydrofuran (5 mL) were added to the residue. Titanium (IV) chloride (667 µL, 6.07 mmol) was added dropwise to the reaction mixture on a dry ice-ethanol bath (−78° C.), and stirred for 45 minutes at 0° C. The reaction mixture was then stirred for further 60 minutes at room temperature. Water, ethyl acetate and tetrahydrofuran were added to the reaction mixture on an ice bath (0° C.), and the organic layer was separated. This organic layer was washed with water and saturated aqueous sodium chloride, and dried over anhydrous magnesium sulfate, and the solvent was evaporated under a reduced pressure to obtain the title compound (484 mg, 91%) as a crude product.

$^1$H-NMR Spectrum (DMSO-$d_6$) δ (ppm): 2.42 (3H, s), 3.82 (2H, s), 5.33 (2H, s), 6.76 (1H, d, J=7.6 Hz), 6.92 (1H, d, J=7.6 Hz), 7.27 (2H, d, J=8.0 Hz), 7.44 (2H, d, J=8.0 Hz), 7.70 (1H, t, J=7.6 Hz), 11.8 (1H, brs).

Example 4

3-(3-(4-Butoxymethyl-benzyl)-isoxazol-5-yl)-pyridin-2-ylamine

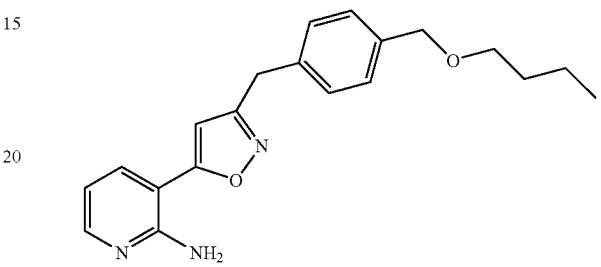

To a solution of 4-butoxymethyl-phenyl-acetohydroximoyl chloride (28 mg, 0.11 mmol) described in Manufacturing Example 4-1-4 and 3-ethynyl-pyridin-2-ylamine (13 mg, 0.11 mmol) described in Manufacturing Example 1-2-3 in tetrahydrofuran (1 mL) was added triethylamine (31 µL, 0.22 mmol) at room temperature, which was stirred for 70 minutes at room temperature. The reaction solution was partitioned into water and ethyl acetate at room temperature. The organic layer was washed with saturated aqueous sodium chloride and dried over anhydrous magnesium sulfate, and the solvent was evaporated under a reduced pressure. The residue was purified by NH silica gel column chromatography (heptane:ethyl acetate=2:1) and then further purified by reverse-phase high performance liquid chromatography (using an acetonitrile-water mobile phase containing 0.1% trifluoroacetic acid) to obtain the title compound (2.3 mg, 5%) as a trifluoroacetic acid salt.

MS m/e (ESI) (MH$^+$) 338.14 (MH$^+$)

The starting material, 4-butoxymethyl-phenyl-acetohydroximoyl chloride, was synthesized as follows.

Manufacturing Example 4-1-1

1-Bromo-4-butoxymethyl-benzene

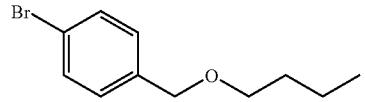

To a solution of 4-bromobenzyl alcohol (10.0 g, 53.5 mmol) in N,N-dimethylformamide (200 mL) was added sodium hydride (3.08 g, 64.2 mmol, 50% in oil) at 0° C. This mixture was stirred for 5 minutes at 0° C., and 1-bromobutane (7.47 mL, 69.3 mmol) was added thereto at 0° C. This mixture was stirred for 40 minutes at room temperature and then stirred for 25 minutes at 70° C. The reaction solution was partitioned into water and ethyl acetate at 0° C. The organic layer was washed with water and saturated aqueous sodium chloride, and dried over anhydrous magnesium sulfate, and the solvent was evaporated under a reduced pressure. The residue was purified by silica gel column chromatography (heptane:ethyl acetate=20:1) to obtain the title compound (11.5 g, 89%).

$^1$H-NMR Spectrum (CDCl$_3$) δ (ppm): 0.919 (3H, t, J=7.3 Hz), 1.35-1.44 (2H, m), 1.56-1.63 (2H, m), 3.46 (2H, t, J=6.6 Hz), 4.45 (2H, s), 7.21 (2H, d, J=8.1 Hz), 7.45-7.48 (2H, m).

Manufacturing Example 4-1-2

4-Butoxymethyl-benzaldehyde

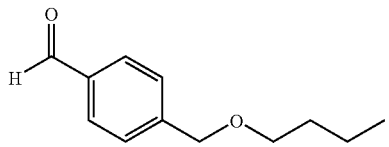

To a solution of 1-bromo-4-butoxymethyl-benzene (11.5 g, 47.3 mmol) described in Manufacturing Example 4-1-1 in tetrahydrofuran (200 mL) was added n-butyl lithium (32.5 mL, 1.6 M hexane solution, 52.0 mmol) at −78° C. This mixture was stirred for 55 minutes at −78° C., and N,N-dimethylformamide (4.4 mL, 56.8 mmol) was added thereto at −78° C. This mixture was warmed to room temperature, and stirred for 20 minutes. The reaction solution was partitioned into water and ethyl acetate at 0° C. The organic layer was washed with saturated aqueous sodium chloride and dried over anhydrous magnesium sulfate, and the solvent was evaporated under a reduced pressure. The residue was purified by silica gel column chromatography (heptane:ethyl acetate=10:1) to obtain the title compound (7.39 g, 81%).

$^1$H-NMR Spectrum (CDCl$_3$) δ (ppm): 0.936 (3H, t, J=7.3 Hz), 1.37-1.47 (2H, m), 1.60-1.67 (2H, m), 3.52 (2H, t, J=6.6 Hz), 4.58 (2H, s), 7.51 (2H, d, J=7.9 Hz), 7.86 (2H, m), 10.0 (1H, s).

Manufacturing Example 4-1-3

1-Butoxymethyl-4-(2-nitroethyl)-benzene

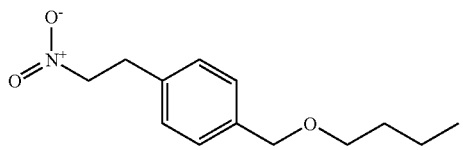

To a solution of 4-butoxymethyl-benzaldehyde (7.39 g, 3.84 mmol) described in Manufacturing Example 4-1-2 in methanol (140 mL) was added nitromethane (2.70 mL, 49.9 mmol) followed by sodium methoxide (1.49 M methanol solution, 9.41 mL, 46.1 mmol) at 0° C. The reaction solution was stirred for 30 minutes at room temperature, and 5 N aqueous hydrochloric acid solution (120 mL) was added thereto and stirred for further 25 minutes. This reaction solution was partitioned into saturated aqueous sodium chloride and ethyl acetate at 0° C. The organic layer was washed with saturated aqueous sodium chloride and dried over anhydrous magnesium sulfate, and the solvent was evaporated under a reduced pressure. To a solution of the resulting residue in dimethyl sulfoxide (100 mL) and acetic acid (6 mL) was added sodium borohydride (1.84 g, 46.1 mmol) at room temperature while cooling appropriately. This solution was then stirred for 80 minutes at room temperature. The reaction solution was partitioned into water and ethyl acetate. The organic layer was washed with saturated aqueous sodium chloride and dried over anhydrous magnesium sulfate, and the solvent was evaporated under a reduced pressure. The residue was purified by silica gel column chromatography (heptane:ethyl acetate=4:1) to obtain the title compound (2.68 g, 29%).

$^1$H-NMR Spectrum (CDCl$_3$) δ (ppm): 0.918 (3H, t, J=7.3 Hz), 1.37-1.42 (2H, m), 1.56-1.63 (2H, m), 3.31 (2H, t, J=7.3 Hz), 3.47 (2H, t, J=6.6 Hz), 4.47 (2H, s), 4.60 (2H, t, J=7.3 Hz), 7.18 (2H, d, J=8.2 Hz), 7.30 (2H, d, J=8.2 Hz).

Manufacturing Example 4-1-4

4-Butoxymethyl-phenyl-acetohydroximoyl chloride

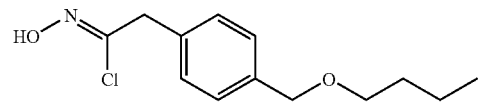

To a solution of 1-butoxymethyl-4-(2-nitroethyl)-benzene (55 mg, 0.23 mmol) described in Manufacturing Example 4-1-3 in methanol (2 mL) was added sodium methoxide (1.49 M methanol solution, 47.3 μL, 0.23 mmol) at 0° C. The reaction solution was stirred for 35 minutes at room temperature, and concentrated under a reduced pressure. To a solution of the residue in methylene chloride (2 mL) was added titanium (IV) chloride (28 μL, 0.23 mmol) under nitrogen atmosphere at −78° C., which was then stirred for 30 minutes at 0° C. The reaction solution was partitioned into water and ethyl acetate at 0° C. The organic layer was washed with saturated aqueous sodium chloride and dried over anhydrous magnesium sulfate, and the magnesium sulfate was removed by filtration. The organic layer was filtered with silica gel, and the filtrate was evaporated under a reduced pressure to obtain the title compound (59 mg, 99%) as a crude product.

$^1$H-NMR Spectrum (CDCl$_3$) δ (ppm): 0.90-0.94 (3H, m), 1.36-1.44 (2H, m), 1.56-1.64 (2H, m), 3.46-3.49 (2H, m), 3.79 (2H, s), 4.50 (2H, s), 7.23-7.26 (2H, m), 7.30-7.34 (2H, m), 8.29 (1H, s).

Example 5

3-(3-(4-(2-Fluoro-benzyloxy)-benzyl)-isoxazol-5-yl)-pyridin-2-ylamine

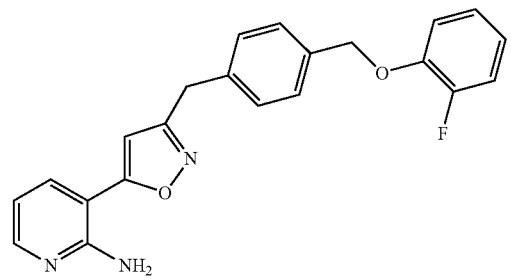

To a mixture of 4-(5-(2-amino-pyridin-3-yl)isoxazol-3-yl-methyl)-phenol (4.2 mg, 0.016 mmol) described in Manufacturing Example 5-1-1 and methanol (0.4 mL) was added 1 N aqueous sodium hydroxide solution (16 μL, 0.016 mmol). This mixture was concentrated under a reduced pressure. To a mixture of the residue and N,N-dimethylformamide (0.5 mL) was added 2-fluorobenzyl bromide (2.3 μL, 0.019 mmol), which was stirred for 1 hour at room temperature. The reaction mixture was then purified directly by reverse-phase high performance liquid chromatography (using an acetonitrile-water mobile phase containing 0.1% trifluoroacetic acid) to obtain the title compound (3.3 mg, 43%) as a trifluoroacetic acid salt.

MS m/e (ESI) 376.14 (MH⁺)

The starting material, 4-(5-(2-amino-pyridin-3-yl)isoxazol-3-ylmethyl)-phenol, was synthesized as follows.

Manufacturing Example 5-1-1

4-(5-(2-Amino-pyridin-3-yl)isoxazol-3-ylmethyl)-phenol

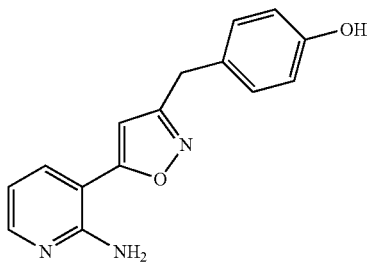

To a mixture of 3-(3-(4-benzyloxy-benzyl)-isoxazol-5-yl)-pyridin-2-ylamine (32 mg, 0.090 mmol) described in Example 1 and trifluoroacetic acid (1 mL) was added thioanisole (45 mg, 0.36 mmol) at room temperature, which was stirred for 2 hours at the same temperature. To a mixture of saturated aqueous sodium hydrogencarbonate solution and ethyl acetate was added the reaction mixture. The organic layer was separated and washed with saturated aqueous sodium chloride, and the solvent was evaporated under a reduced pressure. The residue was purified by silica gel column chromatography (ethyl acetate:heptane=4:1) to obtain the title compound (24 mg, 100%).

¹H-NMR Spectrum (DMSO-d₆) δ (ppm): 3.90 (2H, s), 6.25 (2H, brs), 6.68-6.72 (3H, m), 6.76 (1H, s), 7.11 (2H, d, J=8.6 Hz), 7.87 (1H, dd, J=1.5, 7.7 Hz), 8.10 (1H, brs), 9.29 (1H, s).

Example 6

3-(3-(4-(3-Fluoro-benzyloxy)-benzyl)-isoxazol-5-yl)-pyridin-2-ylamine

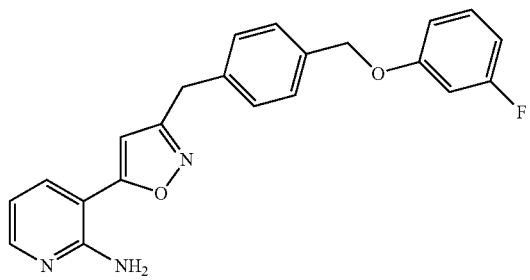

To a mixture of 4-(5-(2-amino-pyridin-3-yl)isoxazol-3-yl-methyl)-phenol (4.2 mg, 0.016 mmol) described in Manufacturing Example 5-1-1 and methanol (0.4 mL) was added 1 N aqueous sodium hydroxide solution (16 μL, 0.016 mmol), which was then concentrated under a reduced pressure. To a mixture of the residue and N,N-dimethylformamide (0.5 mL) was added 3-fluorobenzyl bromide (2.3 μL, 0.019 mmol), which was stirred for 1 hour at room temperature. The reaction mixture was purified directly by reverse-phase high performance liquid chromatography (using an acetonitrile-water mobile phase containing 0.1% trifluoroacetic acid) to obtain the title compound (4.3 mg, 55%) as a trifluoroacetic acid salt.

MS m/e (ESI) 376.12 (MH⁺)

Example 7

3-(3-(4-(4-Fluoro-benzyloxy)-benzyl)-isoxazol-5-yl)-pyridin-2-ylamine

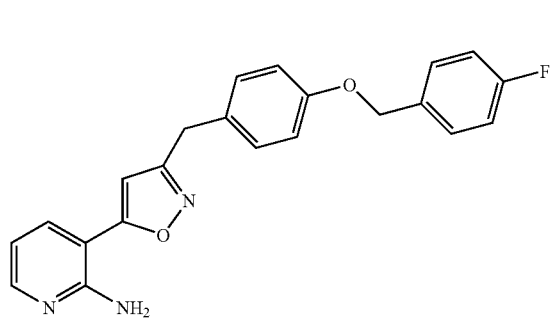

To a mixture of 4-(5-(2-amino-pyridin-3-yl)isoxazol-3-yl-methyl)-phenol (4.2 mg, 0.016 mmol) described in Manufacturing Example 5-1-1 and methanol (0.4 mL) was added 1 N aqueous sodium hydroxide solution (16 μL, 0.016 mmol), which was then concentrated under a reduced pressure. To a mixture of the residue and N,N-dimethylformamide (0.5 mL) was added 4-fluorobenzyl bromide (2.3 μL, 0.019 mmol), which was stirred for 1 hour at room temperature. The reaction mixture was purified as is by reverse-phase high performance liquid chromatography (using an acetonitrile-water mobile phase containing 0.1% trifluoroacetic acid) to obtain the title compound (3.1 mg, 39%) as a trifluoroacetic acid salt.

MS m/e (ESI) 376.12 (MH⁺)

Example 8

3-(3-(4-Cyclopropylmethoxy-benzyl)-isoxazol-5-yl)-pyridin-2-ylamine

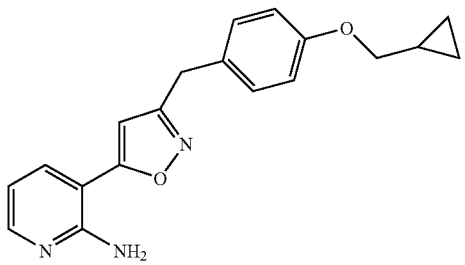

To a mixture of 4-(5-(2-amino-pyridin-3-yl)isoxazol-3-yl-methyl)-phenol (4.2 mg, 0.016 mmol) described in Manufacturing Example 5-1-1 and methanol (0.4 mL) was added 1 N aqueous sodium hydroxide solution (16 μL, 0.016 mmol), which was then concentrated under a reduced pressure. To a mixture of the residue and N,N-dimethylformamide (0.5 mL) were added cyclopropylmethyl bromide (2.3 μL, 0.019 mmol) and sodium iodide (1 mg, 7 μmol) at room temperature, which was stirred for 2 hours at 60° C. The reaction mixture was cooled to room temperature and then purified as is by reverse-phase high performance liquid chromatography (using an acetonitrile-water mobile phase containing 0.1% trifluoroacetic acid). The eluate was neutralized by triethylamine while being concentrated. The solvent was evaporated under a reduced pressure. The residue was washed with water to obtain the title compound (1.6 mg, 30%).

MS m/e (ESI) 322.19 (MH$^+$)

Example 9

3-(3-(4-(Pyridin-2-ylmethoxy)-benzyl)-isoxazol-5-yl)-pyridin-2-ylamine

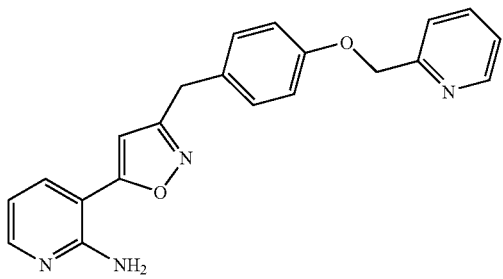

To a mixture of 4-(5-(2-amino-pyridin-3-yl)isoxazol-3-yl-methyl)-phenol (4.2 mg, 0.016 mmol) described in Manufacturing Example 5-1-1 and methanol (0.4 mL) was added 1 N aqueous sodium hydroxide solution (16 μL, 0.016 mmol), which was then concentrated under a reduced pressure. To a mixture of the residue and N,N-dimethylformamide (0.5 mL) was added 2-picolyl chloride (3.1 mg, 0.019 mmol), which was stirred for 2 hours at room temperature. The reaction mixture was purified as is by reverse-phase high performance liquid chromatography (using an acetonitrile-water mobile phase containing 0.1% trifluoroacetic acid) to obtain the title compound (3.6 mg, 39%) as a ditrifuoroacetic acid salt.

MS m/e (ESI) 359.16 (MH$^+$)

Example 10

3-(3-(4-(6-Methyl-pyridin-2-ylmethoxy)-benzyl)-isoxazol-5-yl)-pyridin-2-ylamine

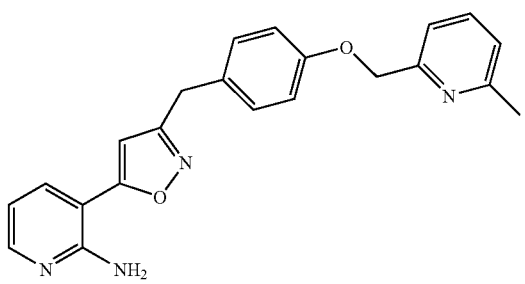

Methanol (3 mL) and 1 N aqueous sodium hydroxide solution (0.18 mL) were added to 4-(5-(2-amino-pyridin-3-yl) isoxazol-3-ylmethyl)-phenol (50 mg, 0.19 mmol) described in Manufacturing Example 5-1-1, which was then dissolved by irradiating ultrasonic wave. This solution was concentrated under a reduced pressure. To the resulting residue were added 2-chloromethyl-6-methyl-pyridine (31.8 mg, 0.22 mmol) described in Manufacturing Example 10-1-1 and N,N-dimethylformamide (2 mL), which was stirred for 20 minutes at 60° C. The reaction solution was partitioned into water and ethyl acetate. The organic layer was separated, and the solvent was evaporated under a reduced pressure. The residue was purified by NH silica gel column chromatography (heptane: ethyl acetate=1:1) to obtain the title compound (36 mg, 51.7%).

$^1$H-NMR Spectrum (DMSO-d$_6$) δ (ppm): 2.48 (3H, s), 3.96 (2H, s), 5.10 (2H, s), 6.25 (2H, brs), 6.69 (1H, dd, J=4.8, 8.0 Hz), 6.79 (1H, s), 6.97 (2H, d, J=8.0 Hz), 7.18 (1H, d, J=7.6 Hz), 7.25 (2H, d, J=8.0 Hz), 7.27 (1H, d, J=7.6 Hz), 7.70 (1H, dd, J=7.6, 7.6 Hz), 7.86 (1H, d, J=8.0 Hz), 8.08 (1H, d, J=4.8 Hz).

The starting material, 2-chloromethyl-6-methyl-pyridine, was obtained as follows.

Manufacturing Example 10-1-1

2-Chloromethyl-6-methyl-pyridine

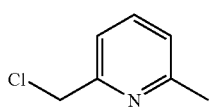

A solution of (6-methyl-pyridin-2-yl)-methanol (1.44 g, 11.7 mmol), thionyl chloride (1.45 mL, 19.9 mmol) and methylene chloride (20 mL) was stirred under reflux for 40 minutes. The reaction solution was cooled to room temperature and then concentrated under a reduced pressure. The residue was partitioned into sodium bicarbonate solution and diethyl ether. The organic layer was concentrated under a reduced pressure, and the residue was purified by silica gel chromatography (ethyl acetate) to obtain the title compound (1.42 g, 85.8%).

¹H-NMR Spectrum (DMSO-d₆) δ (ppm): 2.47 (3H, s), 4.72 (2H, s), 7.22 (1H, d, J=7.6 Hz), 7.33 (1H, d, J=7.6 Hz), 7.72 (1H, dd, J=7.6, 7.6 Hz).

Example 11

3-(3-(4-(4-Methyl-pyridin-2-ylmethoxy)-benzyl)-isoxazol-5-yl)-pyridin-2-ylamine

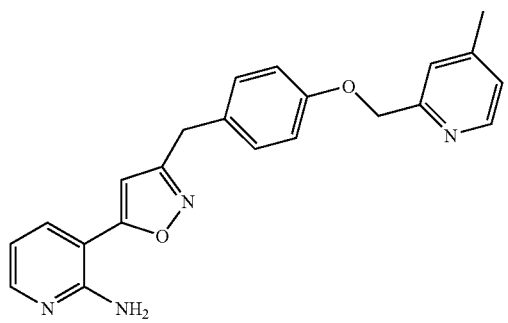

Methanol (3 mL) and 1 N aqueous sodium hydroxide solution (0.18 mL) were added to 4-(5-(2-amino-pyridine-3-yl) isoxazole-3-ylmethyl)-phenol (50 mg, 0.19 mmol) described in Manufacturing Example 5-1-1, which was then dissolved by irradiating ultrasonic wave. This solution was concentrated under a reduced pressure. To the resulting residue were added 2-chloromethyl-4-methyl-pyridine (31.8 mg, 0.22 mmol) described in Manufacturing Example 11-1-4 and N,N-dimethylformamide (2 mL), which was stirred for 10 minutes at 60° C. The reaction solution was partitioned into water and ethyl acetate. The organic layer was separated, and the solvent was evaporated under a reduced pressure. The residue was purified by NH silica gel column chromatography (heptane: ethyl acetate=1:1) to obtain the title compound (21 mg, 30.2%).

¹H-NMR Spectrum (DMSO-d₆) δ (ppm): 2.33 (3H, s), 3.96 (2H, s), 5.11 (2H, s), 6.25 (2H, brs), 6.69 (1H, dd, J=4.8, 8.0 Hz), 6.79 (1H, s), 6.98 (2H, d, J=8.4 Hz), 7.17 (1H, d, J=7.6 Hz), 7.25 (2H, d, J=8.4 Hz), 7.34 (1H, s), 7.87 (1H, d, J=7.6 Hz), 8.09 (1H, d, J=4.8 Hz), 8.41 (1H, d, J=4.8 Hz).

The starting material, 2-chloromethyl-4-methyl-pyridine, was synthesized as follows.

Manufacturing Example 11-1-1

2,4-Dimethyl-pyridine 1-oxide

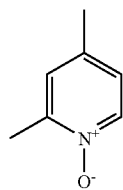

To a solution of 2,4-lutidine (2.0 g, 18.7 mmol) in methylene chloride (100 mL) was added 3-chloroperoxybenzoic acid (5.07 g, 29.4 mmol), which was stirred for 20 minutes at room temperature. A small amount of saturated aqueous sodium hydrogen sulfite solution was added to the reaction solution, and the organic layer was separated after vigorous stirring. This organic layer was washed with 5 N aqueous sodium hydroxide solution (5.9 mL), and dried over anhydrous magnesium sulfate. The solvent was evaporated under a reduced pressure to obtain the title compound (1.54 g, 66.9%). The title compound was used in the following reaction without being purified.

Manufacturing Example 11-1-2

Acetic acid 4-methyl-pyridin-2-ylmethyl ester

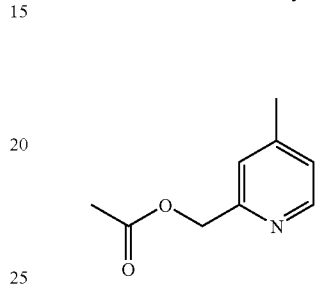

Acetic anhydride (30 mL) was added to 2,4-dimethyl-pyridine 1-oxide (1.93 g, 15.7 mmol) described in Manufacturing Example 11-1-1, and the mixture was stirred for 10 minutes at 110° C. The reaction solution was allowed to room temperature and concentrated under a reduced pressure. The resulting residue was purified by silica gel column chromatography (heptane:ethyl acetate=1:2, then ethyl acetate) to obtain the title compound (774 mg, 29.8%).

¹H-NMR Spectrum (DMSO-d₆) δ (ppm): 2.11 (3H, s), 2.32 (3H, s), 5.09 (2H, s), 7.16 (1H, d, J=5.2 Hz), 7.23 (1H, s), 8.39 (1H, d, J=5.2 Hz).

Manufacturing Example 11-1-3

(4-Methyl-pyridin-2-yl)-methanol

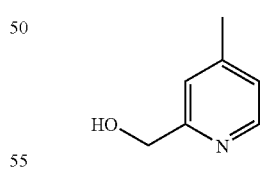

5 N Aqueous sodium hydroxide solution (2 mL) and methanol (4 mL) were added to acetic acid 4-methyl-pyridin-2-ylmethyl ester (774 mg, 4.69 mmol) described in Manufacturing Example 11-1-2, and this mixture was stirred for 10 minutes at 60° C. The reaction solution was partitioned into water and ethyl acetate. The separated aqueous layer was further extracted with ethyl acetate twice. The ethyl acetate layers were combined and dried over anhydrous magnesium sulfate, and the solvent was evaporated under a reduced pressure to obtain the title compound (410 mg, 71.0%).

$^1$H-NMR Spectrum (DMSO-d$_6$) δ (ppm): 2.32 (3H, s), 4.52 (2H, brs), 5.35 (1H, brs), 7.06 (1H, d, J=5.2 Hz), 7.29 (1H, s), 8.32 (1H, d, J=5.2 Hz).

Manufacturing Example 11-1-4

2-Chloromethyl-4-methyl-pyridine

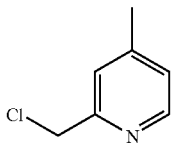

A mixture solution of (4-methyl-pyridine-2-yl)-methanol (410 mg, 3.33 mmol) described in Manufacturing Example 11-1-3, thionyl chloride (0.49 mL, 6.66 mmol) and methylene chloride (10 mL) was stirred under reflux for 5 minutes. The reaction solution was allowed to room temperature and concentrated under a reduced pressure. The resulting residue was partitioned into diethyl ether and saturated sodium bicarbonate solution. The organic layer was purified by silica gel column chromatography (ethyl acetate) to obtain the title compound (340 mg, 72.1%).

$^1$H-NMR Spectrum (DMSO-d$_6$) δ (ppm): 2.37 (3H, s), 4.72 (2H, s), 7.20 (1H, d, J=5.2 Hz), 7.38 (1H, s), 8.40 (1H, d, J=5.2 Hz).

Example 12

3-(3-(6-Benzyloxy-pyridin-3-ylmethyl)-isoxazol-5-yl)-pyridin-2-ylamine

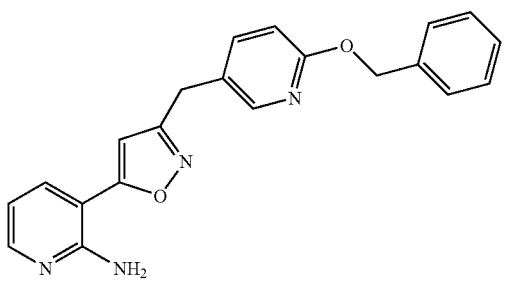

To a solution of 3-ethynyl-pyridin-2-ylamine (400 mg, 3.39 mmol) described in Manufacturing Example 1-2-3 in anhydrous tetrahydrofuran (20 mL) was added (2-benzyloxy-pyridin-5-yl)-acetohydroximoyl chloride (2.50 g, 9.03 mmol) under nitrogen atmosphere at room temperature. Triethylamine (1.89 mL, 13.6 mmol) was then added dropwise thereto, and stirred for 1.5 hours at room temperature. The reaction mixture was partitioned into water and ethyl acetate at room temperature. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=1:3 then 1:2) to obtain the title compound (315 mg, 26%).

$^1$H-NMR Spectrum (DMSO-d$_6$) δ (ppm): 4.00 (2H, s), 5.34 (2H, s), 6.27 (2H, brs), 6.70 (1H, dd, J=4.8, 7.6 Hz), 6.84 (1H, s), 6.86 (1H, d, J=8.8 Hz), 7.31-7.44 (5H, m), 7.69 (1H, dd, J=2.4, 8.4 Hz), 7.87 (1H, dd, J=2.0, 7.4 Hz), 8.09 (1H, dd, J=2.4, 4.8 Hz), 8.17 (1H, d, J=2.4 Hz).

The starting material, (2-benzyloxy-pyridin-5-yl)-acetohydroximoyl chloride, was synthesized as follows.

Manufacturing Example 12-1-1

2-Benzyloxy-5-bromopyridine

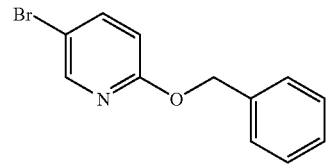

To a solution of phenyl-methanol (20.5 g, 190 mmol) in N,N-dimethylformamide (200 mL) was added sodium hydride (7.6 g, 190 mmol) under nitrogen atmosphere on an ice bath (0° C.), which was stirred for 30 minutes at room temperature. 2,5-Dibromopyridine was then added thereto on the ice bath (0° C.), and stirred for 60 minutes at room temperature. The reaction mixture was partitioned into water and ethyl acetate on the ice bath (0° C.). The organic layer was washed with water and saturated aqueous sodium chloride, and dried over anhydrous magnesium sulfate, and the solvent was evaporated under a reduced pressure. The residue was purified by silica gel column chromatography (ethyl acetate: heptane=1:20 then 1:10) to obtain the title compound (15.1 g, 90%).

$^1$H-NMR Spectrum (CDCl$_3$) δ (ppm): 5.34 (2H, s), 6.71-6.73 (1H, m), 7.32-7.45 (5H, m), 7.64-7.67 (1H, m), 8.20-8.21 (1H, m).

Manufacturing Example 12-1-2

6-Benzyloxy-pyridin-3-carbaldehyde

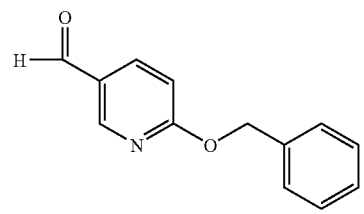

To a solution of 2-benzyloxy-5-bromopyridine (15.1 g, 57.0 mmol) described in Manufacturing Example 12-1-1 in anhydrous tetrahydrofuran (250 mL) were added dropwise n-butyl lithium (2.67 M n-hexane solution, 25.6 mL, 68.4 mmol) under nitrogen atmosphere on a dry ice-ethanol bath (−78° C.), which was stirred for 30 minutes at −78° C. N,N-Dimethylformamide (6.60 mL, 85.5 mmol) was then added thereto at −78° C., and stirred for 30 minutes. Water and ethyl acetate were added to the reaction mixture, and the organic layer was separated after stirring for 10 minutes at room temperature. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=1:7 then 1:5) to obtain the title compound (4.87 g, 40%).

¹H-NMR Spectrum (CDCl₃) δ (ppm): 5.49 (2H, s), 6.89-6.92 (1H, m), 7.34-7.48 (5H, m), 8.07-8.10 (1H, m), 8.64-8.65 (1H, m), 9.97 (1H, s).

Manufacturing Example 12-1-3

2-Benzyloxy-5-((E)-2-nitro-vinyl)-pyridine

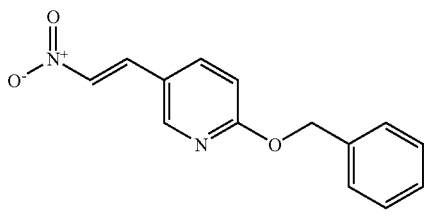

To a solution of 6-benzyloxy-pyridin-3-carbaldehyde (4.87 g, 22.8 mmol) described in Manufacturing Example 12-1-2 in acetic acid (30 mL) were added nitromethane (6.96 g, 114 mmol) and ammonium acetate (3.51 g, 45.6 mmol) under nitrogen atmosphere at room temperature, which was stirred for 2.5 hours at 110° C. The reaction mixture was partitioned into water and ethyl acetate. The organic layer was washed with water and saturated aqueous sodium chloride, and dried over anhydrous magnesium sulfate, and the solvent was evaporated under a reduced pressure to obtain the title compound (5.60 g, 96%) as a crude product.

¹H-NMR Spectrum (DMSO-d₆) δ (ppm): 5.43 (2H, s), 7.01 (1H, d, J=8.8 Hz), 7.34-7.47 (5H, m), 8.16 (1H, d, J=13.6 Hz), 8.24 (1H, d, J=13.6 Hz), 8.27 (1H, dd, J=2.4, 8.8 Hz), 8.64 (1H, d, J=2.4 Hz).

Manufacturing Example 12-1-4

2-Benzyloxy-5-(2-nitro-ethyl)pyridine

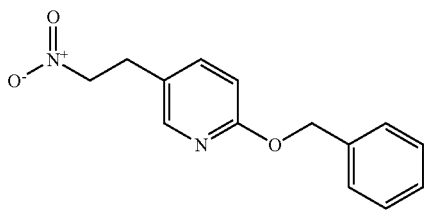

To a solution of 2-benzyloxy-5-((E)-2-nitro-vinyl)-pyridine (5.80 g, 22.8 mmol) described in Manufacturing Example 12-1-3 and acetic acid (5.80 mL) in dimethyl sulfoxide (70 mL) was added sodium borohydride (1.44 g, 36.2 mmol) under nitrogen atmosphere at room temperature while cooling appropriately, which was stirred for 10 minutes at room temperature. The reaction mixture was partitioned into water and ethyl acetate. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=1:4) to obtain the title compound (2.50 g, 43%).

¹H-NMR Spectrum (DMSO-d₆) δ (ppm): 3.17 (2H, t, J=6.8 Hz), 4.84 (2H, d, J=6.8 Hz), 5.31 (2H, s), 6.84 (1H, d, J=8.4 Hz), 7.31-7.42 (5H, m), 7.68 (1H, dd, J=2.4, 8.4 Hz), 8.06 (1H, d, J=2.4 Hz).

Manufacturing Example 12-1-5

(2-Benzyloxy-pyridin-5-yl)-acetohydroximoyl chloride

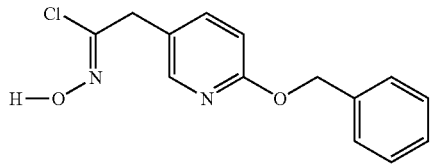

To a solution of 2-benzyloxy-5-(2-nitro-ethyl)pyridine (3.97 g, 15.4 mmol) described in Manufacturing Example 12-1-4 in methanol (25 mL) was added lithium methoxide (1.17 g, 30.8 mmol) under nitrogen atmosphere at room temperature, which was stirred at room temperature for 30 minutes. The reaction mixture was concentrated under a reduced pressure. Anhydrous methylene chloride (30 mL) and anhydrous tetrahydrofuran (20 mL) were added to the residue. Titanium (IV) chloride (5.42 mL, 49.3 mmol) was added dropwise into the reaction mixture on a dry ice-ethanol bath (−78° C.), and stirred for 45 minutes at 0° C. Water, ethyl acetate and tetrahydrofuran were added to the reaction mixture on an ice bath (0° C.), and the organic layer was separated. The organic layer was washed with water and saturated aqueous sodium chloride, and dried over anhydrous magnesium sulfate, and the solvent was evaporated under a reduced pressure to obtain the title compound (3.4 g, 80%) as a crude product.

¹H-NMR Spectrum (DMSO-d₆) δ (ppm): 3.79 (2H, s), 5.34 (2H, s), 6.87 (1H, d, J=8.4 Hz), 7.30-7.62 (5H, m), 7.61 (1H, dd, J=2.4, 8.4 Hz), 7.08 (1H, d, J=2.4 Hz), 11.8 (1H, s).

Example 13

3-(3-(4-Benzyloxy-benzyl)-isoxazol-5-yl)-pyridin-2,6-diamine

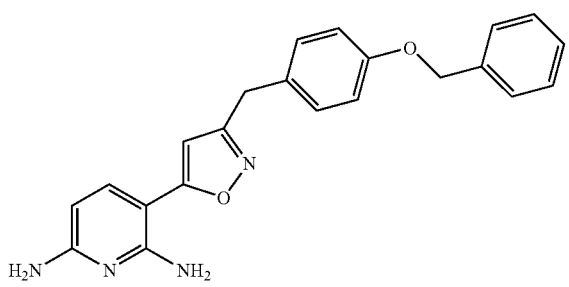

To a mixture of 4-benzyloxy-phenyl-acetohydroximoyl chloride (140 mg, 0.51 mmol) described in Manufacturing Example 1-1-3 and tetrahydrofuran (10 mL) were added 3-ethynyl-pyridin-2,6-diamine (102 mg, 0.76 mmol) described in Manufacturing Example 13-1-3 and triethylamine (0.71 mL, 5.1 mmol), which was stirred overnight at room temperature. The reaction mixture was then stirred for further 1.5 hours at 55° C. The reaction solution was cooled to room temperature and concentrated under a reduced pressure. The residue was filtered by NH silica gel column chromatography (ethyl acetate) to obtain a crude product. The crude product was purified by reverse-phase high performance liquid chromatography (using an acetonitrile-water mobile phase containing 0.1% trifluoroacetic acid). The solvent was evaporated under a reduced pressure, and the residue was filtered with NH silica gel to obtain the title compound (51 mg, 27%).

$^1$H-NMR Spectrum (DMSO-d$_6$) δ (ppm): 3.87 (2H, s), 5.07 (2H, s), 5.79 (2H, brs), 5.82 (1H, d, J=8.6 Hz), 6.10 (2H, brs), 6.34 (1H, s), 6.94-6.98 (2H, m), 7.20-7.24 (2H, m), 7.30-7.45 (5H, m), 7.51 (1H, d, J=8.4 Hz).

The starting material, 3-ethynyl-pyridin-2,6-diamine, was synthesized as follows.

Manufacturing Example 13-1-1

3-Iodo-pyridin-2,6-diamine

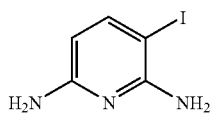

2,6-Diaminopyridine (100 g, 916 mmol) was dissolved in dimethyl sulfoxide (400 mL), and N-iodosuccinimide (100 g, 445 mmol) was added in one portion while stirring at room temperature. The reaction solution was stirring for 10 minutes at room temperature. Water (3.5 L) was added to the reaction solution, and the precipitated solids were filtered out. The resulting aqueous layer was extracted with ethyl acetate (1.3 L) 3 times. The ethyl acetate layers were combined and the solvent was evaporated under a reduced pressure. The residue was purified by silica gel chromatography (heptane:ethyl acetate=2:3) to obtain the title compound (23.8 g, 22.8%).

$^1$H-NMR Spectrum (DMSO-d$_6$) δ (ppm): 5.41 (2H, brs), 5.57 (1H, d, J=8.0 Hz), 5.64 (2H, brs), 7.37 (1H, d, J=8.0 Hz).

Manufacturing Example 13-1-2

3-Trimethylsilanylethynyl-pyridin-2,6-diamine

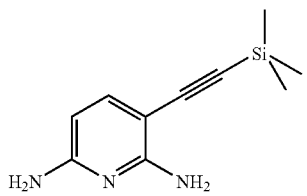

To a mixture of 3-iodo-pyridin-2,6-diamine (20.0 g, 85.2 mmol) described in Manufacturing Example 13-1-1, trimethylsilyl acetylene (24.2 mL, 170 mmol), copper (I) iodide (3.25 g, 17.0 mmol) N,N-diisopropylethylamine (19.1 g, 148 mmol) and N-methylpyrrolidinone (286 mL) was added tetrakis(triphenylphosphine)palladium (0) (9.81 g, 8.52 mmol) under argon atmosphere, which was stirred for 30 minutes at room temperature. The reaction solution was partitioned into water and ethyl acetate. The ethyl acetate layer was washed with water 4 times and dried over sodium sulfate, and the solvent was evaporated under a reduced pressure. The residue was purified by NH silica gel chromatography (heptane:ethyl acetate=4:1 then 1:1). The solids obtained by concentrating the eluate under a reduced pressure were washed with heptane containing a small amount of ethyl acetate to obtain the title compound (10.5 g, 60.0%).

$^1$H-NMR Spectrum (DMSO-d$_6$) δ (ppm): 0.20 (9H, s), 5.53 (2H, brs), 5.66 (1H, d, J=8.0 Hz), 5.95 (2H, brs), 7.11 (1H, d, J=8.0 Hz).

Manufacturing Example 13-1-3

3-Ethynyl-pyridin-2,6-diamine

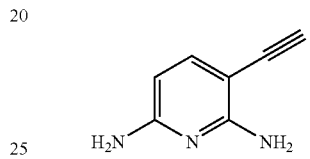

To a solution of 3-trimethylsilanylethynyl-pyridin-2,6-diamine (7.0 g, 34.1 mmol) described in Manufacturing Example 13-1-2 in tetrahydrofuran (100 mL) was added tetrabutylammonium fluoride (1M tetrahydrofuran solution, 17 mL, 17 mmol) on an ice bath, which was stirred for 10 minutes at room temperature. Water was added to the reaction solution, which was then extracted with ethyl acetate 3 times. The extract was dried over sodium sulfate, and the solvent was evaporated under a reduced pressure. The residue was purified by silica gel chromatography (ethyl acetate) to obtain the title compound (3.35 g, 73.8%).

$^1$H-NMR Spectrum (DMSO-d$_6$) δ (ppm): 4.08 (1H, s), 5.57 (2H, brs), 5.68 (1H, d, J=8.0 Hz), 5.89 (2H, brs), 7.14 (1H, d, J=8.0 Hz).

Example 14

3-(3-(4-Pyridin-2-yloxymethyl)-benzyl)-isoxazol-5-yl)-pyridine-2,6-diamine

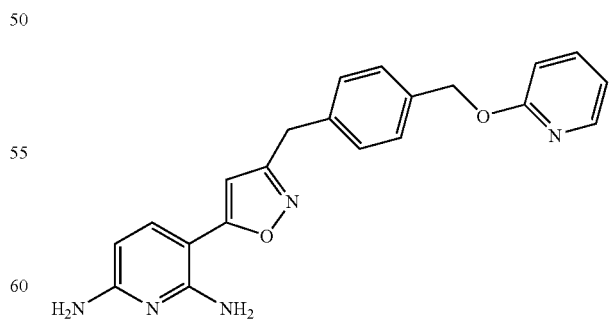

To a solution of 3-ethynyl-pyridin-2,6-diamine (120 mg, 0.90 mmol) described in Manufacturing Example 13-1-3 and 4-(pyridine-2-yloxymethyl)-phenyl-acetohydroximoyl chloride (390 mg, 1.41 mmol) described in Manufacturing Example 2-1-5 in tetrahydrofuran (5.0 mL) was added triethylamine (502 μL, 3.6 mmol) at 0° C. The reaction mixture was stirred for 1 hour and 30 minutes at room temperature. The mixture was partitioned into ethyl acetate and water. The organic layer was separated, washed with water and saturated aqueous sodium chloride, and dried over anhydrous magnesium sulfate, and the solvent was evaporated under a reduced pressure. The residue was purified by silica gel column chromatography (heptane:ethyl acetate=1:1, then ethyl acetate) to obtain the title compound (290 mg, 86.2%).

$^1$H-NMR Spectrum (DMSO-$d_6$) δ (ppm): 3.95 (2H, s), 5.31 (2H, s), 5.79 (2H, brs), 5.82 (1H, d, J=8.4 Hz), 6.11 (2H, brs), 6.37 (1H, s), 6.84-6.86 (1H, m), 6.97-7.00 (1H, m), 7.31 (2H, d, J=8.2 Hz), 7.39 (2H, d, J=8.2 Hz), 7.51 (1H, d, J=8.4 Hz), 7.69-7.73 (1H, m), 8.16-8.18 (1H, m).

Example 15

3-(3-(4-(6-Methyl-pyridin-2-yloxymethyl)-benzyl)-isoxazol-5-yl)-pyridin-2,6-diamine

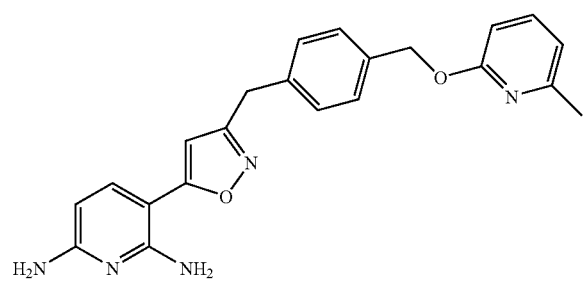

To a solution of 3-ethynyl-pyridin-2,6-diamine (300 mg, 2.25 mmol) described in Manufacturing Example 13-1-3 in anhydrous tetrahydrofuran (30 mL) was added (4-(6-methyl-pyridin-2-yloxymethyl)-phenyl)-acetohydroximoyl chloride (1.50 g, 5.16 mmol) described in Manufacturing Example 3-1-5 under nitrogen atmosphere at room temperature. Triethylamine (1.25 mL, 9.00 mmol) was then added dropwise at room temperature, and stirred for 1.5 hours at room temperature. Water and ethyl acetate were added to the reaction mixture at room temperature, and the organic layer was separated. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=2:1) to obtain the title compound (637 mg, 73%).

$^1$H-NMR Spectrum (DMSO-$d_6$) δ (ppm): 2.39 (3H, s), 3.96 (2H, s), 5.29 (2H, s), 5.80 (2H, brs), 5.83 (1H, d, J=8.8 Hz), 6.11 (2H, brs), 6.37 (1H, s), 6.63 (1H, dd, J=0.4, 8.2 Hz), 6.83 (1H, dd, J=0.4, 7.4 Hz), 7.31 (2H, d, J=8.0 Hz), 7.41 (2H, d, J=8.4 Hz), 7.51 (1H, d, J=8.4 Hz), 7.58 (1H, t, J=8.0 Hz).

Example 16

3-(3-(4-Butoxymethyl-benzyl)-isoxazol-5-yl)-pyridin-2,6-diamine

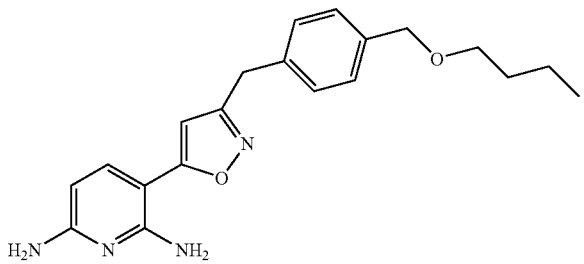

To a solution of 3-ethynyl-pyridin-2,6-diamine (14.6 mg, 0.11 mmol) described in Manufacturing Example 13-1-3 and 4-butoxymethyl-phenyl-acetohydroximoyl chloride (28 mg, 0.11 mmol) described in Manufacturing Example 4-1-4 in tetrahydrofuran was added triethylamine (31 μL, 0.22 mmol), which was stirred for 4 hours at room temperature. The reaction solution was partitioned into water and ethyl acetate at room temperature. The organic layer was washed with saturated aqueous sodium chloride and dried over anhydrous magnesium sulfate, and the solvent was evaporated under a reduced pressure. The residue was purified by NH silica gel column chromatography (heptane:ethyl acetate=2:1) and then purified again by reverse-phase high performance liquid chromatography (using an acetonitrile-water mobile phase containing 0.1% trifluoroacetic acid) to obtain the title compound (6.7 mg, 13%) as a trifluoroacetic acid salt.

MS m/e (ESI) 353.34 (MH$^+$)

Example 17

3-(3-(4-Phenoxy-benzyl)-isoxazol-5-yl)-pyridin-2,6-diamine

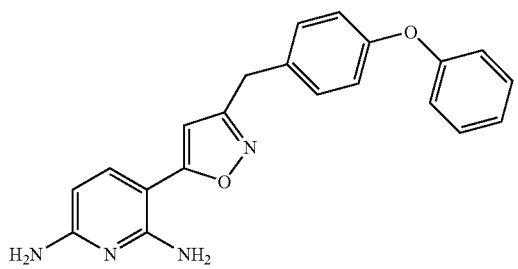

To a solution of 3-ethynyl-pyridin-2,6-diamine (170 mg, 28 mmol) described in Manufacturing Example 13-1-3 in anhydrous tetrahydrofuran (10 mL) was added (4-phenoxy-benzene)-acetohydroximoyl chloride (652 mg, 2.49 mmol) described in Manufacturing Example 17-1-4 under nitrogen atmosphere at room temperature. Triethylamine (714 μL, 5.12 mmol) was then added dropwise, and stirred for 1 hour at room temperature. The reaction mixture was partitioned into water and ethyl acetate at room temperature. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=1:2 then 2:1) to obtain the title compound (314 mg, 68%).

$^1$H-NMR Spectrum (DMSO-d$_6$) δ (ppm): 4.00 (2H, s), 4.74 (2H, brs), 5.50 (2H, brs), 5.94 (1H, d, J=8.8 Hz), 6.03 (1H, s), 6.96-7.02 (2H, m), 7.08-7.12 (1H, m), 7.22-7.26 (5H, m), 7.30-7.35 (1H, m), 7.52 (1H, d, J=8.8 Hz).

The starting material, (4-phenoxy-benzene)-acetohydroximoyl chloride, was synthesized as follows.

Manufacturing Example 17-1-1

Sodium 2-nitro-1-(4-phenoxy-phenyl)-ethanolate

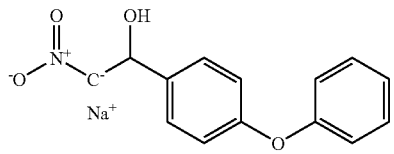

To a solution of 4-phenoxybenzaldehyde (1.5 g, 7.56 mmol) in methanol (12 mL) was added dropwise sodium methoxide (1.49 M methanol solution, 0.19 mL, 0.91 mmol) under nitrogen atmosphere at room temperature. Nitromethane (530 μL, 9.84 mmol) was added dropwise to the reaction solution on an ice bath (0° C.). Sodium methoxide (1.49 M methanol solution, 1.66 mL, 8.16 mmol) was added dropwise thereto at room temperature, and the solution was stirred for 30 minutes at room temperature. The precipitated solids were filtered and dried under reduced pressure, and the solids were dried azeotropically with toluene to obtain the title compound (1.17 g, 55%).

$^1$H-NMR Spectrum (DMSO-d$_6$) δ (ppm): 5.38 (1H, m), 5.73 (1H, d, J=5.2 Hz), 6.58 (1H, d, J=4.4 Hz), 6.91-7.00 (4H, m), 7.09-7.13 (1H, m), 7.34-7.39 (4H, m).

Manufacturing Example 17-1-2

1-((E)-2-Nitro-vinyl)-4-phenoxy-benzene

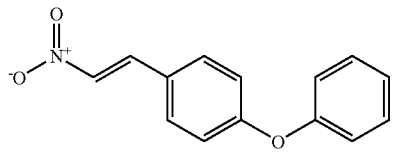

A solution of sodium 2-nitro-1-(4-phenoxy-phenyl)-ethanolate (1.17 g, 4.16 mmol) described in Manufacturing Example 17-1-1, acetic anhydride (510 mg, 4.99 mmol) and triethylamine (696 μL, 4.99 mmol) in anhydrous tetrahydrofuran (20 mL) was stirred overnight under nitrogen atmosphere at room temperature. The reaction mixture was partitioned into water and ethyl acetate at room temperature. The organic layer was washed with water and saturated aqueous sodium chloride, and dried over anhydrous magnesium sulfate, and the solvent was evaporated under a reduced pressure to obtain the title compound (1.4 g, 70%, purity: ca. 50%) as a crude product.

Manufacturing Example 17-1-3

1-(2-Nitro-ethyl)-4-phenoxy-benzene

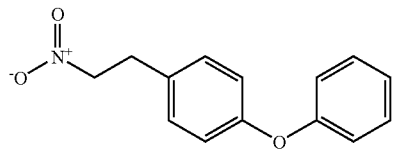

To a solution of 1-((E)-2-nitro-vinyl)-4-phenoxy-benzene (1.40 g, 2.90 mmol, purity: 50%) described in Manufacturing Example 17-1-2 in methanol (15 mL) was added sodium borohydride (274 mg, 7.25 mmol) at room temperature while cooling appropriately under nitrogen atmosphere, which was stirred for 10 minutes at room temperature. Water was then added dropwise at room temperature while cooling appropriately. The reaction mixture was extracted with ethyl acetate. The organic layer was washed with water and saturated aqueous sodium chloride, and dried over anhydrous magnesium sulfate, and the solvent was evaporated under a reduced pressure. The residue was purified by silica gel column chromatography (ethyl acetate:heptane=1:5) to obtain the title compound (199 mg, 28%).

$^1$H-NMR Spectrum (DMSO-d$_6$) δ (ppm): 3.21 (2H, t, J=6.8 Hz), 4.84 (2H, t, J=6.8 Hz), 6.94-7.00 (4H, m), 7.11-7.15 (1H, m), 7.28-7.30 (2H, m), 7.36-7.40 (2H, m).

Manufacturing Example 17-1-4

(4-Phenoxy-benzene)-acetohydroximoyl chloride

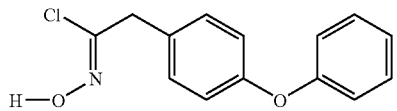

To a solution of 1-(2-nitro-ethyl)-4-phenoxy-benzene (100 mg, 0.41 mmol) described in Manufacturing Example 17-1-3 in methanol (3 mL) was added sodium methoxide (1.49 M methanol solution, 83.9 μL, 0.41 mmol) under nitrogen atmosphere, which was stirred for 30 minutes at room temperature. The reaction mixture was concentrated under a reduced pressure. Anhydrous methylene chloride (3 mL) was added to the residue. Titanium (IV) chloride (54.2 μL, 0.49 mmol) was added dropwise to the reaction mixture on an ice bath (0° C.), and stirred for 30 minutes at room temperature. Water, ethyl acetate and tetrahydrofuran were added on the ice bath (0° C.) to partition the reaction mixture. The organic layer was washed with water and saturated aqueous sodium chloride, and dried over anhydrous magnesium sulfate, and the solvent was evaporated under a reduced pressure. The residue was purified by silica gel column chromatography (ethyl acetate:heptane=1:5) to obtain the title compound (51 mg, 47%).

$^1$H-NMR Spectrum (DMSO-d$_6$) δ (ppm): 3.80 (2H, s), 6.96-7.03 (4H, m), 7.12-7.16 (1H, m), 7.26-7.28 (2H, m), 7.36-7.41 (2H, m), 11.7 (1H, s).

Example 18

3-(3-(4-(2-Fluoro-benzyloxy)-benzyl)-isoxazol-5-y)-pyridin-2,6-diamine

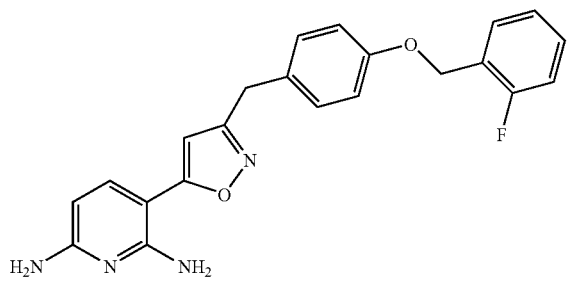

To a solution of 4-(5-(2,6-diamino-pyridin-3-yl)-isoxazol-3-ylmethyl)-phenol (72.4 mg, 0.26 mmol) described in Manufacturing Example 18-1-1 in tetrahydrofuran (3 mL) was added 5 N aqueous sodium hydroxide solution (51.2 μL, 0.26 mmol), which was irradiated by ultrasonic wave for 5 minutes. Next, the reaction solution was concentrated under a reduced pressure to obtain solids (77.9 mg). To a solution of the resulting solids (14.5 mg, 0.05 mmol) in N,N-dimethylformamide (1 mL) was added 2-fluorobenzyl bromide (11.5 μL, 0.10 mmol), which was stirred for 2 hours at room temperature. The reaction solution was partitioned into water and ethyl acetate. The organic layer was washed with water and saturated aqueous sodium chloride, and dried over anhydrous magnesium sulfate, and the solvent was evaporated under a reduced pressure. The residue was purified by silica gel column chromatography (ethyl acetate) and then further purified by reverse-phase high performance liquid chromatography (using an acetonitrile-water mobile phase containing 0.1% trifluoroacetic acid) to obtain the title compound (6.7 mg, 36%) as a trifluoroacetic acid salt.

$^1$H-NMR Spectrum (CDCl$_3$) δ (ppm): 3.96 (2H, s), 4.57 (2H, brs), 5.12 (2H, s), 5.90 (2H, brs), 5.91 (1H, d, J=8.4 Hz), 5.98 (1H, s), 6.95 (2H, d, J=8.4 Hz), 7.05-7.11 (1H, m), 7.14-7.24 (1H, m), 7.20 (2H, d, J=8.4 Hz), 7.28-7.33 (1H, m), 7.48 (1H, d, J=8.4 Hz), 7.45-7.51 (1H, m).

MS m/e (ESI) 391.01 (MH$^+$)

Manufacturing Example 18-1-1

4-(5-(2,6-Diamino-pyridine-3-yl)-isoxazol-3-ylmethyl)-phenol

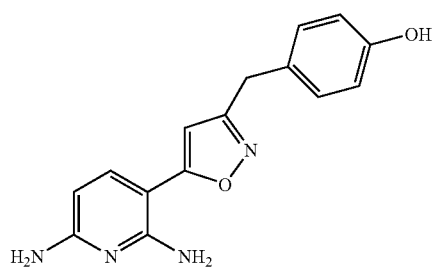

To a solution of 3-(3-(4-benzyloxy-benzyl)-isoxazol-5-yl)-pyridin-2,6-diamine (100 mg, 0.27 mmol) described in Example 13 in trifluoroacetic acid (3 mL) was added thioanisole (126 μL) at room temperature, which was stirred for 2 hours at room temperature. Saturated aqueous sodium hydrogen carbonate solution was added to the reaction solution at 0° C., which was then extracted with ethyl acetate. The organic layer was washed with water and saturated aqueous sodium chloride, and dried over anhydrous magnesium sulfate, and the solvent was evaporated under a reduced pressure. The residue was purified by silica gel column chromatography (ethyl acetate) to obtain the title compound (72.4 mg, 95%).

$^1$H-NMR Spectrum (DMSO-d$_6$) δ (ppm): 3.82 (2H, s), 5.79 (2H, brs), 5.83 (1H, d, J=8.4 Hz), 6.10 (2H, brs), 6.32 (1H, s), 6.70 (2H, d, J=8.4 Hz), 7.09 (2H, d, J=8.4 Hz), 7.51 (1H, d, J=8.4 Hz), 9.27 (1H, s).

Example 19

3-(3-(4-(3-Fluoro-benzyloxy)-benzyl)-isoxazol-5-yl)-pyridin-2,6-diamine

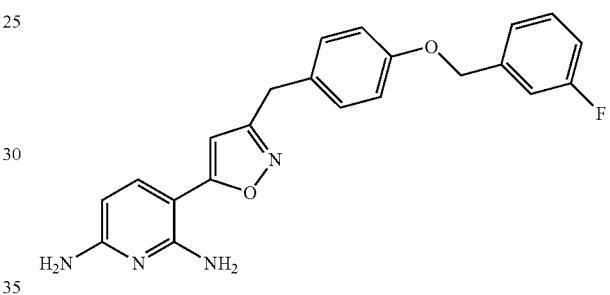

To a solution of 4-(5-(2,6-diamino-pyridin-3-yl)-isoxazol-3-ylmethyl)-phenol (72.4 mg, 0.26 mmol) described in Manufacturing Example 18-1-1 in tetrahydrofuran (3 mL) was added 5 N aqueous sodium hydroxide solution (51.2 μL, 0.26 mmol), which was irradiated by ultrasonic wave for 5 minutes. Next, the reaction solution was concentrated under a reduced pressure to obtain solids (77.9 mg). To a solution of the resulting solids (11.3 mg, 0.04 mmol) in N,N-dimethylformamide (1 mL) was added 3-fluorobenzyl bromide (9.1 μL, 0.07 mmol), which was stirred for 2 hours at room temperature. The reaction solution was partitioned into water and ethyl acetate. The organic layer was washed with water and saturated aqueous sodium chloride, and dried over anhydrous magnesium sulfate, and the solvent was evaporated under a reduced pressure. The residue was purified by silica gel column chromatography (ethyl acetate), and further purified by reverse-phase high performance liquid chromatography (using an acetonitrile-water mobile phase containing 0.1% trifluoroacetic acid) to obtain the title compound (6.7 mg, 36%) as a trifluoroacetic acid salt.

MS m/e (ESI) 391.34 (MH$^+$)

Example 20

3-(3-(4-(4-Fluoro-benzyloxy)-benzyl)-isoxazol-5-yl)-pyridin-2,6-diamine

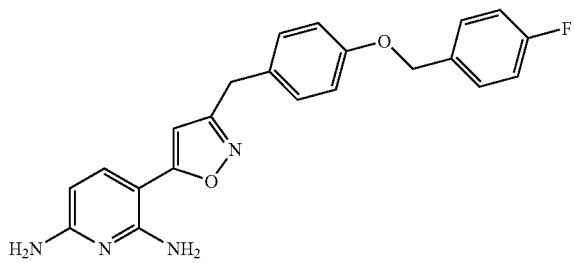

To a solution of 4-(5-(2,6-diamino-pyridin-3-yl)-isoxazol-3-ylmethyl)-phenol (72.4 mg, 0.26 mmol) described in Manufacturing Example 18-1-1 in tetrahydrofuran (3 mL) was added 5 N aqueous sodium hydroxide solution (51.2 μL, 0.26 mmol), which was irradiated by ultrasonic wave for 5 minutes. Next, the reaction solution was concentrated under a reduced pressure to obtain solids (77.9 mg). To a solution of the resulting solids (13.7 mg, 0.05 mmol) in N,N-dimethylformamide (1 mL) was added 4-fluorobenzyl bromide (11.2 μL, 0.09 mmol), which was stirred for 2.5 hours at room temperature. The reaction solution was partitioned into water and ethyl acetate. The organic layer was washed with water and saturated aqueous sodium chloride, and dried over anhydrous magnesium sulfate, and the solvent was evaporated under a reduced pressure. The residue was purified by silica gel column chromatography (ethyl acetate), the mixture was purified by reverse-phase high performance liquid chromatography (using an acetonitrile-water mobile phase containing 0.1% trifluoroacetic acid) and then purified by preparative thin-layer chromatography (ethyl acetate:hexane=1:1) to obtain the title compound (4.0 mg, 18%).

$^1$H-NMR Spectrum (CDCl$_3$-d$_6$) δ (ppm): 3.96 (2H, s), 4.53 (2H, brs), 5.00 (2H, s), 5.30 (2H, brs), 5.91 (1H, d, J=8.0 Hz), 5.98 (1H, s), 6.92 (2H, dd, J=2.0, 6.8 Hz), 7.05-7.15 (2H, m), 7.20 (2H, d, J=8.4 Hz), 7.26-7.46 (2H, m), 7.48 (1H, d, J=8.0 Hz).

MS m/e (ESI) 391.04 (MH$^+$)

Example 21

3-(3-(4-Cyclopropylmethoxy-benzyl)-isoxazol-5-yl)-pyridin-2,6-diamine

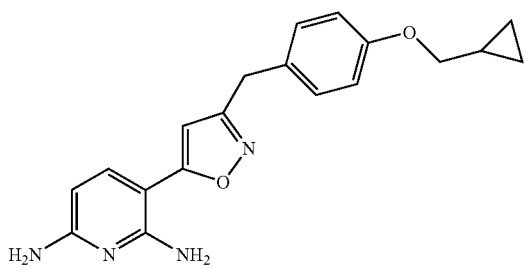

To a solution of 4-(5-(2,6-diamino-pyridin-3-yl)-isoxazol-3-ylmethyl)-phenol (72.4 mg, 0.26 mmol) described in Manufacturing Example 18-1-1 in tetrahydrofuran (3 mL) was added 5 N aqueous sodium hydroxide solution (51.2 μL, 0.26 mmol), which was irradiated by ultrasonic wave for 5 minutes. Next, the reaction solution was concentrated under a reduced pressure to obtain solids (77.9 mg). To a solution of the resulting solids (8.3 mg, 0.03 mmol) in N,N-dimethylformamide (1 mL) was added cyclopropylmethyl bromide (5.3 μL, 0.06 mmol), which was stirred for 5 hours at room temperature. The mixture was purified by reverse-phase high performance liquid chromatography (using an acetonitrile-water mobile phase containing 0.1% trifluoroacetic acid), and then further purified by preparative thin-layer chromatography (ethyl acetate) to obtain the title compound (1.1 mg, 12%).

$^1$H-NMR Spectrum (CDCl$_3$-d$_6$) δ (ppm): 0.33-0.36 (2H, m), 0.63-0.66 (2H, m), 1.24-1.29 (1H, s), 3.79 (2H, d, J=4.8 Hz), 3.96 (2H, s), 4.57 (2H, brs), 5.34 (2H, brs), 5.92 (1H, d, J=8.4 Hz), 5.99 (1H, s), 6.87 (2H, dd, J=2.0, 6.8 Hz), 7.19 (2H, dd, J=2.0, 6.8 Hz), 7.49 (1H, d, J=8.4 Hz).

MS m/e (ESI) 337.11 (MH$^+$)

Example 22

3-(3-(4-(Pyridin-2-ylmethoxy)-benzyl)-isoxazol-5-yl)-pyridin-2,6-diamine

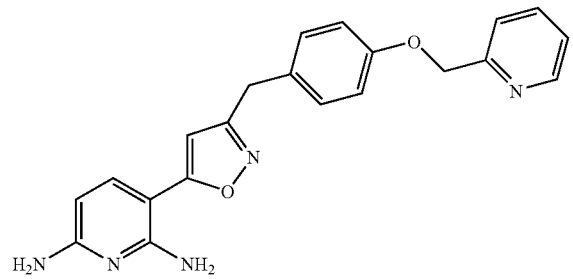

To a solution of 4-(5-(2,6-diamino-pyridin-3-yl)-isoxazol-3-ylmethyl)-phenol (49.7 mg, 0.18 mmol) described in Manufacturing Example 18-1-1 in tetrahydrofuran (3 mL) was added 5 N aqueous sodium hydroxide solution (35.2 μL, 0.18 mmol), which was irradiated by ultrasonic wave for 5 minutes. Next, the reaction solution was concentrated under a reduced pressure to obtain solids (90.6 mg). The resulting solids were made into an N,N-dimethylformamide (3 mL) solution. Tetrahydrofuran (390 μL) and 1 N aqueous sodium hydroxide solution (390 μL, 0.39 mol) were added to 2-picolyl chloride hydrochloride (50 mg, 0.39 mmol), and then the organic layer was separated to obtain tetrahydrofuran solution of 2-picolyl chloride. A part of the solution (0.30 mL) was added to the aforementioned N,N-dimethylformamide solution, and stirred for 15 hours at room temperature. The reaction solution was partitioned into water and ethyl acetate. The organic layer was washed with water and saturated aqueous sodium chloride, and dried over anhydrous magnesium sulfate, and the solvent was evaporated under a reduced pressure. The residue was purified by silica gel column chromatography (ethyl acetate) to obtain the title compound (42.5 mg, 38%).

$^1$H-NMR Spectrum (DMSO-d$_6$) δ (ppm): 3.88 (2H, s), 5.15 (2H, s), 5.79 (2H, brs), 5.83 (1H, dd, J=1.2, 8.4 Hz), 6.11 (2H, brs), 6.35 (1H, s), 6.97 (2H, d, J=8.0 Hz), 1.22 (2H, d, J=8.4 Hz), 7.33 (1H, dd, J=5.2, 8.0 Hz), 7.49 (1H, d, J=8.0 Hz), 7.51 (1H, d, J=8.0), 7.82 (1H, dd, J=8.0, 8.0 Hz), 8.57 (1H, dd, J=0.8, 4.8 Hz).
MS m/e (ESI) 374.28 (MH+).

Example 23

3-(3-(4-(6-Methyl-pyridin-2-ylmethoxy)-benzyl)-isoxazol-5-yl)-pyridin-2,6-diamine

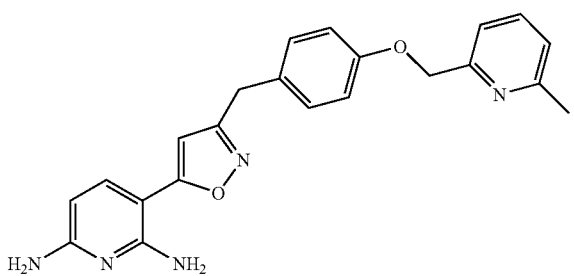

To 4-(5-(2,6-diamino-pyridin-3-yl)-isoxazol-3-ylmethyl)-phenol (150 mg, 0.53 mmol) described in Manufacturing Example 18-1-1 were added methanol (3 mL) and 1 N aqueous sodium hydroxide solution (0.53 mL), which was then dissolved by irradiating ultrasonic wave. This solution was concentrated under a reduced pressure. To the resulting residue was added 2-chloromethyl-6-methyl-pyridine (90.2 mg, 0.64 moL) described in manufacturing Example 10-1-1 and N,N-dimethylformamide (2 mL), which was stirred for 2 hours and 50 minutes at 60° C. The reaction solution was partitioned into water and ethyl acetate. The organic layer was evaporated under a reduced pressure. The residue was purified by NH silica gel column chromatography (heptane:ethyl acetate=1:2, then ethyl acetate) to obtain the title compound (106 mg, 51.5%).
$^1$H-NMR Spectrum (DMSO-$d_6$) δ (ppm): 2.48 (3H, s), 3.88 (2H, s), 5.10 (2H, s), 5.78 (2H, brs), 5.82 (1H, d, J=8.4 Hz), 6.10 (2H, brs), 6.34 (1H, s), 6.96 (2H, d, J=8.0 Hz), 7.18 (1H, d, J=8.0 Hz), 7.22 (2H, d, J=8.0 Hz), 7.27 (1H, d, J=8.0 Hz), 7.50 (1H, d, J=8.4 Hz), 7.70 (1H, dd, J=8.0, 8.0 Hz).

Example 24

3-(3-(4-(4-Methyl-pyridin-2-ylmethoxy)-benzyl)-isoxazol-5-yl)-pyridin-2,6-diamine

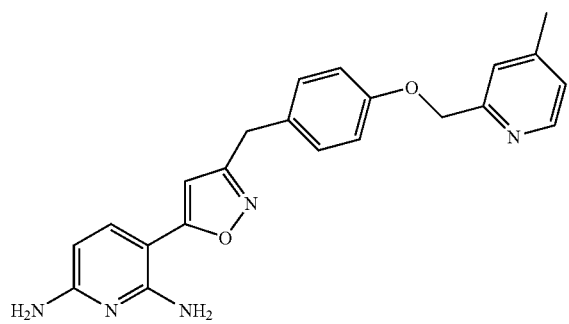

To 4-(5-(2,6-diamino-pyridin-3-yl)-isoxazol-3-ylmethyl)-phenol (80 mg, 0.28 mmol) described in Manufacturing Example 18-1-1 were added methanol (4 mL) and 1 N aqueous sodium hydroxide solution (0.29 mL), which was then dissolved by irradiating ultrasonic wave. This solution was concentrated under a reduced pressure. To the resulting residue was added 2-chloromethyl-4-methyl-pyridine (50.9 mg, 0.36 moL) described in Manufacturing Example 11-1-4 and N,N-dimethylformamide (3 mL), which was stirred for 10 minutes at 60° C. The reaction solution was partitioned into water and ethyl acetate. The organic layer was evaporated under a reduced pressure. The residue was purified by NH silica gel column chromatography (heptane:ethyl acetate=1:2, then ethyl acetate) to obtain the title compound (40 mg, 36.5%).

$^1$H-NMR Spectrum (DMSO-$d_6$) δ (ppm): 2.32 (3H, s), 3.88 (2H, s), 5.10 (2H, s), 5.79 (2H, brs), 5.82 (1H, d, J=8.4 Hz), 6.10 (2H, brs), 6.35 (1H, s), 6.97 (2H, d, J=8.0 Hz), 7.15 (1H, d, J=5.2 Hz), 7.22 (2H, d, J=8.0 Hz), 7.34 (1H, s), 7.50 (1H, d, J=8.4 Hz), 8.41 (1H, d, J=5.2 Hz).

Example 25

3-(3-(6-Benzyloxy-pyridin-3-ylmethyl)-isoxazol-5-yl)-pyridin-2,6-diamine

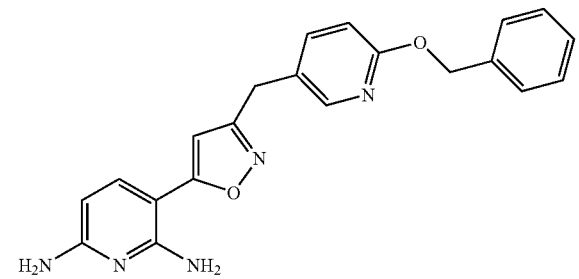

To a solution of 3-ethynyl-pyridin-2,6-diamine (230 mg, 1.73 mmol) described in Manufacturing Example 13-1-3 in anhydrous tetrahydrofuran (20 mL) was added (2-benzyloxy-pyridin-5-yl)-acetohydroximoyl chloride (1.00 g, 3.61 mmol) described in Manufacturing Example 12-1-5 under nitrogen atmosphere at room temperature. Triethylamine (965 μL, 6.92 mmol) was added dropwise to the mixture and stirred for 1.5 hours at room temperature. The reaction mixture was partitioned into water and ethyl acetate at room temperature. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=2:1) to obtain the title compound (470 mg, 73%).
$^1$H-NMR Spectrum (DMSO-$d_6$) δ (ppm): 3.92 (2H, s), 5.33 (2H, s), 5.81 (2H, brs), 5.83 (1H, d, J=8.4 Hz), 6.11 (2H, brs), 6.40 (1H, s), 6.85 (1H, d, J=8.8 Hz), 7.31-7.39 (3H, m), 7.42-7.44 (2H, m), 7.52 (1H, d, J=8.4 Hz), 7.66 (1H, dd, J=2.4, 8.4 Hz), 8.14 (1H, d, J=2.4 Hz).

Example 26

3-(3-(4-Benzyloxy-benzyl)-isoxazol-5-yl)-6-methoxymethyl-pyridin-2-ylamine

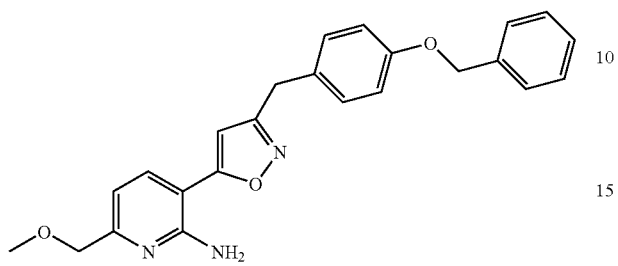

To a mixture of (4-benzyloxy-phenyl)-acetohydroximoyl chloride (19 mg, 0.069 mmol) described in Manufacturing Example 1-1-3 and tetrahydrofuran (1 mL) were added 3-ethynyl-6-methoxymethyl-pyridin-2-ylamine (8.6 mg, 0.053 mmol) described in Manufacturing Example 26-1-7 and triethylamine (15 μL, 0.11 mmol) at room temperature, which was stirred for 5.5 hours at room temperature. Water was added at room temperature to the reaction mixture, which was then extracted with ethyl acetate-tetrahydrofuran (3:2). The organic layer was washed with saturated aqueous sodium chloride, and the solvent was evaporated under a reduced pressure. The residue was purified by NH silica gel column chromatography (ethyl acetate:heptane=2:3) to obtain the title compound (8.8 mg, 41%).

$^1$H-NMR Spectrum (CDCl$_3$) δ (ppm): 3.47 (3H, s), 3.99 (2H, s), 4.42 (2H, s), 5.05 (2H, s), 5.50 (2H, brs), 6.23 (1H, s), 6.82 (1H, d, J=7.9 Hz), 6.93-6.97 (2H, m), 7.18-7.22 (2H, m), 7.31-7.44 (5H, m), 7.72 (1H, d, J=7.7 Hz).

The starting material, 3-ethynyl-6-methoxymethyl-pyridin-2-ylamine, was synthesized as follows.

Manufacturing Example 26-1-1

2-Amino-6-chloro-nicotinic acid

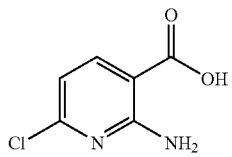

A mixture of 2,6-dichloro-nicotinic acid (31 g, 0.14 mol) and 28% aqueous ammonia solution (200 mL) was stirred in a sealed tube for 10 hours at 135° C. This reaction solution was cooled to room temperature, and the excess ammonia gas was removed under a reduced pressure. Water was added to the residue to a total of 1000 mL, the mixture was cooled to 0° C., and citric acid was added to a pH being about 6. The precipitated solids were filtered out to obtain the title compound (12 g, 49%).

$^1$H-NMR Spectrum (DMSO-d$_6$) δ (ppm): 6.63 (1H, d, J=8.1 Hz), 7.55 (2H, brs), 8.02 (1H, d, J=8.1 Hz).

Manufacturing Example 26-1-2

2-Amino-6-chloro-nicotinic acid methyl ester

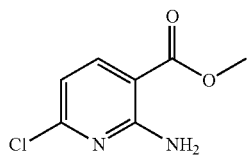

Concentrated sulfuric acid (25 mL) and 2-amino-6-chloro-nicotinic acid (4.3 g, 25 mmol) described in Manufacturing Example 26-1-1 were added to methanol (50 mL) on an ice bath, and stirred at 70° C. for 5 hours. The reaction mixture was cooled and then neutralized by addition of aqueous sodium hydrogen carbonate (90 g) solution. The precipitated solids were filtered to obtain the title compound (3.2 g, 17 mmol, 68%).

$^1$H-NMR Spectrum (CDCl$_3$) δ (ppm): 3.88 (3H, s), 6.62 (1H, d, J=8.2 Hz), 8.05 (1H, d, J=8.1 Hz).

Manufacturing Example 26-1-3

Tributyl-methoxymethyl-stannane

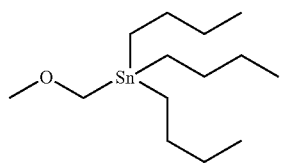

To a mixture of diisopropylamine (9.4 mL, 67 mmol) and tetrahydrofuran (150 mL) was added dropwise n-butyl lithium (2.4 M n-hexane solution, 25 mL, 61 mmol) at −78° C., which was stirred for 30 minutes at the same temperature. Tributyltin hydride (16 mL, 61 mmol) was added dropwise to the reaction mixture at the same temperature, and stirred for 30 minutes at 0° C. The reaction mixture was cooled to −78° C., and chloromethyl methyl ether (4.6 mL, 61 mmol) was added dropwise thereto. The reaction mixture was gradually warmed to room temperature. Water was added to the reaction mixture, which was then extracted with diethyl ether. The organic layer was washed with saturated aqueous sodium chloride, and the solvent was evaporated under a reduced pressure. The residue was purified by neutral silica gel column chromatography (ethyl acetate:heptane=1:30) to obtain the title compound (18 g, 86%).

$^1$H-NMR Spectrum (CDCl$_3$) δ (ppm): 0.88-0.93 (15H, m), 1.26-1.35 (6H, m), 1.47-1.55 (6H, m), 3.30 (3H, s), 3.71 (2H, t, J=6.8 Hz).

Manufacturing Example 26-1-4

2-Amino-6-methoxymethyl-nicotinic acid methyl ester

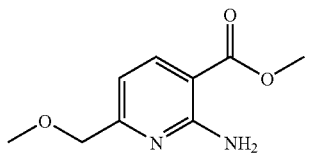

A mixture of 2-amino-6-chloro-nicotinic acid methyl ester (1.4 g, 7.6 mmol) described in Manufacturing Example 26-1-2, tributyl-methoxymethyl-stannane (3.1 g, 9.1 mmol) described in Manufacturing Example 26-1-3, tetrakis(triphenylphosphine)palladium (440 mg, 0.38 mmol) and N-methylpyrrolidinone (20 mL) was stirred for 3.5 hours at 130° C. The reaction mixture was cooled to room temperature, and aqueous potassium fluoride solution and ethyl acetate were added to the reaction mixture, which was then filtered through a Celite pad. The organic layer was separated and washed with saturated aqueous sodium chloride, and the solvent was evaporated under a reduced pressure. The residue was purified by silica gel column chromatography (ethyl acetate:heptane=1:2) to obtain the title compound (0.93 g, 63%).

$^1$H-NMR Spectrum (CDCl$_3$) δ (ppm): 3.47 (3H, s), 3.88 (3H, s), 4.41 (2H, s), 6.74 (1H, d, J=7.9 Hz), 8.14 (1H, d, J=7.9 Hz).

Manufacturing Example 26-1-5

(2-Amino-6-methoxymethyl-pyridin-3-yl)methanol

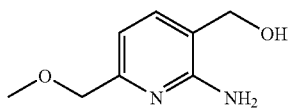

To a mixture of lithium aluminum hydride (80%, 220 mg, 4.6 mmol) and tetrahydrofuran (5 mL) was added 2-amino-6-methoxymethyl-nicotinic acid methyl ester (300 mg, 1.5 mmol) described in Manufacturing Example 26-1-4 at 0° C., which was stirred for 20 minutes at the same temperature. An aqueous 28% ammonia solution was added dropwise to the reaction mixture at 0° C. The mixture was warmed to room temperature and filtered. The filtrate was concentrated under a reduced pressure to obtain the title compound (260 mg, 100%).

$^1$H-NMR Spectrum (CDCl$_3$) δ (ppm): 3.45 (3H, s), 4.39 (2H, s), 4.62 (2H, s), 5.03 (2H, brs), 6.70 (1H, d, J=7.3 Hz), 7.31 (1H, d, J=7.5 Hz).

Manufacturing Example 26-1-6

2-Amino-6-methoxymethyl-pyridine-3-carbaldehyde

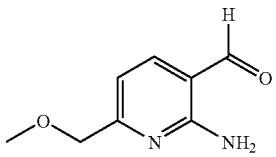

To a mixture of (2-amino-6-methoxymethyl-pyridin-3-yl)methanol (260 mg, 1.5 mmol) described in Manufacturing Example 26-1-5 and methylene chloride (15 mL) was added manganese dioxide (1.3 g, 15 mmol), which was stirred overnight at room temperature. The reaction mixture was filtered through a Celite pad, and the filtrate was concentrated under a reduced pressure. The residue was purified by silica gel column chromatography (ethyl acetate:heptane=3:2) to obtain the title compound (210 mg, 81%).

$^1$H-NMR Spectrum (CDCl$_3$) δ (ppm): 3.48 (3H, s), 4.44 (2H, s), 6.87 (1H, d, J=7.9 Hz), 7.82 (1H, d, J=7.7 Hz), 9.84 (1H, s).

Manufacturing Example 26-1-7

3-Ethynyl-6-methoxymethyl-pyridin-2-ylamine

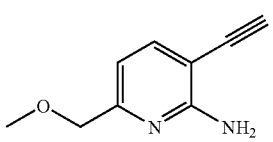

To a mixture of diisopropylamine (0.15 mL, 1.1 mmol) and tetrahydrofuran (2 mL) was added dropwise n-butyl lithium (1.6 M n-hexane solution, 0.68 mL, 1.1 mmol) at −78° C., which was stirred for 30 minutes at that temperature. Trimethysilyl diazomethane (2 M n-hexane solution, 0.50 mL, 0.99 mmol) was added to the reaction mixture at −78° C., and stirred for 30 minutes at that temperature. A mixture of 2-amino-6-methoxymethyl-pyridine-3-carbaldehyde (150 mg, 0.90 mmol) described in Manufacturing Example 26-1-6 and tetrahydrofuran (1.5 mL) was added dropwise to the reaction mixture at −78° C., and stirred for 30 minutes at 0° C. The reaction mixture was cooled to −78° C., and a mixture of acetic acid (0.10 mL) and tetrahydrofuran (1 mL) was added dropwise to the reaction mixture. This reaction mixture was gradually warmed to 0° C., and partitioned into water and ethyl acetate. The organic layer was washed with saturated aqueous sodium chloride, and the solvent was evaporated under a reduced pressure. The residue was purified by silica gel column chromatography (ethyl acetate:heptane=2:3) to obtain the title compound (73 mg, 50%).

$^1$H-NMR Spectrum (CDCl$_3$) δ (ppm): 3.40 (1H, s), 3.45 (3H, s), 4.39 (2H, s), 5.07 (2H, brs), 6.72 (1H, d, J=7.7 Hz), 7.58 (1H, d, J=7.5 Hz).

Example 27

6-Methoxymethyl-3-(3-(4-pyridin-2-yloxymethyl)-benzyl)-isoxazol-5-yl)-pyridin-2-ylamine

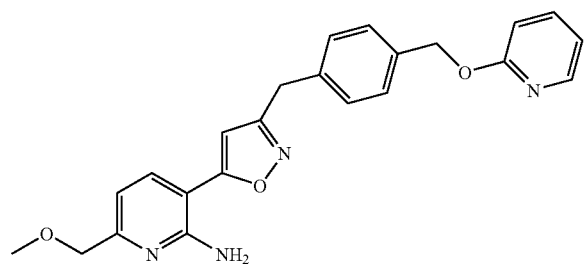

To a mixture of 4-(pyridin-2-yloxymethyl)-phenyl-acetohydroximoyl chloride (18 mg, 0.064 mmol) described in Manufacturing Example 2-1-5 and tetrahydrofuran (1 mL) were added 3-ethynyl-6-methoxymethyl-pyridin-2-ylamine (8.6 mg, 0.053 mmol) described in Manufacturing Example 26-1-7 and triethylamine (15 μL, 0.11 mmol), which was stirred for 2 hours at room temperature. The reaction mixture was partitioned into water and ethyl acetate at room temperature. The organic layer was washed with saturated aqueous sodium chloride, and the solvent was evaporated under a reduced pressure. The residue was purified by NH silica gel column chromatography (ethyl acetate:heptane=2:3) to obtain the title compound (10 mg, 48%).

$^1$H-NMR Spectrum (CDCl$_3$) δ (ppm): 3.47 (3H, s), 4.07 (2H, s), 4.44 (2H, s), 5.37 (2H, s), 5.56 (2H, brs), 6.25 (1H, s), 6.79-6.84 (2H, m), 6.87-6.91 (1H, m), 7.30 (2H, d, J=7.9 Hz), 7.44 (2H, d, J=7.9 Hz), 7.57-7.61 (1H, m), 7.73 (1H, d, J=7.9 Hz), 8.18 (1H, d, J=4.2 Hz).

Example 28

5-(3-(4-Benzyloxy-benzyl)-isoxazol-5-yl)-pyridin-2-ylamine

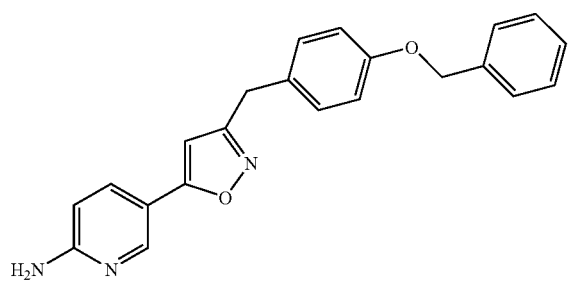

To a solution of 5-ethynyl-pyridin-2-ylamine (10 mg, 85 μmol) described in Manufacturing Example 28-1-3 and 4-benzyloxy-phenyl-acetohydroximoyl chloride (70 mg, 0.25 mmol) described in Manufacturing Example 1-1-3 in tetrahydrofuran (2 mL) was added triethylamine (35 μL, 0.25 mmol) at room temperature, which was stirred for 3 hours and 40 minutes at room temperature. The reaction solution was partitioned into water and ethyl acetate at 0° C. The organic layer was washed with saturated aqueous sodium chloride and dried over anhydrous magnesium sulfate, and the solvent was evaporated under a reduced pressure. The residue was purified by reverse-phase high performance liquid chromatography (using an acetonitrile-water mobile phase containing 0.1% trifluoroacetic acid) to obtain the title compound (1 mg, 3%) as a trifluoroacetic acid salt.

MS m/e (ESI) 358.00 (MH$^+$)

The starting material, 5-ethynyl-pyridin-2-ylamine, was synthesized as follows.

Manufacturing Example 28-1-1

2-Nitro-5-trimethylsilanylethynyl-pyridine

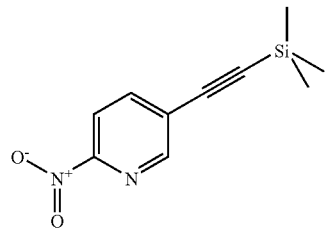

To a solution of 5-bromo-2-nitropyridine (1.00 g, 4.93 mmol) in N-methylpyrrolidinone (20 mL) were added trimethylsilyl acetylene (1.39 mL, 9.85 mmol), tetrakis(triphenylphosphine)palladium (0) (114 mg, 985 μmol), copper (I) iodide (37.5 mg, 197 μmol) and N,N-diisopropylethylamine (1.72 mL, 9.85 mmol) at room temperature, which was stirred under nitrogen atmosphere for 4 hours at 65° C. The reaction solution was partitioned into water and ethyl acetate at 0° C. The organic layer was washed with water and saturated aqueous sodium chloride, and dried over anhydrous magnesium sulfate, and the solvent was concentrated under a reduced pressure. The residue was purified by silica gel column chromatography (heptane:ethyl acetate=6:1) to obtain the title compound (490 mg, 45%).

$^1$H-NMR Spectrum (CDCl$_3$) δ (ppm): 0.298 (9H, s), 8.03-8.05 (1H, m), 8.22 (1H, J=8.4 Hz), 8.66 (1H, d, J=2.0 Hz).

Manufacturing Example 28-1-2

5-Trimethylsilanylethynyl-pyridin-2-ylamine

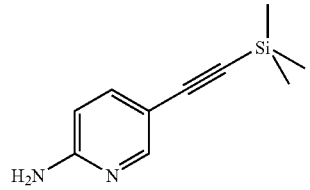

To a solution of 2-nitro-5-trimethylsilanylethynyl-pyridine (405 mg, 1.84 mmol) described in Manufacturing Example 28-1-1 in tetrahydrofuran (10 mL) and water (5 mL) were added iron powder (514 mg, 9.21 mmol) and ammonium chloride (197 mg, 3.69 mmol) at room temperature, which was stirred for 75 minutes at 70° C. The reaction solution was cooled to room temperature and filtered through a Celite pad, and the filtrate was concentrated under a reduced pressure.

The residue was purified by silica gel column chromatography (heptane:ethyl acetate=1:1) to obtain the title compound (319 mg, 91%).

¹H-NMR Spectrum (CDCl₃) δ (ppm): 0.237 (9H, s), 4.73 (2H, brs), 6.44 (1H, d, J=8:6 Hz), 7.51 (1H, dd, J=2.2, 8.4 Hz), 8.19 (1H, d, J=2.2 Hz).

Manufacturing Example 28-1-3

5-Ethynyl-pyridin-2-ylamine

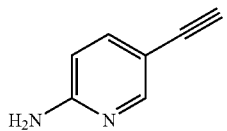

To a solution of 5-trimethylsilanylethynyl-pyridin-2-ylamine (26 mg, 137 µmol) described in Manufacturing Example 28-1-2 in tetrahydrofuran (1 mL) and methanol (1 mL) was added potassium carbonate (37.9 mg, 274 µmol) at room temperature, which was stirred for 1 hour at room temperature. The reaction solution was partitioned into water and ethyl acetate at 0° C. The organic layer was washed with saturated aqueous sodium chloride, and dried over anhydrous magnesium sulfate, and the solvent was concentrated under a reduced pressure. The residue was purified by NH silica gel column chromatography (heptane:ethyl acetate=1:1) to obtain the title compound (16 mg, 99%).

¹H-NMR Spectrum (CDCl₃) δ (ppm): 3.07 (1H, s), 4.73 (2H, brs), 6.46 (1H, d, J=8.6 Hz), 7.53 (1H, dd, J=2.2, 8.6 Hz), 8.21 (1H, s).

Example 29

3-(5-(4-Benzyloxy-benzyl)-isoxazol-3-yl)-pyridin-2-ylamine

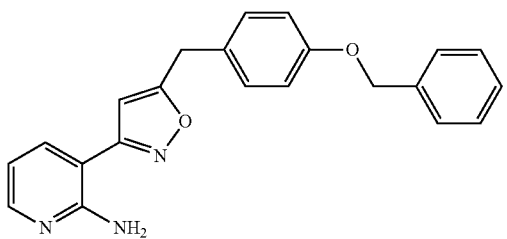

To a solution of 3-(5-(4-benzyloxy-benzyl)-isoxazol-3-yl)-5-chloro-pyridin-2-ylamine (50 mg, 0.13 mmol) described in Manufacturing Example 29-2-3 in N-methylpyrrolidinone (2 mL) were added formic acid (7.3 µL, 0.19 mmol), N,N-diisopropylethylamine (67 µL, 0.38 mmol) and tetrakis(triphenylphosphine)palladium (0) (15 mg, 13 µmol) under nitrogen atmosphere at room temperature, which was stirred for 2 hours and 20 minutes at 100° C. Water and ethyl acetate were added to the reaction solution at room temperature, which was then filtered through a Celite pad. The filtrate was partitioned into water and ethyl acetate. The organic layer was washed with saturated aqueous sodium chloride and dried over anhydrous magnesium sulfate, and the solvent was evaporated under a reduced pressure. The residue was purified by reverse-phase high performance liquid chromatography (using an acetonitrile-water mobile phase containing 0.1% trifluoroacetic acid) and then purified again by NH silica gel column chromatography (heptane:ethyl acetate=1:1) to obtain the title compound (5 mg, 11%).

¹H-NMR Spectrum (CDCl₃) δ (ppm): 4.07 (2H, s), 5.07 (2H, s), 6.24 (1H, s), 6.34 (2H, brs), 6.67 (1H, dd, J=4.9, 7.5 Hz), 6.95-6.98 (2H, m), 7.20-7.23 (2H, m), 7.31-7.45 (5H, m), 7.66 (1H, dd, J=1.7, 7.5 Hz), 8.11 (1H, dd, J=1.7, 4.9 Hz).

MS m/e (ESI) 358.20 (MH⁺)

The starting material, 3-(5-(4-benzyloxy-benzyl)-isoxazol-3-yl)-5-chloro-pyridin-2-ylamine, was synthesized as follows.

Manufacturing Example 29-1-1

2-Amino-pyridine-3-carbaldehyde oxime

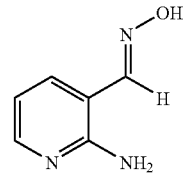

To a solution of 2-amino-3-formylpyridine (1.00 g, 8.19 mmol) in pyridine (20 mL) was added hydroxylamine hydrochloride (854 mg, 12.3 mmol) at room temperature, which was stirred for 1 hour and 40 minutes at room temperature. The reaction solution was partitioned into water and ethyl acetate. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:methanol=10:1) to obtain the title compound (951 mg, 85%).

¹H-NMR Spectrum (DMSO-d₆) δ (ppm): 6.60 (1H, dd, J=4.8, 7.3 Hz), 6.94 (2H, s), 7.55 (1H, m), 7.96 (1H, dd, J=1.7, 4.8 Hz), 8.22 (1H, s), 11.2 (1H, s).

Manufacturing Example 29-1-2

2-Amino-5-chloro-N-hydroxypyridin-3-carboxyimidoyl chloride

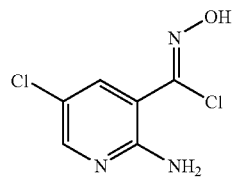

To a solution of 2-amino-pyridine-3-carbaldehyde oxime (951 mg, 6.93 mmol) described in Manufacturing Example 29-1-1 in N,N-dimethylformamide (20 mL) was added N-chlorosuccinimide (2.22 g, 16.6 mmol) at room temperature, which was stirred at room temperature for 5 hours and 30 minutes. The reaction solution was partitioned into water and ethyl acetate at room temperature. The organic layer was washed with water and saturated aqueous sodium chloride, and dried over anhydrous magnesium sulfate, and the solvent was concentrated under a reduced pressure. The residue was purified by silica gel column chromatography (hepane:ethyl acetate=1:1) to obtain the title compound (249 mg, 17%).

$^1$H-NMR Spectrum (DMSO-d$_6$) δ (ppm): 7.24 (2H, brs), 7.91-7.92 (1H, m), 8.06-8.07 (1H, m), 12.6 (1H, s).

Manufacturing Example 29-2-1

(3-(4-Benzyloxy-phenyl)-prop-1-ynyl)-trimethyl-silane

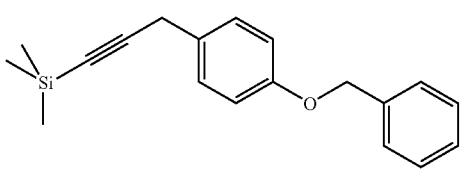

To a solution of trimethylsilyl acetylene (851 μL, 6.02 mmol) in tetrahydrofuran (20 mL) was added ethyl magnesium bromide (3 M diethyl ether solution, 1.86 mL, 5.59 mmol) under nitrogen atmosphere at room temperature, which was stirred for 40 minutes at 65° C. The reaction solution was cooled to room temperature, and copper (I) bromide (308 mg, 2.16 mmol) and 4-benzyloxybenzyl chloride (1.00 g, 4.30 mmol) were added to the reaction solution and stirred for 8 hours and 45 minutes at 65° C. Saturated ammonium chloride solution was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (heptane:ethyl acetate=30:1) to obtain the title compound (911 mg, 72%).

$^1$H-NMR Spectrum (CDCl$_3$) δ (ppm): 0.18 (9H, s), 3.59 (2H, s), 5.06 (2H, s), 6.92-6.95 (2H, m), 7.23-7.26 (2H, m), 7.30-7.34 (1H, m), 7.36-7.40 (2H, m), 7.42-7.44 (2H, m).

Manufacturing Example 29-2-2

1-Benzyloxy-4-prop-2-ynyl-benzene

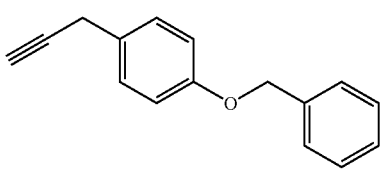

To a solution of (3-(4-benzyloxy-phenyl)-prop-1-ynyl)-trimethyl-silane (911 mg, 3.09 mmol) described in Manufacturing Example 29-2-1 in methanol (20 mL) was added potassium carbonate (854 mg, 6.18 mmol) at room temperature, which was stirred for 4 hours and 10 minutes at room temperature. The reaction solution was partitioned into water and ethyl acetate at room temperature. The organic layer was washed with saturated aqueous sodium chloride and dried over anhydrous magnesium sulfate, and the solvent was evaporated under a reduced pressure. The residue was purified by silica gel column chromatography (heptane:ethyl acetate=20:1) to obtain the title compound (618 mg, 90%).

$^1$H-NMR Spectrum (CDCl$_3$) (ppm): δ 2.16 (1H, t, J=2.4 Hz), 3.54 (2H, d, J=2.4 Hz), 5.05 (2H, s), 6.91-6.94 (2H, m), 7.24-7.26 (2H, m), 7.29-7.43 (5H, m).

Manufacturing Example 29-2-3

3-(5-(4-Benzyloxy-benzyl)-isoxazol-3-yl)-5-chloro-pyridin-2-ylamine

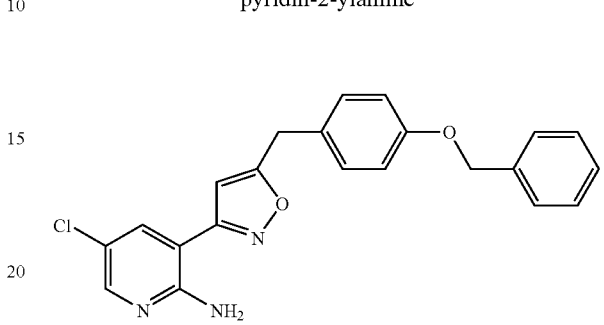

To a solution of 2-amino-5-chloro-N-hydroxypyridin-3-carboxyimidoyl chloride (100 mg, 485 μmol) described in Manufacturing Example 29-1-2 in diethyl ether (2 mL) and tetrahydrofuran (1 mL) were added 1-benzyloxy-4-prop-2-ynyl-benzene (113 mg, 509 μmol) described in Manufacturing Example 29-2-2 and triethylamine (81 μL, 582 μmol), which was stirred for 4 hours and 5 minutes at room temperature. The reaction solution was concentrated under a reduced pressure. The residue was purified by NH silica gel column chromatography (heptane:ethyl acetate=5:1) to obtain the title compound (59 mg, 31%).

$^1$H-NMR Spectrum (DMSO-d$_6$) δ (ppm): 4.11 (2H, s), 5.07 (2H, s), 6.97-6.99 (3H, m), 7.05 (2H, s), 7.24 (2H, d, J=8.6 Hz), 7.29-7.32 (1H, m), 7.37 (2H, m), 7.42 (2H, m), 8.07 (1H, d, J=2.6 Hz), 8.11 (1H, d, J=2.6 Hz).

Example 30

3-(5-(4-(Pyridin-2-yloxymethyl)-benzyl)-isoxazol-3-yl)-pyridin-2-ylamine

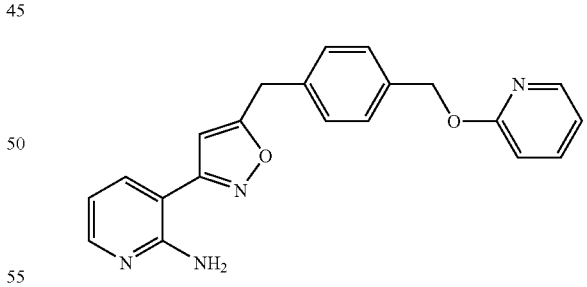

To a solution of 5-chloro-3-(5-(4-(pyridin-2-yloxymethyl)-benzyl)-isoxazol-3-yl)-pyridin-2-ylamine (37 mg, 94 μmol) described in Manufacturing Example 30-1-3 in N-methyl-2-pyrrolidinone (2 mL) were added formic acid (5.3 μL, 0.14 mmol), N,N-diisopropylethylamine (49 μL, 0.28 mmol) and bis(tri-tert-butylphosphine)palladium (0) (9.6 mg, 19 μmol) at room temperature, which was stirred under nitrogen atmosphere for 1 hour and 25 minutes at 100° C. Water and ethyl acetate were added to the reaction solution at room temperature, which was then filtered through a Celite pad.

The filtrate was partitioned into water and ethyl acetate. The organic layer was washed with water and saturated aqueous sodium chloride, and dried over anhydrous magnesium sulfate, and the solvent was evaporated under a reduced pressure. The residue was purified by reverse-phase high performance liquid chromatography (using an acetonitrile-water mobile phase containing 0.1% trifluoroacetic acid), and then further purified by silica gel column chromatography (heptane:ethyl acetate=1:1) to obtain the title compound (0.66 mg, 2.0%).

$^1$H-NMR Spectrum (CDCl$_3$) δ (ppm): 4.14 (2H, s), 5.39 (2H, s), 6.27 (1H, s), 6.49 (2H, brs), 6.69 (1H, dd, J=4.9, 7.5 Hz), 6.81 (1H, d, J=8.4 Hz), 6.88-6.91 (1H, m), 7.31 (2H, d, J=8.0 Hz), 7.47 (2H, d, J=8.0 Hz), 7.57-7.62 (1H, m), 7.68 (1H, dd, J=1.8, 7.5 Hz), 8.09 (1H, dd, J=1.8, 4.9 Hz), 8.17-8.19 (1H, m).

MS m/e (ESI) 359.11 (MH$^+$)

The starting material, 5-chloro-3-(5-(4-(pyridin-2-yloxymethyl)-benzyl)-isoxazol-3-yl)-pyridin-2-ylamine, was synthesized as follows.

Manufacturing Example 30-1-1

2-(4-Chloromethyl-benzyloxy)-pyridine

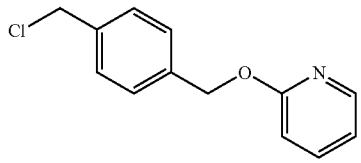

A mixture of (4-(pyridin-2-yloxymethyl)-phenyl)methanol (540 mg, 2.51 mmol) described in Manufacturing Example 2-1-1, triphenylphosphine (856 mg, 3.27 mmol) and carbon tetrachloride (10.8 g, 10.2 mmol) was stirred under reflux for 2 hours and 10 minutes. The reaction solution was cooled to room temperature, and concentrated under a reduced pressure. The residue was purified by silica gel column chromatography (heptane:acetic acid=8:1) to obtain the title compound (300 mg, 51.1%).

$^1$H-NMR Spectrum (DMSO-d$_6$) δ (ppm): 4.76 (2H, s), 5.35 (2H, s), 6.86-6.90 (1H, m), 6.97-7.20 (1H, m), 7.44 (4H, s), 7.70-7.76 (1H, m), 8.15-8.18 (1H m).

Manufacturing Example 30-1-2

2-(4-Prop-2-ynyl-benzyloxy)-pyridine

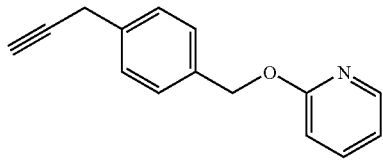

To a solution of trimethylsilyl acetylene (496 μL, 3.51 mmol) in tetrahydrofuran (15 mL) was added ethyl magnesium bromide (3 M diethyl ether solution, 1.09 mL, 3.28 mmol) under nitrogen atmosphere at room temperature, which was stirred for 30 minutes at 65° C. The reaction solution was cooled to room temperature, and copper (I) bromide (168 mg, 1.17 mmol) and 2-(4-chloromethyl-benzyloxy)-pyridine (548 mg, 2.34 mmol) manufactured in Manufacturing Example 30-1-1 were added thereto and stirred for 15 hours and 10 minutes at 65° C. The reaction solution was partitioned into saturated aqueous ammonium chloride solution and ethyl acetate at room temperature. The organic layer was washed with saturated aqueous sodium chloride, and dried over anhydrous magnesium sulfate, and the solvent was evaporated under a reduced pressure. To a solution of the resulting residue in methanol (5 mL) and tetrahydrofuran (10 mL) was added potassium carbonate (647 mg, 4.68 mmol), which was stirred for 3 hours and 25 minutes at room temperature. The reaction solution was partitioned into water and ethyl acetate at room temperature. The organic layer was washed with saturated aqueous sodium chloride and dried over anhydrous magnesium sulfate, and the solvent was evaporated under a reduced pressure. The residue was purified by silica gel column chromatography (heptane:ethyl acetate=20:1) to obtain a mixture of the title compound and 2-(4-chloromethyl-benzyloxy)-pyridine (448 mg, target purity 20%, 17%).

$^1$H-NMR Spectrum (DMSO-d$_6$) δ (ppm): 3.04 (1H, m), 3.61 (2H, d, J=2.6 Hz), 5.30 (2H, s), 6.83-6.87 (1H, m), 6.95-6.99 (1H, m), 7.30-7.32 (2H, s), 7.36-7.40 (2H, m), 7.68-7.73 (1H, m), 8.14-8.16 (1H, m).

Manufacturing Example 30-1-3

5-Chloro-3-(5-(4-(pyridin-2-yloxymethyl)-benzyl)-isoxazol-3-yl)-pyridin-2-ylamine

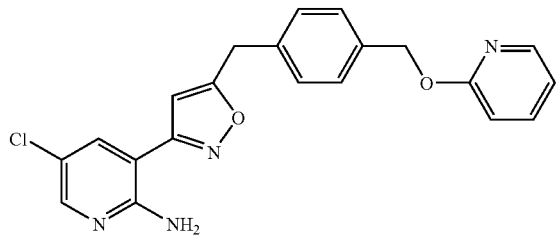

To a solution of 2-amino-5-chloro-N-hydroxypyridine-3-carboxyimidoyl chloride (50 mg, 242 μmol) described in Manufacturing Example 29-1-2 in tetrahydrofuran (5 mL) were added triethylamine (41 μL, 292 μmol) and 2-(4-prop-2-ynyl-benzyloxy)-pyridine (271 mg, 243 μmol, purity: 20%) described in Manufacturing Example 30-1-2 at room temperature, which was stirred for 30 minutes at room temperature, and further stirred under reflux for 2 hours and 25 minutes. The reaction solution was cooled to room temperature, and concentrated under a reduced pressure. The residue was purified by NH silica gel column chromatography (heptane:ethyl acetate=5:1) to obtain the title compound (37 mg, 39%).

$^1$H-NMR Spectrum (DMSO-d$_6$) δ (ppm): 4.22 (2H, s), 5.34 (2H, s), 6.86 (1H, d, J=8.2 Hz), 6.97-7.01 (1H, m), 7.04 (1H, s), 7.07 (2H, brs), 7.34 (2H, d, J=8.0 Hz), 7.44 (2H, d, J=8.0 Hz), 7.70-7.74 (1H, m), 8.09 (1H, d, J=2.6 Hz), 8.14 (1H, d, J=2.6 Hz), 8.16-8.18 (1H, m).

Example 31

3-(1-(4-Benzyloxy-benzyl)-1H-pyrazol-4-yl)-pyridin-2-ylamine

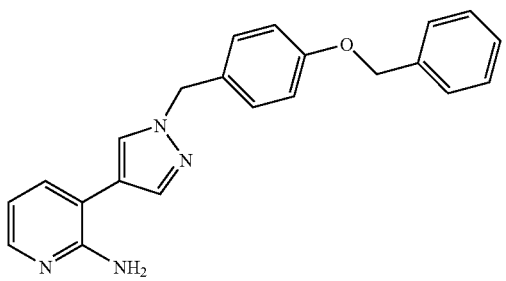

To a solution of 2-amino-3-bromopyridine (44.1 mg, 0.26 mmol) in anhydrous tetrahydrofuran (7 mL) were added 1-(4-benzyloxy-benzyl)-4-tributylstannanyl-1H-pyrazole (141 mg, 0.26 mmol) described in Manufacturing Example 31-1-2, copper (I) iodide (19.4 mg, 0.10 mmol) and bis(triphenylphosphine)palladium (II) (35.8 mg, 0.05 mmol) under nitrogen atmosphere, which was stirred for 4 hours at 70° C. Water and ethyl acetate were added to the reaction mixture at room temperature, which was then filtered through a Celite pad, and the filtrate was partitioned into water and ethyl acetate. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=2:1, then ethyl acetate) to obtain the title compound (1.8 mg, 2%).

$^1$H-NMR Spectrum (DMSO-$d_6$) δ (ppm): 5.09 (2H, s), 5.26 (2H, s), 5.87 (2H, brs), 6.61 (1H, dd, J=4.8, 7.2 Hz), 6.98 (2H, d, J=8.8 Hz), 7.27 (2H, d, J=8.8 Hz), 7.32-7.44 (5H, m), 7.47-7.49 (1H, m), 7.74 (1H, s), 7.86 (1H, dd, J=1.6, 5.0 Hz), 8.13 (1H, s).

The starting material, 1-(4-benzyloxy-benzyl)-4-tributylstannanyl-1H-pyrazole, was synthesized as follows.

Manufacturing Method 31-1-1

1-(4-Benzyloxy-benzyl)-4-bromo-1H-pyrazole

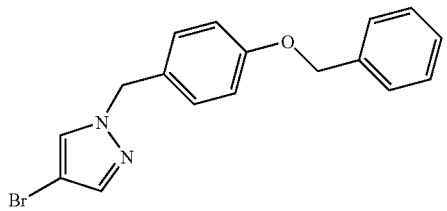

To a solution of 2-bromopyrazole (500 mg, 3.40 mmol) in N,N-dimethylformamide (10 mL) was added sodium hydride (196 mg, 4.08 mmol, 60% in oil) on an ice bath (0° C.) under nitrogen atmosphere, which was stirred for 30 minutes at room temperature. 4-Benzyloxybenzyl chloride (791 mg, 3.40 mmol) was then added and stirred for 60 minutes at room temperature. The reaction mixture was partitioned into water and ethyl acetate at room temperature. The organic layer was washed with water and saturated aqueous sodium chloride, and dried over anhydrous magnesium sulfate, and the solvent was evaporated under a reduced pressure. The residue was purified by silica gel column chromatography (ethyl acetate:heptane=1:5) to obtain the title compound (1.1 g, 94%).

$^1$H-NMR Spectrum (DMSO-$d_6$) δ (ppm): 5.04 (2H, s), 5.17 (2H, s), 6.94 (2H, d, J=8.8 Hz), 7.17 (2H, d, J=8.8 Hz), 7.31 (1H, s), 7.33-7.41 (5H, m), 7.47 (1H, m).

Manufacturing Example 31-1-2

1-(4-Benzyloxy-benzyl)-4-tributylstannanyl-1H-pyrazole

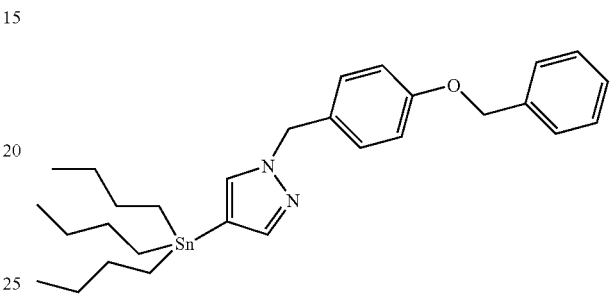

To a solution of 1-(4-benzyloxy-benzyl)-4-bromo-1H-pyrazole (1.10 g, 3.20 mmol) described in Manufacturing Example 31-1-1 in xylene (20 mL) were added tetrakis(triphenylphosphine)palladium (0) (370 mg, 0.32 mmol) and hexa-n-butyl stannane (5.57 g, 9.60 mmol) under nitrogen atmosphere, which was stirred for 2 hours at 140° C. Water and ethyl acetate were added to the reaction mixture at room temperature, which was then filtered through a Celite pad, and the filtrate was partitioned into water and ethyl acetate. The organic layer was washed with water and saturated aqueous sodium chloride, and dried over anhydrous magnesium sulfate, and the solvent was evaporated under a reduced pressure. The residue was purified by silica gel column chromatography (ethyl acetate:heptane=1:5) to obtain the title compound (141 mg, 8%).

$^1$H-NMR Spectrum (CDCl$_3$) δ (ppm): 0.87 (9H, t, J=7.2 Hz), 0.92-1.00 (6H, m), 1.26-1.35 (6H, m), 1.46-1.54 (6H, m), 5.05 (2H, s), 5.27 (2H, s), 6.93-6.95 (2H, m), 7.14-7.17 (2H, m), 7.23 (1H, s), 7.31-7.43 (5H, m), 7.46 (1H, s).

Example 32

3-(1-(4-(Pyridin-2-yloxymethyl)-benzyl)-1H-pyrazol-4-yl)-pyridin-2-ylamine

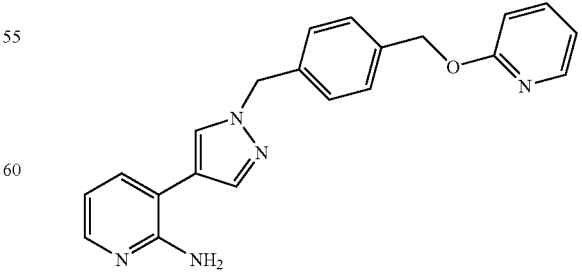

To a solution of 3-(1H-pyrazol-4-yl)-pyridin-2-ylamine (150 mg, 0.94 mmol) described in Manufacturing Example 32-1-4 in N,N-dimethylformamide (10 mL) was added sodium hydride (48.7 mg, 1.22 mmol, 60% in oil) on an ice bath (0° C.) under nitrogen atmosphere. Following 40 minutes of stirring at room temperature, 2-(4-chloromethyl-benzyloxy)-pyridine (228 mg, 0.98 mmol) described in Manufacturing Example 30-1-1 was added and stirred for 30 minutes at room temperature. The reaction mixture was partitioned into water and ethyl acetate at room temperature. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=2:1, then ethyl acetate) to obtain the title compound (307 mg, 92%).

$^1$H-NMR Spectrum (DMSO-d$_6$) δ (ppm): 5.33 (2H, s), 5.35 (2H, s), 5.60 (2H, brs), 6.61 (1H, dd, J=4.8, 7.4 Hz), 6.84-6.87 (1H, m), 6.96-7.00 (1H, m), 7.30-7.43 (1H, m), 7.31 (2H, d, J=8.4 Hz), 7.42 (1H, t, J=8.4 Hz), 7.48 (1H, dd, J=2.0, 7.2 Hz), 7.69-7.73 (1H, m), 7.76 (1H, d, J=1.2 Hz), 7.87 (1H, dd, J=2.0, 5.0 Hz), 8.15-8.17 (1H, m), 8.18 (1H, d, J=0.8 Hz).

The starting material, 3-(1H-pyrazol-4-yl)-pyridin-2-ylamine, was synthesized as follows.

Manufacturing Example 32-1-1

4-Bromo-1-trityl-1H-pyrazole

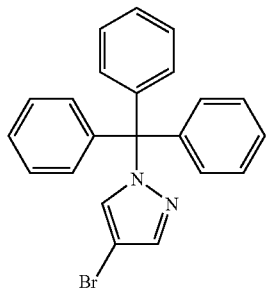

To a solution of 4-bromopyrazole (10.0 g, 68.0 mmol) in N,N-dimethylformamide (100 mL) was added dropwise triethylamine (23.7 mL, 170 mmol) under nitrogen atmosphere at room temperature. Trityl chloride (37.9 g, 136 mmol) was added to the reaction solution on an ice bath (0° C.), and stirred for 3 hours at 70° C. Water (400 mL) was added to the reaction solution to precipitate the solids. The precipitated solids were filtered and dried under a reduced pressure. The solids were then azeotropically dried with toluene to obtain the title compound (22.9 g, 87%).

$^1$H-NMR Spectrum (DMSO-d$_6$) δ (ppm): 7.04-7.07 (6H, m), 7.35-7.38 (9H, m), 7.52 (1H, d, J=0.4 Hz), 7.76 (1H, d, J=0.8 Hz).

Manufacturing Example 32-1-2

4-(4,4,5,5-Tetramethyl-(1,3,2)dioxaborolan-2-yl)-1-trityl-1H-pyrazole

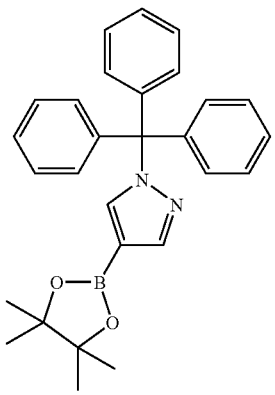

A mixture of 4-bromo-4-trityl-1H-pyrazole (4.8 g, 12.3 mmol) described in Manufacturing Example 32-1-1, bis(pinacolate)diboran (5.0 g, 19.7 mmol), potassium acetate (3.62 g, 36.9 mmoL), 1,1' bis(diphenylphosphino)ferrocene dichloropalladium (II) (450 mg, 0.62 mmol) and dimethyl sulfoxide (50 mL) was stirred under argon atmosphere for 17 hours and 10 minutes at 80° C. The reaction solution was allowed to room temperature, and partitioned into water and ethyl acetate. The organic layer was concentrated under a reduced pressure. The residue was purified by silica gel chromatography (heptane:ethyl acetate=4:1). Heptane was added to the solids obtained by concentrating the eluate under a reduced pressure, which were then irradiated by ultrasonic wave and filtered to obtain the title compound (1.51 g, 28.0%).

$^1$H-NMR Spectrum (CDCl$_3$) δ (ppm): 1.30 (12H, s), 7.10-7.16 (6H, m), 7.26-7.31 (9H, m), 7.75 (1H, s), 7.94 (1H, s).

Manufacturing Example 32-1-3

3-(1-Trityl-1H-pyrazol-4-yl)-pyridin-2-ylamine

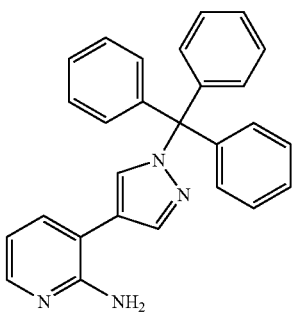

4-(4,4,5,5-Tetramethyl-(1,3,2)dioxaborolan-2-yl)-1-trityl-1H-pyrazole (3.2 g, 7.33 mmol) described in Manufacturing Example 32-1-2, 3-bromo-pyridine-2-ylamine (1.14 g, 6.60 mmol), tetrakis(triphenylphosphine)palladium (0) (424 mg, 0.37 mmol), toluene (40 mL), 2 M aqueous sodium carbonate solution (10 mL) and ethanol (20 mL) were stirred for 1 hour at 95° C. The reaction solution was allowed to room temperature, and partitioned into water and ethyl acetate. The ethyl acetate layer was washed with water once, and the solvent was evaporated under a reduced pressure. The residue was purified by silica gel chromatography (heptane:ethyl acetate=1:2) to obtain the title compound (2.3 g, 78.0%).

¹H-NMR Spectrum (DMSO-d₆) δ (ppm): 5.52 (2H, brs), 6.57 (1H, dd, J=7.2, 4.8 Hz), 7.10-7.16 (6H, m), 7.28-7.38 (9H, m), 7.42 (1H, d, J=7.2 Hz), 7.66 (1H, s), 7.84 (1H, d, J=4.8 Hz), 7.92 (1H, s).

Manufacturing Example 32-1-4

3-(1H-Pyrazol-4-yl)-pyridin-2-ylamine

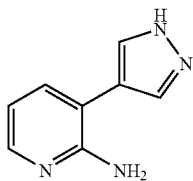

3-(1-Trityl-1H-pyrazol-4-yl)-pyridin-2-ylamine (2.3 g, 5.71 mmol) described in Manufacturing Example 32-1-3, 2 N hydrochloric acid (15 mL), methanol (15 mL) and tetrahydrofuran (10 mL) were stirred for 30 minutes at 70° C. The reaction solution was allowed to room temperature, and partitioned into water and ethyl acetate. Saturated sodium bicarbonate solution was added to the separated aqueous layer, which was then extracted with ethyl acetate 6 times. The ethyl acetate layers were combined and the solvent was evaporated under a reduced pressure. The residue was purified by silica gel chromatography (ethyl acetate, then ethyl acetate:methanol=10:1) to obtain the title compound (625 mg, 68.3%).

¹H-NMR Spectrum (DMSO-d₆) δ (ppm): 5.59 (2H, brs), 6.62 (1H, dd, J=4.8, 7.6 Hz), 7.49 (1H, d, J=7.2 Hz), 7.88 (1H, d, J=4.8 Hz), 7.72-8.15 (2H, brs), 12.9 (1H, brs).

Example 33

3-(1-(4-Butoxymethyl-benzyl)-1H-pyrazol-4-yl)-pyridin-2-ylamine

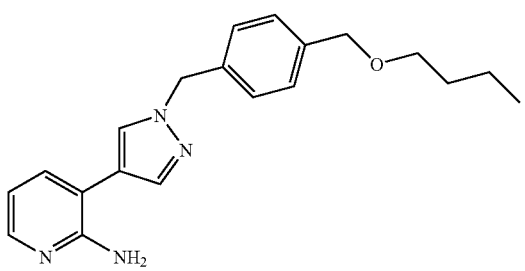

To a mixture of 3-(1H-pyrazol-4-yl)-pyridin-2-ylamine (20 mg, 0.13 mmol) described in Manufacturing Example 32-1-4 and N,N-dimethylformamide (1 mL) was added sodium hydride (6.8 mg, 0.19 mmol, 66% in oil), which was stirred for 30 minutes at room temperature. 1-Butoxymethyl-4-chloromethyl-benzene (29 mg, 0.14 mmol) described in Manufacturing Example 33-1-4 was added to the reaction mixture at room temperature, and stirred for 1.5 hours at 40° C. The reaction mixture was cooled and partitioned into water and ethyl acetate. The organic layer was washed with saturated aqueous sodium chloride, and the solvent was evaporated under a reduced pressure. The residue was purified by NH silica gel column chromatography (ethyl acetate:heptane=2:1) to obtain the title compound (33 mg, 78%).

¹H-NMR Spectrum (CDCl₃) δ (ppm): 0.92 (3H, t, J=7.4 Hz), 1.35-1.44 (2H, m), 1.56-1.62 (2H, m), 3.48 (2H, t, J=6.6 Hz), 4.49 (2H, s), 4.61 (2H, brs), 5.34 (2H, s), 5.70 (1H, dd, J=5.0, 7.4 Hz), 7.27 (2H, d, J=8.1 Hz), 7.35 (2H, d, J=8.1 Hz), 7.39 (1H, dd, J=1.8, 7.3 Hz), 7.58 (1H, s), 7.73 (1H, d, J=0.7 Hz), 8.00 (1H, dd, J=1.8, 5.1 Hz).

The starting material, 1-butoxymethyl-4-chloromethyl-benzene, was synthesized as follows.

Manufacturing Example 33-1-1

4-Butoxymethyl-benzonitrile

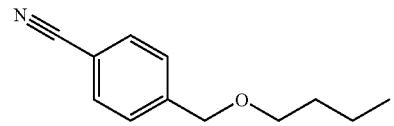

To a mixture of sodium hydride (270 mg, 11 mmol, 66% in oil) and tetrahydrofuran (20 mL) was added n-butanol (1.1 mL, 12 mmol) at 0° C., which was stirred for 45 minutes at room temperature. The reaction mixture was cooled to 0° C., and a mixture of 4-cyanobenzyl bromide (1.5 g, 7.4 mmol) and tetrahydrofuran (10 mL) was added dropwise at that temperature. The reaction mixture was stirred for 3 hours at room temperature, and N,N-dimethylformamide (10 mL) was added to the reaction mixture and stirred for further 4.5 hours at the same temperature. The reaction mixture was partitioned into water and diethyl ether. The organic layer was washed with saturated aqueous sodium chloride, and the solvent was evaporated under a reduced pressure. The residue was purified by NH silica gel column chromatography (ethyl acetate:heptane=1:6) to obtain the title compound (1.2 g, 84%).

¹H-NMR Spectrum (CDCl₃) δ (ppm): 0.93 (3H, t, J=7.3 Hz), 1.37-1.46 (2H, m), 1.59-1.66 (2H, m), 3.50 (2H, t, J=6.6 Hz), 4.55 (2H, s), 7.43-7.46 (2H, m), 7.62-7.65 (2H, m).

Manufacturing Example 33-1-2

4-Butoxymethyl-benzylamine

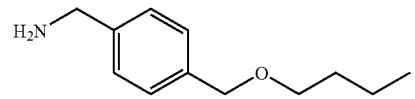

To a mixture of lithium aluminum hydride (600 mg, 13 mmol, purity: 80%) and tetrahydrofuran (10 mL) was added a mixture of 4-butoxymethyl-benzonitrile (600 mg, 3.2 mmol) described in Manufacturing Example 33-1-1 and tetrahydrofuran (10 mL) at 0° C., which was stirred for 4 hours at room temperature. 28% Aqueous ammonia solution was added dropwise to the reaction mixture at 0° C. The reaction mixture was warmed to room temperature and filtered. The filtrate was concentrated under a reduced pressure to obtain the title compound (620 mg, 101%) as a crude product.

¹H-NMR Spectrum (CDCl₃) δ (ppm): 0.92 (3H, t, J=7.3 Hz), 1.37-1.44 (2H, m), 1.56-1.63 (2H, m), 3.47 (2H, t, J=6.6 Hz), 3.86 (2H, s), 4.49 (2H, s), 7.27-7.32 (4H, m).

Manufacturing Example 33-1-3

(4-Butoxymethyl-phenyl)-methanol

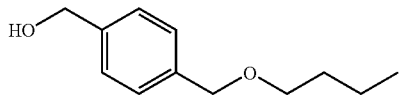

To a mixture of 4-butoxymethyl-benzylamine (250 mg, 1.3 mmol) described in Manufacturing Example 33-1-2, acetic acid (2 mL) and water (2 mL) was added sodium nitrite (1.1 g, 16 mmol) at 0° C., which was stirred for 40 minutes at room temperature. The reaction mixture was partitioned into ethyl acetate and water. The organic layer was washed with saturated aqueous sodium hydrogen carbonate solution and saturated aqueous sodium chloride, and the solvent was evaporated under a reduced pressure. Methanol (2 mL) and potassium carbonate (360 mg, 2.6 mmol) were added to the residue, and the reaction mixture was stirred for 1.5 hours at room temperature. The reaction mixture was concentrated under a reduced pressure. The residue was purified by neutral silica gel column chromatography (ethyl acetate:heptane=1:1) to obtain the title compound (200 mg, 78%).

¹H-NMR Spectrum (CDCl₃) δ (ppm): 0.92 (3H, t, J=7.3 Hz), 1.35-1.44 (2H, m), 1.57-1.64 (2H, m), 3.47 (2H, t, J=6.6 Hz), 4.50 (2H, s), 4.69 (2H, s), 7.34 (4H, s).

Manufacturing Example 33-1-4

1-Butoxymethyl-4-chloromethyl-benzene

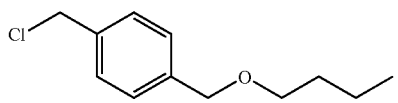

A mixture of (4-butoxymethyl-phenyl)-methanol (190 mg, 0.98 mmol) described in Manufacturing Example 33-1-3, triphenylphosphine (310 mg, 1.2 mmol) and carbon tetrachloride (3 mL) was stirred under reflux for 7 hours. The reaction mixture was cooled to room temperature, and concentrated under a reduced pressure. The residue was purified by neutral silica gel column chromatography (ethyl acetate:heptane=1:15) to obtain the title compound (180 mg, 86%).

¹H-NMR Spectrum (CDCl₃) δ (ppm): 0.92 (3H, t, J=7.3 Hz), 1.35-1.45 (2H, m), 1.57-1.64 (2H, m), 3.47 (2H, t, J=6.6 Hz), 4.50 (2H, s), 4.59 (2H, s), 7.32-7.38 (4H, m).

Example 34

3-(1-(4-Phenoxy-benzyl)-1H-pyrazol-4-yl)-pyridin-2-ylamine

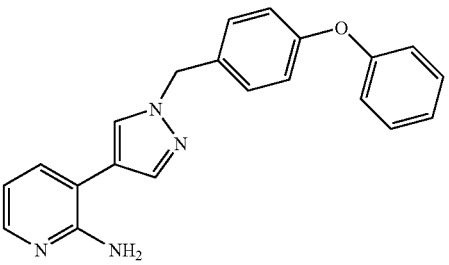

To a solution of 3-(1H-pyrazol-4-yl)-pyridin-2-ylamine (20 mg, 0.13 mmol) described in Manufacturing Example 32-1-4 in N,N-dimethylformamide (10 mL) was added sodium hydride (7.5 mg, 0.19 mmol, 60% in oil) under nitrogen atmosphere on an ice bath (0° C.), which was stirred for 30 minutes at room temperature. 1-Chloromethyl-4-phenoxy-benzene (32.8 mg, 0.15 mmol) described in Manufacturing Example 34-1-1 was then added to the mixture and stirred for 30 minutes at room temperature. The reaction mixture was partitioned into water and ethyl acetate at room temperature. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=2:1, then ethyl acetate only) to obtain the title compound (41 mg, 86%, purity: 90%).

¹H-NMR Spectrum (DMSO-d₆) δ (ppm): 5.33 (2H, s), 5.60 (2H, brs), 6.61 (1H, dd, J=4.8, 7.4 Hz), 6.98-7.01 (2H, m), 7.12-7.16 (1H, m), 7.34-7.40 (2H, m), 7.48-7.65 (5H, m), 7.77 (1H, s), 7.87 (1H, dd, J=1.2, 5.0 Hz), 8.18 (1H, s).

The starting material, 1-chloromethyl-4-phenoxy-benzene, was synthesized as follows.

Manufacturing Example 34-1-1

1-Chloromethyl-4-phenoxy-benzene

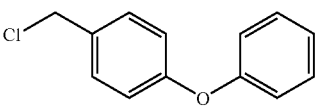

To a solution of (4-phenoxy-phenyl)-methanol (408 mg, 2.04 mmol) in carbon tetrachloride (8.2 mL) was added triphenylphosphine (642 mg, 2.45 mmol) under nitrogen atmosphere at room temperature, and the reaction solution was stirred under reflux for 7 hours and 40 minutes. The reaction mixture was cooled to room temperature and concentrated under a reduced pressure. The residue was purified by silica gel column chromatography (heptane:ethyl acetate=10:1) to obtain the title compound (409 mg, 92%).

$^1$H-NMR Spectrum (DMSO-d$_6$) δ (ppm): 4.76 (2H, s), 6.98-7.05 (4H, m), 7.15-7.19 (1H, m), 7.39-7.46 (4H, m).

Example 35

3-(1-(3-Phenoxy-benzyl)-1H-pyrazol-4-yl)-pyridin-2-ylamine

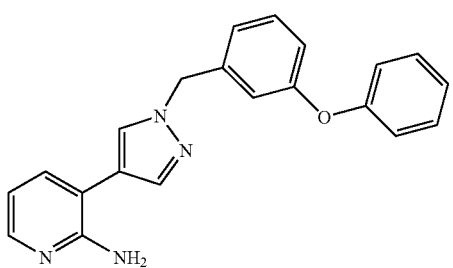

To a solution of 3-(1H-pyrazol-4-yl)-pyridin-2-ylamine (20 mg, 0.13 mmol) described in Manufacturing Example 32-1-4 in N,N-dimethylformamide (10 mL) was added sodium hydride (7.5 mg, 0.19 mmol, 60% in oil) under nitrogen atmosphere on an ice bath (0° C.), which was stirred for 40 minutes at room temperature. 1-Chloromethyl-3-phenoxybenzene (32.8 mg, 0.15 mmol) described in Manufacturing Example 35-1-1 was then added and stirred for 30 minutes at room temperature. The reaction mixture was partitioned into water and ethyl acetate at room temperature. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=2:1, then ethyl acetate only) to obtain the title compound (20 mg, 47%).

$^1$H-NMR Spectrum (DMSO-d$_6$) δ (ppm): 5.35 (2H, s), 5.59 (2H, brs), 6.62 (1H, dd, J=1.2, 7.4 Hz), 6.90-6.95 (2H, m), 6.99-7.06 (3H, m), 7.13-7.17 (1H, m), 7.34-7.41 (3H, m), 7.48 (1H, dd, J=2.0, 7.4 Hz), 7.70 (1H, d, J=0.8 Hz), 7.87 (1H, dd, J=2.0, 5.0 Hz), 8.18 (1H, d, J=0.8 Hz).

The starting material, 1-chloromethyl-3-phenoxy-benzene, was synthesized as follows.

Manufacturing Example 35-1-1

1-Chloromethyl-3-phenoxy-benzene

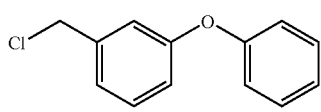

To a solution of (3-phenoxy-phenyl)-methanol (2.00 g, 10.0 mmol) in carbon tetrachloride (40 mL) was added triphenylphosphine (3.15 g, 12.0 mmol) at room temperature. The reaction solution was stirred under nitrogen atmosphere for 5 hours and 40 minutes under reflux. The reaction mixture was cooled to room temperature and concentrated under a reduced pressure. The residue was purified by silica gel column chromatography (heptane:ethyl acetate=10:1) to obtain the title compound (2.05 g, 94%).

$^1$H-NMR Spectrum (DMSO-d$_6$) δ (ppm): 4.37 (2H, s), 6.94-6.97 (1H, m), 7.00-7.03 (2H, m), 7.05-7.06 (1H, m), 7.13-7.20 (3H, m), 7.37-7.41 (2H, m).

Example 36

3-(1-(4-Benzyloxy-benzyl)-1H-pyrazol-4-yl)-pyridin-2,6-diamine

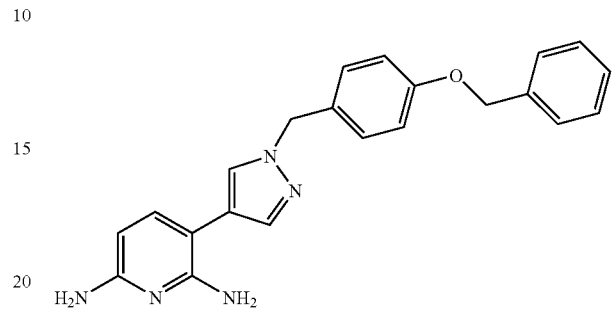

To a solution of 3-(1H-pyrazol-4-yl)-pyridin-2,6-diamine (25 mg, 0.14 mmol) described in Manufacturing Example 36-1-2 in N,N-dimethylformamide (10 mL) was added sodium hydride (8.6 mg, 0.22 mmol, 60% in oil) under nitrogen atmosphere on an ice bath (0° C.), which was stirred for 30 minutes at room temperature. 4-Benzyloxybenzyl chloride (49.9 mg, 0.22 mmol) was then added and stirred for 30 minutes at room temperature. The reaction mixture was partitioned into water and ethyl acetate at room temperature. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=2:1, then ethyl acetate only) to obtain the title compound (24.0 mg, 45%).

$^1$H-NMR Spectrum (DMSO-d$_6$) δ (ppm): 5.06 (2H, brs), 5.09 (2H, s), 5.21 (2H, s), 5.43 (2H, brs), 5.77 (1H, d, J=8.0 Hz), 6.97-7.00 (2H, m), 7.15 (1H, d, J=8.0 Hz), 7.23-7.26 (2H, m), 7.30-7.34 (1H, m), 7.36-7.44 (4H, m), 7.56 (1H, d, J=1.2 Hz), 7.90 (1H, d, J=1.2 Hz).

The starting material, 3-(1H-pyrazol-4-yl)-pyridin-2,6-diamine, was synthesized as follows.

Manufacturing Example 36-1-1

3-(1-Trityl-1H-pyrazol-4-yl)-pyridin-2,6-diamine

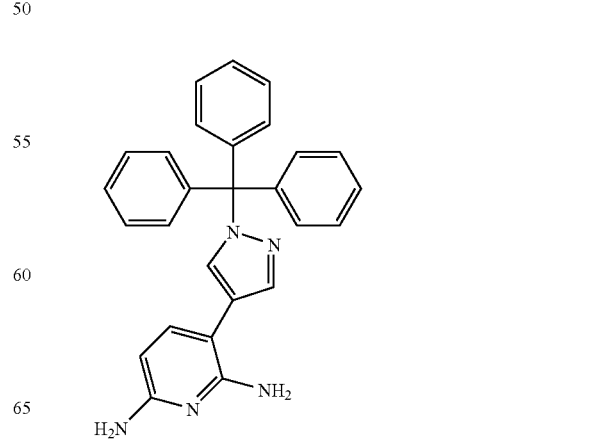

To a solution of 3-iodo-pyridin-2,6-diamine (3.3 g, 7.74 mmol, purity: 70%) described in Manufacturing Example 13-1-1 in toluene (50 mL) were added ethanol (25 mL), 2 N aqueous sodium carbonate solution (12.5 mL), 4-(4,4,5,5-tetramethyl-(1,3,2)dioxaborolan-2-yl)-1-trityl-1H-pyrazole (3.3 g, 7.56 mmol) described in Manufacturing Example 32-1-2 and tetrakis(triphenylphosphine)palladium (0) (1.02 g, 0.88 mmol) under nitrogen atmosphere, which was stirred for 2.5 hours at 95° C. Water and ethyl acetate were added to the reaction mixture at room temperature, which was then filtered through a Celite pad, and the filtrate was partitioned into water and ethyl acetate. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=1:2 then 2:1 then 5:1) to obtain the title compound (2.4 g, 73%).

$^1$H-NMR Spectrum (CDCl$_3$) δ (ppm): 4.63 (2H, brs), 4.79 (2H, brs), 5.90 (1H, d, J=8.0 Hz), 7.16-7.20 (6H, m), 7.29-7.32 (10H, m), 7.45 (1H, s), 7.77 (1H, s).

Manufacturing Example 36-1-2

3-(1H-pyrazol-4-yl)-pyridin-2,6-diamine

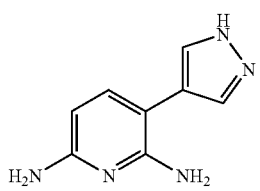

To a solution of 3-(1-trityl-1H-pyrazol-4-yl)-pyridin-2,6-diamine (10.0 g, 25.7 mmol) described in Manufacturing Example 36-1-1 in methylene chloride (14 mL) was added trifluoroacetic acid (7 mL) under nitrogen atmosphere, which was stirred for 1 hour at room temperature. The reaction mixture was concentrated under a reduced pressure. The residue was purified by NH silica gel column chromatography (ethyl acetate, then ethyl acetate:methanol=10:1) to obtain the title compound (600 mg, 60%).

$^1$H-NMR Spectrum (DMSO-d$_6$) δ (ppm): 5.04 (2H, brs), 5.41 (2H, brs), 5.78 (1H, d, J=8.4 Hz), 7.16 (1H, d, J=8.0 Hz), 7.62 (1H, brs), 7.78 (1H, brs), 12.8 (1H, brs).

Example 37

3-(1-(4-(Pyridin-2-yloxymethyl)-benzyl)-1H-pyrazol-4-yl)-pyridin-2,6-diamine

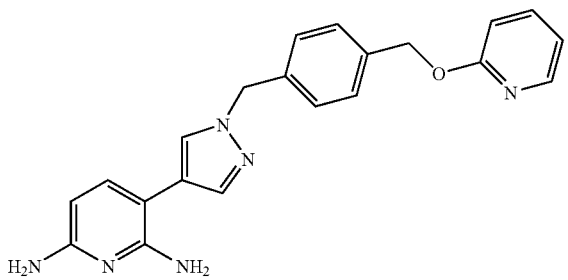

To a solution of 3-(1H-pyrazol-4-yl)-pyridin-2,6-diamine (25 mg, 0.14 mmol) described in Manufacturing Example 36-1-2 in N,N-dimethylformamide (3 mL) was added sodium hydride (8.6 mg, 0.22 mmol, 60% in oil) under nitrogen atmosphere on an ice bath (0° C.). Following 30 minutes of stirring at room temperature, 2-(4-chloromethyl-benzyloxy)-pyridine (43.4 mg, 0.19 mmol) described in Manufacturing Example 30-1-1 was added and stirred for 30 minutes at 60° C. The reaction mixture was partitioned into water and ethyl acetate at room temperature. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=2:1, then ethyl acetate only) to obtain the title compound (22.8 mg, 43%).

$^1$H-NMR Spectrum (DMSO-d$_6$) δ (ppm): 5.07 (2H, brs), 5.30 (2H, s), 5.32 (2H, s), 5.43 (2H, brs), 5.78 (1H, d, J=8.0 Hz), 6.84-6.86 (1H, m), 6.96-7.00 (1H, m), 7.16 (1H, d, J=8.0 Hz), 7.28 (2H, d, J=8.0 Hz), 7.41 (2H, d, J=7.6 Hz), 7.58 (1H, s), 7.69-7.73 (1H, m), 7.94 (1H, s), 8.15-8.17 (1H, m).

Example 38

3-(1-(4-Butoxymethyl-benzyl)-1H-pyrazol-4-yl)-pyridin-2,6-diamine

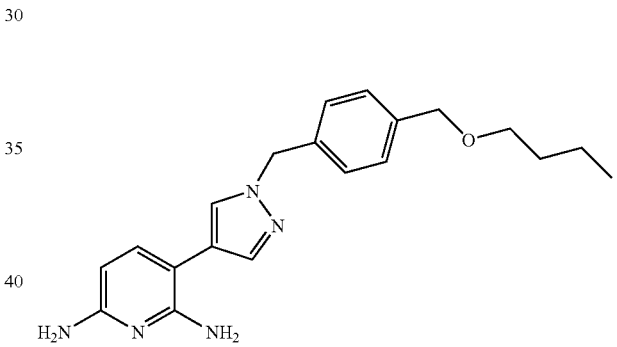

To a solution of 3-(1H-pyrazol-4-yl)-pyridin-2,6-diamine (20 mg, 0.11 mmol) described in Manufacturing Example 36-1-2 in N,N-dimethylformamide (4 mL) was added sodium hydride (5.9 mg, 0.15 mmol, 60% in oil) under nitrogen atmosphere on an ice bath (0° C.) Following 30 minutes of stirring at room temperature, 1-butoxymethyl-4-chloromethyl-benzene (26.7 mg, 0.13 mmol) described in Manufacturing Example 33-1-4 was added and stirred for 30 minutes at room temperature. The reaction mixture was partitioned into water and ethyl acetate at room temperature. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=2:1, then ethyl acetate) to obtain the title compound (29.0 mg, 72%).

$^1$H-NMR Spectrum (DMSO-d$_6$) δ (ppm): 0.864 (3H, d, J=7.6 Hz), 1.30-1.35 (2H, m), 1.47-1.54 (2H, m), 3.40 (2H, d, J=6.4 Hz), 4.42 (2H, s), 5.07 (2H, brs), 5.29 (2H, s), 5.43 (2H, brs), 5.78 (1H, d, J=8.4 Hz), 7.16 (1H, t, J=8.0 Hz), 7.24-7.29 (4H, m), 7.58 (1H, s), 7.93 (1H, s).

Example 39

3-(4-(4-Benzyloxy-benzyl)-pyrazol-1-yl)-pyridin-2-ylamine

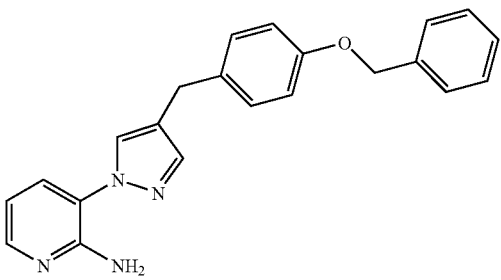

To a mixture of 3-(4-bromo-pyrazol-1-yl)-pyridin-2-ylamine (34 mg, 0.14 mmol) described in Manufacturing Example 39-1-4, (4-benzyloxy-benzyl)-tributyl-stannane (84 mg, 0.17 mmol) described in Manufacturing Example 39-2-1 and N-methylpyrrolidinone (1.5 mL) were added tri-o-tolylphosphine (17 mg, 0.057 mmol) and palladium (II) acetate (3.2 mg, 0.014 mmol) at room temperature, which was stirred for 5 hours at 120° C. The reaction mixture was cooled to room temperature, and filtered after addition of an aqueous potassium fluoride solution and ethyl acetate. The organic layer was separated, washed with saturated aqueous sodium chloride, and the solvent was evaporated under a reduced pressure. The residue was purified by reverse-phase high performance liquid chromatography (using an acetonitrile-water mobile phase containing 0.1% trifluoroacetic acid) to obtain the title compound (2.6 mg, 4%) as a trifluoroacetic acid salt.

MS m/e (ESI) 357.18 (MH$^+$)

The starting material, 3-(4-bromo-pyrazol-1-yl)-pyridin-2-ylamine, was synthesized as follows.

Manufacturing Example 39-1-1

2,2-Dimethyl-N-pyridin-2-yl-propionamide

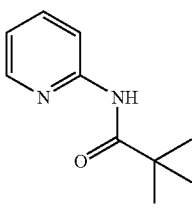

To a solution of 2-aminopyridine (50.0 g, 531 mmol) in methylene chloride (500 mL) were added triethylamine (81.4 mL, 584 mmol) and pivaloyl chloride (71.9 mL, 584 mmol) at 0° C., which was stirred for 4 hours and 30 minutes at room temperature. The reaction solution was partitioned into water and methylene chloride. The organic layer was washed with water and saturated aqueous sodium chloride, and dried over anhydrous magnesium sulfate, and the solvent was evaporated under a reduced pressure. To a solution of the resulting residue in methanol (300 mL) was added potassium carbonate (73.4 g, 531 mmol) at 0° C., which was stirred for 90 minutes at room temperature. The reaction solution was partitioned into water and ethyl acetate at room temperature. The organic layer was washed with saturated aqueous sodium chloride and dried over anhydrous magnesium sulfate, and the solvent was evaporated under a reduced pressure. Heptane (300 mL) was added to the residue, and the precipitated solids were filtered to obtain the title compound (80.2 g, 85%). The filtrate was then concentrated under a reduced pressure, and the residue was purified by silica gel column chromatography (heptane:ethyl acetate=2:1) to obtain the title compound (12.2 g, 13%).

$^1$H-NMR Spectrum (DMSO-d$_6$) δ (ppm): 1.22 (9H, s), 7.06-7.09 (1H, m), 7.72-7.77 (1H, m), 8.01-8.03 (1H, m), 8.29-8.31 (1H, m), 9.71 (1H, s).

Manufacturing Example 39-1-2

N-(3-Iodo-pyridin-2-yl)-2,2-dimethyl-propionamide

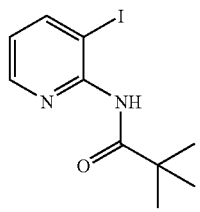

To a mixture of 2,2-dimethyl-N-pyridin-2-yl-propionamide (3.0 g, 17 mmol) described in Manufacturing Example 39-1-1, N,N,N',N'-tetramethylethylenediamine (6.3 mL, 42 mmol) and tetrahydrofuran (60 mL) was added dropwise n-butyl lithium (1.6 M n-hexane solution, 30 mL, 47 mmol) at –78° C., which was stirred overnight at 0° C. Iodine (6.8 g, 27 mmol) was added to the reaction mixture at –78° C., and stirred for 1.5 hours at 0° C. Water and saturated aqueous sodium thiosulfate solution were added to the reaction mixture, which was then extracted with ethyl acetate. The organic layer was washed with saturated aqueous sodium chloride, and the solvent was evaporated under a reduced pressure. The residue was purified by silica gel column chromatography (ethyl acetate:heptane=2:1) to obtain the title compound (2.9 g, 57%).

$^1$H-NMR Spectrum (CDCl$_3$) δ (ppm): 1.38 (9H, s), 6.85 (1H, dd, J=4.8, 7.9 Hz), 7.94 (1H, brs), 8.11 (1H, dd, J=1.7, 7.9 Hz), 8.46 (1H, dd, J=1.7, 4.6 Hz).

Manufacturing Example 39-1-3

N-(3-(4-Bromo-pyrazol-1-yl)-pyridin-2-yl)-2,2-dimethyl-propionamide

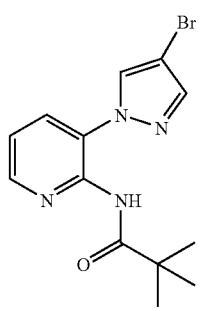

To a mixture of N-(3-iodo-pyridin-2-yl)-2,2-dimethyl-propionamide (380 mg, 1.2 mmol) described in Manufacturing Example 39-1-2 and toluene (10 mL) were added 4-bromopyrazole (160 mg, 1.1 mmol), copper (I) iodide (11 mg, 0.056 mmol), trans-1,2-cyclohexanediamine (26 mg, 0.22 mmol) and potassium carbonate (340 mg, 2.5 mmol) at room temperature, which was stirred overnight at 110° C. The reaction mixture was concentrated under a reduced pressure. The residue was purified by NH silica gel column chromatography (ethyl acetate:heptane=2:1) to obtain the title compound (190 mg, 52%).

$^1$H-NMR Spectrum (DMSO-d$_6$) δ (ppm): 1.10 (9H, s), 7.45 (1H, dd, J=4.8, 8.1 Hz), 7.84 (1H, s), 8.00 (1H, dd, J=1.7, 7.9 Hz), 8.23 (1H, s), 8.47 (1H, dd, J=1.7, 4.8 Hz), 9.83 (1H, brs).

Manufacturing Example 39-1-4

3-(4-Bromo-pyrazol-1-yl)-pyridin-2-ylamine

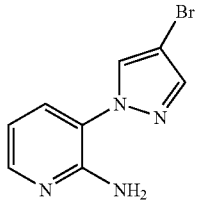

A mixture of N-(3-(4-bromo-pyrazol-1-yl)-pyridin-2-yl)-2,2-dimethyl-propionamide (380 mg, 1.2 mmol) described in Manufacturing Example 39-1-3 and aqueous 2.5 N hydrochloric acid solution (2 mL) was stirred overnight at 105° C. The reaction mixture was cooled to 0° C., and 5 N sodium hydroxide solution (1 mL) was added. The resulting solids were filtered to obtain the title compound (100 mg, 72%).

$^1$H-NMR Spectrum (DMSO-d$_6$) δ (ppm): 6.34 (2H, brs), 6.69 (1H, dd, J=4.8, 7.7 Hz), 7.62 (1H, dd, J=1.7, 7.7 Hz), 7.90 (1H, s), 8.02 (1H, dd, J=1.7, 4.8 Hz), 8.45 (1H, s).

The starting material, (4-benzyloxy-benzyl)-tributyl-stannane, was synthesized as follows.

Manufacturing Example 39-2-1

(4-Benzyloxy-benzyl)-tributyl-stannane

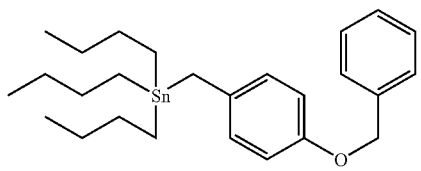

To a mixture of diisopropylamine (1.1 mL, 7.7 mmol) and tetrahydrofuran (20 mL) was added dropwise n-butyl lithium (1.6 M n-hexane solution, 4.5 mL, 7.1 mmol) at −78° C., which was stirred for 30 minutes at that temperature. Tributyltin hydride (1.7 mL, 6.5 mmol) was added dropwise to the reaction mixture at the same temperature and then stirred for 30 minutes at 0° C. The reaction mixture was cooled to −78° C., and a mixture of 4-benzyloxybenzyl chloride (1.5 g, 6.5 mmol) and tetrahydrofuran (10 mL) was added dropwise at that temperature. The reaction mixture was gradually warmed to room temperature. The reaction mixture was partitioned into water and n-heptane. The organic layer was washed with saturated aqueous sodium chloride, and the solvent was evaporated under a reduced pressure. The residue was purified by neutral silica gel column chromatography (ethyl acetate:heptane=1:30) to obtain the title compound (2.6 g, 83%).

$^1$H-NMR Spectrum (CDCl$_3$) δ (ppm): 0.77-0.81 (6H, m), 0.86 (9H, t, J=7.3 Hz), 1.21-1.30 (6H, m), 1.38-1.46 (6H, m), 2.24 (2H, s), 5.01 (2H, s), 6.80-6.83 (2H, m), 6.88-6.91 (2H, m), 7.29-7.44 (5H, m).

Example 40

3-(3-(6-Phenoxy-pyridin-3-ylmethyl)-isoxazol-5-yl)-pyridin-2,6-diamine

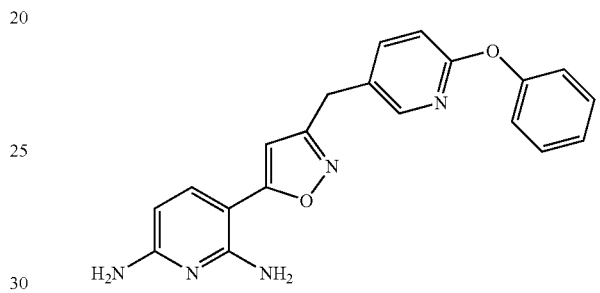

To a solution of (2-phenoxy-pyridin-5-yl)-acetohydroximoyl chloride (59.1 mg, 225 μmol) described in Manufacturing Example 40-1-4 and 3-ethynyl-pyridin-2,6-diamine (20.0 mg, 150 μmol) described in Manufacturing Example 13-1-3 in tetrahydrofuran (1.3 mL) was added triethylamine (41.8 μL, 300 μmol) at room temperature, which was stirred for 65 minutes at 50° C. The reaction solution was allowed to room temperature and partitioned into water and ethyl acetate. The organic layer was separated, washed with saturated aqueous sodium chloride, dried over anhydrous magnesium sulfate and filtered. The filtrate was concentrated under a reduced pressure. The residue was purified by NH silica gel column chromatography (ethyl acetate:methanol=10:1) to obtain the title compound (52 mg, 97%).

$^1$H-NMR Spectrum (DMSO-d$_6$) δ (ppm): 3.93 (2H, s), 5.79 (2H, s), 5.81 (1H, d, J=8.4 Hz), 6.10 (2H, s), 6.40 (1H, s), 6.97 (1H, d, J=8.4 Hz), 7.08-7.10 (2H, m), 7.16-7.20 (1H, m), 7.37-7.41 (2H, m), 7.50 (1H, d, J=8.4 Hz), 7.76 (1H, dd, J=2.2, 8.4 Hz), 8.11 (1H, d, J=2.4 Hz).

The starting material, (2-phenoxy-pyridin-5-yl)-acetohydroximoyl chloride, was synthesized as follows.

Manufacturing Example 40-1-1

5-Bromo-2-phenoxy-pyridine

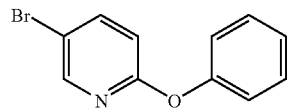

To a solution of phenol (1.97 g, 20.9 mmol) in N,N-dimethylformamide (100 mL) was added sodium hydride (1.00 g, 20.9 mmol) at 0° C., which was stirred for 5 minutes at 0° C. 2,5-Dibromopyridine (4.50 g, 19.0 mmol) was then added to this reaction solution at 0° C., and stirred for 40 minutes at room temperature. The reaction solution was then stirred for further 3 hours at 120° C. After allowing to room temperature, the reaction solution was partitioned into water and ethyl acetate. The organic layer was separated, washed with water and saturated aqueous sodium chloride, dried over anhydrous magnesium sulfate and filtered. The filtrate was concentrated under a reduced pressure. The residue was purified by silica gel column chromatography (heptane:ethyl acetate=6:1) to obtain the title compound (3.85 g, 81%).

$^1$H-NMR Spectrum (DMSO-d$_6$) δ (ppm): 7.02 (1H, dd, J=0.55, 8.8 Hz), 7.11-7.14 (2H, m), 7.19-7.23 (1H, m), 7.38-7.43 (2H, m), 8.04 (1H, dd, J=2.6, 8.8 Hz), 8.25 (1H, dd, J=0.55, 2.6 Hz).

Manufacturing Example 40-1-2

6-Phenoxy-pyridine-3-carbaldehyde

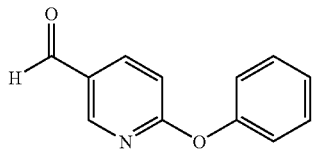

To a solution of 5-bromo-2-phenoxy-pyridine (3.85 g, 15.4 mmol) described in Manufacturing Example 40-1-1 in tetrahydrofuran (60 mL) was added n-butyl lithium (10.6 mL, 1.60 M hexane solution, 16.9 mmol) under nitrogen atmosphere at −78° C., which was stirred for 35 minutes at −78° C. N,N-Dimethylformamide (1.55 mL, 20.0 mmol) was then added to this reaction solution at −78° C., which was stirred for further 10 minutes at room temperature. After allowing to room temperature, the reaction solution was partitioned into water and ethyl acetate. The organic layer was separated, washed with saturated aqueous sodium chloride, dried over anhydrous magnesium sulfate and filtered. The filtrate was concentrated under a reduced pressure. The residue was purified by NH silica gel column chromatography (heptane:ethyl acetate=5:1) to obtain the title compound (1.12 g, 37%).

$^1$H-NMR Spectrum (CDCl$_3$) δ (ppm): 7.04 (1H, d, J=8.6 Hz), 7.17 (2H, d, J=7.5 Hz), 7.26-7.31 (1H, m), 7.44-7.48 (2H, m), 8.19 (1H, dd, J=2.2, 8.6 Hz), 8.63 (1H, d, J=2.2 Hz), 9.99 (1H, s).

Manufacturing Example 40-1-3

5-(2-Nitro-ethyl)-2-phenoxy-pyridine

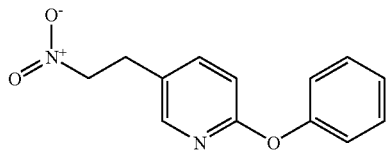

To a solution of 6-phenoxy-pyridine-3-carbaldehyde (1.12 g, 5.62 mmol) described in Manufacturing Example 40-1-2 in acetic acid (10 mL) were added nitromethane (1.52 mL, 28.1 mmol) and ammonium acetate (866 mg, 11.2 mmol) under nitrogen atmosphere, which was stirred for 3 hours at 100° C. After being cooled to room temperature, the reaction solution was partitioned into water and ethyl acetate. The organic layer was separated, washed with saturated aqueous sodium chloride, dried over anhydrous magnesium sulfate and filtered. The filtrate was concentrated under a reduced pressure. The resulting residue was dissolved in dimethyl sulfoxide (17 mL) and acetic acid (3 mL). Sodium borohydride (336 mg, 8.43 mmol) was added to this solution at room temperature while cooling appropriately, and stirred for 30 minutes at room temperature. The reaction solution was partitioned by addition of sodium hydrogencarbonate, water and ethyl acetate. The organic layer was separated, washed with water and saturated aqueous sodium chloride, dried over anhydrous magnesium sulfate and filtered. The filtrate was concentrated under a reduced pressure. The residue was purified by NH silica gel column chromatography (heptane:ethyl acetate=3:1) to obtain the title compound (753 mg, 55%).

$^1$H-NMR Spectrum (CDCl$_3$) δ (ppm): 3.28 (2H, t, J=7.1 Hz), 4.60 (2H, t, J=7.1 Hz), 6.88 (1H, d, J=8.8 Hz), 7.11-7.14 (2H, m), 7.20-7.24 (1H, m), 7.39-7.43 (2H, m), 7.55 (1H, ddd, J=0.37, 2.6, 8.4 Hz), 8.07 (1H, d, J=2.4 Hz).

Manufacturing Example 40-1-4

(2-Phenoxy-pyridin-5-yl)-acetohydroximoyl chloride

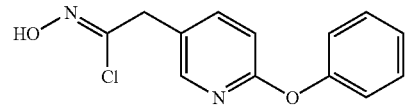

To a solution of 5-(2-nitro-ethyl)-2-phenoxy-pyridine (753 mg, 3.08 mmol) described in Manufacturing Example 40-1-3 in methanol (10 mL) was added lithium methoxide (234 mg, 6.16 mmol), which was stirred for 90 minutes at room temperature. The reaction solution was concentrated under a reduced pressure. The resulting residue was suspended in a mixture solution of tetrahydrofuran (10 mL) and methylene chloride (10 mL). Titanium (IV) chloride (745 μL, 6.87 mmol) was added to the suspension under nitrogen atmosphere at −78° C., and stirred for 140 minutes at 0° C. The reaction solution was partitioned into water and ethyl acetate at 0° C. The organic layer was separated, washed with saturated aqueous sodium chloride, dried over anhydrous magnesium sulfate and filtered. The filtrate was concentrated under a reduced pressure to obtain the title compound (785 mg, 97%) as a crude product.

$^1$H-NMR Spectrum (DMSO-d$_6$) δ (ppm): 3.81 (2H, s), 6.99 (1H, dd, J=0.73, 8.4 Hz), 7.09-7.12 (2H, m), 7.17-7.21 (1H, m), 7.38-7.42 (2H, m), 7.72 (1H, dd, J=2.6, 8.4 Hz), 8.03 (1H, dd, J=0.55, 2.6 Hz), 11.8 (1H, s).

Example 41

3-(3-(4-(5-Fluoro-pyridin-2-ylmethoxy)-benzyl)-isoxazol-5-yl)-pyridin-2-ylamine

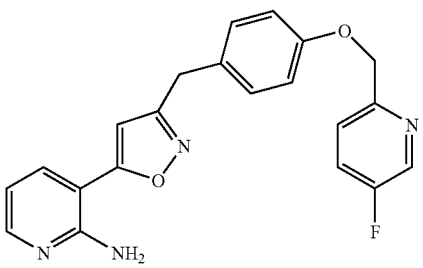

Tetrahydrofuran (10 mL) and 5 N aqueous sodium hydroxide solution (448 µL, 2.24 mmol) were added to 4-(5-(2-amino-pyridin-3-yl)-isoxazol-3-ylmethyl)-phenol (600 mg, 2.24 mmol) described in Manufacturing Example 5-1-1, which was irradiated by ultrasonic wave for 1 minute. The reaction solution was then concentrated under a reduced pressure to obtain a white solid. 2-Chloromethyl-5-fluoro-pyridine (359 mg, 2.46 mol) described in Manufacturing Example 41-2 and N,N-dimethylformamide (10 mL) were added to the resulting white solid and stirred for 1 hour at 60° C. After being cooled to room temperature, the reaction solution was partitioned into water and ethyl acetate. The organic layer was separated and concentrated under a reduced pressure. The residue was purified by NH silica gel column chromatography (heptane:ethyl acetate=1:1) to obtain the title compound (650 mg, 77%).

$^1$H-NMR Spectrum (DMSO-$d_6$) δ (ppm): 3.96 (2H, s), 5.15 (2H, s), 6.25 (2H, brs), 6.69 (1H, dd, J=4.8, 8.0 Hz), 6.79 (1H, s), 6.99 (2H, d, J=8.4 Hz), 7.25 (2H, d, J=8.8 Hz), 7.59 (1H, dd, J=4.8, 8.8 Hz), 7.76 (1H, ddd, J=2.8, 8.8, 8.8 Hz), 7.86 (1H, dd, J=2.0, 7.6 Hz), 8.08 (1H, dd, J=2.0, 4.8 Hz), 8.57 (1H, d, J=3.2 Hz).

2-Chloromethyl-5-fluoro-pyridine was synthesized as follows.

Manufacturing Example 41-1-1

(5-Fluoro-pyridin-2-yl)-methanol

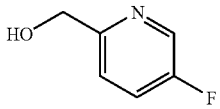

To a solution of 2-bromo-5-fluoropyridine (3.67 g, 20.8 mmol) in toluene (100 mL) was added dropwise n-butyl lithium (15.6 mL, 1.6 M hexane solution, 25.0 mmol) under nitrogen atmosphere at −78° C., which was stirred for 30 minutes. N,N-Dimethylformamide (8.05 mL, 104.0 mmol) was added dropwise to this solution at −78° C., and stirred for 20 minutes at 0° C. This reaction solution was vigorously stirred after addition of water and tetrahydrofuran. The organic layer was separated, washed with water and saturated aqueous sodium chloride, dried over anhydrous magnesium sulfate and filtered. Sodium borohydride (1.58 g, 41.8 mmol) was added to the filtrate at 0° C., and stirred for 1 hour at room temperature. This reaction solution was partitioned by addition of water and tetrahydrofuran. The organic layer was separated, washed with saturated aqueous sodium chloride, dried over anhydrous magnesium sulfate and filtered. The filtrate was concentrated under a reduced pressure. The resulting residue was purified by NH silica gel column chromatography (hexane:diethyl ether=1:2) to obtain the title compound (945 mg, 36%).

$^1$H-NMR Spectrum (CDCl$_3$) δ (ppm): 4.75 (2H, s), 7.29 (1H, dd, J=4.4, 8.8 Hz), 7.43 (1H, ddd, J=2.8, 8.4, 8.4 Hz), 8.42 (1H, d, J=2.8 Hz).

Manufacturing Example 41-1-2

2-Chloromethyl-5-fluoro-pyridine

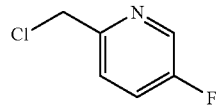

To a solution of (5-fluoro-pyridin-2-yl)-methanol (945 mg, 7.43 mmol) described in Manufacturing Example 41-1-1 in methylene chloride (70 mL) was added dropwise thionyl chloride (813 µL, 11.1 mmol) at room temperature, which was stirred for 30 minutes. This reaction solution was partitioned by addition of water, sodium hydrogencarbonate and methylene chloride. The organic layer was separated, washed with saturated aqueous sodium chloride, dried over anhydrous magnesium sulfate and filtered. The filtrate was concentrated under a reduced pressure. The residue was purified by NH silica gel column chromatography (hexane:diethyl ether=1:1) to obtain the title compound (761.1 mg, 70%).

$^1$H-NMR Spectrum (CDCl$_3$) δ (ppm): 4.67 (2H, s), 7.26-7.51 (2H, m), 8.43 (1H, d, J=2.8 Hz).

Example 42

3-(3-(4-(5-Methyl-pyridin-2-ylmethoxy)-benzyl)-isoxazol-5-yl)-pyridin-2-ylamine

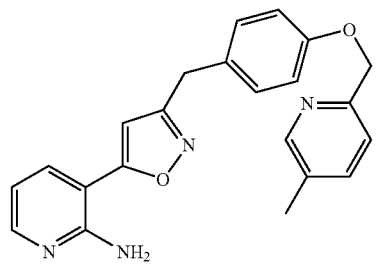

4-(5-(2-Amino-pyridin-3-yl)isoxazol-3-ylmethyl)-phenol (50 mg, 0.19 mmol) described in Manufacturing Example 5-1-1 and the 2-chloromethyl-5-methyl-pyridine (32 mg, 0.23 mmol) described in Manufacturing Example 42-1-2 were used to obtain the title compound (23 mg, 33%) according to the methods similar to those of Example 10.

$^1$H-NMR Spectrum (DMSO-$d_6$) δ (ppm): 2.29 (3H, s), 3.95 (2H, s), 5.11 (2H, s), 6.25 (2H, brs), 6.69 (1H, dd, J=4.8, 8.0 Hz), 6.79 (1H, s), 6.97 (2H, d, J=8.4 Hz), 7.24 (2H, d, J=8.4 Hz), 7.38 (1H, d, J=8.0 Hz), 7.62 (1H, d, J=8.0 Hz), 7.86 (1H, dd, J=1.6, 8.0 Hz), 8.08 (1H, dd, J=1.6, 4.8 Hz), 8.40 (1H, s).

The starting material, 2-chloromethyl-5-methyl-pyridine was synthesized as follows.

Manufacturing Example 42-1-1

(5-Methyl-pyridin-2-yl)-methanol

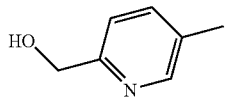

The title compound (1.1 g) was obtained according to the method described in Manufacturing Example 11-1-1 through Manufacturing Example 11-1-3.

$^1$H-NMR Spectrum (DMSO-$d_6$) δ (ppm): 2.27 (3H, s), 4.45 (2H, d, J=5.6 Hz), 5.31 (1H, t, J=5.6 Hz), 7.34 (1H, d, J=8.0 Hz), 7.59 (1H, dd, J=1.6, 8.0 Hz), 8.31 (1H, d, J=1.6 Hz).

Manufacturing Example 42-1-2

2-Chloromethyl-5-methyl-pyridine

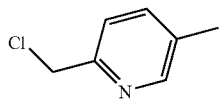

A mixed solution of (5-methyl-pyridine-2-yl)-methanol (500 mg, 4.1 mmol) described in Manufacturing Example 11-1-1, thionyl chloride (0.59 mL, 8.1 mmol) and methylene chloride (10 mL) was stirred for 5 minutes under reflux. The reaction solution was cooled to room temperature and concentrated under a reduced pressure. The resulting residue was partitioned into diethyl ether and saturated sodium bicarbonate solution. The organic layer was separated and passed through a glass filter lined with silica gel (eluted with ethyl acetate). The eluate was concentrated to obtain the title compound (440 mg, 76%) as a crude product. The resulting compound was used in the following reaction without further purification.

Example 43

3-(3-(4-(4-Methyl-pyridin-2-yloxymethyl)-benzyl)-isoxazol-5-yl)-pyridin-2-ylamine

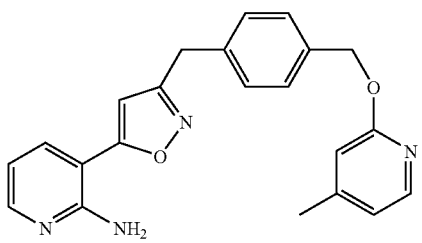

To a tetrahydrofuran (7.00 mL) solution of (4-(4-methyl-pyridin-2-yloxymethyl)-phenyl)-acetohydroximoyl chloride (270 mg, 0.930 mmol) described in Manufacturing Example 43-1-5 and 3-ethynyl-pyridin-2-ylamine (40.0 mg, 0.339 mmol) described in Manufacturing Example 1-2-3 was added triethylamine (189 μL, 1.36 mmol) at room temperature, which was stirred at room temperature for 4 hours. Water was added to the reaction solution at room temperature, which was then extracted with ethyl acetate. The organic layer was separated, washed with saturated aqueous sodium chloride, dried over anhydrous magnesium sulfate, and filtered. The filtrate was evaporated under a reduced pressure, and the residue was purified by NH silica gel column chromatography (ethyl acetate:heptane=1:3→1:2) to obtain the title compound (28.9 mg, 20.6%).

$^1$H-NMR Spectrum (DMSO-$d_6$) δ (ppm): 2.26 (3H, s), 4.03 (2H, s), 5.30 (2H, s), 6.25 (2H, brs), 6.68-6.70 (2H, m), 6.80 (1H, s), 6.81-6.82 (1H, m), 7.32 (2H, d, J=8.0 Hz), 7.39 (2H, d, J=8.0 Hz), 7.86-7.88 (1H, m), 8.00-8.02 (1H, m), 8.08-8.09 (1H, m).

The starting material, (4-(4-methyl-pyridin-2-yloxymethyl)-phenyl)-acetohydroximoyl chloride, was synthesized as follows.

Manufacturing Example 43-1-1

2-(4-Bromo-benzyloxy)-4-methyl-pyridine

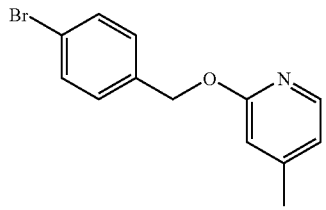

To a mixture of 4-bromobenzyl alcohol (4.54 g, 24.3 mmol) and N,N-dimethylformamide (50.0 mL) were added sodium hydride (1.00 g, 25.0 mmol, 60% in oil) was added at 0° C. under nitrogen atmosphere, which was stirred for 50 minutes at room temperature. 2-Fluoro-4-methylpyridine (1.80 g, 16.2 mmol) was then added thereto at 0° C., and stirred for 2 hours and 30 minutes at room temperature. Water was added to the reaction solution at room temperature, which was then extracted with ethyl acetate. The organic layer was separated, washed with saturated aqueous sodium chloride, and filtered. The filtrate was evaporated under a reduced pressure, and the residue was purified by silica gel column chromatography (ethyl acetate:heptane=1:15) to obtain the title compound (2.65 g, 58.8%).

$^1$H-NMR Spectrum (CDCl$_3$) δ (ppm): 2.28 (3H, s), 5.31 (2H, s), 6.60-6.61 (1H, m), 6.69-6.71 (1H, m), 7.29-7.32 (2H, m), 7.46-7.48 (2H, m), 8.00-8.01 (1H, m).

Manufacturing Example 43-1-2

4-(4-Methyl-pyridin-2-yloxymethyl)-benzaldehyde

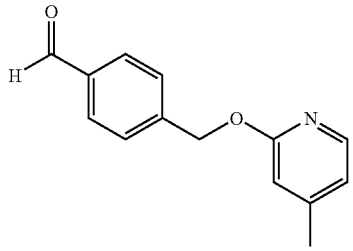

To a tetrahydrofuran (150 mL) solution of 2-(4-bromobenzyloxy)-4-methyl-pyridine (5.70 g, 20.5 mmol) described in Manufacturing Example 43-1-1 was added dropwise n-butyl lithium (2.67 M n-hexane solution, 9.21 mL, 24.6 mmol) on a dry ice-ethanol bath (−78° C.) under nitrogen atmosphere, which was stirred for 20 minutes at −78° C. N,N-dimethylformamide (3.16 mL, 41.0 mmol) was then added dropwise thereto and stirred for 10 minutes at −78° C. The reaction solution was allowed to room temperature, water was added, and the solution was extracted with ethyl acetate. The organic layer was separated and washed with saturated aqueous sodium chloride, and the solvent was evaporated under a reduced pressure. The residue was purified by silica gel column chromatography (ethyl acetate:heptane=1:3) to obtain the title compound (2.58 g, 55.4%).

$^1$H-NMR Spectrum (CDCl$_3$) δ (ppm): 2.31 (3H, s), 5.45 (2H, s), 6.66-6.67 (1H, m), 6.72-6.74 (1H, m), 7.58-7.60 (2H, m), 7.85-7.88 (2H, m), 8.00-8.01 (1H, m), 10.0 (1H, s).

Manufacturing Example 43-1-3

4-Methyl-2-(4-((E)-2-nitro-vinyl)-benzyloxy)-pyridine

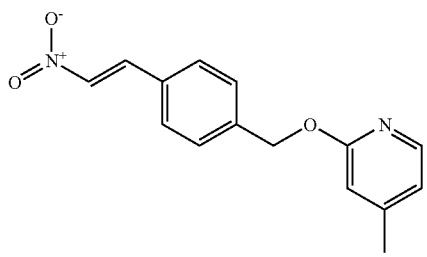

To an acetic acid (20.0 mL) solution of 4-(4-methyl-pyridin-2-yloxymethyl)-benzaldehyde (2.60 g, 11.5 mmol) described in Manufacturing Example 43-1-2 were added nitromethane (3.50 g, 57.3 mmol) and ammonium acetate (1.76 g, 22.9 mmol) at room temperature under nitrogen atmosphere, which was stirred for 4 hours at 100° C. Water and ethyl acetate were added to the reaction mixture, and the organic layer was extracted with ethyl acetate. The organic layer was separated, washed with water and saturated aqueous sodium chloride, dried over anhydrous magnesium sulfate, and filtered. The filtrate was concentrated under a reduced pressure to obtain the title compound (3.40 g) as a crude product.

$^1$H-NMR Spectrum (DMSO-d$_6$) δ (ppm): 2.28 (3H, s), 5.39 (2H, s), 6.75 (1H, m), 6.84-6.85 (1H, m), 7.50-7.53 (2H, m), 7.85-7.87 (2H, m), 8.00-8.02 (1H, m), 8.13 (1H, d, J=13.6 Hz), 8.23 (1H, d, J=13.6 Hz).

Manufacturing Example 43-1-4

4-Methyl-2-(4-(2-nitro-ethyl)-benzyloxy)pyridine

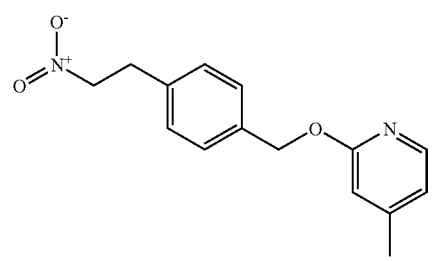

To a dimethyl sulfoxide (50 mL) solution of 4-methyl-2-(4-((E)-2-nitro-vinyl)-benzyloxy)-pyridine (3.10 g, 11.5 mmol) described in Manufacturing Example 43-1-3 and acetic acid (3.10 mL) was added sodium borohydride (733 mg, 18.4 mmol) at room temperature while cooling appropriately under nitrogen atmosphere, which was stirred for 10 minutes. Water was then added dropwise into the reaction solution at room temperature while cooling appropriately, and the reaction mixture was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:5→1:2) to obtain the title compound (1.10 g, 35.1%).

$^1$H-NMR Spectrum (DMSO-d$_6$) δ (ppm): 2.27 (3H, s), 3.22 (2H, t, J=6.8 Hz), 4.84 (2H, t, J=6.8 Hz), 5.29 (2H, s), 6.69 (1H, s), 6.82 (1H, d, J=5.2 Hz), 7.27 (2H, d, J=8.0 Hz), 7.37 (2H, d, J=8.0 Hz), 8.02 (1H, d, J=5.2 Hz).

Manufacturing Example 43-1-5

(4-(4-Methyl-pyridin-2-yloxymethyl)-phenyl)-acetohydroximoyl chloride

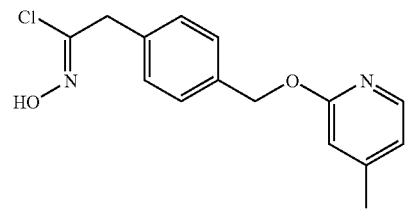

To a methanol (10.0 mL) solution of 4-methyl-2-(4-(2-nitro-ethyl)-benzyloxy)pyridine (500 mg, 1.84 mmol) described in Manufacturing Example 43-1-4 was added lithium methoxide (140 mg, 3.68 mmol) under nitrogen atmosphere at room temperature, which was stirred for 30 minutes at room temperature. The solvent was evaporated from the reaction mixture under a reduced pressure, and anhydrous dichloromethane (10.0 mL) and anhydrous tetrahydrofuran (5.00 mL) were added to the residue. Titanium (IV) chloride (667 μL, 6.07 mmol) was added dropwise into the reaction mixture on a dry ice-ethanol bath (−78° C.), and stirred for 45 minutes at 0° C. and then for 60 minutes at room temperature. Water, ethyl acetate and tetrahydrofuran were added to the reaction mixture on an ice bath (0° C.), and the organic layer was separated. The organic layer was washed with water and saturated aqueous sodium chloride, dried over anhydrous magnesium sulfate, and filtered. The filtrate was concentrated under a reduced pressure to obtain the title compound (409 mg, 76.5%) as a crude product.

$^1$H-NMR Spectrum (DMSO-$d_6$) δ (ppm): 2.27 (3H, s), 3.82 (2H, s), 5.31 (2H, s), 6.70 (1H, s), 6.82-6.84 (1H, m), 7.24-7.28 (2H, m), 7.39-7.41 (2H, m), 8.01-8.03 (1H, m), 11.73 (1H, s).

Example 44

3-(3-(4-(5-Methyl-pyridin-2-yloxymethyl)-benzyl)-isoxazol-5-yl)-pyridin-2-ylamine

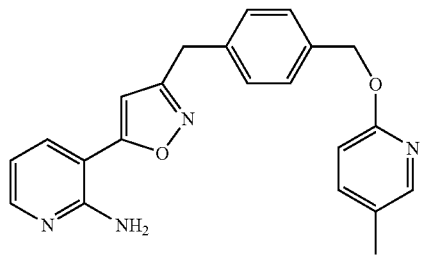

To a tetrahydrofuran (7.00 mL) solution of (4-(5-methyl-pyridin-2-yloxymethyl)-phenyl)-acetohydroximoyl chloride (246 mg, 0.846 mmol) described in Manufacturing Example 44-1-5 and 3-ethynyl-pyridin-2-ylamine (40.0 mg, 0.339 mmol) described in Manufacturing Example 1-2-3 was added triethylamine (189 μL, 1.36 mmol) at room temperature, which was stirred for 4 hours at room temperature. Water was added to the reaction solution at room temperature, which was then extracted with ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (ethyl acetate:heptane=1:3→1:2) to obtain the title compound (21.3 mg, 16.9%).

$^1$H-NMR Spectrum (DMSO-$d_6$) δ (ppm): 2.20 (3H, s), 4.03 (2H, s), 5.28 (2H, s), 6.25 (2H, brs), 6.68-6.71 (1H, m), 6.75-6.77 (1H, m), 6.81 (1H, s), 7.32 (2H, d, J=8.0 Hz), 7.39 (2H, d, J=8.0 Hz), 7.52-7.55 (1H, m), 7.85-7.88 (1H, m), 7.96-7.97 (1H, m), 8.08-8.09 (1H, m).

The starting material, (4-(5-methyl-pyridin-2-yloxymethyl)-phenyl)-acetohydroximoyl chloride, was synthesized as follows.

Manufacturing Example 44-1-1

2-(4-Bromo-benzyloxy)-5-methyl-pyridine

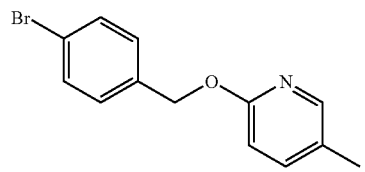

To an N,N-dimethylformamide (50.0 mL) solution of 4-bromobenzyl alcohol (4.54 g, 24.3 mmol) was added sodium hydride (1.00 g, 25.0 mmol, 60% in oil) under nitrogen atmosphere at 0° C., which was stirred for 30 minutes at room temperature. 2-Fluoro-5-methylpyridine (1.80 g, 16.2 mmol) was then added at 0° C., and stirred for 5 hours at room temperature. Water was added to the reaction solution at room temperature, which was then extracted with ethyl acetate. The organic layer was separated and washed with saturated aqueous sodium chloride, and the solvent was evaporated under a reduced pressure. The residue was purified by silica gel column chromatography (ethyl acetate:heptane=1:15) to obtain the title compound (2.67 g, 59.3%).

$^1$H-NMR Spectrum (CDCl$_3$) δ (ppm): 2.24 (3H, s), 5.30 (2H, s), 6.70-6.72 (1H, m), 7.31-7.33 (2H, m), 7.38-7.41 (1H, m), 7.46-7.49 (2H, m), 7.95-7.96 (1H, m).

Manufacturing Example 44-1-2

4-(5-Methyl-pyridin-2-yloxymethyl)-benzaldehyde

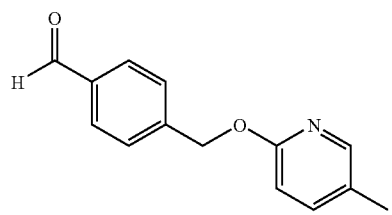

To a tetrahydrofuran (150 mL) solution of 2-(4-bromo-benzyloxy)-5-methyl-pyridine (5.40 g, 19.4 mmol) described in Manufacturing Example 44-1-1 was added dropwise n-butyl lithium (2.67 M n-hexane solution, 8.73 mL, 23.3 mmol) on a dry ice-ethanol bath (−78° C.) under nitrogen atmosphere, which was stirred for 30 minutes at −78° C. N,N-dimethylformamide (2.99 mL, 38.8 mmol) was then added dropwise thereto, which was stirred for 10 minutes at −78° C. Water was added to the reaction solution at room temperature, which was then extracted with ethyl acetate. The organic layer was separated and washed with saturated aqueous sodium chloride, and the solvent was evaporated under a reduced pressure. The residue was purified by silica gel column chromatography (ethyl acetate:heptane=1:6→1:4) to obtain the title compound (2.93 g, 66.5%).

$^1$H-NMR Spectrum (CDCl$_3$) δ (ppm): 2.21 (3H, s), 5.41 (2H, s), 6.72-6.74 (1H, m), 7.38-7.41 (1H, m), 7.56-7.58 (2H, m), 7.83-7.85 (2H, m), 7.92-7.93 (1H, m), 9.97 (1H, s).

Manufacturing Example 44-1-3

5-Methyl-2-(4-((E)-2-nitro-vinyl)-benzyloxy)-pyridine

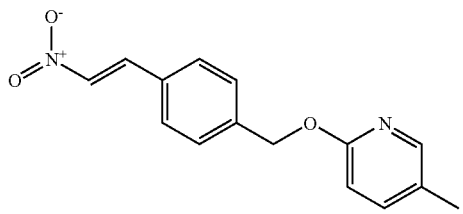

To an acetic acid (20.0 mL) solution of 4-(5-methyl-pyridin-2-yloxymethyl)-benzaldehyde (2.93 g, 12.9 mmol) described in Manufacturing Example 44-1-2 were added nitromethane (3.94 g, 64.5 mmol) and ammonium acetate (1.99 g, 25.8 mmol) under nitrogen atmosphere at room temperature, which was stirred for 2.5 hours at 100° C. Water and ethyl acetate were added to the reaction mixture, and the organic layer was extracted with ethyl acetate. This organic layer was washed with water and saturated aqueous sodium chloride, dried over anhydrous magnesium sulfate, and filtered. The filtrate was concentrated under a reduced pressure to obtain the title compound (3.50 g) as a crude product.

$^1$H-NMR Spectrum (DMSO-d$_6$) δ (ppm): 2.21 (3H, s), 5.38 (2H, s), 6.82-6.84 (1H, m), 7.52 (2H, d, J=8.4 Hz), 7.55-7.58 (1H, m), 7.85 (2H, d, J=8.4 Hz), 7.96-7.97 (1H, m), 8.12 (1H, d, J=13.6 Hz), 8.22 (1H, d, J=13.6 Hz).

Manufacturing Example 44-1-4

5-Methyl-2-(4-(2-nitro-ethyl)-benzyloxy)pyridine

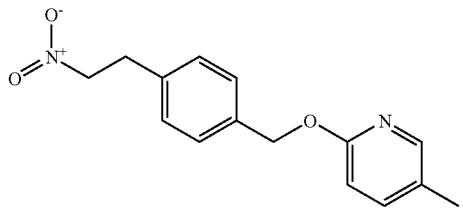

To a dimethyl sulfoxide (40.0 mL) solution of 5-methyl-2-(4-((E)-2-nitro-vinyl)-benzyloxy)-pyridine (3.50 g, 12.9 mmol) described in Manufacturing Example 44-1-3 and acetic acid (3.50 mL) was added sodium borohydride (822 mg, 20.6 mmol) at room temperature while cooling appropriately under nitrogen atmosphere, which was stirred for 10 minutes. Water was then added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:4) to obtain the title compound (1.91 g, 54.3%).

$^1$H-NMR Spectrum (DMSO-d$_6$) δ (ppm): 2.20 (3H, s), 3.22 (2H, t, J=6.8 Hz), 4.84 (2H, t, J=6.8 Hz), 5.27 (2H, s), 6.76-6.78 (1H, m), 7.27 (2H, d, J=8.0 Hz), 7.36 (2H, d, J=8.0 Hz), 7.52-7.55 (1H, m), 7.97-7.98 (1H, m).

Manufacturing Example 44-1-5

(4-(5-Methyl-pyridin-2-yloxymethyl)-phenyl)-acetohydroximoyl chloride

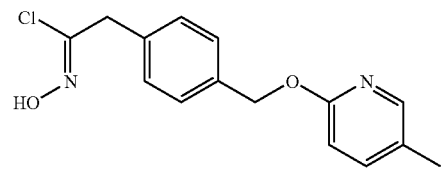

To a methanol (30 mL) solution of 5-methyl-2-(4-(2-nitro-ethyl)-benzyloxy)pyridine (700 mg, 2.57 mmol) described in Manufacturing Example 44-1-4 was added lithium methoxide (195 mg, 5.14 mmol) under nitrogen atmosphere at room temperature, which was stirred for 30 minutes at room temperature. The reaction mixture was concentrated under a reduced pressure, and anhydrous dichloromethane (15.0 mL) and anhydrous tetrahydrofuran (10.0 mL) were added to the residue. Titanium (IV) chloride (904 μL, 8.22 mmol) was added dropwise into the reaction mixture on a dry ice-ethanol bath (−78° C.), and then stirred for 45 minutes at room temperature. Water, ethyl acetate and tetrahydrofuran were added to the reaction mixture, and the organic layer was extracted with ethyl acetate. This organic layer was washed with water and saturated aqueous sodium chloride, dried over anhydrous magnesium sulfate, and filtered. The filtrate was concentrated under a reduced pressure to obtain the title compound (569 mg, 76.1%) as a raw product.

$^1$H-NMR Spectrum (DMSO-d$_6$) δ (ppm): 2.02 (3H, s), 3.81 (2H, s), 5.29 (2H, s), 6.77-6.79 (1H, m), 7.25 (2H, d, J=8.0 Hz), 7.40 (2H, d, J=8.0 Hz), 7.53-7.55 (1H, m), 7.97-7.98 (1H, m), 11.74 (1H, s).

Example 45

3-(3-(4-(6-Fluoro-pyridin-2-ylmethoxy)-benzyl)-isoxazol-5-yl)-pyridin-2-ylamine

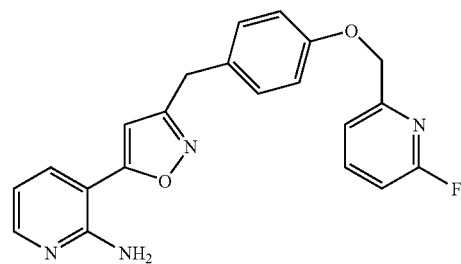

Tetrahydrofuran (3 mL) and a 5 N aqueous sodium hydroxide solution (36.0 μL, 0.18 mmol) were added to 4-(5-(2-amino-pyridin-3-yl)-isoxazol-3-ylmethyl)-phenol (48.2 mg, 0.18 mmol) described in Manufacturing Example 5-1-1, which was dissolved by irradating ultrasonic wave for 1 minute. The reaction mixture was then concentrated under a reduced pressure to obtain a white solid. This solid and 2-chloromethyl-6-fluoro-pyridine (63.2 mg, 0.43 mmol)

described in Manufacturing Example 45-1-1 were added to N,N-dimethylformamide (3 mL), which was stirred for 3 hours at room temperature. This mixture was partitioned into water and ethyl acetate. This organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (47.9 mg, 59%).

$^1$H-NMR Spectrum (CDCl$_3$) δ (ppm): 4.00 (2H, s), 5.12 (2H, s), 5.40 (2H, br s), 6.24 (1H, s), 6.71 (1H, dd, J=4.8, 7.6 Hz), 6.87 (1H, dd, J=2.8, 8.4 Hz), 6.94 (2H, d, J=8.8 Hz), 7.21 (2H, d, J=8.8 Hz), 7.40-7.42 (1H, m), 7.70 (1H, dd, J=1.6, 7.6 Hz), 7.81 (1H, q, J=8.0 Hz), 8.13 (1H, dd, J=1.6, 4.8 Hz)

The starting material, 2-chloromethyl-6-fluoro-pyridine, was synthesized as follows.

Manufacturing Example 45-1-1

2-Chloromethyl-6-fluoro-pyridine

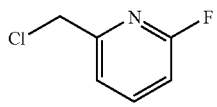

A mixture of 2-fluoro-6-methylpyridine (420 mg, 3.78 mmol), N-chlorosuccimide (757 mg, 5.67 mmol), 75% benzoyl peroxide (24.4 mg, 0.08 mmol), acetic acid (13 μL, 0.23 mmol) and acetonitrile (7 mL) was stirred for 3 hours and 30 minutes at 85° C. The reaction mixture was cooled, water was added, and the mixture was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by silica gel column chromatography (heptane:ethyl acetate=1:1) to obtain the title compound (370.7 mg, 67%).

$^1$H-NMR Spectrum (DMSO-d$_6$) δ (ppm): 4.75 (2H, s), 7.17-7.19 (1H, m), 7.50-7.52 (1H, m), 8.02-8.08 (1H, m).

Example 46

3-(3-(4-(5-Methyl-furan-2-ylmethyl)-benzyl)-isoxazol-5-yl)-pyridin-2-ylamine

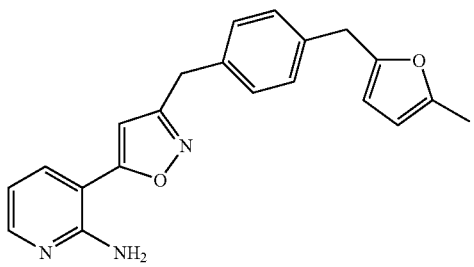

To a mixture of (4-(5-methyl-furan-2-ylmethyl)-phenyl)-acetohydroximoyl chloride (11 mg, 0.043 mmol) described in Manufacturing Example 46-1-6 and tetrahydrofuran (1 mL) were added 3-ethynyl-pyridin-2-ylamine (4.0 mg, 0.034 mmol) described in Manufacturing Example 1-2-3 and triethylamine (9.4 μL, 0.068 mmol) at room temperature, which was stirred for 3 hours at 45° C. The reaction mixture was cooled to room temperature, water was added at the same temperature, and the mixture was extracted with ethyl acetate. The organic layer was washed with saturated aqueous sodium chloride, and was concentrated under a reduced pressure. The residue was purified by NH silica gel column chromatography (ethyl acetate:heptane=2:3) to obtain the title compound (5.1 mg, 41%).

$^1$H-NMR Spectrum (CDCl$_3$) δ (ppm): 2.24 (3H, s), 3.90 (2H, s), 4.03 (2H, s), 5.53 (2H, br s), 5.85 (1H, d, J=2.9 Hz), 5.87 (1H, d, J=2.9 Hz), 6.26 (1H, s), 6.72 (1H, dd, J=5.0, 7.6 Hz), 7.21 (4H, s), 7.72 (1H, d, J=7.7 Hz), 8.12 (1H, dd, J=1.8, 4.9 Hz).

The starting material, (4-(5-methyl-furan-2-ylmethyl)-phenyl)-acetohydroximoyl chloride, was synthesized as follows.

Manufacturing Example 46-1-1

4-(Hydroxy-(5-methyl-furan-2-yl)-methyl)-benzaldehyde

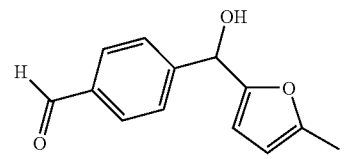

To a mixture of 4-bromobenzaldehyde dimethyl acetal (2.0 mL, 12 mmol) and diethyl ether (30 mL) was added dropwise n-butyl lithium (1.6 M n-hexane solution, 9.0 mL, 14 mmol) at −78° C., which was stirred for 20 minutes at the same temperature. 5-Methylfurfural (1.3 mL, 13 mmol) was added dropwise into the reaction mixture at that temperature, and stirred for 50 minutes at 0° C. Water and ethyl acetate were added to extract the reaction mixture. The organic layer was washed with saturated aqueous sodium chloride, and the solvent was evaporated under a reduced pressure. The residue was purified by silica gel column chromatography (ethyl acetate:heptane=1:2) to obtain the title compound (320 mg, 12%).

$^1$H-NMR Spectrum (CDCl$_3$) δ (ppm): 2.28 (3H, s), 5.86 (1H, s), 5.90-5.91 (1H, m), 5.98 (1H, d, J=3.1 Hz), 7.63 (2H, d, J=8.4 Hz), 7.89 (2H, d, J=7.9 Hz), 10.03 (1H, s).

Manufacturing Example 46-1-2

(4-(5-Methyl-furan-2-ylmethyl)-phenyl)-methanol

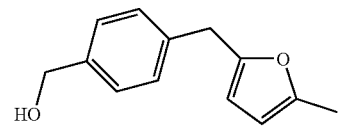

To a mixture of lithium aluminumhydride (230 mg, 4.9 mmol) and tetrahydrofuran (15 mL) was added aluminum chloride (830 mg, 6.2 mmol) at 0° C., which was stirred for 30 minutes at room temperature. A mixture of 4-(hydroxy-(5-methyl-furan-2-yl)-methyl)-benzaldehyde (320 mg, 1.5 mmol) described in Manufacturing Example 46-1-1 and tetrahydrofuran (5 mL) was added dropwise into the reaction mixture at 0° C., and stirred for 2 hours at that temperature. A 28% aqueous ammonia solution was added dropwise into the reaction mixture at the same temperature to quench the excess reagent. The reaction mixture was cooled to room temperature, and filtered by being passed through a Celite bed. The filtrate was concentrated under a reduced pressure to obtain the title compound (330 mg) as a crude product. This compound was used in the following reaction without further purification.

Manufacturing Example 46-1-3

4-(5-Methyl-furan-2-ylmethyl)-benzaldehyde

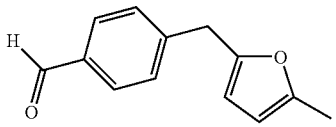

To a mixture of (4-(5-methyl-furan-2-ylmethyl)-phenyl)-methanol (350 mg, 1.7 mmol) obtained in Manufacturing Example 46-1-2 and dichloromethane (10 mL) was added manganese dioxide (3.5 g, 4.7 mmol) at room temperature, which was stirred overnight at room temperature. The reaction mixture was filtered through a Celite pad, and the filtrate was concentrated under a reduced pressure. The residue was purified by silica gel column chromatography (ethyl acetate:heptane=1:6) to obtain the title compound (100 mg, 29%).

$^1$H-NMR Spectrum (CDCl$_3$) δ (ppm): 2.25 (3H, s), 3.99 (2H, s), 5.876-5.883 (1H, m), 5.92 (1H, d, J=3.1 Hz), 7.39-7.41 (2H, m), 7.81-7.83 (2H, m), 9.99 (1H, s).

Manufacturing Example 46-1-4

2-Methyl-5-(4-((E)-2-nitro-vinyl)-benzyl)-furan

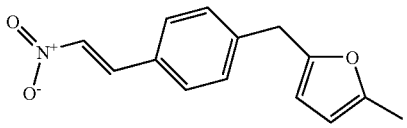

To a mixture of 4-(5-methyl-furan-2-ylmethyl)-benzaldehyde (96 mg, 0.48 mmol) described in Manufacturing Example 46-1-3 and acetic acid (1 mL) were added nitromethane (190 μL, 3.6 mmol) and ammonium acetate (110 mg, 1.4 mmol) at room temperature, which was stirred for 3 hours at 100° C. The reaction mixture was cooled to room temperature, and extracted by addition of water and ethyl acetate. The organic layer was washed with saturated aqueous sodium chloride and dried over magnesium sulfate. The filtrate was concentrated under a reduced pressure to obtain the title compound (120 mg) as a crude product. This compound was used in the following reaction without further purification.

Manufacturing Example 46-1-5

2-Methyl-5-(4-(2-nitro-ethyl)-benzyl)-furan

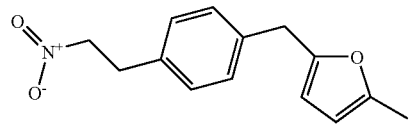

To a mixture of 2-methyl-5-(4-((E)-2-nitro-vinyl)-benzyl)-furan (120 mg) described in Manufacturing Example 46-1-4, acetic acid (0.2 mL) and dimethyl sulfoxide (3.4 mL) was added sodium borohydride (29 mg, 0.77 mmol) at room temperature while cooling appropriately, which was stirred for 20 minutes at room temperature. Water was added to the reaction mixture, which was then extracted with ethyl acetate. The organic layer was washed with saturated aqueous sodium chloride, and was concentrated under a reduced pressure. The residue was purified by neutral silica gel column chromatography (ethyl acetate:heptane=1:5) to obtain the title compound (90 mg, 77%).

$^1$H-NMR Spectrum (CDCl$_3$) δ (ppm): 2.24 (3H, s), 3.30 (2H, t, J=7.4 Hz), 3.89 (2H, s), 4.59 (2H, t, J=7.4 Hz), 5.85-5.87 (2H, m), 7.14 (2H, d, J=8.2 Hz), 7.20 (2H, d, J=8.2 Hz).

Manufacturing Example 46-1-6

(4-(5-Methyl-furan-2-ylmethyl)-phenyl)-acetohydroximoyl chloride

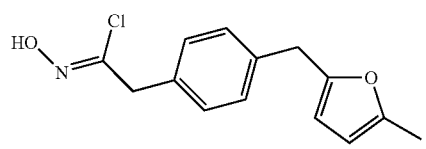

To a mixture of 2-methyl-5-(4-(2-nitro-ethyl)-benzyl)-furan (87 mg, 0.36 mmol) described in Manufacturing Example 46-1-5 and methanol (2 mL) was added lithium methoxide (27 mg, 0.71 mmol) at room temperature, which was stirred for 15 minutes at room temperature. The solvent was evaporated from the reaction mixture under a reduced pressure. Titanium (IV) chloride (86 μL, 0.78 mmol) was added at −78° C. to a mixture of the resulting residue, methylene chloride (2 mL) and tetrahydrofuran (1 mL), which was stirred for 1 hour at 0° C. The reaction mixture was cooled to −78° C., water (5 mL) was added, and the temperature was gradually raised to room temperature. The reaction mixture was extracted by addition of ethyl acetate and water. The organic layer was washed with water until the pH became about 5. The organic layer was washed with saturated aqueous sodium chloride and dried over anhydrous magnesium sulfate. Thereafter, the organic layer was filtered and the filtrate was concentrated under a reduced pressure to obtain the title compound (79 mg, 84%).

Example 47

3-(3-(4-(2-Methyl-pyridin-4-ylmethoxy)-benzyl)-isoxazol-5-yl)-pyridin-2-ylamine

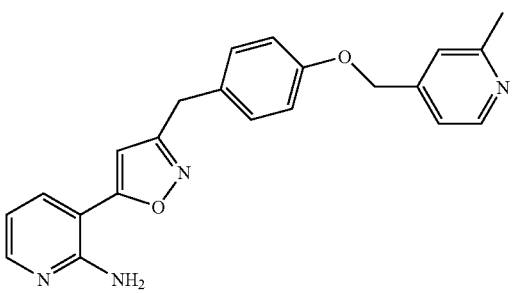

(2-Methyl-pyridin-4-yl)-methanol (40 mg, 0.33 mmol) described in Manufacturing Example 47-1-1, thionyl chloride (0.047 ml, 0.65 mmol) and methylene chloride (4.0 ml) were stirred for 5 minutes at 60° C. Sodium bicarbonate solution and ethyl acetate were added to separate the reaction solution, and the ethyl acetate layer was dried over sodium sulfate. The solvent was evaporated under a reduced pressure to obtain 4-chloromethyl-2-methyl-pyridine as a crude product.

2 N Sodium hydroxide (0.16 ml, 0.32 mmol) and methanol (1.0 ml) were added to dissolve 4-(5-(2-amino-pyridin-3-yl) isoxazol-3-ylmethyl)-phenol (87 mg, 0.33 mmol) described in Manufacturing Example 5-1-1, and methanol was evaporated under a reduced pressure. A solution of the aforementioned 4-chloromethyl-2-methyl-pyridine dissolved in dimethylformamide (1 ml) was added to the residue and stirred for 10 minutes at 60° C. Water and ethyl acetate were added to separate the reaction solution, the resulting ethyl acetate layer was concentrated under a reduced pressure, and the residue was purified by silica gel column chromatography (heptane: ethyl acetate=1:3) to obtain the title compound (47 mg, 39%).

$^1$H-NMR Spectrum (DMSO-d$_6$) δ (ppm): 2.47 (3H, s), 3.96 (2H, s), 5.11 (2H, s), 6.25 (2H, brs), 6.68 (1H, dd, J=4.8, 8.0 Hz), 6.79 (1H, s), 6.97 (2H, d, J=8.8 Hz), 7.20 (1H, d, J=5.2 Hz), 7.25 (2H, d, J=8.8 Hz), 7.29 (1H, s), 7.86 (1H, dd, J=2.0, 8.0 Hz), 8.08 (1H, dd, J=2.0, 4.8 Hz), 8.42 (1H, d, J=5.2 Hz).

The starting material, (2-methyl-pyridin-4-yl)-methanol, was synthesized as follows.

Manufacturing Example 47-1-1

(2-Methyl-pyridin-4-yl)-methanol

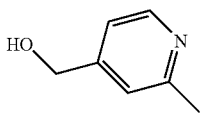

The title compound (200 mg) was obtained according to the methods similar to those of Manufacturing Example 11-1-1 through Manufacturing Example 11-1-3.

$^1$H-NMR Spectrum (CDCl$_3$) δ (ppm): 2.24 (3H, s), 3.78 (2H, s), 3.90 (2H, s), 5.85-5.87 (2H, m), 7.20 (4H, s).

Example 48

3-(3-(5-p-Tolyloxy-thiophen-2-ylmethyl)-isoxazol-5-yl)-pyridin-2-ylamine

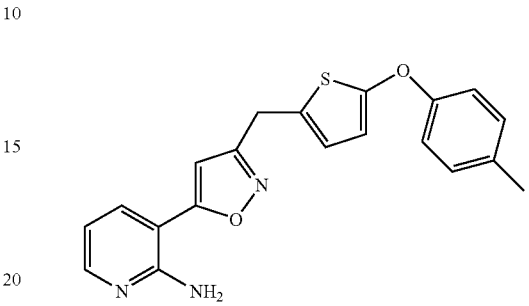

To a tetrahydrofuran (7.00 mL) solution of (5-p-tolyloxy-thiophen-2-yl)-acetohydroximoyl chloride (191 mg, 0.678 mmol) described in Manufacturing Example 48-1-5 and 3-ethynyl-pyridin-2-ylamine (40.0 mg, 0.339 mmol) described in Manufacturing Example 1-2-3 was added triethylamine (189 μL, 1.36 mmol) at room temperature, which was stirred for 4 hours at room temperature. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1: 3) to obtain the title compound (2.03 mg, 1.65%).

$^1$H-NMR Spectrum (DMSO-d$_6$) δ (ppm): 2.32 (3H, s), 4.14 (2H, s), 5.54 (2H, brs), 6.34-6.36 (1H, m), 6.40 (1H, s), 6.62-6.63 (1H, m), 6.73-6.77 (1H, m), 6.98-7.00 (2H, m), 7.11-7.13 (2H, m), 7.76-7.78 (1H, m), 8.14-8.15 (1H, m).

The starting material, (5-p-tolyloxy-thiophen-2-yl)-acetohydroximoyl chloride, was synthesized as follows.

Manufacturing Example 48-1-1

5-p-Tolyloxy-thiophene-2-carbonitrile

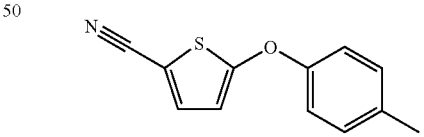

To a dimethyl sulfoxide (100 mL) solution of 5-nitro-2-thiophenecarbonitrile (6.30 g, 40.9 mmol) were added p-cresol (8.85 g, 81.8 mmol) and potassium carbonate (11.3 g, 81.8 mmol) under nitrogen atmosphere, which was stirred for 5 hours at 60° C. The reaction solution was cooled to room temperature, and extracted with ethyl acetate after addition of water. The organic layer was washed with saturated aqueous sodium chloride, and the solvent was evaporated under a reduced pressure. The residue was purified by NH silica gel column chromatography (ethyl acetate:heptane=1:3→2:1) to obtain the title compound (6.95 g, 78.9%).

¹H-NMR Spectrum (CDCl₃) δ (ppm): 2.36 (3H, s), 6.38-6.39 (1H, m), 7.03-7.05 (2H, m), 7.18-7.20 (2H, m), 7.33-7.35 (1H, m).

Manufacturing Example 48-1-2

5-p-Tolyloxy-thiophene-2-carbaldehyde

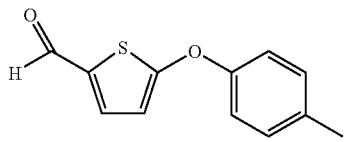

To a tetrahydrofuran (70.0 mL) solution of 5-p-tolyloxy-thiophene-2-carbonitrile (2.00 g, 9.29 mmol) described in Manufacturing Example 48-1-1 was added dropwise diisobutyl aluminum hydride (0.97 M n-hexane solution, 23.9 mL, 23.2 mmol) on a dry ice-ethanol bath (−78° C.) under nitrogen atmosphere, which was stirred for 3 hours at room temperature. The reaction mixture was cooled to room temperature and extracted with ethyl acetate after addition of water. The organic layer was washed with saturated aqueous sodium chloride, and the solvent was evaporated under a reduced pressure. The residue was purified by silica gel column chromatography (ethyl acetate:heptane=1:5) to obtain the title compound (958 mg, 47.2%).

¹H-NMR Spectrum (CDCl₃) δ (ppm): 2.36 (3H, s), 6.47 (1H, d, J=4.0 Hz), 7.08 (2H, d, J=8.0 Hz), 7.20 (2H, d, J=8.0 Hz), 7.51 (1H, d, J=4.0 Hz), 9.69 (1H, s).

Manufacturing Example 48-1-3

2-((E)-2-Nitro-vinyl)-5-p-tolyloxy-thiophene

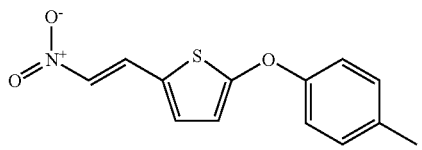

To an acetic acid (20.0 mL) solution of 5-p-tolyloxy-thiophene-2-carbaldehyde (2.30 g, 10.5 mmol) described in Manufacturing Example 48-1-2 were added nitromethane (3.20 g, 52.5 mmol) and ammonium acetate (1.62 g, 21.0 mmol) under nitrogen atmosphere at room temperature, which was stirred for 2.5 hours at 100° C. Water and ethyl acetate were added to the reaction mixture, and the organic layer was extracted with ethyl acetate. The organic layer was washed with water and saturated aqueous sodium chloride, dried over anhydrous magnesium sulfate, and filtered. The solvent was evaporated from the filtrate under a reduced pressure to obtain the title compound (2.50 g) as a crude product.

¹H-NMR Spectrum (DMSO-d₆) δ (ppm): 2.32 (3H, s), 6.70 (1H, d, J=4.0 Hz), 7.18 (2H, d, J=8.0 Hz), 7.28 (2H, d, J=8.0 Hz), 7.65 (1H, d, J=4.0 Hz), 7.78 (1H, d, J=12.8 Hz), 8.26 (1H, d, J=12.8 Hz).

Manufacturing Example 48-1-4

2-(2-Nitro-ethyl)-5-p-tolyloxy-thiophene

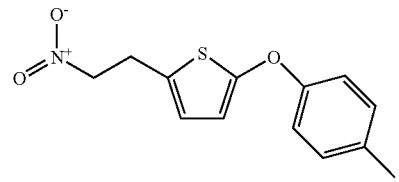

To a dimethyl sulfoxide (30.0 mL) solution of 2-((E)-2-nitro-vinyl)-5-p-tolyloxy-thiophene (2.50 g, 9.57 mmol) described in Manufacturing Example 48-1-3 and acetic acid (2.50 mL) was added sodium borohydride (610 mg, 20.6 mmol) at room temperature while cooling appropriately under nitrogen atmosphere, which was stirred for 30 minutes at room temperature. Water was then added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under a reduced pressure and the residue was purified by NH silica gel column chromatography (ethyl acetate:heptane=1:4) to obtain the title compound (1.20 g, 47.6%).

¹H-NMR Spectrum (DMSO-d₆) δ (ppm): 2.28 (3H, s), 3.33 (2H, t, J=6.4 Hz), 4.81 (2H, t, J=6.4 Hz), 6.45-6.46 (1H, m), 6.67-6.69 (1H, m), 6.98-7.00 (2H, m), 7.17-7.20 (2H, m).

Manufacturing Example 48-1-5

(5-p-Tolyloxy-thiophen-2-yl)-acetohydroximoyl chloride

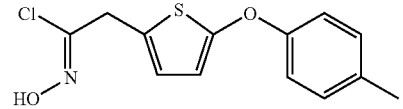

To a methanol (10.0 mL) solution of 2-(2-nitro-ethyl)-5-p-tolyloxy-thiophene (500 mg, 1.90 mmol) described in Manufacturing Example 48-1-4 was added lithium methoxide (144 mg, 3.80 mmol) under nitrogen atmosphere at room temperature, which was stirred for 30 minutes at room temperature. The solvent was evaporated from the reaction mixture under a reduced pressure, and anhydrous dichloromethane (15.0 ml) and anhydrous tetrahydrofuran (10.0 ml) were added to the residue. Titanium (IV) chloride (668 μL, 6.08 mmol) was added dropwise into the reaction mixture on a dry ice-ethanol bath (−78° C.), which was stirred for 45 minutes at room temperature. Water, ethyl acetate and tetrahydrofuran were added to the reaction mixture on an ice bath (0° C.), and the organic layer was extracted with ethyl acetate. This organic layer was washed with water and saturated aqueous sodium chloride, dried over anhydrous magnesium sulfate, and filtered. The solvent was evaporated from the filtrate under a reduced pressure to obtain the title compound (530 mg, 99.0%) as a crude product.

$^1$H-NMR Spectrum (DMSO-$d_6$) δ (ppm): 2.28 (3H, s), 3.94 (2H, s), 6.48 (1H, d, J=3.6 Hz), 6.74 (1H, d, J=3.6 Hz), 7.00-7.01 (2H, m), 7.18-7.20 (2H, m), 11.81 (1H, s).

Example 49

3-(3-(4-(Pyridin-4-ylmethoxy)-benzyl)-isoxazol-5-yl)-pyridin-2-ylamine

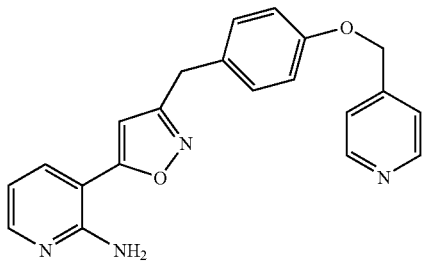

Tetrahydrofuran (3 mL) and a 5 N aqueous sodium hydroxide solution (22.4 μL, 0.11 mmol) were added to 4-(5-(2-amino-pyridine-3-yl)-isoxazole-3-ylmethyl)-phenol (30 mg, 0.11 mmol) described in Manufacturing Example 5-1-1, which was dissolved by irradiating ultrasonic wave for 1 minute. Next, the reaction solution was concentrated under a reduced pressure to obtain a white solid. The resulting solid was suspended in N,N-dimethylformamide (1 mL). Meanwhile, THF (390 μL) and 1 N aqueous sodium hydroxide solution (390 μL, 0.39 mmol) were added to 4-(chloromethyl)pyridine hydrochloride (50 mg, 0.39 mmol) and then the organic layer was separated to obtain a tetrahydrofuran solution of 4-(chloromethyl)pyridine. A part of this tetrahydrofuran solution (224 μL) was added to the N,N-dimethylformamide suspension prepared above, and stirred for 45 minutes at 60° C. This mixture was cooled to room temperature, and partitioned into water and ethyl acetate. The organic layer was separated, washed with water and saturated aqueous sodium chloride, dried over anhydrous magnesium sulfate, and filtered. The filtrate was concentrated under a reduced pressure and the residue was purified by NH silica gel column chromatography (ethyl acetate) to obtain the title compound (36 mg, 88%).

$^1$H-NMR Spectrum (DMSO-$d_6$) δ (ppm): 3.97 (2H, s), 5.17 (2H, s), 6.26 (2H, brs), 6.68-6.72 (1H, m), 6.79 (1H, s), 6.99 (2H, d, J=8.4 Hz), 7.26 (2H, d, J=8.8 Hz), 7.43 (2H, d, J=6.0 Hz), 7.87 (1H, dd, J=2.0, 7.6 Hz), 8.09 (1H, dd, J=1.6, 4.8 Hz), 8.57 (2H, dd, J=1.6, 4.4 Hz).

Example 50

3-(3-(4-(Pyridin-3-ylmethoxy)-benzyl)-isoxazol-5-yl)-pyridin-2-ylamine

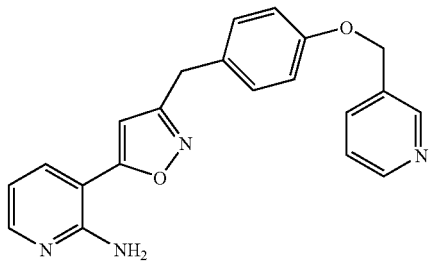

Tetrahydrofuran (3 mL) and a 5 N aqueous sodium hydroxide solution (22.4 μL, 0.11 mmol) were added to 4-(5-(2-amino-pyridin-3-yl)-isoxazol-3-ylmethyl)-phenol (30 mg, 0.11 mmol) described in Manufacturing Example 5-1-1, which was dissolved by irradiating ultrasonic wave for 1 minute. Next, the reaction solution was concentrated under a reduced pressure to obtain a white solid. This solid was suspended in N,N-dimethylformamide (1 mL). Meanwhile, THF (390 μL) and a 1 N aqueous sodium hydroxide solution (390 μL, 0.39 mmol) were added to 3-(chloromethyl)pyridine hydrochloride (50 mg, 0.39 mmol), and then the organic layer was separated to obtain a tetrahydrofuran solution of 3-(chloromethyl)pyridine. A part of this tetrahydrofuran solution (224 μL) was added to the N,N-dimethylformamide suspension prepared above, and stirred for 45 minutes at 60° C. This mixture was cooled to room temperature, and partitioned into water and ethyl acetate. The organic layer was separated, washed with water and saturated aqueous sodium chloride, dried over anhydrous magnesium sulfate, and filtered. The filtrate was concentrated under a reduced pressure and the residue was purified by NH silica gel column chromatography (ethyl acetate) to obtain the title compound (40.0 mg, 100%).

$^1$H-NMR Spectrum (DMSO-$d_6$) δ (ppm): 3.97 (2H, s), 5.13 (2H, s), 6.25 (2H, brs), 6.67-6.74 (1H, m), 6.78 (1H, s), 7.00 (2H, d, J=8.0 Hz), 7.26 (2H, d, J=7.6 Hz), 7.40-7.46 (1H, m), 7.85-7.89 (2H, m), 8.09 (1H, d, J=4.8 Hz), 8.54 (1H, d, J=4.8 Hz), 8.65-8.68 (1H, m).

Example 51

3-(3-(4-(4-Chloro-pyridin-2-ylmethoxy)-benzyl)-isoxazol-5-yl)-pyridin-2-ylamine

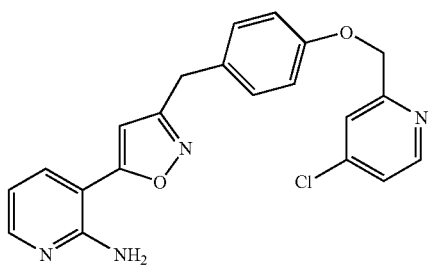

Tetrahydrofuran (3 mL) and 5 N aqueous sodium hydroxide solution (22.4 μL, 0.11 mmol) were added to 4-(5-(2- amino-pyridine-3-yl)-isoxazole-3-ylmethyl)-phenol (30 mg, 0.11 mmol) described in Manufacturing Example 5-1-1, which was dissolved by irradiating ultrasonic wave for 1 minute. Next, the reaction solution was concentrated under a reduced pressure to obtain a white solid. An N,N-dimethylformamide (1 mL) solution of 4-chloro-2-chloromethyl-pyridine (36.3 mg, 0.22 mmol) described in Manufacturing Example 51-1-2 was added to a suspension of this solid and N,N-dimethylformamide (1 mL), which was stirred for 1 hour at 60° C. This mixture was cooled to room temperature, and partitioned into water and ethyl acetate. The organic layer was separated, washed with water and saturated aqueous sodium chloride, dried over anhydrous magnesium sulfate, and filtered. The filtrate was concentrated under a reduced pressure and the residue was purified by NH silica gel column chromatography (heptane:ethyl acetate=1:1) to obtain the title compound (36.6 mg, 83%).

$^1$H-NMR Spectrum (DMSO-d$_6$) δ (ppm): 3.97 (2H, s), 5.17 (2H, s), 6.26 (2H, brs), 6.69 (1H, dd, J=4.8, 8.0 Hz), 6.79 (1H, s), 7.01 (2H, d, J=8.4 Hz), 7.26 (2H, d, J=8.4 Hz), 7.51 (1H, dd, J=2.0, 5.2 Hz), 7.61 (1H, d, J=2.0 Hz), 7.87 (1H, dd, J=2.0, 8.0 Hz), 8.08 (1H, dd, J=2.0, 4.8 Hz), 8.55 (1H, d, J=5.2 Hz).

The starting material, 4-chloro-2-chloromethyl-pyridine, was synthesized as follows.

Manufacturing Example 51-1-1

(4-Chloro-pyridin-2-yl)-methanol

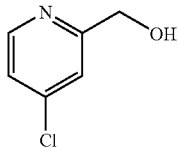

To a mixture of 4-chloro-2-picoline (1.0 g, 7.84 mmol) and dichloromethane (20 mL), was added m-chloroperbenzoic acid (3.5 g, 13.2 mmol) on an ice bath, which was stirred for 1.5 hours at room temperature. Water and sodium hydrogencarbonate were added to the reaction, followed by extraction with dichloromethane. The organic layer was separated, washed with water and saturated aqueous sodium chloride, dried over anhydrous magnesium sulfate, and filtered. Acetic anhydride (20 mL) was added to the residue obtained by concentrating the filtrate under a reduced pressure, and this was stirred for 1 hour at 100° C. The reaction mixture was cooled to room temperature and concentrated under a reduced pressure. A 5 N aqueous sodium hydroxide solution (1.57 mL, 7.87 mmol) was added to a mixture of the resulting residue and methanol (20 mL) on an ice bath, which was stirred for 1.5 hours at room temperature. Water was added to the mixture, which was then extracted with ethyl acetate. The organic layer was separated, washed with water and saturated aqueous sodium chloride, dried over anhydrous magnesium sulfate, and filtered. The filtrate was concentrated under a reduced pressure and the residue was purified by NH silica gel column chromatography (heptane:ethyl acetate=6:1) to obtain the title compound (200 mg, 18%).

$^1$H-NMR Spectrum (CDCl$_3$) δ (ppm): 4.76 (2H, s), 7.23-7.25 (1H, m), 7.32-7.33 (1H, m), 8.46 (1H, d, J=5.6 Hz).

Manufacturing Example 51-1-2

4-Chloro-2-chloromethyl-pyridine

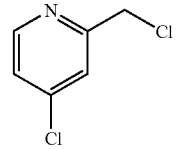

To a mixture of (4-chloro-pyridine-2-yl)-methanol (146.8 mg, 1.0 mmol) described in Manufacturing Example 51-1-1 and toluene (3 mL) was added thionyl chloride (112 μL, 1.53 mmol) on an ice bath, which was stirred for 1 hour 15 minutes at room temperature. Saturated aqueous sodium hydrogencarbonate solution was added to the reaction mixture, which was then extracted with ethyl acetate. The organic layer was separated, washed with water and saturated aqueous sodium chloride, dried over anhydrous magnesium sulfate, and filtered. The filtrate was concentrated under a reduced pressure and the residue was purified by NH silica gel column chromatography (heptane:ethyl acetate=4:1) to obtain the title compound (97 mg, 59%).

$^1$H-NMR Spectrum (CDCl$_3$) δ (ppm): 4.65 (2H, s), 7.26-7.28 (1H, m), 7.52-7.53 (1H, m), 8.48 (1H, d, J=5.6 Hz).

Example 52

3-(3-(4-(6-Chloro-pyridin-2-ylmethoxy)-benzyl)-isoxazol-5-yl)-pyridin-2-ylamine

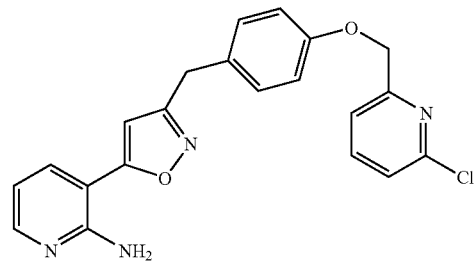

Tetrahydrofuran (3 mL) and a 5 N aqueous sodium hydroxide solution (22.4 μL, 0.11 mmol) were added to 4-(5-(2-amino-pyridin-3-yl)isoxazol-3-ylmethyl)-phenol (30 mg, 0.11 mmol) described in Manufacturing Example 5-1-1, which was dissolved by irradiating ultrasonic wave for 1 minute. The reaction solution was then concentrated under a reduced pressure to obtain a white solid. An N,N-dimethylformamide (1 mL) solution of 2-chloro-6-chloromethyl-pyridine (36.3 mg, 0.22 mmol) described in Manufacturing Example 52-1-2 was added to a suspension of this solid and N,N-dimethylformamide (1 mL), which was stirred for 1 hour at 60° C. This mixture was cooled to room temperature and partitioned into water and ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (39.5 mg, 90%).

¹H-NMR Spectrum (DMSO-d₆) δ (ppm): 3.97 (2H, s), 5.15 (2H, s), 6.26 (2H, brs), 6.69 (1H, dd, J=4.8, 8.0 Hz), 6.79 (1H, s), 6.99 (2H, d, J=8.4 Hz), 7.26 (2H, d, J=8.4 Hz), 7.46-7.52 (2H, m), 7.85-7.92 (2H, m), 8.08 (1H, dd, J=2.0, 4.8 Hz).

The starting material, 2-chloro-6-chloromethyl-pyridine, was synthesized as follows.

Manufacturing Example 52-1-1

(6-Chloro-pyridin-2-yl)-methanol

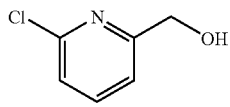

To a mixture of 2-chloro-6-methylpyridine (1.0 g, 7.84 mmol) and dichloromethane (20 mL) was added m-chloroperbenzoic acid (3.5 g, 13.2 mmol) on an ice bath, which was stirred for 1.5 hours at 40° C. Water and sodium hydrogencarbonate were added to the reaction mixture, which was then extracted with dichloromethane. The organic layer was separated, washed with water and saturated aqueous sodium chloride, dried over anhydrous magnesium sulfate, and filtered. The filtrate was concentrated under a reduced pressure. Acetic anhydride (20 mL) was added to the resulting residue and stirred for 1 hour at 100° C. The reaction mixture was cooled to room temperature and concentrated under a reduced pressure. A 5 N aqueous sodium hydroxide solution (4 mL, 20.1 mmol) was added to a mixture of the resulting residue and methanol (20 mL) on an ice bath, which was stirred for 30 minutes. Water was added to this mixture, which was then extracted with ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=3:1) to obtain the title compound (200.0 mg, 18%).

¹H-NMR Spectrum (CDCl₃) δ (ppm): 3.08 (1H, brs), 4.75 (2H, d, J=5.2 Hz), 7.23-7.27 (2H, m), 7.64-7.69 (1H, m).

Manufacturing Example 52-1-2

2-Chloro-6-chloromethyl-pyridine

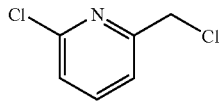

To a mixture of (6-chloro-pyridine-2-yl)-methanol (200 mg, 1.39 mmol) described in Manufacturing Example 52-1-1 and toluene (3 mL) was added thionyl chloride (152 μL, 2.09 mmol) on an ice bath, which was stirred for 2 hours at room temperature. Saturated aqueous sodium hydrogencarbonate solution was added to the reaction mixture, which was then extracted with ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=4:1) to obtain the title compound (163.2 mg, 73%).

¹H-NMR Spectrum (CDCl₃) δ (ppm): 4.64 (2H, s), 7.29 (1H, d, J=8.0 Hz), 7.44 (1H, d, J=7.6 Hz), 7.70 (1H, dd, J=7.6, 8.0 Hz).

Example 53

3-(3-(6-Phenoxy-pyridin-3-ylmethyl)-isoxazol-5-yl)-pyridin-2-ylamine

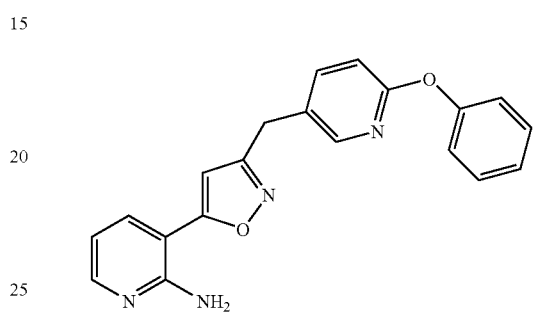

To a tetrahydrofuran (2 mL) solution of (2-phenoxy-pyridin-5-yl)-acetohydroximoyl chloride (100 mg, 0.381 mmol) described in Manufacturing Example 40-1-4 and 3-ethynyl-pyridin-2-ylamine (30 mg, 0.25 mmol) described in Manufacturing Example 1-2-3 was added triethylamine (71 μL, 0.51 mmol) under nitrogen atmosphere, which was stirred for 3 hours at 50° C. Water was added to the reaction mixture at room temperature, which was then extracted with ethyl acetate. The organic layer was separated, washed with water and saturated aqueous sodium chloride, dried over anhydrous magnesium sulfate, and filtered. The filtrate was concentrated under a reduced pressure, and the residue was purified by silica gel column chromatography (ethyl acetate:methanol=10:1) to obtain the title compound (27 mg, 31%).

¹H-NMR Spectrum (DMSO-d₆) δ (ppm): 4.02 (2H, s), 6.26 (2H, s), 6.68 (1H, dd, J=4.8, 7.7 Hz), 6.83 (1H, s), 6.98 (1H, d, J=8.6 Hz), 7.09 (2H, d, J=7.5 Hz), 7.18 (1H, t, J=7.3 Hz), 7.39 (2H, t, J=7.5 Hz), 7.79 (1H, dd, J=2.4, 8.6 Hz), 7.85 (1H, dd, J=1.8, 7.7 Hz), 8.07 (1H, dd, J=1.8, 4.8 Hz), 8.13 (1H, d, J=2.2 Hz).

Example 54

3-(3-(6-Phenoxymethyl-pyridin-3-ylmethyl)-isoxazol-5-yl)-pyridin-2-ylamine

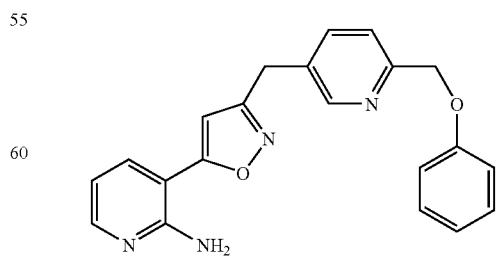

To a tetrahydrofuran (3.00 mL) solution of (6-phenoxymethyl-pyridin-3-yl)-acetohydroximoyl chloride (80.0 mg, 0.289 mmol) described in Manufacturing Example 54-1-6 and 3-ethynyl-pyridin-2-ylamine (20.0 mg, 0.169 mmol) described in Manufacturing Example 1-2-3 was added triethylamine (70.7 µL, 0.507 mmol) at room temperature, which was stirred for 4.5 hours at 60° C. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=2:1→3:1) to obtain the title compound (4.00 mg, 6.60%).

¹H-NMR Spectrum (DMSO-d₆) δ (ppm): 4.10 (2H, s), 5.16 (2H, s), 6.27 (2H, brs), 6.69-6.72 (1H, m), 6.87 (1H, s), 6.92-7.02 (3H, m), 7.27-7.31 (2H, m), 7.48-7.50 (1H, m), 7.78-7.79 (1H, m), 7.86-7.88 (1H, m), 8.09-8.10 (1H, m), 8.58-8.59 (1H, m).

The starting material, (6-phenoxymethyl-pyridin-3-yl)-acetohydroximoyl chloride, was synthesized as follows.

Manufacturing Example 54-1-1

(5-Bromo-pyridin-2-yl)-methanol

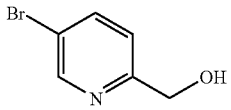

To a toluene (300 mL) solution of 2,5-dibromopyridine (10.0 g, 42.2 mmol) was added dropwise n-butyl lithium (2.55 M n-hexane solution, 18.2 mL, 46.4 mmol) on a dry ice-ethanol bath (−78° C.) under nitrogen atmosphere, which was stirred for 2 hours at −78° C. N,N-dimethylformamide (3.7 g, 50.6 mmol) was then added dropwise thereto and stirred for 10 minutes at −78° C. Sodium borohydride (3.20 g, 84.4 mmol) and methanol (20.0 mL) were then added and stirred for 30 minutes at room temperature. Water was added to the reaction solution, which was then extracted with ethyl acetate. The organic layer was washed with saturated aqueous sodium chloride, and the solvent was evaporated under a reduced pressure. The residue was purified by silica gel column chromatography (ethyl acetate:heptane=1:1→2:1) to obtain the title compound (4.70 g, 59.2%).

¹H-NMR Spectrum (DMSO-d₆) δ (ppm): 4.54 (2H, d, J=5.6 Hz), 5.28 (1H, t, J=5.6 Hz), 7.44-7.47 (1H, m), 8.03-8.05 (1H, m), 8.59-8.60 (1H, m).

Manufacturing Example 54-1-2

5-Bromo-2-chloromethyl-pyridine hydrochloride

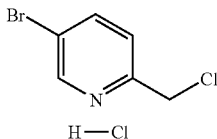

To a toluene (20.0 mL) solution of (5-bromo-pyridin-2-yl)-methanol (4.70 g, 25.0 mmol) described in Manufacturing Example 54-1-1 was added dropwise thionyl chloride (3.65 mL, 50.1 mmol) on an ice bath (0° C.) under nitrogen atmosphere, which was stirred for 5 minutes at room temperature. The solvent was evaporated under a reduced pressure to obtain the title compound (4.2 g, 69.2%) as a hydrochloride.

¹H-NMR Spectrum (DMSO-d₆) δ (ppm): 4.78 (2H, s), 7.55-7.57 (1H, m), 8.11-8.14 (1H, m), 8.70-8.72 (1H, m).

Manufacturing Example 54-1-3

5-Bromo-2-phenoxymethyl-pyridine

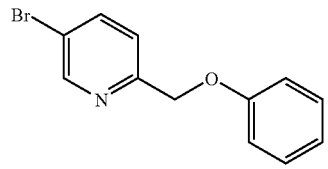

To an N,N-dimethylformamide (40.0 mL) solution of phenol (1.92 g, 20.4 mmol) was added sodium hydride (815 mg, 20.4 mmol, 60% in oil) on an ice bath (0° C.) under nitrogen atmosphere, which was stirred for 20 minutes at room temperature. To the reaction solution was then added a mixture of 5-bromo-2-chloromethyl-pyridine hydrochloride (4.2 g, 20.4 mmol) described in Manufacturing Example 54-1-2 and triethylamine (28.0 mL, 20.4 mmol), which was stirred first for 30 minutes at room temperature and then for 45 minutes at 70° C. Water and ethyl acetate were added to the reaction mixture, and the organic layer was extracted with ethyl acetate. This organic layer was washed with water and saturated aqueous sodium chloride, dried over anhydrous magnesium sulfate, and filtered. The solvent was evaporated from the filtrate under a reduced pressure, and the residue was purified by silica gel column chromatography (ethyl acetate:heptane=1:10) to obtain the title compound (4.40 g, 81.7%).

¹H-NMR Spectrum (CDCl₃) δ (ppm): 5.15 (2H, s), 6.95-6.99 (3H, m), 7.25-7.31 (2H, m), 7.42-7.45 (1H, m), 7.81-7.83 (1H, m), 8.64-8.65 (1H, m).

Manufacturing Example 54-1-4

6-Phenoxymethyl-pyridin-3-carbaldehyde

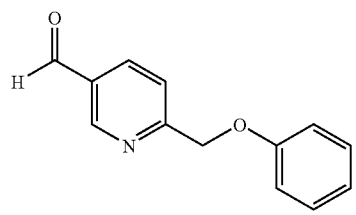

To a diethyl ether (250 mL) solution of 5-bromo-2-phenoxymethyl-pyridine (4.40 g, 16.6 mmol) described in Manufacturing Example 54-1-3 was added n-butyl lithium (2.55 M n-hexane solution, 8.46 mL, 21.6 mmol) on a dry ice-ethanol bath (−78° C.) under nitrogen atmosphere, which was stirred for 40 minutes at −78° C. N,N-dimethylformamide (1.93 mL, 25.0 mmol) was then added dropwise thereto and stirred for 20 minutes at −78° C. The reaction solution was allowed to room temperature, water was added, and the solution was extracted with ethyl acetate. The organic layer was washed with saturated aqueous sodium chloride, and the solvent was evaporated under a reduced pressure. The residue was purified by silica gel column chromatography (ethyl acetate:heptane=1:3) to obtain the title compound (1.00 g, 28.3%).

$^1$H-NMR Spectrum (CDCl$_3$) δ (ppm): 5.29 (2H, s), 6.97-7.01 (3H, m), 7.29-7.33 (2H, m), 7.73-7.75 (1H, m), 8.19-8.21 (1H, m), 9.05-9.06 (1H, m), 10.12 (1H, s).

Manufacturing Example 54-1-5

5-(2-Nitro-ethyl)-2-phenoxymethyl-pyridine

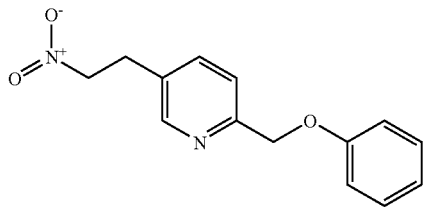

To a methanol (20.0 mL) solution of 6-phenoxymethyl-pyridine-3-carbaldehyde (1.00 g, 4.69 mmol) described in Manufacturing Example 54-1-4 was added lithium methoxide (21.4 mg, 0.56 mmol) under nitrogen atmosphere at room temperature. This was cooled to 0° C., and nitromethane (372 mg, 6.10 mmol) and lithium methoxide (193 mg, 5.07 mmol) were added and stirred for 10 minutes at room temperature. The reaction solution was then concentrated under a reduced pressure. Tetrahydrofuran (20.0 mL) was added to the residue, and then acetic anhydride (6.24 g, 61.1 mmol) and triethylamine (1.42 mL, 10.2 mmol) were added and stirred for 1 hour at 70° C. Water and ethyl acetate were added to the reaction mixture, and the organic layer was extracted with ethyl acetate. This organic layer was washed with water and saturated aqueous sodium chloride, dried over anhydrous magnesium sulfate, and filtered. The solvent was evaporated from the filtrate under a reduced pressure. Methanol (20.0 mL) was added to the residue, and sodium borohydride (263 mg, 6.96 mmol) was then added on an ice bath (0° C.). Following 5 minutes of stirring at 0° C., water was added dropwise at 0° C. The reaction mixture was extracted with ethyl acetate, and the organic layer was washed with water and saturated aqueous sodium chloride, dried over anhydrous magnesium sulfate, and filtered. The solvent was evaporated from the filtrate under a reduced pressure, and the residue was purified by NH silica gel column chromatography (ethyl acetate:heptane=1:1) to obtain the title compound (170 mg, 14.2%).

$^1$H-NMR Spectrum (DMSO-d$_6$) δ (ppm): 3.25 (2H, t, J=6.8 Hz), 4.91 (2H, t, J=6.8 Hz), 5.14 (2H, s), 6.93-6.97 (1H, m), 7.00-7.02 (2H, m), 7.27-7.31 (2H, m), 7.46-7.48 (1H, m), 7.75-7.78 (1H, m), 8.49-8.50 (1H, m).

Manufacturing Example 54-1-6

(6-Phenoxymethyl-pyridin-3-yl)-acetohydroximoyl chloride

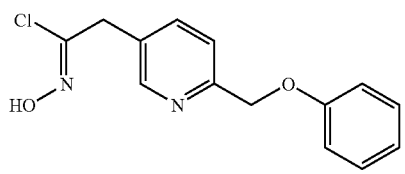

To a methanol (7.00 mL) solution of 5-(2-nitro-ethyl)-2-phenoxymethyl-pyridine (170 mg, 0.658 mmol) described in Manufacturing Example 54-1-5 was added lithium methoxide (50.0 mg, 1.32 mmol) under nitrogen atmosphere at room temperature, which was stirred for 30 minutes at room temperature. The solvent was evaporated from the reaction mixture under a reduced pressure, and anhydrous dichloromethane (10.0 ml) and anhydrous tetrahydrofuran (5.00 ml) were added to the residue. Titanium (IV) chloride (231 μL, 2.11 mmol) was added dropwise into the reaction mixture on a dry ice-ethanol bath (−78° C.), which was stirred for 30 minutes at room temperature. Water, ethyl acetate and tetrahydrofuran were added to the reaction mixture on an ice bath (0° C.), and the organic layer was extracted with ethyl acetate. This organic layer was washed with water and saturated aqueous sodium chloride, dried over anhydrous magnesium sulfate, and filtered. The solvent was evaporated from the filtrate under a reduced pressure to obtain the title compound (169 mg) as a crude product.

$^1$H-NMR Spectrum (DMSO-d$_6$) δ (ppm): 3.90 (2H, s), 5.17 (2H, s), 6.93-6.97 (1H, m), 7.01-7.03 (2H, m), 7.27-7.30 (2H, m), 7.49-7.51 (1H, m), 7.72-7.74 (1H, m), 8.49-8.50 (1H, m), 11.83 (1H, s).

Example 55

3-(3-(4-(6-Fluoro-pyridin-2-yloxymethyl)-benzyl)-isoxazol-5-yl)-pyridin-2-ylamine

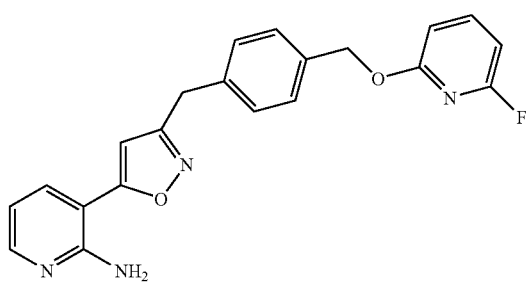

To a tetrahydrofuran (3 mL) solution of (4-(6-fluoro-pyridin-2-yloxymethyl)-phenyl)acetohydroximoyl chloride (200 mg, 0.679 mmol) described in Manufacturing Example 55-1-5 and 3-ethynyl-pyridin-2-ylamine (50 mg, 0.423 mmol) described in Manufacturing Example 1-2-3 was added triethylamine (237 μL, 1.7 mmol) at room temperature, which was stirred for 2 hours at 50° C. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (heptane:ethyl acetate=4:1→2:1) to obtain the title compound (59 mg, 23%).

$^1$H-NMR Spectrum (CDCl$_3$) δ (ppm): 4.07 (2H, s), 5.32 (2H, s), 5.64 (2H, brs), 6.27 (1H, s), 6.47-6.50 (1H, m), 6.64-6.67 (1H, m), 6.71-6.74 (1H, m), 7.30 (2H, d, J=8.4 Hz), 7.43 (2H, d, J=8.4 Hz), 7.63-7.69 (1H, m), 7.72-7.75 (1H, m), 8.11-8.12 (1H, m).

The starting material, (4-(6-fluoro-pyridin-2-yloxymethyl)-phenyl)acetohydroximoyl chloride, was synthesized as follows.

Manufacturing Example 55-1-1

4-(6-Fluoro-pyridin-2-yloxymethyl)-benzonitrile

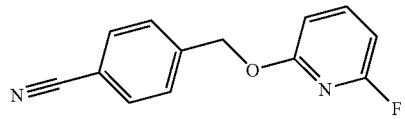

To an N,N-dimethylformamide (50 mL) solution of 2,6-difluoropyridine (5 g, 43.4 mmol) and 4-(hydroxymethyl)benzonitrile (8.67 g, 65.1 mmol) was added sodium hydride (2.56 g, 65.1 mmol, 60% in oil) at room temperature. This mixture was stirred for 4 hours at 70° C. This mixture was partitioned into ethyl acetate and water. The organic layer was separated, washed with water, dried over anhydrous magnesium sulfate, and filtered. The filtrate was concentrated under a reduced pressure, and the residue was purified by NH-silica gel column chromatography (heptane:ethyl acetate=10:1-4:1) to obtain the title compound (5.99 g, 61%).

$^1$H-NMR Spectrum (CDCl$_3$) δ (ppm): 5.41 (2H, s), 6.74-6.77 (1H, m), 6.87-6.89 (1H, m), 7.63-7.66 (2H, m), 7.85-7.88 (2H, m), 7.90-7.96 (1H, m).

Manufacturing Example 55-1-2

4-(6-Fluoro-pyridin-2-yloxymethyl)-benzaldehyde

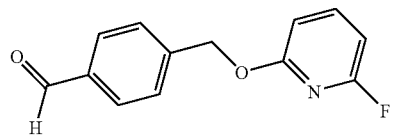

To a toluene (41 mL) solution of 4-(6-fluoro-pyridin-2-yloxymethyl)-benzonitrile (5.99 g, 26.2 mmol) described in Manufacturing Example 55-1-1 was added diisobutyl aluminum hydride (1.01 M toluene solution, 39.3 mmol) under nitrogen atmosphere at −70° C. to −78° C. This mixture was stirred for 2 hours at room temperature. This mixture was partitioned into ethyl acetate and 20% aqueous Rochelle salt solution. After removal of insoluble matter by filtrating through a Celite bed, the filtrate was partitioned. The organic layer was separated, washed with saturated aqueous sodium chloride, dried over anhydrous magnesium sulfate, and filtered. The filtrate was concentrated under a reduced pressure, and the residue was purified by silica gel column chromatography (heptane:ethyl acetate=10:1-4:1) to obtain the title compound (4.57 g, 75%).

$^1$H-NMR Spectrum (CDCl$_3$) δ (ppm): 5.43 (2H, s), 6.50-6.53 (1H, m), 6.70-6.72 (1H, m), 7.60-7.62 (2H, m), 7.66-7.72 (1H, m), 7.88-7.91 (2H, m), 10.0 (1H, s).

Manufacturing Example 55-1-3

2-Fluoro-6-(4-(E)-2-nitro-vinyl)-benzyloxy)-pyridine

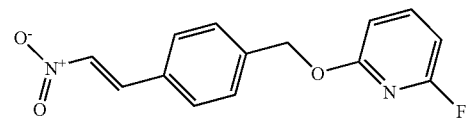

A mixture of 4-(6-fluoro-pyridin-2-yloxymethyl)-benzaldehyde (4.57 g, 19.8 mmol) described in Manufacturing Example 55-1-2, nitromethane (2.13 mL, 39.6 mmol), ammonium acetate (2.29 g, 29.7 mmol) and acetic acid (45.7 mL) was stirred for 19 hours at 100° C. This mixture was cooled to room temperature and concentrated under a reduced pressure. The residue was dissolved in ethyl acetate, washed with water and saturated aqueous sodium chloride, dried over anhydrous magnesium sulfate, and filtered. The filtrate was concentrated under a reduced pressure, and the residue was purified by silica gel column chromatography (heptane:ethyl acetate=4:1) to obtain the title compound (3.44 g, 63%).

$^1$H-NMR Spectrum (CDCl$_3$) δ (ppm): 5.39 (2H, s), 6.50-6.53 (1H, m), 6.68-6.71 (1H, m), 7.52-7.61 (5H, m), 7.66-7.72 (1H, m), 8.03-8.99 (1H, m).

Manufacturing Example 55-1-4

2-Fluoro-6-(4-(2-nitro-ethyl)-benzyloxy)-pyridine

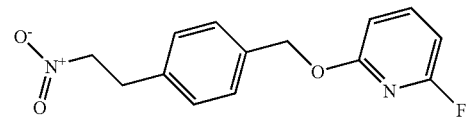

To a dimethyl sulfoxide (58.5 mL) solution of 2-fluoro-6-(4-(E)-2-nitro-vinyl)-benzyloxy)-pyridine (3.44 g, 12.5 mmol) described in Manufacturing Example 55-1-3 and acetic acid (3.44 mL) was added sodium borohydride (757 mg, 20 mmol) at room temperature while cooling appropriately. This mixture was stirred for 4 hours at room temperature. This mixture was partitioned into ethyl acetate and water. The organic layer was separated, washed with saturated aqueous sodium chloride, dried over anhydrous magnesium sulfate, and filtered. The filtrate was concentrated under a reduced pressure, and the residue was purified by silica gel column chromatography (heptane:ethyl acetate=10:1-4:1) to obtain the title compound (1.6 g, 46%).

¹H-NMR Spectrum (CDCl₃) δ (ppm): 3.31-3.35 (2H, m), 4.60-4.63 (2H, m), 5.31 (2H, s), 6.48-6.50 (1H, m), 6.64-6.67 (1H, m), 7.22-7.24 (2H, m), 7.41-7.43 (2H, m), 7.63-7.69 (1H, m).

Manufacturing Example 55-1-5

(4-(6-Fluoro-pyridin-2-yloxymethyl)-phenyl)acetohydroximoyl chloride

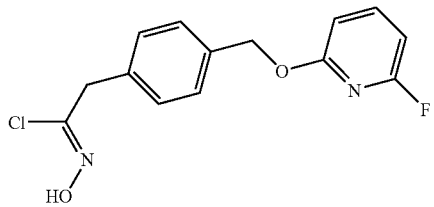

To a methanol (20 mL) solution of 2-fluoro-6-(4-(2-nitroethyl)-benzyloxy)-pyridine (1.6 g, 5.79 mmol) described in Manufacturing Example 55-1-4 was added lithium methoxide (449 mg, 11.6 mmol). This mixture was stirred for 1 hour at room temperature. The mixture was concentrated under a reduced pressure, water in the residue was azeotropically distilled with toluene, and this residue was diluted with methylene chloride (24 mL) and tetrahydrofuran (12 mL). This was cooled to −78° C., and titanium (IV) tetrachloride (2.04 mL, 18.5 mmol) was added dropwise into the suspension. This mixture was stirred for 2 hours at room temperature. This mixture was cooled to −78° C., and partitioned into ethyl acetate and ice water. The organic layer was separated, washed with saturated aqueous sodium chloride, dried over anhydrous magnesium sulfate, and filtered. The filtrate was concentrated under a reduced pressure, and the residue was triturated in ethyl acetate. The solid was collected and dried under reduced pressure to obtain the title compound (1.36 g). This compound was used in the following reaction without further purification.

Example 56

3-(3-4-(5-Fluoro-pyridin-2-yloxymethyl)-benzyl)-isoxazol-5-yl)-pyridin-2-ylamine

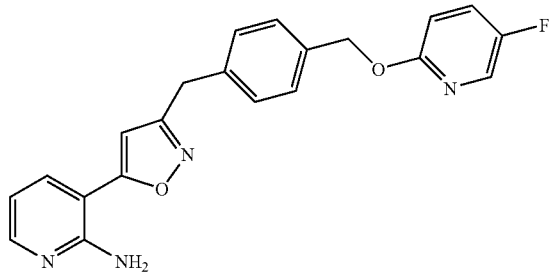

To a tetrahydrofuran (5 mL) solution of ((4-(5-fluoro-pyridin-2-yloxymethyl)-phenyl)acetohydroximoyl chloride (800 mg, 2.72 mmol) described in Manufacturing example 56-1-5 and 3-ethynyl-pyridin-2-ylamine (200 mg, 1.69 mmol) described in Manufacturing Example 1-2-3 was added triethylamine (948 μL, 6.8 mmol) at room temperature, which was stirred for 4 hours at 50° C. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (heptane:ethyl acetate=4:1-2:1) to obtain the title compound (214 mg, 21%).

¹H-NMR Spectrum (CDCl₃) δ (ppm): 4.08 (2H, s), 5.08 (2H, s), 5.54 (2H, brs), 6.27 (1H, s), 6.71-6.74 (1H, m), 7.13-7.16 (1H, m), 7.31-7.39 (5H, m), 7.71-7.73 (1H, m), 8.11-8.14 (2H, m).

The starting material, (4-(5-fluoro-pyridin-2-yloxymethyl)-phenyl)acetohydroximoyl chloride, was synthesized as follows.

Manufacturing Example 56-1-1

4-(5-Fluoro-pyridin-2-yloxymethyl)-benzonitrile

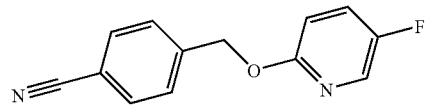

To an N,N-dimethylformamide (50 mL) solution of 2-bromo-5-fluoropyridine (5 g, 28.4 mmol) and 4-(hydroxymethyl)-benzonitrile (5.67 g, 42.4 mmol) was added sodium hydride (1.7 g, 42.4 mmol, 60% in oil) at room temperature. The mixture was stirred for 3 hours at 70° C. The mixture was partitioned into ethyl acetate and water. The organic layer was separated, washed with water, dried over anhydrous magnesium sulfate, and filtered. The filtrate was concentrated under a reduced pressure, and the residue was purified by NH-silica gel column chromatography (heptane:ethyl acetate=4:1-2:1-1:1-ethyl acetate) to obtain the title compound (5.5 g, 85%).

¹H-NMR Spectrum (CDCl₃) δ (ppm): 5.15 (2H, s), 7.14-7.17 (1H, m), 7.39-7.41 (1H, m), 7.53-7.55 (2H, m), 7.70-7.72 (2H, m), 8.12-8.13 (1H, m).

Manufacturing Example 56-1-2

4-(5-Fluoro-pyridin-2-yloxymethyl)benzaldehyde

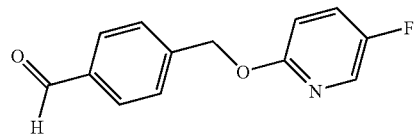

To a toluene solution (37 mL) of 4-(5-fluoro-pyridin-2-yloxymethyl)-benzonitrile (5.5 g, 24.1 mmol) described in Manufacturing Example 56-1-1 was added diisobutyl aluminum hydride (35.8 mL, 1.01 M toluene solution, 36.2 mmol) under nitrogen atmosphere at −70° C. to −78° C. This mixture was stirred for 3 hours at room temperature. This mixture was partitioned into ethyl acetate and 20% aqueous Rochelle salt solution. After removal of insoluble matter by filtrating through a Celite pad, the filtrate was partitioned. The organic layer was separated, washed with saturated aqueous sodium chloride, dried over anhydrous magnesium sulfate, and filtered. The filtrate was concentrated under a reduced pressure, and the residue was purified by silica gel column chromatography (heptane:ethyl acetate=4:1-2:1) to obtain the title compound (2.71 g, 49%).

$^1$H-NMR Spectrum (DMSO-$d_6$) δ (ppm): 5.31-5.33 (2H, m), 7.46-7.50 (1H, m), 7.57-7.59 (1H, m), 7.64-7.69 (2H, m), 7.88-7.96 (2H, m), 8.21-8.22 (1H, m), 10.0 (1H, s).

Manufacturing Example 56-1-3

5-Fluoro-2-(4-((E)-nitro-vinyl)-benzyloxy)-pyridine

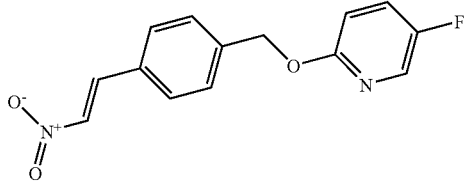

A mixture of 4-(5-fluoro-pyridin-2-yloxymethyl)benzaldehyde (2.71 g, 11.7 mmol) described in Manufacturing Example 56-1-2, nitromethane (1.26 mL, 23.4 mmol), ammonium acetate (1.35 g, 17.6 mmol) and acetic acid (30 mL) was stirred for 10 hours at 100° C. This mixture was cooled to room temperature, concentrated under a reduced pressure, and diluted with ethyl acetate. The organic layer was washed with water, dried over anhydrous magnesium sulfate, and filtered. The filtrate was concentrated under a reduced pressure to obtain the title compound (2.9 g).

This compound was used in the following reaction without being purified.

Manufacturing Example 56-1-4

(5-Fluoro-2-(4-(2-nitro-ethyl)-benzyloxy)-pyridine

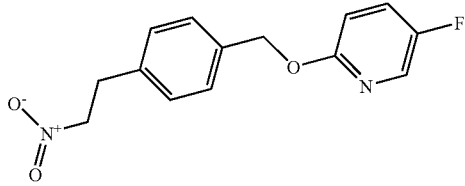

To a dimethyl sulfoxide (49 mL) solution of 5-fluoro-2-(4-((E)-nitro-vinyl)-benzyloxy)-pyridine (2.9 g, 10.6 mmol) described in Manufacturing Example 56-1-3 and acetic acid (2.9 mL) was added sodium borohydride (642 mg, 17 mmol) at room temperature while cooling appropriately. This mixture was stirred for 1 hour at room temperature. This mixture was partitioned into ethyl acetate and water. The organic layer was separated, washed with saturated aqueous sodium chloride, dried over anhydrous magnesium sulfate, and filtered. The filtrate was concentrated under a reduced pressure, and the residue was purified by NH-silica gel column chromatography (heptane:ethyl acetate=10:1) to obtain the title compound (1.63 g, 56%).

$^1$H-NMR Spectrum (DMSO-$d_6$) δ (ppm): 3.21-3.25 (2H, m), 4.83-4.87 (2H, m), 5.15 (2H, s), 7.31 (2H, d, J=8 Hz), 7.40 (2H, d, J=8 Hz), 7.44-7.48 (1H, m), 7.54-7.57 (1H, m), 8.18-8.19 (1H, m).

Manufacturing Example 56-1-5

(4-(5-Fluoro-pyridin-2-yloxymethyl)-phenyl)acetohydroximoyl chloride

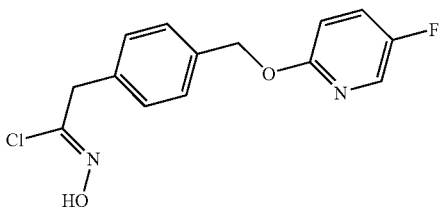

To a methanol (20 mL) solution of (5-fluoro-2-(4-(2-nitro-ethyl)-benzyloxy)-pyridine (1.63 g, 5.9 mmol) described in Manufacturing Example 56-1-4 was added lithium methoxide (448 mg, 11.8 mmol). This mixture was stirred for 2 hours at room temperature. This mixture was concentrated under a reduced pressure, water in the residue was azeotropically distilled with toluene, and the residue was diluted with methylene chloride (24 mL) and tetrahydrofuran (12 mL). This was cooled to −78° C., and titanium (IV) tetrachloride (2.07 mL, 18.9 mmol) was added dropwise into the suspension. This mixture was stirred for 2 hours at room temperature. This mixture was cooled to −78° C. and partitioned into ethyl acetate and ice water. The organic layer was separated, washed with saturated aqueous sodium chloride, dried over anhydrous magnesium sulfate, and filtered. The filtrate was concentrated under a reduced pressure, and the residue was pulverized in ethyl acetate. This solid was collected and dried under a reduced pressure to obtain the title compound (1.75 g).

This compound was used in the following reaction without further purification.

Example 57

3-(3-(1-Benzyl-1H-pyrrol-3-ylmethyl)-isoxazol-5-yl)-pyridin-2-ylamine

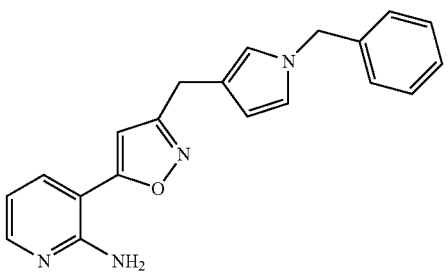

The title compound (27 mg, 7.3%) was obtained according to the methods similar to those of Example 3 using 3-ethynyl-pyridin-2-ylamine (74 mg, 0.56 mmol) described in Manufacturing Example 1-2-3 and (1-benzyl-1H-pyrrol-3-yl)-acetohydroximoyl chloride (280 mg, 1.1 mmol) described in Manufacturing Example 57-1-3.

$^1$H-NMR Spectrum (DMSO-$d_6$) δ (ppm): 3.78 (2H, s), 5.03 (2H, s), 5.99 (1H, d, J=2.0 Hz), 6.24 (2H, brs), 6.68-6.80 (4H, m), 7.18 (2H, d, J=8.4 Hz), 7.23-7.36 (3H, m), 7.87 (1H, dd, J=2.0, 8.0 Hz), 8.08 (1H, dd, J=2.0, 4.8 Hz).

The starting material, (1-benzyl-1H-pyrrol-3-yl)acetohydroximoyl chloride, was synthesized as follows.

Manufacturing Example 57-1-1

1-Benzyl-3-((E)-2-nitro-vinyl)-1H-pyrrole

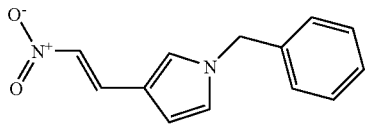

The title compound (3.0 g, 85%) was obtained according to the methods similar to those of Manufacturing Example 3-1-3 using 1-benzyl-1H-pyrrole-3-carbaldehyde (2.9 g, 15 mmol).
$^1$H-NMR Spectrum (DMSO-$d_6$) δ (ppm): 5.16 (2H, s), 6.60-6.63 (1H, m), 6.99 (1H, dd, J=2.0, 2.0 Hz), 7.22-7.40 (5H, m), 7.60 (1H, dd, J=2.0, 2.0 Hz), 7.80 (1H, d, J=13.2 Hz), 8.03 (1H, d, J=13.2 Hz).

Manufacturing Example 57-1-2

1-Benzyl-3-(2-nitro-ethyl)-1H-pyrrole

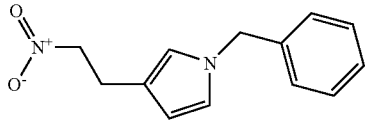

The title compound (2.3 g, 75%) was obtained according to the methods similar to those of Manufacturing Example 3-1-4 using the 1-benzyl-3-((E)-2-nitro-vinyl)-1H-pyrrole (3.0 g, 13 mmol) described in Manufacturing Example 57-1-1.
$^1$H-NMR Spectrum (DMSO-$d_6$) δ (ppm): 3.00 (2H, d, J=6.8 Hz), 4.67 (2H, d, J=6.8 Hz), 5.01 (2H, s), 5.92 (1H, dd, J=2.0, 2.0 Hz), 6.66 (1H, dd, J=2.0, 2.0 Hz), 6.73 (1H, dd, J=2.0, 2.0 Hz), 7.13-7.17 (2H, m), 7.23-7.35 (3H, m).

Manufacturing Example 57-1-3

(1-Benzyl-1H-pyrrol-3-yl)acetohydroximoyl chloride

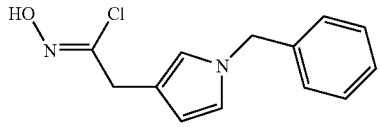

The title compound (550 mg, 51%) was obtained according to the methods similar to those of Manufacturing Example 3-1-5 using the 1-benzyl-3-(2-nitro-ethyl)-1H-pyrrole (280 mg, 1.1 mmol) described in Manufacturing Example 57-1-2.
$^1$H-NMR Spectrum (DMSO-$d_6$) δ (ppm): 3.57 (2H, s), 5.03 (2H, s), 5.97 (1H, dd, J=2.0, 2.0 Hz), 6.77 (1H, dd, J=2.0, 2.0 Hz), 6.79 (1H, dd, J=2.0, 2.0 Hz), 7.15-7.22 (2H, m), 7.23-7.40 (3H, m), 11.46 (1H, s).

Example 58

3-(3-(6-(4-Fluoro-benzyloxy)-pyridin-3-ylmethyl)-isoxazol-5-yl)-pyridin-2-ylamine

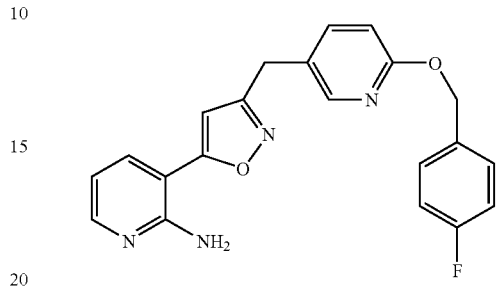

To a tetrahydrofuran (10.0 mL) solution of (6-(4-fluoro-benzyloxy)-pyridin-3-yl)-acetohydroximoyl chloride (150 mg, 0.508 mmol) described in Manufacturing Example 58-1-5 and 3-ethynyl-pyridin-2-ylamine (30.0 mg, 0.254 mmol) described in Manufacturing Example 1-2-3 was added triethylamine (106 μL, 0.762 mmol) at room temperature, which was stirred for 4 hours at 60° C. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1:2) to obtain the title compound (21.2 mg, 22.2%).
$^1$H-NMR Spectrum (DMSO-$d_6$) δ (ppm): 4.00 (2H, s), 5.31 (2H, s), 6.27 (2H, brs), 6.68-6.71 (1H, m), 6.83 (1H, s), 6.84-6.86 (1H, m), 7.17-7.22 (2H, m), 7.47-7.51 (2H, m), 7.67-7.70 (1H, m), 7.86-7.88 (1H, m), 8.08-8.10 (1H, m), 8.16-8.17 (1H, m).

The starting material, (6-(4-fluoro-benzyloxy)-pyridin-3-yl)-acetohydroximoyl chloride, was synthesized as follows.

Manufacturing Example 58-1-1

5-Bromo-2-(4-fluoro-benzyloxy)-pyridine

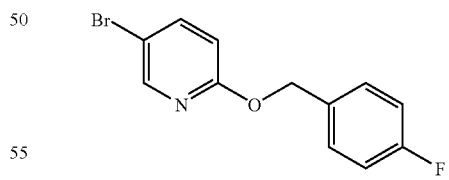

To an N,N-dimethylformamide (30.0 mL) solution of 4-fluorobenzyl alcohol (2.60 g, 20.6 mmol) was added sodium hydride (0.88 g, 22.2 mmol, 60% in oil) under nitrogen atmosphere at 0° C., which was stirred for 10 minutes at room temperature. Next, 2,5-dibromopyridine (3.50 g, 14.8 mmol) was added at 0° C., and stirred for 19 hours at room temperature. Water was added to the reaction solution at room temperature, which was then extracted with ethyl acetate. The organic layer was washed with saturated aqueous sodium chloride, and the solvent was evaporated under a reduced pressure. The residue was purified by silica gel column chromatography (ethyl acetate:heptane=1:5) to obtain the title compound (3.75 g, 89.8%).

¹H-NMR Spectrum (CDCl₃) δ (ppm): 5.29 (2H, s), 6.68-6.70 (1H, m), 7.02-7.06 (2H, m), 7.38-7.42 (2H, m), 7.61-7.64 (1H, m), 8.19-8.20 (1H, m).

Manufacturing Example 58-1-2

6-(4-Fluoro-benzyloxy)-pyridine-3-carbaldehyde

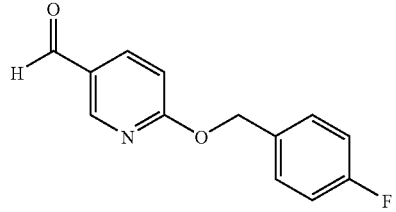

To a diethyl ether (150 mL) solution of 5-bromo-2-(4-fluoro-benzyloxy)-pyridine (3.75 g 13.3 mmol) described in Manufacturing Example 58-1-1 was added n-butyl lithium (2.55 M n-hexane solution, 6.26 mL, 16.0 mmol) on a dry ice-ethanol bath (−78° C.) under nitrogen atmosphere, which was stirred for 30 minutes at −78° C. N,N-dimethylformamide (1.54 mL, 20.0 mmol) was then added dropwise and stirred for 5 minutes at −78° C. The reaction solution was allowed to room temperature, water was added, and the solution was extracted with ethyl acetate. The organic layer was washed with saturated aqueous sodium chloride, and the solvent was evaporated under a reduced pressure. The residue was purified by silica gel column chromatography (ethyl acetate:heptane=1:3) to obtain the title compound (2.23 g, 72.5%).

¹H-NMR Spectrum (CDCl₃) δ (ppm): 5.45 (2H, s), 6.87-6.90 (1H, m), 7.05-7.09 (2H, m), 7.42-7.46 (2H, m), 8.07-8.10 (1H, m), 8.64-8.65 (1H, m), 9.96 (1H, s).

Manufacturing Example 58-1-3

2-(4-Fluoro-benzyloxy)-5-((E)-2-nitro-vinyl)-pyridine

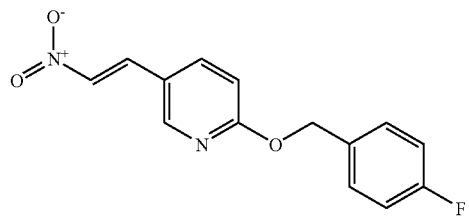

To an acetic acid (20.0 mL) solution of 6-(4-fluoro-benzyloxy)-pyridine-3-carbaldehyde (2.23 g, 9.64 mmol) described in Manufacturing Example 58-1-2 were added nitromethane (2.94 g, 48.2 mmol) and ammonium acetate (1.49 g, 19.3 mmol) under nitrogen atmosphere, which was stirred for 2.5 hours at 105° C. Water and ethyl acetate were added to the reaction mixture, and the organic layer was extracted with ethyl acetate. This organic layer was washed with water and saturated aqueous sodium chloride, dried over anhydrous magnesium sulfate, and filtered. The solvent was evaporated from the filtrate under a reduced pressure to obtain the title compound (2.60 g) as a crude product.

¹H-NMR Spectrum (DMSO-d₆) δ (ppm): 5.41 (2H, s), 7.00-7.02 (1H, m), 7.18-7.24 (2H, m), 7.50-7.54 (2H, m), 8.14-8.18 (1H, m), 8.22-8.26 (1H, m), 8.26-8.29 (1H, m), 8.64-8.65 (1H, m).

Manufacturing Example 58-1-4

2-(4-Fluoro-benzyloxy)-5-(2-nitro-ethyl)-pyridine

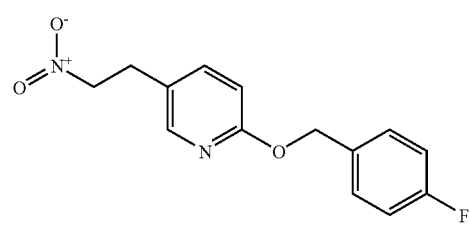

To a dimethyl sulfoxide (20.0 mL) solution of 2-(4-fluoro-benzyloxy)-5-((E)-2-nitro-vinyl)-pyridine (2.60 g, 9.48 mmol) described in Manufacturing Example 58-1-3 and acetic acid (3.00 mL) was added sodium borohydride (574 mg, 15.2 mmol) at room temperature while cooling appropriately under nitrogen atmosphere, which was stirred for 20 minutes. Water was then added dropwise at room temperature while cooling appropriately to quench sodium borohydride. The reaction mixture was extracted with ethyl acetate, and the organic layer was washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:5) to obtain the title compound (785 mg, 30.0%).

¹H-NMR Spectrum (DMSO-d₆) δ (ppm): 3.18 (2H, t, J=6.8 Hz), 4.85 (2H, t, J=6.8 Hz), 5.31 (2H, s), 6.84-6.86 (1H, m), 7.18-7.23 (2H, m), 7.48-7.52 (2H, m), 7.68-7.70 (1H, m), 8.07-8.08 (1H, m).

Manufacturing Example 58-1-5

(6-(4-Fluoro-benzyloxy)-pyridin-3-yl)-acetohydroximoyl chloride

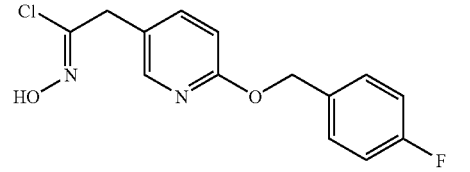

To a methanol (20.0 mL) solution of 2-(4-fluoro-benzyloxy)-5-(2-nitro-ethyl)-pyridine (785 mg, 2.84 mmol) described in Manufacturing Example 58-1-4 was added lithium methoxide (216 mg, 5.68 mmol) under nitrogen atmosphere at room temperature, which was stirred for 30 minutes at room temperature. The solvent was evaporated from the reaction mixture under a reduced pressure, and anhydrous dichloromethane (20.0 mL) and anhydrous tetrahydrofuran (5.00 mL) were added to the residue. Titanium (IV) chloride (998 μL, 9.09 mmol) was added dropwise into the reaction mixture on a dry ice-ethanol bath (−78° C.), which was stirred for 45 minutes at room temperature. Water, ethyl acetate and tetrahydrofuran were added to the reaction mixture on an ice bath (0° C.), and the organic layer was extracted with ethyl acetate. This organic layer was washed with water and saturated aqueous sodium chloride, dried over anhydrous magnesium sulfate, and filtered. The solvent was evaporated from the filtrate under a reduced pressure to obtain the title compound (801 mg, 95.7%) as a crude product.

$^1$H-NMR Spectrum (DMSO-d$_6$) δ (ppm): 3.79 (2H, s), 5.31 (2H, s), 6.85-6.87 (1H, m), 7.18-7.22 (2H, m), 7.48-7.52 (2H, m), 7.60-7.62 (1H, m), 8.07-8.08 (1H, m), 11.76 (1H, s).

Manufacturing Example 59

3-(3-(4-(4-Fluoro-pyridin-2-yloxymethyl)-benzyl)-isoxazol-5-yl)-pyridin-2-ylamine

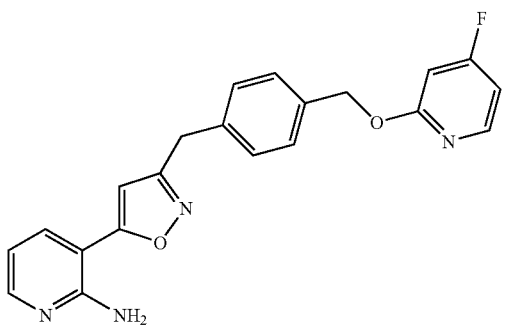

To a tetrahydrofuran (3 mL) solution of (4-(4-fluoro-pyridin-2-yloxymethyl)-phenyl)-acetohydroximoyl chloride (200 mg, 0.679 mmol) described in Manufacturing Example 59-1-5 and 3-ethynyl-pyridin-2-ylamine (50 mg, 0.423 mmol) described in Manufacturing Example 1-2-3 was added triethylamine (237 μL, 1.7 mmol) at room temperature, which was stirred for 4 hours at 50° C. Water was added to the reaction solution at room temperature, which was then extracted with ethyl acetate. The organic layer was washed with saturated aqueous sodium chloride, and dried over anhydrous magnesium sulfate, and the solvent was evaporated under a reduced pressure. The residue was purified by NH silica gel column chromatography (heptane:ethyl acetate=4:1-2:1-1:1) to obtain the title compound (57 mg, 22%).

$^1$H-NMR Spectrum (CDCl$_3$) δ (ppm): 4.09 (2H, s), 5.09 (2H, s), 5.84 (2H, brs), 6.30 (1H, s), 6.74-6.77 (1H, m), 6.80-6.82 (1H, m), 6.90-6.91 (1H, m), 7.33-7.42 (3H, m), 7.76-7.78 (1H, m), 8.09-8.11 (1H, m), 8.19-8.21 (2H, m).

The starting material, (4-(4-fluoro-pyridin-2-yloxymethyl)-phenyl)-acetohydroximoyl chloride, was synthesized as follows.

Manufacturing Example 59-1-1

4-(4-Fluoro-pyridin-2-yloxymethyl)-benzonitrile

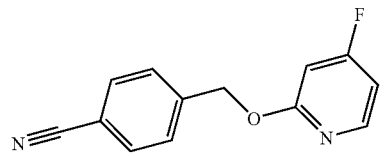

To an N,N-dimethylformamide (15 mL) solution of 2-chloro-4-fluoropyridine (2.88 g, 21.9 mmol) and 4-(hydroxymethyl)benzonitrile (4.37 g, 32.9 mmol) was added sodium hydride (1.29 g, 32.9 mmol, 60% in oil) at room temperature. This mixture was stirred for 4 hours at 70° C. This mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=4:1-2:1) to obtain the title compound (4.08 g, 82%).

$^1$H-NMR Spectrum (CDCl$_3$) δ (ppm): 5.17 (2H, s), 6.81-6.83 (1H, m), 6.908-6.913 (1H, m), 7.52-7.54 (2H, m), 7.70-7.73 (2H, m), 8.23-8.24 (1H, m).

Manufacturing Example 59-1-2

4-(4-Fluoro-pyridin-2-yloxymethyl)-benzaldehyde

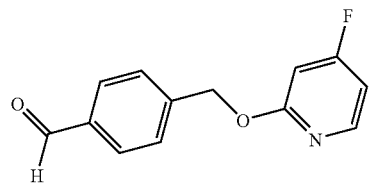

To a toluene solution (28 mL) of 4-(4-fluoro-pyridin-2-yloxymethyl)-benzonitrile (4.08 g, 17.9 mmol) described in Manufacturing Example 59-1-1 was added diisobutyl aluminum hydride (26.6 mL, 1.01 M toluene solution, 26.9 mmol) under nitrogen atmosphere at −70° C. to −78° C. This mixture was stirred for 3 hours at room temperature. This mixture was partitioned into ethyl acetate and 20% aqueous Rochelle salt solution. After the insoluble material had been removed by filtering through a Celite pad, the filtrate was partitioned. This organic layer was washed with water and saturated aqueous sodium chloride, dried over anhydrous magnesium sulfate, and filtered. The filtrate was concentrated under a reduced pressure, and the residue was purified by silica gel column chromatography (heptane:ethyl acetate=4:1-2:1) to obtain the title compound (1.5 g, 36%).

¹H-NMR Spectrum (CDCl₃) δ (ppm): 5.20 (2H, s), 6.82-6.84 (1H, m), 6.92-6.93 (1H, m), 7.57-7.59 (2H, m), 7.93-7.95 (2H, m), 8.22-8.24 (1H, m), 10.0 (1H, s).

Manufacturing Example 59-1-3

4-Fluoro-2-(4-((E)-2-nitro-vinyl)-benzyloxy)-pyridine

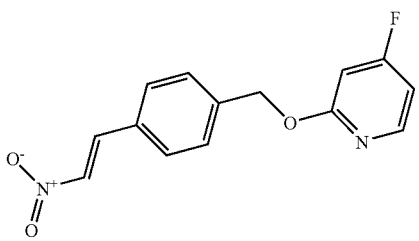

A mixture of the 4-(4-fluoro-pyridine-2-yloxymethyl)-benzaldehyde (1.5 g, 6.49 mmol) described in Manufacturing Example 59-1-2, nitromethane (698 μL, 13 mmol), ammonium acetate (750 mg, 9.74 mmol) and acetic acid (15 mL) was stirred for 6 hours at 100° C. This mixture was cooled to room temperature, concentrated under a reduced pressure, and diluted with ethyl acetate. The organic layer was washed with water, dried over anhydrous magnesium sulfate, and filtered. The filtrate was concentrated under a reduced pressure to obtain the title compound (1.72 g).

This compound was used in the following reaction without being purified.

¹H-NMR Spectrum (CDCl₃) δ (ppm): 5.16 (2H, s), 6.82-6.84 (1H, m), 6.917-6.923 (1H, m), 7.49-7.51 (2H, m), 7.59-7.62 (3H, m), 8.00-8.04 (1H, m), 8.23-8.24 (1H, m).

Manufacturing Example 59-1-4

4-Fluoro-2-(4-(2-nitro-ethyl)-benzyloxy)-pyridine

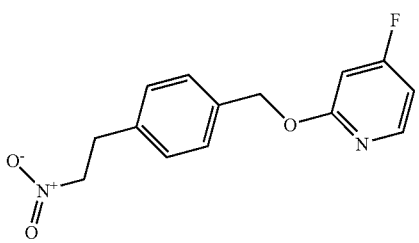

To an acetic acid (1.7 mL) and dimethyl sulfoxide (29 mL) solution of 4-fluoro-2-(4-((E)-2-nitro-vinyl)-benzyloxy)-pyridine (1.72 g, 6.27 mmol) described in Manufacturing Example 59-1-3 was added sodium borohydride (380 mg, 10 mmol) at room temperature while cooling appropriately. This mixture was stirred for 5 hours at room temperature. This mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by silica gel column chromatography (heptane:ethyl acetate=4:1-1:1) to obtain the title compound (960 mg, 55%).

¹H-NMR Spectrum (CDCl₃) δ (ppm): 3.33-3.37 (2H, m), 4.61-4.65 (2H, m), 5.09 (2H, s), 6.81-6.83 (1H, m), 6.91-6.92 (1H, m), 7.25-7.27 (3H, m), 7.36-7.38 (1H, m), 8.20-8.22 (1H, m).

Manufacturing Example 59-1-5

(4-(4-Fluoro-pyridin-2-yloxymethyl)-phenyl)-acetohydroximoyl chloride

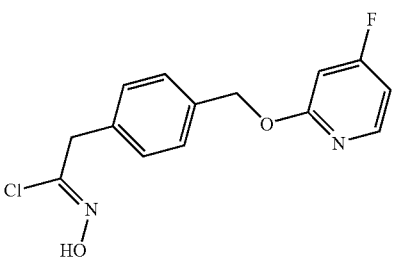

To a methanol (12 mL) solution of 4-fluoro-2-(4-(2-nitro-ethyl)-benzyloxy)-pyridine (960 mg, 3.47 mmol) described in Manufacturing Example 59-1-4 was added lithium methoxide (264 mg, 6.94 mmol). This mixture was stirred for 1 hour at room temperature. This mixture was concentrated under a reduced pressure, water in the residue was azeotropically distilled with toluene, and that residue was diluted with methylene chloride (14 mL) and tetrahydrofuran (7.2 mL). This was cooled to −78° C., and titanium (IV) tetrachloride (1.22 mL, 11.1 mmol) was added dropwise into the suspension. This mixture was stirred for 2 hours at room temperature. This mixture was cooled to −78° C., and partitioned into ethyl acetate and ice water. The organic layer was separated, washed with saturated aqueous sodium chloride, dried over anhydrous magnesium sulfate, and filtered. The filtrate was concentrated under a reduced pressure, and the residue was pulverized in ethyl acetate. This solid was collected and dried under a reduced pressure to obtain the title compound (969 mg).

This compound was used in the following reaction without further purification.

Example 60

3-(3-(3-(Pyridin-2-ylmethoxy)-benzyl)-isoxazol-5-yl)-pyridin-2-ylamine

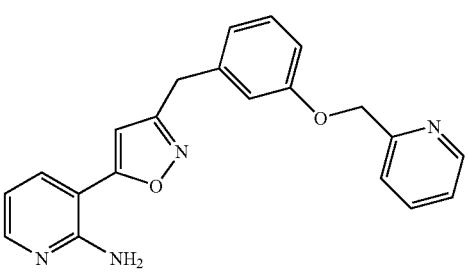

To a tetrahydrofuran (3 mL) solution of 3-(pyridin-2-ylmethoxy)-phenyl)-acetohydroximoyl chloride (200 mg, 0.723 mmol) described in Manufacturing Example 60-1-4 and 3-ethynyl-pyridin-2-ylamine (55 mg, 0.461 mmol)

described in Manufacturing Example 1-2-3 was added triethylamine (252 μL, 1.81 mmol) at room temperature, which was stirred for 2 hours at 50° C. Water was added to the reaction mixture at room temperature, which was then extracted with ethyl acetate. The organic layer was washed with water and saturated aqueous sodium chloride and dried over anhydrous magnesium sulfate, and the solvent was evaporated under a reduced pressure. The residue was purified by NH silica gel column chromatography (heptane:ethyl acetate=4:1-2:1-1:1) to obtain the title compound (52 mg, 20%).

$^1$H-NMR Spectrum (CDCl$_3$) δ (ppm): 4.03 (2H, s), 5.20 (2H, s), 5.80 (2H, brs), 6.26 (1H, s), 6.73-6.76 (1H, m), 6.89-6.91 (4H, m), 7.19-7.24 (1H, m), 7.50-7.51 (1H, m), 7.68-7.77 (2H, m), 8.09-8.11 (1H, m), 8.57-8.59 (1H, m).

The starting material, 3-(pyridin-2-ylmethoxy)-phenyl)-acetohydroximoyl chloride, was synthesized as follows.

Manufacturing Example 60-1-1

3-(Pyridin-2-ylmethoxy)-benzaldehyde

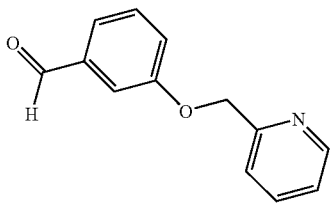

3-Hydroxybenzaldehyde (3 g, 24.6 mmol) and potassium carbonate (10.2 g, 73.8 mmol) were suspended in N,N-dimethylformamide (60 mL). 2-Picolyl chloride hydrochloride (4.44 g, 27.1 mmol) was added to this suspension, and stirred for 14 hours at room temperature. This mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=4:1-2:1-1:1) to obtain the title compound (2.98 g, 57%).

$^1$H-NMR Spectrum (CDCl$_3$) δ (ppm): 5.27 (2H, s), 7.24-7.29 (2H, m), 7.44-7.52 (4H, m), 7.71-7.76 (1H, m), 8.62-8.63 (1H, m), 9.98 (1H, s).

Manufacturing Example 60-1-2

2-(3-((E)-2-nitro-vinyl)-phenoxymethyl)-pyridine

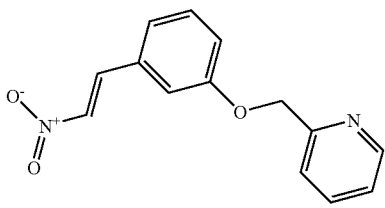

A mixture of 3-(pyridin-2-ylmethoxy)-benzaldehyde (2.98 g, 14 mmol) described in Manufacturing Example 60-1-1, nitromethane (1.51 mL, 28 mmol), ammonium acetate (1.62 g, 21 mmol) and acetic acid (30 mL) was stirred for 6 hours at 100° C. This mixture was cooled to room temperature, concentrated under a reduced pressure, and diluted with ethyl acetate. The organic layer was washed with water, dried over anhydrous magnesium sulfate, and filtered. The filtrate was concentrated under a reduced pressure, and the residue was purified by silica gel column chromatography (heptane:ethyl acetate=4:1-2:1-1:1) to obtain the title compound (2.56 g, 71%).

$^1$H-NMR Spectrum (CDCl$_3$) δ (ppm): 5.27 (2H, s), 7.12-7.17 (3H, m), 7.28-7.30 (1H, m), 7.35-7.39 (1H, m), 7.52-7.58 (2H, m), 7.74-7.78 (1H, m), 7.94-7.97 (1H, m), 8.62-8.64 (1H, m).

Manufacturing Example 60-1-3

2-(3-(2-Nitro-ethyl)-phenoxymethyl)-pyridine

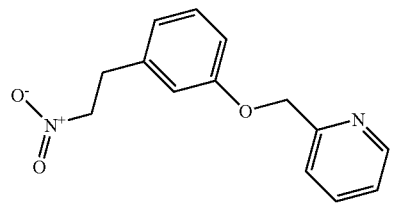

To an acetic acid (2.5 mL) and dimethyl sulfoxide (43 mL) solution of 2-(3-((E)-2-nitro-vinyl)-phenoxymethyl)-pyridine (2.56 g, 10 mmol) described in Manufacturing Example 60-1-2 was added sodium borohydride (605 mg, 16 mmol) at room temperature while cooling appropriately. This mixture was stirred for 1.5 hours at room temperature. This mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=10:1-4:1-1:1) to obtain the title compound (1.66 g, 64%).

$^1$H-NMR Spectrum (DMSO-d$_6$) δ (ppm): 3.20-3.23 (2H, m), 4.83-4.87 (2H, m), 5.44 (2H, s), 6.86-6.89 (1H, m), 6.91-6.93 (1H, m), 7.00 (1H, m), 7.26-7.30 (1H, m), 7.64-7.67 (1H, m), 7.86-7.88 (1H, m), 8.21-8.24 (1H, m), 8.75-8.76 (1H, m).

Manufacturing Example 60-1-4

3-(Pyridin-2-ylmethoxy)-phenyl)-acetohydroximoyl chloride

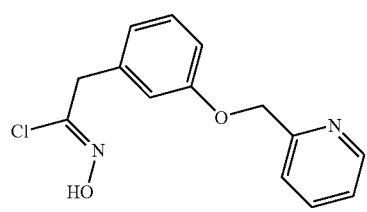

To a methanol (20 mL) solution of 2-(3-(2-nitro-ethyl)-phenoxymethyl)-pyridine (1.66 g, 6.43 mmol) described in Manufacturing Example 60-1-3 was added lithium methoxide (488 mg, 12.9 mmol). This mixture was stirred for 1 hour at room temperature. This mixture was concentrated under a reduced pressure, water in the residue was azeotropically distilled with toluene, and that residue was diluted with methylene chloride (24 mL) and tetrahydrofuran (12 mL). This was cooled to −78° C., and titanium (IV) tetrachloride (2.26 mL, 20.6 mmol) was added dropwise into the suspension. This mixture was stirred for 2 hours at room temperature. This mixture was cooled to −78° C., and partitioned into ethyl acetate and ice water. The organic layer was separated, washed with saturated aqueous sodium chloride, dried over anhydrous magnesium sulfate, and filtered. The filtrate was concentrated under a reduced pressure to obtain the title compound (1.25 g).

This compound was used in the following reaction without further purification.

Example 61

3-(3-(3-Benzyloxy-benzyl)-isoxazol-5-yl)-pyridin-2-ylamine

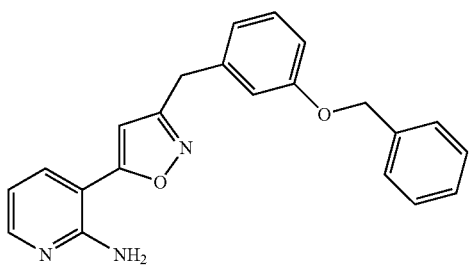

To a tetrahydrofuran (3 mL) solution of (3-benzyloxy-phenyl)-acetohydroximoyl chloride (200 mg, 0.724 mmol) described in Manufacturing Example 61-1-4 and 3-ethynyl-pyridin-2-ylamine (55 mg, 0.462 mmol) described in Manufacturing Example 1-2-3 was added triethylamine (252 μL, 1.81 mmol) at room temperature, which was stirred for 4 hours at 50° C. Water was added to the reaction solution at room temperature, which was then extracted with ethyl acetate. The organic layer was washed with water and saturated aqueous sodium chloride and dried over anhydrous magnesium sulfate, and the solvent was evaporated under a reduced pressure. The residue was purified by NH silica gel column chromatography (heptane:ethyl acetate=4:1-2:1) to obtain the title compound (58 mg, 22%).

$^1$H-NMR Spectrum (CDCl$_3$) δ (ppm): 4.03 (2H, s), 5.05 (2H, s), 5.68 (2H, brs), 6.24 (1H, s), 6.72-6.75 (1H, m), 6.88-6.90 (3H, m), 7.30-7.43 (6H, m), 7.72-7.74 (1H, m), 8.10-8.12 (1H, m).

The starting material, (3-benzyloxy-phenyl)-acetohydroximoyl chloride, was synthesized as follows.

Manufacturing Example 61-1-1

3-Benzyloxy-benzaldehyde

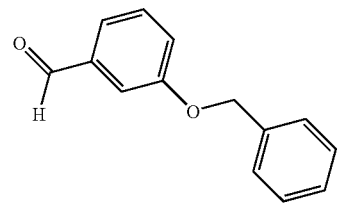

3-Hydroxybenzaldehyde (3 g, 24.6 mmol) and potassium carbonate (10.2 g, 73.8 mmol) were suspended in N,N-dimethylformamide (60 mL). Benzyl bromide (3.21 mL, 27.1 mmol) was added to this suspension, and stirred for 14 hours at room temperature. This mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=4:1-1:1) to obtain the title compound (5.16 g, 99%).

$^1$H-NMR Spectrum (CDCl$_3$) δ (ppm): 5.13 (2H, s), 7.24-7.25 (1H, m), 7.35-7.49 (8H, m), 9.98 (1H, s).

Manufacturing Example 61-1-2

1-Benzyloxy-3-((E)-2-nitro-vinyl)-benzene

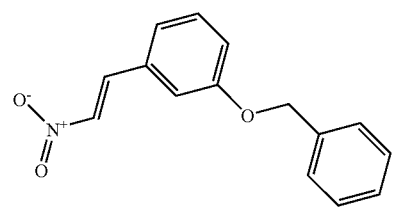

A mixture of 3-benzyloxy-benzaldehyde (5.16 g, 24.3 mmol) described in Manufacturing Example 61-1-1, nitromethane (2.16 mL, 48.6 mmol), ammonium acetate (2.81 g, 36.5 mmol) and acetic acid (50 mL) was stirred for 6 hours at 100° C. This mixture was cooled to room temperature, concentrated under a reduced pressure, and diluted with ethyl acetate. The organic layer was washed with water, dried over anhydrous magnesium sulfate, and filtered. The filtrate was concentrated under a reduced pressure, and the residue was purified by silica gel column chromatography (heptane:ethyl acetate=4:1-2:1-1:1) to obtain the title compound (5.50 g, 89%).

¹H-NMR Spectrum (CDCl₃) δ (ppm): 5.11 (2H, s), 7.10-7.16 (3H, m), 7.35-7.45 (6H, m), 7.53-7.57 (1H, m), 7.95-7.98 (1H, m).

Manufacturing Example 61-1-3

1-Benzyloxy-3-(2-nitro-ethyl)-benzene

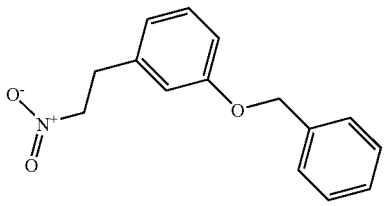

To an acetic acid (5.5 mL) and dimethyl sulfoxide (94 mL) solution of 1-benzyloxy-3-((E)-2-nitro-vinyl)-benzene (5.5 g, 21.5 mmol) described in Manufacturing Example 61-1-2 was added sodium borohydride (1.3 g, 34.4 mmol) at room temperature while cooling appropriately. This mixture was stirred for 1.5 hours at room temperature. This mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=10:1-4:1) to obtain the title compound (3.14 g, 57%).

¹H-NMR Spectrum (CDCl₃) δ (ppm): 3.17-3.21 (2H, m), 4.83-4.86 (2H, m), 5.07 (2H, s), 6.84-6.86 (1H, m), 6.88-6.90 (1H, m), 6.96-6.97 (1H, m), 7.20-7.24 (1H, m), 7.31-7.35 (1H, m), 7.37-7.41 (2H, m), 7.44-7.46 (2H, m).

Manufacturing Example 61-1-4

(3-Benzyloxy-phenyl)-acetohydroximoyl chloride

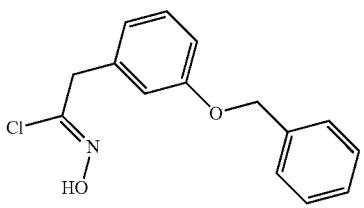

To a methanol (40 mL) solution of 1-benzyloxy-3-(2-nitro-ethyl)-benzene (3.14 g, 12.2 mmol) described in Manufacturing Example 61-1-3 was added lithium methoxide (927 mg, 24.4 mmol). This mixture was stirred for 1 hour at room temperature. This mixture was concentrated under a reduced pressure, water in the residue was azeotropically distilled with toluene, and that residue was diluted with methylene chloride (48 mL) and tetrahydrofuran (24 mL). This was cooled to −78° C., and titanium (IV) tetrachloride (2.95 mL, 26.8 mmol) was added dropwise into the suspension. This mixture was stirred for 2 hours at room temperature. This mixture was cooled to −78° C., and partitioned into ethyl acetate and ice water. The organic layer was separated, washed with saturated aqueous sodium chloride, dried over anhydrous magnesium sulfate, and filtered. The filtrate was concentrated under a reduced pressure to obtain the title compound (3.48 g).

This compound was used in the subsequent reaction without further purification.

Example 62

3-(3-(4-(5-Chloro-furan-2-ylmethyl)-benzyl)-isoxazol-5-yl)-pyridin-2-ylamine

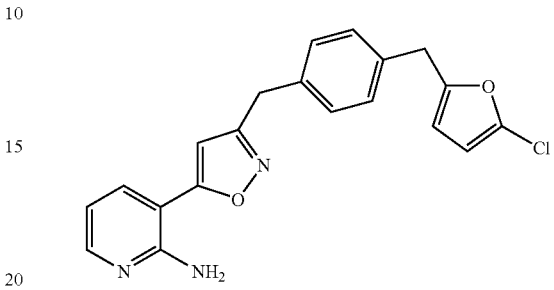

To a mixture of (4-(5-chloro-furan-2-ylmethyl)-phenyl)-acetohydroximoyl chloride (25 mg, 0.088 mmol) described in Manufacturing Example 62-1-6 and tetrahydrofuran (1 mL) were added 3-ethynyl-pyridin-2-ylamine (8.0 mg, 0.068 mmol) described in Manufacturing Example 1-2-3 and triethylamine (19 μL, 0.14 mmol) at room temperature, which was stirred for 1 hour at 55° C. The mixture was cooled to room temperature and water was added at the same temperature, followed by extraction with ethyl acetate. The organic layer was washed with saturated aqueous sodium chloride, and the solvent was evaporated under a reduced pressure. The residue was purified by reverse-phase high performance liquid chromatography (using an acetonitrile-water mobile phase containing 0.1% trifluoracetic acid) to obtain the title compound as a crude product, and this was then purified by NH silica gel column chromatography (ethyl acetate:heptane=1:1) to obtain the title compound (3.8 mg, 15%).

¹H-NMR Spectrum (CDCl₃) δ (ppm): 3.90 (2H, s), 4.04 (2H, s), 5.54 (2H, br s), 5.99 (1H, td, J=0.9, 3.3 Hz), 6.04 (1H, d, J=3.1 Hz), 6.27 (1H, s), 6.72 (1H, dd, J=4.9, 7.7 Hz), 7.19-7.25 (4H, m), 7.73 (1H, dd, J=1.8, 7.7 Hz), 8.12 (1H, dd, J=1.8, 4.9 Hz).

The starting material, (4-(5-chloro-furan-2-ylmethyl)-phenyl)-acetohydroximoyl chloride, was synthesized as follows.

Manufacturing Example 62-1-1

4-((5-Chloro-furan-2-yl)-hydroxy-methyl)-benzonitrile

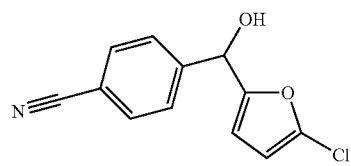

To a mixture of 4-iodobenzonitrile (3.0 g, 13 mmol) and tetrahydrofuran (40 mL) was added dropwise isopropyl magnesium chloride (1-2 M diethyl ether solution, 11 mL, 11-22 mmol) at −78° C., which was stirred for 1 hour at 0° C. The reaction mixture was cooled to −78° C., 5-chloro-2-furaldehyde (2.2 g, 17 mmol) was added at that temperature, and the temperature was gradually raised to 0° C. Following 30 minutes of stirring at 0° C., saturated aqueous ammonium chloride solution, water and ethyl acetate were added to extract the reaction mixture. The organic layer was washed successively with saturated aqueous sodium hydrogencarbonate solution and saturated aqueous sodium chloride, and the solvent was evaporated under a reduced pressure. Ethyl acetate was added to the residue, which was then filtered with NH silica gel. The filtrate was concentrated under a reduced pressure to obtain the title compound (3.2 g) as a crude product. This compound was used in the subsequent reaction without further purification.

Manufacturing Example 62-1-2

4-(5-Chloro-furan-2-ylmethyl)-benzylamine

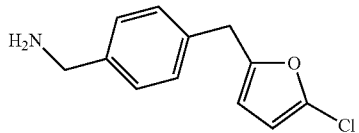

To a mixture of lithium aluminum hydride (3.3 g, 69 mmol) and tetrahydrofuran (100 mL) was added aluminum chloride (13 g, 96 mmol) at 0° C., which was stirred for 1 hour at room temperature. A mixture of 4-((5-chloro-furan-2-yl)-hydroxymethyl)-benzonitrile (3.2 g) described in Manufacturing Example 62-1-1 and tetrahydrofuran was added dropwise into the reaction mixture, and stirred for 1 hour at room temperature. A 28% aqueous ammonia solution was added dropwise into the reaction mixture at 0° C. to quench the excess reagent. The reaction mixture was allowed to room temperature and filtered through a Celite pad. The solvent was evaporated from the filtrate under a reduced pressure, and the residue was filtered after addition of diethyl ether. The filtrate was concentrated under a reduced pressure to obtain the title compound (2.6 g) as a crude product.

$^1$H-NMR Spectrum (CDCl$_3$) δ (ppm): 3.85 (2H, s), 3.90 (2H, s), 5.97 (1H, td, J=0.9, 3.1 Hz), 6.04 (1H, d, J=3.1 Hz), 7.20 (2H, d, J=8.2 Hz), 7.26 (2H, d, J=7.9 Hz).

Manufacturing Example 62-1-3

(4-(5-Chloro-furan-2-ylmethyl)-phenyl)-methanol

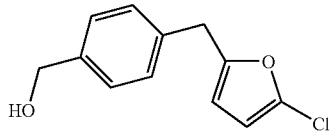

To a mixture of 4-(5-chloro-furan-2-ylmethyl)-benzylamine (2.6 g) described in Manufacturing Example 62-1-2, acetic acid (25 mL) and water (25 mL) was added sodium nitrite (9.8 g, 140 mmol) at 0° C., which was stirred for 40 minutes at room temperature. Water and ethyl acetate were added to extract the reaction mixture. The organic layer was washed successively with water, saturated sodium hydrogencarbonate and saturated aqueous sodium chloride, and the solvent was evaporated under a reduced pressure. Methanol (25 mL) was added to the residue at 0° C., followed by addition of potassium carbonate (3.3 g, 24 mmol) at the same temperature. This was stirred for 1 hour at the same temperature. Water and ethyl acetate were added to extract the reaction mixture. The organic layer was washed successively with water, saturated sodium hydrogencarbonate and saturated aqueous sodium chloride, and the organic layer was concentrated under a reduced pressure. The residue was purified by neutral silica gel column chromatography (ethyl acetate:heptane=1:2) to obtain the title compound (1.2 mg, 44%).

$^1$H-NMR Spectrum (CDCl$_3$) δ (ppm): 3.91 (2H, s), 4.68 (2H, s), 5.97 (1H, d, J=3.1 Hz), 6.04 (1H, d, J=3.1 Hz), 7.23 (2H, d, J=8.1 Hz), 7.32 (2H, d, J=8.1 Hz).

Manufacturing Example 62-1-4

4-(5-Chloro-furan-2-ylmethyl)-benzaldehyde

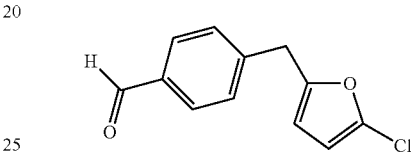

To a mixture of (4-(5-chloro-furan-2-ylmethyl)-phenyl)-methanol (650 mg, 2.9 mmol) described in Manufacturing Example 62-1-3 and dichloromethane (20 mL) was added manganese dioxide (6.5 g, 75 mmol) at room temperature, which was stirred overnight at room temperature. The reaction mixture was filtered through a Celite pad. The filtrate was evaporated under a reduced pressure to obtain the title compound (530 mg, 83%).

$^1$H-NMR Spectrum (CDCl$_3$) δ (ppm): 4.00 (2H, s), 6.04-6.05 (1H, m), 6.07-6.08 (1H, m), 7.40 (2H, d, J=7.9 Hz), 7.84 (2H, d, J=7.9 Hz), 10.00 (1H, s).

Manufacturing Example 62-1-5

2-Chloro-5-(4-(2-nitro-ethyl)-benzyl)-furan

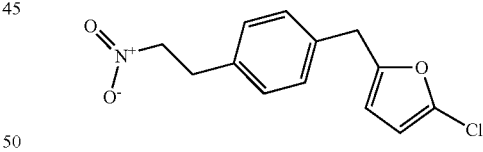

To a mixture of 4-(5-chloro-furan-2-ylmethyl)-benzaldehyde (270 mg, 1.2 mmol) described in Manufacturing Example 62-1-4 and acetic acid (3 mL) were added nitromethane (500 μL, 9.3 mmol) and ammonium acetate (290 mg, 3.7 mmol) at room temperature, which was stirred for 3 hours at 100° C. The reaction mixture was cooled to room temperature, and extracted by addition of water and ethyl acetate. This organic layer was washed with saturated aqueous sodium chloride and dried over anhydrous magnesium sulfate, and was concentrated under a reduced pressure. To a mixture of acetic acid (0.6 mL) and dimethyl sulfoxide (10 mL) was added sodium borohydride (76 mg, 2.0 mmol) at room temperature while cooling appropriately, which was stirred for 10 minutes at room temperature. Water was added to the reaction solution at room temperature, which was then extracted with ethyl acetate. The organic layer was washed with saturated aqueous sodium chloride. The organic layer was concentrated under a reduced pressure, and the residue was purified by neutral silica gel column chromatography (ethyl acetate:heptane=1:5) to obtain the title compound (210 mg, 62%).

$^1$H-NMR Spectrum (CDCl$_3$) δ (ppm): 3.30 (2H, t, J=7.4 Hz), 3.89 (2H, s), 4.60 (2H, t, J=7.4 Hz), 5.97 (1H, d, J=3.1 Hz), 6.04 (1H, d, J=3.1 Hz), 7.15 (2H, d, J=8.2 Hz), 7.19 (2H, d, J=8.2 Hz).

Manufacturing Example 62-1-6

(4-(5-Chloro-furan-2-ylmethyl)-phenyl)-acetohydroximoyl chloride

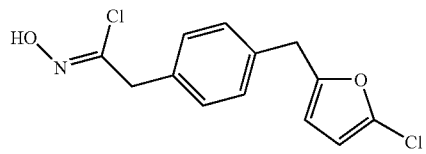

To a mixture of 2-chloro-5-(4-(2-nitro-ethyl)-benzyl)furan (100 mg, 0.38 mmol) described in Manufacturing Example 62-1-5 and methanol (2 mL) was added lithium methoxide (29 mg, 0.75 mmol) at room temperature, which was stirred for 10 minutes at room temperature. The solvent was evaporated from the reaction mixture under a reduced pressure. Titanium (IV) chloride (91 μL, 0.83 mmol) was added at –78° C. to a mixture of the resulting residue, methylene chloride (2 mL) and tetrahydrofuran (1 mL), and stirred for 1 hour at 0° C. The reaction mixture was cooled to –78° C., water (1 mL) was added, and the temperature was gradually raised to room temperature. Ethyl acetate and water were added to extract the reaction mixture. The organic layer was washed with water until the pH became roughly 5. The organic layer was washed with saturated aqueous sodium chloride, and dried over anhydrous magnesium sulfate. The organic layer was concentrated under a reduced pressure to obtain the title compound (110 mg, 84%).

$^1$H-NMR Spectrum (CDCl$_3$) δ (ppm): 3.78 (2H, s), 3.91 (2H, s), 5.97-5.99 (1H, m), 6.04 (1H, d, J=3.3 Hz), 7.21 (4H, d, J=1.7 Hz).

Example 63

3-(3-(4-(5-Chloro-pyridin-2-ylmethoxy)-benzyl)-isoxazol-5-yl)-pyridin-2-ylamine

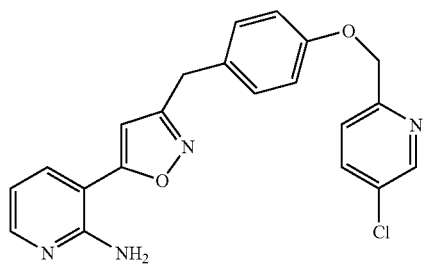

Tetrahydrofuran (3 mL) and a 5 N aqueous sodium hydroxide solution (22.4 μL, 0.11 mmol) were added to 4-(5-(2-amino-pyridine-3-yl)-isoxazole-3-ylmethyl)-phenol (30 mg, 0.11 mmol) described in Manufacturing Example 5-1-1, which was dissolved by irradiating ultrasonic wave for 1 minute. The reaction solution was then concentrated under a reduced pressure to obtain a white solid. An N,N-dimethylformamide (1 mL) solution of 5-chloro-2-chloromethyl-pyridine (20 mg, 0.12 mmol) described in Manufacturing Example 63-1-2 was added to a suspension of this solid and N,N-dimethylformamide (1 mL), and stirred for 1 hour at 60° C. This mixture was cooled to room temperature and partitioned into water and ethyl acetate. The organic layer was separated, washed with saturated aqueous sodium chloride, dried over anhydrous magnesium sulfate, and filtered. The filtrate was concentrated under a reduced pressure, and the resulting residue was purified by NH silica gel column chromatography (heptane:ethyl acetate=1:1) to obtain the title compound (41.1 mg, 93%).

$^1$H-NMR Spectrum (DMSO-d$_6$) δ (ppm): 3.97 (2H, s), 5.17 (2H, s), 6.26 (2H, brs), 6.68-6.72 (1H, m), 6.80 (1H, s), 6.99 (2H, d, J=8.4 Hz), 7.26 (2H, d, J=8.8 Hz), 7.55 (1H, d, J=8.4 Hz), 7.87 (1H, dd, J=1.6, 8.0 Hz), 7.97 (1H, dd, J=2.4, 8.4 Hz), 8.09 (1H, d, J=1.6, 4.8 Hz), 8.64 (1H, d, J=2.4 Hz).

The starting material, 5-chloro-2-chloromethyl-pyridine, was synthesized as follows.

Manufacturing Example 63-1-1

(5-Chloro-pyridin-2-yl)-methanol

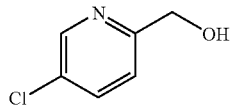

To a mixture of 2-bromo-5-chloropyridine (2.0 g, 10.4 mmol) and toluene (50 ml) was added a 1.6 M n-butyl lithium hexane solution (7.8 mL, 12.5 mmol) at –78° C., which was stirred for 1 hour. N,N-dimethylformamide (4.0 mL, 52.0 mmol) was then added dropwise into the mixture at the same temperature, which was then stirred for a further 15 minutes at room temperature. Water and tetrahydrofuran were added to this reaction solution, followed by vigorous stirring. The organic layer was separated, washed with water and saturated aqueous sodium chloride, dried over anhydrous magnesium sulfate, and filtered. Sodium borohydride (1.18 g, 31.2 mmol) was added at 0° C. to the filtrate, and stirred for 1 hour at room temperature. This reaction solution was partitioned into water and tetrahydrofuran. The organic layer was separated, washed with saturated aqueous sodium chloride, dried over anhydrous magnesium sulfate, and filtered. The filtrate was concentrated under a reduced pressure, and the resulting residue was purified by NH silica gel column chromatography (hexane:diethyl ether=1:2) to obtain the title compound (706 mg, 47%).

$^1$H-NMR Spectrum (CDCl$_3$) δ (ppm): 4.75 (2H, s), 7.25 (1H, dd, J=0.8, 8.4 Hz), 7.68 (1H, dd, J=2.4, 8.4 Hz), 8.53 (1H, d, J=2.4 Hz).

Manufacturing Example 63-1-2

5-Chloro-2-chloromethyl-pyridine

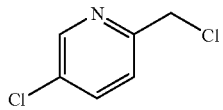

To a mixture of (5-chloro-pyridine-2-yl)-methanol (706 mg, 4.92 mmol) described in Manufacturing Example 63-1-1 and dichloromethane (70 mL) was added thionyl chloride (539 μL, 7.38 mmol), which was stirred for 1 hour at room temperature. Saturated aqueous sodium hydrogencarbonate solution was added to the reaction mixture, which was then extracted with dichloromethane. The organic layer was separated, washed with water and saturated aqueous sodium chloride, dried over anhydrous magnesium sulfate, and filtered. The filtrate was concentrated under a reduced pressure to obtain the title compound (620.0 mg, 78%).

$^1$H-NMR Spectrum (CDCl$_3$) δ (ppm): 4.66 (2H, s), 7.45 (1H, d, J=8.0 Hz), 7.71 (1H, dd, J=2.8, 8.0 Hz), 8.54 (1H, d, J=2.8 Hz).

Example 64

3-(3-(3-Phenoxy-benzyl)-isoxazol-5-yl)-pyridin-2-ylamine

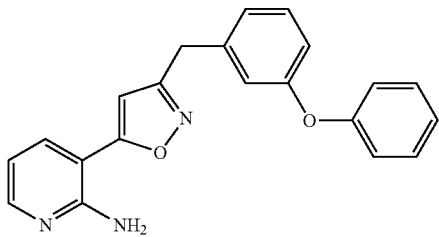

To a tetrahydrofuran (10.0 mL) solution of (3-phenoxyphenyl)-acetohydroximoyl chloride (150 mg, 0.573 mmol) described in Manufacturing Example 64-1-3 and 3-ethynyl-pyridin-2-ylamine (30.0 mg, 0.254 mmol) described in Manufacturing Example 1-2-3 was added triethylamine (106 μL, 0.762 mmol) at room temperature, which was stirred for 2 hours at 60° C. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1:2), the mixture was further purified by reverse-phase high-performance liquid chromatography (using an acetonitrile-water mobile phase containing 0.1% trifluoracetic acid) to obtain the title compound (6.6 mg, 43%) as a trifluoracetic acid salt.

MS m/e (ESI) 344.07 (MH$^+$)

$^1$H-NMR Spectrum (CD$_3$OD) δ (ppm): 4.08 (2H, s), 6.81 (1H, s), 6.85-6.87 (1H, m), 6.96-6.98 (3H, m), 7.03-7.12 (3H, m), 7.29-7.36 (3H, m), 8.03-8.04 (1H, m), 8.32-8.34 (1H, m).

The starting material, (3-phenoxy-phenyl)-acetohydroximoyl chloride, was synthesized as follows.

Manufacturing Example 64-1-1

1-((E)-2-nitro-vinyl)-3-phenoxy-benzene

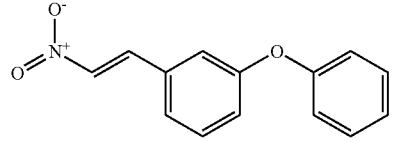

To an acetic acid (20.0 mL) solution of 3-phenoxybenzaldehyde (3.00 g, 15.1 mmol) were added nitromethane (4.61 g, 75.5 mmol) and ammonium acetate (2.33 g, 30.2 mmol) under nitrogen atmosphere at room temperature, which was stirred for 3 hours at 100° C. Water and ethyl acetate were added to the reaction mixture, and the organic layer was extracted with ethyl acetate. The organic layer was washed with saturated aqueous sodium chloride, dried over anhydrous magnesium sulfate, and filtered. The filtrate was concentrated under a reduced pressure to obtain the title compound (3.60 g) as a crude product.

$^1$H-NMR Spectrum (DMSO-d$_6$) δ (ppm): 7.03-7.06 (2H, m), 7.12-7.19 (2H, m), 7.39-7.44 (2H, m), 7.47-7.51 (1H, m), 7.61-7.66 (2H, m), 8.13 (1H, d, J=13.6 Hz), 8.25 (1H, d, J=13.6 Hz).

Manufacturing Example 64-1-2

1-(2-Nitro-ethyl)-3-phenoxy-benzen

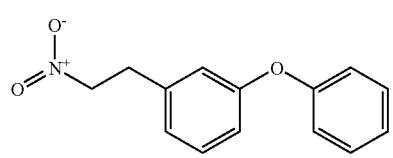

To a dimethyl sulfoxide (30.0 mL) solution of 1-((E)-2-nitro-vinyl)-3-phenoxy-benzene (3.60 g, 14.9 mmol) described in Manufacturing Example 64-1-1 and acetic acid (3.00 mL) was added sodium borohydride (902 mg, 23.8 mmol) at room temperature while cooling appropriately under nitrogen atmosphere, which was stirred for 3 minutes. Water was then added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under a reduce pressure, and the residue was purified by NH silica gel column chromatography (ethyl acetate:heptane=1:5) to obtain the title compound (2.47 g, 68.1%).

$^1$H-NMR Spectrum (DMSO-d$_6$) δ (ppm): 3.22 (2H, t, J=6.8 Hz), 4.84 (2H, t, J=6.8 Hz), 6.85-6.88 (1H, m), 6.98-

7.00 (3H, m), 7.04-7.06 (1H, m), 7.12-7.16 (1H, m), 7.30-7.34 (1H, m), 7.37-7.41 (2H, m).

Manufacturing Example 64-1-3

(3-Phenoxy-phenyl)-acetohydroximoyl chloride

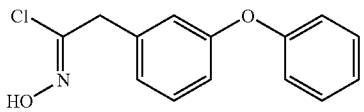

To a methanol (10.0 mL) solution of 1-(2-nitro-ethyl)-3-phenoxy-benzene (800 mg, 3.29 mmol) described in Manufacturing Example 64-1-2 was added lithium methoxide (250 mg, 6.58 mmol) under nitrogen atmosphere at room temperature, which was stirred for 30 minutes at room temperature. The solvent was evaporated from the reaction mixture under a reduced pressure, and anhydrous dichloromethane (20.0 mL) and anhydrous tetrahydrofuran (10.0 mL) were added to the residue. Titanium (IV) chloride (1.08 mL, 9.87 mmol) was added dropwise into the reaction mixture on a dry ice-ethanol bath (−78° C.), and then stirred for 45 minutes at room temperature. Water and ethyl acetate were added to the reaction mixture on an ice bath (0° C.), and the organic layer was extracted with ethyl acetate. The organic layer was washed with water and saturated aqueous sodium chloride, dried over anhydrous magnesium sulfate, and filtered. The filtrate was concentrated to obtain the title compound (860 mg, 100%) as a crude product.

$^1$H-NMR Spectrum (DMSO-d$_6$) δ (ppm): 3.81 (2H, s), 6.90-6.91 (2H, m), 7.00-7.04 (3H, m), 7.13-7.17 (1H, m), 7.34-7.42 (3H, m), 11.75 (1H, s).

Example 65

3-(3-(3-Butoxy-benzyl)-isoxazol-5-yl)-pyridin-2-ylamine

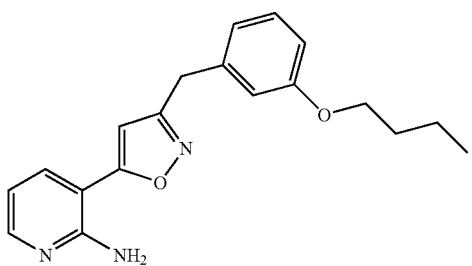

To a tetrahydrofuran (3 mL) solution of (3-butoxy-phenyl)-acetohydroximoyl chloride (150 mg, 0.621 mmol) described in Manufacturing Example 65-1-4 and 3-ethynyl-pyridin-2-ylamine (47 mg, 0.396 mmol) described in Manufacturing Example 1-2-3 was added triethylamine (216 μL, 1.55 mmol) at room temperature, which was stirred for 2 hours at 50° C. Water was added to the reaction solution at room temperature, which was then extracted with ethyl acetate. The organic layer was washed with water and saturated aqueous sodium chloride, and dried over anhydrous magnesium sulfate. The solvent was evaporated under a reduced pressure. The residue was purified by NH silica gel column chromatography (heptane:ethyl acetate=4:1-2:1) to obtain the title compound (33 mg, 8%).

$^1$H-NMR Spectrum (CDCl$_3$) δ (ppm): 0.95-0.99 (3H, m), 1.46-1.51 (2H, m), 1.72-1.79 (2H, m), 3.93-3.96 (2H, m), 4.02 (2H, s), 5.51 (2H, brs), 6.27 (1H, s), 6.70-6.73 (1H, m), 6.79-6.86 (4H, m), 7.71-7.73 (1H, m), 8.12-8.13 (1H, m).

The starting material, (3-butoxy-phenyl)-acetohydroximoyl chloride, was synthesized as follows.

Manufacturing Example 65-1-1

3-Butoxy-benzaldehyde

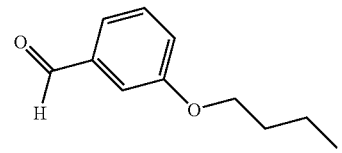

3-Hydroxybenzaldehyde (3 g, 24.6 mmol) and potassium carbonate (10.2 g, 73.8 mmol) were suspended in N,N-dimethylformamide (60 mL). 1-Bromobutane (3.17 mL, 29.5 mmol) was added to this suspension and stirred for 19 hours at room temperature. This mixture was partitioned into ethyl acetate and water. This organic layer was separated, washed with water, dried over anhydrous magnesium sulfate, and filtered. The filtrate was concentrated under a reduced pressure to obtain the title compound (4.23 g).

$^1$H-NMR Spectrum (CDCl$_3$) δ (ppm): 0.97-1.01 (3H, m), 1.48-1.56 (2H, m), 1.76-1.81 (2H, m), 4.01-4.04 (2H, m), 7.16-7.19 (1H, m), 7.384-7.390 (1H, m), 7.43-7.45 (2H, m), 9.97 (1H, s).

Manufacturing Example 65-1-2

1-Butoxy-3-((E)-2-nitro-vinyl)-benzene

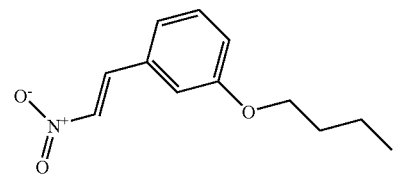

A mixture of 3-butoxy-benzaldehyde (4.23 g, 23.7 mmol) described in Manufacturing Example 65-1-1, nitromethane (2.55 mL, 47.7 mmol), ammonium acetate (2.74 g, 35.6 mmol) and acetic acid (40 mL) was stirred for 5 hours at 100° C. This mixture was cooled to room temperature, concentrated under a reduced pressure, and diluted with ethyl acetate. The organic layer was washed with water and saturated aqueous sodium chloride, dried over anhydrous magnesium sulfate, and filtered. The filtrate was concentrated under a reduced pressure, and the residue was purified by silica gel column chromatography (heptane:ethyl acetate=4:1-1:1) to obtain the title compound (3.92 g, 75%).

$^1$H-NMR Spectrum (DMSO-d$_6$) δ (ppm): 0.93-0.96 (3H, m), 1.42-1.47 (2H, m), 1.68-1.75 (2H, m), 3.97-4.05 (2H, m), 7.07-7.10 (1H, m), 7.35-7.41 (2H, m), 7.458-7.462 (1H, m), 8.09 (1H, d, J=13.6 Hz), 8.27 (1H, d, J=13.6 Hz).

Manufacturing Example 65-1-3

1-Butoxy-3-(2-nitro-ethyl)-benzene

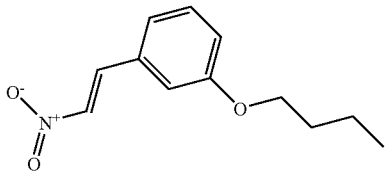

To an acetic acid (3.9 mL) and dimethyl sulfoxide (67 mL) solution of 1-butoxy-3-((E)-2-nitro-vinyl)-benzene (3.92 g, 17.7 mmol) described in Manufacturing Example 65-1-2 was added sodium borohydride (1.07 g, 28.3 mmol) at room temperature while cooling appropriately. This mixture was stirred for 4 hours at room temperature. This mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=10:1) to obtain the title compound (2.29 g, 58%).

$^1$H-NMR Spectrum (CDCl$_3$) δ (ppm): 0.91-0.95 (3H, m), 1.38-1.47 (2H, m), 1.65-1.70 (2H, m), 3.16-3.20 (2H, m), 3.92-3.95 (2H, m), 4.82-4.86 (2H, m), 6.78-6.82 (2H, m), 6.85-6.86 (1H, m), 7.18-7.22 (1H, m).

Manufacturing Example 65-1-4

(3-Butoxy-phenyl)-acetohydroximoyl chloride

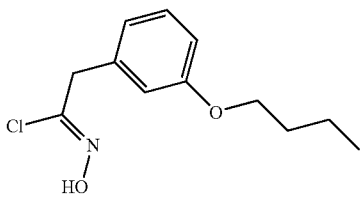

To a methanol (28 mL) solution of 1-butoxy-3-(2-nitro-ethyl)-benzene (2.29 g, 10.3 mmol) described in Manufacturing Example 65-1-3 was added lithium methoxide (782 mg, 20.6 mmol). This mixture was stirred for 1 hour at room temperature. The mixture was concentrated under a reduced pressure, water in the residue was azeotropically distilled with toluene, and that residue was diluted with methylene chloride (33 mL) and tetrahydrofuran (16.5 mL). This was cooled to −78° C., and titanium (IV) tetrachloride (2.49 mL, 22.7 mmol) was added dropwise into the suspension. This mixture was stirred for 2 hours at room temperature. This mixture was cooled to −78° C., and partitioned into ethyl acetate and ice water. The organic layer was separated, washed with saturated aqueous sodium chloride, dried over anhydrous magnesium sulfate, and filtered. The filtrate was concentrated under a reduced pressure to obtain the title compound (2.85 g). This compound was used in the following reaction without further purification.

Example 66

3-(3-(3-Cyclopropylmethoxy-benzyl)-isoxazol-5-yl)-pyridin-2-ylamine

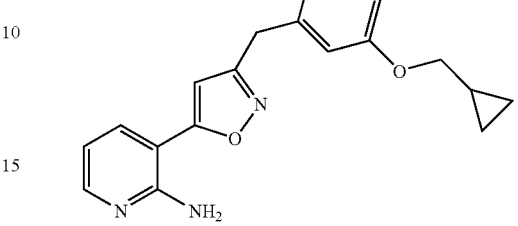

To a tetrahydrofuran (3 mL) solution of (3-cyclopropylmethoxy-phenyl)-acetohydroximoyl chloride (150 mg, 0.624 mmol) described in Manufacturing Example 66-1-4 and 3-ethynyl-pyridin-2-ylamine (47 mg, 0.398 mmol) described in Manufacturing Example 1-2-3 was added triethylamine (220 μL, 1.56 mmol) at room temperature, which was stirred for 2 hours at 50° C. Water was added to the reaction solution at room temperature, which was then extracted with ethyl acetate. The organic layer was washed with water and saturated aqueous sodium chloride, and dried over anhydrous magnesium sulfate. The solvent was evaporated under a reduced pressure. The residue was purified by NH silica gel column chromatography (heptane:ethyl acetate=4:1-2:1) to obtain the title compound (26 mg, 13%).

$^1$H-NMR Spectrum (CDCl$_3$) δ (ppm): 0.32-0.36 (2H, m), 0.62-0.66 (2H, m), 1.24-1.28 (1H, m), 3.78-3.80 (2H, m), 4.02 (2H, s), 5.55 (2H, brs), 6.27 (1H, s), 6.70-6.74 (1H, m), 6.79-6.87 (3H, m), 7.22-7.24 (1H, m), 7.71-7.74 (1H, m), 8.11-8.13 (1H, m).

The starting material, (3-cyclopropylmethoxy-phenyl)-acetohydroximoyl chloride, was synthesized as follows.

Manufacturing Example 66-1-1

3-Cyclopropylmethoxy-benzaldehyde

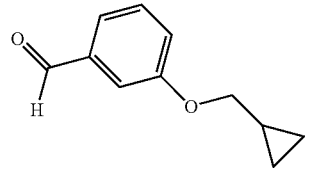

3-Hydroxybenzaldehyde (3 g, 24.6 mmol) and potassium carbonate (10.2 g, 73.8 mmol) were suspended in N,N-dimethylformamide (60 mL). Cyclopropyl methyl chloride (2.86 mL, 29.5 mmol) was added to this suspension, and stirred for 19 hours at room temperature. This mixture was partitioned into ethyl acetate and water. The organic layer was separated, washed with water, dried over anhydrous magnesium sulfate, and filtered. The filtrate was concentrated under a reduced pressure to obtain the title compound (4.32 g).

$^1$H-NMR Spectrum (CDCl$_3$) δ (ppm): 0.36-0.39 (2H, m), 0.65-0.69 (2H, m), 1.24-1.29 (1H, m), 3.86-3.88 (2H, m), 7.18-7.21 (1H, m), 7.37-7.38 (1H, m), 7.44-7.45 (2H, m), 9.97 (1H, s).

Manufacturing Example 66-1-2

1-Cyclopropylmethoxy-3-((E)-2-nitro-vinyl)-benzene

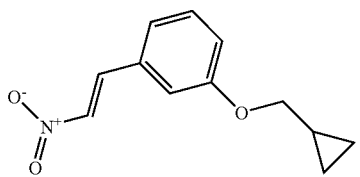

A mixture of 3-cyclopropylmethoxy-benzaldehyde (4.32 g, 24.5 mmol) described in Manufacturing Example 66-1-1, nitromethane (2.64 mL, 49 mmol), ammonium acetate (2.83 g, 36.8 mmol) and acetic acid (40 mL) was stirred for 5 hours at 100° C. This mixture was cooled to room temperature, concentrated under a reduced pressure, and diluted with ethyl acetate. The organic layer was washed with water and saturated aqueous sodium chloride, dried over anhydrous magnesium sulfate, and filtered. The filtrate was concentrated under a reduced pressure, and the residue was purified by silica gel column chromatography (heptane:ethyl acetate=4:1-1:1) to obtain the title compound (3.73 g, 69%).

$^1$H-NMR Spectrum (DMSO-$d_6$) δ (ppm): 0.31-0.36 (2H, m), 0.56-0.61 (2H, m), 1.22-1.26 (1H, m), 3.86-3.91 (2H, m), 7.08-7.11 (1H, m), 7.35-7.41 (2H, m), 7.45-7.46 (1H, m), 8.08 (1H, d, J=14 Hz), 8.27 (1H, d, J=14 Hz).

Manufacturing Example 66-1-3

1-Cyclopropylmethoxy-3-(2-nitro-ethyl)-benzene

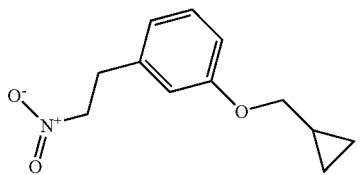

To an acetic acid (3.7 mL) and dimethyl sulfoxide (63 mL) solution of 1-cyclopropylmethoxy-3-((E)-2-nitro-vinyl)-benzene (3.73 g, 17 mmol) described in Manufacturing Example 66-1-2 was added sodium borohydride (1.03 g, 27.2 mmol) at room temperature while cooling appropriately. This mixture was stirred for 4 hours at room temperature. That mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=10:1) to obtain the title compound (2.21 g, 59%).

$^1$H-NMR Spectrum (DMSO-$d_6$) δ (ppm): 0.30-0.32 (2H, m), 0.54-0.57 (2H, m), 1.17-1.24 (1H, m), 3.17-3.19 (2H, m), 3.78-3.80 (2H, m), 4.82-4.85 (2H, m), 6.77-6.82 (2H, m), 6.85-6.86 (1H, m), 7.17-7.21 (1H, m).

Manufacturing Example 66-1-4

(3-Cyclopropylmethoxy-phenyl)-acetohydroximoyl chloride

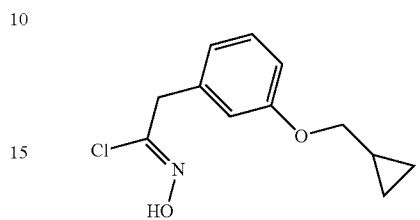

To a methanol (27 mL) solution of 1-cyclopropylmethoxy-3-(2-nitro-ethyl)-benzene (2.21 g, 10 mmol) described in Manufacturing Example 66-1-3 was added lithium methoxide (759 mg, 20 mmol). This mixture was stirred for 1 hour at room temperature. The mixture was concentrated under a reduced pressure, water in the residue was azeotropically distilled with toluene, and that residue was diluted with methylene chloride (32 mL) and tetrahydrofuran (16 mL). This was cooled to −78° C., and titanium (IV) tetrachloride (2.42 mL, 22 mmol) was added dropwise into the suspension. This mixture was stirred for 2 hours at room temperature. The mixture was cooled to −78° C. and partitioned into ethyl acetate and ice water. The organic layer was separated, washed with saturated aqueous sodium chloride, dried over anhydrous magnesium sulfate, and filtered. The filtrate was concentrated under a reduced pressure to obtain the title compound (2.5 g). This compound was used in the following reaction without further purification.

Example 67

3-(3-(4-Butoxy-benzyl)-isoxazol-5-yl)-pyridin-2-ylamine

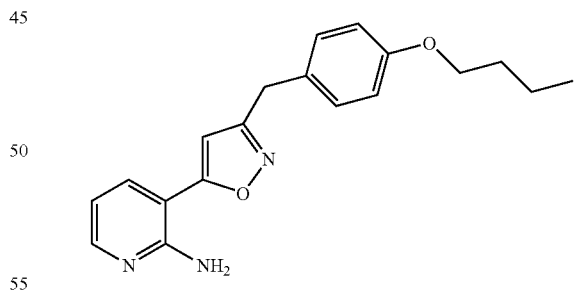

To a tetrahydrofuran (3 mL) solution of (4-butoxy-phenyl)-acetohydroximoyl chloride (150 mg, 0.619 mmol) described in Manufacturing Example 67-1-4 and 3-ethynyl-pyridin-2-ylamine (47 mg, 0.395 mmol) described in Manufacturing Example 1-2-3 was added triethylamine (216 μL, 1.55 mmol) at room temperature, which was stirred for 2 hours at 50° C. Water was added to the reaction solution at room temperature, which was then extracted with ethyl acetate. The organic layer was washed with water and saturated aqueous sodium chloride, and dried over anhydrous magnesium sulfate. The solvent was devaporated under a reduced pressure. The residue was purified by NH silica gel column chromatography (heptane:ethyl acetate=4:1-2:1) to obtain the title compound (27 mg, 14%).

$^1$H-NMR Spectrum (CDCl$_3$) δ (ppm): 0.95-0.99 (3H, m), 1.44-1.53 (2H, m), 1.72-1.79 (2H, m), 3.93-3.96 (2H, m), 4.00 (2H, s), 5.65 (2H, brs), 6.25 (1H, s), 6.71-6.74 (1H, m), 6.86-6.88 (2H, m), 7.17-7.20 (2H, m), 7.72-7.75 (1H, m), 8.10-8.12 (1H, m).

The starting material, (4-butoxy-phenyl)-acetohydroximoyl chloride, was synthesized as follows.

Manufacturing Example 67-1-1

4-Butoxy-benzaldehyde

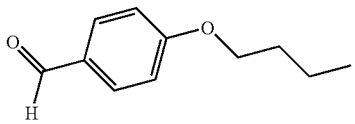

4-Hydroxybenzaldehyde (3 g, 24.6 mmol) and potassium carbonate (10.2 g, 73.8 mmol) were suspended in N,N-dimethylformamide (60 mL). 1-Bromobutane (3.17 mL, 29.5 mmol) was added to this suspension, and stirred for 17 hours at room temperature. The mixture was partitioned into ethyl acetate and water. The organic layer was separated, washed with water, dried over anhydrous magnesium sulfate, and filtered. The filtrate was concentrated under a reduced pressure to obtain the title compound (4.72 g).

$^1$H-NMR Spectrum (CDCl$_3$) δ (ppm): 0.97-1.01 (3H, m), 1.48-1.54 (2H, m), 1.79-1.82 (2H, m), 4.03-4.07 (2H, m), 6.98-7.00 (2H, m), 7.82-7.84 (2H, m), 9.88 (1H, s).

Manufacturing Example 67-1-2

1-Butoxy-4-((E)-2-nitro-vinyl)-benzene

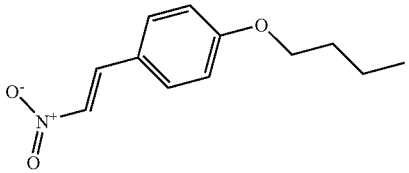

A mixture of 4-butoxy-benzaldehyde (4.72 g, 26.5 mmol) described in Manufacturing Example 67-1-1, nitromethane (2.85 mL, 53 mmol), ammonium acetate (3.06 g, 39.8 mmol) and acetic acid (40 mL) was stirred for 13 hours at 100° C. This mixture was cooled to room temperature, concentrated under a reduced pressure, and diluted with ethyl acetate. The organic layer was washed with water and saturated aqueous sodium chloride, dried over anhydrous magnesium sulfate, and filtered. The filtrate was concentrated under a reduced pressure, and the residue was purified by silica gel column chromatography (heptane:ethyl acetate=4:1-1:1) to obtain the title compound (4.44 g, 76%).

$^1$H-NMR Spectrum (DMSO-d$_6$) δ (ppm): 0.92-0.95 (3H, m), 1.41-1.46 (2H, m), 1.67-1.74 (2H, m), 4.04-4.09 (2H, m), 7.13 (2H, d, J=8.8 Hz), 7.82 (2H, d, J=8.8 Hz), 8.09 (1H, d, J=13.6 Hz), 8.13 (1H, d, J=13.6 Hz).

Manufacturing Example 67-1-3

1-Butoxy-4-(2-nitro-ethyl)-benzene

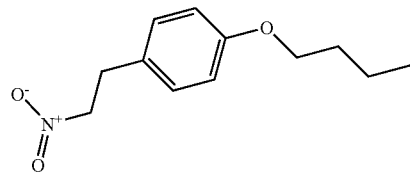

To an acetic acid (4.4 mL) and dimethyl sulfoxide (75 mL) solution of 1-butoxy-4-((E)-2-nitro-vinyl)-benzene (4.44 g, 20.1 mmol) described in Manufacturing Example 67-1-2 was added sodium borohydride (1.22 g, 32.2 mmol) at room temperature while cooling appropriately. This mixture was stirred for 4 hours at room temperature. The mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=10:1) to obtain the title compound (3.42 g, 76%).

$^1$H-NMR Spectrum (CDCl$_3$) δ (ppm): 0.90-0.95 (3H, m), 1.37-1.47 (2H, m), 1.63-1.70 (2H, m), 3.12-3.16 (2H, m), 3.91-3.94 (2H, m), 4.76-4.80 (2H, m), 6.83-6.87 (2H, m), 7.14-7.18 (2H, m).

Manufacturing Example 67-1-4

(4-Butoxy-phenyl)-acetohydroximoyl chloride

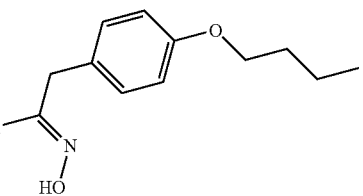

To a methanol (42 mL) solution of 1-butoxy-4-(2-nitroethyl)-benzene (3.42 g, 15.3 mmol) described in Manufacturing Example 67-1-3 was added lithium methoxide (1.16 g, 30.6 mmol). This mixture was stirred for 1 hour at room temperature. The mixture was concentrated under a reduced pressure, water in the residue was azeotropically distilled with toluene, and that residue was diluted with methylene chloride (50 mL) and tetrahydrofuran (25 mL). This was cooled to −78° C., and titanium (IV) tetrachloride (3.7 mL, 33.7 mmol) was added dropwise into the suspension. This mixture was stirred for 2 hours at room temperature. This mixture was cooled to −78° C., and partitioned into ethyl acetate and ice water. The organic layer was separated, washed with saturated aqueous sodium chloride, dried over anhydrous magnesium sulfate, and filtered. The filtrate was concentrated under a reduced pressure to obtain the title compound (3.5 g). This compound was used in the following reaction without further purification.

Example 68

3-(3-(4-Benzylamino-benzyl)-isoxazol-5-yl)-pyridin-2-ylamine

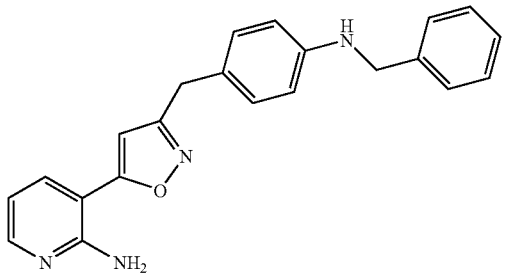

To a tetrahydrofuran (3 mL) solution of (4-benzylamino-phenyl)-acetohydroximoyl chloride (150 mg, 0.546 mmol) described in Manufacturing Example 68-1-4 and 3-ethynyl-pyridin-2-ylamine (41 mg, 0.348 mmol) described in Manufacturing Example 1-2-3 was added triethylamine (190 μL, 1.37 mmol) at room temperature, which was stirred for 7 hours at 50° C. Water was added to the reaction solution at room temperature, which was then extracted with ethyl acetate. The organic layer was washed with water and saturated aqueous sodium chloride, and dried over anhydrous magnesium sulfate. The solvent was evaporated under a reduced pressure. The residue was purified by NH silica gel column chromatography (heptane:ethyl acetate=4:1-2:1) to obtain the title compound (14 mg, 7%).

$^1$H-NMR Spectrum (CDCl$_3$) δ (ppm): 3.94 (2H, s), 4.32 (2H, s), 5.69 (2H, brs), 6.26 (1H, s), 6.59-6.62 (2H, m), 6.71-6.74 (1H, m), 7.06-7.09 (2H, m), 7.24-7.38 (4H, m), 7.73-7.75 (1H, m), 8.09-8.10 (1H, m).
(It was not observed that the proton on the amino group of NH—CH2Ph appeared on the NMR chart.)

The starting material, (4-benzylamino-phenyl)-acetohydroximoyl chloride, was synthesized as follows.

Manufacturing Example 68-1-1

4-Benzylamino-benzaldehyde

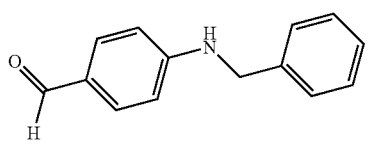

To a toluene (35 mL) solution of 4-benzylamino-benzonitrile (5 g, 24 mmol) was added diisobutyl aluminum hydride (35.6 mL, 1.01 M toluene solution, 36 mmol) under nitrogen atmosphere at −70° C. to −78° C. This mixture was stirred for 5 hours at room temperature. The mixture was partitioned into ethyl acetate and 20% aqueous Rochelle salt solution. After removal of insoluble matter by filtering through a Celite pad, the filtrate was partitioned. The organic layer was separated, washed with saturated aqueous sodium chloride, dried over anhydrous magnesium sulfate, and filtered. The filtrate was concentrated under a reduced pressure to obtain the title compound (5 g, 99%). This compound was used in the following reaction without further purification.

Manufacturing Example 68-1-2

Benzyl-(4-((E)-2-nitro-vinyl)-phenyl)-amine

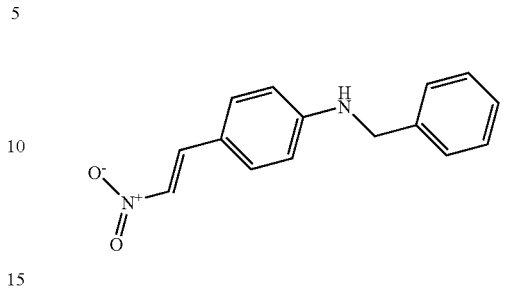

A mixture of 4-benzylamino-benzaldehyde (5 g, 23.7 mmol) described in Manufacturing Example 68-1-1, nitromethane (2.55 mL, 47.7 mmol), ammonium acetate (2.74 g, 35.6 mmol) and acetic acid (50 mL) was stirred for 6 hours at 100° C. This mixture was cooled to room temperature, concentrated under a reduced pressure, and diluted with ethyl acetate. The organic layer was washed with saturated aqueous sodium chloride, dried over anhydrous magnesium sulfate, and filtered. The filtrate was concentrated under a reduced pressure to obtain the title compound (5.82 g).

$^1$H-NMR Spectrum (CDCl$_3$) δ (ppm): 4.41-4.43 (2H, m), 4.68 (1H, brs), 6.62-6.67 (2H, m), 7.25-7.39 (6H, m), 7.47-7.50 (1H, m), 7.69-7.71 (1H, m), 7.93-7.96 (1H, m).

Manufacturing Example 68-1-3

Benzyl-(4-(2-nitro-ethyl)-phenyl)-amine

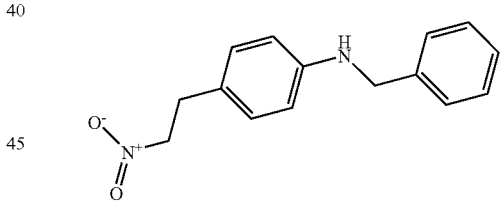

To an acetic acid (5.8 mL) and dimethyl sulfoxide (100 mL) solution of benzyl-(4-((E)-2-nitro-vinyl)-phenyl)-amine (5.82 g, 22.9 mmol) described in Manufacturing Example 68-1-2 was added sodium borohydride (1.39 g, 36.6 mmol) at room temperature while cooling appropriately. This mixture was stirred for 1 hour at room temperature. The mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=4:1-2:1) to obtain the title compound (2.79 g, 48%).

$^1$H-NMR Spectrum (CDCl$_3$) δ (ppm): 3.19-3.22 (2H, m), 4.32 (2H, s), 4.52-4.56 (3H, m), 6.60-6.62 (2H, m), 7.00-7.02 (2H, m), 7.27-7.37 (5H, m).

Manufacturing Example 68-1-4

(4-Benzylamino-phenyl)-acetohydroximoyl chloride

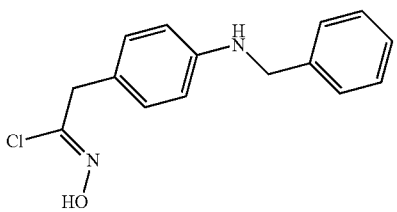

To a methanol (12 mL) solution of benzyl-(4-(2-nitroethyl)-phenyl)-amine (1 g, 3.91 mmol) described in Manufacturing Example 68-1-3 was added lithium methoxide (297 mg, 30.6 mmol). This mixture was stirred for 1 hour at room temperature. The mixture was concentrated under a reduced pressure, water in the residue was azeotropically distilled with toluene, and that residue was diluted with methylene chloride (15 mL) and tetrahydrofuran (7.6 mL). This was cooled to −78° C., and titanium (IV) tetrachloride (945 µL, 8.6 mmol) was added dropwise into the suspension. This mixture was stirred for 1 hour at room temperature. This mixture was cooled to −78° C., and partitioned into ethyl acetate and ice water. The organic layer was separated, washed with saturated aqueous sodium chloride, dried over anhydrous magnesium sulfate, and filtered. The filtrate was concentrated under a reduced pressure to obtain the title compound (1.1 g). This compound was used in the following reaction without further purification.

Example 69

3-(3-(4-Phenylamino-benzyl)-isoxazol-5-yl)-pyridin-2-ylamine

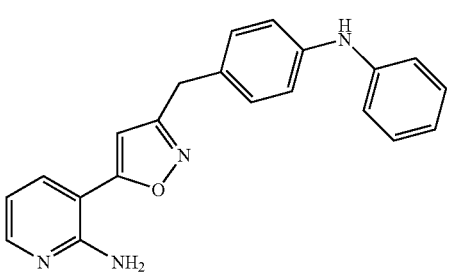

To a tetrahydrofuran (3 mL) solution of (4-phenylamino-phenyl)-acetohydroximoyl chloride (150 mg, 0.576 mmol) described in Manufacturing Example 69-1-4 and 3-ethynyl-pyridin-2-ylamine (43 mg, 0.367 mmol) described in Manufacturing Example 1-2-3 was added triethylamine (201 µL, 1.44 mmol) at room temperature, which was stirred for 7 hours at 50° C. Water was added to the reaction solution at room temperature, which was then extracted with ethyl acetate. The organic layer was washed with water and saturated aqueous sodium chloride, and dried over anhydrous magnesium sulfate. The solvent was evaporated under a reduced pressure. The residue was purified by NH silica gel column chromatography (heptane:ethyl acetate=4:1-2:1) to obtain the title compound (48 mg, 24%).

$^1$H-NMR Spectrum (CDCl$_3$) δ (ppm): 4.00 (2H, s), 5.58 (2H, brs), 5.70 (1H, brs), 6.29 (1H, s), 6.71-6.74 (1H, m), 6.91-6.95 (1H, m), 7.03-7.07 (4H, m), 7.16-7.19 (2H, m), 7.24-7.28 (2H, m), 7.73-7.75 (1H, m), 8.11-8.13 (1H, m).

The starting material, (4-phenylamino-phenyl)-acetohydroximoyl chloride, was synthesized as follows.

Manufacturing Example 69-1-1

4-Phenylamino-benzaldehyde

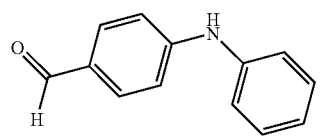

To a toluene (20 mL) solution of 4-phenylamino-benzonitrile (3 g, 15.4 mmol) was added diisobutyl aluminum hydride (22.9 mL, 1.01 M toluene solution, 23.1 mmol) under nitrogen atmosphere at −78° C. This mixture was stirred for 5 hours at room temperature. The mixture was partitioned into ethyl acetate and 20% aqueous Rochelle salt solution. After removal of insoluble matter by filtering through a Celite pad, the filtrate was partitioned. The organic layer was separated, washed with saturated aqueous sodium chloride, dried over anhydrous magnesium sulfate, and filtered. The filtrate was concentrated under a reduced pressure to obtain the title compound (3 g, 98%). This compound was used in the following reaction without further purification.

Manufacturing Example 69-1-2

(4-((E)-2-nitro-vinyl)-phenyl)-phenyl-amine

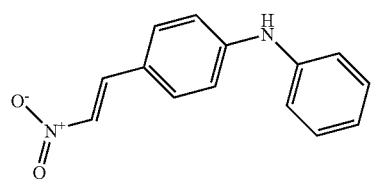

A mixture of 4-phenylamino-benzaldehyde (3 g, 15.2 mmol) described in Manufacturing Example 69-1-1, nitromethane (1.63 mL, 30.4 mmol), ammonium acetate (1.76 g, 22.8 mmol) and acetic acid (30 mL) was stirred for 6 hours at 100° C. This mixture was cooled to room temperature, concentrated under a reduced pressure, and diluted with ethyl acetate. The organic layer was washed with water and saturated aqueous sodium chloride, dried over anhydrous magnesium sulfate, and filtered. The filtrate was concentrated under a reduced pressure to obtain the title compound (3.2 g). This compound was used in the following reaction without being purified.

Manufacturing Example 69-1-3

(4-(2-Nitro-ethyl)-phenyl)-phenyl-amine

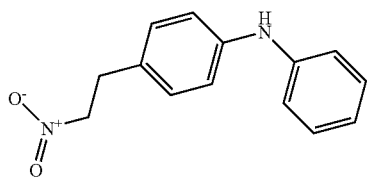

To an acetic acid (3.2 mL) and dimethyl sulfoxide (54 mL) solution of (4-((E)-2-nitro-vinyl)-phenyl)-phenyl-amine (3.2 g, 13.4 mmol) described in Manufacturing Example 69-1-2 was added sodium borohydride (811 mg, 21.4 mmol) at room temperature while cooling appropriately. This mixture was stirred for 1 hour at room temperature. The mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=4:1-2:1) to obtain the title compound (2.01 g, 62%).

$^1$H-NMR Spectrum (CDCl$_3$) δ (ppm): 3.24-3.28 (2H, m), 4.56-4.60 (2H, m), 5.81 (1H, brs), 6.93-6.98 (1H, m), 7.00-7.12 (6H, m), 7.24-7.29 (2H, m).

Manufacturing Example 69-1-4

(4-Phenylamino-phenyl)-acetohydroximoyl chloride

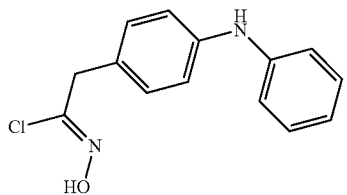

To a methanol (12 mL) solution of (4-(2-nitro-ethyl)-phenyl)-phenyl-amine (1 g, 4.13 mmol) described in Manufacturing Example 69-1-3 was added lithium methoxide (314 mg, 8.26 mmol). This mixture was stirred for 1 hour at room temperature. The mixture was concentrated under a reduced pressure, water in the residue was azeotropically distilled with toluene, and that residue was diluted with methylene chloride (15 mL) and tetrahydrofuran (7.6 mL). This was cooled to −78° C., and titanium (IV) tetrachloride (999 μL, 9.09 mmol) was added dropwise into the suspension. The mixture was stirred for 1 hour at room temperature. This mixture was cooled to −78° C., and partitioned into ethyl acetate and ice water. The organic layer was separated, washed with saturated aqueous sodium chloride, dried over anhydrous magnesium sulfate, and filtered. The filtrate was concentrated under a reduced pressure to obtain the title compound (1.2 g). This compound was used in the following reaction without further purification.

Example 70

3-(3-(4-Butyl-benzyl)-isoxazol-5-yl)-pyridin-2-ylamine

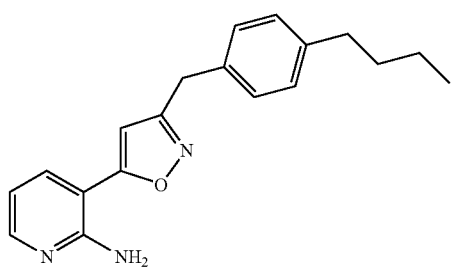

To a tetrahydrofuran (3 mL) solution of (4-butyl-phenyl)-acetohydroximoyl chloride (150 mg, 0.665 mmol) described in Manufacturing Example 70-1-3 and 3-ethynyl-pyridin-2-ylamine (50 mg, 0.424 mmol) described in Manufacturing Example 1-2-3 was added triethylamine (232 μL, 1.66 mmol) at room temperature, which was stirred for 8 hours at 50° C. Water was added to the reaction solution at room temperature, which was then extracted with ethyl acetate. The organic layer was washed with water and saturated aqueous sodium chloride, and dried over anhydrous magnesium sulfate, and the solvent was evaporated under a reduced pressure. The residue was purified by NH silica gel column chromatography (heptane:ethyl acetate=4:1-2:1) to obtain the title compound (55 mg, 18%).

$^1$H-NMR Spectrum (CDCl$_3$) δ (ppm): 0.91-0.94 (3H, m), 1.31-1.40 (2H, m), 1.55-1.63 (2H, m), 2.57-2.61 (2H, m), 4.03 (2H, s), 5.53 (2H, brs), 6.26 (1H, s), 6.70-6.73 (1H, m), 7.14-7.20 (4H, m), 7.71-7.73 (1H, m), 8.11-8.13 (1H, m).

The starting material, (4-butyl-phenyl)-acetohydroximoyl chloride, was synthesized as follows.

Manufacturing Example 70-1-1

1-butyl-4-((E)-2-nitro-vinyl)-benzene

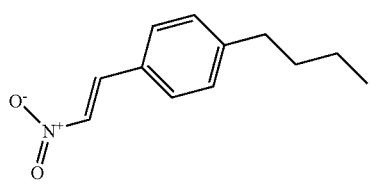

A mixture of 4-n-butylbenzaldehyde (5 g, 30.8 mmol), nitromethane (3.31 mL, 61.6 mmol), ammonium acetate (3.56 g, 46.2 mmol) and acetic acid (50 mL) was stirred for 5 hours at 100° C. The mixture was cooled to room temperature, concentrated under a reduced pressure, and diluted with ethyl acetate. The organic layer was washed with water and saturated aqueous sodium chloride, dried over anhydrous magnesium sulfate, and filtered. The filtrate was concentrated under a reduced pressure to obtain the title compound (5.7 g). This compound was used in the subsequent reaction without being purified.

¹H-NMR Spectrum (CDCl₃) δ (ppm): 0.92-0.95 (3H, m), 1.34-1.39 (2H, m), 1.58-1.65 (2H, m), 2.64-2.68 (2H, m), 7.25-7.27 (2H, m), 7.45-7.48 (2H, m), 7.56-7.59 (1H, m), 7.98-8.02 (1H, m).

Manufacturing Example 70-1-2

1-Butyl-4-(2-nitro-ethyl)-benzene

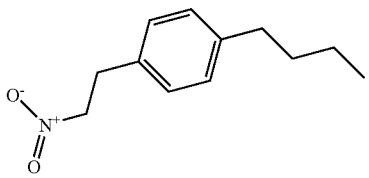

To an acetic acid (5.7 mL) and dimethyl sulfoxide (95 mL) solution of 1-butyl-4-((E)-2-nitro-vinyl)-benzene (5.7 g, 27.8 mmol) described in Manufacturing Example 70-1-1 was added sodium borohydride (1.68 g, 44.5 mmol) at room temperature while cooling appropriately. This mixture was stirred for 3 hours at room temperature. The mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=4:1-2:1) to obtain the title compound (1.48 g, 26%).

¹H-NMR Spectrum (CDCl₃) δ (ppm): 0.90-0.94 (3H, m), 1.31-1.37 (2H, m), 1.54-1.61 (2H, m), 2.56-2.60 (2H, m), 3.27-3.30 (2H, m), 4.57-4.61 (2H, m), 7.10-7.15 (4H, m).

Manufacturing Example 70-1-3

(4-Butyl-phenyl)-acetohydroximoyl chloride

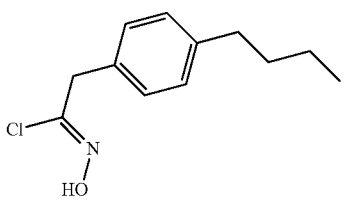

To a methanol (18 mL) solution of 1-butyl-4-(2-nitro-ethyl)-benzene (1.48 g, 7.14 mmol) described in Manufacturing Example 70-1-2 was added lithium methoxide (542 mg, 14.3 mmol). This mixture was stirred for 1 hour at room temperature. The mixture was concentrated under a reduced pressure, water in the residue was azeotropically distilled with toluene, and that residue was diluted with methylene chloride (22 mL) and tetrahydrofuran (11 mL). This was cooled to −78° C., and titanium (IV) tetrachloride (1.7 mL, 15.7 mmol) was added dropwise into the suspension. This mixture was stirred for 1 hour at room temperature. This mixture was cooled to −78° C., and partitioned into ethyl acetate and ice water. The organic layer was separated, washed with saturated aqueous sodium chloride, dried over anhydrous magnesium sulfate, and filtered. The filtrate was concentrated under a reduced pressure to obtain the title compound (1.5 g). This compound was used in the subsequent reaction without further purification.

Example 71

3-(3-(6-(3-Fluoro-phenoxy)-pyridin-3-ylmethyl)-isoxazol-5-yl)-pyridin-2-ylamine

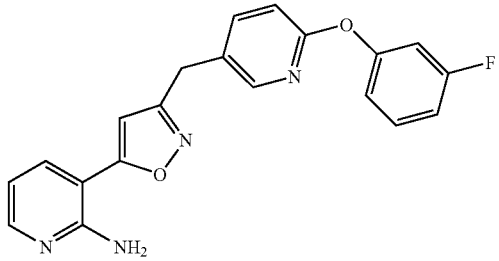

To a tetrahydrofuran (4 mL) solution of 3-ethynyl-pyridin-2-ylamine (20 mg, 0.17 mmol) described in Manufacturing Example 1-2-3 and (6-(3-fluoro-phenoxy)-pyridin-3-yl)-acetohydroximoyl chloride (95 mg, 0.34 mmol) described in Manufacturing Example 71-1-4 was added triethylamine (47 μL, 0.34 mmol), which was stirred for 3 hours at 50° C. under nitrogen atmosphere. Water was added to the reaction solution at room temperature, which was then extracted with ethyl acetate. The organic layer was separated, washed with saturated aqueous sodium chloride, dried over anhydrous magnesium sulfate, and filtered. The filtrate was concentrated under a reduced pressure, and the filtrate was purified by NH silica gel column chromatography (ethyl acetate:methanol=20:1) and further purified by reverse-phase high-performance liquid chromatography (using an acetonitrile-water mobile phase containing 0.1% trifluoracetic acid) to obtain the title compound (33 mg, 33%) as a ditrifluoracetic acid salt.

MS m/e (ESI) (MH⁺) 363.01 (MH⁺)

The starting material, (6-(3-fluoro-phenoxy)-pyridin-3-yl)-acetohydroximoyl chloride, was synthesized as follows.

Manufacturing Example 71-1-1

5-Bromo-2-(3-fluoro-phenoxy)-pyridine

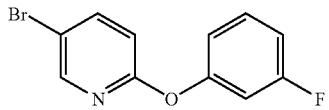

To an N,N-dimethylformamide (100 mL) solution of 3-fluorophenol (3.30 g, 29.4 mmol) was added sodium hydride (1.41 g, 29.4 mmol, 50% in oil), which was stirred for 10 minutes at 0° C. 2,5-Dibromopyridine (4.64 g, 19.6 mmol) was then added to this mixture at 0° C., followed by 7 hours and 45 minutes of stirring at 110° C. Water was added to the reaction solution at room temperature, which was then extracted with ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=3:1) to obtain the title compound (5.81 g, quant.).

¹H-NMR Spectrum (DMSO-d₆) δ (ppm): 7.00-7.02 (1H, m), 7.08-7.13 (3H, m), 7.43-7.49 (1H, m), 8.09 (1H, dd, J=2.8, 8.8 Hz), 8.31 (1H, d, J=2.8 Hz).

Manufacturing Example 71-1-2

6-(3-Fluoro-phenoxy)-pyridine-3-carbaldehyde

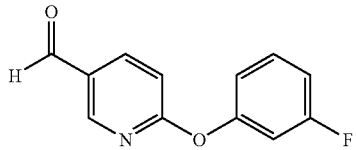

To a diethyl ether (100 mL) solution of 5-bromo-2-(3-fluoro-phenoxy)-pyridine (5.81 g, 21.7 mmol) described in Manufacturing Example 71-1-1 was added n-butyl lithium (13.8 mL, 1.57 M n-hexane solution, 21.7 mmol) under nitrogen atmosphere at −78° C., which was stirred for 40 minutes at −78° C. N,N-Dimethylformamide (2.02 mL, 26.0 mmol) was then added to the mixture at −78° C., and stirred for 25 minutes as the temperature was gradually raised to 0° C. Water was added to the reaction solution at 0° C., which was then extracted with ethyl acetate. The organic layer was separated, washed with 1 N aqueous sodium hydroxide solution and saturated aqueous sodium chloride, dried over anhydrous magnesium sulfate, and filtered. The filtrate was concentrated under a reduced pressure, and the residue was purified by silica gel column chromatography (heptane:ethyl acetate=5:1) to obtain the title compound (2.47 g, 52%).

¹H-NMR Spectrum (CDCl₃) δ (ppm): 6.91-7.01 (3H, m), 7.06 (1H, d, J=8.8 Hz), 7.37-7.42 (1H, m), 8.20 (1H, dd, J=2.4, 8.4 Hz), 8.62 (1H, d, J=2.4 Hz), 9.98 (1H, s).

Manufacturing Example 71-1-3

2-(3-Fluoro-phenoxy)-5-(2-nitro-ethyl)-pyridine

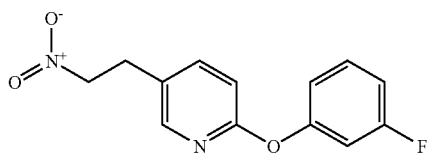

To an acetic acid (20 mL) solution of 6-(3-fluoro-phenoxy)-pyridine-3-carbaldehyde (2.47 g, 11.4 mmol) described in Manufacturing Example 71-1-2 was added nitromethane (3.09 mL, 57.0 mmol) and ammonium acetate (1.76 g, 22.8 mmol), which was stirred for 6 hours at 100° C. Water was added to the reaction solution at room temperature, which was then extracted with ethyl acetate. The organic layer was separated, washed with saturated aqueous sodium chloride, dried over anhydrous magnesium sulfate, and filtered. The filtrate was concentrated under a reduced pressure. To a dimethyl sulfoxide (35 mL) and acetic acid (5 mL) solution of the residue was added sodium borohydride (681 mg, 17.1 mmol), which was stirred for 40 minutes at room temperature. Sodium hydrogencarbonate and water were added to the reaction mixture at room temperature while cooling appropriately, which was then extracted with ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (heptane:ethyl acetate=2:1) to obtain the title compound (1.96 g, 66%).

¹H-NMR Spectrum (CDCl₃) δ (ppm): 3.30 (2H, t, J=7.1 Hz), 4.61 (2H, t, J=7.1 Hz), 6.86-6.94 (4H, m), 7.32-7.38 (1H, m), 7.58 (1H, dd, J=2.6, 8.4 Hz), 8.07 (1H, d, J=2.2 Hz).

Manufacturing Example 71-1-4

(6-(3-Fluoro-phenoxy)-pyridin-3-yl)-acetohydroximoyl chloride

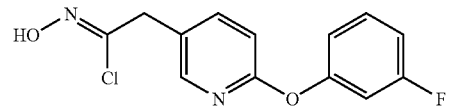

To a methanol (20 mL) solution of 2-(3-fluoro-phenoxy)-5-(2-nitro-ethyl)-pyridine (1.96 g, 7.47 mmol) described in Manufacturing Example 71-1-3 was added lithium methoxide (567 mg, 14.9 mmol), which was stirred for 35 minutes at room temperature. The reaction mixture was concentrated under a reduced pressure. Titanium (IV) tetrachloride (1.81 mL, 16.4 mmol) was added under nitrogen atmosphere to a tetrahydrofuran (20 mL) and methylene chloride (20 mL) suspension of the residue, and stirred for 1 hour 15 minutes at 0° C. Water was added to the reaction mixture at 0° C., which was then extracted with ethyl acetate. The organic layer was separated, washed with saturated aqueous sodium chloride, dried over anhydrous magnesium sulfate, and filtered. The filtrate was concentrated under a reduced pressure to obtain the title compound (2.1 g, quant.). This compound was used in the subsequent reaction without further purification.

¹H-NMR Spectrum (CDCl₃) δ (ppm): 3.77 (2H, s), 6.87-6.95 (4H, m), 7.31-7.38 (1H, m), 7.65 (1H, dd, J=2.6, 8.4 Hz), 8.12 (1H, d, J=2.6 Hz).

Example 72

3-(3-(6-(4-Fluoro-phenoxymethyl)-pyridin-3-ylmethyl)-isoxazol-5-yl)-pyridin-2-ylamine

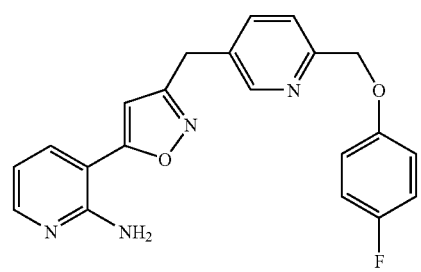

To a methanol (5.00 mL) solution of 2-(4-fluoro-phenoxymethyl)-5-(2-nitro-ethyl)-pyridine (50.0 mg, 0.181 mmol) described in Manufacturing Example 72-1-3 was added lithium methoxide (13.7 mg, 0.362 mmol) under nitrogen atmosphere at room temperature, which was stirred for 30 minutes at room temperature. The solvent was evaporated from the reaction mixture under a reduced pressure, and anhydrous dichloromethane (4.00 ml) and anhydrous tetrahydrofuran (2.00 ml) were added to the residue. Titanium (IV) chloride (63.7 μL, 0.579 mmol) was added dropwise into the reaction mixture on a dry ice-ethanol bath (−78° C.), and stirred for 40 minutes at 0° C. Water and ethyl acetate were added to the reaction mixture on an ice bath (0° C.), and the organic layer was extracted with ethyl acetate. This organic layer was washed with water and saturated aqueous sodium chloride, dried over anhydrous magnesium sulfate, and filtered. The filtrate was concentrated under a reduced pressure to obtain a crude product (43.0 mg). To a tetrahydrofuran (5.00 mL) solution of this crude product (23.0 mg) and 3-ethynyl-pyridin-2-ylamine described in Manufacturing Example 1-2-3 (3.44 mg, 0.029 mmol) was added triethylamine (12.2 μL, 0.083 mmol) at room temperature, which was stirred for 2 hours at room temperature. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1: 2), the mixture was further purified by reverse-phase high-performance liquid chromatography (using an acetonitrile-water mobile phase containing 0.1% trifluoracetic acid) to obtain the title compound (3.62 mg, 25.4%) as a ditrifluoracetic acid salt.

MS m/e (ESI) 377.18 (MH$^+$)

The starting material, 2-(4-fluoro-phenoxymethyl)-5-(2-nitro-ethyl)-pyridine, was synthesized as follows.

Manufacturing Example 72-1-1

5-Bromo-2-(4-fluoro-phenoxymethyl)-pyridine

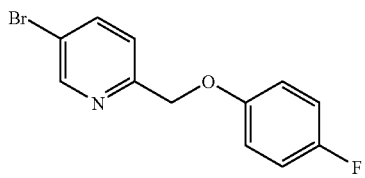

To an N,N-dimethylformamide (40.0 mL) solution of 4-fluorophenol (3.00 g, 26.8 mmol) was added sodium hydride (1.00 g, 25.0 mmol, 60% in oil) on an ice bath (0° C.) under nitrogen atmosphere, which was stirred for 20 minutes at room temperature. To the reaction solution was then added a mixture of 5-bromo-2-chloromethyl-pyridine hydrochloride (4.6 g, 22.3 mmol) described in Manufacturing Example 54-1-2 and triethylamine (30.6 mL, 20.4 mmol), which was stirred for 10 minutes at room temperature. Water and ethyl acetate were added to the reaction mixture, and the organic layer was extracted with ethyl acetate. This organic layer was washed with water and saturated aqueous sodium chloride, dried over anhydrous magnesium sulfate, and filtered. The solvent was evaporated from the filtrate under a reduced pressure, and the residue was purified by silica gel column chromatography (ethyl acetate:heptane=1:4) to obtain the title compound (4.0 g, 63.6%).

$^1$H-NMR Spectrum (CDCl$_3$) δ (ppm): 5.10 (2H, s), 6.88-6.91 (2H, m), 6.95-6.99 (2H, m), 7.40-7.42 (1H, m), 7.81-7.84 (1H, m), 8.64-8.65 (1H, m).

Manufacturing Example 72-1-2

6-(4-Fluoro-phenoxymethyl)-pyridine-3-carbaldehyde

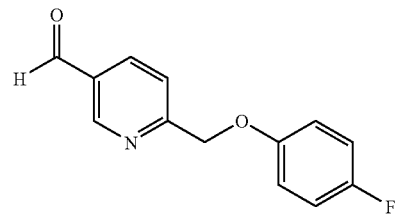

To a diethyl ether (100 mL) solution of 5-bromo-2-(4-fluoro-phenoxymethyl)-pyridine (4.00 g, 14.2 mmol) described in Manufacturing Example 72-1-1 was added dropwise n-butyl lithium (2.55 M n-hexane solution, 6.13 mL, 15.6 mmol) on a dry ice-ethanol bath (−78° C.) under nitrogen atmosphere, which was stirred for 40 minutes at −78° C. N,N-dimethylformamide (1.32 mL, 17.0 mmol) was then added dropwise and stirred for 5 minutes at −78° C. The reaction solution was cooled to room temperature and water was added, followed by extraction with ethyl acetate. The organic layer was washed with saturated aqueous sodium chloride, and the solvent was evaporated under a reduced pressure. The residue was purified by silica gel column chromatography (ethyl acetate:heptane=1:4) to obtain the title compound (1.00 g, 30.5%).

$^1$H-NMR Spectrum (CDCl$_3$) δ ppm): 5.25 (2H, s), 6.91-7.02 (4H, m), 7.71-7.75 (1H, m), 8.19-8.22 (1H, m), 9.04-9.05 (1H, m), 10.12 (1H, s).

Manufacturing Example 72-1-3

2-(4-Fluoro-phenoxymethyl)-5-(2-nitro-ethyl)-pyridine

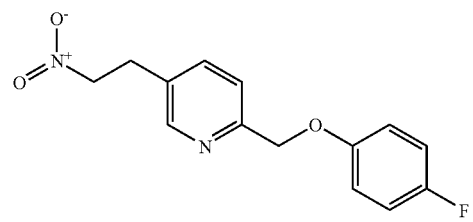

To an acetic acid (5.00 mL) solution of 6-(4-fluoro-phenoxymethyl)-pyridine-3-carbaldehyde (500 mg, 1.30 mmol) described in Manufacturing Example 72-1-2 were added nitromethane (923 mg, 15.1 mmol) and ammonium acetate (333 mg, 4.32 mmol) under nitrogen atmosphere, which was stirred for 2 hours at 105° C. Water and ethyl acetate were added to the reaction mixture, and the organic layer was extracted with ethyl acetate. The organic layer was washed with water and saturated aqueous sodium chloride, dried over anhydrous magnesium sulfate, and filtered. The solvent was evaporated from the filtrate under a reduced pressure. Dimethyl sulfoxide (10.0 mL) and acetic acid (600 μL) were added to the residue, and sodium borohydride (131 mg, 3.46 mmol) was then added at room temperature while cooling appropriately. Following 20 minutes of stirring, water was added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:1) to obtain the title compound (50 mg, 8.38%).

$^1$H-NMR Spectrum (DMSO-d$_6$) δ (ppm): 3.36 (2H, t, J=6.8 Hz), 4.96 (2H, t, J=6.8 Hz), 5.40 (2H, s), 7.01-7.05 (2H, m), 7.16-7.20 (2H, m), 7.84 (1H, d, J=8.0 Hz), 8.17 (1H, dd, J=2.0, 8.4 Hz), 8.75 (1H, s).

Example 73

3-(3-(4-Phenylaminomethyl-benzyl)-isoxazol-5-yl)-pyridin-2-ylamine

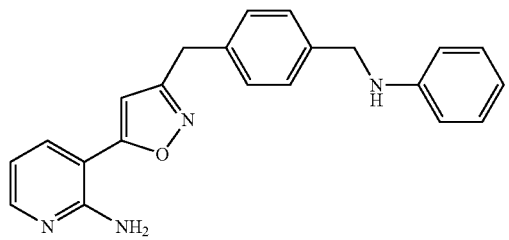

To a tetrahydrofuran (3 mL) solution of (4-phenylaminomethyl-phenyl)-acetohydroximoyl chloride (150 mg, 0.546 mmol) described in Manufacturing Example 73-1-6 and 3-ethynyl-pyridin-2-ylamine (41 mg, 0.348 mmol) described in Manufacturing Example 1-2-3 was added triethylamine (104 μL, 0.748 mmol), which was stirred for 7 hours at room temperature. Water was added to the reaction solution at room temperature, which was then extracted with ethyl acetate. The organic layer was washed with water and saturated aqueous sodium chloride and dried over anhydrous magnesium sulfate, and the solvent was evaporated under a reduced pressure. The residue was purified by NH silica gel column chromatography (heptane:ethyl acetate=1:1-1:2) to obtain the title compound (11 mg, 6%).

$^1$H-NMR Spectrum (CDCl$_3$) δ (ppm): 4.05 (2H, s), 4.32 (2H, s), 5.39 (2H, brs), 6.26 (1H, s), 6.62-6.64 (2H, m), 6.69-6.74 (2H, m), 7.15-7.23 (5H, m), 7.34-7.36 (2H, m), 7.69-7.72 (1H, m), 8.13-8.15 (1H, m).

The starting material, (4-phenylaminomethyl-phenyl)-acetohydroximoyl chloride, was synthesized as follows.

Manufacturing Example 73-1-1

4-[1,3]Dioxolan-2-ylbenzaldehyde

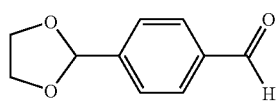

To a tetrahydrofuran (100 mL) solution of 2-(4-bromophenyl)-1,3-dioxolane (8 g, 34.9 mmol) was added dropwise n-butyl lithium (19.6 mL, 2.67 M hexane solution, 52.4 mmol) at −78° C. After 1 hour of stirring at −78° C., N-formylmorpholine (4.42 g, 38.4 mmol) was added to the mixture, and stirred for 3 hours at the same temperature. This mixture was partitioned into diethyl ether and water. The organic layer was separated, washed with saturated aqueous sodium chloride, dried over anhydrous magnesium sulfate, and filtered. The filtrate was concentrated under a reduced pressure to obtain the title compound (6.3 g). This compound was used in the subsequent reaction without being purified.

$^1$H-NMR Spectrum (CDCl$_3$) δ (ppm): 4.04-4.16 (4H, m), 5.89 (1H, s), 7.65-7.67 (2H, m), 7.90-7.92 (2H, m), 10.0 (1H, s).

Manufacturing Example 73-1-2

(4-[1,3]Dioxolane-2-yl-benzyl)-phenyl-amine

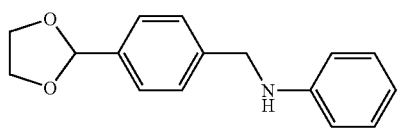

To a tetrahydrofuran (200 mL) solution of 4-[1,3]dioxolane-2-ylbenzaldehyde (6.32 g, 35.5 mmol) described in Manufacturing Example 73-1-1, aniline (2.08 mL, 35.5 mmol) and acetic acid (10.2 mL, 178 mmol) was added sodium triacetoxyborohydride (15 g, 71 mmol). This mixture was stirred for 1 hour at room temperature. This mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=4:1) to obtain the title compound (4.16 g, 46%).

$^1$H-NMR Spectrum (CDCl$_3$) δ (ppm): 4.02-4.15 (5H, m), 4.35 (2H, s), 5.81 (1H, s), 6.61-6.63 (2H, m), 6.69-6.73 (1H, m), 7.14-7.18 (2H, m), 7.38-7.40 (2H, m), 7.45-7.47 (2H, m).

Manufacturing Example 73-1-3

4-Phenylaminomethyl-benzaldehyde

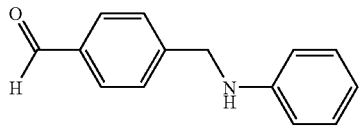

To a mixture solution of methanol and tetrahydrofuran (1:1, 20 mL) of (4-[1,3]dioxolane-2-yl-benzyl)-phenyl-amine (4.16 g, 16.3 mmol) described in Manufacturing Example 73-1-2 was added 5N hydrochloric acid (20 mL). This mixture was stirred for 1 hour at room temperature. This mixture was neutralized with saturated aqueous sodium hydrogencarbonate solution, and extracted with ethyl acetate.

The organic layer was separated, washed with water, dried over anhydrous magnesium sulfate, and filtered. The filtrate was concentrated under a reduced pressure to obtain the title compound (3.5 g). This compound was used in the subsequent reaction without being purified.

$^1$H-NMR Spectrum (CDCl$_3$) δ (ppm): 4.19 (1H, brs), 4.45 (2H, s), 6.59-6.62 (2H, m), 6.72-6.76 (1H, m), 7.15-7.20 (2H, m), 7.53-7.55 (2H, m), 7.84-7.87 (2H, m), 10.0 (1H, s).

Manufacturing Example 73-1-4

(4-((E)-2-nitro-vinyl)-benzyl)-phenyl-amine

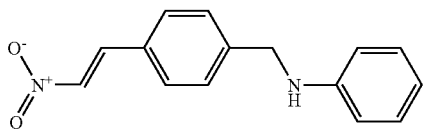

A mixture of 4-phenylaminomethyl-benzaldehyde (3.5 g, 16.6 mmol) described in Manufacturing Example 73-1-3, nitromethane (4.46 mL, 83 mmol), ammonium acetate (2.56 g, 33.2 mmol) and acetic acid (30 mL) was stirred for 4 hours at 100° C. This mixture was cooled to room temperature, concentrated under a reduced pressure, and diluted with ethyl acetate. The organic layer was washed with water and saturated aqueous sodium chloride, dried over anhydrous magnesium sulfate, and filtered. The filtrate was concentrated under a reduced pressure, and the residue was purified by silica gel column chromatography (heptane:ethyl acetate=10:1-4:1) to obtain the title compound (1.53 g, 36%).

$^1$H-NMR Spectrum (CDCl$_3$) δ (ppm): 4.16 (1H, brs), 4.42 (2H, m), 6.60-6.62 (2H, m), 6.72-6.76 (1H, m), 7.15-7.19 (2H, m), 7.45-7.47 (2H, m), 7.51-7.53 (2H, m), 7.58 (1H, d, J=13.6 Hz), 8.00 (1H, d, J=13.6 Hz).

Manufacturing Example 73-1-5

(4-(2-Nitro-ethyl)-benzyl)-phenyl-amine

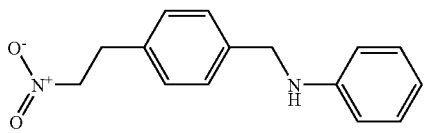

To an acetic acid (1.5 mL) and dimethyl sulfoxide (26 mL) solution of (4-((E)-2-nitro-vinyl)-benzyl)-phenyl-amine (1.53 g, 6.02 mmol) described in Manufacturing Example 73-1-4 was added sodium borohydride (364 mg, 9.63 mmol) at room temperature while cooling appropriately. This mixture was stirred for 1.5 hours at room temperature. This mixture was partitioned into ethyl acetate and water. The organic layer was separated, washed with water, dried over anhydrous magnesium sulfate, and filtered. The filtrate was concentrated under a reduced pressure to obtain the title compound (1.5 g). This compound was used in the subsequent reaction without being purified.

$^1$H-NMR Spectrum (CDCl$_3$) δ (ppm): 3.29-3.33 (2H, m), 4.32 (2H, s), 4.59-4.62 (2H, m), 6.61-6.63 (2H, m), 6.70-6.74 (1H, m), 7.15-7.20 (4H, m), 7.33-7.35 (2H, m).

Manufacturing Example 73-1-6

(4-Phenylaminomethyl-phenyl)-acetohydroximoyl chloride

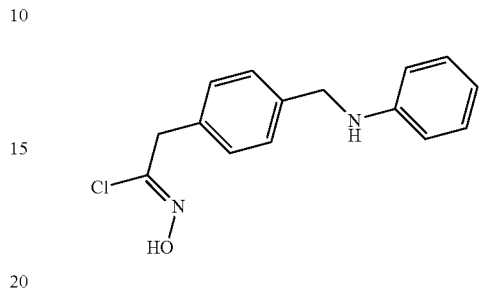

To a methanol (24 mL) solution of (4-(2-nitro-ethyl)-benzyl)-phenyl-amine (1.5 g, 5.66 mmol) described in Manufacturing Example 73-1-5 was added lithium methoxide (430 mg, 11.3 mmol). This mixture was stirred for 1 hour at room temperature. This mixture was concentrated under a reduced pressure, water in the residue was azeotropically distilled with toluene, and that residue was diluted with methylene chloride (25 mL) and tetrahydrofuran (12.5 mL). This was cooled to −78° C., and titanium (IV) tetrachloride (1.99 mL, 18.1 mmol) was added dropwise into the suspension. This mixture was stirred for 1 hour at room temperature. This mixture was cooled to −78° C. and partitioned into ethyl acetate and ice water. The organic layer was separated, washed with saturated aqueous sodium chloride, dried over anhydrous magnesium sulfate, and filtered. The filtrate was concentrated under a reduced pressure to obtain the title compound (1.5 g). This compound was used in the subsequent reaction without further purification.

Example 74

3-(3-(6-(2-Fluoro-phenoxy)-pyridin-3-ylmethyl)-isoxazol-5-yl)-pyridin-2-ylamine

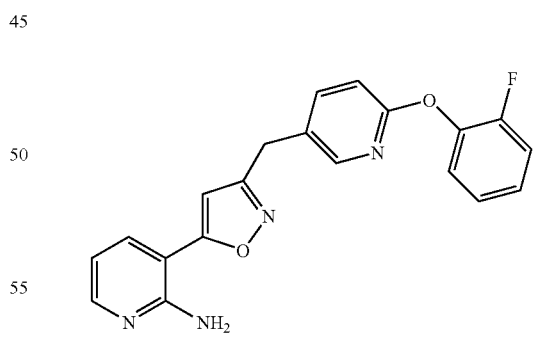

To a tetrahydrofuran (1 mL) solution of 3-ethynyl-pyridin-2-ylamine (9.0 mg, 0.076 mmol) described in Manufacturing Example 1-2-3 and (6-(2-fluoro-phenoxy)-pyridine-3-yl)-acetohydroximoyl chloride (28 mg) described in Manufacturing Example 74-1-4 was added triethylamine (21 μL, 0.15 mmol), which was stirred for 5 hours at 55° C. The mixture was cooled to room temperature and water was added at that temperature, followed by extraction with ethyl acetate. The organic layer was washed with saturated aqueous sodium chloride, and was concentrated under a reduced pressure. The residue was purified by NH silica gel column chromatography (ethyl acetate:heptane=2:1) to obtain the title compound as a crude product. This was then purified by reverse-phase high-performance liquid chromatography (using an acetonitrile-water mobile phase containing 0.1% trifluoracetic acid). Triethylamine was added to make the solvent basic when concentrating the mobile phase, and the eluate was concentrated under a reduced pressure. The resulting residue was washed with water to obtain the title compound (1.0 mg, 4%).

$^1$H-NMR Spectrum (CDCl$_3$) δ (ppm): 4.01 (2H, s), 5.53 (2H, brs), 6.27 (1H, s), 6.73 (1H, dd, J=4.9, 7.7 Hz), 6.98 (1H, d, J=8.4 Hz), 7.14-7.25 (4H, m), 7.63 (1H, dd, J=2.4, 8.4 Hz), 7.72 (1H, dd, J=1.8, 7.7 Hz), 8.09 (1H, d, J=2.4 Hz), 8.14 (1H, dd, J=1.9, 4.9 Hz).

The starting material, (6-(2-fluoro-phenoxy)-pyridin-3-yl)-acetohydroximoyl chloride, was synthesized as follows.

Manufacturing Example 74-1-1

5-Bromo-2-(2-fluoro-phenoxy)-pyridine

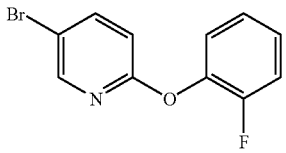

To a mixture of 2-fluorophenol (2.1 g, 19 mmol), 2,5-dibromopyridine (3.0 g, 13 mmol) and N,N-dimethylformamide (30 mL) was added sodium hydride (730 mg, 15 mmol, 50% in oil) at 0° C., which was stirred for 10 minutes at room temperature. The reaction mixture was then stirred for 5 hours at 110° C. The reaction mixture was cooled to room temperature and water was added, followed by extraction with ethyl acetate. The organic layer was washed twice with water and then washed with saturated aqueous sodium chloride, was concentrated under a reduced pressure. The residue was purified by NH silica gel column chromatography (heptane:ethyl acetate=15:1) to obtain the title compound (940 mg, 28%).

$^1$H-NMR Spectrum (CDCl$_3$) δ (ppm): 6.91-6.93 (1H, m), 7.16-7.24 (4H, m), 7.79 (1H, ddd, J=0.6, 2.6, 8.6 Hz), 8.17 (1H, dd, J=0.6, 2.6 Hz).

Manufacturing Example 74-1-2

6-(2-Fluoro-phenoxy)-pyridine-3-carbaldehyde

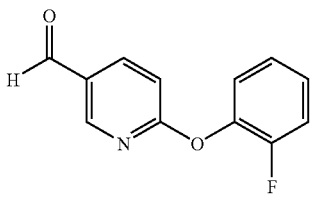

To a mixture of 5-bromo-2-(2-fluoro-phenoxy)-pyridine (500 mg, 1.9 mmol) described in Manufacturing Example 74-1-1 and tetrahydrofuran (7 mL) was added n-butyl lithium (1.7 mL, 1.5 M n-hexane solution, 2.6 mmol) under nitrogen atmosphere at −78° C. N,N-dimethylformamide (0.29 mL, 3.7 mmol) was added to the reaction mixture at the same temperature, and the temperature was then gradually raised to 0° C. Water was added to the reaction solution, which was then extracted with ethyl acetate. The organic layer was washed with saturated aqueous sodium chloride, and was concentrated under a reduced pressure. The residue was purified by silica gel column chromatography (heptane:ethyl acetate=2:1) to obtain the title compound (210 mg, 53%).

$^1$H-NMR Spectrum (CDCl$_3$) δ (ppm): 7.12-7.15 (1H, m), 7.20-7.31 (4H, m), 8.22 (1H, dd, J=2.4, 8.6 Hz), 8.60 (1H, dd, J=0.6, 2.4 Hz), 9.99 (1H, d, J=0.6 Hz).

Manufacturing Example 74-1-3

2-(2-Fluoro-phenoxy)-5-(2-nitro-ethyl)-pyridine

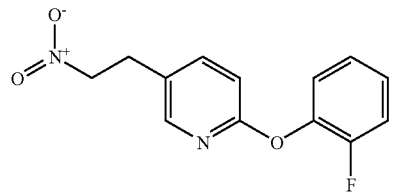

To a mixture of 6-(2-fluoro-phenoxy)-pyridine-3-carbaldehyde (210 mg, 0.97 mmol) described in Manufacturing Example 74-1-2 and acetic acid (3 mL) were added nitromethane (0.39 mL, 7.3 mmol) and ammonium acetate (220 mg, 2.9 mmol), which was stirred for 3 hours at 100° C. The reaction mixture was cooled to room temperature and water was added thereto, followed by extraction with ethyl acetate. The organic layer was washed with saturated aqueous sodium chloride and dried over anhydrous magnesium sulfate, and was concentrated under a reduced pressure. A mixture of dimethyl sulfoxide (3 mL) and acetic acid (0.2 mL) was added to the resulting residue, and sodium borohydride (58 mg, 1.5 mmol) was added to the reaction mixture at room temperature while cooling appropriately. The reaction mixture was stirred for 10 minutes. Water was added to the reaction solution at room temperature, which was then extracted with ethyl acetate. The organic layer was washed with saturated aqueous sodium chloride, and was concentrated under a reduced pressure. The residue was purified by NH silica gel column chromatography (heptane:ethyl acetate=2:1) to obtain the title compound (150 mg, 61%).

$^1$H-NMR Spectrum (CDCl$_3$) δ (ppm): 3.28 (2H, t, J=7.1 Hz), 4.59 (2H, t, J=7.1 Hz), 6.97 (1H, d, J=8.4 Hz), 7.15-7.24 (4H, m), 7.57 (1H, dd, J=2.6, 8.4 Hz), 8.00 (1H, d, J=2.6 Hz).

Manufacturing Example 74-1-4

(6-(2-Fluoro-phenoxy)-pyridin-3-yl)-acetohydroximoyl chloride

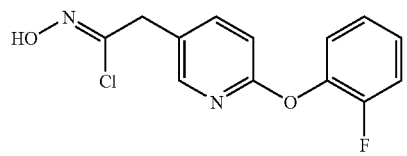

To a mixture of 2-(2-fluoro-phenoxy)-5-(2-nitro-ethyl)-pyridine (150 mg, 0.59 mmol) described in Manufacturing Example 74-1-3 and methanol (1.5 mL) was added lithium methoxide (45 mg, 1.2 mmol) at room temperature, which was stirred for 5 minutes at room temperature. The solvent was evaporated from the reaction mixture under a reduced pressure. Titanium (IV) chloride (140 μL, 1.3 mmol) was added at −78° C. to a mixture of the resulting residue, methylene chloride (2 mL) and tetrahydrofuran (1 mL), and stirred for 80 minutes at 0° C. The reaction mixture was cooled to −78° C., water (1 mL) was added, and the temperature was gradually raised to room temperature. Water was added to the reaction solution at room temperature, which was then extracted with ethyl acetate. The organic layer was washed with water until the pH was 5, and then washed with saturated aqueous sodium chloride. The organic layer was dried over anhydrous magnesium sulfate, and was concentrated under a reduced pressure to obtain the title compound (160 mg) as a crude product. This compound was used in the subsequent reaction without further purification.

$^1$H-NMR Spectrum (CDCl$_3$) δ (ppm): 3.74 (2H, s), 6.97 (1H, d, J=8.4 Hz), 7.15-7.25 (4H, m), 7.63 (1H, dd, J=2.4, 8.4 Hz), 8.04 (1H, d, J=2.0 Hz).

Example 75

3-(3-(6-(4-Fluoro-phenoxy)-pyridin-3-ylmethyl)-isoxazol-5-yl)-pyridin-2-ylamine

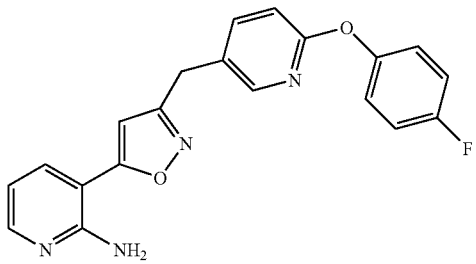

To a mixture of (6-(4-fluoro-phenoxy)-pyridin-3-yl)-acetohydroximoyl chloride (25 mg) described in Manufacturing Example 75-1-4 and tetrahydrofuran (1 mL) were added 3-ethynyl-pyridin-2-ylamine (6.0 mg, 0.051 mmol) described in Manufacturing Example 1-2-3 and triethylamine (21 μL, 0.15 mmol), which was stirred for 5 hours at 55° C. The reaction mixture was cooled to room temperature and water was added thereto at that temperature, followed by extraction with ethyl acetate. The organic layer was washed with saturated aqueous sodium chloride, and was concentrated under a reduced pressure. The residue was purified by NH silica gel column chromatography (ethyl acetate:heptane=2:1) to obtain the title compound (5.9 mg, 32%).

$^1$H-NMR Spectrum (CDCl$_3$) δ (ppm): 4.02 (2H, s), 5.41 (2H, br s), 6.27 (1H, s), 6.73 (1H, dd, J=4.8, 7.7 Hz), 6.90 (1H, d, J=8.4 Hz), 7.06-7.12 (4H, m), 7.62 (1H, dd, J=2.6, 8.4 Hz), 7.71 (1H, dd, J=1.7, 7.6 Hz), 8.13 (1H, d, J=2.6 Hz), 8.16 (1H, dd, J=1.7, 4.9 Hz).

The starting material, (6-(4-fluoro-phenoxy)-pyridin-3-yl)-acetohydroximoyl chloride, was synthesized as follows.

Manufacturing Example 75-1-1

5-Bromo-2-(4-fluoro-phenoxy)-pyridine

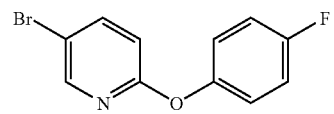

To a mixture of 4-fluorophenol (2.1 g, 19 mmol), 2,5-dibromopyridine (3.0 g, 13 mmol) and N,N-dimethylformamide (30 mL) was added sodium hydride (730 mg, 15 mmol, 50% in oil) at 0° C., which was stirred for 10 minutes at room temperature. The reaction mixture was then stirred for 5 hours at 110° C. The reaction mixture was cooled to room temperature and water was added thereto, followed by extraction with ethyl acetate. The organic layer was washed with water twice, and then washed with saturated aqueous sodium chloride, and was concentrated under a reduced pressure, and the residue was purified by NH silica gel column chromatography (heptane:ethyl acetate=15:1) to obtain the title compound (2.6 g, 75%).

$^1$H-NMR Spectrum (CDCl$_3$) δ (ppm): 6.83-6.85 (1H, m), 7.09 (4H, d, J=6.4 Hz), 7.76-7.79 (1H, m), 8.20 (1H, dd, J=0.6, 2.6 Hz).

Manufacturing Example 75-1-2

6-(4-Fluoro-phenoxy)-pyridine-3-carbaldehyde

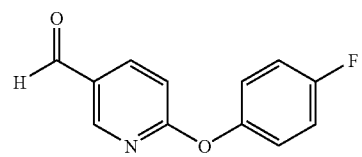

To a mixture of 5-bromo-2-(4-fluoro-phenoxy)-pyridine (940 mg, 3.5 mmol) described in Manufacturing Example 75-1-1 and tetrahydrofuran (10 mL) was added n-butyl lithium (1.7 mL, 1.5 M n-hexane solution, 2.6 mmol) under nitrogen atmosphere at −78° C., which was stirred for 30 minutes at that temperature. N,N-dimethylformamide (0.54 mL, 7.0 mmol) was added to the reaction mixture at the same temperature, and the temperature was gradually raised to 0° C. Water was added to the reaction solution, which was then extracted with ethyl acetate. The organic layer was washed with saturated aqueous sodium chloride, and was concentrated under a reduced pressure. The residue was purified by silica gel column chromatography (heptane:ethyl acetate=2:1) to obtain the title compound (280 mg, 36%).

$^1$H-NMR Spectrum (CDCl$_3$) δ (ppm): 7.04-7.06 (1H, m), 7.13-7.15 (4H, m), 8.20 (1H, ddd, J=0.9, 2.4, 8.6 Hz), 8.61 (1H, dd, J=0.6, 2.4 Hz), 9.99 (1H, d, J=0.6 Hz).

Manufacturing Example 75-1-3

2-(4-Fluoro-phenoxy)-5-(2-nitro-ethyl)-pyridine

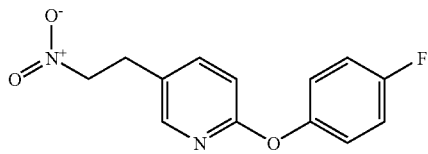

To a mixture of 6-(4-fluoro-phenoxy)-pyridine-3-carbaldehyde (150 mg, 0.69 mmol) described in Manufacturing Example 75-1-2 and acetic acid (2 mL) were added nitromethane (0.28 mL, 5.2 mmol) and ammonium acetate (160 mg, 2.1 mmol), which was stirred for 3 hours at 100° C. The reaction mixture was cooled to room temperature and water was added thereto, followed by extraction with ethyl acetate. The organic layer was washed with saturated aqueous sodium chloride and dried over anhydrous magnesium sulfate, and was concentrated under a reduced pressure. A mixture of dimethyl sulfoxide (3 mL) and acetic acid (0.2 mL) was added to the resulting residue, and sodium borohydride (42 mg, 1.1 mmol) was added at room temperature while cooling appropriately. The reaction mixture was stirred for 10 minutes at that temperature. Water was added at room temperature to the reaction solution at room temperature, which was then extracted with ethyl acetate. The organic layer was washed with saturated aqueous sodium chloride, and was concentrated under a reduced pressure. The residue was purified by NH silica gel column chromatography (heptane:ethyl acetate=1:1) to obtain the title compound (130 mg, 70%).

$^1$H-NMR Spectrum (CDCl$_3$) δ (ppm): 3.28 (2H, t, J=7.1 Hz), 4.60 (2H, t, J=7.1 Hz), 6.89 (1H, dd, J=0.4, 8.4 Hz), 7.09 (4H, d, J=6.4 Hz), 7.55 (1H, dd, J=2.6, 8.4 Hz), 8.03 (1H, d, J=2.2 Hz).

Manufacturing Example 75-1-4

(6-(4-Fluoro-phenoxy)-pyridin-3-yl)-acetohydroximoyl chloride

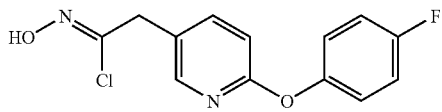

To a mixture of 2-(4-fluoro-phenoxy)-5-(2-nitro-ethyl)-pyridine (120 mg, 0.46 mmol) described in Manufacturing Example 75-1-3 and methanol (2 mL) was added lithium methoxide (35 mg, 0.91 mmol) at room temperature, which was stirred for 5 minutes at room temperature. The reaction mixture was concentrated under a reduced pressure. A mixture of methylene chloride (2 mL) and tetrahydrofuran (1 mL) was added to the residue, and titanium (IV) chloride (110 µL, 1.0 mmol) was added to the reaction mixture at −78° C. and stirred for 100 minutes at 0° C. The reaction mixture was cooled to 0° C., water (1 mL) was added, and the temperature was gradually raised to room temperature. Water was added to the reaction solution, which was then extracted with ethyl acetate. The organic layer was washed with water until the pH was 5, and then washed with saturated aqueous sodium chloride. The organic layer was dried over anhydrous magnesium sulfate, and was concentrated under a reduced pressure to obtain the title compound (130 mg) as a crude product. This compound was used in the subsequent reaction without further purification.

Example 76

3-(3-(4-(Pyridin-3-yloxy)-benzyl)-isoxazol-5-yl)-pyridin-2-ylamine

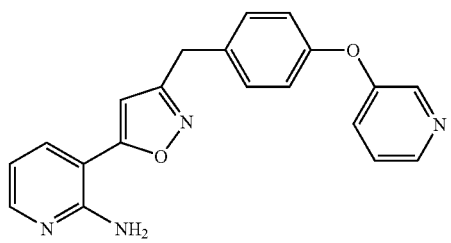

To a methanol (10.0 mL) solution of 3-(4-(2-nitro-ethyl)-phenoxy)-pyridine (819 mg, 3.35 mmol) described in Manufacturing Example 76-1-3 was added lithium methoxide (254 mg, 6.70 mmol) under nitrogen atmosphere at room temperature, which was stirred for 30 minutes at room temperature. The solvent was evaporated from the reaction mixture under a reduced pressure, and anhydrous dichloromethane (15.0 ml) and anhydrous tetrahydrofuran (7.00 mL) were added to the residue. Titanium (IV) chloride (1.18 mL, 10.7 mmol) was added dropwise to the reaction mixture on a dry ice-ethanol bath (−78° C.), and stirred for 30 minutes at room temperature. Sodium bicarbonate solution and ethyl acetate were added to the reaction mixture on an ice bath (0° C.), which was then filtered through a Celite pad. The organic layer of the filtrate was extracted with ethyl acetate, and that organic layer was washed with water and saturated aqueous sodium chloride, dried over anhydrous magnesium sulfate, and filtered. The filtrate was concentrated under a reduced pressure to obtain a crude product (400 mg). To a tetrahydrofuran (5.00 mL) solution of this crude product (250 mg) and 3-ethynyl-pyridin-2-ylamine described in Manufacturing Example 1-2-3 (40.0 mg, 0.339 mmol) was added triethylamine (142 µL, 1.02 mmol) at room temperature, which was stirred for 3 hours at 60° C. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1:1), the mixture was further purified by reverse-phase high-performance liquid chromatography (using an acetonitrile-water mobile phase containing 0.1% trifluoroacetic acid) to obtain the title compound (11.7 mg, 10.0%) as a ditrifluoracetic acid salt.

MS m/e (ESI) 345.13 (MH$^+$)

$^1$H-NMR Spectrum (CD$_3$OD) δ (ppm): 4.17 (2H, s), 6.89 (1H, s), 7.06-7.10 (1H, m), 7.19-7.22 (2H, m), 7.48-8.50 (2H, m), 7.94-7.98 (1H, m), 8.04-8.06 (1H, m), 8.08-8.11 (1H, m), 8.37-8.39 (1H, m), 8.55 (1H, d, J=5.6 Hz), 8.60 (1H, d, J=2.8 Hz).

The starting material, 3-(4-(2-nitro-ethyl)phenoxy)-pyridine, was synthesized as follows.

Manufacturing Example 76-1-1

4-(Pyridine-3-yloxy)-benzaldehyde

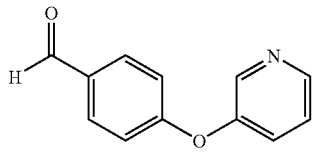

To an N,N-dimethylformamide (30.0 mL) solution of 3-hydroxypyridine (3.00 g, 31.5 mmol) and 4-fluorobenzaldehyde (5.08 g, 41.0 mmol) was added potassium carbonate (8.71 g, 63.0 mmol) under nitrogen atmosphere, which was stirred for 17 hours at 70° C. The reaction mixture was then cooled to room temperature and water was added thereto, followed by extraction with ethyl acetate. The organic layer was washed with saturated aqueous sodium chloride, and the solvent was evaporated under a reduced pressure. The residue was purified by silica gel column chromatography (ethyl acetate:heptane=1:1→3:1) to obtain the title compound (1.70 g, 27.1%).

$^1$H-NMR Spectrum (CDCl$_3$) δ (ppm): 7.09-7.11 (2H, s), 7.35-7.39 (1H, m), 7.41-7.44 (1H, m), 7.88-7.91 (2H, m), 8.48-8.51 (2H, m), 9.96 (1H, s).

Manufacturing Example 76-1-2

3-(4-((E)-2-Nitro-vinyl)-phenoxy)-pyridine

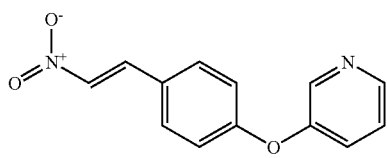

To an acetic acid (17.0 mL) solution of 4-(pyridine-3-yloxy)-benzaldehyde (1.70 g, 8.53 mmol) described in Manufacturing Example 76-1-1 were added nitromethane (2.60 g, 42.7 mmol) and ammonium acetate (1.32 g, 17.1 mmol) under nitrogen atmosphere, which was stirred for 3 hours at 110° C. Water and ethyl acetate were added to the reaction solution, and the organic layer was then extracted with ethyl acetate. The organic layer was washed with water and saturated aqueous sodium chloride, dried over anhydrous magnesium sulfate, and filtered. The filtrate was concentrated under a reduced pressure to obtain the title compound (2.00 g) as a crude product.

$^1$H-NMR Spectrum (DMSO-d$_6$) δ (ppm): 7.12-7.14 (2H, m), 7.48-7.51 (1H, m), 7.57-7.61 (1H, m), 7.91-7.94 (2H, m), 8.16-8.19 (2H, m), 8.46-8.47 (2H, m).

Manufacturing Example 76-1-3

3-(4-(2-Nitro-ethyl)-phenoxy)-pyridine

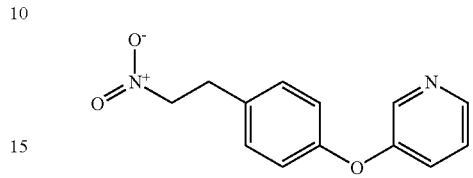

To a dimethyl sulfoxide (15.0 mL) solution of 3-(4-((E)-2-nitro-vinyl)-phenoxy)-pyridine (2.00 g, 8.26 mmol) described in Manufacturing Example 76-1-2 and acetic acid (2.00 mL) was added sodium borohydride (500 mg, 13.2 mmol) at room temperature while cooling appropriately under nitrogen atmosphere, which was stirred for 30 minutes at room temperature. Water was then added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:3→1:2) to obtain the title compound (819 mg, 40.6%).

$^1$H-NMR Spectrum (DMSO-d$_6$) δ (ppm): 3.26 (2H, t, J=6.8 Hz), 4.88 (2H, t, J=6.8 Hz), 7.17 (2H, d, J=8.4 Hz), 7.40 (2H, d, J=8.4 Hz), 7.68-7.76 (2H, m), 8.23 (1H, s), 8.35 (1H, d, J=5.2 Hz).

Example 77

3-(3-(4-(Thiophen-3-ylmethoxy)-benzyl)-isoxazol-5-yl)-pyridin-2-ylamine

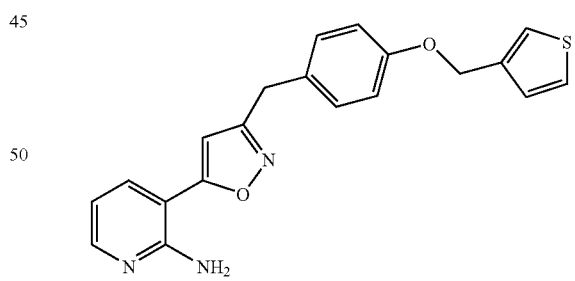

To a tetrahydrofuran (3 mL) solution of (4-(thiophen-3-ylmethoxy)-phenyl)-acetohydroximoyl chloride (150 mg, 0.532 mmol) described in Manufacturing Example 77-1-4 and 3-ethynyl-pyridin-2-ylamine (40 mg, 0.339 mmol) described in Manufacturing Example 1-2-3 was added triethylamine (185 μL, 1.33 mmol), which was stirred for 3 hours at 50° C. Water was added to the reaction solution at room temperature, which was then extracted with ethyl acetate. The organic layer was washed with water and saturated aqueous sodium chloride and dried over anhydrous magnesium sulfate, and the solvent was evaporated under a reduced pressure. The residue was purified by NH silica gel column chromatography (heptane:ethyl acetate=4:1-2:1-1:1) to obtain the title compound (46 mg, 24%).

¹H-NMR Spectrum (CDCl₃) δ (ppm): 4.00 (2H, s), 5.06 (2H, s), 5.41 (2H, brs), 6.24 (1H, s), 6.69-6.72 (1H, m), 6.93-6.95 (2H, m), 7.14-7.15 (1H, m), 7.19-7.22 (2H, m), 7.31-7.35 (2H, m), 7.69-7.71 (1H, m), 8.13-8.14 (1H, m).

The starting material, (4-(thiophen-3-ylmethoxy)-phenyl)-acetohydroximoyl chloride, was synthesized as follows.

Manufacturing Example 77-1-1

4-(Thiophen-3-ylmethoxy)-benzaldehyde

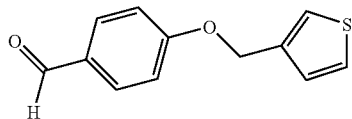

To a tetrahydrofuran (250 mL) solution of diethylazodicarboxylate (16.1 mL, 40.9 mmol) were added 4-hydroxybenzaldehyde (5 g, 40.9 mmol), 3-thiophene methanol (3.86 mL, 40.9 mmol) and PS-triphenylphosphine (29 g, 1.41 mmol/g, 40.9 mmol). This mixture was stirred for 7 hours at room temperature. This mixture was concentrated under a reduced pressure, and the residue was purified by silica gel column chromatography (heptane:ethyl acetate=2:1) to obtain the title compound (3.61 g, 40%).

¹H-NMR Spectrum (CDCl₃) δ (ppm): 5.17 (2H, s), 7.07-7.09 (2H, m), 7.15-7.17 (1H, m), 7.35-7.39 (2H, m), 7.84-7.86 (2H, m), 9.90 (1H, s).

Manufacturing Example 77-1-2

3-(4-((E)-2-Nitro-vinyl)-phenoxymethyl)-thiophene

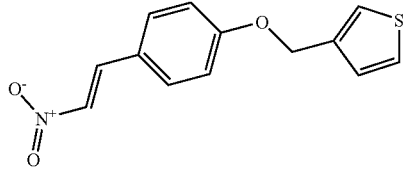

A mixture of 4-(thiophen-3-ylmethoxy)-benzaldehyde (3.61 g, 16.5 mmol) described in Manufacturing Example 77-1-1, nitromethane (4.44 mL, 82.5 mmol), ammonium acetate (2.54 g, 33 mmol) and acetic acid (36 mL) was stirred for 5 hours at 100° C. This mixture was cooled to room temperature, concentrated under a reduced pressure, and diluted with ethyl acetate. The organic layer was washed with water and saturated aqueous sodium chloride, dried over anhydrous magnesium sulfate, and filtered. The filtrate was concentrated under a reduced pressure to obtain the title compound (4.1 g).

¹H-NMR Spectrum (CDCl₃) δ (ppm): 5.14 (2H, s), 7.01-7.03 (2H, m), 7.14-7.16 (1H, m), 7.34-7.35 (1H, m), 7.37-7.39 (1H, m), 7.50-7.54 (3H, m), 7.96-8.00 (1H, m).

Manufacturing Example 77-1-3

3-(4-(2-Nitro-ethyl)-phenoxymethyl)-thiophene

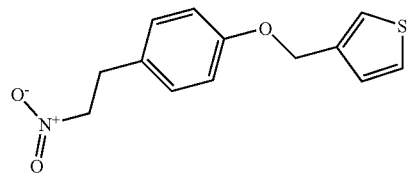

To an acetic acid (4.1 mL) and dimethyl sulfoxide (70 mL) solution of 3-(4-((E)-2-nitro-vinyl)-phenoxymethyl)-thiophene (4.1 g, 15.7 mmol) described in Manufacturing Example 77-1-2 was added sodium borohydride (950 mg, 25.1 mmol) at room temperature while cooling appropriately. This mixture was stirred for 1.5 hours at room temperature. The mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=4:1-2:1) to obtain the title compound (1.93 g, 47%).

¹H-NMR Spectrum (CDCl₃) δ (ppm): 3.24-3.28 (2H, m), 4.55-4.59 (2H, m), 5.05 (2H, s), 6.91-6.93 (2H, m), 7.11-7.15 (3H, m), 7.31-7.32 (1H, m), 7.34-7.36 (1H, m).

Manufacturing Example 77-1-4

(4-(Thiophen-3-ylmethoxy)-phenyl)-acetohydroximoyl chloride

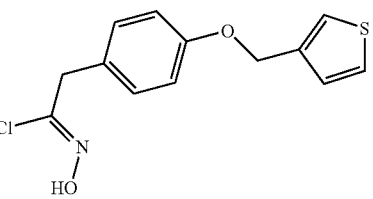

To a methanol (12 mL) solution of 3-(4-(2-nitro-ethyl)-phenoxymethyl)-thiophene (1 g, 3.8 mmol) described in Manufacturing Example 77-1-3 was added lithium methoxide (289 mg, 7.6 mmol). This mixture was stirred for 1.5 hours at room temperature. The mixture was concentrated under a reduced pressure, water in the residue was azeotropically distilled with toluene, and that residue was diluted with methylene chloride (16 mL) and tetrahydrofuran (8 mL). This was cooled to −78° C., and titanium (IV) tetrachloride (1.34 mL, 12.2 mmol) was added dropwise into the suspension. This mixture was stirred for 1 hour at room temperature. This mixture was cooled to −78° C. and partitioned into ethyl acetate and ice water. The organic layer was separated, washed with saturated aqueous sodium chloride, dried over anhydrous magnesium sulfate, and filtered. The filtrate was concentrated under a reduced pressure to obtain the title compound (1.1 g). This compound was used in the subsequent reaction without further purification.

Manufacturing Example 78

3-(3-(4-Cyclopentyloxy-benzyl)-isoxazol-5-yl)-pyridin-2-ylamine

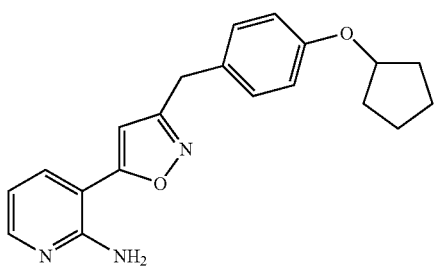

To a tetrahydrofuran (3 mL) solution of (4-cyclopentyloxy-phenyl)-acetohydroximoyl chloride (150 mg, 0.592 mmol) described in Manufacturing Example 78-1-4 and 3-ethynyl-pyridin-2-ylamine described in Manufacturing Example 1-2-3 (45 mg, 0.378 mmol) was added triethylamine (206 μL, 1.48 mmol), which was stirred for 3 hours at 50° C. Water was added to the reaction solution at room temperature, which was then extracted with ethyl acetate. The organic layer was washed with water and saturated aqueous sodium chloride and dried over anhydrous magnesium sulfate, and the solvent was evaporated under a reduced pressure. The residue was purified by NH silica gel column chromatography (heptane:ethyl acetate=4:1-2:1) to obtain the title compound (44 mg, 22%).

$^1$H-NMR Spectrum (CDCl$_3$) δ (ppm): 1.57-1.75 (2H, m), 1.75-1.92 (6H, m), 3.98 (2H, s), 4.71-4.75 (1H, m), 5.39 (2H, brs), 6.24 (1H, s), 6.69-6.72 (1H, m), 6.82-6.85 (2H, m), 7.16-7.18 (2H, m), 7.69-7.71 (1H, m), 8.12-8.14 (1H, m).

The starting material, (4-cyclopentyloxy-phenyl)-acetohydroximoyl chloride, was synthesized as follows.

Manufacturing Example 78-1-1

4-Cyclopentyloxy-benzaldehyde

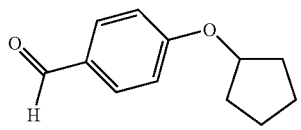

To a tetrahydrofuran (250 mL) solution of diethylazodicarboxylate (16.1 mL, 40.9 mmol) were added 4-hydroxybenzaldehyde (5 g, 40.9 mmol), cyclopentanol (3.71 mL, 40.9 mmol) and triphenylphosphine (10.7 g, 40.9 mmol). This mixture was stirred for 30 minutes at room temperature. The mixture was concentrated under a reduced pressure, and the residue was purified by silica gel column chromatography (heptane:ethyl acetate=2:1) to obtain the title compound (4.36 g, 56%).

$^1$H-NMR Spectrum (CDCl$_3$) δ (ppm): 1.61-1.70 (2H, m), 1.77-2.00 (6H, m), 4.84-4.87 (1H, m), 6.95-6.98 (2H, m), 7.80-7.83 (2H, m), 9.87 (1H, s).

Manufacturing Example 78-1-2

1-Cyclopentyloxy-4-((E)-2-nitro-vinyl-benzene

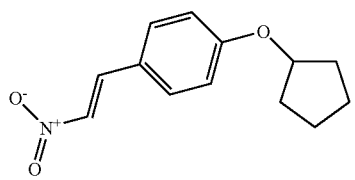

A mixture of 4-cyclopentyloxy-benzaldehyde (4.36 g, 22.9 mmol) described in Manufacturing Example 78-1-1, nitromethane (6.16 mL, 115 mmol), ammonium acetate (3.53 g, 33 mmol) and acetic acid (45 mL) was stirred for 14 hours at 100° C. This mixture was cooled to room temperature, concentrated under a reduced pressure, and diluted with ethyl acetate. The organic layer was washed with water and saturated aqueous sodium chloride, dried over anhydrous magnesium sulfate, and filtered. The filtrate was concentrated under a reduced pressure to obtain the title compound (4.8 g).

$^1$H-NMR Spectrum (CDCl$_3$) δ (ppm): 1.61-1.66 (2H, m), 1.78-1.97 (6H, m), 4.80-4.84 (1H, m), 6.90-6.93 (2H, m), 7.46-7.53 (3H, m), 7.96-7.99 (1H, m).

Manufacturing Example 78-1-3

1-Cyclopentyloxy-4-(2-nitro-ethyl)-benzene

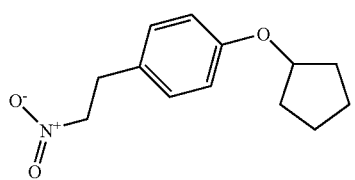

To an acetic acid (4.8 mL) and dimethyl sulfoxide (82 mL) solution of 1-cyclopentyloxy-4-((E)-2-nitro-vinyl-benzene (4.8 g, 20.4 mmol) described in Manufacturing Example 78-1-2 was added sodium borohydride (1.23 g, 32.6 mmol) at room temperature while cooling appropriately. The mixture was stirred for 1.5 hours at room temperature. This mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=4:1-2:1) to obtain the title compound (3.24 g, 68%).

$^1$H-NMR Spectrum (CDCl$_3$) δ (ppm): 1.59-1.65 (2H, m), 1.76-1.92 (6H, m), 3.23-3.27 (2H, m), 4.55-4.58 (2H, m), 4.70-4.74 (1H, m), 6.80-6.84 (2H, m), 7.07-7.11 (2H, m).

Manufacturing Example 78-1-4

(4-Cyclopentyloxy-phenyl)-acetohydroximoyl chloride

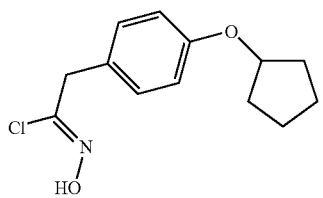

To a methanol (12 mL) solution of 1-cyclopentyloxy-4-(2-nitro-ethyl)-benzene (1 g, 4.26 mmol) described in Manufacturing Example 78-1-3 was added lithium methoxide (356 mg, 9.37 mmol). This mixture was stirred for 1.5 hours at room temperature. The mixture was concentrated under a reduced pressure, water in the residue was azeotropically distilled with toluene, and that residue was diluted with methylene chloride (16 mL) and tetrahydrofuran (8 mL). This was cooled to −78° C., and titanium (IV) tetrachloride (1.03 mL, 9.37 mmol) was added dropwise into the suspension. This mixture was stirred for 1 hour at room temperature. This mixture was cooled to −78° C. and partitioned into ethyl acetate and ice water. The organic layer was separated, washed with saturated aqueous sodium chloride, dried over anhydrous magnesium sulfate, and filtered. The filtrate was concentrated under a reduced pressure to obtain the title compound (1.1 g). This compound was used in the subsequent reaction without further purification.

Example 79

3-(3-(4-Cyclohexyloxy-benzyl)-isoxazol-5-yl)-pyridin-2-ylamine

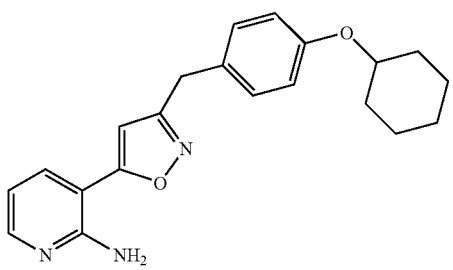

To a tetrahydrofuran (3 mL) solution of (4-cyclohexyloxy-phenyl)-acetohydroximoyl chloride (150 mg, 0.56 mmol) described in Manufacturing Example 79-1-4 and 3-ethynyl-pyridin-2-ylamine (42 mg, 0.357 mmol) described in Manufacturing Example 1-2-3 was added triethylamine (195 µL, 1.4 mmol), which was stirred for 4 hours at 50° C. Water was added to the reaction solution at room temperature, which was then extracted with ethyl acetate. The organic layer was washed with water and saturated aqueous sodium chloride and dried over anhydrous magnesium sulfate, and the solvent was evaporated under a reduced pressure. The residue was purified by NH silica gel column chromatography (heptane:ethyl acetate=4:1-2:1) to obtain the title compound (37 mg, 19%).

$^1$H-NMR Spectrum (CDCl$_3$) δ (ppm): 1.29-1.41 (3H, m), 1.47-1.56 (3H, m), 1.79-1.80 (2H, m), 1.96-1.99 (2H, m), 3.99 (2H, s), 4.18-4.24 (1H, m), 5.38 (2H, brs), 6.25 (1H, s), 6.69-6.72 (1H, m), 6.85-6.88 (2H, m), 7.12-7.18 (2H, m), 7.69-7.71 (1H, m), 8.13-8.14 (1H, m).

The starting material, (4-cyclohexyloxy-phenyl)-acetohydroximoyl chloride, was synthesized as follows.

Manufacturing Example 79-1-1

4-Cyclohexyloxy-benzaldehyde

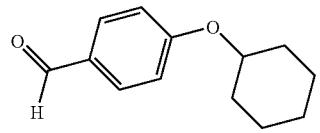

To a tetrahydrofuran (250 mL) solution of diethylazodicarboxylate (16.1 mL, 40.9 mmol) were added 4-hydroxybenzaldehyde (5 g, 40.9 mmol), cyclohexanol (4.31 mL, 40.9 mmol) and triphenylphosphine (10.7 g, 40.9 mmol). This mixture was stirred for 30 hours at room temperature. The mixture was concentrated under a reduced pressure, and the residue was purified by silica gel column chromatography (heptane:ethyl acetate=2:1) to obtain the title compound (2.84 g, 34%).

$^1$H-NMR Spectrum (CDCl$_3$) δ (ppm): 1.31-1.46 (4H, m), 1.53-1.63 (2H, m), 1.80-1.86 (2H, m), 1.98-2.02 (2H, m), 4.35-4.41 (1H, m), 6.97-7.00 (2H, m), 7.80-7.84 (2H, m), 9.87 (1H, s).

Manufacturing Example 79-1-2

1-Cyclohexyloxy-4-((E)-2-nitro-vinyl)-benzene

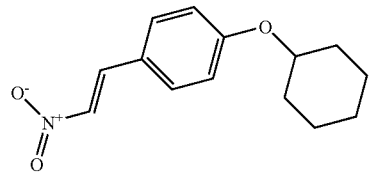

A mixture of 4-cyclohexyloxy-benzaldehyde (2.84 g, 13.9 mmol) described in Manufacturing Example 79-1-1, nitromethane (3.74 mL, 69.5 mmol), ammonium acetate (2.14 g, 27.8 mmol) and acetic acid (30 mL) was stirred for 14 hours at 100° C. This mixture was cooled to room temperature, concentrated under a reduced pressure, and diluted with ethyl acetate. The organic layer was washed with saturated aqueous sodium chloride, dried over anhydrous magnesium sulfate, and filtered. The filtrate was concentrated under a reduced pressure to obtain the title compound (3.3 g).

$^1$H-NMR Spectrum (CDCl$_3$) δ (ppm): 1.34-1.45 (3H, m), 1.51-1.61 (3H, m), 1.80-1.82 (2H, m), 1.98-2.00 (2H, m), 4.31-4.36 (1H, m), 6.91-6.95 (2H, m), 7.45-7.50 (2H, m), 7.53-7.57 (1H, m), 7.96-7.99 (1H, m).

Manufacturing Example 79-1-3

1-Cyclohexyloxy-4-(2-nitro-ethyl)-benzene

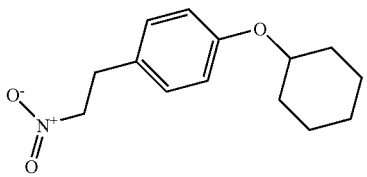

To an acetic acid (3.3 mL) and dimethyl sulfoxide (55 mL) solution of 1-cyclohexyloxy-4-((E)-2-nitro-vinyl)-benzene (3.3 g, 13.1 mmol) described in Manufacturing Example 79-1-2 was added sodium borohydride (793 mg, 21 mmol) at room temperature while cooling appropriately. This mixture was stirred for 1 hour at room temperature. This mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=4:1) to obtain the title compound (1.45 g, 44%).

$^1$H-NMR Spectrum (CDCl$_3$) δ (ppm): 1.26-1.43 (3H, m), 1.46-1.58 (3H, m), 1.79-1.81 (2H, m), 1.95-1.98 (2H, m), 3.23-3.27 (2H, m), 4.17-4.24 (1H, m), 4.55-4.58 (2H, m), 6.83-6.87 (2H, m), 7.08-7.10 (2H, m).

Manufacturing Example 79-1-4

(4-Cyclohexyloxy-phenyl)-acetohydroximoyl chloride

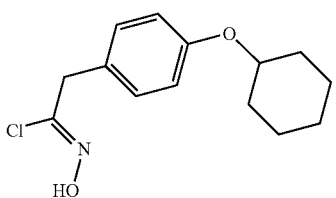

To a methanol (17 mL) solution of 1-cyclohexyloxy-4-(2-nitro-ethyl)-benzene (1.45 g, 5.82 mmol) described in Manufacturing Example 79-1-3 was added lithium methoxide (442 mg, 11.6 mmol). This mixture was stirred for 2 hours at room temperature. The mixture was concentrated under a reduced pressure, water in the residue was azeotropically distilled with toluene, and that residue was diluted with methylene chloride (24 mL) and tetrahydrofuran (12 mL). This was cooled to −78° C., and titanium (IV) tetrachloride (1.41 mL, 12.8 mmol) was added dropwise into the suspension. This mixture was stirred for 1.5 hours at room temperature. This mixture was cooled to −78° C. and partitioned into ethyl acetate and ice water. The organic layer was separated, washed with saturated aqueous sodium chloride, dried over anhydrous magnesium sulfate, and filtered. The filtrate was concentrated under a reduced pressure to obtain the title compound (1.5 g). This compound was used in the subsequent reaction without further purification.

Example 80

3-(3-(4-(2-Furan-2-yl-ethyl)-benzyl)-isoxazol-5-yl)-pyridin-2-ylamine

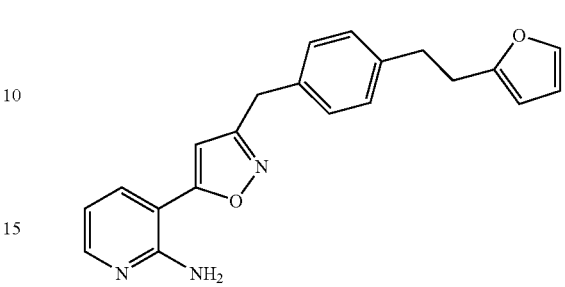

To an anhydrous tetrahydrofuran (5 mL) solution of 3-ethynyl-pyridin-2-ylamine (33.1 mg, 0.281 mmol) described in Manufacturing Example 1-2-3 was added (4-(2-furan-2-yl-ethyl) phenyl)-acetohydroximoyl chloride (224 mg, 0.85 mmol) described in Manufacturing Example 80-1-7 under nitrogen atmosphere at room temperature. Triethylamine (0.24 mL, 1.7 mmol) was then added dropwise, followed by 1.5 hours of stirring at 60° C. The reaction mixture was partitioned into water and ethyl acetate at room temperature. The organic layer was washed with water and saturated aqueous sodium chloride and dried over anhydrous magnesium sulfate, and the solvent was evaporated under a reduced pressure. The residue was purified by NH silica gel column chromatography (ethyl acetate:heptane=1:9 then 3:7) to obtain the title compound (39.6 mg, 40.8%).

$^1$H-NMR Spectrum (CDCl$_3$) δ (ppm): 2.88-2.98 (4H, m), 4.03 (2H, s), 5.41 (2H, brs), 5.97 (1H, d, J=3.2 Hz), 6.25 (1H, s), 6.27 (1H, dd, J=2.0, 3.2 Hz), 6.71 (1H, dd, J=4.8, 8.0 Hz), 7.15 (2H, d, J=8.4 Hz), 7.20 (2H, d, J=8.4 Hz), 7.31 (1H, d, J=2.0 Hz), 7.70 (1H, dd, J=2.0, 8.0 Hz), 8.13 (1H, dd, J=2.0, 4.8 Hz).

The starting material, ((4-(2-furan-2-yl-ethyl) phenyl)-acetohydroximoyl chloride, was synthesized as follows.

Manufacturing Example 80-1-1

4-((E)-2-furan-2-yl-vinyl)-benzoic acid ethyl ester

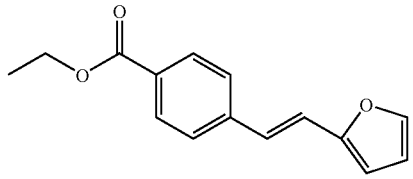

60% Sodium hydride (0.48 g, 12 mmol) was suspended in anhydrous tetrahydrofuran (10 mL) under nitrogen atmosphere, and diethyl 4-ethoxycarbonyl benzylphosphonate (3.6 g, 12 mmol) prepared from ethyl 4-bromomethylbenzoate and triethylphosphite according to the methods as similar to those of Manufacturing Example 93-1-1 was added at room temperature and stirred for 30 minutes at room temperature. Furfural (1 g, 10.4 mmol) was then added at room temperature, and stirred for 2 hours at room temperature. The reaction mixture was partitioned into water and ethyl acetate on an ice bath (0° C.). The organic layer was washed with water and saturated aqueous sodium chloride and dried over anhydrous magnesium sulfate, and the solvent was evaporated under a reduced pressure. The residue was purified by NH silica gel column chromatography (ethyl acetate:heptane=1:20) to obtain the title compound (1.07 g, 42%).

$^1$H-NMR Spectrum (CDCl$_3$) δ (ppm): 1.40 (3H, t, J=5.2 Hz), 4.38 (2H, q, J=5.2 Hz), 6.40-6.48 (2H, m), 6.99 (1H, d, J=16 Hz), 7.05 (1H, d, J=16 Hz), 7.43 (1H, m), 7.50 (2H, dd, J=2.0, 6.4 Hz), 8.01 (2H, dd, J=2.0, 6.4 Hz).

Manufacturing Example 80-1-2

4-(2-Furan-2-yl-ethyl)-benzoic acid ethyl ester

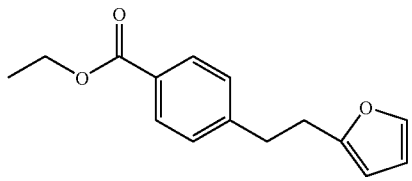

To an anhydrous tetrahydrofuran (25 mL) solution of 4-((E)-2-furan-2-yl-vinyl)-benzoic acid ethyl ester (1.07 g, 4.4 mmol) described in Manufacturing Example 80-1-1 was added 10% palladium-carbon (50% hydrate, 500 mg), which was added for 2 hours under a hydrogen atmosphere at room temperature. The reaction product was filtered, and the filtrate was concentrated under a reduced pressure. The residue was purified by silica gel column chromatography (t-butylmethyl ether:heptane=5:95) to obtain the title compound (706 mg, 65.4%).

$^1$H-NMR Spectrum (CDCl$_3$) δ (ppm): 1.39 (3H, t, J=7.2 Hz), 2.90-3.08 (4H, m), 4.36 (2H, q, J=7.2 Hz), 5.94 (1H, m), 6.26 (1H, m), 7.21 (2H, d, J=8.0 Hz), 7.32 (1H, m), 7.95 (2H, d, J=8.0 Hz).

Manufacturing Example 80-1-3

(4-(2-Furan-2-yl-ethyl)-phenyl)-methanol

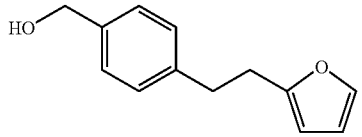

To an anhydrous tetrahydrofuran (10 mL) solution of ethyl 4-(2-furan-2-yl-ethyl)-benzoic acid ethyl ester (706 mg, 2.89 mmol) described in Manufacturing Example 80-1-2 was added diisobutyl aluminum hydride (0.97 M toluene solution, 7.45 mL, 7.23 mmol) on a dry ice-ethanol bath (−78° C.) under nitrogen atmosphere. After 30 minutes of stirring, 15% aqueous potassium sodium tartrate solution (40 mL) was added to the reaction solution, and stirred for 30 minutes at room temperature. Ethyl acetate (100 mL) was added, and the organic layer and water layer were separated. The organic layer was washed with water and saturated aqueous sodium chloride and dried over anhydrous magnesium sulfate, and the solvent was evaporated under a reduced pressure to obtain the title compound (580 mg, 99%).

$^1$H-NMR Spectrum (CDCl$_3$) δ (ppm): 1.58 (1H, t, J=6.0 Hz), 2.90-3.00 (4H, m), 4.66 (2H, d, J=6.0 Hz), 5.96 (1H, m), 6.27 (1H, m), 7.17 (2H, d, J=8.0 Hz), 7.28 (2H, d, J=8.0 Hz), 7.32 (1H, m).

Manufacturing Example 80-1-4

4-(2-Furan-2-yl-ethyl)-benzaldehyde

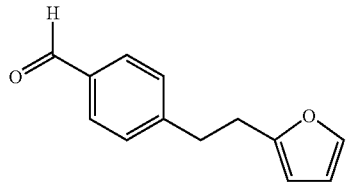

To an ethyl acetate (50 mL) solution of (4-(2-furan-2-yl-ethyl)-phenyl)-methanol (580 mg, 2.87 mmol) described in Manufacturing Example 80-1-3 was added activated manganese dioxide (8 g, 92 mmol), which was stirred for 12 hours at room temperature. The reaction solution was suction filtered through a Celite pad, and washed with ethyl acetate (50 mL). The filtrate was concentrated under a reduced pressure to obtain the title compound (480 mg, 83.5%).

$^1$H-NMR Spectrum (CDCl$_3$) δ (ppm): 2.94-3.08 (4H, m), 5.96 (1H, m), 6.27 (1H, m), 7.32 (3H, d, J=8.0 Hz), 7.80 (2H, d, J=8.0 Hz), 9.98 (1H, s).

Manufacturing Example 80-1-5

4-(2-Furan-2-yl-ethyl)-((E)-2-nitro-vinyl)-benzene

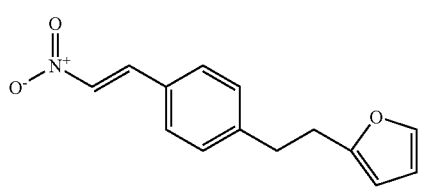

To an acetic acid (5 mL) solution of 4-(2-furan-2-yl-ethyl)-benzaldehyde (480 mg, 2.4 mmol) described in Manufacturing Example 80-1-4 were added nitromethane (732 mg, 12 mmol) and ammonium acetate (370 mg, 4.8 mmol) under nitrogen atmosphere at room temperature, which was stirred for 2 hours at 120° C. The reaction mixture was partitioned into water and ethyl acetate. The organic layer was washed with water and saturated aqueous sodium chloride and dried over anhydrous magnesium sulfate, and the solvent was evaporated under a reduced pressure to obtain the title compound (554 mg, 95%) as a crude product.

$^1$H-NMR Spectrum (CDCl$_3$) δ (ppm): 2.90-3.08 (4H, m), 5.95 (1H, m), 6.27 (1H, m), 7.23 (2H, d, J=8.0 Hz), 7.32 (1H, m), 7.46 (2H, d, J=8.0 Hz), 7.57 (1H, d, J=13.6 Hz), 7.99 (1H, d, J=13.6 Hz).

Manufacturing Example 80-1-6

4-(2-Furan-2-yl-ethyl)-(2-nitro-ethyl)-benzene

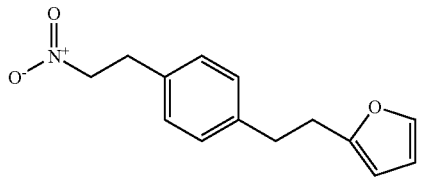

To a mixed tetrahydrofuran-dimethyl sulfoxide (1:1, 10 mL) solution of 4-(2-furan-2-yl-ethyl)-((E)-2-nitro-vinyl)-benzene (554 mg, 2.28 mmol) described in Manufacturing Example 80-1-5 and acetic acid (0.5 mL) was added sodium borohydride (129 mg, 3.42 mmol) at room temperature while cooling appropriately under nitrogen atmosphere, which was stirred for 10 minutes at room temperature. Water was added dropwise into this reaction solution at room temperature while cooling appropriately. The reaction mixture was partitioned into water and ethyl acetate. The organic layer was washed with water and saturated aqueous sodium chloride and dried over anhydrous magnesium sulfate, and the solvent was evaporated under a reduced pressure. The residue was purified by NH silica gel column chromatography (t-butylmethyl ether:heptane=5:95) to obtain the title compound (300 mg, 53%).

$^1$H-NMR Spectrum (CDCl$_3$) δ (ppm): 2.88-2.96 (4H, m), 3.29 (2H, t, J=7.2 Hz), 4.59 (2H, t, J=7.2 Hz), 5.95 (1H, m), 6.27 (1H, m), 7.10-7.16 (4H, m), 7.32 (1H, m)

Manufacturing Example 80-1-7

(4-(2-Furan-2-yl-ethyl) phenyl)-acetohydroximoyl chloride

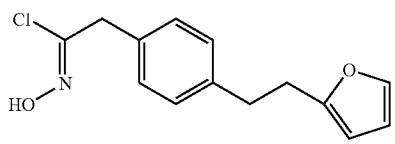

To a methanol (5 mL) solution of 4-(2-furan-2-yl-ethyl)-(2-nitro-ethyl)-benzene (300 mg, 1.22 mmol) described in Manufacturing Example 80-1-6 was added lithium methoxide (92.7 mg, 2.44 mmol) under nitrogen atmosphere at room temperature, which was stirred for 30 minutes at room temperature. The reaction mixture was concentrated under a reduced pressure. Anhydrous methylene chloride (7 mL) and anhydrous tetrahydrofuran (3 mL) were added to the residue. A titanium (IV) chloride (2.7 mL, 1 M dichloromethane solution 2.7 mmol) was added dropwise into the reaction mixture on a dry ice-ethanol bath (−78° C.), which was stirred for 45 minutes at 0° C. Water and ethyl acetate were added to the reaction mixture on an ice bath (0° C.), and the organic layer was separated. This organic layer was washed with saturated aqueous sodium chloride and dried over anhydrous magnesium sulfate, and the solvent was evaporated under a reduced pressure to obtain the title compound (324 mg, 100%).

$^1$H-NMR Spectrum (CDCl$_3$) δ (ppm): 2.88-2.96 (4H, m), 3.77 (2H, s), 5.96 (1H, m), 6.27 (1H, m), 7.15 (2H, d, J=8.4 Hz), 7.19 (2H, d, J=8.4 Hz), 7.32 (1H, m), 7.36 (1H, s).

Example 81

3-(3-(4-(3-Fluoro-phenoxy)-benzyl)-isoxazol-5-yl)-pyridin-2-ylamine

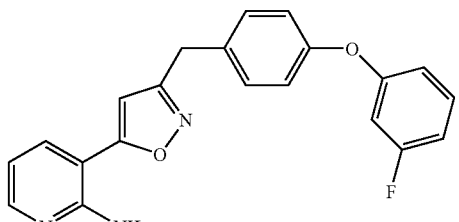

To a tetrahydrofuran (5.00 mL) solution of (4-(3-fluoro-phenoxy)-phenyl)-acetohydroximoyl chloride (290 mg, 1.04 mmol) described in Manufacturing Example 81-1-2 and 3-ethynyl-pyridin-2-ylamine described in Manufacturing Example 1-2-3 (50.0 mg, 0.423 mmol) was added triethylamine (177 μL, 1.27 mmol) at room temperature, which was stirred for 30 minutes at 60° C. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1:5) to obtain the title compound (38.7 mg, 25.3%).

$^1$H-NMR Spectrum (DMSO-d$_6$) δ (ppm): 4.05 (2H, s), 6.27 (2H, brs), 6.70 (1H, dd, J=3.2, 8.0 Hz), 6.79-6.93 (2H, m), 6.84 (1H, s), 6.95 (1H, m), 7.04-7.06 (2H, m), 7.37-7.43 (3H, m), 7.88 (1H, dd, J=1.6, 8.0 Hz), 8.08-8.10 (1H, m).

The starting material, (4-(3-fluoro-phenoxy)-phenyl)-acetohydroximoyl chloride, was synthesized as follows.

Manufacturing Example 81-1-1

1-(3-Fluoro-phenoxy)-4-(2-nitro-ethyl)-benzene

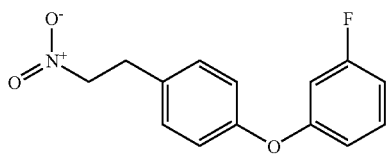

To an N,N-dimethylformamide (30.0 mL) solution of 3-fluorophenol (5.43 g, 48.4 mmol) and 4-fluorobenzaldehyde (3.00 g, 24.2 mmol) was added potassium carbonate (10.1 g, 72.5 mmol) under nitrogen atmosphere, which was stirred for 16 hours at 80° C. The reaction mixture was cooled to room temperature and water was added, followed by extraction with ethyl acetate. The organic layer was washed with saturated aqueous sodium chloride, and the solvent was evaporated under a reduced pressure. The residue was purified by silica gel column chromatography (ethyl acetate:heptane=1:15→1:10) to obtain a mixture with the starting material (6.00 g). To an acetic acid (50.0 mL) solution of this mixture (6.0 g) were added nitromethane (6.78 g, 111 mmol) and ammonium acetate (3.42 g, 44.4 mmol) at room temperature, which was stirred for 4 hours at 110° C. Water and ethyl acetate were added to the reaction mixture, and the organic layer was extracted with ethyl acetate. The organic layer was washed with water and saturated aqueous sodium chloride, dried over anhydrous magnesium sulfate, and filtered. The filtrate was concentrated under a reduced pressure to obtain a crude product (5.5 g). To a dimethyl sulfoxide (40.0 mL) solution of this crude product (5.5 g) and acetic acid (5.00 mL) was added sodium borohydride (1.28 g, 33.9 mmol) at room temperature while cooling appropriately, which was stirred for 5 minutes at room temperature. Water was then added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:5) to obtain the title compound (2.10 g, 37.9%).

$^1$H-NMR Spectrum (DMSO-$d_6$) δ (ppm): 3.24 (2H, t, J=6.8 Hz), 4.86 (2H, t, J=6.8 Hz), 6.78-6.85 (2H, m), 6.94-6.98 (1H, m), 7.03 (2H, d, J=8.0 Hz), 7.33 (2H, d, J=8.0 Hz), 7.40-7.42 (1H, m).

Manufacturing Example 81-1-2

(4-(3-Fluoro-phenoxy)-phenyl)-acetohydroximoyl chloride

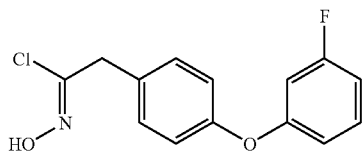

To a methanol (10.0 mL) solution of 1-(3-fluoro-phenoxy)-4-(2-nitro-ethyl)-benzene (500 mg, 1.91 mmol) described in Manufacturing Example 81-1-1 was added lithium methoxide (145 mg, 3.82 mmol) under nitrogen atmosphere at room temperature, which was stirred for 30 minutes at room temperature. The solvent was evaporated from the filtrate under a reduced pressure, and anhydrous dichloromethane (20.0 mL) and anhydrous tetrahydrofuran (10.0 mL) were added to the residue. Titanium (IV) chloride (525 μL, 4.78 mmol) was added dropwise into the reaction mixture on a dry ice-ethanol bath (−78° C.), which was stirred for 40 minutes at room temperature. Water and ethyl acetate were added to the reaction mixture on an ice bath (0° C.), and the organic layer was extracted with ethyl acetate. The organic layer was washed with water and saturated aqueous sodium chloride, dried over anhydrous magnesium sulfate, and filtered. The filtrate was concentrated under a reduced pressure to obtain the title compound (490 mg, 91.7%) as a crude product.

$^1$H-NMR Spectrum (DMSO-$d_6$) δ (ppm): 3.83 (2H, s), 6.80-6.89 (2H, m), 6.95-7.00 (1H, m), 7.05 (2H, d, J=8.4 Hz), 7.31 (2H, d, J=8.4 Hz), 7.38-7.45 (1H, m), 11.75 (1H, s).

Example 82

3-(3-(4-(2-(Tetrahydrofuran-2-yl)-ethyl)-benzyl)-isoxazol-5-yl)-pyridin-2-ylamine

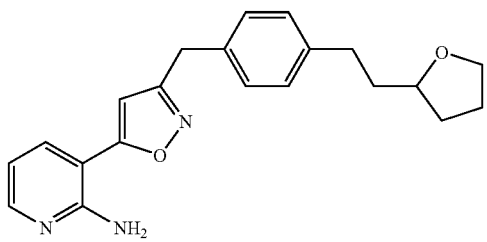

To an anhydrous tetrahydrofuran (5 mL) solution of 3-ethynyl-pyridin-2-ylamine described in Manufacturing Example 1-2-3 (43.7 mg, 0.37 mmol) was added (4-(2-tetrahydrofuran-2-yl-ethyl) phenyl)-acetohydroximoyl chloride (300 mg, 1.12 mmol) described in Manufacturing Example 82-1-6 under nitrogen atmosphere at room temperature. Triethylamine (0.31 mL, 2.24 mmol) was then added dropwise and stirred for 2 hours at 60° C. The reaction mixture was partitioned into water and ethyl acetate at room temperature. The organic layer was washed with water and saturated aqueous sodium chloride, and dried over anhydrous magnesium sulfate, and the solvent was evaporated under a reduced pressure. The residue was purified by silica gel column chromatography (ethyl acetate:heptane=1:9 then 3:7) to obtain the title compound (68 mg, 53%).

$^1$H-NMR Spectrum (CDCl$_3$) δ (ppm): 1.40-1.55 (1H, m), 1.70-2.00 (5H, m), 2.60-2.80 (2H, m), 3.70-3.90 (3H, m), 4.02 (2H, s), 5.41 (2H, brs), 6.25 (1H, s), 6.70 (1H, dd, J=4.8, 8.0 Hz), 7.16-7.24 (4H, m), 7.70 (1H, dd, J=2.0, 8.0 Hz), 8.13 (1H, dd, J=2.0, 4.8 Hz).

The starting material, (4-(2-tetrahydrofuran-2-yl-ethyl) phenyl)-acetohydroximoyl chloride, was synthesized as follows.

Manufacturing Example 82-1-1

4-(2-(Tetrahydrofuran-2-yl)-ethyl)-benzoic acid ethyl ester

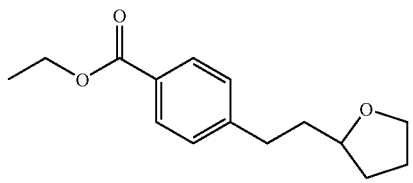

To an anhydrous tetrahydrofuran (25 mL) solution of 4-((E)-2-furan-2-yl-vinyl)-benzoic acid ethyl ester (2.2 g, 9.39 mmol) described in Manufacturing Example 80-1-1 was added 10% palladium-carbon (50% hydrate, 1 g), which was stirred for 6 hours under hydrogen atmosphere at room temperature. The reaction liquid was filtered, and the filtrate was concentrated under a reduced pressure to obtain the title compound (2.2 g, 100%) as a crude product.

Manufacturing Example 82-1-2

(4-(2-(Tetrahydrofuran-2-yl)-ethyl)-phenyl)-methanol

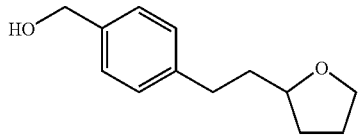

To an anhydrous tetrahydrofuran (20 mL) solution of ethyl 4-(2-(tetrahydrofuran-2-yl)-ethyl)-benzoic acid ethyl ester (2.2 g, 9.39 mmol) described in Manufacturing Example 82-1-1 was added diisobutyl aluminum hydride (0.97 M toluene solution, 24.2 mL, 23.5 mmol) on a dry ice-ethanol bath (−78° C.) under nitrogen atmosphere. After stirring for 30 minutes, 15% aqueous potassium sodium tartrate solution (100 mL) was added to the reaction liquid, and stirred for 30 minutes at room temperature. After addition of ethyl acetate (200 mL), the organic layer and water layer were separated. The organic layer was washed with water and saturated aqueous sodium chloride, and dried over anhydrous magnesium sulfate, and the solvent was evaporated under a reduced pressure. The residue was purified by silica gel column chromatography (ethyl acetate:heptane=1:9 then 2:8) to obtain the title compound (600 mg, 31%).

$^1$H-NMR Spectrum (CDCl$_3$) δ (ppm): 1.40-1.55 (1H, m), 1.63 (1H, t, J=6.0 Hz), 1.70-2.00 (5H, m), 2.60-2.80 (2H, m), 3.70-3.90 (3H, m), 4.66 (2H, d, J=6.0 Hz), 7.21 (2H, d, J=8.0 Hz), 7.28 (2H, d, J=8.0 Hz).

Manufacturing Example 82-1-3

4-(2-(Tetrahydrofuran-2-yl)-ethyl)-benzaldehyde

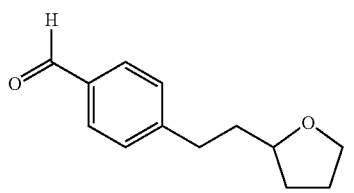

To an ethyl acetate (50 mL) solution of (4-(2-(tetrahydrofuran-2-yl)-ethyl)-phenyl)-methanol (600 mg, 2.91 mmol) described in Manufacturing Example 82-1-2 was added active manganese dioxide (10 g, 115 mmol), which was stirred for 12 hours at room temperature. The reaction liquid was suction filtered through a Celite pad, and washed with ethyl acetate (50 mL). The filtrate was concentrated under a reduced pressure to obtain the title compound (565 mg, 95%).

$^1$H-NMR Spectrum (CDCl$_3$) δ (ppm): 1.40-1.55 (1H, m), 1.70-2.00 (5H, m), 2.60-2.80 (2H, m), 3.70-3.90 (3H, m), 7.37 (2H, d, J=8.4 Hz), 7.80 (2H, d, J=8.0 Hz), 9.97 (1H, s).

Manufacturing Example 82-1-4

4-(2-(Tetrahydrofuran-2-yl)-ethyl)-((E)-2-nitro-vinyl)-benzene

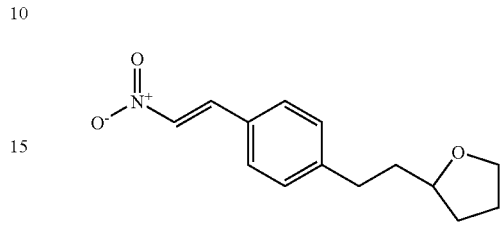

To an acetic acid (10 mL) solution of 4-(2-(tetrahydrofuran-2-yl)-ethyl)-benzaldehyde (565 mg, 2.77 mmol) described in Manufacturing Example 82-1-3 were added nitromethane (1.69 g, 27.7 mmol) and ammonium acetate (427 mg, 5.54 mmol) under nitrogen atmosphere at room temperature, which was stirred for 4 hours at 120° C. The reaction mixture was partitioned into water and ethyl acetate. The organic layer was washed with water and saturated aqueous sodium chloride, and dried over anhydrous magnesium sulfate, and the solvent was evaporated under a reduced pressure to obtain the title compound (646 mg, 94%) as a crude product.

$^1$H-NMR Spectrum (CDCl$_3$) δ (ppm): 1.40-1.55 (1H, m), 1.70-2.00 (5H, m), 2.60-2.80 (2H, m), 3.70-3.90 (3H, m), 7.29 (2H, d, J=8.0 Hz), 7.47 (2H, d, J=8.0 Hz), 7.57 (1H, d, J=13.6 Hz), 7.99 (1H, d, J=13.6 Hz).

Manufacturing Example 82-1-5

4-(2-(Tetrahydrofuran-2-yl)-ethyl)-(2-nitro-ethyl)-benzene

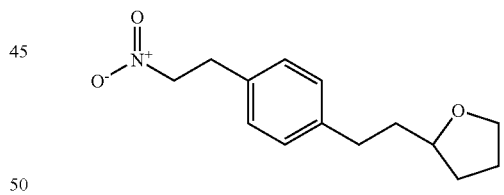

To a mixed tetrahydrofuran-dimethyl sulfoxide (1:1, 10 mL) solution of 4-(2-(tetrahydrofuran-2-yl)-ethyl)-((E)-2-nitro-vinyl)-benzene (646 mg, 2.61 mmol) described in Manufacturing Example 82-1-4 and acetic acid (0.6 mL) was added sodium borohydride (148 mg, 3.92 mmol) at room temperature while cooling appropriately under nitrogen atmosphere, which was stirred for 10 minutes at room temperature. Water was added dropwise into the reaction mixture at room temperature while cooling appropriately. The reaction mixture was partitioned into water and ethyl acetate. The organic layer was washed with water and saturated aqueous sodium chloride, and dried over anhydrous magnesium sulfate, and the solvent was evaporated under a reduced pressure. The residue was purified by NH-silica gel column chromatography (ethyl acetate:heptane=2:8) to obtain the title compound (421 mg, 65%).

¹H-NMR Spectrum (CDCl₃) δ (ppm): 1.40-1.55 (1H, m), 1.70-2.00 (5H, m), 2.60-2.80 (2H, m), 3.29 (2H, t, J=7.2 Hz), 3.70-3.90 (3H, m), 4.59 (2H, t, J=7.2 Hz), 7.11 (2H, d, J=8.4 Hz), 7.17 (2H, d, J=8.4 Hz)

Manufacturing Example 82-1-6

(4-(2-(Tetrahydrofuran-2-yl)-ethyl) phenyl)-acetohydroximoyl chloride

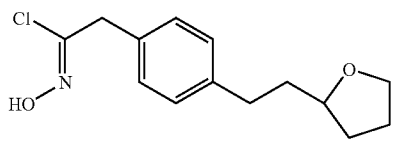

To a methanol (5 mL) solution of 4-(2-(tetrahydrofuran-2-yl)-ethyl)-(2-nitro-ethyl)-benzene (421 mg, 1.69 mmol) described in Manufacturing Example 82-1-5 was added lithium methoxide (128 mg, 3.38 mmol) under nitrogen atmosphere at room temperature, and which was stirred for 30 minutes at room temperature. The reaction mixture was concentrated under a reduced pressure. Anhydrous methylene chloride (10 mL) and anhydrous tetrahydrofuran (5 mL) were added to the residue. A titanium (IV) chloride (1 M dichloromethane solution, 3.7 mL, 3.72 mmol) was added dropwise into the reaction mixture on a dry ice-ethanol bath (−78° C.), which was stirred for 45 minutes at 0° C. Water and ethyl acetate were added to the reaction mixture on an ice bath (0° C.), and the organic layer was separated. The organic layer was washed with water and saturated aqueous sodium chloride and dried over anhydrous magnesium sulfate, and the solvent was evaporated under a reduced pressure to obtain the title compound (445 mg, 98%) as a crude product.

¹H-NMR Spectrum (CDCl₃) δ (ppm): 1.40-1.55 (1H, m), 1.70-2.00 (5H, m), 2.60-2.80 (2H, m), 3.70-3.90 (3H, m), 3.77 (2H, s), 7.18 (4H, brs), 7.51 (1H, brs).

Example 83

3-(3-(4-(2-(Fluoro-phenoxy)-benzyl)-isoxazol-5-yl)-pyridin-2-ylamine

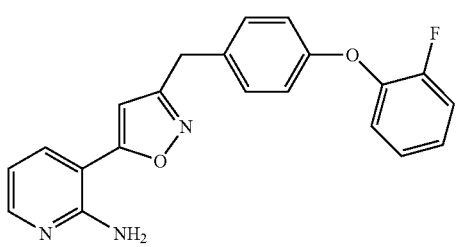

To a tetrahydrofuran (10.0 mL) solution of (4-(2-fluoro-phenoxy)-phenyl)-acetohydroximoyl chloride (290 mg, 1.04 mmol) described in Manufacturing Example 83-1-3 and 3-ethynyl-pyridin-2-ylamine (50.0 mg, 0.423 mmol) described in Manufacturing Example 1-2-3 was added triethylamine (177 µL, 1.27 mmol) at room temperature, which was stirred for 30 minutes at 60° C. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1:5) to obtain the title compound (57.0 mg, 37.3%).

¹H-NMR Spectrum (DMSO-d₆) δ (ppm): 4.02 (2H, s), 6.27 (2H, brs), 6.81-6.72 (1H, m), 6.82 (1H, s), 6.94 (2H, d, J=8.4 Hz), 7.13-7.18 (1H, m), 7.20-7.25 (2H, m), 7.33 (2H, d, J=8.4 Hz), 7.36-7.41 (1H, m), 7.87-7.89 (1H, m), 8.08-8.10 (1H, m).

The starting material, (4-(2-fluoro-phenoxy)-phenyl)-acetohydroximoyl chloride, was synthesized as follows.

Manufacturing Example 83-1-1

4-(2-Fluoro-phenoxy)-benzaldehyde

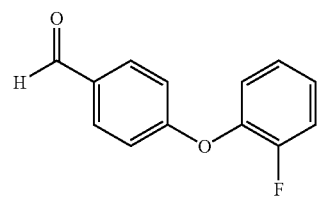

To an N,N-dimethylformamide (30.0 mL) solution of 2-fluorophenol (5.43 g, 48.4 mmol) and 4-fluorobenzaldehyde (3.00 g, 24.2 mmol) was added potassium carbonate (10.1 g, 72.5 mmol) under nitrogen atmosphere, which was stirred for 16 hours at 80° C. Water was added to the reaction solution at room temperature, which was then extracted with ethyl acetate. The organic layer was washed with saturated aqueous sodium chloride, and the solvent was evaporated under a reduced pressure. The residue was purified by silica gel column chromatography (ethyl acetate:heptane=1:15→1:10) to obtain the title compound (5.20 g, 99.4%).

¹H-NMR Spectrum (CDCl₃) δ (ppm): 7.04 (2H, d, J=8.8 Hz), 7.17-7.24 (4H, m), 7.85 (2H, d, J=8.8 Hz), 9.91 (1H, s)

Manufacturing Example 83-1-2

1-(2-Fluoro-phenoxy)-4-(2-nitro-ethyl)-benzene

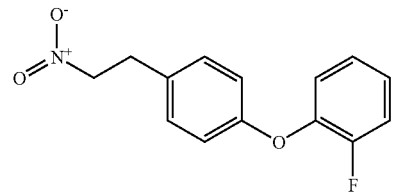

To an acetic acid (30.0 mL) solution of 4-(2-fluoro-phenoxy)-benzaldehyde (3.00 g, 13.9 mmol) described in Manufacturing Example 83-1-1 were added nitromethane (4.24 g, 69.5 mmol) and ammonium acetate (2.14 g, 27.8 mmol) under nitrogen atmosphere, which was stirred for 3 hours at 110° C. Water and ethyl acetate were added to the reaction mixture, and the organic layer was extracted with ethyl acetate. The organic layer was washed with water and saturated aqueous sodium chloride, dried over anhydrous magnesium sulfate, and filtered. The filtrate was concentrated under a reduced pressure to obtain a crude product (3.60 g). To a dimethyl sulfoxide (50.0 mL) solution of this crude product (3.60 g) and acetic acid (3.00 mL) was added sodium borohydride (789 mg, 20.9 mmol) at room temperature while cooling appropriately, which was stirred for 20 minutes at room temperature. Water was then added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:10→1:5) to obtain the title compound (1.80 g, 49.6%).

$^1$H-NMR Spectrum (DMSO-d$_6$) δ (ppm): 3.20 (2H, d, J=7.2 Hz), 4.83 (2H, d, J=7.2 Hz), 6.91-6.93 (2H, m), 7.13-7.17 (1H, m), 7.20-7.29 (4H, m), 7.36-7.41 (1H, m).

Manufacturing Example 83-1-3

(4-(2-Fluoro-phenoxy)-phenyl)-acetohydroximoyl chloride

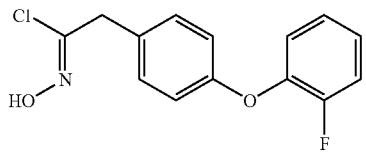

To a methanol (20.0 mL) solution of 1-(2-fluoro-phenoxy)-4-(2-nitro-ethyl)-benzene (1.80 g, 6.89 mmol) described in Manufacturing Example 83-1-2 was added lithium methoxide (524 mg, 13.8 mmol) under nitrogen atmosphere at room temperature, which was stirred for 30 minutes at room temperature. The reaction mixture was concentrated under a reduced pressure, and anhydrous dichloromethane (15.0 mL) and anhydrous tetrahydrofuran (5.00 mL) were added to the residue. Titanium (IV) chloride (1.74 mL, 15.8 mmol) was added dropwise into the reaction mixture on a dry ice-ethanol bath (−78° C.), which was stirred for 30 minutes at room temperature. Water, ethyl acetate and tetrahydrofuran were added to the reaction mixture on an ice bath (0° C.), and the organic layer was extracted with ethyl acetate. This organic layer was washed with water and saturated aqueous sodium chloride, dried over anhydrous magnesium sulfate, and filtered. The filtrate was concentrated under a reduced pressure to obtain the title compound (2.00 g, 51.9%) as a crude product.

$^1$H-NMR Spectrum (DMSO-d$_6$) δ (ppm): 3.79 (2H, s), 6.93-6.95 (2H, m), 7.16-7.27 (5H, m), 7.28-7.42 (1H, m), 11.73 (1H, s).

Example 84

3-(3-(3-Pyridin-2-yl-benzyl)-isoxazol-5-yl)-pyridin-2-ylamine

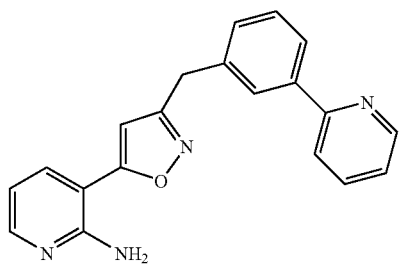

To a mixture of (3-(pyridin-2-yl)-phenyl)-acetohydroximoyl chloride (100 mg) described in Manufacturing Example 84-1-3 and tetrahydrofuran (2 mL) were added 3-ethynyl-pyridin-2-ylamine (10 mg, 0.20 mmol) described in Manufacturing Example 1-2-3 and triethylamine (71 μL, 0.51 mmol) at room temperature, which was stirred for 2.5 hours at 55° C. The reaction mixture was cooled to room temperature, and water was added at that temperature, followed by extraction with ethyl acetate. The organic layer was washed with saturated aqueous sodium chloride, and was concentrated under a reduced pressure. The residue was purified by NH silica gel column chromatography (ethyl acetate:heptane=2:1) to obtain the title compound as a crude product. This was then purified by reverse-phase high-performance liquid chromatography (using an acetonitrile-water mobile phase containing 0.1% trifluoracetic acid) to obtain the title compound (7.2 mg, 15%) as a ditrifluoracetic acid salt.

MS m/e (ESI) 329.20 (MH$^+$)

The starting material, (3-(pyridin-2-yl)-phenyl)-acetohydroximoyl chloride, was synthesized as follows.

Manufacturing Example 84-1-1

3-Pyridin-2-yl-benzaldehyde

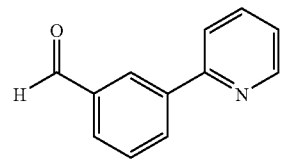

To a mixture of 3-bromobenzaldehyde (930 mg, 5.0 mmol) and toluene (10 mL) were added tri-n-butyl (2-pyridyl) tin (2.1 g, 5.6 mmol) and bis(triphenylphosphine)palladium (II) chloride (350 mg, 0.50 mmol), and the reaction mixture was refluxed for 5 hours. The reaction mixture was cooled to room temperature, and saturated aqueous potassium fluoride solution (1 mL) was added at that temperature and stirred for 30 minutes at room temperature. Water and ethyl acetate were added to the reaction mixture, which was then filtered through a Celite pad. The organic layer of the filtrate was separated and washed with saturated aqueous sodium chloride. The solvent was evaporated under a reduced pressure, and the residue was purified by silica gel column chromatography (heptane:ethyl acetate=2:1) to obtain the title compound (530 mg, 58%).

$^1$H-NMR Spectrum (CDCl$_3$) δ (ppm): 7.28-7.32 (1H, m), 7.65 (1H, t, J=7.7 Hz), 7.80-7.82 (2H, m), 7.93-7.95 (1H, m), 8.29-8.31 (1H, m), 8.50-8.51 (1H, m), 8.72-8.74 (1H, m), 10.12 (1H, s).

Manufacturing Example 84-1-2

2-(3-(2-Nitro-ethyl)-phenyl)-pyridine

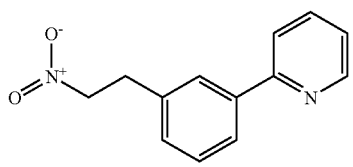

To a mixture of 3-pyridin-2-yl-benzaldehyde (290 mg, 1.6 mmol) described in Manufacturing Example 84-1-1 and acetic acid (5 mL) were added nitromethane (0.65 mL, 12 mmol) and ammonium acetate (370 mg, 4.8 mmol), which was stirred for 2 hours at 100° C. The reaction mixture was cooled to room temperature and water was added, followed by extraction with ethyl acetate. The organic layer was washed with saturated aqueous sodium chloride and dried over anhydrous magnesium sulfate, and the solvent was evaporated under a reduced pressure. A mixture of dimethyl sulfoxide (6 mL) and acetic acid (0.4 mL) was added to the resulting residue, and sodium borohydride (97 mg, 2.6 mmol) was added at room temperature while cooling appropriately. The reaction mixture was stirred for 10 minutes at the same temperature. Water was added to the reaction mixture at room temperature, which was then extracted with ethyl acetate. The organic layer was washed with saturated aqueous sodium chloride, and was concentrated under a reduced pressure. The resulting residue was purified by NH silica gel column chromatography (heptane:ethyl acetate=2:1) to obtain the title compound (260 mg, 71%).

$^1$H-NMR Spectrum (CDCl$_3$) δ (ppm): 3.41 (2H, t, J=7.5 Hz), 4.67 (2H, t, J=7.5 Hz), 7.24-7.27 (2H, m), 7.44 (1H, t, J=7.7 Hz), 7.70-7.79 (2H, m), 7.85 (1H, d, J=7.9 Hz), 7.90 (1H, s), 8.68-8.70 (1H, m).

Manufacturing Example 84-1-3

(3-(Pyridin-2-yl)-phenyl)-acetohydroximoyl chloride

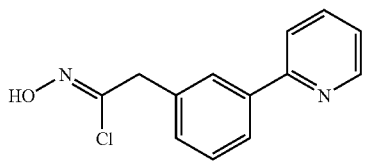

To a mixture of 2-(3-(2-nitro-ethyl)-phenyl)-pyridine (260 mg, 1.1 mmol) described in Manufacturing Example 84-1-2 and methanol (4 mL) was added lithium methoxide (86 mg, 2.3 mmol) at room temperature, which was stirred for 5 minutes at room temperature. The reaction mixture was concentrated under a reduced pressure. A mixture of methylene chloride (6 mL) and tetrahydrofuran (3 mL) was added to the resulting residue, and titanium (IV) chloride (400 μL, 3.6 mmol) was added to the reaction mixture at −78° C. and stirred for 60 minutes at 0° C. The reaction mixture was cooled to 0° C. and saturated aqueous sodium hydrogencarbonate solution was added at that temperature, followed by water and ethyl acetate. The reaction mixture was filtered through a Celite pad, and the organic layer of the filtrate was separated. The organic layer was washed with water and saturated aqueous sodium chloride, and dried over anhydrous magnesium sulfate, and was then filtered. The filtrate was concentrated under a reduced pressure to obtain the title compound (160 mg) as a crude product. This compound was used in the subsequent reaction without further purification.

Example 85

3-(3-Biphenyl-3-ylmethyl-isoxazol-5-yl)-pyridin-2-ylamine

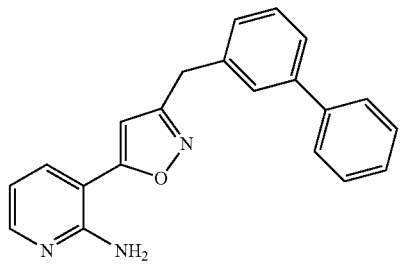

To a mixture of biphenyl-3-yl-acetohydroximoyl chloride (120 mg) described in Manufacturing Example 85-1-3 and tetrahydrofuran (6 mL) were added 3-ethynyl-pyridin-2-ylamine (28 mg, 0.24 mmol) described in Manufacturing Example 1-2-3 and triethylamine (200 μL, 1.4 mmol) at room temperature, which was stirred for 2.5 hours at 55° C. The reaction mixture was cooled to room temperature and water was added at that temperature, followed by extraction with ethyl acetate. The organic layer was washed with saturated aqueous sodium chloride, and was concentrated under a reduced pressure. The residue was purified by NH silica gel column chromatography (ethyl acetate:heptane=2:1) to obtain the title compound (27 mg, 34%).

$^1$H-NMR Spectrum (CDCl$_3$) δ (ppm): 4.13 (2H, s), 5.41 (2H, br s), 6.28 (1H, s), 6.70 (1H, dd, J=4.9, 7.7 Hz), 7.27 (1H, d, J=7.7 Hz), 7.33-7.37 (1H, m), 7.40-7.46 (3H, m), 7.50 (2H, d, J=6.8 Hz), 7.56-7.59 (2H, m), 7.70 (1H, dd, J=1.8, 7.7 Hz), 8.13 (1H, dd, J=1.7, 4.9 Hz).

The starting material, biphenyl-3-yl-acetohydroximoyl chloride, was synthesized as follows.

Manufacturing Example 85-1-1

3-Phenyl-benzaldehyde

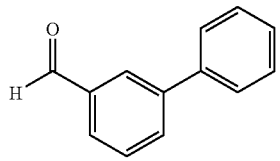

To a mixture of 3-bromobiphenyl (0.50 mL, 3.0 mmol) and tetrahydrofuran (8 mL) was added n-butyl lithium (2.6 mL, 1.5 M n-hexane solution, 3.9 mmol) under nitrogen atmosphere at −78° C., which was stirred for 20 minutes at that temperature. N,N-dimethylformamide (0.35 mL, 4.5 mmol) was added to the reaction mixture at the same temperature, and the temperature was gradually raised to 0° C. Water was added to the reaction mixture, which was then extracted with ethyl acetate. The organic layer was washed with saturated aqueous sodium chloride, and was concentrated under a reduced pressure. The residue was purified by silica gel column chromatography (heptane:ethyl acetate=6:1) to obtain the title compound (430 mg, 79%).

$^1$H-NMR Spectrum (CDCl$_3$) δ (ppm): 7.38-7.42 (1H, m), 7.46-7.50 (2H, m), 7.60-7.64 (3H, m), 7.86 (2H, dd, J=1.7, 7.9 Hz), 8.11 (1H, t, J=1.8 Hz), 10.09 (1H, s).

Manufacturing Example 85-1-2

3-(2-Nitro-ethyl)-biphenyl

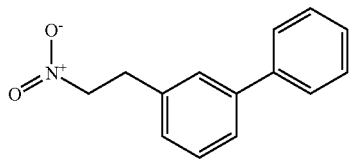

To a mixture of 3-phenyl-benzaldehyde (430 mg, 2.4 mmol) described in Manufacturing Example 85-1-1 and acetic acid (7 mL) were added nitromethane (0.95 mL, 18 mmol) and ammonium acetate (540 mg, 7.1 mmol), which was stirred for 2.5 hours at 100° C. The reaction mixture was cooled to room temperature, and water was added at the same temperature, followed by extraction with ethyl acetate. The organic layer was washed with saturated aqueous sodium chloride and dried over anhydrous magnesium sulfate, and the solvent was evaporated under a reduced pressure. A mixture of dimethyl sulfoxide (9.3 mL) and acetic acid (0.62 mL) was added to the resulting residue, and sodium borohydride (140 mg, 3.8 mmol) was added to the reaction mixture at room temperature while cooling appropriately. The reaction mixture was stirred for 10 minutes at the same temperature. Water was added to the reaction solution at room temperature, which was then extracted with ethyl acetate. The organic layer was washed with saturated aqueous sodium chloride, and was concentrated under a reduced pressure. The resulting residue was purified by NH silica gel column chromatography (heptane:ethyl acetate=5:1) to obtain the title compound (380 mg, 71%).

$^1$H-NMR Spectrum (CDCl$_3$) δ (ppm): 3.39 (2H, t, J=7.4 Hz), 4.64-4.68 (2H, m), 7.18-7.20 (1H, m), 7.34-7.52 (6H, m), 7.55-7.57 (2H, m).

Manufacturing Example 85-1-3

Biphenyl-3-yl-acetohydroximoyl chloride

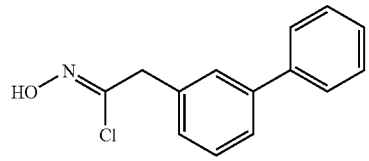

To a mixture of 3-(2-nitro-ethyl)-biphenyl (380 mg, 1.7 mmol) described in Manufacturing Example 85-1-2 and methanol (6 mL) was added lithium methoxide (130 mg, 3.4 mmol) at room temperature, which was stirred for 5 minutes at room temperature. The solvent was evaporated from the reaction mixture under a reduced pressure. A mixture of methylene chloride (7 mL) and tetrahydrofuran (3.5 mL) was added to the resulting residue at room temperature, and titanium (IV) chloride (410 μL, 3.7 mmol) was added at −78° C. to the reaction mixture at −78° C., which was stirred for 60 minutes at 0° C. The reaction mixture was cooled to 0° C., water was added at that temperature, and ethyl acetate was then added at room temperature to extract the mixture. The organic layer was washed successively with water, saturated aqueous sodium hydrogencarbonate solution and saturated aqueous sodium chloride, and the organic layer was dried over magnesium sulfate, and then filtered. The filtrate was concentrated under a reduced pressure to obtain the title compound (420 mg) as raw product. This compound was used in the subsequent reaction without further purification.

Example 86

3-(3-(4-Phenoxymethyl-benzyl)-isoxazol-5-yl)-pyridin-2-ylamine

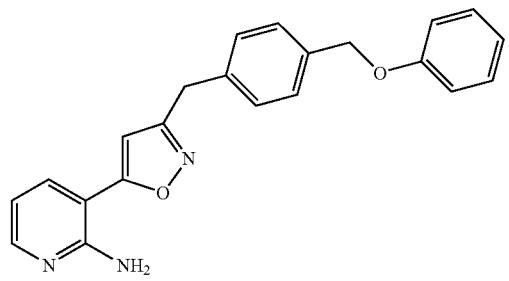

To a tetrahydrofuran (3 mL) solution of (4-phenoxymethyl-phenyl)-acetohydroximoyl chloride (150 mg, 0.545 mmol) described in Manufacturing Example 86-1-5 and 3-ethynyl-pyridin-2-ylamine (41 mg, 0.348 mmol) described in Manufacturing Example 1-2-3 was added triethylamine (104 μL, 0.747 mmol), which was stirred for 2 hours at 50° C. Water was added to the reaction solution at room temperature, which was then extracted with ethyl acetate. The organic layer was washed with water and saturated aqueous sodium chloride and dried over anhydrous magnesium sulfate, and the solvent was evaporated under a reduced pressure. The residue was purified by NH silica gel column chromatography (heptane:ethyl acetate=4:1-2:1) to obtain the title compound (39 mg, 20%).

$^1$H-NMR Spectrum (CDCl$_3$) δ (ppm): 4.07 (2H, s), 5.05 (2H, s), 5.39 (2H, brs), 6.25 (1H, s), 6.70-6.73 (1H, m), 6.95-6.98 (3H, m), 7.29-7.32 (4H, m), 7.41-7.43 (2H, m), 7.69-7.72 (1H, m), 8.13-8.15 (1H, m).

The starting material, (4-phenoxymethyl-phenyl)-acetohydroximoyl chloride, was synthesized as follows.

Manufacturing Example 86-1-1

1-Bromo-4-phenoxymethyl-benzene

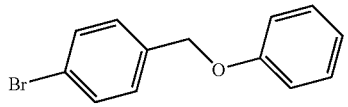

To an N,N-dimethylformamide (50 mL) solution of 4-bromobenzyl bromide (5 g, 20 mmol) and phenol (2.26 g, 24 mmol) was added potassium carbonate (8.29 g, 60 mmol). This mixture was stirred for 1 hour at room temperature. This mixture was partitioned into ethyl acetate and water. The organic layer was separated, washed with water, dried over anhydrous magnesium sulfate, and filtered. The filtrate was concentrated under a reduced pressure, and the residue was purified by NH-silica gel column chromatography (heptane:ethyl acetate=4:1) to obtain the title compound (4.69 g, 89%).

$^1$H-NMR Spectrum (CDCl$_3$) δ (ppm): 5.02 (2H, s), 6.94-6.99 (3H, m), 7.27-7.33 (4H, m), 7.49-7.52 (2H, m).

Manufacturing Example 86-1-2

4-Phenoxymethyl-benzaldehyde

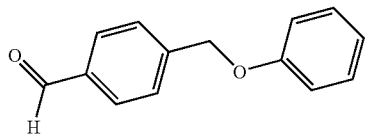

To a tetrahydrofuran solution (50 mL) of 1-bromo-4-phenoxymethyl-benzene (4.69 g, 17.8 mmol) described in Manufacturing Example 86-1-1 was added dropwise n-butyl lithium (16.8 mL, 1.59 M hexane solution, 26.7 mmol) at −78° C. After 40 minutes of stirring at −78° C., N-formylmorpholine (2.25 g, 19.6 mmol) was added to this mixture, which was then stirred for a further 30 minutes at that temperature. This mixture was partitioned into diethyl ether and water. The organic layer was separated, washed with saturated aqueous sodium chloride, dried over anhydrous magnesium sulfate, and filtered. The filtrate was concentrated under a reduced pressure to obtain the title compound (3.8 g). This compound was used in the subsequent reaction without purification.

$^1$H-NMR Spectrum (CDCl$_3$) δ (ppm): 5.16 (2H, s), 6.96-6.99 (3H, m), 7.29-7.33 (2H, m), 7.60-7.62 (2H, m), 7.90-7.92 (2H, m), 10.0 (1H, s).

Manufacturing Example 86-1-3

1-((E)-2-Nitro-vinyl)-4-phenoxymethyl-benzene

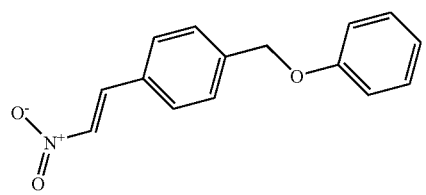

A mixture of 4-phenoxymethyl-benzaldehyde described in Manufacturing Example 86-1-2 (3.8 g, 17.8 mmol), nitromethane (4.79 mL, 89 mmol), ammonium acetate (2.74 g, 35.6 mmol) and acetic acid (38 mL) was stirred for 3 hours at 100° C. This mixture was cooled to room temperature, concentrated under a reduced pressure, and diluted with ethyl acetate. The organic layer was washed with water and saturated aqueous sodium chloride, dried over anhydrous magnesium sulfate, and filtered. The filtrate was concentrated under a reduced pressure to obtain the title compound (4.1 g).

$^1$H-NMR Spectrum (CDCl$_3$) δ (ppm): 5.13 (2H, s), 6.96-7.01 (4H, m), 7.29-7.33 (2H, m), 7.52-7.62 (4H, m), 8.00-8.03 (1H, m).

Manufacturing Example 86-1-4

1-(2-Nitro-ethyl)-4-phenoxymethyl-benzene

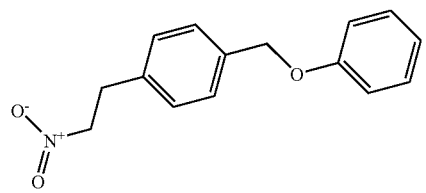

To an acetic acid (4.1 mL) and dimethyl sulfoxide (70 mL) solution of 1-((E)-2-nitro-vinyl)-4-phenoxymethyl-benzene (4.1 g, 16.2 mmol) described in Manufacturing Example 86-1-3 was added sodium borohydride (981 mg, 25.9 mmol) at room temperature while cooling appropriately. This mixture was stirred for 1 hour at room temperature. The mixture was partitioned into ethyl acetate and water. The organic layer was separated, washed with water, dried over anhydrous magnesium sulfate, and filtered. The filtrate was concentrated under a reduced pressure, and the residue was purified by silica gel column chromatography (heptane:ethyl acetate=4:1) to obtain the title compound (2.11 g, 51%).

$^1$H-NMR Spectrum (DMSO-d$_6$) δ (ppm): 3.21-3.24 (2H, m), 4.83-4.87 (2H, m), 5.06 (2H, s), 6.91-6.95 (1H, m), 6.98-7.01 (2H, m), 7.27-7.31 (4H, m), 7.38-7.40 (2H, m).

Manufacturing Example 86-1-5

(4-Phenoxymethyl-phenyl)-acetohydroximoyl chloride

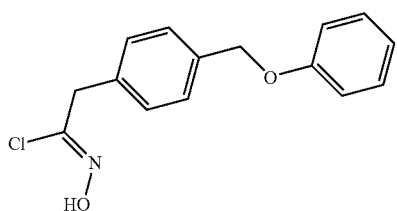

To a methanol solution (12 mL) of 1-(2-nitro-ethyl)-4-phenoxymethyl-benzene described in Manufacturing Example 86-1-4 (1 g, 3.89 mmol) was added lithium methoxide (295 mg, 7.78 mmol). This mixture was stirred for 1 hour at room temperature. The mixture was concentrated under a reduced pressure, water in the residue was azeotropically distilled with toluene, and that residue was diluted with methylene chloride (16 mL) and tetrahydrofuran (8 mL). This was cooled to −78° C., and titanium (IV) tetrachloride (940 µL, 8.56 mmol) was added dropwise into the suspension. The mixture was stirred for 1.5 hours at room temperature. This mixture was cooled to −78° C., and partitioned into ethyl acetate and ice water. The organic layer was separated, washed with saturated aqueous sodium chloride, dried over anhydrous magnesium sulfate, and filtered. The filtrate was concentrated under a reduced pressure to obtain the title compound (1 g). This compound was used in the subsequent reaction without further purification.

Example 87

3-(3-(3-Fluoro-4-(pyridin-2-ylmethoxy)-benzyl)-isoxazol-5-yl)-pyridin-2-ylamine

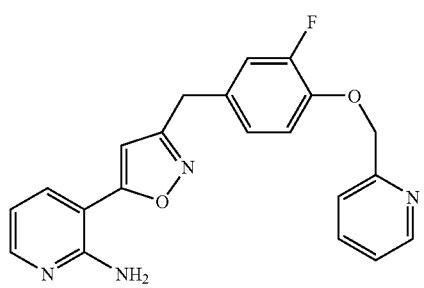

To a methanol (20.0 mL) solution of 2-(2-fluoro-4-(2-nitro-ethyl)-phenoxy)pyridine (500 mg, 1.81 mmol) described in Manufacturing Example 87-1-3 was added lithium methoxide (137 mg, 3.61 mmol) under nitrogen atmosphere at room temperature, which was stirred for 30 minutes at room temperature. The solvent was evaporated from the reaction mixture under a reduced pressure, and anhydrous dichloromethane (15.0 mL) and anhydrous tetrahydrofuran (7.00 mL) were added to the residue. Titanium (IV) chloride (656 µL, 5.97 mmol) was added dropwise into the reaction mixture on a dry ice-ethanol bath (−78° C.), which was stirred for 30 minutes at that temperature. Sodium hydrogencarbonate and ethyl acetate were added to the reaction mixture on an ice cooling (0° C.), which was then filtered through a Celite pad. The organic layer of the filtrate was extracted with ethyl acetate, and that organic layer was washed with water and saturated aqueous sodium chloride, dried over anhydrous magnesium sulfate, and filtered. The filtrate was concentrated under a reduced pressure to obtain a crude product (300 mg). To a tetrahydrofuran (5.00 mL) solution of this crude product (150 mg) and 3-ethynyl-pyridin-2-ylamine (30.0 mg, 0.254 mmol) described in Manufacturing Example 1-2-3 was added triethylamine (106 µL, 0.762 mmol) at room temperature, which was stirred for 30 minutes at 50° C. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1:1), the mixture was further purified by reverse-phase high-performance liquid chromatography (using an acetonitrile-water mobile phase containing 0.1% trifluoracetic acid) to obtain the title compound (6.9 mg, 4.49%) as a ditrifluoroacetic acid salt.

MS m/e (ESI) 377.15 (MH$^+$)

The starting material, 2-(2-fluoro-4-(2-nitro-ethyl)-phenoxy)pyridine, was synthesized as follows.

Manufacturing Example 87-1-1

3-Fluoro-4-(pyridin-2-ylmethoxy)-benzaldehyde

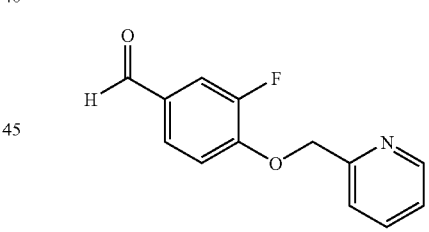

To an N,N-dimethylformamide (40.0 mL) solution of 2-(hydroxymethyl)-pyridine (3.00 g, 27.5 mmol) was added sodium hydride (1.00 g, 25.0 mmol, 60% in oil) under nitrogen atmosphere at 0° C., which was stirred for 20 minutes at room temperature. 3,4-Difluorobenzaldehyde (4.69 g, 33.0 mmol) was then added at 0° C., and stirred for 20 minutes at room temperature. Water was added to the reaction solution at room temperature, which was then extracted with ethyl acetate. The organic layer was washed with saturated aqueous sodium chloride, and the solvent was evaporated under a reduced pressure. The residue was purified by silica gel column chromatography (ethyl acetate:heptane=1:1→2:1) to obtain the title compound (2.90 g, 45.6%).

$^1$H-NMR Spectrum (CDCl$_3$) δ (ppm): 5.36 (2H, s), 7.15 (1H, t, J=8.0 Hz), 7.26-7.29 (1H, m), 7.55-7.67 (3H, m), 7.74-7.78 (1H, m), 8.61-8.63 (1H, m), 9.86-9.87 (1H, m).

Manufacturing Example 87-1-2

2-(2-Fluoro-4-((E)-2-nitro-vinyl)-phenoxymethyl)-pyridine

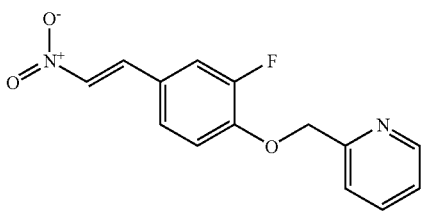

To an acetic acid (25.0 mL) solution of 3-fluoro-4-(pyridin-2-ylmethoxy)-benzaldehyde (2.80 g, 12.1 mmol) described in Manufacturing Example 87-1-1 were added nitromethane (3.69 g, 60.5 mmol) and ammonium acetate (1.87 g, 24.2 mmol) under nitrogen atmosphere at room temperature, which was stirred for 2 hours at 110° C. Water and ethyl acetate were added to the reaction mixture, and the organic layer was extracted with ethyl acetate. The organic layer was washed with water and saturated aqueous sodium chloride, dried over anhydrous magnesium sulfate, and filtered. The filtrate was concentrated under a reduced pressure to obtain the title compound (3.00 g) as a crude product.

$^1$H-NMR Spectrum (DMSO-d$_6$) δ (ppm): 5.35 (2H, s), 7.34-7.40 (2H, s), 7.54-6.84 (1H, d, J=8.0 Hz), 7.67 (1H, d, J=8.0 Hz), 7.85-7.92 (2H, m), 8.09 (1H, d, J=13.4 Hz), 1.19 (1H, d, J=13.4 Hz), 8.60 (1H, d, J=4.0 Hz).

Manufacturing Example 87-1-3

2-(2-Fluoro-4-(2-nitro-ethyl)-phenoxymethyl)pyridine

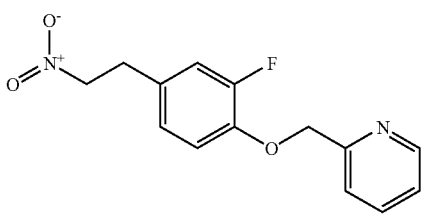

To a dimethyl sulfoxide (30.0 mL) solution of 2-(2-fluoro-4-((E)-2-nitro-vinyl)-phenoxymethyl)-pyridine (3.00 g, 10.9 mmol) described in Manufacturing Example 87-1-2 and acetic acid (3.00 mL) was added sodium borohydride (660 mg, 17.4 mmol) at room temperature while cooling appropriately under nitrogen atmosphere, which was stirred for 20 minutes at room temperature. Water was then added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under a reduced pressure, and the residue was crystallized with a tetrahydrofuran-ethyl acetate-heptane system and filtered to obtain the title compound (1.50 g, 49.8%).

$^1$H-NMR Spectrum (DMSO-d$_6$) δ (ppm): 3.18 (2H, t, J=6.8 Hz), 4.84 (2H, t, J=6.8 Hz), 5.50 (2H, s), 7.06-7.08 (2H, m), 7.28-7.31 (1H, m), 7.65-7.69 (1H, m), 7.88 (1H, d, J=8.0 Hz), 8.23-8.27 (1H, m), 8.76 (1H, J=5.6 Hz).

Example 88

3-(3-(4-(Thiazol-2-ylmethoxy)-benzyl)-isoxazol-5-yl)-pyridin-2-ylamine

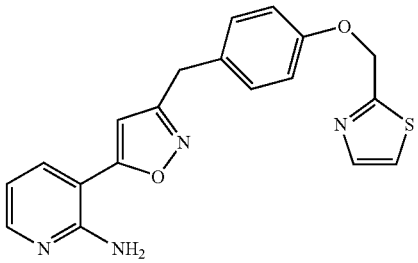

To 4-(5-(2-amino-pyridin-3-yl)-isoxazol-3-ylmethyl)-phenol (50.0 mg, 0.19 mmol) described in Manufacturing Example 5-1-1 were added tetrahydrofuran (3 mL) and a 5N aqueous sodium hydroxide solution (37.3 μL, 0.19 mmol), which was dissolved by irraidiating ultrasonic wave for 1 minute. The reaction mixture was then concentrated under a reduced pressure to obtain a white solid. An N,N-dimethylformamide (1 mL) solution of 2-chloromethyl-thiazole (29.8 mg, 0.22 mmol) described in Manufacturing Example 88-1-2 was added to a suspension of this solid and N,N-dimethylformamide (2 mL), which was stirred for 1 hour at 60° C. This mixture was cooled to room temperature, and partitioned into water and ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (53.0 mg, 78%).

$^1$H-NMR Spectrum (DMSO-d$_6$) δ (ppm): 3.97 (2H, s), 5.42 (2H, s), 6.25 (2H, brs), 6.68-6.71 (1H, m), 6.79 (1H, s), 7.03 (2H, d, J=8.8 Hz), 7.27 (2H, d, J=8.8 Hz), 7.77 (1H, d, J=3.2 Hz), 7.83 (1H, d, J=3.2 Hz), 7.85-7.88 (1H, m), 8.08 (1H, dd, J=2.0, 4.8 Hz).

The starting material, 2-chloromethyl-thiazole, was synthesized as follows.

Manufacturing Example 88-1-1

Thiazole-2-yl-methanol

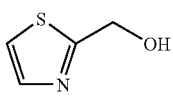

To a mixture of 2-formylthiazole (300 mg, 2.65 mmol) and methanol (30 mL) was added sodium borohydride (201.0 mg, 5.30 mmol) at 0° C., which was stirred for 1 hour at room temperature. Water was added to this reaction mixture, which was then extracted with ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (diethyl ether) to obtain the title compound (251.2 mg, 82%).

$^1$H-NMR Spectrum (DMSO-d$_6$) δ (ppm): 4.74 (2H, d, J=6.0 Hz), 6.04 (1H, t, J=6.0 Hz), 7.63-7.65 (1H, m), 7.73-7.75 (1H, m).

Manufacturing Example 88-1-2

2-Chloromethyl-thiazole

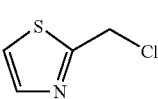

To a mixture of thiazole-2-yl-methanol (251 mg, 2.18 mmol) described in Manufacturing Example 88-1-1 and dichloromethane (10 mL) was added thionyl chloride (191 μL, 2.62 mmol) at room temperature, which was stirred for 30 minutes. Saturated aqueous sodium hydrogencarbonate solution was added to the reaction mixture, which was then extracted with dichloromethane. The organic layer was separated, washed with water and saturated aqueous sodium chloride, dried over anhydrous magnesium sulfate, and filtered. The filtrate was concentrated under a reduced pressure to obtain the title compound (220.5 mg, 76%).

$^1$H-NMR Spectrum (DMSO-d$_6$) δ (ppm): 5.11 (2H, s), 7.81-7.83 (2H, m).

Example 89

3-(3-(6-(3,4-Difluoro-benzyloxy)-pyridin-3-ylmethyl)-isoxazol-5-yl)-pyridin-2-ylamine

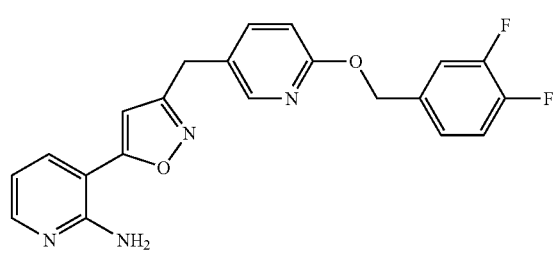

The title compound (23 mg, 17%) was obtained according to the methods similar to those of Example 3 using 3-ethynyl-pyridin-2-ylamine (40 mg, 0.34 mmol) described in Manufacturing Example 1-2-3 and (6-(3,4-difluoro-benzyloxy)-pyridin-3-yl)-acetohydroximoyl chloride (210 mg, 0.68 mmol) described in Manufacturing Example 89-1-1.

$^1$H-NMR Spectrum (DMSO-d$_6$) δ (ppm): 4.01 (2H, s), 5.32 (2H, s), 6.27 (2H, brs), 6.70 (1H, ddd, J=2.0, 4.8, 8.0 Hz), 6.83 (1H, d, J=2.0 Hz), 6.88 (1H, d, J=8.8 Hz), 7.28-7.34 (1H, m), 7.39-7.48 (1H, m), 7.49-7.56 (1H, m), 7.68-7.73 (1H, m), 7.85-7.89 (1H, m), 8.08-8.12 (1H, m), 8.17 (1H, s).

The starting material, (6-(3,4-difluoro-benzyloxy)-pyridin-3-yl)-acetohydroximoyl chloride was synthesized as follows.

Manufacturing Example 89-1-1

(6-(3,4-Difluoro-benzyloxy)-pyridin-3-yl)-acetohydroximoyl chloride

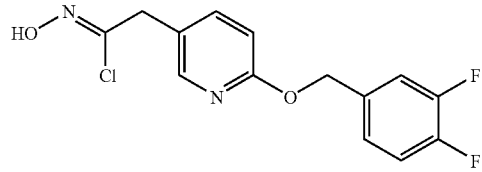

The title compound (810 mg) was obtained according to the methods similar to those of Manufacturing Examples 12-1-1 through 12-1-5 using 3,4-difluoro-benzyl alcohol.

$^1$H-NMR Spectrum (DMSO-d$_6$) δ (ppm): 3.80 (2H, s), 5.32 (2H, s), 6.89 (1H, d, J=8.0 Hz), 7.29-7.34 (1H, m), 7.40-7.49 (1H, m), 7.50-7.57 (1H, m), 7.62 (1H, d, J=8.0 Hz), 8.08 (1H, s), 11.76 (1H, s).

Example 90

3-(3-(6-(2,4-Difluoro-benzyloxy)-pyridin-3-ylmethyl)-isoxazol-5-yl)-pyridin-2-ylamine

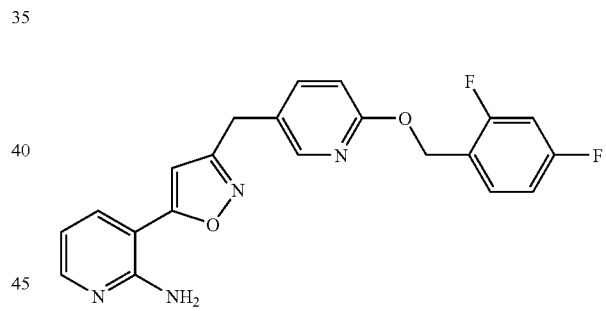

The title compound (45 mg, 34%) was obtained according to the methods similar to those of Example 3 using 3-ethynyl-pyridin-2-ylamine (40 mg, 0.34 mmol) described in Manufacturing Example 1-2-3 and (6-(2,4-difluoro-benzyloxy)-pyridin-3-yl)-acetohydroximoyl chloride (210 mg, 0.68 mmol) described in Manufacturing Example 90-1-1.

$^1$H-NMR Spectrum (DMSO-d$_6$) δ (ppm): 4.01 (2H, s), 5.34 (2H, s), 6.27 (2H, brs), 6.70 (1H, dd, J=4.8, 8.0 Hz), 6.84 (1H, s), 6.85 (1H, d, J=8.0 Hz), 7.08-7.14 (1H, m), 7.26-7.33 (1H, m), 7.57-7.64 (1H, m), 7.69 (1H, dd, J=2.4, 8.0 Hz), 7.87 (1H, dd, J=2.0, 8.0 Hz), 8.09 (1H, dd, J=2.0, 4.8 Hz), 8.18 (1H, d, J=2.4 Hz).

The starting material, (6-(2,4-difluoro-benzyloxy)-pyridin-3-yl)-acetohydroximoyl chloride, was synthesized as follows.

Manufacturing Example 90-1-1

(6-(2,4-Difluoro-benzyloxy)-pyridin-3-yl)-acetohydroximoyl chloride

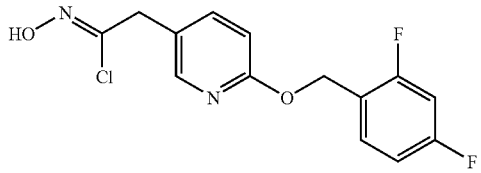

The title compound (600 mg) was obtained according to the methods similar to those of Manufacturing Examples 12-1-1 through 12-1-5 using 2,4-difluoro-benzyl alcohol.

$^1$H-NMR Spectrum (DMSO-d$_6$) δ (ppm): 3.80 (2H, s), 5.34 (2H, s), 6.86 (1H, d, J=8.0 Hz), 7.08-7.14 (1H, m), 7.26-7.33 (1H, m), 7.58 (2H, m), 8.09 (1H, s), 11.75 (1H, s).

Example 91

3-(3-(5-(4-Fluoro-phenoxy)-thiophen-2-ylmethyl)-isoxazol-5-yl)-pyridin-2-ylamine

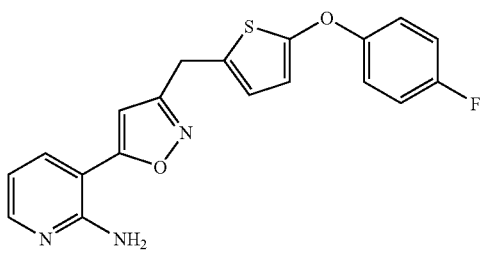

To a tetrahydrofuran (5.00 mL) solution of (5-(4-fluoro-phenoxy)-thiophen-2-yl)-acetohydroximoyl chloride (250 mg, 0.875 mmol) described in Manufacturing Example 91-1-4 and 3-ethynyl-pyridin-2-ylamine (50.0 mg, 0.423 mmol) described in Manufacturing Example 1-2-3 was added triethylamine (177 μL, 1.27 mmol) at room temperature, which was stirred for 30 minutes at 60° C. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1:2→1:1) to obtain the title compound (11.2 mg, 7.21%).

$^1$H-NMR Spectrum (DMSO-d$_6$) δ (ppm): 4.17 (2H, s), 6.28 (2H, brs), 6.53 (1H, d, J=4.0 Hz), 6.69-6.73 (1H, m), 6.78 (1H, d, J=4.0 Hz), 6.88 (1H, s), 7.13-7.17 (2H, m), 7.20-7.25 (2H, m), 7.88-7.91 (1H, m), 8.09-8.11 (1H, m).

The starting material, (5-(4-fluoro-phenoxy)-thiophen-2-yl)-acetohydroximoyl chloride, was synthesized as follows.

Manufacturing Example 91-1-1

5-(4-Fluoro-phenoxy)-thiophene-2-carbonitrile

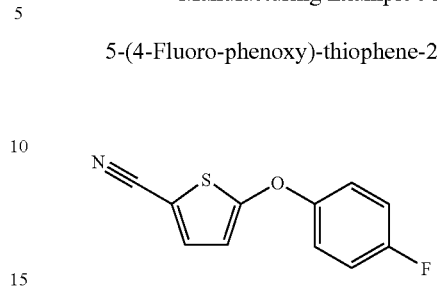

To a dimethyl sulfoxide (100 mL) solution of 5-nitro-2-thiophene carbonitrile (5.00 g, 32.4 mmol) were added 4-fluorophenol (5.45 g, 48.6 mmol) and potassium carbonate (11.2 g, 81.0 mmol) under nitrogen atmosphere, which was stirred for 16 hours at 60° C. The reaction solution was cooled to room temperature and water was added, followed by extraction with ethyl acetate. The organic layer was washed with saturated aqueous sodium chloride, and the solvent was evaporated under a reduced pressure. The residue was purified by NH silica gel column chromatography (ethyl acetate:heptane=1:10→1:5) to obtain the title compound (6.10 g, 85.9%).

$^1$H-NMR Spectrum (CDCl$_3$) δ (ppm): 6.40 (1H, d, J=4.4 Hz), 7.07-7.16 (4H, m), 7.36 (1H, d, J=4.4 Hz).

Manufacturing Example 91-1-2

5-(4-Fluoro-phenoxy)-thiophene-2-carbaldehyde

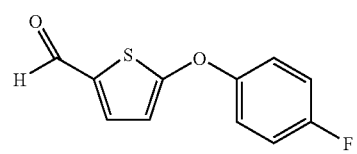

To a tetrahydrofuran (150 mL) solution of 5-(4-fluoro-phenoxy)-thiophene-2-carbonitrile (6.10 g, 27.8 mmol) described in Manufacturing Example 91-1-1 was added dropwise diisobutyl aluminum hydride (0.97 M n-hexane solution, 43.0 mL, 41.7 mmol) on a dry ice-ethanol bath (−78° C.) under nitrogen atmosphere, which was stirred for 2 hours at room temperature. The reaction solution was added to water, followed by extraction with ethyl acetate. The organic layer was washed with saturated aqueous sodium chloride, and the solvent was evaporated under a reduced pressure. The residue was purified by silica gel column chromatography (ethyl acetate:heptane=1:5) to obtain the title compound (3.4 g, 55.0%).

$^1$H-NMR Spectrum (CDCl$_3$) δ (ppm): 6.48-6.49 (1H, m), 7.08-7.12 (2H, m), 7.16-7.19 (2H, m), 7.52-7.54 (1H, m), 9.71 (1H, s).

Manufacturing Example 91-1-3

2-(4-Fluoro-phenoxy)-5-(2-nitro-ethyl)-thiophene

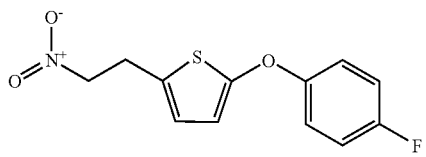

To an acetic acid (20.0 mL) solution of 5-(4-fluoro-phenoxy)-thiophene-2-carbaldehyde (2.60 g, 11.7 mmol) described in Manufacturing Example 91-1-2 were added nitromethane (3.57 g, 58.5 mmol) and ammonium acetate (1.80 g, 23.4 mmol) under nitrogen atmosphere at room temperature, which was stirred for 4 hours at 110° C. Water and ethyl acetate were added to the reaction mixture, and the organic layer was extracted with ethyl acetate. This organic layer was washed with water and saturated aqueous sodium chloride, dried over anhydrous magnesium sulfate, and filtered. The filtrate was concentrated under a reduced pressure to obtain a crude product (3.00 g). To a dimethyl sulfoxide (30.0 mL) solution of this crude product (3.00 g) and acetic acid (3.00 mL) was added sodium borohydride (684 g, 18.1 mol) at room temperature while cooling appropriately, which was stirred for 20 minutes at room temperature. Water was then added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:5) to obtain the title compound (1.38 g, 45.7%).

$^1$H-NMR Spectrum (DMSO-d$_6$) δ (ppm): 3.34 (2H, t, J=6.8 Hz), 4.82 (2H, t, J=6.4 Hz), 6.50 (1H, d, J=3.6 Hz), 6.69-6.71 (1H, m), 7.12-7.16 (2H, m), 7.21-7.26 (2H, m).

Manufacturing Example 91-1-4

(5-(4-Fluoro-phenoxy)-thiophen-2-yl)-acetohydroximoyl chloride

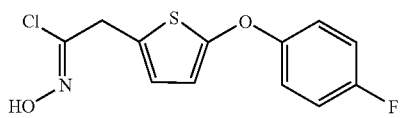

To a methanol (20.0 mL) solution of 2-(4-fluoro-phenoxy)-5-(2-nitro-ethyl)-thiophene (500 mg, 1.87 mmol) described in Manufacturing Example 91-1-3 was added lithium methoxide (142 mg, 3.74 mmol) under nitrogen atmosphere at room temperature, which was stirred for 30 minutes at room temperature. The solvent was evaporated from the reaction mixture under a reduced pressure, and anhydrous dichloromethane (10.0 ml) and anhydrous tetrahydrofuran (5.00 mL) were added to the residue. Titanium (IV) chloride (514 μL, 4.68 mmol) was added dropwise into the reaction mixture on a dry ice-ethanol bath (−78° C.), which was stirred for 30 minutes at room temperature. Water, ethyl acetate and tetrahydrofuran were added to the reaction mixture on an ice cooling (0° C.), and the organic layer was extracted with ethyl acetate. This organic layer was washed with water and saturated aqueous sodium chloride, dried over anhydrous magnesium sulfate, and filtered. The solvent was evaporated from the filtrate under a reduced pressure to obtain the title compound (500 mg, 93.6%) as a crude product.

$^1$H-NMR Spectrum (DMSO-d$_6$) δ (ppm): 3.95 (2H, s), 6.52 (1H, d, J=4.0 Hz), 6.76 (1H, d, J=4.0 Hz), 7.14-7.26 (4H, m), 11.82 (1H, s).

Example 92

3-(3-(5-(4-Methyl-benzyl)-thiophen-2-ylmethyl)-isoxazol-5-yl)-pyridin-2-ylamine

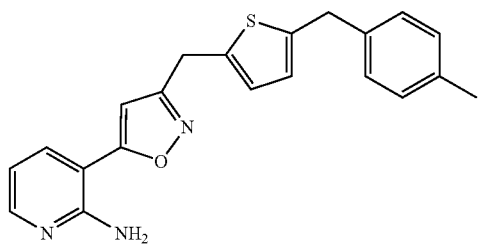

To a tetrahydrofuran (5.00 mL) solution of (5-(4-(methyl-benzyl)-thiophen-2-yl)-acetohydroximoyl chloride (250 mg, 0.894 mmol) described in Manufacturing Example 92-1-5 and 3-ethynyl-pyridin-2-ylamine (50.0 mg, 0.423 mmol) described in Manufacturing Example 1-2-3 was added triethylamine (177 μL, 1.27 mmol) at room temperature, which was stirred for 2 hours at 60° C. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1:3→1:2) to obtain the title compound (27.7 mg, 18.1%).

$^1$H-NMR Spectrum (DMSO-d$_6$) δ (ppm): 2.26 (3H, s), 4.02 (2H, s), 4.15 (2H, s), 6.26 (2H, brs), 6.68-6.72 (2H, m), 6.80-6.81 (1H, m), 6.84 (1H, s), 7.08-7.14 (4H, m), 7.88 (1H, dd, J=2.0, 7.6 Hz), 8.09 (1H, dd, J=2.0, 4.8 Hz).

The starting material, 5-(4-(methyl-benzyl)-5-thiophen-2-yl)-acetohydroximoyl chloride, was synthesized as follows.

Manufacturing Example 92-1-1

(5-Bromo-thiophen-2-yl)-p-tolyl-methanol

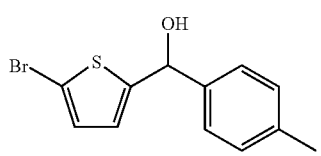

To an anhydrous tetrahydrofuran (70.0 mL) solution of 2,5-dibromothiophene (5.00 g, 19.6 mmol) was added dropwise n-butyl lithium (2.55 M n-hexane solution, 7.69 mL, 19.6 mmol) on a dry ice-ethanol bath (−78° C.) under nitrogen atmosphere, which was stirred for 20 minutes at −78° C. p-Tolaldehyde (2.35 g, 19.6 mmol) was then added dropwise and stirred for 10 minutes at −78° C. The reaction mixture was allowed to room temperature and water was added, followed by extraction with ethyl acetate. The organic layer was washed with saturated aqueous sodium chloride, and the solvent was evaporated under a reduced pressure. The residue was purified by NH silica gel column chromatography (ethyl acetate:heptane=1:5→1:1) to obtain the title compound (4.30 g, 77.5%).

$^1$H-NMR Spectrum (CDCl$_3$) δ (ppm): 2.34 (3H, s), 2.62 (1H, brs), 5.84 (1H, d, J=4.0 Hz), 6.56-6.57 (1H, m), 6.84 (1H, d, J=4.0 Hz), 7.15-7.17 (2H, m), 7.25-7.27 (2H, m).

Manufacturing Example 92-1-2

5-(4-Methyl-benzyl)-thiophene-2-carbaldehyde

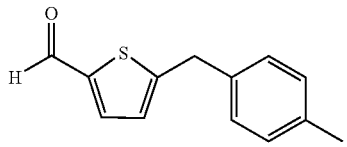

To an acetonitrile (50.0 mL) solution of sodium iodide (11.4 g, 76.0 mmol) was added dropwise chlorotrimethylsilane (9.65 mL, 76.0 mmol) under nitrogen atmosphere, which was stirred for 1.5 hours at room temperature. The reaction solution was cooled to −30° C., and an acetonitrile (10.0 mL) solution of (5-bromo-thiophene-2-yl)-p-tolyl-methanol (4.30 g, 15.2 mmol) described in Manufacturing Example 92-1-1 was added dropwise and stirred for 1.5 hours at room temperature. Water was added to the reaction solution, which was then extracted with ethyl acetate. The organic layer was washed with saturated aqueous sodium chloride, and the solvent was evaporated under a reduced pressure. The residue was purified by silica gel column chromatography (ethyl acetate:heptane=1:10) to obtain a mixture (4.30 g). To a tetrahydrofuran (40.0 mL) solution of this mixture (2.30 g) was added dropwise n-butyl lithium (1.57 M n-hexane solution, 6.03 mL, 9.47 mmol) on a dry ice-ethanol bath (−78° C.), which was stirred for 10 minutes at −78° C. N,N-dimethylformamide (864 µL, 11.2 mmol) was then added dropwise at −78° C., and stirred for 5 minutes at −78° C. The reaction solution was allowed to room temperature and water was added, followed by extraction with ethyl acetate. The organic layer was washed with saturated aqueous sodium chloride, and the solvent was evaporated under a reduced pressure. The residue was purified by silica gel column chromatography (ethyl acetate:heptane=1:10) to obtain the title compound (1.05 g, 56.4%).

$^1$H-NMR Spectrum: (CDCl$_3$) δ (ppm): 2.33 (3H, s), 4.14 (2H, s), 6.89 (1H, d, J=3.6 Hz), 7.13 (4H, s), 7.59 (1H, d, J=3.6 Hz), 9.79 (1H, s).

Manufacturing Example 92-1-3

2-(4-Methyl-benzyl)-5-((E)-2-nitro-vinyl)-thiophene

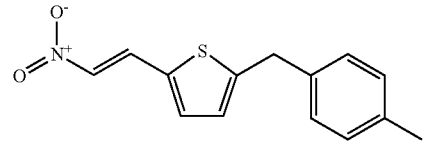

To an acetic acid (10.0 mL) solution of 5-(4-methyl-benzyl)-thiophene-2-carbaldehyde (1.05 g, 4.85 mmol) described in Manufacturing Example 91-1-2 were added nitromethane (1.48 g, 24.3 mmol) and ammonium acetate (748 mg, 9.70 mmol) under nitrogen atmosphere at room temperature, which was stirred for 4 hours at 110° C. Water and ethyl acetate were added to the reaction mixture, and the organic layer was extracted with ethyl acetate. The organic layer was washed with water and saturated aqueous sodium chloride, dried over anhydrous magnesium sulfate, and filtered. The filtrate was concentrated under a reduced pressure to obtain the title compound (1.20 g) as a crude product.

$^1$H-NMR Spectrum (DMSO-d$_6$) δ (ppm): 2.27 (3H, s), 4.16 (2H, s), 7.04 (1H, d, J=3.6 Hz), 7.14-7.18 (4H, m), 7.66 (1H, d, J=3.6 Hz), 7.83 (1H, d, J=13.2 Hz), 8.27 (1H, d, J=13.2 Hz).

Manufacturing Example 92-1-4

2-(4-Methyl-benzyl)-5-(2-nitro-ethyl)-thiophene

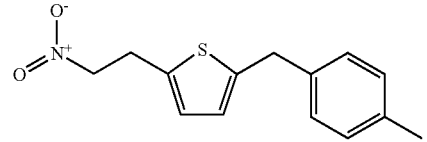

To a dimethyl sulfoxide (20.0 mL) solution of 2-(4-methyl-benzyl)-5-((E)-2-nitro-vinyl)-thiophene (1.20 g, 4.63 mmol) described in Manufacturing Example 92-1-3 and acetic acid (1.20 mL) was added sodium borohydride (280 mg, 7.41 mmol) at room temperature while cooling appropriately under nitrogen atmosphere, which was stirred for 20 minutes at room temperature. Water was then added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under a reduced pressure, and the residue was crystallized with a tetrahydrofuran-ethyl acetate-heptane system and filtered to obtain the title compound (525 mg, 43.4%).

$^1$H-NMR Spectrum (DMSO-d$_6$) δ (ppm): 2.26 (3H, s), 3.33 (2H, t, J=6.4 Hz), 4.01 (2H, s), 4.78 (2H, t, J=6.4 Hz), 6.68-6.69 (1H, m), 6.72-6.73 (1H, m), 7.11 (4H, s).

Manufacturing Example 92-1-5

(5-(4-Methyl-benzyl)-thiophen-2-yl)-acetohydroximoyl chloride

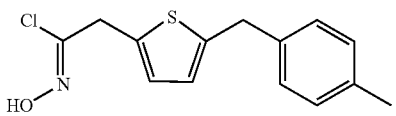

To a methanol (20.0 mL) solution of 2-(4-methyl-benzyl)-5-(2-nitro-ethyl)-thiophene described in Manufacturing Example 92-1-4 (525 mg, 2.01 mmol) was added lithium methoxide (153 mg, 4.02 mmol) under nitrogen atmosphere at room temperature, which was stirred for 30 minutes at room temperature. The reaction mixture was concentrated under a reduced pressure, and anhydrous dichloromethane (20.0 mL) and anhydrous tetrahydrofuran (10.0 ml) were added to the residue. Titanium (IV) chloride (582 µL, 5.30 mmol) was added dropwise into the reaction mixture on a dry ice-ethanol bath (−78° C.), which was then stirred for 30 minutes at room temperature. Water, ethyl acetate and tetrahydrofuran were added to the reaction mixture on an ice bath (0° C.), and the organic layer was separated. This organic layer was washed with water and saturated aqueous sodium chloride, dried over anhydrous magnesium sulfate, and filtered. The filtrate was concentrated under a reduced pressure to obtain the title compound (520 mg, 92.5%) as a crude product.

$^1$H-NMR Spectrum (DMSO-$d_6$) δ (ppm): 2.26 (3H, s), 3.93 (2H, s), 4.02 (2H, s), 6.71 (1H, d, J=3.2 Hz), 6.78 (1H, d, J=3.2 Hz), 7.09-7.15 (4H, m), 11.76 (1H, s).

Example 93

3-(3-(4-(2-Pyridin-2-yl-ethyl)-benzyl)-isoxazol-5-yl)-pyridin-2-ylamine

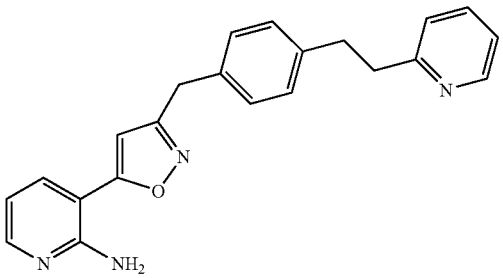

To an anhydrous tetrahydrofuran (5 mL) solution of 3-ethynyl-pyridin-2-ylamine (39 mg, 0.33 mmol) described in Manufacturing Example 1-2-3 was added (4-(2-pyridin-2-yl-ethyl)-phenyl)-acetohydroximoyl chloride hydrochloride (310 mg, 1.0 mmol) described in Manufacturing Example 93-1-8 under nitrogen atmosphere at room temperature. Triethylamine (0.42 mL, 3.0 mmol) was then added dropwise, and stirred for 2 hours at 60° C. The reaction mixture was partitioned into water and ethyl acetate at room temperature. The organic layer was washed with water and saturated aqueous sodium chloride and dried over anhydrous magnesium sulfate, and the solvent was evaporated under a reduced pressure. The residue was purified by NH silica gel column chromatography (ethyl acetate:heptane=3:7 then 4:6), and the resulting crude product was further purified by silica gel thin-layer chromatography (ethyl acetate) to obtain the title compound (21.2 mg, 18%).

$^1$H-NMR Spectrum (CDCl$_3$) δ (ppm): 3.00-3.16 (4H, m), 4.02 (2H, s), 5.42 (2H, brs), 6.25 (1H, s), 6.71 (1H, dd, J=4.8, 8.0 Hz), 7.10-7.25 (6H, m), 7.55-7.60 (1H, m), 7.70 (1H, dd, J=2.0, 8.0 Hz), 8.13 (1H, dd, J=2.0, 4.8 Hz), 8.56 (1H, m).

The starting material, (4-(2-pyridin-2-yl-ethyl)phenyl)-acetohydroximoyl chloride hydrochloride, was synthesized as follows.

Manufacturing Example 93-1-1

Diethyl 4-methoxycarbonyl benzylphosphonate

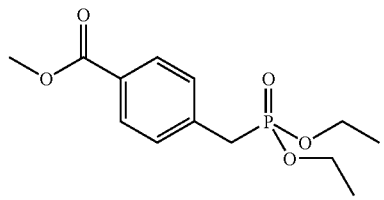

Methyl 4-(bromomethyl)benzoate (50 g, 218 mmol) and triethyl phosphite (43.5 g, 262 mmol) were mixed, stirred for 30 minutes at 100° C. and then stirred for 30 minutes at 120° C. The reaction solution was evaporated under a reduced pressure (165-175° C., 1 mmHg) to obtain the title compound (58.6 g, 94%).

$^1$H-NMR Spectrum (CDCl$_3$) δ (ppm): 1.24 (6H, t, J=7.2 Hz), 3.20 (2H, d, J=22 Hz), 3.91 (3H, s), 3.98-4.18 (4H, m), 7.38 (2H, dd, J=2.4, 8.4 Hz), 7.99 (2H, J=8.4 Hz).

Manufacturing Example 93-1-2

Methyl 4-(2-pyridin-2-yl-ethylenyl)benzoate

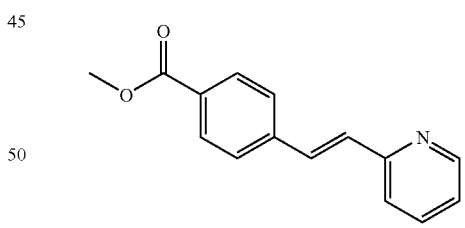

Sodium hydride (0.97 g, 24.2 mmol, 60% in oil) was suspended in anhydrous tetrahydrofuran (20 mL) under nitrogen atmosphere, diethyl 4-methoxycarbonyl benzylphosphonate (6.96 g, 24.2 mmol) described in Manufacturing Example 93-1-1 was added at room temperature, and methanol (0.5 mL) was added followed by 30 minutes of stirring at room temperature. Next, 2-pyridinecarboxyaldehyde (2 g, 18.7 mmol) was added at room temperature and stirred for 1 hour at room temperature. The reaction mixture was partitioned into water and ethyl acetate on an ice bath (0° C.). The organic layer was washed with water and saturated aqueous sodium chloride and dried over anhydrous magnesium sulfate, and the solvent was evaporated under a reduced pressure. The residue was purified by silica gel column chromatography (ethyl acetate:heptane=1:9) to obtain the title compound (3.71 g, 83%).

$^1$H-NMR Spectrum (CDCl$_3$) δ (ppm): 3.93 (3H, s), 7.19 (1H, dd, J=4.8, 7.6 Hz), 7.27 (1H, d, J=16 Hz), 7.41 (1H, d, J=7.6 Hz), 7.63 (2H, d, J=8.8 Hz), 7.66 (1H, d, J=16 Hz), 7.69 (1H, t, J=8.0 Hz), 8.05 (2H, d, J=8.8 Hz), 8.63 (1H, d, J=4.8 Hz).

Manufacturing Example 93-1-3

Methyl 4-(2-pyridin-2-yl-ethyl)benzoate

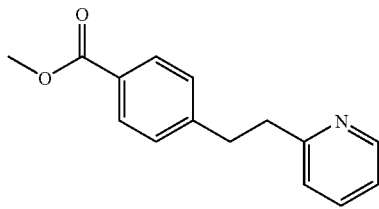

To an anhydrous tetrahydrofuran (25 mL) solution of methyl 4-(2-pyridin-2-yl-ethylenyl)benzoate (3.71 g, 15.5 mmol) described in Manufacturing Example 93-1-2 was added 10% palladium-carbon (50% hydrate, 1 g), which was stirred under hydrogen atmosphere for 2 hours at room temperature. The reaction mixture was filtered, and the filtrate was concentrated under a reduced pressure to obtain the title compound (3.71 g, 99%).

$^1$H-NMR Spectrum (CDCl$_3$) δ (ppm): 3.11 (4H, m), 3.90 (3H, s), 7.04 (1H, d, J=7.6 Hz), 7.12 (1H, dd, J=6.0, 7.6 Hz), 7.24 (2H, d, J=8.4 Hz), 7.55 (1H, t, J=7.6 Hz), 7.94 (2H, d, J=8.4 Hz), 8.56 (1H, d, J=6.0 Hz).

Manufacturing Example 93-1-4

4-(2-Pyridin-2-yl-ethyl)benzyl alcohol

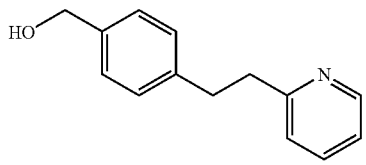

To an anhydrous tetrahydrofuran (50 mL) solution of methyl 4-(2-pyridin-2-yl-ethyl)benzoate 3.71 g, 15.4 mmol) described in Manufacturing Example 93-1-3 was added diisobutyl ammonium hydride (0.97 M toluene solution, 39.7 mL, 38.5 mmol) on a dry ice-ethanol bath (−78° C.) under nitrogen atmosphere. After 30 minutes of stirring, 15% aqueous potassium sodium tartrate solution (100 mL) was added to the reaction mixture, and stirred for 30 minutes at room temperature. Ethyl acetate (100 mL) was added, and the organic layer and water layer were separated. The organic layer was washed with water and saturated aqueous sodium chloride and dried over anhydrous magnesium sulfate, and the solvent was evaporated under a reduced pressure to obtain the title compound (3.16 g, 96%).

$^1$H-NMR Spectrum (CDCl$_3$) δ (ppm): 1.79 (1H, brs), 3.07 (4H, m), 4.66 (2H, s), 7.07 (1H, d, J=7.6 Hz), 7.12 (1H, dd, J=6.0, 7.6 Hz), 7.19 (2H, d, J=8.0 Hz), 7.28 (2H, d, J=8.0 Hz), 7.57 (1H, t, J=7.6 Hz), 8.56 (1H, d, J=6.0 Hz).

Manufacturing Example 93-1-5

4-(2-Pyridin-2-yl-ethyl)benzaldehyde

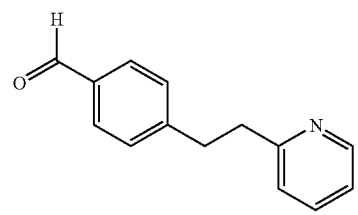

To an ethyl acetate (100 mL) solution of 4-(2-pyridin-2-yl-ethyl)benzyl alcohol (3.16 g, 14.8 mmol) described in Manufacturing Example 93-1-4 was added activated manganese dioxide (45 g, 518 mmol), which was stirred for 4 hours at room temperature. The reaction mixture was filtered through a Celite pad, and washed with ethyl acetate (100 mL). The filtrate was concentrated under a reduced pressure to obtain the title compound (2.57 g, 82%).

$^1$H-NMR Spectrum (CDCl$_3$) δ (ppm): 3.10-3.20 (4H, m), 7.07 (1H, d, J=7.6 Hz), 7.12 (1H, dd, J=6.0, 7.6 Hz), 7.34 (2H, d, J=8.0 Hz), 7.57 (1H, t, J=7.6 Hz), 7.79 (2H, d, J=8.0 Hz), 8.56 (1H, d, J=6.0 Hz), 9.97 (1H, s).

Manufacturing Example 93-1-6

4-(2-Pyridin-2-yl-ethyl)-((E)-2-nitro-vinyl)-benzene

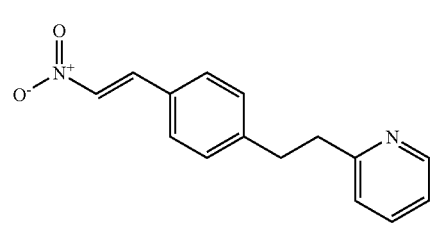

To an acetic acid (30 mL) solution of 4-(2-pyridin-2-yl-ethyl)benzaldehyde (2.57 g, 12.2 mmol) described in Manufacturing Example 93-1-5 were added nitromethane (7.45 g, 122 mmol) and ammonium acetate (1.88 g, 24.4 mmol) under nitrogen atmosphere at room temperature, which was stirred for 3 hours at 120° C. The reaction mixture was partitioned into water and ethyl acetate. The organic layer was washed with water and saturated aqueous sodium chloride and dried over anhydrous magnesium sulfate, and the solvent was evaporation under a reduced pressure to obtain the title compound (2.83 g, 91%) as a raw product.

$^1$H-NMR Spectrum (CDCl$_3$) δ (ppm): 3.10-3.20 (4H, m), 7.07 (1H, d, J=7.6 Hz), 7.12 (1H, dd, J=6.0, 7.6 Hz), 7.26 (2H, d, J=8.0 Hz), 7.45 (2H, d, J=8.0 Hz), 7.56 (1H, d, J=13.6 Hz), 7.57 (1H, t, J=7.6 Hz), 7.98 (1H, d, J=13.6 Hz), 8.56 (1H, d, J=6.0 Hz).

Manufacturing Example 93-1-7

4-(2-Pyridin-2-yl-ethyl)-(2-nitro-ethyl)-benzene

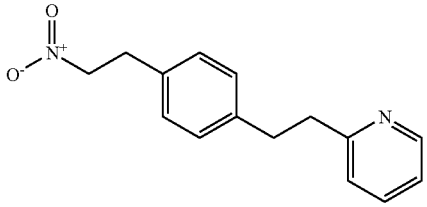

To a mixed tetrahydrofuran-dimethyl sulfoxide (1:1) solution of 4-(2-pyridin-2-yl-ethyl)-((E)-2-nitro-vinyl)-benzene (2.83 g, 11.1 mmol) described in Manufacturing Example 93-1-6 and acetic acid (3 mL) was added sodium borohydride (630 mg, 16.7 mmol) at room temperature while cooling appropriately under nitrogen atmosphere, which was stirred for 15 minutes at room temperature. Water was added dropwise into this reaction mixture at room temperature while cooling appropriately. The reaction mixture was partitioned into water and ethyl acetate. The organic layer was washed with water and saturated aqueous sodium chloride and dried over anhydrous magnesium sulfate, and the solvent was evaporated under a reduced pressure. The residue was purified by NH silica gel column chromatography (ethyl acetate:heptane=1:9 then 2:8) to obtain the title compound (2.11 g, 74%).

$^1$H-NMR Spectrum (CDCl$_3$) δ (ppm): 3.07 (2H, t, J=7.6 Hz), 3.29 (2H, t, J=7.2 Hz), 3.47 (2H, t, J=7.6 Hz), 4.60 (2H, t, J=7.2 Hz), 7.13 (2H, d, J=8.0 Hz), 7.19 (2H, d, J=8.0 Hz), 7.19 (1H, d, J=7.6 Hz), 7.30 (1H, dd, J=6.0, 7.6 Hz), 7.78 (1H, t, J=7.6 Hz), 8.78 (1H, d, J=7.6 Hz).

Manufacturing Example 93-1-8

(4-(2-Pyridin-2-yl-ethyl)-phenyl)-acetohydroximoyl chloride hydrochloride

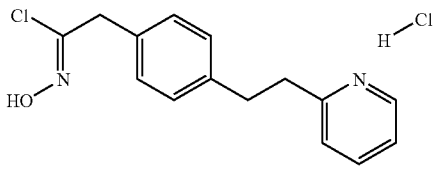

To a methanol (30 mL) solution of 4-(2-pyridin-2-yl-ethyl)-(2-nitro-ethyl)-benzene (1 g, 3.9 mmol) described in Manufacturing Example 93-1-7 was added lithium methoxide (296 mg, 7.8 mmol) under nitrogen atmosphere at room temperature, which was stirred for 30 minutes at room temperature. The reaction mixture was concentrated under a reduced pressure. Anhydrous methylene chloride (20 mL) and anhydrous tetrahydrofuran (10 mL) were added to the residue. Titanium (IV) chloride (1 M dichloromethane solution, 12.5 mL, 12.5 mmol) was added dropwise into the reaction mixture on a dry ice-ethanol bath (−78° C.), which was stirred for 30 minutes at 0° C. Water and ethyl acetate were added to the reaction mixture on an ice bath (0° C.), which was then neutralized by addition of a 10% aqueous sodium hydrogencarbonate solution. The reaction liquid including precipitate was filtered through a Celite pad and washed with ethyl acetate. The organic layer was separated from the filtrate. This organic layer was washed with water and saturated aqueous sodium chloride and dried over anhydrous magnesium sulfate, and the anhydrous magnesium sulfate was filtered. A 4 N hydrochloric acid-ethyl acetate solution (4 mL) was added to the filtrate, and the solvent was evaporated under a reduced pressure to obtain the title compound (324 mg, 100%).

$^1$H-NMR Spectrum (DMSO-d6) δ (ppm): 3.08 (2H, t, J=7.6 Hz), 3.32 (2H, t, J=7.6 Hz), 3.78 (2H, s), 7.12-7.26 (4H, m), 7.80-7.94 (2H, m), 8.43 (1H, m), 8.80 (1H, m).

Example 94

3-(3-(3-Fluoro-4-(5-fluoro-pyridin-2-ylmethoxy)-benzyl)-isoxazol-5-yl)-pyridin-2-ylamine

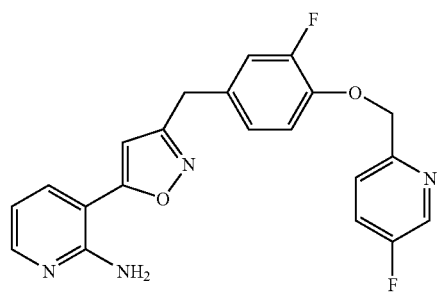

To a tetrahydrofuran (5.00 mL) solution of (3-fluoro-4-(5-fluoro-pyridin-2-ylmethoxy)-phenyl)-acetohydroximoyl chloride (170 mg, 0.554 mmol) described in Manufacturing Example 94-1-3 and 3-ethynyl-pyridin-2-ylamine (40.0 mg, 0.339 mmol) described in Manufacturing Example 1-2-3 was added triethylamine (142 µL, 1.02 mmol) at room temperature, which was stirred for 4 hours at room temperature. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1:3→1:2) to obtain the title compound (18.0 mg, 13.5%).

$^1$H-NMR Spectrum (DMSO-d$_6$) δ (ppm): 3.98 (2H, s), 5.23 (2H, s), 6.27 (2H, brs), 6.70 (1H, dd, J=0.8, 8.0 Hz), 6.82 (1H, s), 7.07 (1H, d, J=8.0 Hz), 7.18-7.26 (2H, m), 7.61 (1H, dd, J=0.8, 8.4 Hz), 7.76-7.81 (1H, m), 7.86-7.88 (1H, m), 8.09 (1H, dd, J=1.6, 4.8 Hz), 8.58-8.59 (1H, m).

The starting material, (3-fluoro-4-(5-fluoro-pyridin-2-ylmethoxy)-phenyl)-acetohydroximoyl chloride, was synthesized as follows.

Manufacturing Example 94-1-1

3-Fluoro-4-(5-fluoro-pyridin-2-ylmethoxy)-benzaldehyde

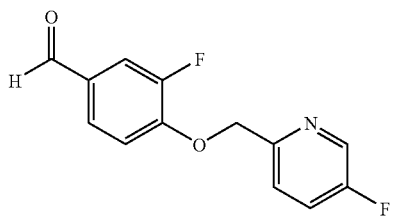

To an N,N-dimethylformamide (20.0 mL) solution of (5-fluoro-pyridin-2-yl)-methanol (760 mg, 5.98 mmol) described in Manufacturing Example 41-1-1 was added sodium hydride (239 mg, 5.98 mmol, 60% in oil) under nitrogen atmosphere at 0° C., which was stirred for 10 minutes at room temperature. 3,4-Difluorobenzaldehyde (935 mg, 6.58 mmol) was then added at room temperature, and stirred for 30 minutes at room temperature. Water was added to the reaction solution at room temperature, which was then extracted with ethyl acetate. The organic layer was washed with saturated aqueous sodium chloride, and the solvent was evaporated under a reduced pressure. The residue was purified by silica gel column chromatography (ethyl acetate:heptane=1:3) to obtain the title compound (629 mg, 42.2%).

$^1$H-NMR Spectrum (CDCl$_3$) δ (ppm): 5.33 (2H, s), 7.15 (1H, t, J=8.0 Hz), 7.45-7.50 (1H, m), 7.57-7.66 (3H, m), 8.47 (1H, d, J=3.2 Hz), 9.87 (1H, d, J=2.0 Hz).

Manufacturing Example 94-1-2

5-Fluoro-2-(2-fluoro-4-(2-nitro-ethyl)-phenoxymethyl)-pyridine

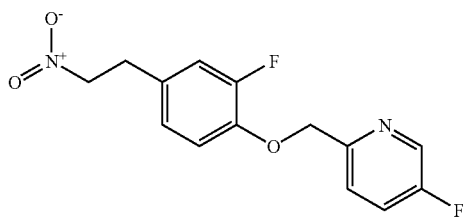

To an acetic acid (8.00 mL) solution of 3-fluoro-4-(5-fluoro-pyridin-2-ylmethoxy)-benzaldehyde (629 mg, 2.52 mmol) described in Manufacturing Example 94-1-1 were added nitromethane (769 mg, 12.6 mmol) and ammonium acetate (388 mg, 5.04 mmol) under nitrogen atmosphere at room temperature, which was stirred for 6 hours at 100° C. Water and ethyl acetate were added to the reaction solution, and the organic layer was extracted with ethyl acetate. The organic layer was washed with water and saturated aqueous sodium chloride, dried over anhydrous magnesium sulfate, and filtered. The filtrate was concentrated under a reduced pressure to obtain a crude product (736 mg). To a dimethyl sulfoxide (10.0 mL) solution of this crude product (736 mg) and acetic acid (700 µL) was added sodium borohydride (153 mg, 4.03 mmol) at room temperature while cooling appropriately, which was stirred for 30 minutes at room temperature. Water was then added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:5) to obtain the title compound (341 mg, 46.0%).

$^1$H-NMR Spectrum (DMSO-d$_6$) δ (ppm): 3.16 (2H, t, J=6.8 Hz), 4.83 (2H, t, J=6.8 Hz), 5.22 (2H, s), 7.01-7.03 (1H, m), 7.16-7.24 (2H, m), 7.59-7.63 (1H, m), 7.77-7.82 (1H, m), 8.59 (1H, d, J=2.8 Hz).

Manufacturing Example 94-1-3

(3-Fluoro-4-(5-fluoro-pyridin-2-ylmethoxy)-phenyl)-acetohydroximoyl chloride

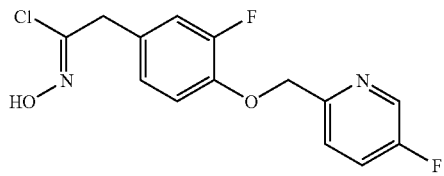

To a methanol (20.0 mL) solution of 5-fluoro-2-(2-fluoro-4-(2-nitro-ethyl)-phenoxymethyl)-pyridine (341 mg, 1.16 mmol) described in Manufacturing Example 94-1-2 was added lithium methoxide (88.1 mg, 2.32 mmol) under nitrogen atmosphere at room temperature, which was stirred for 30 minutes at room temperature. The reaction mixture was concentrated under a reduced pressure, and anhydrous dichloromethane (20.0 mL) and anhydrous tetrahydrofuran (10.0 mL) were added to the residue. Titanium (IV) chloride (408 µL, 3.71 mmol) was added dropwise into the reaction mixture on a dry ice-ethanol bath (−78° C.), which was stirred for 60 minutes at room temperature. Water, ethyl acetate and tetrahydrofuran were added to the reaction mixture on an ice bath (0° C.), and the organic layer was extracted with ethyl acetate. This organic layer was washed with water and saturated aqueous sodium chloride, dried over anhydrous magnesium sulfate, and filtered. The filtrate was concentrated under a reduced pressure to obtain the title compound (340 mg, 93.7%) as a crude product.

$^1$H-NMR Spectrum (DMSO-d$_6$) δ (ppm): 3.77 (2H, s), 5.24 (2H, s), 7.01-7.02 (1H, m), 7.12-7.16 (1H, m), 7.20-7.24 (1H, m), 7.60-7.63 (1H, m), 7.77-7.82 (1H, m), 8.59 (1H, d, J=2.8 Hz), 11.74 (1H, s).

Example 95

3-(3-(2-Fluoro-4-(pyridin-2-ylmethoxy)-benzyl)-isoxazol-5-yl)-pyridin-2-ylamine

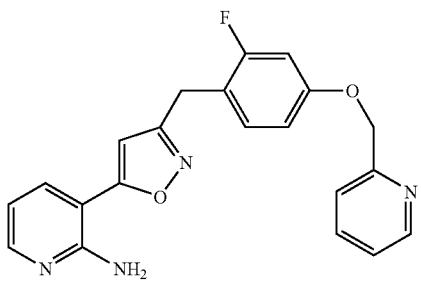

To a methanol (20.0 mL) solution of 2-(3-fluoro-4-(2-nitro-ethyl)-phenoxymethyl)-pyridine (400 mg, 1.45 mmol) described in Manufacturing Example 95-1-3 was added lithium methoxide (110 mg, 2.90 mmol) under nitrogen atmosphere at room temperature, which was stirred for 30 minutes at room temperature. The solvent was evaporated from the reaction mixture under a reduced pressure, and anhydrous dichloromethane (20.0 mL) and anhydrous tetrahydrofuran (10.0 ml) were added to the residue. Titanium (IV) chloride (510 μL, 4.64 mmol) was added dropwise into the reaction mixture on a dry ice-ethanol bath (−78° C.), which was stirred for 60 minutes at room temperature. Water, ethyl acetate and tetrahydrofuran were added to the reaction mixture on an ice bath (0° C.), and the organic layer was extracted with ethyl acetate. The organic layer was washed with water and saturated aqueous sodium chloride, dried over anhydrous magnesium sulfate, and filtered. The filtrate was concentrated under a reduced pressure to obtain a crude product (360 mg). To a tetrahydrofuran (5.00 mL) solution of this crude product (180 mg) and 3-ethynyl-pyridin-2-ylamine (40.0 mg, 0.339 mmol) described in Manufacturing Example 1-2-3 was added triethylamine (142 μL, 1.02 mmol) at room temperature, which was stirred for 1 hour at 60° C. Water was added to the reaction solution at room temperature, which was then extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1:3→1:2) to obtain the title compound (25.2 mg, 19.7%).

$^1$H-NMR Spectrum (DMSO-d$_6$) δ (ppm): 3.98 (2H, s), 5.18 (2H, s), 6.26 (2H, brs), 6.68-6.71 (1H, m), 6.77 (1H, s), 6.86 (1H, dd, J=2.4, 8.4 Hz), 6.95 (1H, dd, J=2.4, 12.0 Hz), 7.29-7.37 (2H, m), 7.51 (1H, d, J=8.0 Hz), 7.82-7.88 (2H, m), 8.08-8.09 (1H, m), 8.57-8.59 (1H, m).

The starting material, 2-(3-fluoro-4-(2-nitro-ethyl)-phenoxymethyl)-pyridine, was synthesized as follows.

Manufacturing Example 95-1-1

2-Fluoro-4-(pyridin-2-ylmethoxy)-benzaldehyde

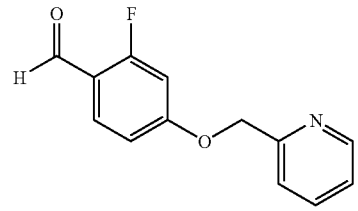

To an N,N-dimethylformamide (10.0 mL) solution of 2-fluoro-4-hydroxy-benzaldehyde (1.60 g, 11.4 mmol) was added sodium hydride (547 mg, 13.7 mmol, 60% in oil) under nitrogen atmosphere at 0° C., which was stirred for 30 minutes at room temperature. 2-Picolyl chloride (2.80 g, 17.1 mmol) was then added at room temperature and stirred for 1 hour at 70° C. Water was added to the reaction solution at room temperature, which was then extracted with ethyl acetate. The organic layer was washed with saturated aqueous sodium chloride, and the solvent was evaporated under a reduced pressure. The residue was purified by silica gel column chromatography (ethyl acetate:heptane=1:3) to obtain the title compound (1.07 g, 40.6%).

$^1$H-NMR Spectrum (CDCl$_3$) δ (ppm): 5.27 (2H, s), 6.74-6.77 (1H, m), 6.87-6.90 (1H, m), 7.26-7.29 (1H, m), 7.47-7.49 (1H, m), 7.73-7.85 (2H, m), 8.62-8.64 (1H, m), 10.21 (1H, s).

Manufacturing Example 95-1-2

2-(3-Fluoro-4-((E)-2-nitro-vinyl)-phenoxymethyl) pyridine

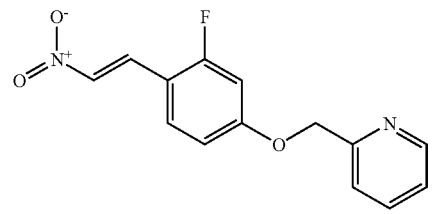

To an acetic acid (15.0 mL) solution of 2-fluoro-4-(pyridin-2-ylmethoxy)-benzaldehyde (1.07 g, 4.63 mmol) described in Manufacturing Example 95-1-1 were added nitromethane (1.41 g, 23.2 mmol) and ammonium acetate (714 mg, 9.26 mmol) under nitrogen atmosphere at room temperature, which was stirred for 2 hours at 100° C. Water and ethyl acetate were added to the reaction mixture, and the organic layer was extracted with ethyl acetate. The organic layer was washed with water and saturated aqueous sodium chloride, dried over anhydrous magnesium sulfate, and filtered. The filtrate was concentrated under a reduced pressure to obtain the title compound (1.20 g) as a crude product.

$^1$H-NMR Spectrum (DMSO-d$_6$) δ (ppm): 5.30 (2H, s), 7.02-7.05 (1H, m), 7.14-7.18 (1H, m), 7.36-7.39 (1H, m), 7.54 (1H, d, J=7.6 Hz), 7.85-7.89 (1H, m), 7.93 (1H, t, J=8.8 Hz), 8.06 (2H, s), 8.59-8.61 (1H, m).

Manufacturing Example 95-1-3

2-(3-Fluoro-4-(2-nitro-ethyl)-phenoxymethyl)-pyridine

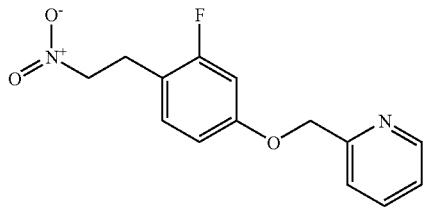

To a dimethyl sulfoxide (20.0 mL) solution of 2-(3-fluoro-4-((E)-2-nitro-vinyl)-phenoxymethyl)pyridine (1.20 g) described in Manufacturing Example 95-1-2 and acetic acid (1.00 mL) was added sodium borohydride (249 mg, 6.57 mmol) at room temperature while cooling appropriately under nitrogen atmosphere, which was stirred for 30 minutes at room temperature. Water was then added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under a reduced pressure, followed by crystallization with an ethyl acetate-heptane system and filtration to obtain the title compound (614 mg, 50.7%).

$^1$H-NMR Spectrum (DMSO-$d_6$) δ (ppm): 3.21 (2H, t, J=7.2 Hz), 4.79 (2H, t, J=7.2 Hz), 5.46 (2H, s), 6.82 (1H, dd, J=2.4, 8.4 Hz), 6.92 (1H, dd, J=2.4, 8.4 Hz), 7.32 (1H, t, J=8.8 Hz), 7.66 (1H, t, J=6.4 Hz), 7.87 (1H, d, J=8.0 Hz), 8.21-8.25 (1H, m), 8.76 (1H, d, J=5.6 Hz).

Example 96

3-(3-(2-Fluoro-4-(5-fluoro-pyridin-2-ylmethoxy)-benzyl)-isoxazol-5-yl)-pyridin-2-ylamine

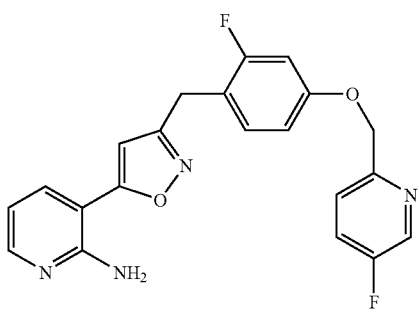

To a tetrahydrofuran (5.00 mL) solution of (2-fluoro-4-(5-fluoro-pyridin-2-ylmethoxy)-phenyl)-acetohydroximoyl chloride (170 mg, 0.554 mmol) described in Manufacturing Example 96-1-4 and 3-ethynyl-pyridin-2-ylamine (40.0 mg, 0.339 mmol) described in Manufacturing Example 1-2-3 was added triethylamine (142 μL, 1.02 mmol) at room temperature, which was stirred for 4 hours at room temperature. Water was added to the reaction solution at room temperature, which was then extracted with ethyl acetate. The organic layer was washed with saturated aqueous sodium chloride and dried over anhydrous magnesium sulfate, and the solvent was devaporated under a reduced pressure. The residue was purified by NH silica gel column chromatography (ethyl acetate:heptane=1:3→1:2) to obtain the title compound (32.0 mg, 23.9%).

$^1$H-NMR Spectrum (DMSO-$d_6$) δ (ppm): 3.99 (2H, s), 5.18 (2H, s), 6.26 (2H, brs), 6.68-6.71 (1H, m), 6.77 (1H, s), 6.86 (1H, dd, J=2.4, 8.4 Hz), 6.96 (1H, dd, J=2.4, 12.0 Hz), 7.31 (1H, t, J=8.8 Hz), 7.61 (1H, dd, J=4.8, 8.8 Hz), 7.78 (1H, ddd, J=2.8, 8.4, 17.2 Hz), 7.87 (1H, dd, J=1.6, 7.6 Hz), 8.08 (1H, dd, J=1.6, 7.6 Hz), 8.59 (1H, d, J=2.8 Hz).

The starting material, (2-fluoro-4-(5-fluoro-pyridin-2-ylmethoxy)-phenyl)-acetohydroximoyl chloride, was synthesized as follows.

Manufacturing Example 96-1-1

2-Fluoro-4-(5-fluoro-pyridin-2-ylmethoxy)-benzaldehyde

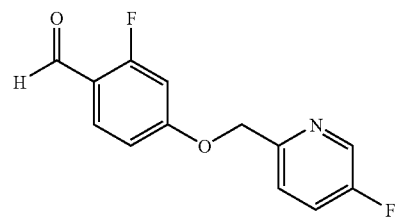

To an N,N-dimethylformamide (20.0 mL) solution of 2-fluoro-4-hydroxy-benzaldehyde (1.48 g, 10.2 mmol) was added sodium hydride (411 mg, 10.3 mmol, 60% in oil) under nitrogen atmosphere at 0° C., which was stirred for 20 minutes at room temperature. 2-Chloromethyl-5-fluoro-pyridine (1.20 g, 8.56 mmol) described in Manufacturing Example 41-1-2 was then added at room temperature, and stirred for 30 minutes at 80° C. Water was added at room temperature to the reaction solution, which was then extracted with ethyl acetate. The organic layer was washed with saturated aqueous sodium chloride, and the solvent was evaporated under a reduced pressure. The residue was purified by silica gel column chromatography (ethyl acetate:heptane=1:5→1:2) to obtain the title compound (901 mg, 42.2%).

$^1$H-NMR Spectrum (CDCl$_3$) δ (ppm): 5.24 (2H, s), 6.73-6.77 (1H, m), 6.87-6.89 (1H, m), 7.46-7.51 (2H, m), 7.84 (1H, t, J=8.4 Hz), 8.48 (1H, d, J=2.8 Hz), 10.22 (1H, s).

Manufacturing Example 96-1-2

5-Fluoro-2-(3-fluoro-4-((E)-2-nitro-vinyl)-phenoxymethyl)-pyridine

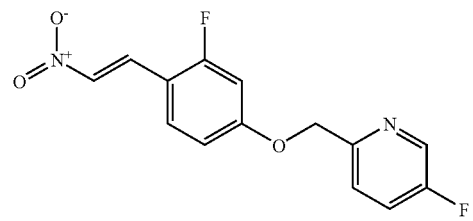

To an acetic acid (20.0 mL) solution of 2-fluoro-4-(5-fluoro-pyridin-2-ylmethoxy)-benzaldehyde (901 mg, 3.62 mmol) described in Manufacturing Example 96-1-1 were added nitromethane (1.10 g, 18.1 mmol) and ammonium acetate (558 mg, 7.24 mmol) under nitrogen atmosphere, which was stirred for 2 hours at 110° C. Water and ethyl acetate were added to the reaction mixture, and the organic layer was extracted with ethyl acetate. The organic layer was washed with water and saturated aqueous sodium chloride, dried over anhydrous magnesium sulfate, and filtered. The filtrate was concentrated under a reduced pressure to obtain the title compound (1.00 g) as a crude product.

$^1$H-NMR Spectrum (DMSO-$d_6$) δ (ppm): 5.30 (2H, s), 7.04 (1H, dd, J=2.4, 8.8 Hz), 7.17 (1H, dd, J=2.4, 7.2 Hz), 7.63-7.66 (1H, m), 7.78-7.83 (1H, m), 7.93 (1H, d, J=8.4 Hz), 8.06 (2H, s), 8.61 (1H, d, J=2.8 Hz).

Manufacturing Example 96-1-3

5-Fluoro-2-(3-fluoro-4-(2-nitro-ethyl)-phenoxymethyl)-pyridine

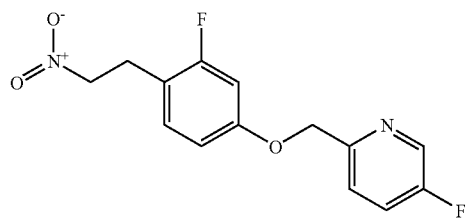

To a dimethyl sulfoxide (20.0 mL)-tetrahydrofuran (5.00 mL) solution of 5-fluoro-2-(3-fluoro-4-((E)-2-nitro-vinyl)-phenoxymethyl)-pyridine (1.00 g, 3.42 mmol) described in Manufacturing Example 96-1-2 and acetic acid (1.00 mL) was added sodium borohydride (207 mg, 5.47 mmol) at room temperature while cooling appropriately under nitrogen atmosphere, which was stirred for 10 minutes at room temperature. Water was then added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under a reduced pressure, and the residue was crystallized with an ethyl acetate:heptane system and filtered to obtain the title compound (346 mg, 34.4%).

$^1$H-NMR Spectrum (DMSO-$d_6$) δ (ppm): 3.20 (2H, t, J=6.8 Hz), 4.79 (2H, t, J=6.8 Hz), 5.17 (2H, s), 6.84 (1H, dd, J=2.4, 8.4 Hz), 6.94 (1H, dd, J=2.4, 12.0 Hz), 7.27 (1H, t, J=8.8 Hz), 7.61 (1H, dd, J=4.4, 8.8 Hz), 8.78 (1H, ddd, J=2.8, 8.8, 17.6 Hz), 8.58-8.59 (1H, m).

Manufacturing Example 96-1-4

(2-Fluoro-4-(5-fluoro-pyridin-2-ylmethoxy)-phenyl)-acetohydroximoyl chloride

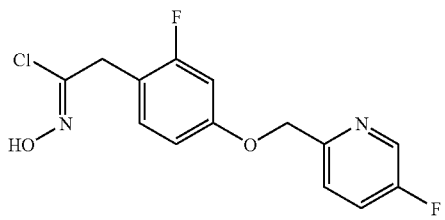

To a methanol (20.0 mL) solution of 5-fluoro-2-(3-fluoro-4-(2-nitro-ethyl)-phenoxymethyl)-pyridine (346 mg, 1.18 mmol) described in Manufacturing Example 96-1-3 was added lithium methoxide (89.6 mg, 2.36 mmol) under nitrogen atmosphere at room temperature, which was stirred for 30 minutes at room temperature. The reaction mixture was concentrated under a reduced pressure, and anhydrous dichloromethane (20.0 mL) and anhydrous tetrahydrofuran (10.0 mL) were added to the residue. Titanium (IV) chloride (584 μL, 5.30 mmol) was added dropwise into the reaction mixture on a dry ice-ethanol bath (−78° C.), which was stirred for 60 minutes at room temperature. Water, ethyl acetate and tetrahydrofuran were added to the reaction mixture on an ice bath (0° C.), and the organic layer was extracted with ethyl acetate. This organic layer was washed with water and saturated aqueous sodium chloride, dried over anhydrous magnesium sulfate, and filtered. The filtrate was concentrated under a reduced pressure to obtain the title compound (300 mg, 81.3%) as a crude product.

$^1$H-NMR Spectrum (DMSO-$d_6$) δ (ppm): 3.79 (2H, s), 5.19 (2H, s), 6.87 (1H, dd, J=2.4, 8.4 Hz), 6.95 (1H, dd, J=2.8, 12.0 Hz), 7.26 (1H, t, J=8.8 Hz), 7.62 (1H, dd, J=4.4, 8.8 Hz), 7.78 (1H, ddd, J=3.2, 8.8, 13.6 Hz), 8.59 (1H, dd, J=0.4, 2.8 Hz), 11.72 (1H, s).

Example 97

3-(3-(6-Phenylsulfanyl-pyridin-3-ylmethyl)-isoxazol-5-yl)-pyridin-2-ylamine

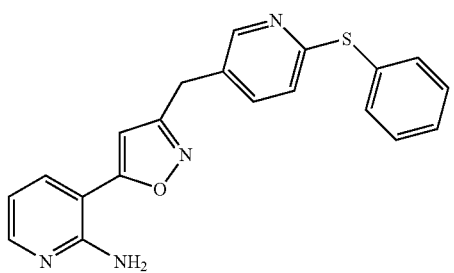

To a tetrahydrofuran (5 mL) solution of (6-phenylsulfanyl-pyridin-3-yl)-acetohydroximoyl chloride (149 mg, 0.54 mmol) described in Manufacturing Example 97-1-4 and 3-ethynyl-pyridin-2-ylamine (15 mg, 0.13 mmol) described in Manufacturing Example 1-2-3 was added triethylamine (80 μL, 0.57 mmol), which was stirred for 4 hours at 50° C. under nitrogen atmosphere. Water was added to the reaction solution at room temperature, which was then extracted with ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (ethyl acetate:methanol=10:1) and then further purified by silica gel column chromatography (ethyl acetate:methanol=10:1) to obtain the title compound (11 mg, 23%).

$^1$H-NMR Spectrum (CDCl$_3$) δ (ppm): 3.99 (2H, s), 5.39 (2H, s), 6.24 (1H, s), 7.72 (1H, dd, J=4.8, 7.7 Hz), 6.87 (1H, d, J=8.2 Hz), 7.38 (1H, dd, J=2.4, 8.2 Hz), 7.40-7.43 (3H, m), 7.58-7.60 (2H, m), 7.70 (1H, dd, J=1.8, 7.7 Hz), 8.15 (1H, dd, J=1.8, 4.8 Hz), 8.40 (1H, d, J=2.4 Hz).

The starting material, (6-phenylsulfanyl-pyridin-3-yl)-acetohydroximoyl chloride, was synthesized as follows.

Manufacturing Example 97-1-1

5-Bromo-2-phenylsulfanyl-pyridine

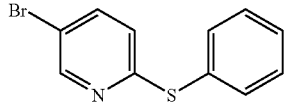

To an N,N-dimethylformamide (20 mL) solution of thiophenol (1.02 g, 9.28 mmol) was added sodium hydride (446 mg, 9.28 mmol, 50% in oil), which was stirred for 15 minutes at room temperature. 2,5-Dibromopyridine (2.00 g, 8.44 mmol) was then added to this reaction mixture and stirred for 35 minutes at room temperature, and then for a further 45 minutes at 55° C. Water was added to the reaction solution at room temperature, which was then extracted with ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (heptane:ethyl acetate:=4:1) to obtain the title compound (2.24 g, quant.).

$^1$H-NMR Spectrum (CDCl$_3$) δ (ppm): 6.78 (1H, dd, J=0.73, 8.4 Hz), 7.42-7.45 (3H, m), 7.56-7.60 (3H, m), 8.47 (1H, dd, J=0.73, 2.6 Hz).

Manufacturing Example 97-1-2

6-Phenylsulfanyl-pyridine-3-carbaldehyde

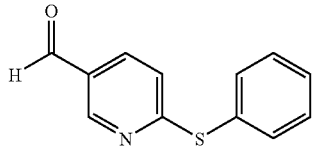

To a tetrahydrofuran (40 mL) solution of 5-bromo-2-phenylsulfanyl-pyridine (2.24 g, 8.42 mmol) described in Manufacturing Example 97-1-1 was added n-butyl lithium (6.35 mL, 1.6 M hexane solution, 10.1 mmol) under nitrogen atmosphere at −78° C., which was stirred for 45 minutes at −78°. Next, N,N-dimethylformamide (848 μL, 10.9 mmol) was added to this reaction mixture, and stirred for 35 minutes as the temperature was gradually raised to room temperature. Water was added to the reaction solution at room temperature, which was then extracted with ethyl acetate. The organic layer was separated, washed with saturated aqueous sodium chloride, dried over anhydrous magnesium sulfate, and filtered. The filtrate was concentrated under a reduced pressure, and the residue was purified by silica gel column chromatography (heptane:ethyl acetate=2:1) to obtain the title compound (583 mg, 32%).

$^1$H-NMR Spectrum (CDCl$_3$) δ (ppm): 6.94 (1H, d, J=8.4 Hz), 7.48-7.52 (3H, m), 7.62-7.65 (2H, m), 7.89 (1H, dd, J=2.4, 8.4 Hz), 8.82 (1H, dd, J=0.73, 2.2 Hz), 9.98 (1H, s).

Manufacturing Example 97-1-3

5-(2-Nitro-ethyl)-2-phenylsulfanyl-pyridine

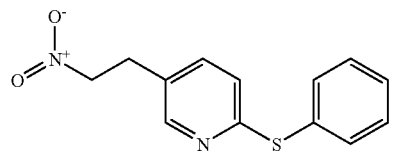

To an acetic acid (10 mL) solution of 6-phenylsulfanyl-pyridine-3-carbaldehyde (583 mg, 2.71 mmol) described in Manufacturing Example 97-1-2 were added nitromethane (734 μL, 13.6 mmol) and ammonium acetate (418 mg, 5.42 mmol), and which was stirred for 4 hours 35 minutes at 100° C. under nitrogen atmosphere. Water was added to the reaction solution at room temperature, which was then extracted with ethyl acetate. The organic layer was separated, washed with saturated aqueous sodium chloride, dried over anhydrous magnesium sulfate, and filtered. The filtrate was concentrated under a reduced pressure. To a dimethyl sulfoxide (10 mL) and acetic acid (1 mL) solution of the residue was added sodium borohydride (205 mg, 5.42 mmol), which was stirred for 55 minutes at room temperature. Sodium hydrogencarbonate and water were added to the reaction mixture at room temperature while cooling appropriately, which was then extracted with ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (212 mg, 30%).

$^1$H-NMR Spectrum (CDCl$_3$) δ (ppm): 3.27 (2H, t, J=6.6 Hz), 4.60 (2H, t, J=6.6 Hz), 6.71 (1H, d, J=8.6 Hz), 7.39 (1H, d, J=8.4 Hz), 7.50-7.58 (3H, m), 7.62-7.64 (2H, m), 8.57 (1H, s).

Manufacturing Example 97-1-4

(6-Phenylsulfanyl-pyridin-3-yl)-acetohydroximoyl chloride

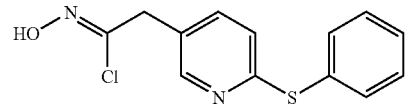

To a methanol (5 mL) solution of 5-(2-nitro-ethyl)-2-phenylsulfanyl-pyridine (212 mg, 0.814 mmol) described in Manufacturing Example 97-1-3 was added lithium methoxide (62 mg, 1.6 mmol), which was stirred for 5 minutes at room temperature. The reaction mixture was concentrated under a reduced pressure, and the residue was suspended in tetrahydrofuran (3 mL) and methylene chloride (3 mL). Titanium (IV) tetrachloride (197 μL, 1.8 mmol) was added to this suspension under a nitrogen atmosphere at −78° C., which was stirred for 1 hour and 30 minutes at 0° C. The mixture was then stirred for another 50 minutes at room temperature, after which water was added at 0° C. to the reaction mixture, which was then extracted with ethyl acetate. The organic layer was separated, washed with saturated aqueous sodium chloride, dried over anhydrous magnesium sulfate, and then filtered. The filtrate was concentrated under a reduced pressure to obtain the title compound (249 mg, quant.). This compound was used in the following reaction without any further purification.

Example 98

3-(3-(4-(3-Methoxy-benzyloxy)-benzyl)-isoxazol-5-yl)-pyridin-2-ylamine

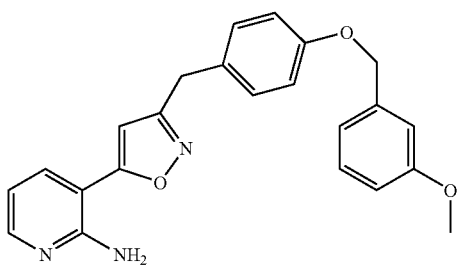

To 4-(5-(2-amino-pyridin-3-yl)-isoxazol-3-ylmethyl)-phenol (30 mg, 0.11 mmol) described in Manufacturing Example 5-1-1 were tetrahydrofuran (3 mL) and a 5N sodium hydroxide aqueous solution (22.4 μL, 0.11 mmol), which was dissolved by irradiating ultrasonic wave for 1 minute. The reaction solution was then concentrated under a reduced pressure, which gave a white solid. To a suspension of this solid in N,N-dimethylformamide (1 mL) was added an N,N-dimethylformamide (1 mL) solution of 3-methoxybenzyl chloride (21.0 mg, 0.13 mmol), which was stirred for 12 hours at 60° C. This mixture was cooled to room temperature and partitioned into water and ethyl acetate. The organic layer was separated, washed with water and saturated aqueous sodium chloride, dried over anhydrous magnesium sulfate, and filtered. The filtrate was concentrated under a reduced pressure, and this residue was purified by NH silica gel column chromatography (heptane:ethyl acetate=1:1) to obtain the title compound (35.1 mg, 81%).

$^1$H-NMR Spectrum (DMSO-$d_6$) δ (ppm): 3.75 (3H, s), 3.95 (2H, s), 5.05 (2H, s), 6.25 (2H, brs), 6.67-6.71 (1H, m), 6.78 (1H, s), 6.86-6.90 (1H, m), 6.96 (1H, d, J=8.4 Hz), 6.97-7.00 (2H, m), 7.24 (2H, d, J=8.8 Hz), 7.29 (1H, t, J=8.0 Hz), 7.85-7.88 (1H, m), 8.07-8.10 (1H, m).

Example 99

3-(3-(4-(6-Methoxy-pyridin-2-ylmethoxy)-benzyl)-isoxazol-5-yl)-pyridin-2-ylamine

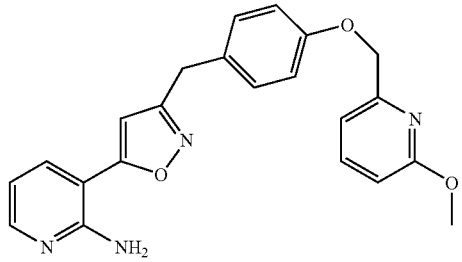

Tetrahydrofuran (3 mL) and a 5N sodium hydroxide aqueous solution (22.4 μL, 0.11 mmol) were added to 4-(5-(2-amino-pyridin-3-yl)-isoxazol-3-ylmethyl)-phenol (30 mg, 0.11 mmol) described in Manufacturing Example 5-1-1, which was dissolved by irradiating ultrasonic wave for 1 minute. The reaction solution was then concentrated under a reduced pressure, which gave a white solid. To a suspension of this solid in N,N-dimethylformamide (1 mL) was added an N,N-dimethylformamide (1 mL) solution of the 2-chloromethyl-6-methoxy-pyridine (21.2 mg, 0.13 mmol) described in Manufacturing Example 99-1-2, which was stirred for 12 hours at 60° C. This reaction mixture was cooled to room temperature and partitioned into water and ethyl acetate. The organic layer was separated, washed with water and saturated aqueous sodium chloride, dried over anhydrous magnesium sulfate, and filtered. The filtrate was concentrated under a reduced pressure, and this residue was purified by NH silica gel column chromatography (heptane:ethyl acetate=1:1) to obtain the title compound (36.7 mg, 84%).

$^1$H-NMR Spectrum (DMSO-$d_6$) δ (ppm): 3.85 (3H, s), 3.96 (2H, s), 5.07 (2H, s), 6.25 (2H, brs), 6.69 (1H, dd, J=4.8, 7.6 Hz), 6.75 (1H, d, 8.0 Hz), 6.79 (1H, s), 6.99 (2H, d, J=8.8 Hz), 7.07 (1H, d, J=7.2 Hz), 7.25 (2H, d, J=8.8 Hz), 7.69-7.74 (1H, m), 7.85-7.88 (1H, m), 8.08 (1H, dd, J=2.0, 4.8 Hz).

The starting material, 2-chloromethyl-6-methoxy-pyridine, was synthesized as follows.

Manufacturing Example 99-1-1

(6-Methoxy-pyridin-2-yl)-methanol

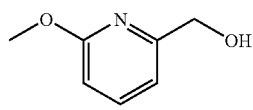

To a mixture of 2-bromo-6-methoxypyridine (500 mg, 2.66 mmol) and toluene (20 mL) was added dropwise n-butyl lithium (1.84 mL, 1.6 M hexane solution, 2.93 mmol) at −78° C., which was stirred for 30 minutes. N,N-dimethylformamide (412 μL, 5.32 mmol) was added dropwise to the mixture at the same temperature, which was stirred for 45 minutes at 0° C. Water and tetrahydrofuran were added to the reaction solution and vigorously stirred. The organic layer was separated, washed with water and saturated aqueous sodium chloride, dried over anhydrous magnesium sulfate, and filtered.

Sodium borohydride (201 mg, 5.31 mmol) was added to this filtrate at 0° C., which was stirred for 2 hours at room temperature. Water was added to the reaction solution, which was then exacted with ethyl acetate. The organic layer was separated, washed with saturated aqueous sodium chloride, dried with anhydrous magnesium sulfate, and then dried. This filtrate was concentrated under a reduced pressure, and the residue was purified by NH silica gel column chromatography (hexane:diethyl ether=2:1) to obtain the title compound (104.8 mg, 28%).

$^1$H-NMR Spectrum (DMSO-$d_6$) δ (ppm): 3.81 (3H, s), 4.47 (2H, d, J=6.0 Hz), 5:34 (1H, t, J=5.6, 6.0 Hz), 6.65 (1H, dd, J=0.8, 8.4 Hz), 7.03-7.05 (1H, m), 7.68 (1H, dd, J=7.2, 8.0 Hz).

Manufacturing Example 99-1-2

2-Chloromethyl-6-methoxy-pyridine

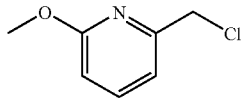

To a mixture of dichloromethane (5 mL) and the (6-methoxy-pyridin-2-yl)-methanol (105 mg, 0.75 mmol) described in Manufacturing Example 99-1-1 was added thionyl chloride (82.4 μL, 1.13 mmol), which was stirred for 30 minutes at room temperature. A saturated sodium hydrogencarbonate aqueous solution was added to this reaction mixture, which was then extracted with dichloromethane. The organic layer was separated, washed with water and saturated aqueous sodium chloride, dried over anhydrous magnesium sulfate, and filtered. The filtrate was concentrated under a reduced pressure to obtain the title compound (105.8 mg, 89%).

$^1$H-NMR Spectrum (DMSO-$d_6$) δ (ppm): 3.85 (3H, s), 4.69 (2H, s), 7.79 (1H, dd, J=0.4, 8.4 Hz), 7.12 (1H, dd, J=0.4, 7.2 Hz), 7.73 (1H, dd, J=7.2, 8.4 Hz).

Example 100

3-(3-(6-(Pyridin-3-yloxy)-pyridin-3-ylmethyl)-isoxazol-5-yl)-pyrindin-2-ylamine

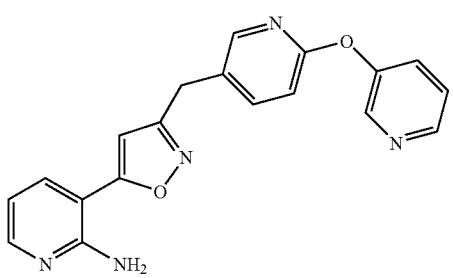

To a mixture of 5-(2-nitroethyl)-2-(pyrdin-3-yloxy)pyridine (157.0 mg, 0.64 mmol) described in Manufacturing Example 100-1-2 and methanol (6 mL) was added lithium methoxide (48.7 mg, 1.28 mmol), which was stirred for 1 hour at room temperature. The reaction solution was concentrated under a reduced pressure, which gave a white solid. To a mixture of a dichloromethane (4 mL) and tetrahydrofuran (2 mL) solution of this solid was added titanium tetrachloride (155.0 μL, 1.41 mmol) under nitrogen atmosphere at −78° C., which was stirred for another 3 hours at 0° C. Water was added to the reaction solution, which was then extracted with ethyl acetate. The organic layer was separated, washed with water and saturated aqueous sodium chloride, dried over anhydrous magnesium sulfate, and filtered. The filtrate was concentrated under a reduced pressure. To a mixture of the residue thus obtained (30.7 mg), 3-ethynyl-pyridin-2-ylamine (13.7 mg, 0.12 mmol) described in Manufacturing Example 1-2-3, tetrahydrofuran (1 mL), and dimethyl sulfoxide (1 mL) was added triethylamine (32.4 μL, 0.23 mmol) at room temperature, which was stirred for 1 hour at 55° C. The reaction mixture was cooled to room temperature, water was added thereto, which was then extracted with ethyl acetate. The organic layer was separated, washed with water and saturated aqueous sodium chloride, dried over anhydrous magnesium sulfate, and filtered. The filtrate was concentrated under a reduced pressure, and the residue thus obtained was purified by reverse-phase high performance liquid chromatography (using an acetonitrile-water mobile phase containing 0.1% trifluoroacetic acid), and then further purified by preparative thin-layer chromatography (NH silica gel, ethyl acetate) to obtain the title compound (1.41 mg, 4%).

$^1$H-NMR Spectrum (CDCl$_3$) δ (ppm): 4.03 (2H, s), 5.39 (2H, brs), 6.28 (1H, s), 6.73 (1H, ddd, J=0.8, 4.8, 7.6 Hz), 6.98 (1H, d, J=8.4 Hz), 7.35 (1H, dd, J=4.8, 8.0 Hz), 7.51-7.54 (1H, m), 7.67 (1H, ddd, J=0.2, 2.4, 8.4 Hz), 7.71 (1H, dd, J=2.0, 7.6 Hz), 8.11 (1H, d, J=2.8 Hz), 8.15-8.17 (1H, m), 8.46 (1H, d, J=4.4 Hz), 8.50 (1H, d, J=2.4 Hz).

The starting material, 5-(2-nitroethyl)-2-(pyridin-3-yloxy) pyridine, was synthesized as follows.

Manufacturing Example 100-1-1

6-(Pyridin-3-yloxy)-pyridine-3-carbaldehyde

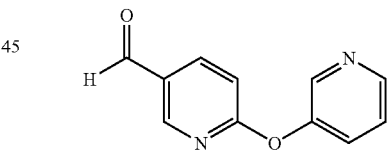

To a suspension of sodium hydride (407 mg, 8.48 mmol, 50% in oil) and N,N-dimethylformamide (45 mL) was added an N,N-dimethylformamide (5 mL) solution of 3-hydroxy-pyridine (806 mg, 8.48 mmol) at 0° C., which was stirred for 30 minutes. An N,N-dimethylformamide (5 mL) solution of 2-chloro-5-formylpyridine (1.0 g, 7.06 mmol) was added to this reaction mixture at the same temperature, which was stirred for 5 hours at 100° C. The reaction mixture was cooled to room temperature, and water was added thereto, which was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate) to obtain the title compound (505.1 mg, 36%).

¹H-NMR Spectrum (DMSO-d₆) δ (ppm): 7.32-7.36 (1H, m), 7.53 (1H, ddd, J=0.8, 4.8, 8.4 Hz), 7.72-7.75 (1H, m), 8.30-8.34 (1H, m), 8.50-8.54 (2H, m), 8.70-8.72 (1H, m), 10.01 (1H, s).

Manufacturing Example 100-1-2

5-(2-Nitroethyl)-2-(pyridin-3-yloxy)pyridine

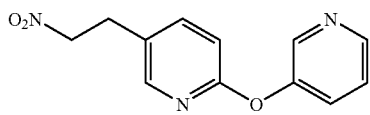

A mixture of 6-(pyridin-3-yloxy)-pyridine-3-carbaldehyde (505.1 mg, 2.52 mmol) described in Manufacturing Example 100-1-1, nitromethane (680 μL, 12.6 mmol), ammonium acetate (388 mg, 5.04 mmol), and acetic acid (20 mL) was stirred for 2.5 hours at 140° C. This reaction mixture was cooled to room temperature and partitioned into water and ethyl acetate. The organic layer was separated, washed with water and saturated aqueous sodium chloride, dried over anhydrous magnesium sulfate, and filtered. The filtrate was concentrated under a reduced pressure. To a mixture of this residue in dimethyl sulfoxide (20 mL) and acetic acid (2 mL) was added sodium borohydride (114.0 mg, 3.02 mmol) at room temperature, which was stirred for 15 minutes. Water was added to this reaction mixture, which was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by silica gel column chromatography (heptane:ethyl acetate=2:1) to obtain the title compound (157.3 mg, 26%).

¹H-NMR Spectrum (DMSO-d₆) δ (ppm): 3.23 (2H, t, J=6.8 Hz), 4.88 (2H, t, J=6.8 Hz), 7.18-7.22 (1H, m), 7.77 (1H, dd, J=5.6, 8.4 Hz), 7.90 (1H, dd, J=2.4, 8.4 Hz), 8.02-8.07 (1H, m), 8.07-8.10 (1H, m), 8.45 (1H, d, J=6.0 Hz), 8.51 (1H, d, J=2.8 Hz).

Example 101

3-(3-(4-(5-Methyl-pyridin-2-yloxy)-benzyl)-isoxazol-5-yl)-pyridin-2,6-diamine

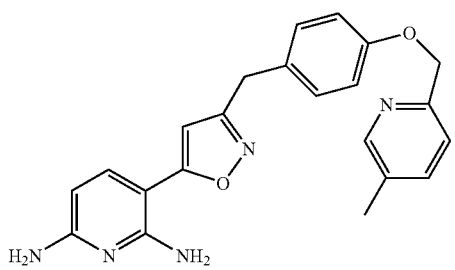

The title compound (120 mg, 57%) was obtained according to the methods similar to those of Example 18, using 4-(5-(2,6-diamino-pyridin-3-yl)-isoxazol-3-ylmethyl)-phenol (150 mg, 0.53 mmol) described in Manufacturing Example 18-1-1 and 2-chloromethyl-5-methyl-pyridine (90 mg, 0.64 mmol) described in Manufacturing Example 42-1-2.

¹H-NMR Spectrum (DMSO-d₆) δ (ppm): 2.29 (3H, s), 3.87 (2H, s), 5.10 (2H, s), 5.78 (2H, brs), 5.82 (1H, d, J=8.0 Hz), 6.10 (2H, brs), 6.34 (1H, s), 6.95 (2H, d, J=8.8 Hz), 7.21 (2H, d, J=8.8 Hz), 7.38 (1H, d, J=8.0 Hz), 7.50 (1H, d, J=8.0 Hz), 7.62 (1H, d, J=8.0 Hz), 8.40 (1H, s).

Example 102

3-(3-(4-(4-Methyl-pyridin-2-yloxymethyl)-benzyl)-isoxazol-5-yl)-pyridin-2,6-diamine

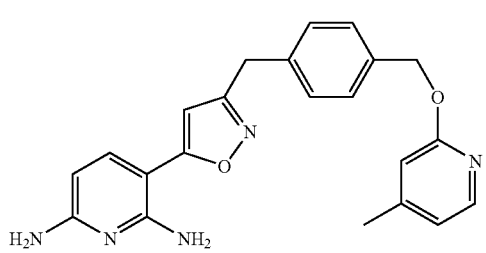

To a tetrahydrofuran (5.00 mL) solution of (4-(4-methyl-pyridin-2-yloxymethyl)-phenyl)-acetohydroximoyl chloride (130 mg, 0.447 mmol) described in Manufacturing Example 43-1-5 and 3-ethynyl-pyridin-2,6-diamine (30.0 mg, 0.226 mmol) described in Manufacturing Example 13-1-3 was added triethylamine (126 μL, 0.903 mmol) at room temperature, which was stirred for 1 hour at room temperature. Water was added to the reaction solution at room temperature, which was extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=2:1) to obtain the title compound (37.4 mg, 42.7%).

¹H-NMR Spectrum (DMSO-d₆) δ (ppm): 2.26 (3H, s), 3.95 (2H, s), 5.30 (2H, s), 5.79 (2H, brs), 5.83 (2H, d, J=8.4 Hz), 6.11 (1H, brs), 6.37 (1H, s), 6.67-6.68 (1H, m), 6.81-6.83 (1H, m), 7.30 (2H, d, J=8.0 Hz), 7.38 (2H, d, J=8.0 Hz), 7.51 (1H, d, J=8.4 Hz), 8.08-8.09 (1H, d, J=5.2 Hz).

Example 103

3-(3-(4-(5-Methyl-pyridin-2-yloxymethyl)-benzyl)-isoxazol-5-yl)-pyridin-2,6-diamine

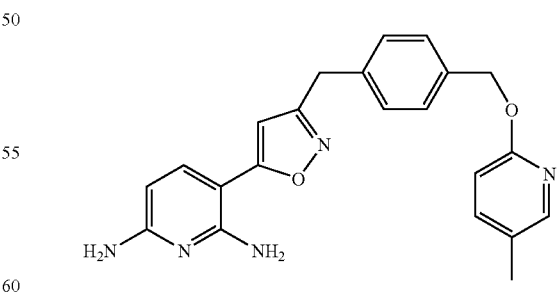

To a tetrahydrofuran (5.00 mL) solution of (4-(5-methyl-pyridin-2-yloxymethyl)-phenyl)-acetohydroximoyl chloride (130 mg, 0.447 mmol) described in Manufacturing Example 44-1-5 and 3-ethynyl-pyridin-2,6-diamine (30.0 mg, 0.226 mmol) described in Manufacturing Example 13-1-3 was added triethylamine (126 μL, 0.903 mmol) at room temperature, which was stirred for 2 hours at room temperature. Water was added to the reaction solution at room temperature, which was extracted with ethyl acetate. The organic layer was washed with saturated sodium chloride solution and dried over anhydrous magnesium sulfate, and the solvent was evaporated under a reduced pressure. The residue was purified by NH silica gel column chromatography (ethyl acetate: heptane=2:1) to obtain the title compound (57.4 mg, 65.6%).

¹H-NMR Spectrum (DMSO-d₆) δ (ppm): 2.20 (3H, s), 3.95 (2H, s), 5.28 (2H, s), 5.79 (2H, brs), 5.82 (1H, d, J=8.4 Hz), 6.11 (2H, brs), 6.36 (1H, s), 6.76 (1H, d, J=8.4 Hz), 7.30 (2H, d, J=8.4 Hz), 7.38 (2H, d, J=8.0 Hz), 7.51 (1H, d, J=8.4 Hz), 7.53-7.55 (1H, m), 7.96-7.97 (1H, m).

Example 104

3-(3-(4-(6-Fluoro-pyridin-2-ylmethoxy)-benzyl)-isoxazol-5-yl)-pyridin-2,6-diamine

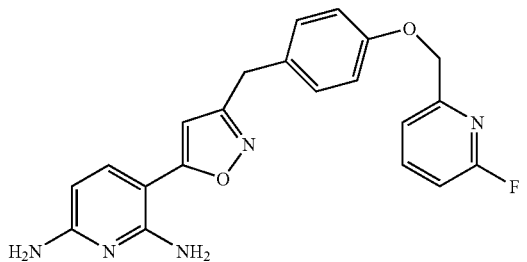

To a tetrahydrofuran (3 mL) solution of 4-(5-(2,6-diamino-pyridin-3-yl)-isoxazol-3-ylmethyl)-phenol (40 mg, 0.14 mmol) described in Manufacturing Example 18-1-1 was added a 5 N sodium hydroxide aqueous solution (28.3 μL, 0.14 mmol), which was dissolved by irradiating ultrasonic wave for 1 minute. The reaction solution was concentrated under a reduced pressure, which gave a white solid. To a suspension of this solid in N,N-dimethylformamide (1 mL) was added an N,N-dimethylformamide (1 mL) solution of 2-chloromethyl-6-fluoro-pyridine (52.7 mg, 0.36 mmol) described in manufacturing Example 45-1-1, which was stirred for 14 hours at room temperature. The reaction mixture was partitioned into water and ethyl acetate. The organic layer was separated, washed with water and saturated aqueous sodium chloride, dried over anhydrous magnesium sulfate, and filtered. The filtrate was concentrated under a reduced pressure. The residue was purified by NH silica gel column chromatography (heptane:ethyl acetate=1:2), and then further purified by reverse-phase high performance liquid chromatography (using an acetonitrile-water mobile phase containing 0.1% trifluoroacetic acid) to obtain the title compound (7.8 mg, 11%) as a trifluoroacetic acid salt.

¹H-NMR Spectrum (CD₃OD) δ (ppm): 3.96 (2H, s), 5.08 (2H, s), 6.15 (1H, d, J=8.8 Hz), 6.42 (1H, s), 6.96 (2H, d, J=8.8 Hz), 6.96-7.00 (1H, m), 7.23 (2H, d, J=8.4 Hz), 7.43-7.46 (1H, m), 7.90 (1H, d, J=8.8 Hz), 7.94 (1H, q, J=8.4, 7.6 Hz).

MS m/e (ESI) 391.99 (MH⁺)

Example 105

3-(3-(4-(5-Methyl-furan-2-ylmethyl)-benzyl)-isoxazol-5-yl)-pyridin-2,6-diamine

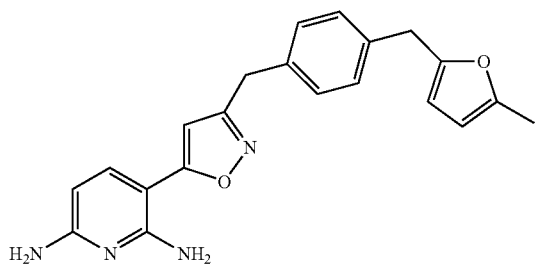

To a mixture of (4-(5-methyl-furan-2-ylmethyl)-phenyl)-acetohydroximoyl chloride (11 mg, 0.043 mmol) described in Manufacturing Example 46-1-6 and tetrahydrofuran (1 mL) were added 3-ethynyl-pyridin-2,6-diamine (4.5 mg, 0.034 mmol) described in Manufacturing Example 13-1-3 and triethylamine (9.4 μL, 0.068 mmol), which was stirred for 3 hours at 40° C. Water was added thereto at the same temperature, which was extracted with ethyl acetate. The organic layer was washed with saturated aqueous sodium chloride, and was concentrated under a reduced pressure. The residue was purified by NH silica gel column chromatography (ethyl acetate:heptane=3:2) to obtain the title compound (9.2 mg, 76%).

¹H-NMR Spectrum (CDCl₃) δ (ppm): 2.24 (3H, s), 3.89 (2H, s), 3.98 (2H, s), 4.53 (2H, br s), 5.31 (2H, br s), 5.84-5.87 (2H, m), 5.91 (1H, d, J=8.2 Hz), 5.99 (1H, s), 7.20 (4H, d, J=2.4 Hz), 7.48 (1H, d, J=8.2 Hz).

Example 106

3-(3-(5-p-Tolyloxy-thiophen-2-ylmethyl)-isoxazol-5-yl)-pyridin-2,6-diamine

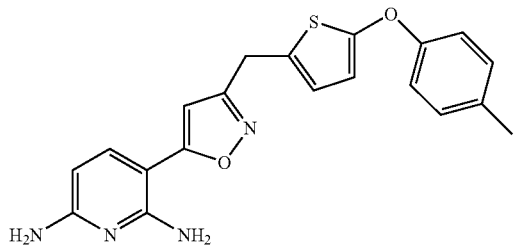

To a tetrahydrofuran (5.00 mL) solution of (5-p-tolyloxy-thiophen-2-yl)-acetohydroximoyl chloride (130 mg, 0.461 mmol) described in Manufacturing Example 48-1-5 and 3-ethynyl-pyridin-2,6-diamine (30.0 mg, 0.226 mmol) described in Manufacturing Example 13-1-3 was added triethylamine (126 μL, 0.903 mmol), which was stirred for 7 hours at 60° C. Water was added to the reaction solution at room temperature, which was extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=2:1) to obtain the title compound (12.0 mg, 14.0%).

$^1$H-NMR Spectrum (CDCl$_3$) δ (ppm): 2.27 (3H, s), 4.08 (2H, s), 5.81 (2H, brs), 5.84 (1H, d, J=8.8 Hz), 6.13 (2H, brs), 6.44 (1H, s), 6.47 (1H, d, J=3.6 Hz), 6.73 (1H, d, J=3.6 Hz), 6.98-7.01 (2H, m), 7.17-7.19 (2H, m), 7.54 (1H, d, J=8.8 Hz).

Example 107

3-(3-(4-(Pyridin-4-ylmethoxy)-benzyl)-isoxazol-5-yl)-pyridin-2,6-diamine

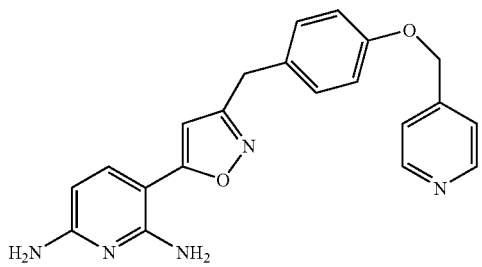

To a tetrahydrofuran (3 mL) solution of 4-(5-(2,6-diamino-pyridin-3-yl)-isoxazol-3-ylmethyl)-phenol (50 mg, 0.18 mmol) described in Manufacturing Example 18-1-1 was added a 5 N sodium hydroxide aqueous solution (35.4 μL, 0.18 mmol), which was dissolved by irraditaing ultrasonic wave for 1 minute. The reaction solution was concentrated under a reduced pressure, which gave a white solid. This solid was suspended in N,N-dimethylformamide (1 mL). Meanwhile, THF (780 μL) and a 1 N sodium hydroxide aqueous solution (780 μL, 0.78 mmol) were added to 4-(chloromethyl)pyridine hydrochloride (100 mg, 0.78 mmol), and then the organic layer was separated to obtain a tetrahydrofuran solution of 4-(chloromethyl)pyridine. A part of this solution (354 μL) was added to the above-mentioned N,N-dimethylformamide suspension and stirred for 14.5 hours at room temperature. This reaction mixture was partitioned into water and ethyl acetate. The organic layer was separated, washed with water and saturated aqueous sodium chloride, dried over anhydrous magnesium sulfate, and filtered. The filtrate was concentrated under a reduced pressure. The residue was purified by NH silica gel column chromatography (ethyl acetate) to obtain the title compound (64.6 mg, 98%).

$^1$H-NMR Spectrum (DMSO-d$_6$) δ (ppm): 3.88 (2H, s), 5.16 (2H, s), 5.79 (2H, brs), 5.82 (1H, d, J=8.4 Hz), 6.10 (2H, brs), 6.34 (1H, s), 6.97 (2H, d, J=8.4 Hz), 7.23 (2H, d, J=8.8 Hz), 7.42 (2H, d, J=5.2 Hz), 7.51 (1H, d, J=8.4 Hz), 8.56 (2H, d, J=5.2 Hz).

Example 108

3-(3-(4-(Pyridin-3-ylmethoxy)-benzyl)-isoxazol-5-yl)-pyridin-2,6-diamine

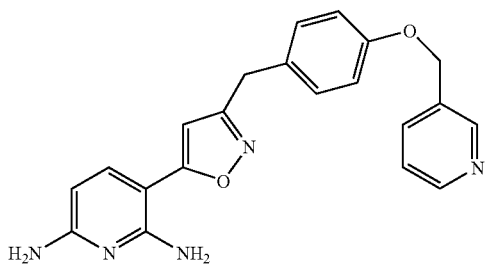

To a tetrahydrofuran (3 mL) solution of 4-(5-(2,6-diamino-pyridin-3-yl)-isoxazol-3-ylmethyl)-phenol (50 mg, 0.18 mmol) described in Manufacturing Example 18-1-1 was added a 5 N sodium hydroxide aqueous solution (35.4 μL, 0.18 mmol), which was dissolved by irradiating ultrasonic wave for 1 minute. The reaction solution was concentrated under a reduced pressure, which gave a white solid. This solid was suspended in N,N-dimethylformamide (1 mL). Meanwhile, THF (780 μL) and a 1 N sodium hydroxide aqueous solution (780 μL, 0.78 mmol) were added to 3-(chloromethyl)pyridine hydrochloride (100 mg, 0.78 mmol), and then the organic layer was separated to obtain a tetrahydrofuran solution of 3-(chloromethyl)pyridine. A part of this solution (354 μL) was added to the above-mentioned N,N-dimethylformamide suspension and stirred for 15 hours at room temperature. This reaction mixture was partitioned into water and ethyl acetate. The organic layer was separated, washed with water and saturated aqueous sodium chloride, dried over anhydrous magnesium sulfate, and filtered. The filtrate was concentrated under a reduced pressure. The residue was purified by NH silica gel column chromatography (ethyl acetate) to obtain the title compound (49.6 mg, 75%).

$^1$H-NMR Spectrum (DMSO-d$_6$) δ (ppm): 3.88 (2H, s), 5.13 (2H, s), 5.79 (2H, brs), 5.83 (1H, d, J=8.4 Hz), 6.11 (2H, brs), 6.34 (1H, s), 6.98 (2H, d, J=8.4 Hz), 7.23 (2H, d, J=8.4 Hz), 7.42 (1H, dd, J=4.8, 8.0 Hz), 7.51 (1H, d, J=8.4 Hz), 7.85 (1H, d, J=8.0 Hz), 8.54 (1H, d, J=4.8 Hz), 8.55-8.58 (1H, m).

Example 109

3-(3-(4-(4-Chloro-pyridin-2-ylmethoxy)-benzyl)-isoxazol-5-yl)-pyridin-2,6-diamine

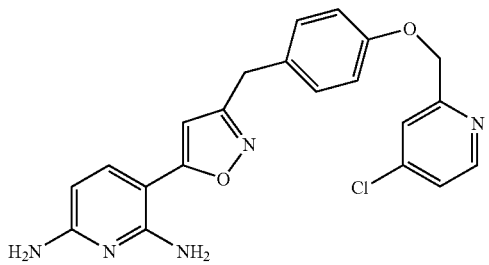

To a tetrahydrofuran (3 mL) solution of 4-(5-(2,6-diamino-pyridin-3-yl)-isoxazol-3-ylmethyl)-phenol (30 mg, 0.11 mmol) described in Manufacturing Example 18-1-1 was added a 5 N sodium hydroxide aqueous solution (21.2 µL, 0.11 mmol), which was dissolved by irradiating ultrasonic wave for 1 minute. The reaction solution was concentrated under a reduced pressure, which gave a white solid. An N,N-dimethylformamide (1 mL) solution of 4-chloro-2-chloromethyl-pyridine (34.3 mg, 0.21 mmol) described in Manufacturing Example 51-1-2 was added to a suspension of this solid in N,N-dimethylformamide (1 mL), which was stirred for 1 hour at 60° C. This reaction mixture was cooled to room temperature and then partitioned into water and ethyl acetate. The organic layer was separated, washed with water and saturated aqueous sodium chloride, dried over anhydrous magnesium sulfate, and filtered. The filtrate was concentrated under a reduced pressure. The residue was purified by NH silica gel column chromatography (heptane:ethyl acetate=1:2), and then further purified by reverse-phase high performance liquid chromatography (using an acetonitrile-water mobile phase containing 0.1% trifluoroacetic acid) to obtain the title compound (5.1 mg, 12%) as a trifluoro acetic acid salt.

$^1$H-NMR Spectrum (CD$_3$OD) δ (ppm): 3.94 (2H, s), 5.16 (2H, s), 5.95 (1H, d, J=8.4 Hz), 6.21 (1H, s), 6.98 (2H, d, J=8.8 Hz), 7.24 (2H, d, J=8.8 Hz), 7.35-7.45 (1H, m), 7.56 (1H, d, J=8.4 Hz), 7.62-7.63 (1H, m), 8.47 (1H, d, J=5.2 Hz).

MS m/e (ESI) 408.21 (MH$^+$)

Example 110

3-(3-(4-(6-Chloro-pyridin-2-ylmethoxy)-benzyl)-isoxazol-5-yl)-pyridin-2,6-diamine

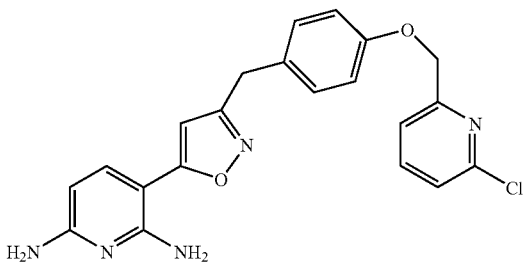

To a tetrahydrofuran (3 mL) solution of 4-(5-(2,6-diamino-pyridin-3-yl)-isoxazol-3-ylmethyl)-phenol (30 mg, 0.11 mmol) described in Manufacturing Example 18-1-1 was added a 5 N sodium hydroxide aqueous solution (21.2 µL, 0.11 mmol), which was dissolved by irradiating ultrasonic wave for 1 minute. The reaction solution was concentrated under a reduced pressure, which gave a white solid. An N,N-dimethylformamide (1 mL) solution of 2-chloro-6-chloromethyl-pyridine (34.3 mg, 0.21 mmol) described in Manufacturing Example 52-1-2 was added to a suspension of this solid in N,N-dimethylformamide (1 mL), which was stirred for 1 hour at 60° C. This reaction mixture was cooled to room temperature and then partitioned into water and ethyl acetate. The organic layer was separated, washed with water and saturated aqueous sodium chloride, dried over anhydrous magnesium sulfate, and filtered. The filtrate was concentrated under a reduced pressure. The residue was purified by NH silica gel column chromatography (heptane:ethyl acetate=1:2), and then further purified by reverse-phase high performance liquid chromatography (using an acetonitrile-water mobile phase containing 0.1% trifluoroacetic acid) to obtain the title compound (15.9 mg, 37%) as a trifluoroacetic acid salt.

$^1$H-NMR Spectrum (CDCl$_3$) δ (ppm): 3.95 (2H, s), 4.56 (2H, brs), 5.15 (2H, s), 5.30 (2H, brs), 5.90 (1H, d, J=8.0 Hz), 5.99 (1H, s), 6.91 (2H, d, J=8.8 Hz), 7.20 (2H, d, J=8.0 Hz), 7.27-7.28 (1H, m), 7.45 (1H, d, J=7.6 Hz), 7.46 (1H, d, J=8.0 Hz), 7.67 (1H, dd, J=7.6, 8.0 Hz).

MS m/e (ESI) 408.19 (MH$^+$)

Example 111

3-(3-(6-Phenoxymethyl-pyridin-3-ylmethyl)-isoxazol-5-yl)-pyridin-2,6-diamine

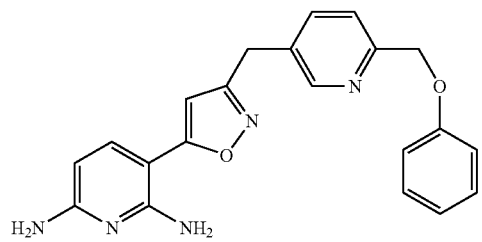

To a tetrahydrofuran (5.00 mL) solution of (6-phenoxymethyl-pyridin-3-yl)-acetohydroximoyl chloride (89.0 mg, 0.322 mmol) described in Manufacturing Example 54-1-6 and 3-ethynyl-pyridin-2,6-diamine (25.0 mg, 0.188 mmol) described in Manufacturing Example 13-1-3 was added triethylamine (78.6 µL, 0.564 mmol) at room temperature, which was stirred for 4.5 hours at room temperature. Water was added to the reaction solution at room temperature, which was extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1:1→3:1) to obtain the title compound (21.0 mg, 29.9%).

$^1$H-NMR Spectrum (DMSO-d$_6$) δ (ppm): 4.02 (2H, s), 5.15 (2H, s), 5.81 (2H, brs), 5.83 (1H, d, J=8.4 Hz), 6.12 (2H, brs), 6.43 (1H, s), 6.92-6.96 (1H, m), 7.01 (2H, d, J=8.4 Hz), 7.27-7.31 (2H, m), 7.50 (2H, dd, J=4.0, 16.4 Hz), 7.74-7.77 (1H, m), 8.56 (1H, d, J=2.4 Hz).

Example 112

3-(3-(4-(5-Fluoro-pyridin-2-ylmethoxy)-benzyl)-isoxazol-5-yl)-pyridin-2,6-diamine

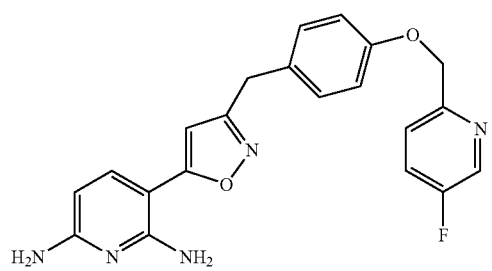

To a tetrahydrofuran (3 mL) solution of 4-(5-(2,6-diamino-pyridin-3-yl)-isoxazol-3-ylmethyl)-phenol (25.5 mg, 0.09 mmol) described in Manufacturing Example 18-1-1 was added a 5 N sodium hydroxide aqueous solution (18.1 µL, 0.09 mmol), which was dissolved by irradiating ultrasonic wave for 1 minute. The reaction solution was concentrated under a reduced pressure, which gave a white solid. An N,N-dimethylformamide (1 mL) solution of 2-chloromethyl-5-fluoro-pyridine (13.2 mg, 0.09 mmol) described in manufacturing Example 41-1-2 was added to a suspension of this solid in N,N-dimethylformamide (1 mL), which was stirred for 1 hour at 60° C. The reaction mixture was cooled to room temperature and then partitioned into water and ethyl acetate. The organic layer was separated, washed with water and saturated aqueous sodium chloride solution, dried over anhydrous magnesium sulfate, and filtered. The filtrate was concentrated under a reduced pressure. The residue was purified by reverse-phase high performance liquid chromatography (using an acetonitrile-water mobile phase containing 0.1% trifluoroacetic acid) to obtain the title compound (23.6 mg, 67%) as a ditrifluoroacetic acid salt.

$^1$H-NMR Spectrum (DMSO-D$_6$) δ (ppm): 3.93 (2H, s), 5.15 (2H, s), 6.04 (1H, d, J=8.4 Hz), 6.53 (1H, s), 6.98 (2H, d, J=8.8 Hz), 7.23 (2H, d, J=8.4 Hz), 7.57-7.61 (1H, m), 7.77 (1H, dt, J=2.8, 8.8 Hz), 7.81-7.86 (1H, m), 8.57 (1H, d, J=2.8 Hz).

MS m/e (ESI) 391.96 (MH$^+$)

Example 113

3-(3-(4-(6-Fluoro-pyridin-2-ylmethoxy)-benzyl)-isoxazol-5-yl)-pyridin-2,6-diamine

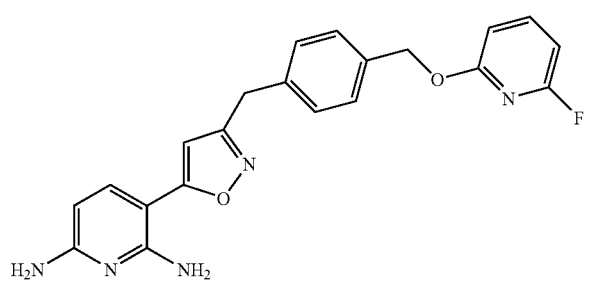

To a tetrahydrofuran (3 mL) solution of (4-(6-fluoro-pyridin-2-yloxymethyl)-phenyl)-acetohydroximoyl chloride (200 mg, 0.678 mmol) described in Manufacturing Example 55-1-5 and 3-ethynyl-pyridin-2,6-diamine (57.6 mg, 0.433 mmol) described in Manufacturing Example 13-1-3 was added triethylamine (236 µL, 1.7 mmol). This mixture was stirred for 2 hours at room temperature. This mixture was partitioned into water and ethyl acetate. The organic layer was separated, washed with water and saturated aqueous sodium chloride, dried over anhydrous magnesium sulfate, and filtered. The filtrate was concentrated under a reduced pressure. The residue was purified by NH silica gel column chromatography (heptane:ethyl acetate=1:1~ethyl acetate) to obtain the title compound (150 mg, 57%).

$^1$H-NMR Spectrum (CDCl$_3$) δ (ppm): 4.02 (2H, s), 4.57 (2H, brs), 5.32 (2H, s), 5.34 (2H, brs), 5.91-5.93 (1H, m), 6.00 (1H, s), 6.47-6.50 (1H, m), 6.64-6.66 (1H, m), 7.30 (2H, d, J=8.0 Hz), 7.42 (2H, d, J=8.0 Hz), 7.48-7.50 (1H, m), 7.62-7.68 (1H, m).

Example 114

3-(3-(4-(5-Fluoro-pyridin-2-ylmethoxy)-benzyl)-isoxazol-5-yl)-pyridin-2,6-diamine

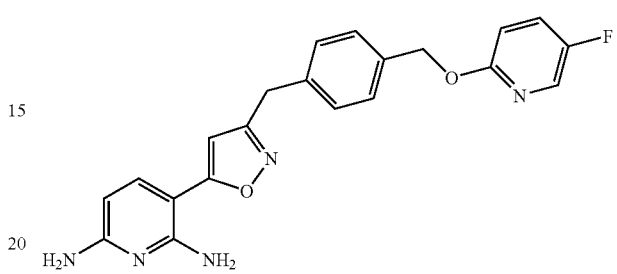

To a tetrahydrofuran (3 mL) solution of (4-(5-fluoro-pyridin-2-yloxymethyl)-phenyl)-acetohydroximoyl chloride (200 mg, 0.679 mmol) described in Manufacturing Example 56-1-5 and 3-ethynyl-pyridin-2,6-diamine (57.7 mg, 0.433 mmol) described in Manufacturing Example 13-1-3 was added triethylamine (237 µL, 1.7 mmol). The mixture was stirred for 4 hours at room temperature. This mixture was partitioned into water and ethyl acetate. The organic layer was separated, washed with water and saturated aqueous sodium chloride, dried over anhydrous magnesium sulfate, and filtered. The filtrate was concentrated under a reduced pressure. The residue was purified by NH silica gel column chromatography (heptane:ethyl acetate=1:1~ethyl acetate) to obtain the title compound (86 mg, 32%).

$^1$H-NMR Spectrum (CDCl$_3$) δ (ppm): 4.03 (2H, s), 4.62 (2H, brs), 5.07 (2H, s), 5.39 (2H, brs), 5.92-5.94 (1H, m), 6.00 (1H, s), 7.13-7.16 (1H, m), 7.31-7.33 (2H, m), 7.35-7.38 (3H, m), 7.49-7.51 (1H, m), 8.11-8.12 (1H, m).

Example 115

3-(3-(1-Benzyl-1H-pyrrol-3-ylmethyl)-isoxazol-5-yl)-pyridin-2,6-diamine

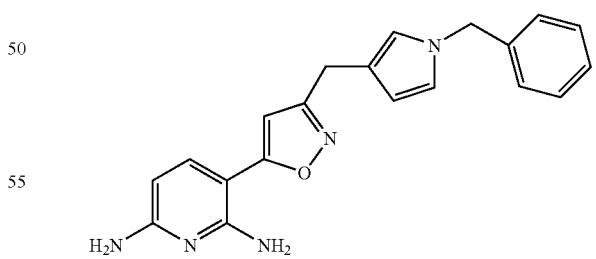

The title compound (7.6 mg, 2.0%) was obtained according to the method similar to those of Example 3, using (1-benzyl-1H-pyrrol-3-yl)acetohydroximoyl chloride (280 mg, 1.1 mmol) described in Manufacturing Example 57-1-3 and 3-ethynyl-pyridin-2,6-diamine (74 mg, 0.56 mmol) described in Manufacturing Example 13-1-3.

$^1$H-NMR Spectrum (DMSO-d$_6$) δ (ppm): 3.70 (2H, s), 5.02 (2H, s), 5.77 (2H, brs), 5.83 (1H, d, J=8.0 Hz), 5.97 (1H, dd, J=2.0, 2.0 Hz), 6.09 (2H, brs), 6.35 (1H, s), 6.70 (1H, dd, J=2.0, 2.0 Hz), 6.74 (1H, dd, J=2.0, 2.0 Hz), 7.18 (2H, d, J=7.6 Hz), 7.23-7.28 (1H, m), 7.30-7.35 (2H, m), 7.51 (1H, d, J=8.0 Hz).

Example 116

3-(3-(6-(4-Fluoro-benzyloxy)-pyridin-3-ylmethyl)-isoxazol-5-yl)-pyridin-2,6-diamine

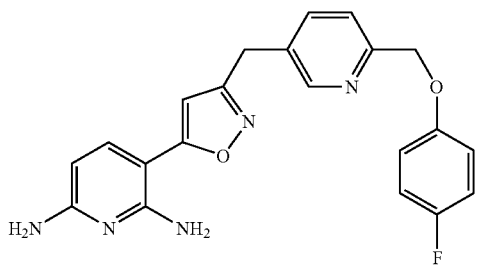

To a tetrahydrofuran (10.0 mL) solution of (6-(4-fluoro-benzyloxy)-pyridin-3-yl)-acetohydroximoyl chloride (133 mg, 0.450 mmol) described in Manufacturing Example 58-1-5 and 3-ethynyl-pyridin-2,6-diamine (30.0 mg, 0.225 mmol) described in Manufacturing Example 13-1-3 was added triethylamine (94.1 µL, 0.675 mmol), which was stirred for 3 hours at room temperature. Water was added to the reaction solution at room temperature, which was extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=3:1) to obtain the title compound (67.4 mg, 76.5%).
$^1$H-NMR Spectrum (DMSO-d$_6$) δ (ppm): 3.92 (2H, s), 5.31 (2H, s), 5.81 (2H, brs), 5.83 (1H, d, J=8.4 Hz), 6.12 (2H, brs), 6.40 (1H, s), 6.84 (1H, d, 8.4 Hz), 7.19 (2H, d, J=8.8 Hz), 7.47-7.53 (3H, m), 7.65-7.67 (1H, m), 8.14 (1H, d, J=2.0 Hz).

Example 117

3-(3-(4-(4-Fluoro-pyridin-2-yloxymethyl)-benzyl)-isoxazol-5-yl)-pyridin-2,6-diamine

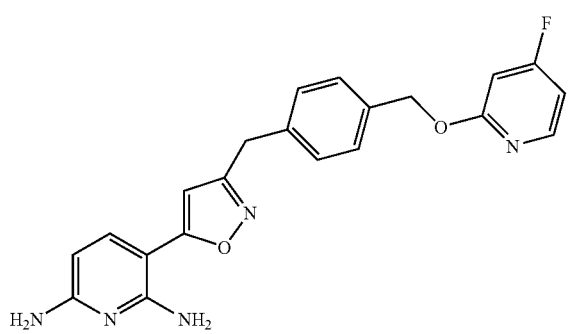

To a tetrahydrofuran (3 mL) solution of (4-(4-fluoro-pyridin-2-yloxymethyl)-phenyl)-acetohydroximoyl chloride (200 mg, 0.679 mmol) described in Manufacturing Example 59-1-5 and 3-ethynyl-pyridin-2,6-diamine (57.7 mg, 0.433 mmol) described in Manufacturing Example 13-1-3 was added triethylamine (237 µL, 1.7 mmol). This mixture was stirred for 4 hours at room temperature. This mixture was partitioned into water and ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1~ethyl acetate) to obtain the title compound (113 mg, 43%).
$^1$H-NMR Spectrum (CD$_3$OD) δ (ppm): 4.02 (2H, s), 5.18 (2H, s), 5.94-5.96 (1H, m), 6.23 (1H, s), 6.99-7.01 (1H, m), 7.097-7.103 (1H, m), 7.34-7.36 (2H, m), 7.40-7.42 (2H, m), 7.54-7.56 (1H, m), 8.14-8.15 (1H, m).

Example 118

3-(3-(3-(Pyridin-2-ylmethoxy)-benzyl)-isoxazol-5-yl)-pyridin-2,6-diamine

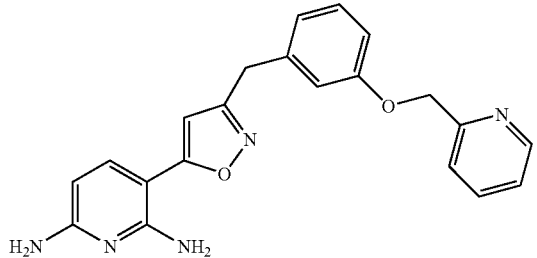

To a tetrahydrofuran (3 mL) solution of 3-(pyridin-2-ylmethoxy)-phenyl)-acetohydroximoyl chloride (200 mg, 0.723 mmol) described in Manufacturing Example 60-1-4 and 3-ethynyl-pyridin-2,6-diamine (61.4 mg, 0.461 mmol) described in Manufacturing Example 13-1-3 was added triethylamine (252 µL, 1.81 mmol). This mixture was stirred for 2 hours at room temperature. This mixture was partitioned into water and ethyl acetate. The organic layer was separated, washed with water and saturated aqueous sodium chloride, dried over anhydrous magnesium sulfate, and filtered. The filtrate was concentrated under a reduced pressure. The residue was purified by NH silica gel column chromatography (heptane:ethyl acetate=1:1~ethyl acetate) to obtain the title compound (87 mg, 32%).
$^1$H-NMR Spectrum (CD$_3$OD) δ (ppm): 3.96 (2H, s), 5.16 (2H, s), 5.94-5.97 (1H, m), 6.17 (1H, s), 6.87-6.92 (3H, m), 7.21-7.25 (1H, m), 7.29-7.32 (1H, m), 7.53-7.57 (2H, m), 7.79-7.84 (1H, m), 8.48-8.50 (1H, m).

Example 119

3-(3-(3-Benzyloxy-benzyl)-isoxazol-5-yl)-pyridin-2,6-diamine

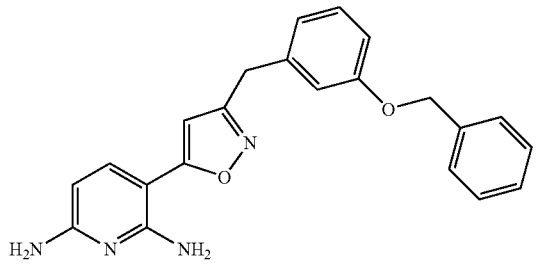

To a tetrahydrofuran (3 mL) solution of (3-benzyloxy-phenyl)-acetohydroximoyl chloride (200 mg, 0.724 mmol) described in Manufacturing Example 61-1-4 and 3-ethynyl-pyridin-2,6-diamine (61.5 mg, 0.462 mmol) described in Manufacturing Example 13-1-3 was added triethylamine (252 μL, 1.81 mmol). This mixture was stirred for 4 hours at room temperature. This mixture was partitioned into water and ethyl acetate. The organic layer was separated, washed with water and saturated aqueous sodium chloride, dried over anhydrous magnesium sulfate, and filtered. The filtrate was concentrated under a reduced pressure. The residue was purified by NH silica gel column chromatography (heptane:ethyl acetate=1:1~ethyl acetate) to obtain the title compound (138 mg, 51%).

$^1$H-NMR Spectrum (CD$_3$OD) δ (ppm): 3.95 (2H, s), 5.07 (2H, s), 5.95-5.97 (1H, m), 6.17 (1H, s), 6.86-6.88 (2H, m), 6.92 (1H, m), 7.20-7.27 (2H, m), 7.31-7.35 (2H, m), 7.39-7.41 (2H, m), 7.53-7.55 (1H, m).

Example 120

3-(3-(4-(5-Chloro-furan-2-ylmethyl)-benzyl)-isoxazol-5-yl)-pyridin-2,6-diamine

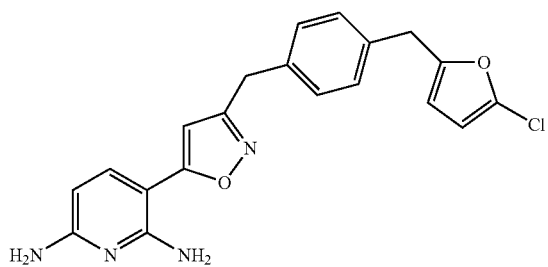

To a mixture of (4-(5-chloro-furan-2-ylmethyl)-phenyl)-acetohydroximoyl chloride (25 mg, 0.088 mmol) described in Manufacturing Example 62-1-6 and tetrahydrofuran (1 mL) were added 3-ethynyl-pyridin-2,6-diamine (9 mg, 0.068 mmol) described in Manufacturing Example 13-1-3 and triethylamine (19 μL, 0.14 mmol), which was stirred for 1 hour at room temperature. Water was added to the reaction mixture at the same temperature, which was extracted with ethyl acetate. The organic layer was washed with saturated aqueous sodium chloride, and was concentrated under a reduced pressure. The residue was purified by reverse-phase high performance liquid chromatography (using an acetonitrile-water mobile phase containing 0.1% trifluoroacetic acid) to obtain the title compound as a trifluoroacetate (10 mg, 28%).

MS m/e (ESI) 381.13 (MH$^+$)

Example 121

3-(3-(5-Phenoxy-pyridin-2-ylmethyl)-isoxazol-5-yl)-pyridin-2,6-diamine

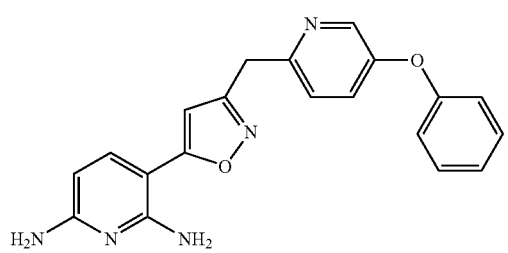

The title compound (26 mg, 34%) was obtained according to the method similar to those of Example 3, using (5-phenoxy-pyridin-2-yl)-acetohydroximoyl chloride (56 mg, 0.21 mmol) described in Manufacturing Example 121-1-5 and 3-ethynyl-pyridin-2,6-diamine (42 mg, 0.32 mmol) described in Manufacturing Example 13-1-3.

$^1$H-NMR Spectrum (DMSO-d$_6$) δ (ppm): 4.11 (2H, s), 5.80 (2H, brs), 5.83 (1H, d, J=8.0 Hz), 6.12 (2H, brs), 6.40 (1H, s), 7.05 (2H, d, J=8.0 Hz), 7.15-7.21 (1H, m), 7.38-7.45 (4H, m), 7.52 (1H, d, J=8.0 Hz), 8.31 (1H, s).

The starting material, (5-phenoxy-pyridin-2-yl)-acetohydroximoyl chloride, was synthesized as follows.

Manufacturing Example 121-1-1

2-Methyl-5-phenoxy-pyridine

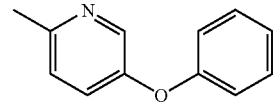

Diphenyliodonium iodide (5.8 g, 14 mmol), 3-hydroxy-6-methylpyridine (1.6 g, 14 mmol), potassium tert-butoxide (1.7 g, 15 mmol), and tetrahydrofuran (60 mL) were stirred for 2.5 hours at 60° C. Water was added to the reaction solution, which was extracted with ethyl acetate. The solvent was evaporated under a reduced pressure, and the residue was purified by silica gel column chromatography (heptane:ethyl acetate=3:1) to obtain the title compound (1.5 g, 56%).

$^1$H-NMR Spectrum (DMSO-d$_6$) δ (ppm): 2.46 (3H, s), 7.00-7.04 (2H, m), 7.13-7.18 (1H, m), 7.28 (1H, d, J=8.4 Hz), 7.37 (1H, dd, J=2.8, 8.4 Hz), 7.37-7.43 (2H, m), 8.24 (1H, d, J=2.8 Hz).

Manufacturing Example 121-1-2

(5-Phenoxy-pyridin-2-yl)-methanol

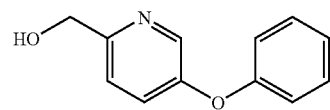

A mixture of 2-methyl-5-phenoxy-pyridine (3.6 g, 19 mmol) described in Manufacturing Example 121-1-1, 3-chloroperoxybenzoic acid (5.6 g, 33 mmol), and methylene chloride (80 mL) was stirred at room temperature for 45 minutes.

Aqueous sodium sulfite was added to the reaction solution, and the organic layer was separated and was washed with 5 N aqueous sodium hydroxide (7 mL). The organic layer was dried over anhydrous magnesium sulfate, and then the solvent was evaporated under a reduced pressure to obtain 2-methyl-5-phenoxy-pyridine 1-oxide (3.3 g). 2-methyl-5-phenoxy-pyridine 1-oxide (3.3 g, 16 mmol) and acetic anhydride (20 mL) were stirred for 40 minutes at 115° C. Acetic anhydride was evaporated under a reduced pressure, aqueous sodium bicarbonate and ethyl acetate were added to the residue, and the organic layer was separated. The ethyl acetate solution was concentrated under a reduced pressure, and the residue was purified by silica gel column chromatography (heptane:ethyl acetate=2:1) to obtain an acetic acid 5-phenoxy-pyridin-2-ylmethyl ester (3.0 g). Acetic acid 5-phenoxy-pyridin-2-ylmethyl ester (3.0 g, 12 mmol), 5 N aqueous sodium hydroxide (8.0 mL), and methanol (20 mL) were stirred for 20 minutes at 60° C. Water and ethyl acetate were added to the reaction solution, and the organic layer was separated. The ethyl acetate layer was dried over anhydrous magnesium sulfate, and then the solvent was evaporated under a reduced pressure to obtain the title compound (2.6 g, 65%).

$^1$H-NMR Spectrum (DMSO-$d_6$) δ (ppm): 4.57 (2H, d, J=6.0 Hz), 5.44 (1H, t, J=6.0 Hz), 7.00-7.08 (2H, m), 7.15-7.20 (1H, m), 7.38-7.53 (4H, m), 8.29 (1H, d, J=2.8 Hz).

Manufacturing Example 121-1-3

5-Phenoxy-pyridine-2-carbaldehyde

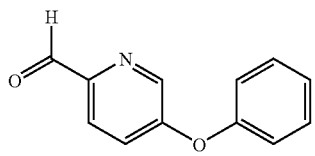

(5-Phenoxy-pyridin-2-yl)-methanol (300 mg, 1.5 mmol) described in Manufacturing Example 121-1-2, magnesium (IV) oxide (1.3 g, 15 mmol), and acetone (10 mL) were stirred under reflux for 20 minutes. More magnesium (IV) oxide (1.5 g, 17 mmol) was then added, which was stirred under reflux for another 20 minutes. The reaction solution was filtered through a Celite pad, and then the filtrate was concentrated under a reduced pressure to obtain the title compound (220 mg, 74%).

$^1$H-NMR Spectrum (DMSO-$d_6$) δ (ppm): 7.20-7.25 (2H, m), 7.29-7.34 (1H, m), 7.47-7.54 (3H, m), 7.95-8.00 (1H, m), 8.57-8.60 (1H, m), 9.94 (1H, s).

Manufacturing Example 121-1-4

2-(2-Nitro-ethyl)-5-phenoxy-pyridine

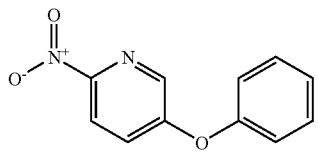

A mixture of 5-phenoxy-pyridine-2-carbaldehyde (700 mg, 3.5 mmol) described in Manufacturing Example 121-1-3, lithium methoxide (170 mg, 4.6 mmol), nitromethane (280 mg, 4.6 mmol), and methanol (10 mL) was dissolved by irradiating ultrasonic wave for 2 minutes at room temperature, after which the reaction solution was concentrated under a reduced pressure. Acetic anhydride (30 mL) and triethylamine (1.1 g, 11 mmol) were added to the residue, which was stirred for 10 minutes at room temperature, after which the reaction solution was concentrated under a reduced pressure. Ethyl acetate was added to the residue, and the organic layer was separated and washed with saturated aqueous sodium chloride once and then dried over anhydrous magnesium sulfate. The solvent was evaporated under a reduced pressure, dimethyl sulfoxide (5.0 mL), acetic acid (0.50 mL), and sodium borohydride (270 mg, 7.0 mmol) were added to the residue, which was stirred for 5 minutes at room temperature. Water and ethyl acetate were added to the reaction solution, and then the ethyl acetate layer was separated and washed with aqueous sodium bicarbonate, water, and saturated aqueous sodium chloride. The solvent was evaporated under a reduced pressure, and the residue was purified first by silica gel column chromatography (heptane:ethyl acetate=2:1) and then NH silica gel column chromatography (heptane:ethyl acetate=4:1 then 2:1) to obtain the title compound (76 mg, 8.9%).

$^1$H-NMR Spectrum (DMSO-$d_6$) δ (ppm): 3.40 (2H, d, J=6.4 Hz), 4.98 (2H, d, J=6.4 Hz), 7.02-7.06 (2H, m), 7.16-7.21 (1H, m), 7.39-7.46 (4H, m), 8.28 (1H, d, J=2.4 Hz).

Manufacturing Example 121-1-5

(5-Phenoxy-pyridin-2-yl)-acetohydroximoyl chloride

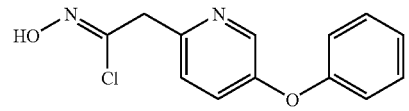

To 2-(2-nitro-ethyl)-5-phenoxy-pyridine (76 mg, 0.31 mmol) described in Manufacturing Example 121-1-4 and methanol (6.0 mL) was added lithium methoxide (24 mg, 0.62 mmol) at room temperature, which was stirred for 3 minutes, and then the solvent was evaporated under a reduced pressure. Methylene chloride (10 mL) was added to the residue, titanium (IV) chloride (0.11 mL, 1.0 mmol) was added at room temperature, which was stirred for 10 minutes. Cold aqueous sodium bicarbonate and ethyl acetate were added to the reaction solution, which was filtered through a Celite pad, and then the organic layer was separated. The organic layer was concentrated under a reduced pressure to obtain the title compound (56 mg, 69%).

$^1$H-NMR Spectrum (DMSO-$d_6$) δ (ppm): 3.99 (2H, s), 7.00-7.10 (2H, m), 7.13-7.22 (1H, m), 7.34-7.48 (4H, m), 8.32 (1H, d, J=2.4 Hz), 11.75 (1H, s).

Example 122

3-(3-(4-(5-Chloro-pyridin-2-ylmethoxy)-benzyl)-isoxazol-5-yl)-pyridin-2,6-diamine

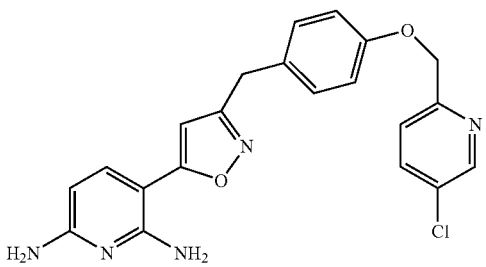

To a tetrahydrofuran (3 mL) solution of 4-(5-(2,6-diamino-pyridin-3-yl)-isoxazol-3-ylmethyl)-phenol (30 mg, 0.11 mmol) described in Manufacturing Example 18-1-1 was added a 5 N sodium hydroxide aqueous solution (21.2 μL, 0.11 mmol), which was dissolved by irradiating ultrasonic wave for 1 minute. The reaction solution was concentrated under a reduced pressure, which gave a white solid. An N,N-dimethylformamide (1 mL) solution of 5-chloro-2-chloromethyl-pyridine (18.9 mg, 0.12 mmol) described in manufacturing Example 63-1-2 was added to a suspension of this solid in N,N-dimethylformamide (1 mL), which was stirred for 1 hour at 60° C. The reaction mixture was cooled to room temperature and then partitioned into water and ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (38.4 mg, 89%).

$^1$H-NMR Spectrum (DMSO-$d_6$) δ (ppm): 3.88 (2H, s), 5.16 (2H, s), 5.79 (2H, brs), 5.82 (1H, d, J=8.4 Hz), 6.11 (2H, brs), 6.34 (1H, s), 6.97 (2H, d, J=8.8 Hz), 7.23 (2H, d, J=8.8 Hz), 7.51 (1H, d, J=8.4 Hz), 7.54 (1H, d, J=8.4 Hz), 7.96 (1H, dd, J=2.4, 8.4 Hz), 8.63 (1H, d, J=2.8 Hz).

Example 123

3-(3-(3-Phenoxy-benzyl)-isoxazol-5-yl)-pyridin-2,6-diamine

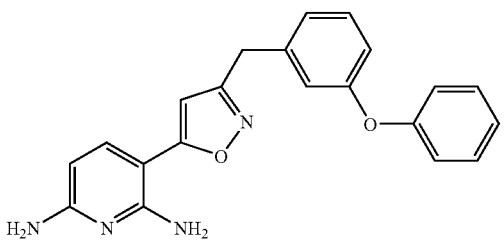

To a tetrahydrofuran (10.0 mL) solution of (3-phenoxy-phenyl)-acetohydroximoyl chloride (133 mg, 0.508 mmol) described in Manufacturing Example 64-1-3 and 3-ethynyl-pyridine-2,6-diamine (30.0 mg, 0.254 mmol) described in Manufacturing Example 13-1-3 was added triethylamine (94.1 μL, 0.675 mmol) at room temperature, which was stirred for 14 hours at room temperature. Water was added to the reaction solution at room temperature, which was extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=3:1) to obtain the title compound (26.1 mg, 80.6%).

$^1$H-NMR Spectrum (CD$_3$OD) δ (ppm): 3.95 (2H, s), 5.81 (2H, brs), 5.84 (1H, d, J=8.4 Hz), 6.12 (2H, brs), 6.38 (1H, s), 6.84-6.87 (1H, m), 6.98-7.02 (3H, m), 7.07 (1H, d, J=8.0 Hz), 7.12-7.16 (1H, m), 7.31-7.41 (3H, m), 7.52 (1H, d, J=8.4 Hz).

Example 124

3-(3-(3-Butoxy-benzyl)-isoxazol-5-yl)-pyridin-2,6-diamine

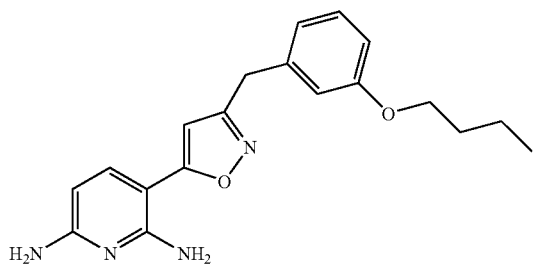

To a tetrahydrofuran (3 mL) solution of (3-butoxy-phenyl)-acetohydroximoyl chloride (150 mg, 0.621 mmol) described in Manufacturing Example 65-1-4 and 3-ethynyl-pyridin-2,6-diamine (52.8 mg, 0.396 mmol) described in Manufacturing Example 13-1-3 was added triethylamine (216 μL, 1.55 mmol). This mixture was stirred for 4 hours at room temperature. The mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:1~ethyl acetate) to obtain the title compound (43 mg, 21%).

$^1$H-NMR Spectrum (CDCl$_3$) δ (ppm): 0.95-0.98 (3H, m), 1.45-1.51 (2H, m), 1.72-1.77 (2H, m), 3.96-3.99 (2H, m), 3.98 (2H, s), 4.59 (2H, brs), 5.36 (2H, brs), 5.91-5.93 (1H, m), 6.01 (1H, s), 6.78-6.86 (4H, m), 7.21-7.24 (1H, m).

Example 125

3-(3-(3-Cyclopropylmethoxy-benzyl)-isoxazol-5-yl)-pyridin-2,6-diamine

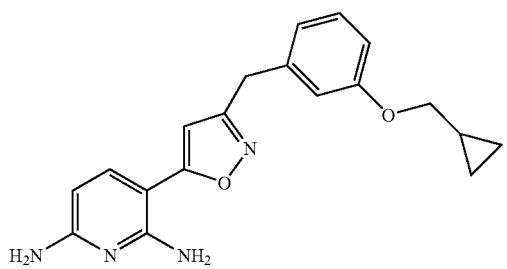

To a tetrahydrofuran (3 mL) solution of (3-cyclopropyl-methoxy-phenyl)-acetohydroximoyl chloride (150 mg, 0.626 mmol) described in Manufacturing Example 66-1-4 and 3-ethynyl-pyridin-2,6-diamine (53.2 mg, 0.399 mmol) described in Manufacturing Example 13-1-3 was added triethylamine (218 μL, 1.57 mmol). This mixture was stirred for 4 hours at room temperature. The mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:1~ethyl acetate) to obtain the title compound (117 mg, 56%).

$^1$H-NMR Spectrum (CDCl$_3$) δ (ppm): 0.32-0.36 (2H, m), 0.61-0.66 (2H, m), 1.22-1.29 (1H, m), 3.77-3.79 (2H, m), 3.98 (2H, s), 4.58 (2H, brs), 5.35 (2H, brs), 5.91-5.93 (1H, m), 6.00 (1H, s), 6.78-6.87 (3H, m), 7.21-7.25 (1H, m), 7.48-7.50 (1H, m).

Example 126

3-(3-(4-Butoxy-benzyl)-isoxazol-5-yl)-pyridin-2,6-diamine

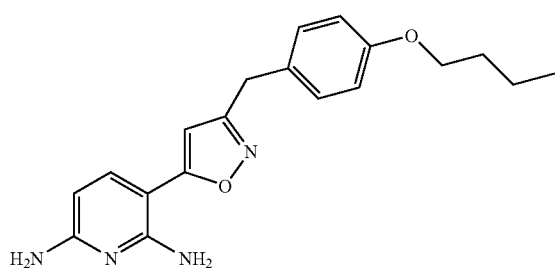

To a tetrahydrofuran (3 mL) solution of (4-butoxy-phenyl)-acetohydroximoyl chloride (150 mg, 0.621 mmol) described in Manufacturing Example 67-1-4 and 3-ethynyl-pyridin-2,6-diamine (52.8 mg, 0.396 mmol) described in Manufacturing Example 13-1-3 was added triethylamine (216 μL, 1.55 mmol). This mixture was stirred for 4 hours at room temperature. The mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:1~ethyl acetate) to obtain the title compound (155 mg, 74%).

$^1$H-NMR Spectrum (CDCl$_3$) δ (ppm): 0.95-0.99 (3H, m), 1.46-1.53 (2H, m), 1.72-1.79 (2H, m), 3.92-3.96 (4H, m), 4.60 (2H, brs), 5.37 (2H, brs), 5.91-5.92 (1H, m), 5.98 (1H, s), 6.84-6.86 (2H, m), 7.17-7.19 (2H, m), 7.48-7.50 (1H, m).

Example 127

3-(3-(5-Benzyloxy-pyridin-2-ylmethyl)-isoxazol-5-yl)-pyridin-2,6-diamine

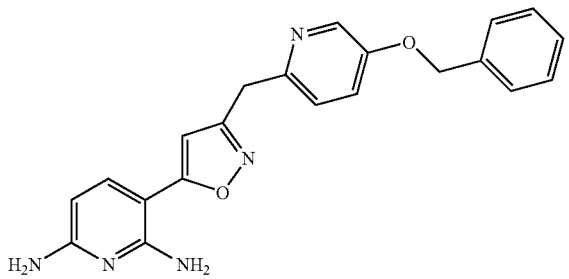

To a mixture of 2-(5-benzyloxy-pyridin-2-yl)-N-hydroxy-acetamidine (50 mg, 0.19 mmol) described in Manufacturing Example 127-1-5 and a 5 N hydrochloric acid aqueous solution (1 mL) was added sodium nitrite (20 mg, 0.29 mmol) at 0° C., which was stirred for 20 minutes at 0° C. Sodium hydrogencarbonate and water were added to the reaction mixture at 0° C., which was extracted with ethyl acetate. The organic layer was separated, washed with saturated aqueous sodium chloride, dried over anhydrous magnesium sulfate, and filtered. The filtrate was concentrated under a reduced pressure. To a tetrahydrofuran (3 mL) solution of this residue were added 3-ethynyl-pyridin-2,6-diamine (10 mg, 0.39 mmol) described in Manufacturing Example 13-1-3 and triethylamine (27 μL, 0.19 mmol), which was stirred for 40 minutes at 50° C. under nitrogen atmosphere. Water was added to the reaction mixture at room temperature, which was extracted with ethyl acetate. The organic layer was separated, washed with saturated aqueous sodium chloride, dried over anhydrous magnesium sulfate, and filtered. The filtrate was concentrated under a reduced pressure. The residue was purified by NH silica gel column chromatography (ethyl acetate:heptane=2:1), and then purified further by reverse-phase high performance liquid chromatography (using an acetonitrile-water mobile phase containing 0.1% trifluoroacetic acid) to obtain the title compound (4.7 mg, 4.0%) as a ditrifluoroacetic acid salt.

MS m/e (ESI) (MH$^+$) 374.01 (MH$^+$)

The starting material, 2-(5-benzyloxy-pyridin-2-yl)-N-hydroxy-acetamidine, was synthesized as follows.

Manufacturing Example 127-1-1

5-Benzyloxy-2-methyl-pyridine

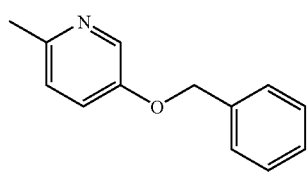

To an N,N-dimethylformamide (50 mL) solution of 3-hydroxy-6-methylpyridine (5.00 g, 45.8 mmol) was added sodium hydride (2.02 g, 50.4 mmol, 60% in oil), which was stirred for 15 minutes at 0° C. Next, benzyl bromide (5.99 mL, 50.4 mmol) was added to this reaction mixture at 0° C., which was stirred for 3.5 hours at room temperature. Water was added to the reaction mixture, which was extracted with ethyl acetate. The organic layer was separated, washed with water and saturated aqueous sodium chloride, dried over anhydrous magnesium sulfate, and filtered. The filtrate was concentrated under a reduced pressure. The residue was purified by silica gel column chromatography (heptane:ethyl acetate=2:1) to obtain the title compound (5.99 g, 66%).

$^1$H-NMR Spectrum (CDCl$_3$) δ (ppm): 2.49 (3H, s), 5.08 (2H, s), 7.05 (1H, d, J=8.6 Hz), 7.17 (1H, dd, J=2.9, 8.4 Hz), 7.31-7.44 (5H, m), 8.27 (1H, d, J=2.9 Hz).

Manufacturing Example 127-1-2

(5-Benzyloxy-pyridin-2-yl)-methanol

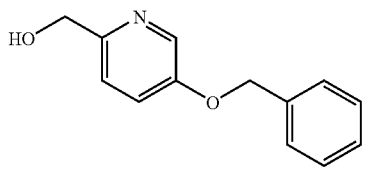

To a methylene chloride (100 mL) solution of 5-benzyloxy-2-methyl-pyridine (5.99 g, 30.1 mmol) described in Manufacturing Example 127-1-1 was added m-chloroperbenzoic acid (8.79 g, 33.1 mmol, purity: 65%) at 0° C., which was stirred for 2 hours at room temperature. Saturated aqueous sodium bicarbonate was added to the reaction mixture at 0° C., which was extracted with methylene chloride. The organic layer was separated, washed with saturated aqueous sodium bicarbonate and saturated aqueous sodium chloride, dried over anhydrous magnesium sulfate, and filtered. The filtrate was concentrated under a reduced pressure to obtain 5-benzyloxy-2-methyl-pyridine-1-oxide (7.71 g). Acetic anhydride (77 mL) was added to 5-benzyloxy-2-methyl-pyridine-1-oxide (7.71 g) thus obtained, which was stirred for 80 minutes at 120° C. This mixture was cooled to room temperature and then concentrated under a reduced pressure. To an ethanol (50 mL) solution of this residue was added a 5 N sodium hydroxide aqueous solution (7 mL), which was stirred for 50 minutes at room temperature. The reaction mixture was concentrated under a reduced pressure. The residue was partitioned into saturated aqueous sodium chloride and ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (4.17 g, 54%).

$^1$H-NMR Spectrum (DMSO-d$_6$) δ (ppm): 4.46 (2H, d, J=5.9 Hz), 5.15 (2H, s), 5.26 (1H, t, J=5.9 Hz), 7.29-7.40 (4H, m), 7.42-7.45 (3H, m), 8.22 (1H, d, J=2.9 Hz).

Manufacturing Example 127-1-3

5-Benzyloxy-2-chloromethyl-pyridine

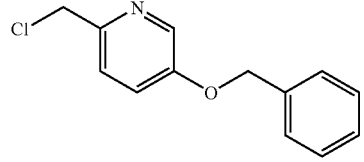

To a carbon tetrachloride (10 mL) solution of (5-benzyloxy-pyridin-2-yl)-methanol (500 mg) described in Manufacturing Example 127-1-2 was added triphenylphosphine (791 mg), which was refluxed for 19 hours and 35 minutes under nitrogen atmosphere. The reaction mixture was cooled to room temperature and then concentrated under a reduced pressure, and the residue was purified by silica gel column chromatography (heptane:ethyl acetate=3:1) to obtain the title compound (386 mg).

$^1$H-NMR Spectrum (CDCl$_3$) δ (ppm): 4.64 (2H, s), 5.12 (2H, s), 7.25-7.28 (1H, m), 7.35-7.44 (6H, m), 8.34 (1H, d, J=2.7 Hz).

Manufacturing Example 127-1-4

(5-Benzyloxy-pyridin-2-yl)-acetonitrile

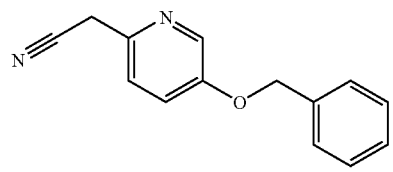

To a solution of 5-benzyloxy-2-chloromethyl-pyridine (2.13 g, 9.11 mmol) described in Manufacturing Example 127-1-3 in ethanol (30 mL) and water (10 mL) was added sodium cyanide (580 mg, 11.8 mmol), which was stirred for 4 hours and 25 minutes under reflux. Water was added to the reaction mixture at room temperature, which was extracted with ethyl acetate. The organic layer was separated, dried over anhydrous magnesium sulfate, and filtered. The filtrate was concentrated under a reduced pressure, and the residue was purified by silica gel column chromatography (heptane:ethyl acetate=1:1) to obtain the title compound (1.77 g, 87%).

$^1$H-NMR Spectrum (CDCl$_3$) δ (ppm): 3.88 (2H, s), 5.12 (2H, s), 7.29 (1H, d, J=2.7 Hz), 7.32-7.42 (6H, m), 8.33 (1H, d, J=2.7 Hz).

Manufacturing Example 127-1-5

2-(5-Benzyloxy-pyridin-2-yl)-N-hydroxy-acetamidine

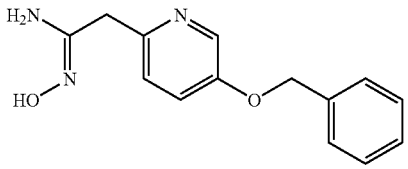

To an ethanol (30 mL) solution of (5-benzyloxy-pyridin-2-yl)-acetonitrile (1.77 g, 7.89 mmol) described in Manufacturing Example 127-1-4 were added hydroxylammonium chloride (848 mg, 11.8 mmol) and potassium carbonate (2.18 g, 15.8 mmol), which was stirred for 11 hours and 20 minutes at 70° C. The mixture was then stirred for another 5 hours and 45 minutes under reflux. Water was added to the reaction mixture at room temperature, which was extracted with ethyl acetate. The organic layer was separated, dried over anhydrous magnesium sulfate, and filtered. The filtrate was concentrated under a reduced pressure, and the residue was purified by silica gel column chromatography (ethyl acetate:methanol=10:1) to obtain the title compound (550 mg, 27%).

$^1$H-NMR Spectrum (DMSO-d$_6$) δ (ppm): 3.61 (2H, s), 5.15 (2H, s), 7.21 (1H, d, J=8.4 Hz), 7.32-7.47 (6H, m), 8.08 (1H, s), 8.22 (1H, d, J=3.1 Hz), 8.32 (1H, s), 9.49 (1H, s).

Example 128

3-(3-(4-Benzylamino-benzyl)-isoxazol-5-yl)-pyridin-2,6-diamine

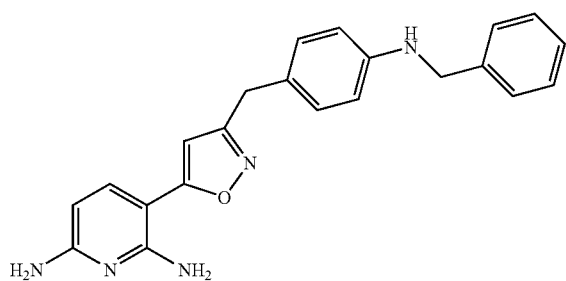

To a tetrahydrofuran (3 mL) solution of (4-benzylamino-phenyl)-acetohydroximoyl chloride (150 mg, 0.546 mmol) described in Manufacturing Example 68-1-4 and 3-ethynyl-pyridin-2,6-diamine (46.4 mg, 0.348 mmol) described in Manufacturing Example 13-1-3 was added triethylamine (190 μL, 1.37 mmol). The mixture was stirred for 6.5 hours at room temperature. This mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1~ethyl acetate) to obtain the title compound (17 mg, 8.4%).

$^1$H-NMR Spectrum (CDCl$_3$) δ (ppm): 3.89 (2H, s), 4.31 (2H, s), 4.52-4.58 (2H, m), 5.33 (2H, brs), 5.90-5.92 (1H, m), 5.99 (1H, s), 6.58-6.62 (2H, m), 7.07-7.09 (2H, m), 7.25-7.38 (5H, m), 7.48-7.52 (1H, m).

Note that it was not observed that protons on the amino groups of NH—CH2Ph appeared on the NMR chart.

Example 129

3-(3-(4-Phenylamino-benzyl)-isoxazol-5-yl)-pyridin-2,6-diamine

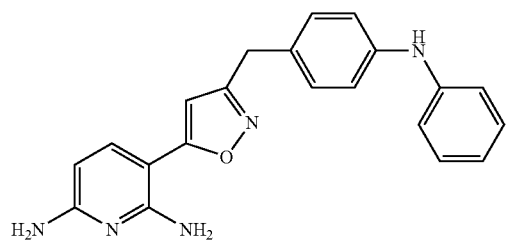

To a tetrahydrofuran (3 mL) solution of (4-phenylamino-phenyl)-acetohydroximoyl chloride (150 mg, 0.576 mmol) described in Manufacturing Example 69-1-4 and 3-ethynyl-pyridin-2,6-diamine (48.9 mg, 0.367 mmol) described in Manufacturing Example 13-1-3 was added triethylamine (201 μL, 1.44 mmol). This mixture was stirred for 6.5 hours at room temperature. The mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1~ethyl acetate) to obtain the title compound (107 mg, 52%).

$^1$H-NMR Spectrum (CDCl$_3$) δ (ppm): 3.96 (2H, s), 4.55 (2H, brs), 5.34 (2H, brs), 5.69 (1H, brs), 5.91-5.94 (1H, m), 6.02 (1H, s), 6.91-6.94 (1H, m), 7.03-7.07 (4H, m), 7.16-7.18 (2H, m), 7.24-7.28 (2H, m), 7.49-7.51 (1H, m).

Example 130

3-(3-(4-Butyl-benzyl)-isoxazol-5-yl)-pyridin-2,6-diamine

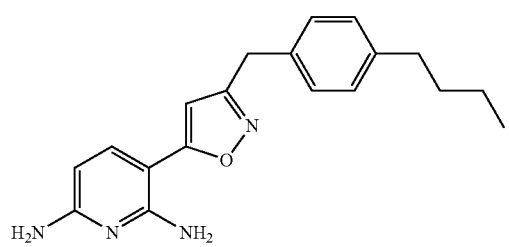

To a tetrahydrofuran (3 mL) solution of (4-butyl-phenyl)-acetohydroximoyl chloride (150 mg, 0.665 mmol) described in Manufacturing Example 70-1-3 and 3-ethynyl-pyridin-2,6, 6-diamine (56.5 mg, 0.424 mmol) described in Manufacturing Example 13-1-3 was added triethylamine (232 μL, 1.66 mmol). This mixture was stirred for 5 hours at room temperature. The mixture was partitioned into ethyl acetate and water. The organic layer was separated, washed with water, dried over anhydrous magnesium sulfate, and filtered. The filtrate was concentrated under a reduced pressure, and the residue was purified by NH silica gel column chromatography (heptane:ethyl acetate=1:1~ethyl acetate) to obtain the title compound (66 mg, 31%).

$^1$H-NMR Spectrum (CDCl$_3$) δ (ppm): 0.90-0.94 (3H, m), 1.30-1.40 (2H, m), 1.55-1.62 (2H, m), 2.57-2.61 (2H, m), 3.98 (2H, s), 4.55 (1H, brs), 5.34 (2H, brs), 5.91-5.93 (2H, m), 6.00 (1H, s), 7.14 (2H, d, J=8.0 Hz), 7.19 (2H, d, J=8.0 Hz), 7.48-7.50 (1H, m).

Example 131

3-(3-(6-(3-Fluoro-phenoxy)-pyridin-3-ylmethyl)-isoxazol-5-yl)-pyridin-2,6-diamine

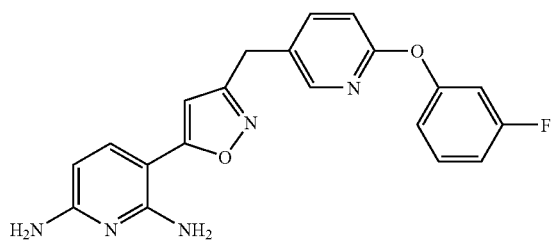

To a tetrahydrofuran (2 mL) solution of 3-ethynyl-pyridin-2,6-diamine (10 mg, 75 μmol) described in Manufacturing Example 13-1-3 and (6-(3-fluoro-phenoxy)-pyridin-3-yl)-acetohydroximoyl chloride (42 mg, 0.15 mmol) described in Manufacturing Example 71-1-4 was added triethylamine (21 μL, 0.15 mmol), which was stirred for 1 hour at 50° C. under nitrogen atmosphere. Water was added at room temperature to the reaction mixture at room temperature, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (ethyl acetate:methanol=20:1) to obtain the title compound (27 mg, 95%).

$^1$H-NMR Spectrum (CDCl$_3$) δ (ppm): 3.98 (2H, s), 4.57 (2H, s), 5.33 (2H, s), 5.94 (1H, dd, J=0.73, 8.2 Hz), 6.01 (1H, s), 6.86-6.94 (4H, m), 7.31-7.37 (1H, m), 7.49 (1H, d, J=8.4 Hz), 7.64 (1H, dd, J=2.6, 8.4 Hz), 8.15 (1H, d, J=2.6 Hz).

Example 132

3-(3-(6-(4-Fluoro-phenoxymethyl)-pyridin-3-ylmethyl)-isoxazol-5-yl)-pyridin-2,6-diamine

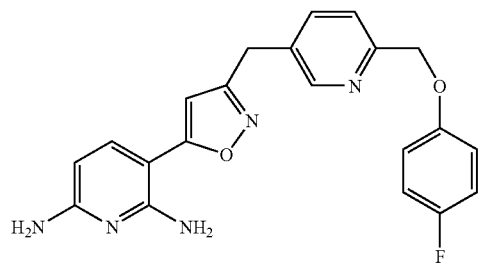

To a methanol (5.00 mL) solution of 2-(4-fluoro-phenoxymethyl)-5-(2-nitro-vinyl)-pyridine (50.0 mg, 0.181 mmol) described in Manufacturing Example 72-1-3 was added lithium methoxide (13.7 mg, 0.362 mmol) under nitrogen atmosphere, which was stirred for 30 minutes at room temperature. The reaction mixture was concentrated under a reduced pressure, and anhydrous dichloromethane (4.00 mL) and anhydrous tetrahydrofuran (2.00 mL) were added to the residue. Titanium (IV) tetrachloride (63.7 μL, 0.579 mmol) was added dropwise to the reaction mixture on a dry ice-ethanol bath (−78° C.), after which the system was stirred for 40 minutes at 0° C. Water and ethyl acetate were added to the reaction mixture on an ice bath (0° C.), and the organic layer was extracted with ethyl acetate. This organic layer was washed with water and saturated aqueous sodium chloride, dried over anhydrous magnesium sulfate, and then filtered. The filtrate was concentrated under a reduced pressure to obtain a crude product (43.0 mg). To a tetrahydrofuran (5.00 mL) solution of 3-ethynyl-pyridin-2,6-diamine (4.00 mg, 0.030 mmol) described in Manufacturing Example 13-1-3 and this crude product (20.0 mg) was added triethylamine (12.5 μL, 0.090 mmol), which was stirred for 2 hours at room temperature. Water was added to the reaction solution at room temperature, which was extracted with ethyl acetate. The organic layer was washed with a saturated aqueous sodium chloride and dried over anhydrous magnesium sulfate, and the solvent was evaporated under a reduced pressure. The residue was purified by reverse-phase high performance liquid chromatography (using an acetonitrile-water mobile phase containing 0.1% trifluoroacetic acid) to obtain the title compound (1.53 mg, 25.4%) as a ditrifluoroacetic acid salt.

MS m/e (ESI) 392.18 (MH$^+$)

Example 133

3-(3-(4-Phenylaminomethyl-benzyl)-isoxazol-5-yl)-pyridin-2,6-diamine

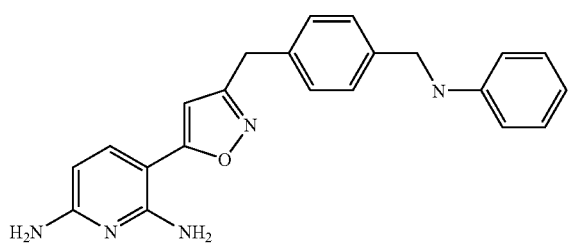

To a tetrahydrofuran (3 mL) solution of (4-phenylaminomethyl-phenyl)-acetohydroximoyl chloride (150 mg, 0.546 mmol) described in Manufacturing Example 73-1-6 and 3-ethynyl-pyridin-2,6-diamine (46.4 mg, 0.348 mmol) described in Manufacturing Example 13-1-3 was added triethylamine (104 μL, 0.748 mmol). This mixture was stirred for 7 hours at room temperature. This mixture was partitioned into ethyl acetate and water. The organic layer was separated, washed with water, dried over anhydrous magnesium sulfate, and filtered. The filtrate was concentrated under a reduced pressure, and the residue was purified by NH silica gel column chromatography (heptane:ethyl acetate=1:1 to 1:2~ethyl acetate) to obtain the title compound (26 mg, 13%).

$^1$H-NMR Spectrum (CDCl$_3$) δ (ppm): 4.00 (2H, s), 4.31 (2H, brs), 4.46 (2H, brs), 5.25 (2H, brs), 5.90-5.92 (1H, m), 5.99 (1H, s), 6.62-6.64 (2H, m), 6.69-6.73 (1H, m), 7.15-7.20 (2H, m), 7.25-7.27 (1H, m), 7.32-7.34 (2H, m), 7.47-7.49 (1H, m).

Note that it was not observed that no protons from the amino groups of NH—CH2Ph appeared on the NMR chart.

Example 134

3-(3-(6-(2-Fluoro-phenoxy)-pyridin-3-ylmethyl)-isoxazol-5-yl)-pyridin-2,6-diamine

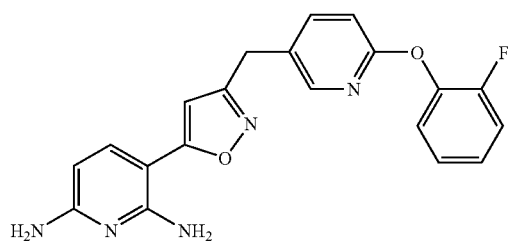

To a mixture of (6-(2-fluoro-phenoxy)-pyridin-3-yl)-acetohydroximoyl chloride (28 mg) described in Manufacturing Example 74-1-4 and tetrahydrofuran (1 mL) were added 3-ethynyl-pyridin-2,6-diamine (10 mg, 0.075 mmol) described in Manufacturing Example 13-1-3 and triethylamine (21 μL, 0.15 mmol), which was stirred for 5 hours at room temperature. Water was added to the reaction mixture at the same temperature, which was extracted with ethyl acetate. The organic layer was washed with saturated aqueous sodium chloride, and was concentrated under a reduced pressure. The residue was purified by NH silica gel column chromatography (ethyl acetate alone) to obtain the title compound (13 mg, 45%).

$^1$H-NMR Spectrum (CDCl$_3$) δ (ppm): 3.96 (2H, s), 4.50 (2H, br s), 5.27 (2H, br s), 5.93 (1H, d, J=8.4 Hz), 5.99 (1H, s), 6.96 (1H, d, J=8.6 Hz), 7.16-7.23 (4H, m), 7.48 (1H, d, J=8.2 Hz), 7.62 (1H, dd, J=2.6, 8.4 Hz), 8.08 (1H, d, J=2.6 Hz).

Example 135

3-(3-(6-(4-Fluoro-phenoxy)-pyridin-3-ylmethyl)-isoxazol-5-yl)-pyridin-2,6-diamine

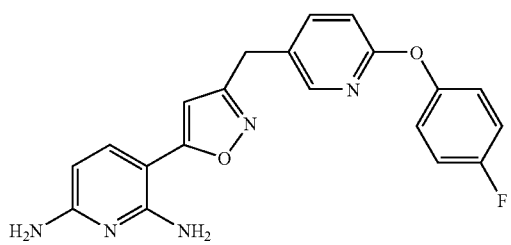

To a mixture of (6-(4-fluoro-phenoxy)-pyridin-3-yl)-acetohydroximoyl chloride (25 mg) described in Manufacturing Example 75-1-4 and tetrahydrofuran (1 mL) were added 3-ethynyl-pyridin-2,6-diamine (8 mg, 0.060 mmol) described in Manufacturing Example 13-1-3 and triethylamine (17 μL, 0.12 mmol), which was stirred for 5 hours at room temperature. Water was added to the reaction mixture at the same temperature, which was extracted with ethyl acetate. The organic layer was washed with saturated aqueous sodium chloride, and was concentrated under a reduced pressure. The residue was purified by NH silica gel column chromatography (ethyl acetate) to obtain the title compound (8.7 mg, 38%).

$^1$H-NMR Spectrum (DMSO-d$_6$) δ (ppm): 3.95 (2H, s), 5.81 (2H, br s), 5.83 (1H, d, J=8.4 Hz), 6.12 (2H, brs), 6.41 (1H, s), 7.00 (1H, d, J=8.4 Hz), 7.14-7.18 (2H, m), 7.21-7.26 (2H, m), 7.52 (1H, d, J=8.4 Hz), 7.78 (1H, dd, J=2.4, 8.4 Hz), 8.12 (1H, d, J=2.6 Hz).

Example 136

3-(3-(4-(Thiophen-3-ylmethoxy)-benzyl)-isoxazol-5-yl)-pyridin-2,6-diamine

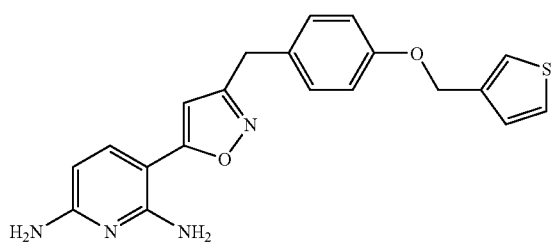

To a tetrahydrofuran (3 mL) solution of (4-(thiophen-3-ylmethoxy)-phenyl)-acetohydroximoyl chloride (150 mg, 0.532 mmol) described in Manufacturing Example 77-1-4 and 3-ethynyl-pyridin-2,6-diamine (45.2 mg, 0.339 mmol)

described in Manufacturing Example 13-1-3 was added triethylamine (185 μL, 1.33 mmol). This reaction mixture was stirred for 1.5 hours at room temperature. This mixture was partitioned into ethyl acetate and water. The organic layer was separated, washed with water, dried over anhydrous magnesium sulfate, and filtered. The filtrate was concentrated under a reduced pressure, and the residue was purified by NH silica gel column chromatography (heptane:ethyl acetate=1:1~ethyl acetate) to obtain the title compound (73 mg, 36%).

$^1$H-NMR Spectrum (DMSO-d$_6$) δ (ppm): 3.87 (2H, s), 5.06 (2H, s), 5.79 (2H, brs), 5.81-5.83 (1H, m), 6.11 (2H, brs), 6.34 (1H, s), 6.94-6.96 (2H, m), 7.15-7.17 (1H, m), 7.20-7.22 (2H, m), 7.50-5.56 (3H, m).

Example 137

3-(3-(4-Cyclopentyloxy-benzyl)-isoxazol-5-yl)-pyridin-2,6-diamine

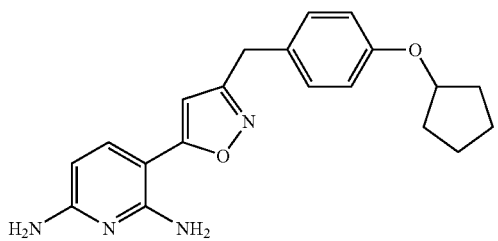

To a tetrahydrofuran (3 mL) solution of (4-cyclopentyloxy-phenyl)-acetohydroximoyl chloride (150 mg, 0.592 mmol) described in Manufacturing Example 78-1-4 and 3-ethynyl-pyridin-2,6-diamine (50.3 mg, 0.378 mmol) described in Manufacturing Example 13-1-3 was added triethylamine (206 μL, 1.48 mmol). This reaction mixture was stirred for 1.5 hours at room temperature. This mixture was partitioned into ethyl acetate and water. The organic layer was separated, washed with water, dried over anhydrous magnesium sulfate, and filtered. The filtrate was concentrated under a reduced pressure, and the residue was purified by NH silica gel column chromatography (heptane:ethyl acetate=1:1~ethyl acetate) to obtain the title compound (64 mg, 31%).

$^1$H-NMR Spectrum (DMSO-d$_6$) δ (ppm): 1.56-1.58 (2H, m), 1.67-1.68 (4H, m), 1.88-1.89 (2H, m), 3.86 (2H, s), 4.76-4.77 (1H, m), 5.79 (2H, brs), 5.81-5.84 (1H, m), 6.10 (2H, brs), 6.34 (1H, s), 6.82-6.84 (2H, m), 7.17-7.19 (2H, m), 7.50-7.52 (1H, m).

Example 138

3-(3-(4-(Pyridin-3-yloxy)-benzyl)-isoxazol-5-yl)-pyridin-2,6-diamine

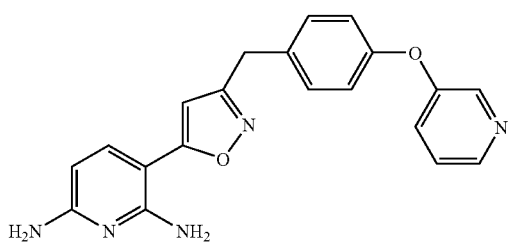

To a methanol (10.0 mL) solution of 3-(4-(2-nitro-ethyl)-phenoxy)-pyridine (819 mg, 3.35 mmol) described in Manufacturing Example 76-1-3 was added lithium methoxide (254 mg, 6.70 mmol), which was stirred for 30 minutes at room temperature. The reaction mixture was concentrated under a reduced pressure, and anhydrous dichloromethane (15.0 mL) and anhydrous tetrahydrofuran (7.00 mL) were added to the residue. Titanium (IV) chloride (1.18 mL, 10.7 mmol) was added dropwise to the reaction mixture on a dry ice-ethanol bath (−78° C.), after which the system was stirred for 30 minutes at room temperature. Aqueous sodium bicarbonate and ethyl acetate were added to the reaction mixture on an ice bath (0° C.), and the mixture was filtered through a Celite pad. The organic layer of the filtrate was extracted with ethyl acetate, and this organic layer was washed with water and saturated aqueous sodium chloride, dried over anhydrous magnesium sulfate, and the filtrate was concentrated under a reduced pressure, which gave a crude product (400 mg). To a tetrahydrofuran (5.00 mL) solution of 3-ethynyl-pyridin-2,6-diamine (40.0 mg, 0.300 mmol) described in Manufacturing Example 13-1-3 and this crude product (150 mg) was added triethylamine (125 μL, 0.900 mmol), which was stirred for 3 hours at 60° C. Water was added to the reaction solution at room temperature, which was extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=3:1→5:1) to obtain the title compound (17.0 mg, 15.8%).

$^1$H-NMR Spectrum (CD$_3$OD) δ (ppm): 3.96 (2H, s), 5.81 (2H, brs), 5.84 (1H, d, J=8.4 Hz), 6.12 (2H, brs), 6.40 (1H, s), 7.04 (2H, d, J=8.8 Hz), 7.36 (2H, d, J=8.8 Hz), 7.40-7.42 (2H, m), 7.53 (1H, d, J=8.4 Hz), 8.35-8.38 (2H, m).

Example 139

3-(3-(4-Cyclohexyloxy-benzyl)-isoxazol-5-yl)-pyridin-2,6-diamine

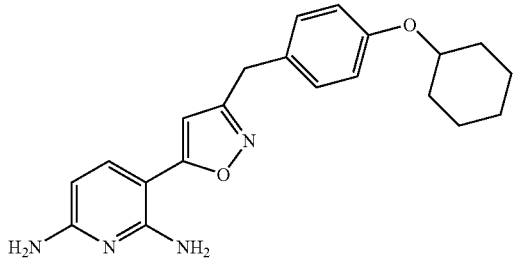

To a tetrahydrofuran (3 mL) solution of (4-cyclohexyloxy-phenyl)-acetohydroximoyl chloride (150 mg, 0.56 mmol) described in Manufacturing Example 79-1-4 and 3-ethynyl-pyridine-2,6-diamine (47.6 mg, 0.357 mmol) described in Manufacturing Example 13-1-3 was added triethylamine (195 μL, 1.4 mmol). This reaction mixture was stirred for 4 hours at room temperature. This mixture was partitioned into ethyl acetate and water. The organic layer was separated, washed with water, dried with anhydrous magnesium sulfate, and filtered. The filtrate was concentrated under a reduced pressure, and the residue was purified by NH silica gel column chromatography (heptane:ethyl acetate=1:1~ethyl acetate) to obtain the title compound (83 mg, 41%).

Example 140

3-(3-(4-(2-Furan-2-yl-ethyl)-benzyl)-isoxazol-5-yl)-pyridin-2,6-diamine

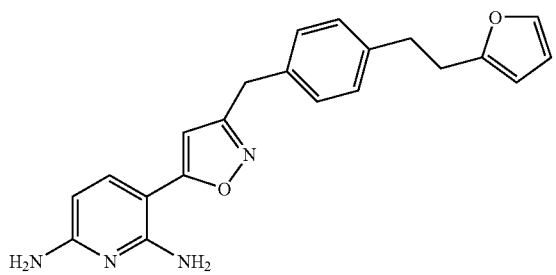

To a mixture of (4-(2-furan-2-yl-ethyl)phenyl)-acetohydroximoyl chloride (100 mg, 0.38 mmol) described in Manufacturing Example 80-1-7 and tetrahydrofuran (3 mL) were added 3-ethynyl-pyridin-2,6-diamine (25.3 mg, 0.19 mmol) described in Manufacturing Example 13-1-3 and triethylamine (0.1 mL, 0.76 mmol), which was stirred for 2 hours at room temperature. Water and ethyl acetate were added to the reaction mixture, and the organic layer was separated. This organic layer was washed with water and saturated aqueous sodium chloride and dried over anhydrous magnesium sulfate, and the solvent was evaporated under a reduced pressure. The residue was purified by NH silica gel column chromatography (ethyl acetate:heptane=1:1 then ethyl acetate) to obtain the title compound (50 mg, 72%).

$^1$H-NMR Spectrum (CDCl$_3$) δ (ppm): 2.88-2.98 (4H, m), 3.98 (2H, s), 4.47 (2H, brs), 5.26 (2H, brs), 5.91 (1H, d, J=8.4 Hz), 5.97 (1H, d, J=3.2 Hz), 5.99 (1H, s), 6.27 (1H, dd, J=2.0, 3.2 Hz), 7.13 (2H, d, J=8.0 Hz), 7.23 (2H, d, J=8.0 Hz), 7.31 (1H, d, J=2.0 Hz), 7.47 (1H, d, J=8.4 Hz).

Example 141

3-(3-(4-(4-Fluoro-phenoxy)-benzyl)-isoxazol-5-yl)-pyridin-2,6-diamine

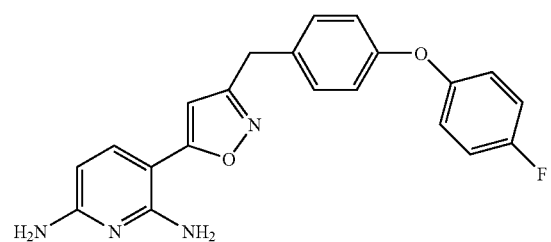

To a tetrahydrofuran (5.00 mL) solution of (4-(4-fluoro-phenoxy)-phenyl)-acetohydroximoyl chloride (290 mg, 1.04 mmol) described in Manufacturing Example 141-1-3 and 3-ethynyl-pyridine-2,6-diamine (40.0 mg, 0.300 mmol) described in Manufacturing Example 13-1-3 was added triethylamine (105 μL, 0.750 mmol) under nitrogen atmosphere at room temperature, which was stirred for 16 hours at room temperature. Water was added at room temperature to the reaction solution at room temperature, which was extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=3:1→ethyl acetate) to obtain the title compound (38.1 mg, 33.7%).

$^1$H-NMR Spectrum (DMSO-d$_6$) δ (ppm): 3.94 (2H, s), 5.81 (2H, brs), 5.83 (1H, d, J=8.0 Hz), 6.12 (2H, brs), 6.39 (1H, s), 6.95 (2H, d, J=8.4 Hz), 7.03-7.06 (2H, m), 7.19-7.24 (2H, m), 7.31 (2H, d, J=8.4 Hz), 7.52 (1H, d, J=8.0 Hz).

The starting material, (4-(4-fluoro-phenoxy)-phenyl)-acetohydroximoyl chloride, was synthesized as follows.

Manufacturing Example 141-1-1

4-(4-Fluoro-phenoxy)-benzaldehyde

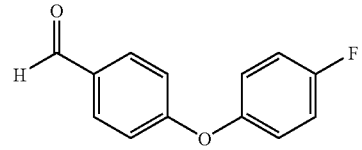

To an N,N-dimethylformamide (40.0 mL) solution of 4-fluorophenol (5.00 g, 44.6 mmol) and 4-fluorobenzaldehyde (4.00 mg, 32.2 mmol) was added potassium carbonate (13.4 g, 96.6 mmol), which was stirred for 21 hours at 80° C. The reaction solution was then cooled to room temperature, water was added thereto, and the reaction solution was extracted with ethyl acetate. The organic layer was washed with saturated aqueous sodium chloride, and the solvent was evaporated under a reduced pressure. The residue was purified by silica gel column chromatography (ethyl acetate:heptane=1:15→1:10) to obtain the title compound (6.60 g, 90.1%).

$^1$H-NMR Spectrum (CDCl$_3$) δ (ppm): 7.02-7.11 (6H, m), 7.85 (2H, d, J=8.8 Hz), 9.91 (1H, s).

Manufacturing Example 141-1-2

4-(4-Fluoro-phenoxy)-1-(2-nitro-ethyl)-benzene

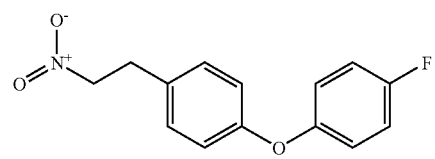

To an acetic acid (30.0 mL) solution of 4-(4-fluoro-phenoxy)-benzaldehyde (3.00 g, 48.4 mmol) described in Manufacturing Example 141-1-1 were added nitromethane (4.03 g, 66.0 mmol) and ammonium acetate (2.03 g, 26.4 mmol) under nitrogen atmosphere at room temperature, which was stirred for 4 hours at 110° C. Water and ethyl acetate were added to the reaction mixture, which was extracted with ethyl acetate. The organic layer was washed with water and a saturated aqueous sodium chloride, dried over anhydrous magnesium sulfate, and filtered. The filtrate was concentrated under a reduced pressure, which gave a crude product (3.4 g). To a dimethyl sulfoxide (30.0 mL) solution of this crude product (3.4 g) and acetic acid (3.00 mL) was added sodium borohydride (793 mg, 21.0 mmol) at room temperature while cooling appropriately, which was stirred for 30 minutes at room temperature. Water was then added dropwise at room temperature while cooling appropriately. The reaction mixture was extracted with ethyl acetate, and the organic layer was washed with water and saturated aqueous sodium chloride, dried over anhydrous magnesium sulfate, and filtered. The filtrate was concentrated under reduced pressure, and the residue was purified by NH silica gel column chromatography (ethyl acetate:heptane=1:3→1:1) to obtain the title compound (1.80 g, 52.6%).

$^1$H-NMR Spectrum (DMSO-d$_6$) δ (ppm): 3.21 (2H, t, J=6.8 Hz), 4.84 (2H, t, J=6.8 Hz), 6.93 (2H, d, J=8.4 Hz), 7.03-7.06 (2H, m), 7.22 (2H, t, J=8.8 Hz), 7.29 (2H, d, J=8.4 Hz).

Manufacturing Example 141-1-3

(4-(4-Fluoro-phenoxy)-phenyl)-acetohydroximoyl chloride

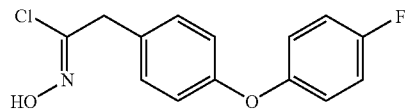

To a methanol (20.0 mL) solution of 4-(4-fluoro-phenoxy)-1-(2-nitro-ethyl)-benzene (500 mg, 1.91 mmol) described in Manufacturing Example 141-1-2 was added lithium methoxide (145 mg, 3.82 mmol) under nitrogen atmosphere at room temperature, which was stirred for 30 minutes at room temperature. The reaction mixture was concentrated under a reduced pressure, and anhydrous dichloromethane (20.0 mL) and anhydrous tetrahydrofuran (5.00 mL) were added to the residue. Titanium (IV) chloride (525 μL, 4.78 mmol) was added dropwise to the reaction mixture on a dry ice-ethanol bath (−78° C.), after which the system was stirred for 30 minutes at room temperature. Water and ethyl acetate were added to the reaction mixture on an ice bath (0° C.), and the organic layer was separated. The organic layer was washed with water and saturated aqueous sodium chloride, dried with anhydrous magnesium sulfate, and then filtered. The filtrate was concentrated under a reduced pressure to obtain the title compound (500 mg, 93.6%).

$^1$H-NMR Spectrum (DMSO-d$_6$) δ (ppm): 3.80 (2H, s), 6.95-6.97 (2H, m), 7.05-7.08 (2H, m), 7.21-7.27 (4H, m), 11.73 (1H, s).

Example 142

3-(3-(4-(3-Fluoro-phenoxy)-benzyl)-isoxazol-5-yl)-pyridin-2,6-diamine

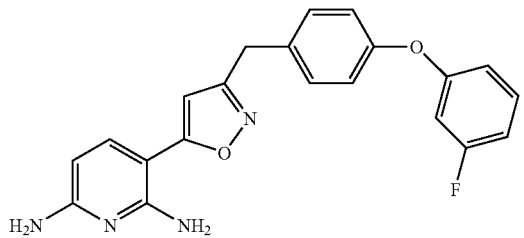

To a tetrahydrofuran (5.00 mL) solution of (4-(3-fluoro-phenoxy)-phenyl)-acetohydroximoyl chloride (210 mg, 0.622 mmol) described in Manufacturing Example 81-1-2 and 3-ethynyl-pyridine-2,6-diamine (30.0 mg, 0.225 mmol) described in Manufacturing Example 13-1-3 was added triethylamine (94.1 μL, 0.675 mmol) at room temperature, which was stirred for 30 minutes at room temperature. Water was added to the reaction solution at room temperature, which was extracted with ethyl acetate. The organic layer washed with saturated aqueous sodium chloride and dried over anhydrous magnesium sulfate, and the solvent was evaporated under a reduced pressure. The residue was purified by NH silica gel column chromatography (ethyl acetate:heptane=2:1) to obtain the title compound (29.0 mg, 34.2%).

$^1$H-NMR Spectrum (DMSO-d$_6$) δ (ppm): 3.97 (2H, s), 5.81 (2H, brs), 5.84 (1H, d, J=8.4 Hz), 6.12 (2H, brs), 6.41 (1H, s), 6.79-6.81 (1H, m), 6.84-6.87 (1H, m), 6.93-6.98 (1H, m), 7.03 (2H, d, J=8.8 Hz), 7.36 (2H, d, J=8.4 Hz), 7.39-7.43 (1H, m), 7.53 (1H, d, J=8.4 Hz).

Example 143

3-(3-(4-(2-Tetrahydrofuran-2-yl)-ethyl)-benzyl)-isoxazol-5-yl)-pyridin-2,6-diamine

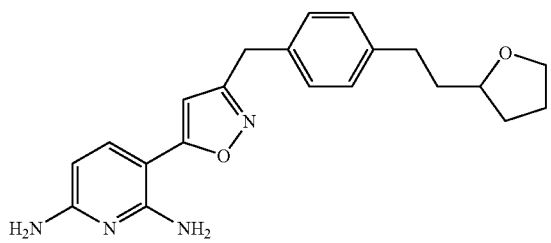

To a mixture of (4-(2-tetrahydrofuran-2-yl-ethyl)-phenyl)-acetohydroximoyl chloride (145 mg, 0.54 mmol) described in Manufacturing Example 82-1-6 and tetrahydrofuran (3 mL) were added 3-ethynyl-pyridin-2,6-diamine (36 mg, 0.27 mmol) described in Manufacturing Example 13-1-3 and triethylamine (0.15 mL, 1.08 mmol), which was stirred for 2 hours at room temperature. Water and ethyl acetate were added to the reaction mixture, and the organic layer was separated. This organic layer was washed with water and saturated aqueous sodium chloride and dried over anhydrous magnesium sulfate, and the solvent was evaporated under a reduced pressure. The residue was purified by NH silica gel column chromatography (ethyl acetate:heptane=1:1 then ethyl acetate) to obtain the title compound (76 mg, 77%).

$^1$H-NMR Spectrum (CDCl$_3$) δ (ppm): 1.40-1.55 (1H, m), 1.70-2.00 (5H, m), 2.60-2.80 (2H, m), 3.70-3.90 (3H, m), 3.91 (2H, s), 4.47 (μL, brs), 5.26 (2H, brs), 5.91 (1H, d, J=8.4 Hz), 5.99 (1H, s), 7.16 (2H, d, J=8.4 Hz), 7.20 (2H, d, J=8.4 Hz), 7.47 (1H, d, J=8.4 Hz).

Example 144

3-(3-(4-(2-Fluoro-phenoxy)-benzyl)-isoxazol-5-yl)-pyridin-2,6-diamine

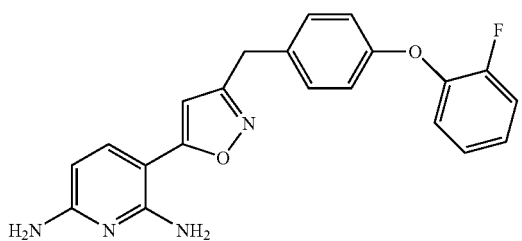

To a tetrahydrofuran (5.00 mL) solution of (4-(2-fluoro-phenoxy)-phenyl)-acetohydroximoyl chloride (210 mg, 0.622 mmol) described in Manufacturing Example 83-1-3 and 3-ethynyl-pyridin-2,6-diamine (30.0 mg, 0.225 mmol) described in Manufacturing Example 13-1-3 was added triethylamine (94.1 μL, 0.675 mmol) at room temperature, which was stirred for 16 hours at room temperature. Water was added at room temperature to the reaction solution at room temperature, which was extracted with ethyl acetate. The organic layer washed with saturated aqueous sodium chloride and dried over anhydrous magnesium sulfate, and the solvent was evaporated under a reduced pressure. The residue was purified by NH silica gel column chromatography (ethyl acetate:heptane=2:1) to obtain the title compound (41.7 mg, 49.2%).

$^1$H-NMR Spectrum (DMSO-d$_6$) δ (ppm): 3.94 (2H, s), 5.81 (2H, brs), 5.82-5.85 (1H, m), 6.12 (2H, brs), 6.39 (1H, s), 6.92-6.95 (2H, m), 7.13-7.24 (3H, m), 7.30-7.32 (2H, m), 7.35-7.41 (1H, m), 7.51-7.54 (1H, m).

Example 145

3-(3-(5-Phenoxy-pyridin-3-ylmethyl)-isoxazol-5-yl)-pyridin-2,6-diamine

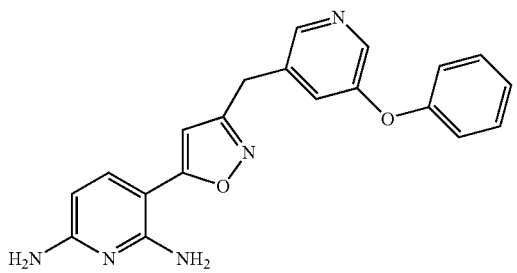

To a methanol (5 mL) solution of 3-(2-nitro-ethyl)-5-phenoxy-pyridine (210 mg, 0.860 mmol) described in Manufacturing Example 145-1-4 was added lithium methoxide (65 mg, 1.72 mmol), which was stirred for 25 minutes at room temperature. The reaction mixture was concentrated under a reduced pressure. To a suspension of this residue in tetrahydrofuran (5 mL) ad methylene chloride (5 mL) was added titanium (IV) tetrachloride (236 μL, 2.15 mmol) under nitrogen atmosphere, which was stirred for 50 minutes at 0° C. Sodium hydrogencarbonate was added to the reaction mixture at 0° C., which was extracted with ethyl acetate. The organic layer was separated, washed with saturated aqueous sodium chloride, dried over anhydrous magnesium sulfate, and filtered. The filtrate was concentrated under a reduced pressure. To a tetrahydrofuran (4 mL) solution of this residue were added 3-ethynyl-pyridin-2,6-diamine (15 mg, 0.11 mmol) described in Manufacturing Example 13-1-3 and triethylamine (240 μL, 1.72 mmol), which was stirred for 1 hour and 15 minutes at 50° C. Water was added to the reaction mixture at room temperature, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by reverse-phase high performance liquid chromatography (using an acetonitrile-water mobile phase containing 0.1% trifluoroacetic acid) to obtain the title compound (5.6 mg, 1.1%) as a ditrifluoroacetic acid salt.

MS m/e (ESI) (MH$^+$) 360.02 (MH$^+$)

The starting material, 3-(2-nitro-ethyl)-5-phenoxy-pyridine, was synthesized as follows.

Manufacturing Example 145-1-1

5-Phenoxy-nicotinic acid methyl ester

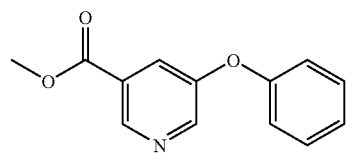

To a solution of 5-hydroxy-nicotinic acid methyl ester (903 mg, 5.90 mmol) in tetrahydrofuran (10 mL) and N,N-dimethylformamide (10 mL) were added diphenyliodonium chloride (1.87 g, 5.90 mmol) and potassium t-butoxide (662 mg, 5.90 mmol) at 0° C., which was stirred for 2 hours and 30 minutes at room temperature. Water was added to the reaction mixture, which was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by silica gel column chromatography (heptane:ethyl acetate=2:1) to obtain the title compound (1.11 g, 82%).

¹H-NMR Spectrum (CDCl₃) δ (ppm): 3.93 (3H, s), 7.04-7.06 (2H, m), 7.19-7.23 (1H, m), 7.39-7.43 (2H, m), 7.83 (1H, dd, J=1.7, 2.9 Hz), 8.57 (1H, d, J=2.9 Hz), 8.95 (1H, d, J=1.7 Hz).

Manufacturing Example 145-1-2

(5-Phenoxy-pyridin-3-yl)-methanol

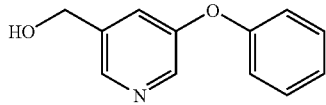

To a suspension of lithium aluminum hydride (689 mg, 14.5 mmol, purity: 80%) in tetrahydrofuran (20 mL) was added 5-phenoxy-nicotinic acid methyl ester (1.11 g, 4.84 mmol) described in Manufacturing Example 145-1-1 at 0° C., which was stirred for 20 minutes at room temperature. First water (689 μL), then a 5 N sodium hydroxide aqueous solution (689 μL), and then water (2.07 mL) were added at 0° C. to the reaction mixture, which was filtered through a Celite pad. The filtrate was concentrated under a reduced pressure, and the residue was purified by NH silica gel column chromatography (heptane:ethyl acetate=1:1) to obtain the title compound (756 mg, 78%).

¹H-NMR Spectrum (CDCl₃) δ (ppm): 1.77 (1H, t, J=5.9 Hz), 4.73 (2H, d, J=5.9 Hz), 7.03-7.06 (2H, m), 7.15-7.19 (1H, m), 7.32-7.33 (1H, m), 7.36-7.40 (2H, m), 8.33-8.34 (2H, m).

Manufacturing Example 145-1-3

5-Phenoxy-pyridine-3-carbaldehyde

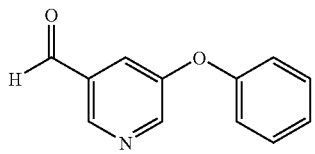

To a methylene chloride (20 mL) solution of (5-phenoxy-pyridin-3-yl)-methanol (756 mg, 3.76 mmol) described in Manufacturing Example 145-1-2 was added manganese (IV) dioxide (3.27 g, 37.6 mmol), which was stirred for 2 hours at room temperature. The insolubles were removed by filtrating through a Celite pad, after which the filtrate was concentrated under a reduced pressure. The residue was purified by silica gel column chromatography (heptane:ethyl acetate=2:1 to 1:1) to obtain the title compound (607 mg, 81%).

¹H-NMR Spectrum (CDCl₃) δ (ppm): 7.06-7.08 (2H, m), 7.22-7.26 (1H, m), 7.41-7.45 (2H, m), 7.64 (1H, dd, J=1.7, 2.9 Hz), 8.66 (1H, d, J=2.9 Hz), 8.79 (1H, d, J=1.7 Hz), 10.1 (1H, s).

Manufacturing Example 145-1-4

3-(2-Nitro-ethyl)-5-phenoxy-pyridine

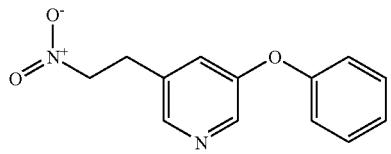

To an acetic acid (15 mL) solution of 5-phenoxy-pyridine-3-carbaldehyde (607 mg, 3.05 mmol) described in Manufacturing Example 145-1-3 were added nitromethane (826 μL, 15.3 mmol) and ammonium acetate (470 mg, 6.10 mmol), which was stirred for 3 hours at 100° C. under nitrogen atmosphere. Water was added at room temperature to the reaction mixture at room temperature, which was extracted with ethyl acetate. The organic layer was separated, washed with saturated aqueous sodium chloride, dried over anhydrous magnesium sulfate, and filtered. The filtrate was concentrated under a reduced pressure. To a solution of this residue in dimethyl sulfoxide (10 mL) and acetic acid (1 mL) was added sodium borohydride (182 mg, 4.58 mmol), which was stirred for 20 minutes at room temperature. Sodium hydrogencarbonate and water were added to the reaction mixture at room temperature while cooling appropriately, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (210 mg, 28%).

¹H-NMR Spectrum (CDCl₃) δ (ppm): 3.34 (2H, t, J=6.8 Hz), 4.65 (2H, t, J=6.8 Hz), 7.05-7.07 (2H, m), 7.28-7.32 (1H, m), 7.38 (1H, s), 7.44-7.48 (2H, m), 8.23-8.24 (2H, m).

Example 146

3-(3-(3-Pyridin-2-yl-benzyl)-isoxazol-5-yl)-pyridin-2,6-diamine

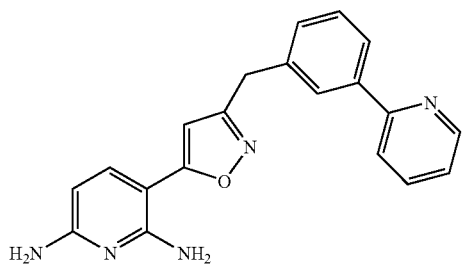

To a mixture of (3-(pyridin-2-yl)-phenyl)-acetohydroximoyl chloride (50 mg) described in Manufacturing Example 84-1-3 and tetrahydrofuran (2 mL) were added 3-ethynylpyridin-2,6-diamine (6.0 mg, 0.045 mmol) described in Manufacturing Example 13-1-3 and triethylamine (38 μL, 0.27 mmol), which was stirred for 2 hours at room temperature. Water was added to the reaction mixture at the same temperature, which was extracted with ethyl acetate. The organic layer was washed with saturated aqueous sodium chloride, and was concentrated under a reduced pressure. The residue was purified by NH silica gel column chromatography (ethyl acetate) to obtain the title compound in a crude product. Then, the residue was purified by reverse-phase high performance liquid chromatography (using an acetonitrile-water mobile phase containing 0.1% trifluoroacetic acid) to obtain the title compound (3.7 mg, 14%) as a ditrifluoroacetic acid salt.

MS m/e (ESI) 344.24 (MH$^+$)

Example 147

3-(3-Biphenyl-3-ylmethyl-isoxazol-5-yl)-pyridin-2,6-diamine

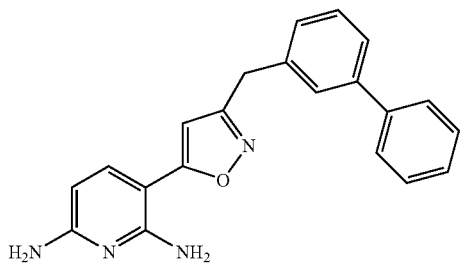

To a mixture of biphenyl-3-yl-acetohydroximoyl chloride (60 mg) described in Manufacturing Example 85-1-3 and tetrahydrofuran (3 mL) were added 3-ethynyl-pyridin-2,6-diamine (15 mg, 0.11 mmol) described in Manufacturing Example 13-1-3 and triethylamine (94 μL, 0.68 mmol), which was stirred for 2 hours at room temperature. Water was added to the reaction mixture at the same temperature, which was extracted with ethyl acetate. The organic layer was washed with saturated aqueous sodium chloride, and was concentrated under a reduced pressure. The residue was purified by NH silica gel column chromatography (ethyl acetate) to obtain the title compound in a crude product. Then, the residue was purified by reverse-phase high performance liquid chromatography (using an acetonitrile-water mobile phase containing 0.1% trifluoroacetic acid) to obtain the title compound (32 mg, 62%) as a trifluoroacetic acid salt.

MS m/e (ESI) 343.18 (MH$^+$)

Example 148

3-(3-(4-Phenoxymethyl-benzyl)-isoxazol-5-yl)-pyridin-2,6-diamine

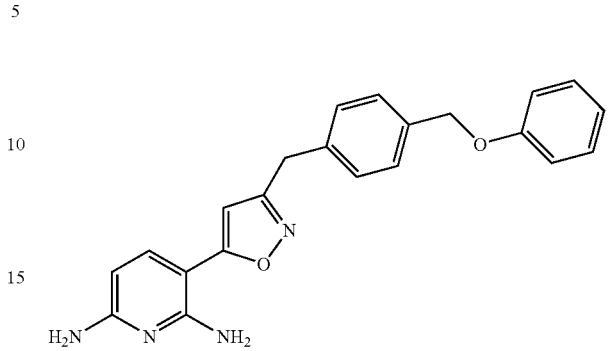

To a tetrahydrofuran (3 mL) solution of (4-phenoxymethyl-phenyl)-acetohydroximoyl chloride (150 mg, 0.545 mmol) described in Manufacturing Example 86-1-5 and 3-ethynyl-pyridin-2,6-diamine (46.3 mg, 0.348 mmol) described in Manufacturing Example 13-1-3 was added triethylamine (104 μL, 0.747 mmol), which was stirred for 1 hour at room temperature. This mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate) to obtain the title compound (45 mg, 22%).
$^1$H-NMR Spectrum (CDCl$_3$) δ (ppm): 4.03 (2H, s), 4.46 (2H, brs), 5.05 (2H, s), 5.25 (2H, brs), 5.91-5.93 (1H, m), 5.99 (1H, s), 6.97-6.99 (3H, m), 7.26-7.32 (4H, m), 7.40-7.42 (2H, m), 7.47-7.49 (1H, m).

Example 149

3-(3-(4-(3-Fluoro-pyridin-2-yloxymethyl)-benzyl)-isoxazol-5-yl)-pyridin-2,6-diamine

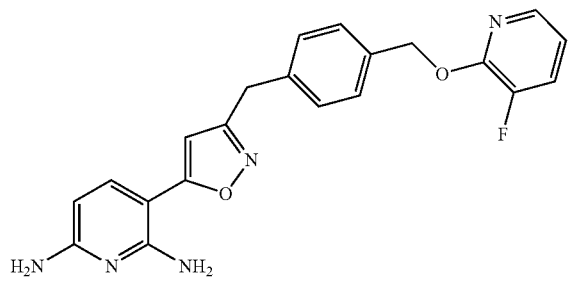

To a tetrahydrofuran (2 mL) solution of (4-(3-fluoro-pyridin-2-yloxymethyl)-phenyl)-acetohydroximoyl chloride (33 mg, 0.11 mmol) described in Manufacturing Example 149-1-4 were added 3-ethynyl-pyridin-2,6-diamine (10 mg, 75 μmol) described in Manufacturing Example 13-1-3 and triethylamine (21 μL, 0.15 mmol), which was stirred for 2 hours and 25 minutes at 50° C. and under nitrogen atmosphere. Water was added to the reaction mixture at room temperature, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (ethyl acetate:methanol=20:1) to obtain the title compound (27 mg, 92%).

¹H-NMR Spectrum (DMSO-d₆) δ (ppm): 3.97 (2H, s), 5.23 (2H, s), 5.80 (2H, s), 5.83 (1H, d, J=8.4 Hz), 6.11 (2H, s), 6.39 (1H, s), 7.35 (2H, d, J=8.2 Hz), 7.39 (1H, dd, J=4.6, 8.2 Hz), 7.43 (2H, d, J=8.2 Hz), 7.51 (1H, d, J=8.4 Hz), 7.66 (1H, dd, J=1.6, 8.4 Hz), 7.98 (1H, dd, J=1.6, 4.8 Hz).

The starting material, (4-(3-fluoro-pyridin-2-yloxymethyl)-phenyl)-acetohydroximoyl chloride, was synthesized as follows.

Manufacturing Example 149-1-1

2-(4-Bromo-benzyloxy)-3-fluoro-pyridine

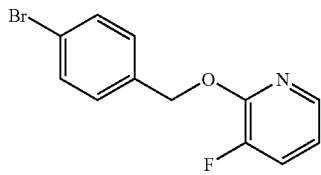

To an N,N-dimethylformamide (15 mL) solution of (4-bromo-phenyl)-methanol (1.56 g, 8.34 mmol) was added sodium hydride (401 mg, 8.35 mmol, 50% in oil), which was stirred for 5 minutes at room temperature. Then, an N,N-dimethylformamide (5 mL) solution of 2-chloro-3-fluoropyridine (967 mg, 7.35 mmol) was added to this mixture, which was stirred for 1 hour and 10 minutes at room temperature. Water was to the reaction mixture at room temperature, which was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=2:1) to obtain the title compound (2.03 g, 98%).

¹H-NMR Spectrum (CDCl₃) δ (ppm): 5.13 (2H, s), 7.17 (1H, dd, J=4.4, 8.1 Hz), 7.20 (1H, dd, J=2.0, 8.1 Hz), 7.34 (2H, d, J=8.4 Hz), 7.54 (2H, d, J=8.4 Hz), 8.02 (1H, dd, J=2.0, 4.4 Hz).

Manufacturing Example 149-1-2

4-(3-Fluoro-pyridin-2-yloxymethyl)-benzaldehyde

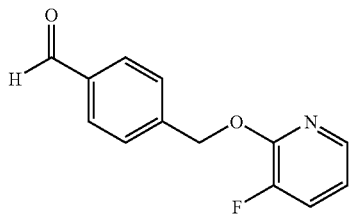

To a tetrahydrofuran (40 mL) solution of 2-(4-bromo-benzyloxy)-3-fluoro-pyridine (2.03 g, 7.20 mmol) described in Manufacturing Example 149-1-1 was added n-Butyl lithium (5.04 mL, 1.6 M hexane solution, 7.92 mmol) under nitrogen atmosphere at −78° C., which was stirred for 45 minutes at −78° C. Then, N,N-dimethylformamide (725 μL, 9.36 mmol) was added to the reaction mixture at −78° C., which was stirred for 1 hour and 10 minutes while the temperature was raised to room temperature. Water was added to the reaction solution at room temperature, which was extracted with ethyl acetate. The organic layer was separated, washed with saturated aqueous sodium chloride, dried over anhydrous magnesium sulfate, and filtered. The residue was purified by silica gel column chromatography (heptane:ethyl acetate=2:1) to obtain the title compound (887 mg, 53%).

¹H-NMR Spectrum (CDCl₃) δ (ppm): 5.26 (2H, s), 7.17-7.26 (2H, m), 7.64 (2H, d, J=8.1 Hz), 7.94 (2H, d, J=8.0 Hz), 8.05 (1H, dd, J=1.8, 4.4 Hz), 10.0 (1H, s).

Manufacturing Example 149-1-3

3-Fluoro-2-(4-(2-nitro-ethyl)-benzyloxy)-pyridine

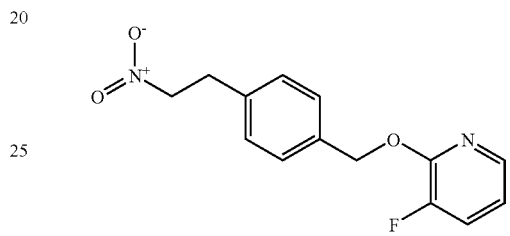

To an acetic acid (20 mL) solution of 4-(3-fluoro-pyridin-2-yloxymethyl)-benzaldehyde (887 mg, 3.84 mmol) described in Manufacturing Example 149-1-2 were added nitromethane (1.04 mL, 19.2 mmol) and ammonium acetate (592 mg, 7.68 mmol), which was stirred under nitrogen atmosphere for 4 hours and 30 minutes at 100° C. Water was added to the reaction mixture at 0° C., which was extracted with ethyl acetate. The organic layer was separated, washed with saturated aqueous sodium chloride, dried over anhydrous magnesium sulfate, and filtered. The filtrated was concentrated under a reduced pressure. To a solution of this residue in dimethyl sulfoxide (20 mL) and acetic acid (1 mL) was added sodium borohydride (291 mg, 7.68 mmol), which was stirred for 30 minutes at room temperature. Sodium hydrogencarbonate and water were added to the reaction solution at room temperature while cooling appropriately, which was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=2:1) to obtain the title compound (674 mg, 64%).

¹H-NMR Spectrum (CDCl₃) δ (ppm): 3.33 (2H, t, J=7.2 Hz), 4.62 (2H, t, J=7.2 Hz), 5.15 (2H, s), 7.16 (1H, dd, J=4.8, 8.0 Hz), 7.20 (1H, dd, J=2.0, 8.0 Hz), 7.23-7.25 (2H, m), 7.41 (2H, d, J=8.4 Hz), 8.00 (1H, dd, J=1.6, 4.4 Hz).

Manufacturing Example 149-1-4

(4-(3-Fluoro-pyridin-2-yloxymethyl)-phenyl)-acetohydroximoyl chloride

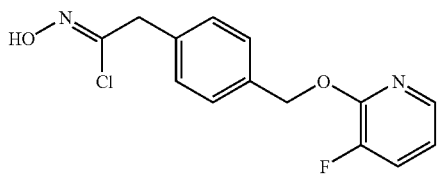

To a methanol (10 mL) solution of 3-fluoro-2-(4-(2-nitroethyl)-benzyloxy)-pyridine (674 mg, 2.44 mmol) described in Manufacturing Example 149-1-3 was added lithium methoxide (185 mg, 4.87 mmol), which was stirred for 5 minutes at room temperature. The reaction mixture was concentrated under a reduced pressure. To a suspension of this residue in tetrahydrofuran (10 mL) and methylene chloride (10 mL) was added titanium (IV) tetrachloride (590 µL, 5.37 mmol) under nitrogen atmosphere at −78° C., which was stirred for 1 hour at 0° C. Water was added to the reaction mixture at 0° C., which was then extracted with ethyl acetate. The organic layer was separated, washed with saturated aqueous sodium chloride, dried over anhydrous magnesium sulfate, and then filtered with neutral silica gel. The filtrate was concentrated under a reduced pressure to obtain the title compound (629 mg, 88%). This compound was used in the following reaction without any further purification.

$^1$H-NMR Spectrum (CDCl$_3$) δ (ppm): 3.82 (2H, s), 5.17 (2H, s), 7.17 (1H, ddd, J=1.4, 4.8, 8.0 Hz), 7.23 (1H, dd, J=1.6, 8.0 Hz), 7.32 (2H, d, J=7.9 Hz), 7.43 (2H, d, J=7.9 Hz), 7.64 (1H, s), 8.01 (1H, dd, J=1.7, 4.6 Hz).

Example 150

3-(3-(3-Fluoro-4-(pyridin-2-ylmethoxy)-benzyl)-isoxazol-5-yl)-pyridin-2,6-diamine

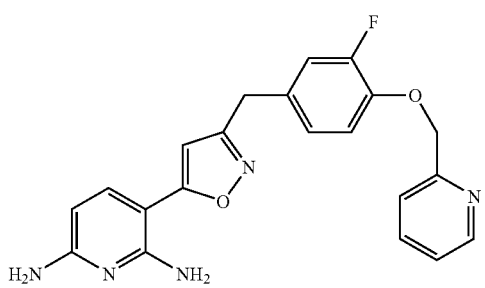

To a methanol (20.0 mL) solution of 2-(2-fluoro-4-(2-nitro-ethyl)-phenoxymethyl)-pyridine (500 mg, 1.81 mmol) described in Manufacturing Example 87-1-3 was added lithium methoxide (137 mg, 3.61 mmol) under nitrogen atmosphere, which was stirred for 30 minutes at room temperature. The reaction mixture was concentrated under a reduced pressure, and dichloromethane (15.0 mL) and anhydrous tetrahydrofuran (7.00 mL) were added to the residue. Titanium (IV) chloride (656 µL, 5.97 mmol) was added dropwise to the reaction mixture on a dry ice-ethanol bath (−78° C.), and which was stirred for 30 minutes at room temperature. Aqueous sodium bicarbonate and ethyl acetate were added to the reaction mixture on an ice bath (0° C.), which was filtered through a Celite pad. The organic layer of the filtrate was extracted with ethyl acetate, and this organic layer was washed with water and saturated aqueous sodium chloride, dried over anhydrous magnesium sulfate, and filtered. The filtrate was concentrated under a reduced pressure to obtain a crude product (300 mg). To a tetrahydrofuran (5.00 mL) solution of this crude product (150 mg) and 3-ethynyl-pyridin-2,6-diamine (30.0 mg, 0.225 mmol) described in Manufacturing Example 13-1-3 was added triethylamine (94.1 µL, 0.675 mmol) at room temperature, which was stirred for 1 hour at room temperature. Water was added to the reaction solution, which was extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=2:1→10:1) to obtain the title compound (35.0 mg, 39.7%).

$^1$H-NMR Spectrum (DMSO-d$_6$) δ (ppm): 3.90 (2H, s), 5.22 (2H, s), 5.80 (2H, brs), 5.83 (1H, d, J=8.8 Hz), 6.12 (2H, brs), 6.38 (1H, s), 7.04 (1H, d, J=8.4 Hz), 7.15-7.23 (2H, m), 7.34-7.37 (1H, m), 7.52 (2H, d, J=8.0 Hz), 7.85 (1H, t, J=8.0 Hz), 8.58 (1H, d, J=8.8 Hz).

Example 151

3-(3-(4-(Thiazol-2-ylmethoxy)-benzyl)-isoxazol-5-yl)-pyridin-2,6-diamine

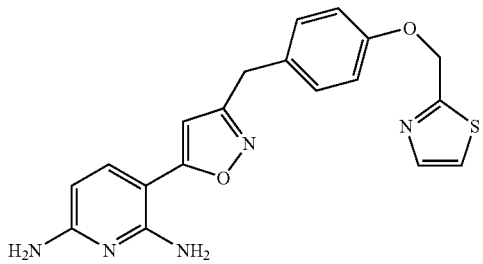

To a tetrahydrofuran (3 mL) solution of 4-(5-(2,6-diaminopyridin-3-yl)-isoxazol-3-ylmethyl)-phenol (50 mg, 0.18 mmol) described in Manufacturing Example 18-1-1 was added a 5 N sodium hydroxide aqueous solution (35.4 µL, 0.18 mmol), which was dissolved by irradiating ultrasonic wave for 1 minute. The reaction solution was concentrated under a reduced pressure, which gave a white solid. To a suspension of this solid in N,N-dimethylformamide (1 mL) was added an N,N-dimethylformamide (1 mL) solution of 2-chloromethyl-thiazole (28.4 mg, 0.21 mmol) described in manufacturing Example 88-1-2, which was stirred for 3 hours at 60° C. The reaction mixture was cooled to room temperature and then partitioned into water and ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate) to obtain the title compound (43.0 mg, 64%).

$^1$H-NMR Spectrum (DMSO-d$_6$) δ (ppm): 3.89 (2H, s), 5.41 (2H, s), 5.79 (2H, brs), 5.82 (1H, d, J=8.8 Hz), 6.11 (2H, brs), 6.35 (1H, s), 7.01 (2H, d, J=8.8 Hz), 7.24 (2H, d, J=8.8 Hz), 7.51 (1H, d, J=8.4 Hz), 7.77 (1H, d, J=3.6 Hz), 7.83 (1H, d, J=3.2 Hz).

Example 152

3-(3-(6-(3,4-Difluoro-benzyloxy)-pyridin-3-ylmethyl)-isoxazol-5-yl)-pyridin-2,6-diamine

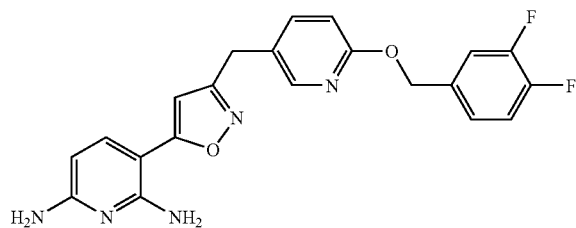

The title compound (90 mg, 73%) was obtained according to the method similar to those of Example 3, using 3-ethynyl-pyridin-2,6-diamine (40 mg, 0.30 mmol) described in Manufacturing Example 13-1-3 and (6-(3,4-difluoro-benzyloxy)-pyridin-3-yl)-acetohydroximoyl chloride (140 mg, 0.45 mmol) described in Manufacturing Example 89-1-1.

$^1$H-NMR Spectrum (DMSO-$d_6$) δ (ppm): 3.92 (2H, s), 5.31 (2H, s), 5.81 (2H, brs), 5.83 (1H, dd, J=1.6, 8.0 Hz), 6.12 (2H, brs), 6.40 (1H, d, J=1.6 Hz), 6.86 (1H, d, J=8.0 Hz), 7.28-7.34 (1H, m), 7.39-7.47 (1H, m), 7.48-7.56 (2H, m), 7.65-7.70 (1H, m), 8.14 (1H, s).

Example 153

3-(3-(6-(2,4-Difluoro-benzyloxy)-pyridin-3-ylmethyl)-isoxazol-5-yl)-pyridin-2,6-diamine

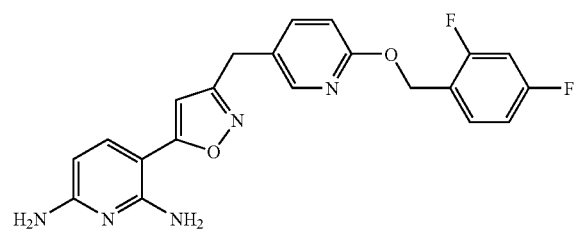

The title compound (62 mg, 67%) was obtained according to the method similar to those of Example 12, using 3-ethynyl-pyridin-2,6-diamine (30 mg, 0.23 mmol) described in Manufacturing Example 13-1-3 and (6-(2,4-difluoro-benzyloxy)-pyridin-3-yl)-acetohydroximoyl chloride (110 mg, 0.34 mmol) described in Manufacturing Example 90-1-1.

$^1$H-NMR Spectrum (DMSO-$d_6$) δ (ppm): 3.92 (2H, s), 5.34 (2H, s), 5.81 (2H, brs), 5.83 (1H, d, J=8.0 Hz), 6.12 (2H, brs), 6.34 (1H, s), 6.83 (1H, d, J=8.0 Hz), 7.07-7.14 (1H, m), 7.25-7.33 (1H, m), 7.51 (1H, d, J=8.0 Hz), 7.56-7.64 (1H, m), 7.66 (1H, dd, J=2.0, 8.0 Hz), 8.15 (1H, d, J=2.0 Hz).

Example 154

3-(3-(6-Pyridin-2-yloxymethyl)-pyridin-3-ylmethyl)-isoxazol-5-yl)-pyridin-2,6-diamine

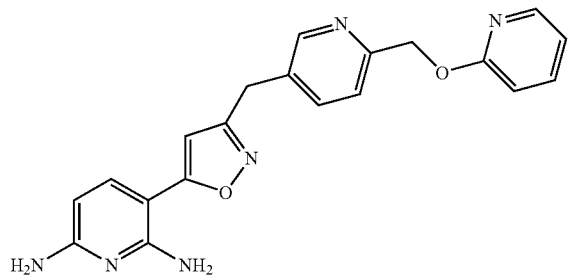

To a tetrahydrofuran (2 mL) solution of (6-(pyridin-2-yloxymethyl)-pyridin-3-yl)-acetohydroximoyl chloride (24 mg) described in Manufacturing Example 154-1-8 were added 3-ethynyl-pyridin-2,6-diamine (5.0 mg, 38 μmol) described in Manufacturing Example 13-1-3 and triethylamine (13 μL, 94 μmol), which was stirred for 1 hour at 50° C. Water was added to the reaction mixture, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (ethyl acetate:methanol=20:1) to obtain the title compound (8.2 mg, 58%).

$^1$H-NMR Spectrum (CDCl$_3$) δ (ppm): 4.03 (2H, s), 4.53 (2H, s), 5.28 (2H, s), 5.50 (2H, s), 5.92 (1H, d, J=8.4 Hz), 6.00 (1H, s), 6.85-6.91 (2H, m), 7.43 (1H, d, J=7.9 Hz), 7.47 (1H, d, J=8.4 Hz), 7.58-7.62 (2H, m), 8.14-8.16 (1H, m), 8.58 (1H, d, J=2.4 Hz).

The starting material, (6-(pyridin-2-yloxymethyl)-pyridin-3-yl)acetohydroximoyl chloride, was synthesized as follows.

Manufacturing Example 154-1-1

6-Bromo-pyridine-3-carbaldehyde

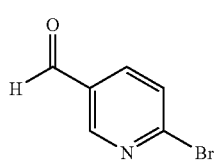

To a diethyl ether (60 mL) solution of 2,5-dibromopyridine (3.00 g, 12.7 mmol) was added n-butyl lithium (7.99 mL, 1.6 M hexane solution, 12.7 mmol) under nitrogen atmosphere at −78° C., which was stirred for 50 minutes at −78° C. Then, N,N-dimethylformamide (1.18 mL, 15.2 mmol) was added to the mixture, which was stirred for 35 minutes while the temperature was raised to room temperature. Water was added to the reaction solution at room temperature, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by silica gel column chromatography (heptane:ethyl acetate=3:1) to obtain the title compound (1.56 g, 66%).

$^1$H-NMR Spectrum (CDCl$_3$) δ (ppm): 7.69 (1H, dd, J=0.73, 8.2 Hz), 8.03 (1H, dd, J=2.4, 8.2 Hz), 8.84 (1H, dd, J=0.73, 2.4 Hz), 10.1 (1H, s).

Manufacturing Example 154-1-2

2-Bromo-5-[1,3]dioxolan-2-yl-pyridine

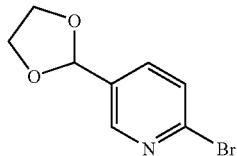

To a toluene (100 mL) solution of 6-bromo-pyridine-3-carbaldehyde (5.0 g, 27 mmol) described in Manufacturing Example 154-1-1 were added ethylene glycol (3.0 mL, 54 mmol) and p-toluenesulfonic acid monohydrate (512 mg, 2.7 mmol), which was refluxed for 3 hours and 40 minutes under nitrogen atmosphere. Sodium hydrogencarbonate and water were added to the reaction mixture, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (6.0 g, 97%).

$^1$H-NMR Spectrum (CDCl$_3$) δ (ppm): 4.03-4.13 (4H, m), 5.83 (1H, s), 7.49-7.52 (1H, m), 7.64-7.67 (1H, m), 8.46 (1H, d, J=2.4 Hz).

Manufacturing Example 154-1-3

5-[1,3]Dioxolan-2-yl-pyridine-2-carbaldehyde

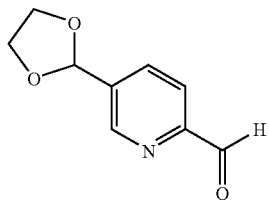

To a tetrahydrofuran (100 mL) solution of 2-bromo-5-[1,3]dioxolan-2-yl-pyridine (4.77 g, 20.7 mmol) described in Manufacturing Example 154-1-2 was added n-butyl lithium (14.3 mL, 1.6 M hexane solution, 22.8 mmol) under nitrogen atmosphere at −78° C., which was stirred for 20 minutes at −78° C. Then, N,N-dimethylformamide (1.92 mL, 24.8 mmol) was added to the reaction mixture, which was stirred for 15 minutes while the temperature was raised to room temperature. Water was added to the reaction mixture at room temperature, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by silica gel column chromatography (heptane:ethyl acetate=2:1) to obtain the title compound (1.73 g, 47%).

$^1$H-NMR Spectrum (CDCl$_3$) δ (ppm): 4.07-4.16 (4H, m), 5.94 (1H, s), 7.98 (2H, s), 8.88 (1H, s), 10.1 (1H, s).

Manufacturing Example 154-1-4

(5-[1,3]Dioxolan-2-yl-pyridin-2-yl)-methanol

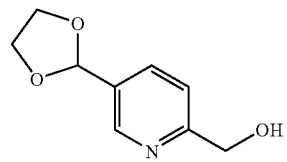

To an ethanol (20 mL) and tetrahydrofuran (20 mL) solution of 5-[1,3]dioxolan-2-yl-pyridine-2-carbaldehyde (1.73 g, 9.66 mmol) described in Manufacturing Example 154-1-3 was added sodium borohydride (731 mg, 19.3 mmol), which was stirred for 25 minutes at room temperature. Water was added to the reaction mixture, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by silica gel column chromatography (heptane:ethyl acetate=1:2) to obtain the title compound (1.37 g, 78%).

$^1$H-NMR Spectrum (CDCl$_3$) δ (ppm): 3.65 (1H, s), 4.05-4.16 (4H, m), 4.78 (2H, s), 5.87 (1H, s), 7.26-7.28 (1H, m), 7.80 (1H, dd, J=2.0, 8.1 Hz), 8.65 (1H, d, J=2.0 Hz).

Manufacturing Example 154-1-5

5-[1,3]Dioxolan-2-yl-2-(pyridin-2-yloxymethyl)-pyridine

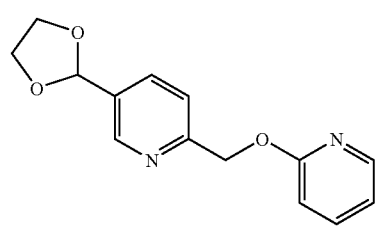

To an N,N-dimethylformamide (40 mL) solution of (5-[1,3]dioxolan-2-yl-pyridin-2-yl)-methanol (1.37 g, 7.56 mmol) described in Manufacturing Example 154-1-4 was added sodium hydride (333 mg, 8.32 mmol, 60% in oil), which was stirred for 5 minutes at 0° C. Next, 2-fluoropyridine (716 μL, 8.32 mmol) was added to the reaction mixture, which was stirred for 45 minutes at 50° C. Water was added to the reaction mixture at room temperature, which was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by silica gel column chromatography (heptane:ethyl acetate=2:1 to 1:1) to obtain the title compound (1.51 g, 77%).

$^1$H-NMR Spectrum (CDCl$_3$) δ (ppm): 4.04-4.15 (4H, m), 5.53 (2H, s), 5.87 (1H, s), 6.86-6.91 (2H, m), 7.47 (1H, d, J=8.1 Hz), 7.58-7.63 (1H, m), 7.79 (1H, dd, J=2.0, 8.2 Hz), 8.14-8.16 (1H, m), 8.70 (1H, d, J=2.0 Hz).

Manufacturing Example 154-1-6

6-(Pyridin-2-yloxymethyl)-pyridine-3-carbaldehyde

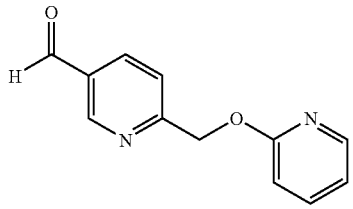

To a solution of 5-[1,3]dioxolan-2-yl-2-(pyridin-2-yloxymethyl)-pyridine (1.51 g, 5.85 mmol) described in Manufacturing Example 154-1-5 in tetrahydrofuran (15 mL) and dimethyl sulfoxide (10 mL) was added a 5 N hydrochloric acid aqueous solution (3 mL), which was stirred for 25 minutes at room temperature, and then for another 1 hour at 20 minutes at 60° C. A 5 N sodium hydroxide aqueous solution was added to the reaction mixture at room temperature, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by silica gel column chromatography (heptane:ethyl acetate=1:1) to obtain the title compound (603 mg, 48%).

$^1$H-NMR Spectrum (CDCl$_3$) δ (ppm): 5.61 (2H, s), 6.90-6.94 (2H, m), 7.26-7.66 (2H, m), 8.12-8.14 (1H, m), 8.17 (1H, dd, J=2.0, 8.1 Hz), 9.05 (1H, d, J=1.7 Hz), 10.1 (1H, s).

Manufacturing Example 154-1-7

5-(2-Nitro-ethyl)-2-(pyridin-2-yloxymethyl)-pyridine

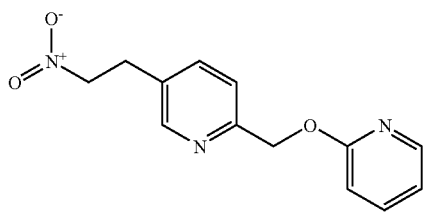

To an acetic acid (20 mL) solution of 6-(pyridine-2-yloxymethyl)-pyridine-3-carbaldehyde (504 mg, 2.35 mmol) described in Manufacturing Example 154-1-6 were added nitromethane (635 μL, 11.8 mmol) and ammonium acetate (363 mg, 4.71 mmol), which was stirred for 4 hours at 100° C. under nitrogen atmosphere. Water was added to the reaction mixture at room temperature, which was extracted with ethyl acetate. The organic layer was separated, washed with saturated aqueous sodium chloride, dried over anhydrous magnesium sulfate, and filtered. The filtrate was concentrated under a reduced pressure. To a solution of this residue in dimethyl sulfoxide (25 mL) and acetic acid (2.5 mL) was added sodium borohydride (178 mg, 4.71 mmol), which was stirred for 25 minutes at room temperature. Sodium hydrogencarbonate and water were added to the reaction mixture at room temperature, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (93 mg, 15%).

$^1$H-NMR Spectrum (CDCl$_3$) δ (ppm): 3.38 (2H, t, J=6.8 Hz), 4.66 (2H, t, J=6.8 Hz), 5.83 (2H, s), 6.90-6.96 (2H, m), 7.63-7.70 (2H, m), 7.78 (1H, dd, J=1.6, 8.0 Hz), 8.14 (1H, dd, J=1.6, 4.8 Hz), 8.68 (1H, d, J=1.2 Hz).

Manufacturing Example 154-1-8

(6-(Pyridin-2-yloxymethyl)-pyridin-3-yl)-acetohydroximoyl chloride

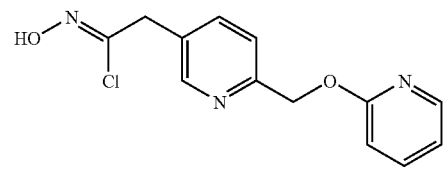

To a methanol (5 mL) solution of 5-(2-nitro-ethyl)-2-(pyridin-2-yloxymethyl)-pyridine (93 mg, 0.36 mmol) described in Manufacturing Example 154-1-7 was added lithium methoxide (27 mg, 0.72 mmol), which was stirred for 5 minutes at room temperature. The reaction mixture was concentrated under a reduced pressure. To a suspension of this residue in tetrahydrofuran (3 mL) and methylene chloride (3 mL) was added titanium (IV) tetrachloride (87 μL, 0.79 mmol) under nitrogen atmosphere at −78° C., which was stirred for 2 hours at 0° C. More titanium (IV) tetrachloride (50 μL, 0.46 mmol) was added at −78° C., which was stirred for 3 hours at 0° C. Water was added to the reaction mixture at 0° C., which was then extracted with ethyl acetate. The organic layer was separated, washed with saturated aqueous sodium chloride, dried over anhydrous magnesium sulfate, and then filtered. The filtrate was concentrated under a reduced pressure to obtain the title compound (24 mg). This compound was used in the following reaction without any further purification.

Example 155

3-(3-(5-(4-Fluoro-phenoxy-thiophen-2-ylmethyl)-isoxazol-5-yl)-pyridin-2,6-diamine

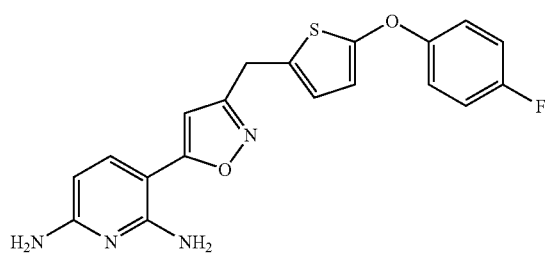

To a tetrahydrofuran (5.00 mL) solution of (5-(4-fluorophenoxy)-thiophen-2-yl)-acetohydroximoyl chloride (250 mg, 0.875 mmol) described in Manufacturing Example 91-1-4 and 3-ethynyl-pyridin-2,6-diamine (50.0 mg, 0.376 mmol) described in Manufacturing Example 13-1-3 was added triethylamine (157 μL, 1.27 mmol) at room temperature, which was stirred for 3 hours at 60° C. Water was added to the reaction mixture at room temperature, which was extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=2:1→3:1) to obtain the title compound (20.9 mg, 14.5%).

$^1$H-NMR Spectrum (DMSO-d$_6$) δ (ppm): 4.09 (2H, s), 5.82 (2H, brs), 5.84 (1H, d, J=8.4 Hz), 6.14 (2H, brs), 6.44 (1H, s), 6.51 (1H, d, J=3.6 Hz), 6.75 (1H, d, J=3.6 Hz), 7.13-7.16 (2H, m), 7.19-7.25 (2H, m), 7.54 (1H, d, J=8.0 Hz).

Example 156

3-(3-(5-(4-Methyl-benzyl)-thiophen-2-ylmethyl)-isoxazol-5-yl)-pyridin-2,6-diamine

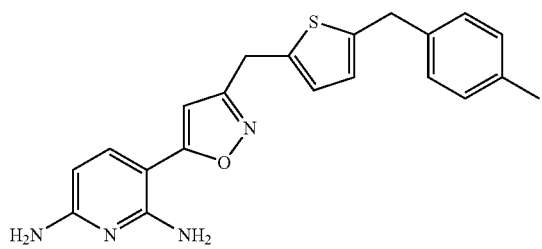

To a tetrahydrofuran (5.00 mL) solution of (5-(4-methyl-benzyl)-thiophen-2-yl)acetohydroximoyl chloride (250 mg, 0.894 mmol) described in Manufacturing Example 92-1-5 and 3-ethynyl-pyridin-2,6-diamine (50.0 mg, 0.376 mmol) described in Manufacturing Example 13-1-3 was added triethylamine (157 μL, 1.13 mmol) at room temperature, which was stirred for 30 minutes at 60° C. Water was added to the reaction solution at room temperature, which was extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=2:1→3:1) to obtain the title compound (49.8 mg, 35.2%).

$^1$H-NMR Spectrum (DMSO-d$_6$) δ (ppm): 2.25 (3H, s), 4.01 (2H, s), 4.07 (2H, s), 5.80 (2H, brs), 5.83 (1H, d, J=8.4 Hz), 6.13 (2H, brs), 6.39 (1H, s), 6.69 (1H, d, J=3.2 Hz), 7.78 (1H, d, J=3.2 Hz), 7.08-7.13 (4H, m), 8.09 (1H, d, J=8.4 Hz).

Example 157

3-(3-(3-Fluoro-4-(5-fluoro-pyridin-2-ylmethoxy)-benzyl)-isoxazol-5-yl)-pyridin-2,6-diamine

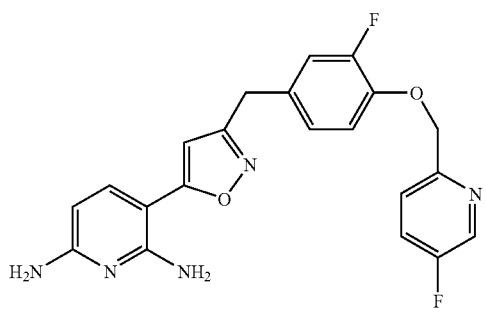

To a tetrahydrofuran (5.00 mL) solution of (3-fluoro-4-(5-fluoro-pyridin-2-ylmethoxy)-phenyl)-acetohydroximoyl chloride (170 mg, 0.554 mmol) described in Manufacturing Example 94-1-3 and 3-ethynyl-pyridin-2,6-diamine (40.0 mg, 0.300 mmol) described in Manufacturing Example 13-1-3 was added triethylamine (125 μL, 0.900 mmol) at room temperature, which was stirred for 30 minutes at room temperature. Water was added to the reaction solution at room temperature, which was extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=2:1→3:1) to obtain the title compound (59.0 mg, 48.0%).

$^1$H-NMR Spectrum (DMSO-d$_6$) δ (ppm): 3.90 (2H, s), 5.22 (2H, s), 5.80 (2H, brs), 5.83 (1H, d, J=8.4 Hz), 6.11 (1H, brs), 6.38 (1H, s), 7.05 (1H, d, J=8.4 Hz), 7.19-7.22 (2H, m), 7.51 (2H, d, J=8.4 Hz), 7.59-7.62 (1H, m), 7.76-7.81 (1H, m), 8.58 (1H, d, J=2.8 Hz).

Example 158

3-(3-(2-Fluoro-4-(pyridin-2-ylmethoxy)-benzyl)-isoxazol-5-yl)-pyridin-2,6-diamine

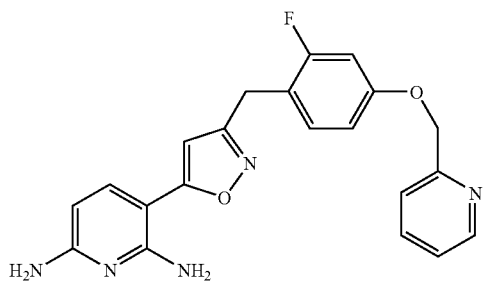

To a methanol (20.0 mL) solution of 2-(3-fluoro-4-(2-nitro-ethyl)-phenoxymethyl)-pyridine (400 mg, 1.45 mmol) described in Manufacturing Example 95-1-3 was added lithium methoxide (110 mg, 2.90 mmol), which was stirred for 30 minutes at room temperature. The reaction mixture was concentrated under a reduced pressure, and anhydrous dichloromethane (20.0 mL) and anhydrous tetrahydrofuran (10.0 mL) were added to the residue. Titanium (IV) chloride (510 μL, 4.64 mmol) was added dropwise to the reaction mixture on a dry ice-ethanol bath (−78° C.), which was stirred for 60 minutes at room temperature. Water, ethyl acetate, and tetrahydrofuran were added to the reaction mixture on an ice bath (0° C.), and the organic layer was extracted with ethyl acetate. This organic layer was washed with water and saturated aqueous sodium chloride, dried over anhydrous magnesium sulfate, and then filtered. The filtrate was concentrated under a reduced pressure to obtain a crude product (360 mg). To a tetrahydrofuran (5.00 mL) solution of 3-ethynyl-pyridin-2,6-diamine (40.0 mg, 0.300 mmol) described in Manufacturing Example 13-1-3 and this crude product (180 mg) was added triethylamine (125 μL, 0.900 mmol) at room temperature, which was stirred for 2 hours at room temperature. Water was added to the reaction solution at room temperature, which was extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=2:1→3:1), and then further purified by reverse-phase high performance liquid chromatography (using an acetonitrile-water mobile phase containing 0.1% trifluoroacetic acid) to obtain the title compound (3.20 mg, 1.72%) as a ditrifluoroacetic acid salt.

MS m/e (ESI) 392.19 (MH+)

Example 159

3-(3-(4-(2-Pyridin-2-yl-ethyl)-benzyl)-isoxazol-5-yl)-pyridin-2,6-diamine

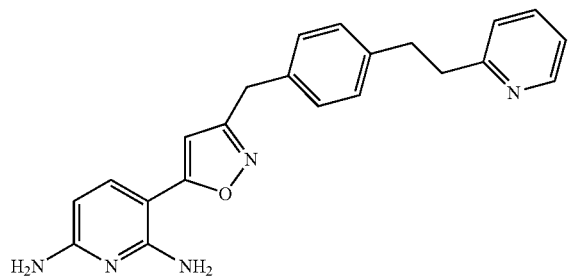

To a mixture of (4-(2-pyridin-2-yl-ethyl)-phenyl)-acetohydroximoyl chloride hydrochloride (780 mg, 2.51 mmol) described in Manufacturing Example 93-1-8 and dimethylformamide (10 mL) were added 3-ethynyl-pyridin-2,6-diamine (96 mg, 0.721 mmol) described in Manufacturing Example 13-1-3 and triethylamine (1.05 mL, 7.53 mmol), which was stirred for 3 hours at room temperature. Water and ethyl acetate were added to the reaction mixture, and the organic layer was separated. This organic layer was washed with water and saturated aqueous sodium chloride and dried over anhydrous magnesium sulfate, and the solvent was evaporated under a reduced pressure. The residue was purified by NH silica gel column chromatography (ethyl acetate:heptane=4:6 then ethyl acetate) to obtain the title compound (80 mg, 30%).

$^1$H-NMR Spectrum (CDCl$_3$) δ (ppm): 3.00-3.10 (4H, m), 3.98 (2H, s), 4.46 (2H, brs), 5.25 (2H, brs), 5.91 (1H, d, J=8.4 Hz), 5.99 (1H, s), 7.07 (1H, d, J=7.6 Hz), 7.12 (1H, dd, J=6.0, 7.6 Hz), 7.15 (2H, d, J=8.0 Hz), 7.19 (2H, d, J=8.0 Hz), 7.48 (1H, d, J=8.4 Hz), 7.57 (1H, t, J=7.6 Hz), 8.56 (1H, d, J=6.0 Hz).

Example 160

3-(3-(1-(3-Fluoro-benzyl)-1H-pyrrol-3-ylmethyl)-isoxazol-5-yl)-pyridin-2,6-diamine

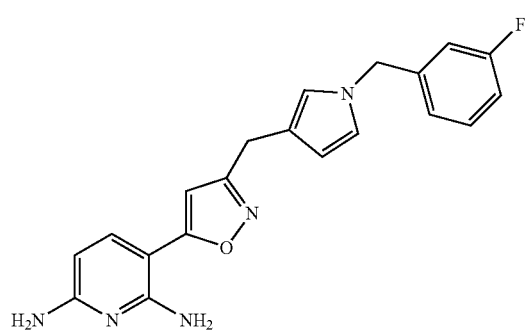

1-(3-fluoro-benzyl)-1H-pyrrol-3-yl)-acetohydroximoyl chloride (1.1 g) was obtained according to the methods similar to those of Manufacturing Example 57-1-3, using 1-(3-fluoro-benzyl)-3-(2-nitro-ethyl)-1H-pyrrole (1.7 g, 6.9 mmol) described in Manufacturing Example 160-1-1. The title compound (4.7 mg, 4.3%) was obtained according to the methods similar to those of Example 12, using 3-ethynyl-pyridin-2,6-diamine (40 mg, 0.30 mmol) described in Manufacturing Example 13-1-3 and the above-mentioned 1-(3-fluoro-benzyl)-1H-pyrrol-3-yl)-acetohydroximoyl chloride (400 mg, 1.5 mmol).

$^1$H-NMR Spectrum (DMSO-d$_6$) δ (ppm): 3.71 (2H, s), 5.05 (2H, s), 5.77 (2H, brs), 5.83 (1H, d, J=8.0 Hz), 5.99 (1H, dd, J=2.0, 2.0 Hz), 6.09 (2H, brs), 6.35 (1H, s), 6.72 (1H, dd, J=2.0, 2.0 Hz), 6.77 (1H, dd, J=2.0, 2.0 Hz), 6.96-7.01 (1H, m), 7.02 (1H, d, J=8.0 Hz), 7.06-7.12 (1H, m), 7.34-7.40 (1H, m), 7.51 (1H, d, J=8.0 Hz).

The starting material, 1-(3-fluoro-benzyl)-3-(2-nitro-ethyl)-1H-pyrrole, was synthesized as follows.

Manufacturing Example 160-1-1

1-(3-Fluoro-benzyl)-3-(2-nitro-ethyl)-1H-pyrrole

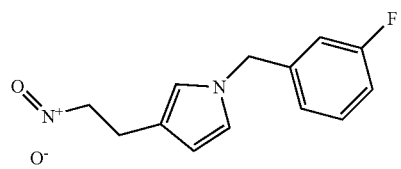

The title compound (1.7 g, 48%) was obtained according to the methods similar to those of Manufacturing Examples 57-1-1 to 57-1-2, using 1-(3-fluoro-benzyl)-1H-pyrrole-3-carbaldehyde (2.9 g, 14 mmol).

$^1$H-NMR Spectrum (DMSO-d$_6$) δ (ppm): 3.00 (2H, t, J=6.8 Hz), 4.67 (2H, t, J=6.8 Hz), 5.05 (2H, s), 5.94 (1H, dd, J=2.0, 2.0 Hz), 6.68 (1H, dd, J=2.0, 2.0 Hz), 6.75 (1H, dd, J=2.0, 2.0 Hz), 6.90-6.95 (1H, m), 6.98 (1H, d, J=8.0 Hz), 7.06-7.12 (1H, m), 7.33-7.49 (1H, m).

Example 161

3-(3-(6-Phenylsulfanyl-pyridin-3-ylmethyl)-isoxazol-5-yl)-pyridin-2,6-diamine

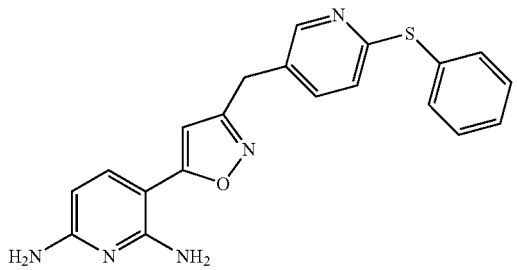

To a tetrahydrofuran (4 mL) solution of the (6-phenylsulfanyl-pyridin-3-yl)-acetohydroximoyl chloride (100 mg, 0.359 mmol) described in Manufacturing Example 97-1-4 and 3-ethynyl-pyridin-2,6-diamine (15 mg, 0.13 mmol) described in Manufacturing Example 13-1-3 was added triethylamine (55 μL, 0.40 mmol), which was stirred under nitrogen atmosphere for 1 hour at 50° C. Water was added to the reaction mixture, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (ethyl acetate:methanol=10:1) to obtain the title compound (25 mg, 58%).

$^1$H-NMR Spectrum (CDCl$_3$) δ (ppm): 3.94 (2H, s), 4.51 (2H, s), 5.26 (2H, s), 5.92 (1H, d, J=8.4 Hz), 5.97 (1H, s), 6.86 (1H, d, J=8.4 Hz), 7.37 (1H, dd, J=2.4, 8.2 Hz), 7.40-7.43 (3H, m), 7.46 (1H, d, J=8.2 Hz), 7.57-7.60 (2H, m), 8.39 (1H, d, J=2.4 Hz).

Example 162

3-(3-(4-(3-Methoxy-benzyloxy)-benzyl)-isoxazol-5-yl)-pyridin-2,6-diamine

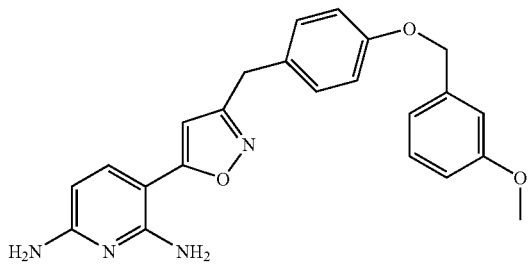

To a tetrahydrofuran (3 mL) solution of 4-(5-(2,6-diaminopyridin-3-yl)-isoxazol-3-ylmethyl)-phenol (30 mg, 0.11 mmol) described in Manufacturing Example 18-1-1 was added a 5 N sodium hydroxide aqueous solution (21.2 μL, 0.11 mmol), which was dissolved by irradiating ultrasonic wave for 1 minute. The reaction solution was concentrated under a reduced pressure, which gave a white solid. To a mixture of this solid and N,N-dimethylformamide (1 mL) was added an N,N-dimethylformamide (1 mL) solution of 3-methoxybenzyl chloride (17.0 mg, 0.11 mmol), which was stirred for 12 hours at 60° C. This reaction mixture was cooled to room temperature, and then partitioned into water and ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate) to obtain the title compound (34.4 mg, 81%).

$^1$H-NMR Spectrum (DMSO-d$_6$) δ (ppm): 3.75 (3H, s), 3.87 (2H, s), 5.05 (2H, s), 5.89 (2H, brs), 5.82 (1H, d, J=8.4 Hz), 6.10 (2H, brs), 6.34 (1H, s), 6.86-6.89 (1H, m), 6.95 (2H, d, J=8.8 Hz), 6.98-7.02 (2H, m), 7.21 (2H, d, J=8.8 Hz), 7.29 (1H, dd, J=8.0, 8.4 Hz), 7.51 (1H, d, J=8.4 Hz).

Example 163

3-(3-(4-(6-Methoxy-pyridin-2-ylmethoxy)-benzyl)-isoxazol-5-yl)-pyridin-2,6-diamine

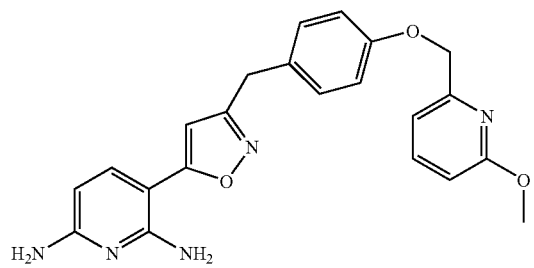

To a tetrahydrofuran (3 mL) solution of 4-(5-(2,6-diaminopyridin-3-yl)-isoxazol-3-ylmethyl)-phenol (30 mg, 0.11 mmol) described in Manufacturing Example 18-1-1 was added a 5 N sodium hydroxide aqueous solution (21.2 μL, 0.11 mmol), which was dissolved by irradiating ultrasonic wave for 1 minute. The reaction solution was concentrated under a reduced pressure, which gave a white solid. To a mixture of this solid and N,N-dimethylformamide (1 mL) was added an N,N-dimethylformamide (1 mL) solution of 2-chloromethyl-6-methoxypyridine (20.0 mg, 0.13 mmol) described in Manufacturing Example 99-1-2, which was stirred for 1 hour at 60° C. This reaction mixture was cooled to room temperature, and then partitioned into water and ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate) to obtain the title compound (26.1 mg, 61%).

$^1$H-NMR Spectrum (DMSO-d$_6$) δ (ppm): 3.85 (3H, s), 3.88 (2H, s), 5.06 (2H, s), 5.79 (2H, brs), 5.82 (1H, d, J=8.4 Hz), 6.11 (2H, brs), 6.34 (1H, s), 6.75 (1H, dd, J=0.8, 8.4 Hz), 6.98 (2H, d, J=8.8 Hz), 7.05-7.08 (1H, m), 7.20-7.24 (2H, m), 7.51 (1H, d, J=8.8 Hz), 7.69-7.74 (1H, m).

Example 164

3-(3-(6-(Pyridin-3-yloxy)-pyridin-3-ylmethyl)-isoxazol-5-yl)-pyridin-2,6-diamine

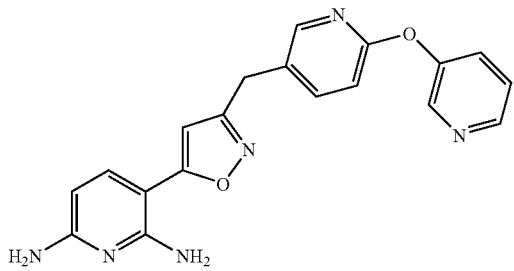

To a mixture of 5-(2-nitro-ethyl)-2-(pyridin-3-yloxy)pyridine (157.0 mg, 0.64 mmol) described in Manufacturing Example 100-1-2 and methanol (6 mL) was added lithium methoxide (48.7 mg, 1.28 mmol) at room temperature, which was stirred for 1 hour. The reaction mixture was then concentrated under a reduced pressure, which gave a white solid. To a mixture of this solid in dichloromethane (4 mL) and tetrahydrofuran (2 mL) was added titanium tetrachloride (155.0 μL, 1.41 mmol) under nitrogen atmosphere at −78° C., which was stirred for 3 hours at 0° C. Water was added to the reaction mixture, which was extracted with ethyl acetate. The organic layer was separated, washed with water and saturated aqueous sodium chloride, dried over anhydrous magnesium sulfate, and then filtered. The filtrate was concentrated under a reduced pressure. To a mixture of the resulting residue (30.7 mg), 3-ethynyl-pyridin-2,6-diamine (15.4 mg, 0.12 mmol) described in Manufacturing Example 13-1-3, tetrahydrofuran (1 mL), and dimethyl sulfoxide (1 mL) was added triethylamine (32.4 μL, 0.23 mmol) at room temperature, which was stirred for 1 hour at 55° C. The reaction mixture was cooled to room temperature, water was added, and the mixture was extracted with ethyl acetate. The organic layer was separated, washed with water and saturated aqueous sodium chloride, dried over anhydrous magnesium sulfate, and filtered. The filtrate was concentrated under a reduced pressure. The residue thus obtained was purified by reverse-phase high performance liquid chromatography (using an acetonitrile-water mobile phase containing 0.1% trifluoroacetic acid), and then further purified by preparative thin-layer chromatography (NH silica gel, ethyl acetate) to obtain the title compound (3.6 mg, 9%).

$^1$H-NMR Spectrum (CDCl$_3$) δ (ppm): 3.98 (2H, s), 4.52 (2H, brs), 5.28 (2H, brs), 5.93 (1H, d, J=8.4 Hz), 6.01 (1H, s), 6.96 (1H, dd, J=0.4, 8.4 Hz), 7.34 (1H, ddd, J=0.8, 4.4, 8.4 Hz), 7.50-7.53 (1H, m), 7.66 (1H, dd, 2.4, 8.4 Hz), 8.10 (1H, dd, J=0.8, 2.4 Hz), 8.45 (1H, dd, J=1.2, 1.6, 4.8, 5.2 Hz), 8.50 (1H, d, J=2.8 Hz).

MS m/e (ESI) 361.05 (MH$^+$)

Example 165

6-Methoxy-3-(3-(4-(5-methyl-furan-2-ylmethyl)-benzyl)-isoxazol-5-yl)-pyridin-2-ylamine

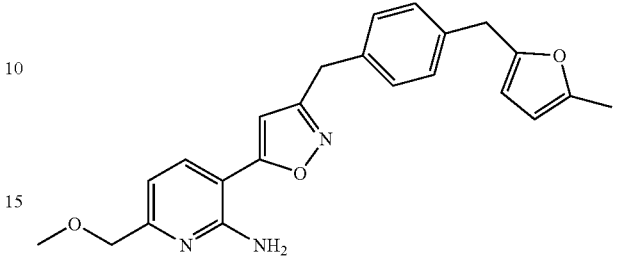

To a mixture of (4-(5-methyl-furan-2-ylmethyl)-phenyl)-acetohydroximoyl chloride (11 mg, 0.043 mmol) described in Manufacturing Example 46-1-6 and tetrahydrofuran (1 mL) were added 3-ethynyl-6-methoxymethyl-pyridin-2-ylmethyl (6.5 mg, 0.035 mmol) described in Manufacturing Example 26-1-7 and triethylamine (9.6 μL, 0.069 mmol), which was stirred for 3 hours at 40° C. The reaction mixture was allowed to room temperature, water was added at the same temperature, and the mixture was extracted with ethyl acetate. The organic layer was washed with saturated aqueous sodium chloride, and the solvent was evaporated under a reduced pressure. The residue was purified by NH silica gel column chromatography (ethyl acetate:heptane=2:3) to obtain the title compound (9.2 mg, 58%, purity: 84%) as a mixture with the starting material 3-ethynyl-6-methoxymethyl-pyridin-2-ylamine.

$^1$H-NMR Spectrum (CDCl$_3$) δ (ppm): 2.24 (3H, s), 3.46 (3H, s), 3.90 (2H, s), 4.02 (2H, s), 4.42 (2H, s), 5.46 (2H, brs), 5.85-5.87 (2H, m), 6.23 (1H, s), 6.81 (1H, d, J=7.9 Hz), 7.21 (4H, s), 7.71 (1H, d, J=7.9 Hz).

Example 166

6-Methoxymethyl-3-(3-(4-(pyridin-2-ylmethoxy)-benzyl)-isoxazol-5-yl)-pyridin-2-ylamine

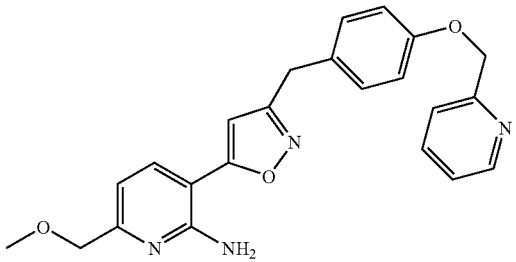

To a methanol (1.5 mL) solution of 4-(5-(2-amino-6-methoxymethyl-pyridin-3-yl)isoxazol-3-ylmethyl)-phenol (50 mg, 0.16 mmol) described in Manufacturing Example 166-1-1 was added a 1 N sodium hydroxide aqueous solution (160 μL, 0.16 mmol), which was concentrated under a reduced pressure. N,N-dimethylformamide (1.5 mL) was added to the residue thus obtained at room temperature, and 2-picolyl chloride (29 mg, 0.23 mmol; this 2-picolyl chloride was prepared by adding a 5 N sodium hydroxide aqueous solution to 2-picolyl chloride hydrochloride) was added to the reaction mixture at the same temperature. The reaction mixture was stirred for 100 minutes at the same temperature. Water was added to the reaction mixture, which was extracted with ethyl acetate. The organic layer was washed with water and saturated aqueous sodium chloride, and was concentrated under a reduced pressure. The residue was purified by NH silica gel column chromatography (ethyl acetate:heptane=4:1) to obtain the title compound (32 mg, 52%).

$^1$H-NMR Spectrum (CDCl$_3$) δ (ppm): 3.46 (3H, s), 3.99 (2H, s), 4.41 (2H, s), 5.20 (2H, s), 5.43 (2H, br s), 6.22 (1H, s), 6.81 (1H, d, J=7.9 Hz), 6.95-6.97 (2H, m), 7.19-7.24 (3H, m), 7.52 (1H, d, J=7.9 Hz), 7.69-7.73 (2H, m), 8.60 (1H, d, J=4.2 Hz).

The starting material, 4-(5-(2-amino-6-methoxymethyl-pyridin-3-yl)-isoxazol-3-ylmethyl)-phenol, was synthesized as follows.

Manufacturing Example 166-1-1

4-(5-(2-Amino-6-methoxymethyl-pyridin-3-yl)-isoxazol-3-ylmethyl)-phenol

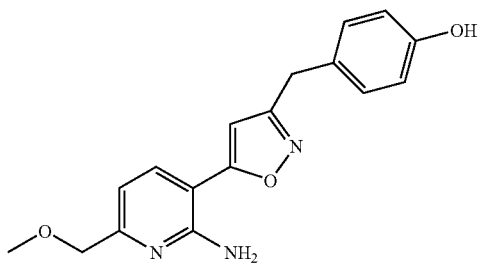

To a mixture of 3-(3-(4-benzyloxy-benzyl)-isoxazol-5-yl)-6-methoxymethyl-pyridin-2-ylamine (30 mg, 0.075 mmol) described in Example 26 and dichloromethane (1 mL) was added boron tribromide (220 μL, 1 M dichloromethane solution, 0.22 mmol) at −78° C., which was stirred for 1 hour at 0° C. The reaction mixture was cooled to −78° C., methanol was added at the same temperature, and the excess boron tribromide was quenched. The reaction mixture was gradually allowed to room temperature, a sodium acetate aqueous solution was added to the reaction mixture at room temperature, which was neutralized, after which water was added, and the mixture was extracted with ethyl acetate. The organic layer was washed with saturated aqueous sodium chloride, and was concentrated under a reduced pressure. The residue was purified by silica gel column chromatography (ethyl acetate:heptane=2:1) to obtain the title compound (4.6 mg, 20%).

$^1$H-NMR Spectrum (CDCl$_3$) δ (ppm): 3.47 (3H, s), 3.98 (2H, s), 4.43 (2H, s), 5.50 (2H, brs), 6.22 (1H, s), 6.78-6.83 (3H, m), 7.13-7.16 (2H, m), 7.73 (1H, d, J=7.9 Hz)

Example 167

6-Methoxymethyl-3-(3-(6-(phenoxy-pyridin-3-ylmethyl)-isoxazol-5-yl)-pyridin-2-ylamine

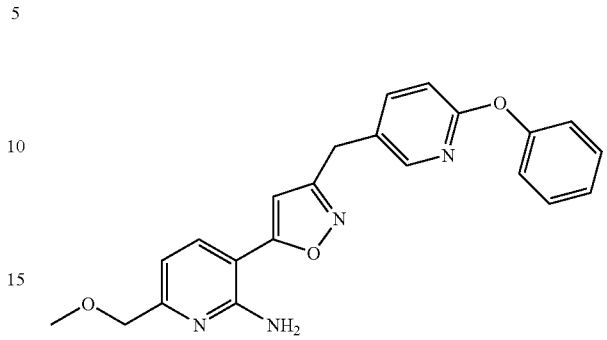

To a tetrahydrofuran (2 mL) solution of (2-phenoxy-pyridin-5-yl)-acetohydroximoyl chloride (93 mg, 0.36 mmol) described in Manufacturing Example 40-1-4 and 3-ethynyl-6-methoxymethyl-pyridin-2-ylamine (32 mg, 0.20 mmol) described in Manufacturing Example 26-1-7 was added triethylamine (55 μL, 0.39 mmol), which was stirred under nitrogen atmosphere for 5 hours and 25 minutes at 50° C. Water was added to the reaction mixture at room temperature, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by silica gel column chromatography (heptane:ethyl acetate=1:1) to obtain the title compound (54 mg, 71%).

$^1$H-NMR Spectrum (DMSO-d$_6$) δ (ppm): 3.35 (3H, s), 4.03 (2H, s), 4.33 (2H, s), 6.31 (2H, s), 6.73 (1H, d, J=7.7 Hz), 6.83 (1H, s), 7.00 (1H, d, J=8.4 Hz), 7.10-7.12 (2H, m), 7.18-7.22 (1H, m), 7.38-7.44 (2H, m), 7.81 (1H, dd, J=2.4, 8.4 Hz), 7.89 (1H, d, J=7.9 Hz), 8.15 (1H, d, J=2.4 Hz).

Example 168

3-(3-(4-(5-Chloro-furan-2-ylmethyl)-benzyl)-isoxazol-5-yl)-6-methoxymethyl-pyridin-2-ylamine

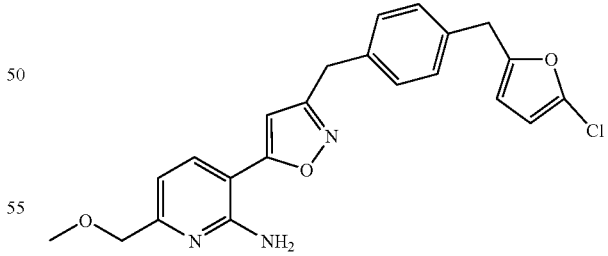

To a mixture of (4-(5-chloro-furan-2-ylmethyl)-phenyl)-acetohydroximoyl chloride (25 mg, 0.088 mmol) described in Manufacturing Example 62-1-6 and tetrahydrofuran (1 mL) were added 3-ethynyl-6-methoxymethyl-pyridin-2-ylamine (11 mg, 0.069 mmol) described in Manufacturing Example 26-1-7 and triethylamine (19 μL, 0.014 mmol), which was stirred for 1 hour at 50° C. The reaction mixture was allowed to room temperature, water was added at the same temperature, and the mixture was extracted with ethyl acetate. The organic layer was washed with saturated aqueous sodium chloride, and was concentrated under a reduced pressure. The residue thus obtained was purified by reverse-phase high performance liquid chromatography (using an acetonitrile-water mobile phase containing 0.1% trifluoroacetic acid) to obtain the title compound as a crude product. This product was then purified by NH silica gel column chromatography (ethyl acetate:heptane=1:1) to obtain the title compound (7.5 mg, 27%).

MS m/e (ESI) 410.10 (MH$^+$)

$^1$H-NMR Spectrum (CDCl$_3$) δ (ppm): 3.46 (3H, s), 3.90 (2H, s), 4.03 (2H, s), 4.42 (2H, s), 5.46 (2H, br s), 5.98-5.99 (1H, m), 6.04-6.05 (1H, m), 6.24 (1H, s), 6.81 (1H, d, J=7.9 Hz), 7.20 (2H, d, J=8.1 Hz), 7.23 (2H, d, J=8.1 Hz), 7.72 (1H, d, J=7.9 Hz).

Example 169

(6-Amino-5-(3-(4-benzyloxy-benzyl)-isoxazol-5-yl)-methanol

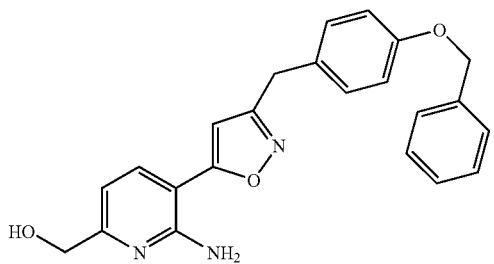

To a mixture of 4-benzyloxy-phenyl-acetohydroximoyl chloride (9.8 mg, 0.043 mmol) described in Manufacturing Example 1-1-3 and tetrahydrofuran (1 mL) were added (6-amino-5-ethynyl-pyridin-2-yl)-methanol (6.1 mg, 0.024 mmol, purity: 57%) described in Manufacturing Example 169-1-2 and triethylamine (6.5 µL, 0.047 mmol), which was stirred for 1 hour at 50° C. The reaction mixture was allowed to room temperature, water was added at the same temperature, and the mixture was extracted with ethyl acetate. The organic layer was washed with saturated aqueous sodium chloride, and was concentrated under a reduced pressure. The residue thus obtained was purified by reverse-phase high performance liquid chromatography (using an acetonitrile-water mobile phase containing 0.1% trifluoroacetic acid) to obtain the title compound as a crude product. This product was then purified by NH silica gel column chromatography (ethyl acetate) to obtain the title compound (3.3 mg, 36%).

MS m/e (ESI) 388.01 (MH$^+$)

$^1$H-NMR Spectrum (CDCl$_3$) δ (ppm): 4.00 (2H, s), 4.63 (2H, s), 5.05 (2H, s), 5.52 (2H, brs), 6.22 (1H, s), 6.63 (1H, d, J=7.9 Hz), 6.93-6.97 (2H, m), 7.19-7.22 (2H, m), 7.30-7.44 (5H, m), 7.70 (1H, d, J=7.9 Hz).

The starting material, (6-amino-5-ethynyl-pyridin-2-yl)-methanol, was synthesized as follows.

Manufacturing Example 169-1-1

2-Amino-6-hydroxymethyl-pyridine-3-carbaldehyde

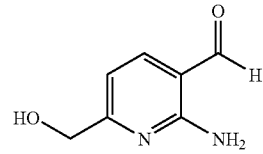

To a mixture of 2-amino-6-methoxymethyl-pyridine-3-carbaldehyde (57 mg, 0.34 mmol) described in Manufacturing Example 26-1-6 and dichloromethane (2 mL) was added boron tribromide (1.0 mL, 1 M dichloromethane solution, 1.0 mmol) at −78° C., which was stirred for 1 hour at 0° C. The reaction mixture was cooled to −78° C., methanol was added at the same temperature, and the excess reagent was quenched. The reaction mixture was gradually allowed to room temperature and was neutralized by adding an ammonium aqueous solution (28%). Water was added to the reaction mixture, which was extracted with ethyl acetate. The organic layer was washed with saturated aqueous sodium chloride, and was concentrated under a reduced pressure. The residue was purified by silica gel column chromatography (ethyl acetate:heptane=4:1) to obtain the title compound (18 mg, 34%).

$^1$H-NMR Spectrum (DMSO-d$_6$) δ (ppm): 4.40 (2H, d, J=5.9 Hz), 5.42 (1H, t, J=5.9 Hz), 6.86 (1H, d, J=7.7 Hz), 7.52 (2H, br s), 8.00 (1H, d, J=7.9 Hz), 9.81 (1H, s).

Manufacturing Example 169-1-2

(6-Amino-5-ethynyl-pyridin-2-yl)-methanol

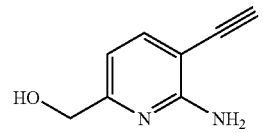

To a mixture of 2-amino-6-hydroxymethyl-pyridine-3-carbaldehyde (16 mg, 0.11 mmol) described in Manufacturing Example 169-1-1 and methanol (1.5 mL) were added dimethyl (1-diazo-2-oxopropyl)phosphonate (30 mg, 0.16 mmol) and potassium carbonate (23 mg, 0.17 mmol) at −10° C., which was stirred for 10 minutes at 0° C., and then for another 6 hours at room temperature. A saturated ammonium chloride aqueous solution and saturated aqueous sodium chloride were added to the reaction mixture at the same temperature, which was extracted with ethyl acetate. The organic layer was washed with saturated aqueous sodium chloride, and was concentrated under a reduced pressure. The residue thus obtained was purified by silica gel column chromatography (ethyl acetate) to obtain the title compound (13 mg, 47%, purity: 57%).

$^1$H-NMR Spectrum (CDCl$_3$) δ (ppm): 3.41 (1H, s), 4.60 (2H, s), 5.12 (2H, br s), 6.56 (1H, d, J=7.5 Hz), 7.56 (1H, d, J=7.7 Hz).

Example 170

3-(3-(4-benzyloxy-benzyl)-isoxazol-5-yl)-6-methyl-pyridin-2-ylamine

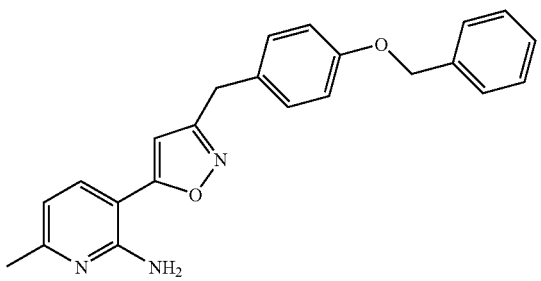

To a tetrahydrofuran (2 mL) solution of 4-benzyloxy-phenyl-acetohydroximoyl chloride (63 mg, 0.23 mmol) described in Manufacturing Example 1-1-3 and 3-ethynyl-6-methyl-pyridin-2-ylamine (20 mg, 0.15 mmol) described in Manufacturing Example 170-1-5 was added triethylamine (42 µL, 0.30 mmol) at room temperature, which was stirred for 4 hours at 50° C. Water was added to the reaction mixture, which was extracted with ethyl acetate. The organic layer was washed with saturated aqueous sodium chloride, dried over anhydrous magnesium sulfate, and filtered, and the filtrate was concentrated under a reduced pressure. The residue was purified by NH silica gel column chromatography (heptane:ethyl acetate=2:1), and then further purified by reverse-phase high performance liquid chromatography (using an acetonitrile-water mobile phase containing 0.1% trifluoroacetic acid) to obtain the title compound (26 mg, 34%) as a trifluoroacetic acid salt.

MS m/e (ESI) (MH$^+$) 372.23 (MH$^+$)

The starting material, 3-ethynyl-6-methyl-pyridin-2-ylamine, was synthesized as follows.

Manufacturing Example 170-1-1

2-Amino-6-chloro-nicotinic acid ethyl ester

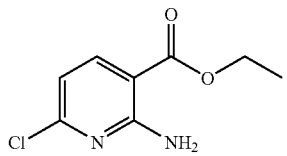

To ethanol (20 mL) were added concentrated sulfuric acid (10 mL) and 2-amino-6-chloro-nicotinic acid (6.3 g, 27 mmol, purity: 75%) described in Manufacturing Example 26-1-1 on an ice bath, which was stirred overnight at 65° C. The reaction mixture was gradually cooled, after which a sodium hydrogencarbonate aqueous solution was added to neutralize the mixture. The precipitated solids were filtered to obtain the title compound (4.1 g, 74%).

$^1$H-NMR Spectrum (CDCl$_3$) δ (ppm): 1.38 (3H, t, J=7.1 Hz), 4.34 (2H, q, J=7.1 Hz), 6.62 (1H, d, J=8.1 Hz), 8.07 (1H, d, J=8.1 Hz).

Manufacturing Example 170-1-2

2-Amino-6-methyl-nicotinic acid ethyl ester

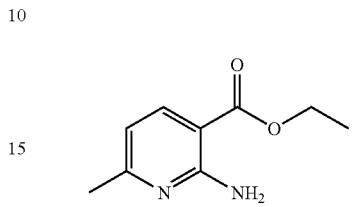

To a N-methylpyrrolidinone (20 mL) solution of 2-amino-6-chloro-nicotinic acid ethyl ester (2.00 g, 7.78 mmol) described in Manufacturing Example 170-1-1 were added tetramethyltin (1.62 mL, 11.7 mmol) and tetrakis(triphenylphosphine)palladium (0) (899 mg, 0.778 mmol), which was stirred under nitrogen atmosphere for 5 hours and 40 minutes at 130° C. Water was added to the reaction mixture at room temperature, which was extracted with ethyl acetate. The organic layer was washed with water and saturated aqueous sodium chloride, dried over anhydrous magnesium sulfate, and filtered, and the filtrate was concentrated under a reduced pressure. The residue thus obtained was purified by NH silica gel column chromatography (heptane:ethyl acetate=3:1), and then further purified by silica gel column chromatography (heptane:ethyl acetate=2:1) to obtain the title compound (670 mg, 48%).

$^1$H-NMR Spectrum (CDCl$_3$) δ (ppm): 1.38 (3H, t, J=7.1 Hz), 2.41 (3H, s), 4.33 (2H, q, J=7.1 Hz), 6.49 (1H, d, J=8.0 Hz), 8.03 (1H, d, J=8.0 Hz).

Manufacturing Example 170-1-3

(2-Amino-6-methyl-pyridin-3-yl)-methanol

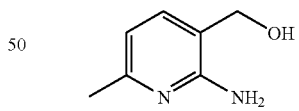

To a tetrahydrofuran (12 mL) solution of lithium aluminum hydride (706 mg, 14.9 mmol, purity: 80%) was added 2-amino-6-methyl-nicotinic acid ethyl ester (670 mg, 3.72 mmol) described in Manufacturing Example 170-1-2 at 0° C., which was stirred for 30 minutes at room temperature. Water (706 µL), a 5 N sodium hydroxide aqueous solution (706 µL), and water (2.12 mL) were added to the reaction mixture in that order at 0° C., which was filtered through a Celite pad. The filtrate was concentrated under a reduced pressure, and the residue was purified by NH silica gel column chromatography (ethyl acetate:methanol=10:1) to obtain the title compound (379 mg, 74%).

¹H-NMR Spectrum (CDCl₃) δ (ppm): 2.38 (3H, s), 4.61 (2H, s), 5.08 (2H, s), 6.48 (1H, d, J=7.2 Hz), 7.23 (1H, d, J=7.2 Hz).

Manufacturing Example 170-1-4

2-Amino-6-methyl-pyridine-3-carbaldehyde

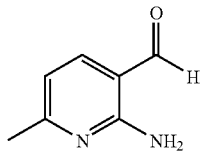

To a methylene chloride (8 mL) solution of (2-amino-6-methyl-pyridin-3-yl)-methanol (379 mg, 2.74 mmol) described in Manufacturing Example 170-1-3 was added manganese (IV) dioxide (1.19 mg, 13.7 mmol) at room temperature, which was stirred for 11 hours at room temperature. The reaction mixture was filtered through a Celite pad, and the filtrate was concentrated under a reduced pressure. The residue was purified by silica gel column chromatography (heptane:ethyl acetate=1:2) to obtain the title compound (328 mg, 88%).

¹H-NMR Spectrum (CDCl₃) δ (ppm): 2.44 (3H, s), 6.61 (1H, d, J=7.9 Hz), 7.69 (1H, d, J=7.9 Hz), 9.80 (1H, s).

Manufacturing Example 170-1-5

3-Ethynyl-6-methyl-pyridin-2-ylamine

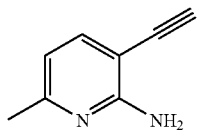

To a tetrahydrofuran (5 mL) solution of diisopropylamine (439 μL, 3.13 mmol) was added n-butyl lithium (1.81 mL, 1.6 M hexane solution, 2.89 mmol) under nitrogen atmosphere at −78° C., which was stirred for 15 minutes at 0° C. Then, trimethylsilyldiazomethane (1.81 mL, 2 M tetrahydrofuran solution, 3.62 mmol) was added to the reaction mixture at −78° C., which was stirred for 30 minutes at −78° C. To the reaction mixture was added a tetrahydrofuran (2 mL) solution of 2-amino-6-methyl-pyridine-3-carbaldehyde (328 mg, 2.41 mmol) described in Manufacturing Example 170-1-4 at −78° C., which was stirred for 25 minutes while the temperature was slowly raised to −30° C. Acetic acid (414 mL, 7.23 mmol) was added to the reaction mixture at −78° C., and the temperature was slowly raised, after which water was added and the mixture was extracted with ethyl acetate. The organic layer was washed with saturated aqueous sodium chloride, dried over anhydrous magnesium sulfate, and filtered. The filtrate was concentrated under a reduced pressure. The residue was purified by NH silica gel column chromatography (heptane:ethyl acetate=2:1) to obtain the title compound (243 mg, 76%).

¹H-NMR Spectrum (CDCl₃) δ (ppm): 2.39 (3H, s), 3.38 (1H, s), 5.07 (2H, s), 6.49 (1H, d, J=7.7 Hz), 7.47 (1H, d, J=7.7 Hz).

Example 171

6-Methyl-3-(3-(4-pyridin-2-yloxymethyl)-benzyl)-isoxazol-5-yl)-pyridin-2-ylamine

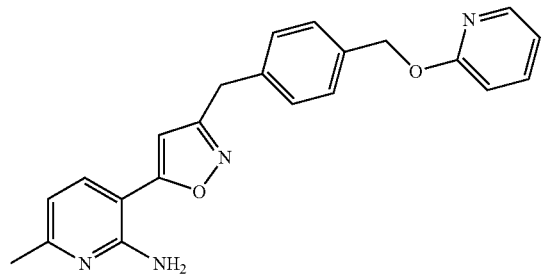

To a tetrahydrofuran (2 mL) solution of 3-ethynyl-6-methyl-pyridin-2-ylamine (20 mg, 0.15 mmol) described in Manufacturing Example 170-1-5 were added 4-(pyridin-2-yloxymethyl)-phenyl-acetohydroximoyl chloride (63 mg, 0.23 mmol) described in Manufacturing Example 2-1-5 and triethylamine (42 μL, 0.30 mmol) at room temperature, which was stirred for 2 hours and 50 minutes at 50° C. Water was added to the reaction mixture at room temperature, which was extracted with ethyl acetate. The organic layer was washed with saturated aqueous sodium chloride, dried over anhydrous magnesium sulfate, and filtered, after which the filtrate was concentrated under a reduced pressure. The residue was purified by NH silica gel column chromatography (heptane:ethyl acetate=2:1), and then further purified by reverse-phase high performance liquid chromatography (using an acetonitrile-water mobile phase containing 0.1% trifluoroacetic acid) to obtain the title compound (29 mg, 32%) as a trifluoroacetic acid salt.

MS m/e (ESI) (MH⁺) 373.19 (MH⁺)

¹H-NMR Spectrum (DMSO-d₆) δ (ppm): 2.28 (3H, s), 4.00 (2H, s), 5.30 (2H, s), 6.17 (2H, s), 6.54 (1H, d, J=7.9 Hz), 6.72 (1H, s), 6.83 (1H, d, J=8.4 Hz), 6.95-6.98 (1H, m), 7.31 (2H, d, J=8.4 Hz), 7.39 (2H, d, J=8.2 Hz), 7.67-7.72 (1H, m), 7.75 (1H, d, J=7.9 Hz), 8.14-8.15 (1H, m).

Example 172

5-chloro-3-(3-(4-pyridin-2-yloxymethyl)-benzyl)-isoxazol-5-yl)-pyridin-2-ylamine

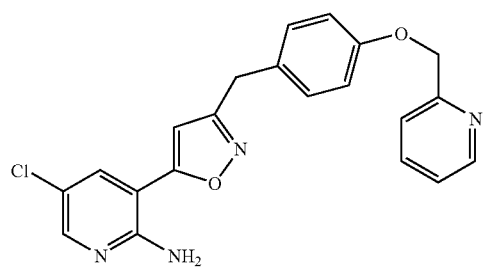

To a mixture of 3-(3-(4-benzyloxy-benzyl)-isoxazol-5-yl)-pyridin-2-ylamine (10.0 mg, 0.03 mmol) described in Example 2 and N,N-dimethylformamide (1 mL) was added N-chlorosuccinimide (3.7 mg, 0.03 mmol), which was stirred for 2 hours at room temperature. This mixture was then stirred for 1 hour at 50° C., and then for another 14 hours at room temperature. Water was added to the reaction mixture, which was extracted with ethyl acetate. The organic layer was separated, washed with water and saturated aqueous sodium chloride, dried over anhydrous magnesium sulfate, and filtered. The filtrate was concentrated under a reduced pressure, and the residue thus obtained was purified by reverse-phase high performance liquid chromatography (using an acetonitrile-water mobile phase containing 0.1% trifluoroacetic acid) to obtain the title compound (4.0 mg, 11%) as a ditrifluoroacetic acid salt.

$^1$H-NMR Spectrum (CD$_3$OD) δ (ppm): 4.08 (2H, s), 5.34 (2H, s), 6.69 (1H, s), 6.93 (1H, d, J=8.4 Hz), 6.99-7.02 (1H, m), 7.33 (2H, d, J=8.0 Hz), 7.42 (2H, d, J=8.0 Hz), 7.75-7.79 (1H, m), 7.96 (1H, d, J=2.4 Hz), 8.04 (1H, d, J=2.8 Hz), 8.12-8.17 (1H, m).

MS m/e (ESI) 393.03 (MH$^+$)

Example 173

3-(3-(4-Benzyloxy-benzyl)-isoxazol-5-yl)-5-fluoro-pyridin-2-ylamine

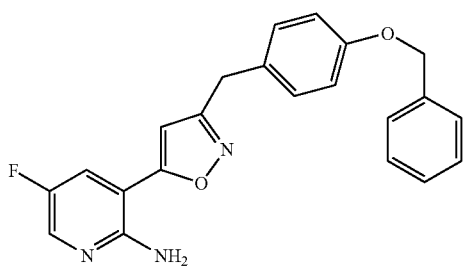

To a tetrahydrofuran (10 mL) mixture of 3-ethynyl-5-fluoro-pyridin-2-ylamine (129 mg, 0.95 mmol) described in Manufacturing Example 173-1-2 and 4-benzyloxy-phenyl-acetohydroximoyl chloride (314 mg, 1.14 mmol) described in Manufacturing Example 1-1-3 was added triethylamine (264 µL, 1.90 mmol) at room temperature, which was stirred for 1 hour at 55° C., and then for another hour at 60° C. This reaction mixture was cooled to room temperature, and then partitioned into ethyl acetate and water. The organic layer was separated, washed with water and saturated aqueous sodium chloride, dried over anhydrous magnesium sulfate, and filtered. The filtrate was concentrated under a reduced pressure, and the residue thus obtained was purified by NH silica gel column chromatography (heptane:ethyl acetate=3:1) to obtain the title compound (212 mg, 60%).

$^1$H-NMR Spectrum (DMSO-d$_6$) δ (ppm): 3.97 (2H, s), 5.08 (2H, s), 6.24 (2H, brs), 6.90 (1H, s), 6.98 (2H, d, J=8.0 Hz), 7.24 (2H, d, J=8.8 Hz), 7.28-7.45 (5H, m), 7.83-7.90 (1H, m), 8.10-8.12 (1H, m).

The starting material, 3-ethynyl-5-fluoro-pyridin-2-ylamine, was synthesized as follows.

Manufacturing Example 173-1-1

5-Fluoro-3-iodo-pyridin-2-ylamine

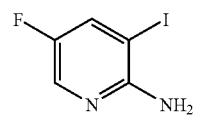

To a mixture of 2-amino-5-fluoropyridine (2.0 g, 17.8 mmol) and dimethyl sulfoxide (50 mL) was added N-iodosuccinimide (4.8 g, 21.4 mmol), which was stirred for 1 hour at room temperature. A suitable amount of acetic acid was added to this mixture, which was stirred for 1 hour at the same temperature, and then stirred for another 3 hours at 55° C. This reaction mixture was cooled to room temperature, after which a saturated sodium hydrogencarbonate aqueous solution was added, and the mixture was extracted with ethyl acetate. The organic layer was separated, washed with water and saturated aqueous sodium chloride, dried over anhydrous magnesium sulfate, and filtered. The filtrate was concentrated under a reduced pressure, and the residue thus obtained was purified by NH silica gel column chromatography (ethyl acetate) to obtain the title compound (751 mg, 18%).

$^1$H-NMR Spectrum (DMSO-d$_6$) δ (ppm): 5.99 (2H, brs), 8.05 (1H, dt, J=2.8, 8.0 Hz), 8.80-8.81 (1H, m).

Manufacturing Example 173-1-2

3-Ethynyl-5-fluoro-pyridin-2-ylamine

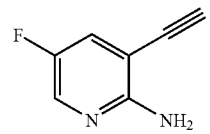

To a mixture of 5-fluoro-3-iodo-pyridin-2-ylamine (751 mg, 3.16 mmol) described in Manufacturing Example 173-1-1, trimethylsilylacetylene (874 µL, 6.32 mmol), copper (I) iodide (60.2 mg, 0.32 mmol), N,N-diisopropylethylamine (1.07 mL, 6.32 mmol), and N-methylpyrrolidinone (15 mL) was added tetrakis(triphenylphosphine)palladium (0) (183 mg, 0.16 mmol), which was stirred for 3 hours under nitrogen atmosphere at 70° C. This reaction solution was cooled to room temperature, and then partitioned into ethyl acetate and water. The organic layer was separated, washed with water and saturated aqueous sodium chloride, dried over anhydrous magnesium sulfate, and filtered. The filtrate was concentrated under a reduced pressure, and the residue thus obtained was purified by NH silica gel column chromatography and then silica gel column chromatography (heptane:ethyl acetate=1:1) to obtain the title compound (129 mg, 30%).

¹H-NMR Spectrum (DMSO-d₆) δ (ppm): 4.56 (1H, s), 6.13 (2H, brs), 7.56 (1H, dd, J=3.2, 8.8 Hz), 7.97 (1H, d, J=3.2 Hz).

Example 174

5-Fluoro-3-(3-(4-(5-fluoro-pyridin-2-ylmethoxy)-benzyl)-isoxazol-5-yl)-pyridin-2-ylamine

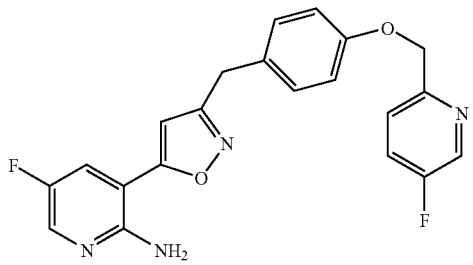

To 4-(5-(2-amino-5-fluoro-pyridin-3-yl)-isoxazol-3-ylmethyl)-phenol (20.0 mg, 0.07 mmol) described in Manufacturing Example 174-1-1 were added tetrahydrofuran (3 mL) and a 5 N sodium hydroxide aqueous solution (14.0 μL, 0.07 mmol), which was dissolved by irradiating ultrasonic wave for 1 minute. Next, the reaction solution was concentrated under a reduced pressure, which gave a white solid. To a mixture of this solid and N,N-dimethylformamide (1 mL) was added an N,N-dimethylformamide (1 mL) solution of 2-chloromethyl-5-fluoro-pyridine (11.2 mg, 0.08 mmol) described in manufacturing Example 41-1-2, which was stirred for 1 hour at 60° C. The reaction mixture was cooled to room temperature and then partitioned into water and ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (24.7 mg, 89%).

¹H-NMR Spectrum (DMSO-d₆) δ (ppm): 3.98 (2H, s), 5.16 (2H, s), 6.25 (2H, brs), 6.91 (1H, s), 7.00 (2H, d, J=8.8 Hz), 7.26 (2H, d, J=8.4 Hz), 7.57-7.63 (1H, m), 7.77 (1H, dt, J=2.8, 8.8 Hz), 7.87 (1H, dd, J=2.8, 9.2 Hz), 8.12 (1H, d, J=3.2 Hz), 8.58 (1H, d, J=3.6 Hz).

The starting material, 4-(5-(2-amino-5-fluoro-pyridin-3-yl)-isoxazol-3-ylmethyl)-phenol, was synthesized as follows.

Manufacturing Example 174-1-1

4-(5-(2-Amino-5-fluoro-pyridin-3-yl)-isoxazol-3-ylmethyl)-phenol

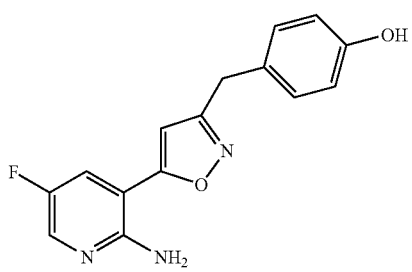

To a trifluoroacetic acid (5 mL) solution of 3-(3-(4-benzyloxy-benzyl)-isoxazol-5-yl)-5-fluoro-pyridin-2-ylamine (180 mg, 0.48 mmol) described in Example 173 was added thioanisole (225 μL, 1.92 mmol), which was stirred for 6 hours at room temperature. A saturated sodium hydrogencarbonate aqueous solution was added to this reaction solution at 0° C., which was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:2~ethyl acetate) to obtain the title compound (134.0 mg, 98%).

¹H-NMR Spectrum (DMSO-d₆) δ (ppm): 3.91 (2H, s), 6.24 (2H, brs), 6.71 (2H, d, J=8.8 Hz), 6.87 (1H, s), 7.10 (2H, d, J=8.8 Hz), 7.86 (1H, dd, J=2.8, 9.2 Hz), 8.11 (1H, d, J=2.8 Hz), 9.32 (1H, brs).

Example 175

3-(3-(4-(4-Chloro-pyridin-2-ylmethoxy)-benzyl)-isoxazol-5-yl)-5-fluoro-pyridin-2-ylamine

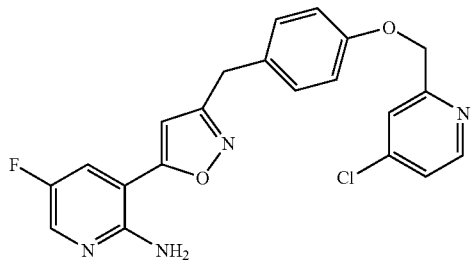

Tetrahydrofuran (3 mL) and a 5 N sodium hydroxide aqueous solution (14.0 μL, 0.07 mmol) were added to 4-(5-(2-amino-5-fluoro-pyridin-3-yl)-isoxazol-3-ylmethyl)-phenol (20.0 mg, 0.07 mmol) described in Manufacturing Example 174-1-1, which was dissolved by irradiating ultrasonic wave for 1 minute. Next, the reaction solution was concentrated under a reduced pressure, which gave a white solid. To a mixture of this solid and N,N-dimethylformamide (1 mL) was added an N,N-dimethylformamide (1 mL) solution of 4-chloromethyl-2-chloromethyl-pyridine (11.4 mg, 0.07 mmol) described in manufacturing Example 51-1-2, which was stirred for 1 hour at 60° C. The reaction mixture was cooled to room temperature and then partitioned into water and ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (24.3 mg, 84%).

¹H-NMR Spectrum (DMSO-d₆) δ (ppm): 3.98 (2H, s), 5.18 (2H, s), 6.24 (2H, brs), 6.90 (1H, s), 7.01 (2H, d, J=7.2

Hz), 7.26 (2H, d, J=7.6 Hz), 7.50-7.54 (1H, m), 7.60-7.64 (1H, m), 7.85-7.89 (1H, m), 8.11-8.13 (1H, m), 8.55-8.57 (1H, m).

Example 176

5-(3-(4-Pyridin-2-yloxymethyl)-benzyl)-isoxazol-5-yl)-pyridin-2-ylamine

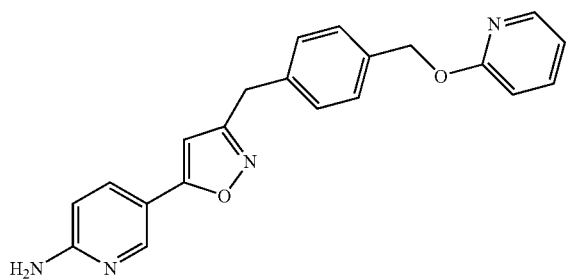

To a tetrahydrofuran (2.0 mL) solution of 5-ethynyl-pyridin-2-ylamine (300 mg, 2.54 mmol) described in Manufacturing Example 28-1-3 were added 4-(pyridin-2-yloxymethyl)-phenyl-acetohydroximoyl chloride (1.05 g, 3.81 mmol) described in Manufacturing Example 2-1-5 and triethylamine (566 μL, 4.06 mmol), which was stirred for 2 hours and 40 minutes at 50° C. Water was added to the reaction mixture at room temperature, which was extracted with ethyl acetate. The organic layer was separated, washed with saturated aqueous sodium chloride, dried over anhydrous magnesium sulfate, and filtered. The filtrate was concentrated under a reduced pressure. The residue was purified by NH silica gel column chromatography (ethyl acetate), and further purified by NH silica gel column chromatography (ethyl acetate:methanol=10:1) to obtain the title compound (196 mg, 22%).

$^1$H-NMR Spectrum (DMSO-$d_6$) δ (ppm): 3.96 (2H, s), 5.30 (2H, s), 6.47 (1H, dd, J=0.73, 8.6 Hz), 6.50 (2H, s), 6.55 (1H, s), 6.83 (1H, d, J=8.2 Hz), 6.95-6.98 (1H, m), 7.28 (2H, d, J=8.1 Hz), 7.38 (2H, d, J=8.1 Hz), 7.67-7.74 (2H, m), 8.14-8.16 (1H, m), 8.36 (1H, d, J=2.4 Hz).

Example 177

5-(3-(4-(Pyridin-2-ylmethoxy)-benzyl)-isoxazol-5-yl)-pyridin-2-ylamine

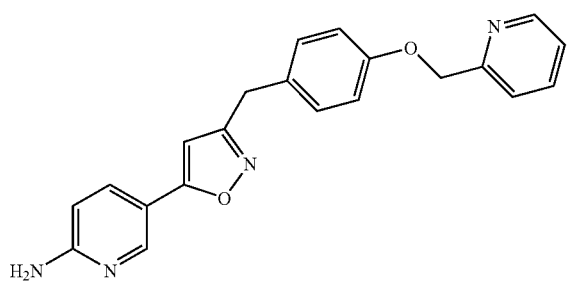

To a tetrahydrofuran (3 mL) and acetone (3 mL) solution of 4-(5-(6-amino-pyridin-3-yl)-isoxazol-3-ylmethyl)-phenol (150 mg, 0.561 mmol) described in Manufacturing Example 177-1-1 was added a 5 N sodium hydroxide aqueous solution (112 μL, 0.561 mmol), which was dissolved by irradiating ultrasonic wave for 1 minute. The reaction solution was concentrated under a reduced pressure, which gave a light-brown sodium salt (162 mg, quant.). A tetrahydrofuran solution of 2-picolyl chloride (prepared by adding a 5 N sodium hydroxide aqueous solution (13 μL, 62 μmol) to a solution of 2-picolyl chloride hydrochloride (10 mg, 62 μmol) in tetrahydrofuran (1 mL) and saturated aqueous sodium chloride (1 mL), stirring for 1 minute, and then separating the tetrahydrofuran layer) was added to a dimethyl sulfoxide (2 mL) solution of sodium salt (15 mg, 52 μmol) obtained above, which was stirred for 30 minutes at 65° C. Water was added to the reaction mixture at room temperature, which was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:methanol=20:1) to obtain the title compound (4.4 mg, 24%).

$^1$H-NMR Spectrum (CDCl$_3$) δ (ppm): 3.97 (2H, s), 4.84 (2H, s), 5.20 (2H, s), 6.13 (1H, s), 6.55 (1H, dd, J=0.73, 8.6 Hz), 6.94-6.97 (2H, m), 7.19-7.24 (3H, m), 7.52 (1H, d, J=7.9 Hz), 7.71 (1H, dt, J=1.8, 7.7 Hz), 7.78 (1H, dd, J=2.4, 8.6 Hz), 8.42 (1H, dd, J=0.73, 2.4 Hz), 8.59-8.60 (1H, m).

The starting material, 4-(5-(6-amino-pyridin-3-yl)-isoxazol-3-ylmethyl)-phenol, was synthesized as follows.

Manufacturing Example 177-1-1

4-(5-(6-Amino-pyridin-3-yl)-isoxazol-3-ylmethyl)-phenol

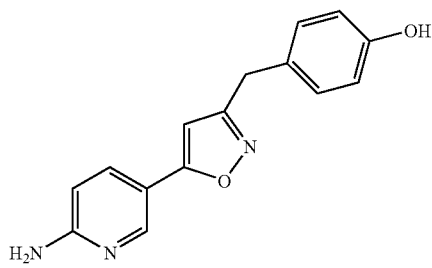

To a trifluoroacetic acid (5 mL) solution of 5-(3-(4-benzyloxy-benzyl)-isoxazol-5-yl)-pyridin-2-ylamine (270 mg, 0.755 mmol) described in Example 28 was added thioanisole (355 μL, 3.02 mmol) at 0° C., which was stirred for 1 hour and 20 minutes at room temperature. Sodium hydrogencarbonate and water were added to the reaction mixture at 0° C., which was extracted with ethyl acetate. The organic layer was separated, washed with saturated aqueous sodium chloride, dried over anhydrous magnesium sulfate, and filtered. The filtrate was concentrated under a reduced pressure, and the residue was purified by silica gel column chromatography (ethyl acetate:methanol=10:1) to obtain the title compound (150 mg, 74%).

$^1$H-NMR Spectrum (DMSO-$d_6$) δ (ppm): 3.84 (2H, s), 6.51 (1H, d, J=8.8 Hz), 6.53 (1H, s), 6.57 (2H, s), 6.70 (2H, d, J=8.4 Hz), 7.08 (2H, d, J=8.4 Hz), 7.76 (1H, dd, J=2.4, 8.8 Hz), 8.37 (1H, d, J=2.4 Hz), 9.28 (1H, s).

Example 178

5-(3-(4-(5-Methyl-furan-2-ylmethyl)-benzyl)-isoxazol-5-yl)-pyridin-2-ylamine

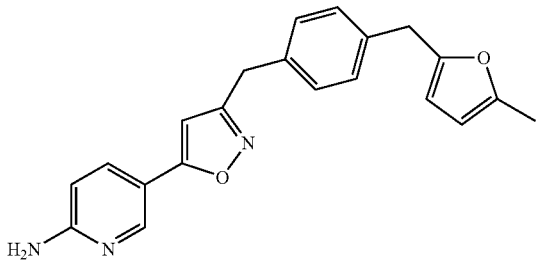

To a mixture of (4-(5-methyl-furan-2-ylmethyl)-phenyl)-acetohydroximoyl chloride (38 mg, 0.14 mmol) described in Manufacturing Example 46-1-6 and tetrahydrofuran (1 mL) were added 5-ethynyl-pyridin-2-ylamine (15 mg, 0.13 mmol) described in Manufacturing Example 28-1-3 and triethylamine (35 μL, 0.25 mmol), which was stirred for 3.5 hours at 50° C. The reaction mixture was allowed to room temperature, and water was added to the system at the same temperature, which was extracted with ethyl acetate. The organic layer was washed with saturated aqueous sodium chloride and was concentrated under a reduced pressure. The residue thus obtained was purified by reverse-phase high performance liquid chromatography (using an acetonitrile-water mobile phase containing 0.1% trifluoroacetic acid), after which triethylamine was added to a mixture of the resulting target product and the mobile phase, thereby rendering the mobile phase basic, and the eluate was concentrated under a reduced pressure. The residue thus obtained was washed with water to obtain the title compound (5.1 mg, 12%).

MS m/e (ESI) 346.05 (MH$^+$)

$^1$H-NMR Spectrum (DMSO-d$_6$) δ (ppm): 2.17 (3H, s), 3.86 (2H, s), 3.94 (2H, s), 5.93 (1H, s), 5.96 (1H, s), 6.49-6.57 (4H, m), 7.17 (2H, d, J=7.9 Hz), 7.23 (2H, d, J=8.1 Hz), 7.75 (1H, d, J=7.1 Hz), 8.38 (1H, s).

Example 179

5-(3-(6-Benzyloxy-pyridin-3-ylmethyl)-isoxazol-5-yl)-pyridin-2-ylamine

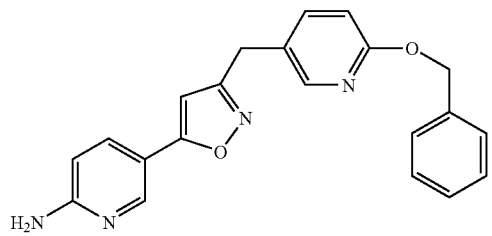

To a tetrahydrofuran (7.00 mL) solution of (2-benzyloxy-pyridin-5-yl)-acetohydroximoyl chloride (191 mg, 0.690 mmol) described in Manufacturing Example 12-1-5 and 5-ethynyl-pyridin-2-ylamine (40.0 mg, 0.339 mmol) described in Manufacturing Example 28-1-3 was added triethylamine (142 μL, 1.02 mmol) under nitrogen atmosphere at room temperature, which was stirred for 3 hours at 60° C. Water was added to the reaction mixture at room temperature, which was extracted with ethyl acetate. The organic layer was washed with saturated aqueous sodium chloride and dried over anhydrous magnesium sulfate, and the solvent was evaporated under a reduced pressure. The residue was purified by NH silica gel column chromatography (ethyl acetate:heptane=1:1→2:1) to obtain the title compound (15.7 mg, 12.9%).

$^1$H-NMR Spectrum (DMSO-d$_6$) δ (ppm): 3.94 (2H, s), 5.33 (2H, s), 6.50 (1H, dd, J=0.8, 8.8 Hz), 6.53 (2H, brs), 6.61 (1H, s), 6.85 (1H, d, J=8.4 Hz), 7.31-7.39 (3H, m), 7.42-7.45 (2H, m), 7.65 (1H, dd, J=2.4, 8.4 Hz), 7.75 (1H, dd, J=2.4, 8.4 Hz), 8.14 (1H, d, J=2.0 Hz), 8.38 (1H, d, J=2.4 Hz).

Example 180

5-(3-(4-Pyridin-4-ylmethoxy)-benzyl)-isoxazol-5-yl)-pyridin-2-ylamine

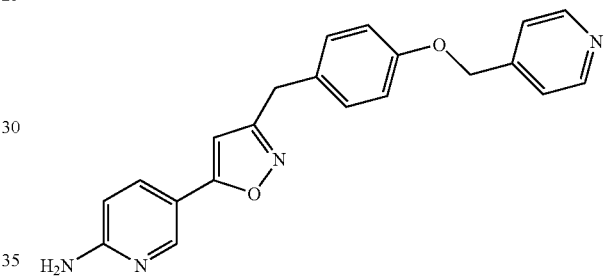

To a tetrahydrofuran (3 mL) and acetone (3 mL) solution of 4-(5-(6-amino-pyridin-3-yl)-isoxazol-3-ylmethyl)-phenol (150 mg, 0.561 mmol) described in Manufacturing Example 177-1-1 was added a 5 N sodium hydroxide aqueous solution (112 μL, 0.561 mmol) at room temperature, which was dissolved by irradiating ultrasonic wave for 1 minute. The reaction solution was concentrated under a reduced pressure, which gave a light-brown sodium salt (162 mg, quant.). A tetrahydrofuran solution of 4-chloromethylpyridine (prepared by adding 5 N sodium hydroxide aqueous solution (21 μL, 0.10 mmol) to a solution of 4-chloromethylpyridine hydrochloride (17 mg, 0.10 mmol) in tetrahydrofuran (1 mL) and saturated aqueous sodium chloride (1 mL), stirring for 1 minute, and then partitioning the tetrahydrofuran layer) was added to a dimethyl sulfoxide (1 mL) solution of the sodium salt (15 mg, 52 μmol) obtained above, which was stirred for 2 hours and 15 minutes at room temperature, and then for another hour at 60° C. Water was added to the reaction mixture at room temperature, which was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate) to obtain the title compound (4.2 mg, 23%).

$^1$H-NMR Spectrum (CDCl$_3$) δ (ppm): 3.98 (2H, s), 4.88 (2H, s), 5.08 (2H, s), 6.13 (1H, s), 6.56 (1H, d, J=8.8 Hz), 6.92 (2H, d, J=8.6 Hz), 7.22 (2H, d, J=8.4 Hz), 7.36 (2H, d, J=5.5 Hz), 7.78 (1H, dd, J=2.4, 9.0 Hz), 8.42 (1H, d, J=2.4 Hz), 8.62 (2H, d, J=6.0 Hz).

Example 181

5-(3-(6-Phenoxy-pyridin-3-ylmethyl)-isoxazol-5-yl)-pyridin-2-ylamine

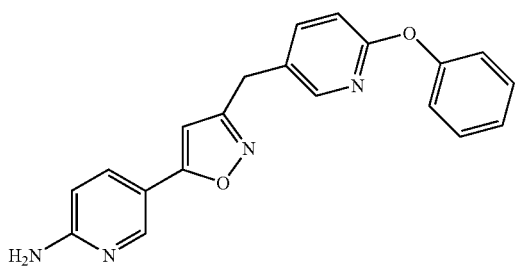

To a tetrahydrofuran (2 mL) solution of 5-ethynyl-pyridin-2-ylamine (30 mg, 0.25 mmol) described in Manufacturing Example 28-1-3 were added (2-phenoxy-pyridin-5-yl)-acetohydroximoyl chloride (100 mg, 0.381 mmol) described in Manufacturing Example 40-1-4 and triethylamine (70.8 μL, 0.508 mmol), which was stirred for 8 hours at 50° C. Water was added to the reaction mixture at room temperature, which was extracted with ethyl acetate. The organic layer was separated, washed with saturated aqueous sodium chloride, dried over anhydrous magnesium sulfate, and filtered. The filtrate was concentrated under a reduced pressure, and the residue was purified by NH silica gel column chromatography (ethyl acetate) to obtain the title compound (26 mg, 30%).

$^1$H-NMR Spectrum (DMSO-$d_6$) δ (ppm): 3.97 (2H, s), 6.48 (1H, dd, J=0.73, 8.6 Hz), 6.52 (2H, s), 6.61 (1H, s), 6.97 (1H, d, J=8.4 Hz), 7.08-7.10 (2H, m), 7.16-7.20 (1H, m), 7.37-7.41 (2H, m), 7.72-7.77 (2H, m), 8.11 (1H, d, J=2.2 Hz), 8.37 (1H, dd, J=0.73, 2.4 Hz).

Example 182

5-(3-(4-(5-Chloro-furan-2-ylmethyl)-benzyl)-isoxazol-5-yl)-pyridin-2-ylamine

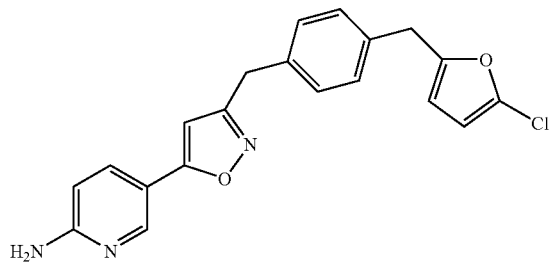

To a mixture of (4-(5-chloro-furan-2-ylmethyl)-phenyl)-acetohydroximoyl chloride (25 mg, 0.088 mmol) described in Manufacturing Example 62-1-6 and tetrahydrofuran (1 mL) were added 5-ethynyl-pyridin-2-ylamine (8.0 mg, 0.068 mmol) described in Manufacturing Example 28-1-3 and triethylamine (19 μL, 0.14 mmol), which was stirred for 1 hour at 50° C. The reaction mixture was allowed to room temperature, and water was added to the system at the same temperature, which was extracted with ethyl acetate. The organic layer was washed with saturated aqueous sodium chloride, and was concentrated under a reduced pressure. The residue thus obtained was purified by reverse-phase high performance liquid chromatography (using an acetonitrile-water mobile phase containing 0.1% trifluoroacetic acid) to obtain the title compound (1.6 mg, 4.9%) as a trifluoroacetic acid salt.

MS m/e (ESI) 366.09 (MH$^+$)

$^1$H-NMR Spectrum (DMSO-$d_6$) δ (ppm): 3.93 (2H, s), 3.98 (2H, s), 6.24-6.25 (1H, m), 6.34-6.35 (1H, m), 6.71 (1H, s), 6.76 (1H, d, J=8.6 Hz), 7.20 (2H, d, J=7.9 Hz), 7.25 (2H, d, J=7.9 Hz), 8.00 (1H, d, J=8.6 Hz), 8.42 (1H, d, J=2.4 Hz).

Example 183

5-(3-(4-(4-Chloro-pyridin-2-ylmethoxy)-benzyl)-isoxazol-5-yl)-pyridin-2-ylamine

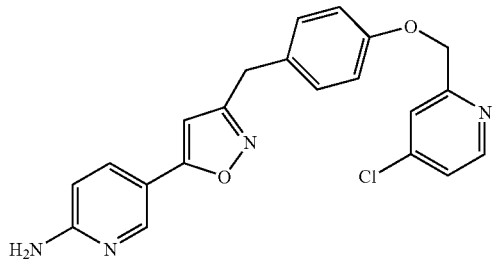

To 4-(5-(6-amino-pyridin-3-yl)-isoxazol-3-ylmethyl)-phenol (20.0 mg, 0.07 mmol) described in Manufacturing Example 177-1-1 were added tetrahydrofuran (3 mL) and a 5 N sodium hydroxide aqueous solution (14.9 μL, 0.07 mmol), which was dissolved by irradiating ultrasonic wave for 1 minute. The reaction solution was concentrated under a reduced pressure, which gave a white solid. To a mixture of the solid obtained above and N,N-dimethylformamide (1 mL) was added an N,N-dimethylformamide (1 mL) solution of 4-chloro-2-chloromethyl-pyridine (13.3 mg, 0.08 mmol) described in Manufacturing Example 51-1-2, which was stirred for 1 hour at 60° C. The reaction mixture was cooled to room temperature and then partitioned into water and ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (7.2 mg, 25%).

$^1$H-NMR Spectrum (DMSO-$d_6$) δ (ppm): 3.89 (2H, s), 5.15 (2H, s), 6.47 (1H, d, J=8.8 Hz), 6.50 (2H, brs), 6.53 (1H, s), 6.85 (1H, s), 6.98 (2H, d, J=8.4 Hz), 7.21 (2H, d, J=8.4 Hz), 7.48 (1H, dd, J=2.4, 5.2 Hz), 7.72 (1H, dd, J=2.4, 8.4 Hz), 8.35 (1H, d, J=2.4 Hz), 8.54 (1H, d, J=5.2 Hz).

Example 184

5-(3-(4-(5-Fluoro-pyridin-2-ylmethoxy)-benzyl)-isoxazol-5-yl)-pyridin-2-ylamine

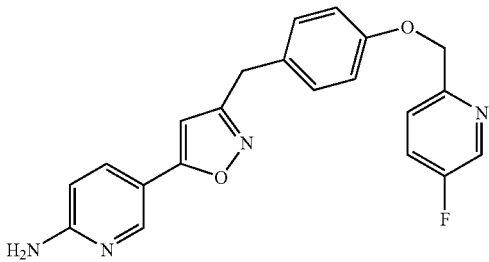

To 4-(5-(6-amino-pyridin-3-yl)-isoxazol-3-ylmethyl)-phenol (20.0 mg, 0.07 mmol) described in Manufacturing Example 177-1-1 were added tetrahydrofuran (3 mL) and a 5 N sodium hydroxide aqueous solution (14.9 µL, 0.07 mmol), which was dissolved by irraditaing ultrasonic wave for 1 minute. The reaction solution was concentrated under a reduced pressure, which gave a white solid. To a mixture of the solid obtained above and N,N-dimethylformamide (1 mL) was added an N,N-dimethylformamide (1 mL) solution of the 2-chloromethyl-5-fluoro-pyridine (12.0 mg, 0.08 mmol) described in Manufacturing Example 41-1-2, which was stirred for 1 hour at 60° C. The reaction mixture was cooled to room temperature and then partitioned into water and ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (3.0 mg, 11%).

$^1$H-NMR Spectrum (CDCl$_3$) δ (ppm): 3.96 (2H, s), 4.73 (2H, brs), 5.16 (2H, s), 6.12 (1H, s), 6.52 (1H, d, J=8.8 Hz), 6.93 (2H, d, J=8.8 Hz), 7.20 (2H, d, J=8.8 Hz), 7.42 (1H, dt, J=2.8, 8.4 Hz), 7.49-7.55 (1H, m), 7.75 (1H, m), 8.42-8.44 (2H, m).

Example 185

5-(3-(6-(2-Fluoro-phenoxy)-pyridin-3-ylmethyl)-isoxazol-5-yl)-pyridin-2-ylamine

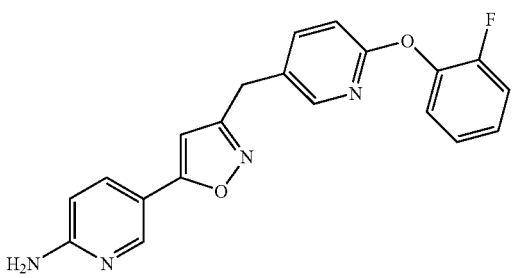

To a mixture of (6-(2-fluoro-phenoxy)-pyridin-3-yl)-acetohydroximoyl chloride (28 mg) described in Manufacturing Example 74-1-4 and tetrahydrofuran (1 mL) were added 5-ethynyl-pyridin-2-ylamine (9.0 mg, 0.076 mmol) described in Manufacturing Example 28-1-3 and triethylamine (21 µL, 0.15 mmol), which was stirred for 5 hours at 50° C. The reaction mixture was allowed to room temperature, water was added at the same temperature, and the mixture was extracted with ethyl acetate. The organic layer was washed with saturated aqueous sodium chloride, and was concentrated under a reduced pressure. The residue was purified by NH silica gel column chromatography (ethyl acetate) to obtain the title compound (4.6 mg, 17%).

$^1$H-NMR Spectrum (CDCl$_3$) δ (ppm): 3.98 (2H, s), 4.73 (2H, brs), 6.14 (1H, s), 6.54 (1H, dd, J=0.7, 8.6 Hz), 6.96 (1H, d, J=8.4 Hz), 7.14-7.26 (4H, m), 7.63 (1H, dd, J=2.6, 8.4 Hz), 7.76 (1H, dd, J=2.4, 8.6 Hz), 8.08 (1H, dd, J=0.6, 2.5 Hz), 8.45 (1H, d, J=2.4 Hz).

Example 186

5-(3-(6-(4-Fluoro-phenoxy)-pyridin-3-ylmethyl)-isoxazol-5-yl)-pyridin-2-ylamine

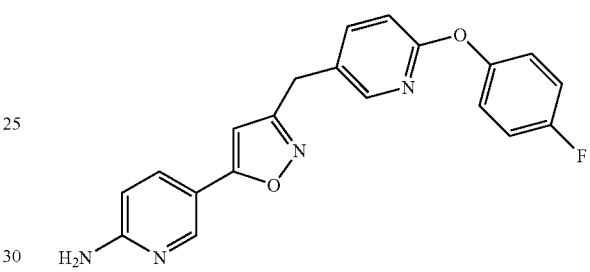

To a mixture of (6-(4-fluoro-phenoxy)-pyridin-3-yl)-acetohydroximoyl chloride (25 mg) described in Manufacturing Example 75-1-4 and tetrahydrofuran (1 mL) were added 5-ethynyl-pyridin-2-ylamine (6.0 mg, 0.051 mmol) described in Manufacturing Example 28-1-3 and triethylamine (14 µL, 0.10 mmol), which was stirred for 5 hours at 50° C. The reaction mixture was allowed to room temperature, water was added at the same temperature, and the mixture was extracted with ethyl acetate. The organic layer was washed with saturated aqueous sodium chloride, and was concentrated under a reduced pressure. The residue was purified by NH silica gel column chromatography (ethyl acetate) to obtain the title compound (3.5 mg, 19%).

$^1$H-NMR Spectrum (CDCl$_3$) δ (ppm): 3.98 (2H, s), 4.72 (2H, brs), 6.15 (1H, s), 6.54 (1H, dd, J=0.7, 8.6 Hz), 6.88 (1H, d, J=8.6 Hz), 7.05-7.12 (4H, m), 7.62 (1H, dd, J=2.6, 8.4 Hz), 7.77 (1H, dd, J=2.2, 8.6 Hz), 8.12 (1H, d, J=2.6 Hz), 8.45 (1H, d, J=2.4 Hz).

Example 187

6-Methyl-5-(3-(4-pyridin-2-yloxymethyl)-benzyl)-isoxazol-5-yl)-pyridin-2-ylamine

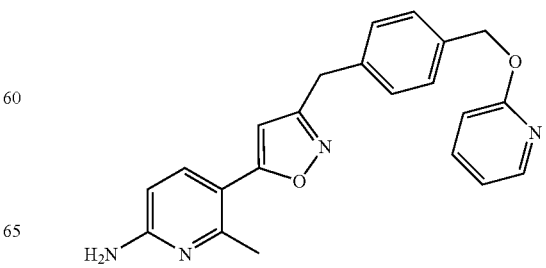

To a mixture of (4-(pyridin-2-yloxymethyl)-phenyl)-acetohydroximoyl chloride (55 mg, 0.20 mmol) described in Manufacturing Example 2-1-5 and tetrahydrofuran (1 mL) were added 5-ethynyl-6-methyl-pyridin-2-ylamine (20 mg, 0.15 mmol) described in Manufacturing Example 187-1-2 and triethylamine (43 μL, 0.31 mmol), which was stirred for 2 hours at 50° C. The reaction mixture was allowed to room temperature, and water was added thereto at the same temperature, which was extracted with ethyl acetate. The organic layer was washed with saturated aqueous sodium chloride, and was concentrated under a reduced pressure. The residue thus obtained was purified by NH silica gel column chromatography (heptane:ethyl acetate=1:2) to obtain the title compound (35 mg, 61%).

$^1$H-NMR Spectrum (CDCl$_3$) δ (ppm): 2.52 (3H, s), 4.06 (2H, s), 4.64 (2H, br s), 5.36 (2H, s), 6.05 (1H, s), 6.40 (1H, d, J=8.4 Hz), 6.79-6.81 (1H, m), 6.87-6.90 (1H, m), 7.31 (2H, d, J=8.1 Hz), 7.43 (2H, d, J=7.9 Hz), 7.56-7.60 (1H, m), 7.74 (1H, d, J=8.4 Hz), 8.16-8.18 (1H, m).

The starting material, 5-ethynyl-6-methyl-pyridin-2-ylamine, was synthesized as follows.

Manufacturing Example 187-1-1

6-Methyl-5-trimethylsilanylethynyl-pyridin-2-ylamine

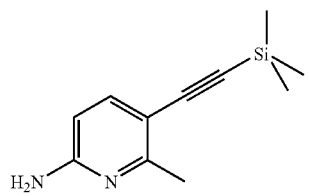

To a mixture of 6-amino-3-bromo-2-methylpyridine (200 mg, 1.0 mmol), trimethylsilylacetylene (0.22 mL, 1.6 mmol), copper (I) iodide (9.9 mg, 0.052 mmol), and 1,4-dioxane (1.5 mL) was added bis(triphenylphosphine)palladium (II) chloride (73 mg, 0.10 mmol), which was stirred under nitrogen atmosphere for 3 hours and 30 minutes at 100° C. The reaction mixture was allowed to room temperature, water was added to the reaction mixture at the same temperature, ethyl acetate was added, and the mixture was filtered through a Celite pad. The organic layer of the filtrate was separated and washed with saturated aqueous sodium chloride, and was concentrated under a reduced pressure, and the residue thus obtained was purified by silica gel column chromatography (heptane:ethyl acetate=2:1) to obtain the title compound (140 mg, 57%, purity: 86%).

$^1$H-NMR Spectrum (CDCl$_3$) δ (ppm): 0.24 (9H, s), 2.50 (3H, s), 4.59 (2H, br s), 6.26 (1H, d, J=8.2 Hz), 7.44 (1H, d, J=8.4 Hz).

Manufacturing Example 187-1-2

5-Ethynyl-6-methyl-pyridin-2-ylamine

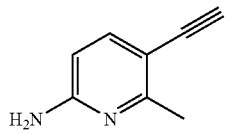

To a mixture of 6-methyl-5-trimethylsilanylethynyl-pyridin-2-ylamine (450 mg, 1.9 mmol) described in Manufacturing Example 187-1-1 and methanol (5 mL) was added potassium carbonate (390 mg, 2.8 mmol), which was stirred for 30 minutes at the same temperature. Water was added to the reaction mixture, which was extracted with ethyl acetate. The organic layer was washed with saturated aqueous sodium chloride, and was concentrated under a reduced pressure. The residue was purified by silica gel column chromatography (heptane:ethyl acetate=1:1) to obtain the title compound (220 mg, 88%).

$^1$H-NMR Spectrum (CDCl$_3$) δ (ppm): 2.52 (3H, s), 3.24 (1H, s), 4.58 (2H, br s), 6.29 (1H, d, J=8.4 Hz), 7.47 (1H, d, J=8.4 Hz).

Example 188

5-(3-(4-Benzyloxy-benzyl)-isoxazol-5-yl)-6-methyl-pyridin-2-ylamine

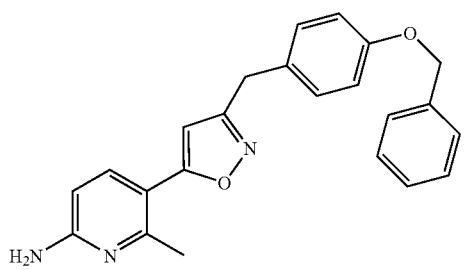

To a mixture of 4-benzyloxy-phenyl-acetohydroximoyl chloride (59 mg, 0.21 mmol) described in Manufacturing Example 1-1-3 and tetrahydrofuran (1 mL) were added 5-ethynyl-6-methyl-pyridin-2-ylamine (22 mg, 0.16 mmol) described in Manufacturing Example 187-1-2 and triethylamine (46 μL, 0.33 mmol), which was stirred for 2 hours at 50° C. The reaction mixture was allowed to room temperature, water was added at the same temperature, and the mixture was extracted with ethyl acetate. The organic layer was washed with saturated aqueous sodium chloride, and was concentrated under a reduced pressure. The residue thus obtained was purified by NH silica gel column chromatography (heptane:ethyl acetate=1:2) to obtain the title compound (35 mg, 57%).

$^1$H-NMR Spectrum (CDCl$_3$) δ (ppm): 2.52 (3H, s), 3.99 (2H, s), 4.60 (2H, br s), 5.05 (2H, s), 6.04 (1H, s), 6.39-6.41 (1H, m), 6.92-6.96 (2H, m), 7.19-7.23 (2H, m), 7.30-7.44 (5H, m), 7.75 (1H, d, J=8.4 Hz).

Example 189

3-(5-(4-(Pyridin-2-ylmethoxy)-benzyl)-isoxazol-3-yl)-pyridin-2-ylamine

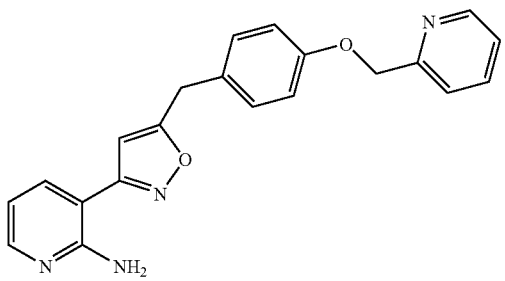

To a N-methylpyrrolidinone (4 mL) solution of 5-chloro-3-(5-(4-(pyridin-2-ylmethoxy)-benzyl)-isoxazol-3-yl)-pyridin-2-ylamine (141 mg, 0.359 mmol) described in Manufacturing Example 189-1-2 were added tetrakis(triphenylphosphine)palladium (0) (42 mg, 36 μmol), formic acid (20 μL, 0.58 mmol), and N,N-diisopropylethylamine (193 μL, 1.08 mmol), which was stirred under nitrogen atmosphere for 5 hours and 35 minutes at 100° C. Water was added to the reaction mixture at room temperature, which was extracted with ethyl acetate. The organic layer was separated, washed with water and saturated aqueous sodium chloride, dried over anhydrous magnesium sulfate, and filtered. The filtrate was concentrated under a reduced pressure. The residue was purified by reverse-phase high performance liquid chromatography (using an acetonitrile-water mobile phase containing 0.1% trifluoroacetic acid), and then further purified by NH silica gel column chromatography (ethyl acetate:methanol=10:1) to obtain the title compound (8.3 mg, 6.5%).

MS m/e (ESI) (MH+) 359.24 (MH+)

$^1$H-NMR Spectrum (CDCl$_3$) δ (ppm): 4.07 (2H, s), 5.21 (2H, s), 6.24 (1H, s), 6.25 (2H, s), 6.66 (1H, dd, J=4.9, 7.7 Hz), 6.96-7.00 (2H, m), 7.20-7.25 (3H, m), 7.52 (1H, d, J=7.9 Hz), 7.64 (1H, dd, J=1.7, 7.5 Hz), 7.72 (1H, dt, J=1.8, 7.7 Hz), 8.11 (1H, dd, J=1.7, 4.8 Hz), 8.59-8.61 (1H, m).

The starting material, 5-chloro-3-(5-(4-(pyridin-2-ylmethoxy)-benzyl)-isoxazol-3-yl)-pyridin-2-ylamine, was synthesized as follows.

Manufacturing Example 189-1-1

4-(3-(2-Amino-5-chloro-pyridin-3-yl)-isoxazol-5-ylmethyl)-phenol

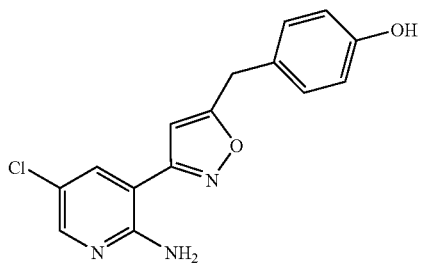

To a trifluoroacetic acid (6 mL) solution of 3-(5-(4-benzyloxy-benzyl)-isoxazol-3-yl)-5-chloro-pyridin-2-ylamine (304 mg, 0.776 mmol) described in Manufacturing Example 29-2-3 was added thioanisole (364 mL, 3.10 mmol) at 0° C., which was stirred for 3 hours at room temperature. To this reaction mixture were added sodium hydrogencarbonate and water at 0° C., which was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:methanol=20:1) to obtain the title compound (146 mg, 62%).

$^1$H-NMR Spectrum (DMSO-d$_6$) δ (ppm): 4.07 (2H, s), 6.74 (2H, d, J=8.4 Hz), 6.98 (1H, s), 7.07 (2H, s), 7.12 (2H, d, J=8.4 Hz), 8.09 (1H, d, J=2.6 Hz), 8.13 (1H, d, J=2.6 Hz), 9.36 (1H, s).

Manufacturing Example 189-1-2

5-Chloro-3-(5-(4-(pyridin-2-ylmethoxy)-benzyl)-isoxazol-3-yl)-pyridin-2-ylamine

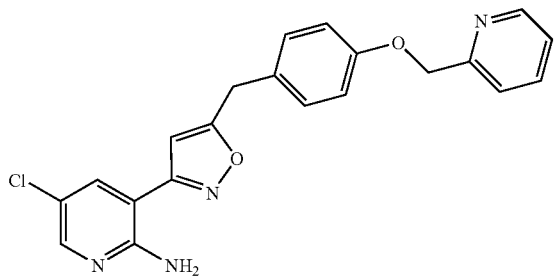

To a tetrahydrofuran (4 mL) solution of 4-(3-(2-amino-5-chloro-pyridin-3-yl)-isoxazol-5-ylmethyl)-phenol (146 mg, 0.484 mmol) described in Manufacturing Example 189-1-1 was added a 5 N sodium hydroxide aqueous solution (96.8 μL, 0.484 mmol) at room temperature, which was dissolved by irradiating ultrasonic wave for 1 minute. The reaction mixture was concentrated under a reduced pressure to obtain a sodium salt. A tetrahydrofuran solution of 2-picolyl chloride (prepared by adding a 5 N sodium hydroxide aqueous solution (242 μL, 1.21 mmol) to a solution of 2-picolyl chloride hydrochloride (198 mg, 1.21 μmol) in tetrahydrofuran (2 mL) water (2 mL), stirring for 1 minute, and then separating the tetrahydrofuran layer) was added at room temperature to an N,N-dimethylformamide (5 mL) solution of the sodium salt obtained above, which was stirred for 2 hours at 60° C. Water was added to the reaction mixture at room temperature, which was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (heptane:ethyl acetate=1:1) to obtain the title compound (141 mg, 74%).

$^1$H-NMR Spectrum (CDCl$_3$) δ (ppm): 4.08 (2H, s), 5.22 (2H, s), 6.22 (1H, s), 6.25 (2H, s), 6.99 (2H, d, J=8.6 Hz), 7.22 (2H, d, J=8.1 Hz), 7.26-7.31 (1H, m), 7.54 (1H, d, J=6.4 Hz), 7.60 (1H, d, J=2.4 Hz), 7.73 (1H, dt, J=1.8, 7.9 Hz), 8.07 (1H, d, J=2.4 Hz), 8.61 (1H, d, J=4.9 Hz).

Example 190

2-Methyl-5-(3-(4-(pyridin-2-yloxymethyl)-benzyl)-isoxazol-5-yl)-pyridine

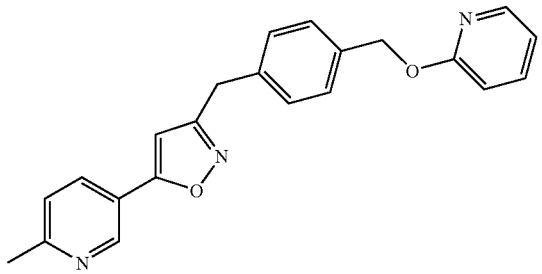

To a tetrahydrofuran (2 mL) solution of 5-ethynyl-2-methyl-pyridine (10 mg, 85 µmol) described in Manufacturing Example 190-1-1 were added 4-(pyridin-2-yloxymethyl)-phenyl-acetohydroximoyl chloride (31 mg, 0.11 mmol) described in Manufacturing Example 2-1-5 and triethylamine (18 µL, 0.13 mmol), which was stirred for 2 hours and 30 minutes at 50° C. Water was added to the reaction mixture at room temperature, which was extracted with ethyl acetate. The organic layer was washed with saturated aqueous sodium chloride, dried over anhydrous magnesium sulfate, and filtered. The filtrated was concentrated under a reduced pressure, and the residue was purified by silica gel column chromatography (heptane:ethyl acetate=1:1) to obtain the title compound (14 mg, 46%).

$^1$H-NMR Spectrum (DMSO-d$_6$) δ (ppm): 2.52 (3H, s), 4.05 (2H, s), 5.32 (2H, s), 6.85 (1H, d, J=8.2 Hz), 6.96 (1H, s), 6.98 (1H, dd, J=5.1, 6.6 Hz), 7.33 (2H, d, J=8.1 Hz), 7.39-7.43 (3H, m), 7.69-7.74 (1H, m), 8.10 (1H, dd, J=2.2, 8.1 Hz), 8.17 (1H, dd, J=2.0, 5.1 Hz), 8.91 (1H, d, J=2.2 Hz).

The starting material, 5-ethynyl-2-methyl-pyridine, was synthesized as follows.

Manufacturing Example 190-1-1

5-Ethynyl-2-methyl-pyridine

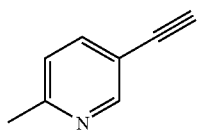

To a N-methylpyrrolidinone (20 mL) solution of 5-bromo-2-methyl-pyridine (1.00 g, 5.81 mmol) were added trimethylsilylacetylene (1.23 mL, 8.72 mmol), tetrakis(triphenylphosphine)palladium (0) (134 mg, 0.116 mmol), copper (I) iodide (44.3 mg, 0.232 mmol), and N,N-diisopropylethylamine (2.02 mL, 11.6 mmol), which was stirred under a nitrogen atmosphere for 13 hours at room temperature. Water was added to the reaction mixture at room temperature, which was extracted with ethyl acetate. The organic layer was separated, washed with water and saturated aqueous sodium chloride, dried over anhydrous magnesium sulfate, and filtered. The filtrate was concentrated under a reduced pressure, and the residue was purified by silica gel column chromatography (heptane:ethyl acetate=5:1) to obtain a mixture (656 mg) of 5-bromo-2-methyl-pyridine and 2-methyl-5-trimethylsilanylethynyl-pyridine. To a methanol (10 mL) solution of this mixture (656 mg) was then added potassium carbonate (956 mg, 6.92 mmol), which was stirred for 2 hours at room temperature. Water was added at room temperature to the reaction mixture at room temperature, which was extracted with diethyl ether. The organic layer was separated, washed with water and saturated aqueous sodium chloride, dried over anhydrous magnesium sulfate, and filtered. The filtrate was concentrated under a reduced pressure, and the residue was purified by silica gel column chromatography (heptane:ethyl acetate=2:1) to obtain the title compound (166 mg, 25%).

$^1$H-NMR Spectrum (CDCl$_3$) δ (ppm): 2.57 (3H, s), 3.17 (1H, s), 7.12 (1H, d, J=8.1 Hz), 7.66 (1H, dd, J=2.0, 8.1 Hz), 8.61 (1H, d, J=1.8 Hz).

Example 191

3-(1-(6-Benzyloxy-pyridin-3-ylmethyl)-1H-pyrazol-4-yl)-pyridin-2-ylamine

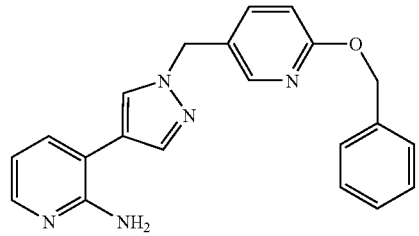

To an N,N-dimethylformamide (5.00 mL) solution of 3-(1H-pyrazol-4-yl)-pyridin-2-ylamine (20.0 mg, 0.125 mmol) described in Manufacturing Example 32-1-4 was added sodium hydride (5.50 g, 0.138 mmol, 60% in oil) on an ice bath (0° C.) under nitrogen atmosphere, which was stirred for 30 minutes at room temperature. Thereafter, 2-benzyloxy-5-chloromethyl-pyridine (49.7 mg, 0.213 mmol) described in Manufacturing Example 191-1-2 was added to this mixture, which was stirred for 30 minutes at room temperature. This mixture was partitioned into ethyl acetate and water at room temperature. The organic layer was washed with water and saturated aqueous sodium chloride, and dried over anhydrous magnesium sulfate, and the solvent was evaporated under a reduced pressure. The residue was purified by NH silica gel column chromatography (ethyl acetate:heptane=2:1→ethyl acetate) to obtain the title compound (31.3 mg, 70.1%).

$^1$H-NMR Spectrum (DMSO-d$_6$) δ (ppm): 5.30 (2H, s), 5.34 (2H, s), 5.61 (2H, brs), 6.61 (1H, dd, J=4.8, 7.2 Hz), 6.87 (1H, d, J=8.0 Hz), 7.31-7.39 (3H, m), 7.42-7.44 (2H, m), 7.48 (1H, dd, J=1.6, 7.2 Hz), 7.72 (1H, dd, J=2.4, 8.4 Hz), 7.75 (1H, d, J=0.8 Hz), 8.87 (1H, dd, J=2.0, 4.8 Hz), 8.18 (1H, d, J=0.8 Hz), 8.20 (1H, d, J=2.8 Hz).

389

The starting material, 2-benzyloxy-5-chloromethyl-pyridine, was synthesized as follows.

Manufacturing Example 191-1-1

(6-Benzyloxy-pyridin-3-yl)-methanol

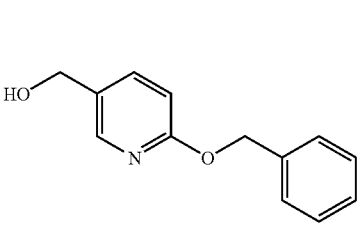

To a methanol (20.0 mL) solution of 6-benzyloxy-pyridine-3-carbaldehyde (2.00 g, 9.38 mmol) described in Manufacturing Example 12-1-2 was added sodium borohydride (426 mg, 11.3 mmol) on an ice bath (0° C.) under nitrogen atmosphere, which was stirred for 10 minutes at room temperature. Water was added to the reaction mixture at room temperature, which was extracted with ethyl acetate. The organic layer was washed with saturated aqueous sodium chloride and dried over anhydrous magnesium sulfate, and the solvent was evaporated under a reduced pressure to obtain the title compound (1.84 g, 91.1%).

$^1$H-NMR Spectrum (CDCl$_3$) δ (ppm): 4.55 (2H, s), 5.39 (2H, s), 6.82 (1H, d, J=8.4 Hz), 7.30-7.45 (5H, m), 7.63-7.66 (1H, m), 8.16 (1H, d, J=2.4 Hz).

Manufacturing Example 191-1-2

2-Benzyloxy-5-chloromethyl-pyridine

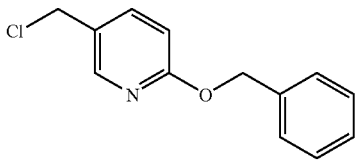

To a dichloromethane (4.00 mL) solution of (6-benzyloxy-pyridin-3-yl)-methanol (1.80 g, 8.36 mmol) described in Manufacturing Example 191-1-1 was added dropwise thionyl chloride (732 μL, 10.0 mmol) on an ice bath (0° C.) under nitrogen atmosphere, which was stirred for 5 minutes at room temperature. Aqueous sodium bicarbonate was added to the reaction solution, which was extracted with ethyl acetate. The organic layer was washed with saturated aqueous sodium chloride and dried over anhydrous magnesium sulfate, and the solvent was evaporated under a reduced pressure to obtain the title compound (1.70 g, 87.0%).

$^1$H-NMR Spectrum (CDCl$_3$) δ (ppm): 4.60 (2H, s), 5.37 (2H, s), 6.80 (1H, d, J=8.4 Hz), 7.31-7.46 (5H, m), 7.61-7.63 (1H, m), 8.11 (1H, d, J=2.4 Hz).

390

Example 192

3-(1-(4-(Pyridin-2-ylmethoxy)-benzyl)-1H-pyrazol-4-yl)-pyridin-2-ylamine

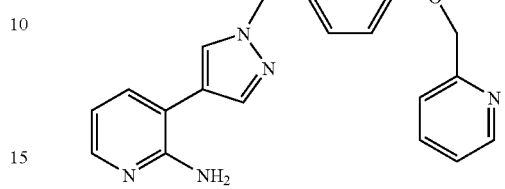

2-(4-chloromethyl-phenoxymethyl)-pyridine was obtained according to the methods similar to those of Manufacturing Example 199-1-1 and Manufacturing 199-1-2 using 4-(pyridine-2-ylmethoxy)-benzaldehyde described in Manufacturing Example 203-1-1.

To an N,N-dimethylformamide (5.00 mL) solution of 3-(1H-pyrazol-4-yl)-pyridin-2-ylamine (20.0 mg, 0.125 mmol) described in Manufacturing Example 32-1-4 was added sodium hydride (5.50 mg, 0.138 mmol, 60% in oil) on an ice bath (0° C.) under nitrogen atmosphere, which was stirred for 30 minutes at room temperature. Thereafter, 2-(4-chloromethyl-benzyloxy)-pyridine (49.7 mg, 0.213 mmol) described in Manufacturing Example 30-1-1 was added to the above mixture, which was stirred for 30 minutes at room temperature. This mixture was partitioned into ethyl acetate and water at room temperature. The organic layer was washed with water and saturated aqueous sodium chloride and dried over anhydrous magnesium sulfate, and the solvent was evaporated under a reduced pressure. The residue was purified by NH silica gel column chromatography (ethyl acetate:heptane=2:1→ethyl acetate) to obtain the title compound (21.9 mg, 49.0%).

2-(4-chloromethyl-phenoxymethyl)-pyridine
$^1$H-NMR Spectrum (CDCl$_3$) δ (ppm): 4.56 (2H, s), 5.21 (2H, s), 6.95-6.99 (2H, m), 7.21-7.23 (1H, m), 7.29-7.32 (2H, m), 7.49-7.51 (1H, m), 7.69-7.73 (1H, m), 8.59-8.61 (1H, m).

the title compound
$^1$H-NMR Spectrum (DMSO-d$_6$) δ (ppm): 5.16 (2H, s), 5.26 (2H, s), 5.59 (2H, brs), 6.61 (1H, dd, J=5.2, 7.2 Hz), 6.99-7.02 (2H, m), 7.26-7.29 (2H, m), 7.32-7.35 (1H, m), 7.46-7.50 (2H, m), 7.74 (1H, s), 7.80-7.84 (1H, m), 7.84-7.87 (1H, m), 8.13 (1H, d, J=1.2 Hz), 8.55-8.58 (1H, m).

Example 193

3-(1-(6-Phenoxy-pyridin-3-ylmethyl)-1H-pyrazol-4-yl)-pyridin-2-ylamine

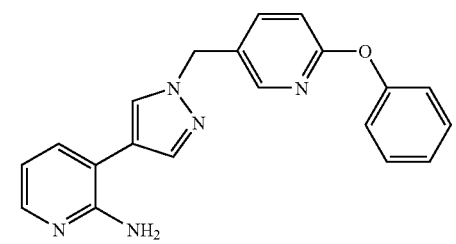

To an N,N-dimethylformamide (5.00 mL) solution of 3-(1H-pyrazol-4-yl)-pyridin-2-ylamine (20.0 mg, 0.125 mmol) described in Manufacturing Example 32-1-4 was added sodium hydride (5.50 mg, 0.138 mmol, 60% in oil) on an ice bath (0° C.) under nitrogen atmosphere, which was stirred for 10 minutes at room temperature. Thereafter, 5-chloromethyl-2-phenoxy-pyridine (49.7 mg, 0.226 mmol) described in Manufacturing Example 193-1-2 was added to the above mixture, which was stirred for 30 minutes at room temperature. The reaction mixture was partitioned into ethyl acetate and water at room temperature. The organic layer was washed with water and saturated aqueous sodium chloride and dried over anhydrous magnesium sulfate, and the solvent was evaporated under a reduced pressure. The residue was purified by NH silica gel column chromatography (ethyl acetate:heptane=2:1→ethyl acetate) to obtain the title compound (25.0 mg, 58.2%).

$^1$H-NMR Spectrum (DMSO-$d_6$) δ (ppm): 5.34 (2H, s), 5.62 (2H, brs), 6.61 (1H, dd, J=4.8, 7.6 Hz), 7.01 (1H, d, J=8.4 Hz), 7.10-7.12 (2H, m), 7.19-7.23 (1H, m), 7.39-7.43 (2H, m), 7.48 (1H, dd, J=2.0, 7.2 Hz), 7.67 (1H, s), 7.83 (1H, dd, J=2.4, 8.4 Hz), 7.87 (1H, dd, J=2.0, 5.2 Hz), 8.16 (1H, d, J=2.8 Hz), 8.19 (1H, s).

The starting material, 5-chloromethyl-2-phenoxy-pyridine, was synthesized as follows.

Manufacturing Example 193-1-1

(6-Phenoxy-pyridin-3-yl)-methanol

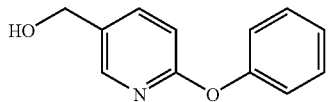

To a diethyl ether (30.0 mL) solution of 5-bromo-2-phenoxy-pyridine (1.02 g, 4.08 mmol) described in Manufacturing Example 40-1-1 was added dropwise n-butyl lithium (2.55 M n-hexane solution, 1.92 mL, 4.90 mmol) on a dry ice-ethanol bath (−78° C.) under nitrogen atmosphere, which was stirred for 30 minutes at −78° C. Thereafter, N,N-dimethylformamide (378 μL, 4.90 mmol) was added dropwise, which was stirred for 10 minutes at −78° C. Then, sodium borohydride (309 mg, 8.16 mmol) and methanol (15.0 mL) were added, which was stirred for 20 minutes at room temperature. Water was added to the reaction mixture, which was extracted with ethyl acetate. The organic layer was washed with saturated aqueous sodium chloride, and the solvent was evaporated under a reduced pressure. The residue was purified by silica gel column chromatography (ethyl acetate:heptane=1:1) to obtain the title compound (2.93 g, 66.5%).

$^1$H-NMR Spectrum (CDCl$_3$) δ (ppm): 4.62 (2H, s), 6.88 (1H, d, J=8.4 Hz), 7.10-7.13 (2H, m), 7.18-7.22 (1H, m), 7.37-7.41 (2H, m), 7.70-7.73 (1H, m), 8.12-8.13 (1H, m).

Manufacturing Example 193-1-2

5-Chloromethyl-2-phenoxy-pyridine

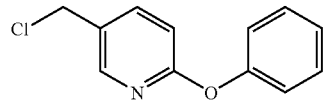

To a dichloromethane (5.00 mL) solution of (6-phenoxy-pyridin-3-yl)-methanol (458 mg, 2.28 mmol) described in Manufacturing Example 193-1-1 was added dropwise thionyl chloride (333 μL, 4.56 mmol) on an ice bath (0° C.) under nitrogen atmosphere, which was stirred for 5 minutes at room temperature. Aqueous sodium bicarbonate was added to the reaction solution at room temperature, which was extracted with ethyl acetate. The organic layer was washed with saturated aqueous sodium chloride and dried over anhydrous magnesium sulfate, and the solvent was evaporated under a reduced pressure to obtain the title compound (450 mg, 89.8%).

$^1$H-NMR Spectrum (CDCl$_3$) δ (ppm): 4.55 (2H, s), 6.91 (1H, d, J=8.8 Hz), 7.12-7.15 (2H, m), 7.20-7.24 (1H, m), 7.38-7.43 (2H, m), 7.72-7.75 (1H, m), 8.17 (1H, d, 2.4 Hz).

Example 194

3-(1-(4-Prop-2-ynyloxymethyl-benzyl)-1H-pyrazol-4-yl)-pyridin-2-ylamine

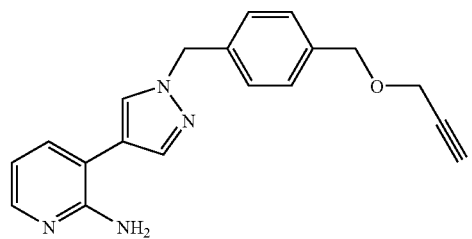

To a mixture of 3-(1H-pyrazol-4-yl)-pyridin-2-ylamine (30 mg, 0.19 mmol) described in Manufacturing Example 32-1-4 and tetrahydrofuran (1 mL) was added sodium hydride (12 mg, 0.24 mmol, 50% in oil) at 0° C., and then N,N-dimethylformamide (1 mL) was added. The reaction mixture was stirred for 10 minutes at room temperature, after which 1-chloromethyl-4-prop-2-ynyloxymethyl-benzene (47 mg, 0.24 mmol) described in Manufacturing Example 194-1-2 was added to this mixture at 0° C., which was stirred for 2 hours at room temperature. Water was added to the reaction mixture, which was extracted with ethyl acetate. The organic layer was washed with saturated aqueous sodium chloride, and was concentrated under a reduced pressure. The residue was purified by NH silica gel column chromatography (ethyl acetate:heptane=4:1) to obtain the title compound (37 mg, 62%).

$^1$H-NMR Spectrum (CDCl$_3$) δ (ppm): 2.47 (1H, t, J=2.4 Hz), 4.18 (2H, d, J=2.4 Hz), 4.56 (2H, br s), 4.61 (2H, s), 5.35

(2H, s), 6.70 (1H, dd, J=5.0, 7.4 Hz), 7.28 (2H, d, J=8.2 Hz), 7.36-7.40 (3H, m), 7.58 (1H, d, J=0.7 Hz), 7.74 (1H, d, J=0.9 Hz), 8.01 (1H, dd, J=1.8, 4.9 Hz).

The starting material, 1-chloromethyl-4-prop-2-ynyloxymethyl-benzene, was synthesized as follows.

Manufacturing Example 194-1-1

(4-Prop-2-ynyloxymethyl-phenyl)-methanol

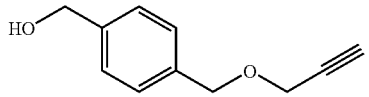

To a mixture of sodium hydride (400 mg, 8.4 mmol, 50% in oil) and tetrahydrofuran (30 mL) was added 1,4-benzenedimethanol (2.3 g, 17 mmol) at 0° C., and then N,N-dimethylformamide (30 mL) was added. The reaction mixture was stirred at room temperature for 10 minutes, after which propargyl bromide (1.0 g, 8.4 mmol) was added dropwise to the reaction mixture at 0° C. The reaction mixture was stirred at room temperature for 1 hour, after which water was added to the reaction mixture, which was extracted with ethyl acetate. The organic layer was washed and saturated aqueous sodium chloride, and was concentrated under a reduced pressure. The residue thus obtained was purified by NH silica gel column chromatography (heptane:ethyl acetate=3:2) to obtain the title compound (860 mg, 58%).

$^1$H-NMR Spectrum (CDCl$_3$) δ (ppm): 1.64 (1H, t, J=6.0 Hz), 2.47 (1H, t, J=2.4 Hz), 4.18 (2H, d, J=2.4 Hz), 4.62 (2H, s), 4.70 (2H, d, J=5.9 Hz), 7.37 (4H, s).

Manufacturing Example 194-1-2

1-Chloromethyl-4-prop-2-ynyloxymethyl-benzene

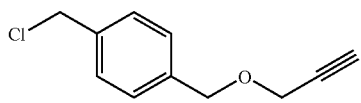

A mixture of (4-prop-2-ynyloxymethyl-phenyl)-methanol (190 mg, 1.1 mmol) described in Manufacturing Example 194-1-1, triphenylphosphine (340 mg, 1.3 mmol), and carbon tetrachloride (3 mL) was stirred for 6 hours under reflux. The reaction mixture was cooled to room temperature, after which the reaction mixture was concentrated under a reduced pressure. The residue was purified by neutral silica gel column chromatography (ethyl acetate:heptane=1:10) to obtain the title compound (180 mg, 84%).

$^1$H-NMR Spectrum (CDCl$_3$) δ (ppm): 2.47 (1H, t, J=2.4 Hz), 4.18 (2H, d, J=2.4 Hz), 4.59 (2H, s), 4.62 (2H, s), 7.35-7.40 (4H, m).

Example 195

3-(1-(4-Cyclopropylmethoxymethyl-benzyl)-1H-pyrazol-4-yl)-pyridin-2-ylamine

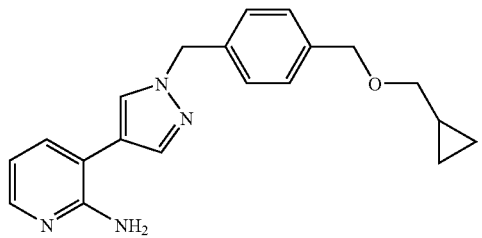

To a mixture of 3-(1-(4-bromo-benzyl)-1H-pyrazol-4-yl)-pyridin-2-ylamine (24 mg, 0.073 mmol) described in Manufacturing Example 195-1-1 and 1,4-dioxane (1.5 mL) were added water (150 µL), cesium carbonate (95 mg, 0.29 mmol), sodium cyclopropylmethoxymethyl trifluoroborate (19 mg, 0.11 mmol) described in Manufacturing Example 195-2-2, palladium (II) acetate (1.6 mg, 0.0073 mmol), and (±)-2,2'-bis(diphenylphosphino)-1,1'-binaphthyl (4.5 mg, 0.0073 mmol) at room temperature, which was stirred for 6 hours at 100° C. under nitrogen atmosphere. The reaction mixture was cooled to room temperature, after which water and ethyl acetate were added and the mixture was filtered through a Celite pad. The organic layer of the filtrate was washed with saturated aqueous sodium chloride, and was concentrated under a reduced pressure. The residue thus obtained was purified by reverse-phase high performance liquid chromatography (using an acetonitrile-water mobile phase containing 0.1% trifluoroacetic acid), after which triethylamine was added to a mixture of the resulting target product and the mobile phase, thereby rendering the mobile phase basic, and the solvent was evaporated under a reduced pressure. The residue thus obtained was filtered through NH silica gel (ethyl acetate) to obtain the title compound (1.6 mg, 6.6%).

MS m/e (ESI) 335.30 (MH$^+$)

The starting material, 3-(1-(4-bromo-benzyl)-1H-pyrazol-4-yl)-pyridin-2-ylamine, was synthesized as follows.

Manufacturing Example 195-1-1

3-(1-(4-Bromo-benzyl)-1H-pyrazol-4-yl)-pyridin-2-ylamine

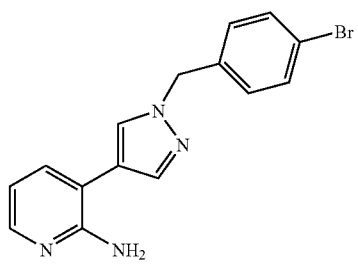

To a mixture of 3-(1H-pyrazol-4-yl)-pyridin-2-ylamine (150 mg, 0.94 mmol) described in Manufacturing Example 32-1-4 and tetrahydrofuran (2 mL) was added sodium hydride (12 mg, 0.24 mmol, 50% in oil) at 0° C., and then N,N-dimethylformamide (2 mL) was added. The reaction mixture was stirred for 10 minutes at room temperature, after which 4-bromobenzyl bromide (260 mg, 1.0 mmol) was added at 0° C. to this mixture, which was stirred for 1 hour at room temperature. Water was added to the reaction mixture, which was extracted with ethyl acetate. The organic layer was washed with saturated aqueous sodium chloride, and was concentrated under a reduced pressure. The residue was purified by NH silica gel column chromatography (ethyl acetate: heptane=4:1) to obtain the title compound (270 mg, 86%).

$^1$H-NMR Spectrum (CDCl$_3$) δ (ppm): 4.55 (2H, brs), 5.30 (2H, s), 6.71 (1H, ddd, J=0.7, 4.9, 7.3 Hz), 7.16 (2H, d, J=8.6 Hz), 7.40 (1H, dd, J=1.7, 7.3 Hz), 7.50 (2H, d, J=8.4 Hz), 7.60 (1H, s), 7.75 (1H, s), 8.02 (1H, dd, J=1.7, 4.9 Hz).

The starting material, sodium cyclopropylmethoxymethyl trifluoroborate, was synthesized as follows.

Manufacturing Example 195-2-1

2-(Bromomethyl)-4,4,5,5-tetramethyl-1,3,2-dioxaborolane

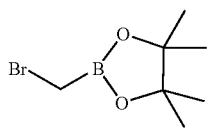

To a mixture of triisopropyl borate (20 g, 110 mmol), dibromomethane (8.6 mL, 120 mmol), and tetrahydrofuran (150 mL) was added dropwise n-butyl lithium (2.6 M n-hexane solution, 39 mL, 100 mmol) over a period of 1.5 hours at −78° C., and then the reaction mixture was stirred for 1.5 hours at the same temperature. This mixture was then stirred for 2 hours at room temperature, after which it was cooled to 0° C., methanesulfonic acid (6.5 mL, 100 mmol) was added to the reaction mixture, and then the reaction mixture was stirred for 1 hour at room temperature. The mixture was cooled to 0° C., pinacol (12 g, 100 mmol) was added to the reaction mixture, and the reaction mixture was then stirred for 1 hour at room temperature. The reaction mixture was concentrated under a reduced pressure, after which the residue thus obtained was distilled under a reduced pressure (74-76° C., 8 mmHg) to obtain the title compound (16 g, 68%).

$^1$H-NMR Spectrum (CDCl$_3$) δ (ppm): 1.29 (12H, s), 2.59 (2H, s).

Manufacturing Example 195-2-2

Sodium cyclopropylmethoxymethyl trifluoroborate

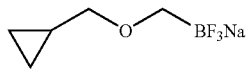

To a mixture of sodium hydride (430 mg, 12 mmol, 66% in oil) and tetrahydrofuran (20 mL) was added cyclopropylmethanol (1.2 mL, 15 mmol) at 0° C., and the reaction mixture was stirred for 30 minutes at room temperature. To the reaction mixture was added 2-(bromomethyl)-4,4,5,5-tetramethyl-1,3,2-dioxaborolane (2.0 g, 9.1 mmol) described in Manufacturing Example 195-2-1 at 0° C., and the reaction mixture was stirred for 1 hour at room temperature, and then for 4 hours at 45° C. The reaction mixture was cooled to 0° C., sodium hydrogenfluoride (2.2 g, 36 mmol) was added, and then water (15 mL) was added dropwise to the reaction mixture at the same temperature. The reaction mixture was raised to room temperature, after which the solvent was evaporated under a reduced pressure. Acetone (100 mL) and methanol (1 mL) were added to the residue thus obtained, which was heated and then gradually cooled to about 40° C., and then filtered. The filtrate was concentrated under a reduced pressure, and the residue was washed with ethyl acetate to obtain the title compound (1.2 g, 75%).

$^1$H-NMR Spectrum (DMSO-d$_6$) δ (ppm): 0.05-0.09 (2H, m), 0.35-0.40 (2H, m), 0.86-0.96 (1H, m), 2.46 (2H, q, J=5.6 Hz), 3.00 (2H, d, J=6.8 Hz).

Example 196

3-(1-(4-Ethoxymethyl-benzyl)-1H-pyrazol-4-yl)-pyridin-2-ylamine

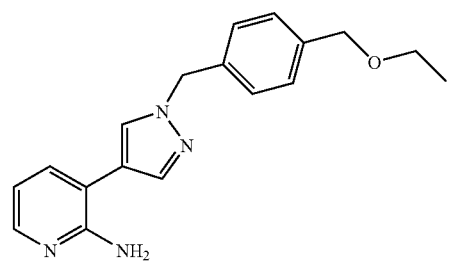

To a mixture of 3-(1-(4-bromo-benzyl)-1H-pyrazol-4-yl)-pyridin-2-ylamine (24 mg, 0.073 mmol) described in Manufacturing Example 195-1-1 and 1,4-dioxane (1.5 mL) were added water (150 μL), cesium carbonate (95 mg, 0.29 mmol), the potassium ethoxymethyl trifluoroborate (18 mg, 0.11 mmol) described in Manufacturing Example 196-1-2, palladium (II) acetate (1.6 mg, 0.0073 mmol), and (±)-2,2'-bis (diphenylphosphino)-1,1'-binaphthyl (4.5 mg, 0.0073 mmol) at room temperature, which was stirred under nitrogen atmosphere for 6 hours at 100° C. The reaction mixture was cooled to room temperature, after which water and ethyl acetate were added and the mixture was filtered through a Celite pad. The organic layer of the filtrate was washed with saturated aqueous sodium chloride, and was concentrated under a reduced pressure. The residue thus obtained was purified by reverse-phase high performance liquid chromatography (using an acetonitrile-water mobile phase containing 0.1% trifluoroacetic acid) to obtain the title compound (5.2 mg, 17%) as a trifluoroacetic acid salt.

MS m/e (ESI) 309.29 (MH$^+$)

The starting material, potassium ethoxymethyl trifluoroborate, was synthesized as follows.

Manufacturing Example 196-1-1

Tributyl-ethoxymethyl-tin

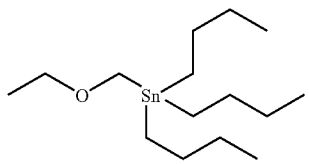

To a mixture of diisopropylamine (2.1 mL, 15 mmol) and tetrahydrofuran (30 mL) was added dropwise n-butyl lithium (2.4 M n-hexane solution, 5.0 mL, 12 mmol) at −78° C., and then the reaction mixture was stirred for 30 minutes. Tributyltin hydride (3.3 mL, 12 mmol) was added dropwise to this mixture at −78° C., and then the reaction mixture was stirred for 40 minutes at 0° C. The reaction mixture was cooled to −78° C., after which ethoxymethyl chloride (1.1 mL, 12 mmol) was added dropwise to the reaction mixture. The reaction mixture was raised to room temperature, diethyl ether and an ammonium chloride aqueous solution were added to the reaction mixture, and the organic layer was separated. The organic layer was washed with saturated aqueous sodium chloride, after which the organic layer was concentrated under a reduced pressure. The residue was purified by neutral silica gel column chromatography (heptane:diethyl ether=30:1) to obtain the title compound (2.8 g, 66%).

$^1$H-NMR Spectrum (CDCl$_3$) δ (ppm): 0.87-0.92 (15H, m), 1.16 (3H, t, J=7.0 Hz), 1.26-1.35 (6H, m), 1.43-1.55 (6H, m), 3.36 (2H, q, J=7.0 Hz), 3.74 (2H, t, J=6.5 Hz).

Manufacturing Example 196-1-2

Potassium Ethoxymethyl Trifluoroborate

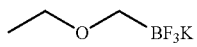

To a mixture of tributyl-ethoxymethyl-tin (1.0 g, 2.9 mmol) described in Manufacturing Example 196-1-1 and tetrahydrofuran (10 mL) was added dropwise n-butyl lithium (1.5 M n-hexane solution, 2.0 mL, 3.2 mmol) at −78° C., and then the reaction mixture was stirred for 30 minutes at the same temperature. To a mixture of triisopropyl borate (0.73 mL, 3.2 mmol) and tetrahydrofuran (10 mL) was added dropwise reaction mixture by cannulation at −78° C. The reaction mixture was stirred for 30 minutes at room temperature. Potassium hydrogenfluoride (1.3 g, 17 mmol) was added at 0° C. to the mixture, and then water (10 mL) was added dropwise to the reaction mixture. The reaction mixture was raised to room temperature, after which the reaction mixture was concentrated under a reduced pressure. The residue thus obtained was washed with diethyl ether (50 mL). Acetone (100 mL) was added to this residue, which was filtered. The filtrate was concentrated under a reduced pressure, and the residue was recrystallized from acetonitrile to obtain the title compound (150 mg, 32%).

$^1$H-NMR Spectrum (DMSO-d$_6$) δ (ppm): 0.99 (3H, t, J=7.0 Hz), 2.42 (2H, q, J=5.6 Hz), 3.18 (2H, q, J=7.0 Hz).

Example 197

3-(1-(4-Cyclobutoxymethyl-benzyl)-1H-pyrazol-4-yl)-pyridin-2-ylamine

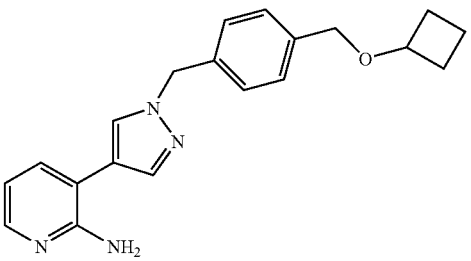

To a mixture of 3-(1-(4-bromo-benzyl)-1H-pyrazol-4-yl)-pyridin-2-ylamine (24 mg, 0.073 mmol) described in Manufacturing Example 195-1-1 and 1,4-dioxane (1.5 mL) were added water (150 μL), cesium carbonate (95 mg, 0.29 mmol), potassium cyclobutoxymethyl trifluoroborate (21 mg, 0.11 mmol) described in Manufacturing Example 197-1-2, palladium (II) acetate (1.6 mg, 0.0073 mmol), and (±)-2,2'-bis(diphenylphosphino)-1,1'-binaphthyl (4.5 mg, 0.0073 mmol) at room temperature, which was stirred under nitrogen atmosphere for 6 hours at 100° C. The reaction mixture was cooled to room temperature, after which water and ethyl acetate were added and the mixture was filtered through a Celite pad. The organic layer of the filtrate was washed with saturated aqueous sodium chloride, and was concentrated under a reduced pressure. The residue thus obtained was purified by reverse-phase high performance liquid chromatography (using an acetonitrile-water mobile phase containing 0.1% trifluoroacetic acid) to obtain the title compound (5.2 mg, 16%) as a trifluoroacetic acid salt.

MS m/e (ESI) 335.19 (MH$^+$)

The starting material, potassium cyclobutoxymethyl trifluoroborate, was synthesized as follows.

Manufacturing Example 197-1-1

Tributyl-cyclobutoxymethyl-tin

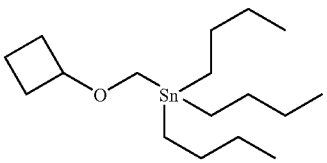

To a mixture of sodium hydride (250 mg, 7.0 mmol, 66% in oil) and tetrahydrofuran (20 mL) were added cyclobutanol (0.55 mL, 7.0 mmol) and N,N-dimethylformamide (20 mL) at 0° C., and then the reaction mixture was stirred for 40 minutes at room temperature. The tributyl-iodomethyl-tin (2.0 g, 4.6 mmol) described in Manufacturing Example 197-2-2 was added dropwise to the reaction mixture at 0° C., and then the reaction mixture was stirred overnight at room temperature. Heptane and water were added to the reaction mixture, and the organic layer was separated. The organic layer was washed and saturated aqueous sodium chloride, and was concentrated under a reduced pressure. The residue was purified by silica gel column chromatography (heptane:ethyl acetate=20:1) to obtain the title compound (1.6 g, 92%).

$^1$H-NMR Spectrum (CDCl$_3$) δ (ppm): 0.81-0.98 (15H, m), 1.26-1.35 (6H, m), 1.43-1.57 (7H, m), 1.65-1.70 (1H, m), 1.80-1.87 (2H, m), 2.14-2.21 (2H, m), 3.57 (2H, dd, J=7.3, 7.0 Hz), 3.68-3.76 (1H, m).

Manufacturing Example 197-1-2

Potassium Cyclobutoxymethyl Trifluoroborate

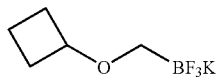

To a mixture of tributyl-cyclobutoxymethyl-tin (1.0 g, 2.7 mmol) described in Manufacturing Example 197-1-1 and tetrahydrofuran (10 mL) was added n-butyl lithium (1.5 M n-hexane solution, 1.7 mL, 2.7 mmol) dropwise at −78° C., and then the reaction mixture was stirred for 60 minutes at the same temperature. A tetrahydrofuran (10 mL) solution of triisopropyl borate (0.80 mL, 3.5 mmol) was added dropwise at to this mixture at −78° C., and then the reaction mixture was stirred for 5 minutes at room temperature. Potassium hydrogenfluoride (1.25 g, 16 mmol) was added to the reaction mixture at 0° C., and then the reaction mixture was stirred for 50 minutes at room temperature. Water (10 mL) was added dropwise to the compound at room temperature, and then the reaction mixture was stirred for further 50 minutes at the same temperature. The reaction mixture was concentrated under a reduced pressure. The residue thus obtained was washed with diethyl ether. Acetone was added to this residue, which was filtered. The filtrate was concentrated under reduced pressure to obtain the title compound (210 mg, 42%).

$^1$H-NMR Spectrum (DMSO-d$_6$) δ (ppm): 1.30-1.42 (1H, m), 1.48-1.58 (1H, m), 1.61-1.73 (2H, m), 1.99-2.08 (2H, m), 2.31 (2H, q, J=5.6 Hz), 3.60 (1H, quin, J=6.8 Hz).

The starting material, tributyl-iodomethyl-tin, was synthesized as follows.

Manufacturing Example 197-2-1

Tributylstannyl-methanol

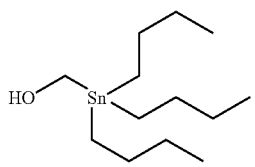

To a mixture of diisopropylamine (62 mL, 0.44 mol) and tetrahydrofuran (1000 mL) were added dropweise n-butyl lithium (2.6 M n-hexane solution, 100 mL, 0.26 mol) and n-butyl lithium (1.6 M n-hexane solution, 95 mL, 0.15 mol) at −78° C., and then the reaction mixture was stirred for 30 minutes. To this mixture was added dropwise tributyltin hydride (100 mL, 0.37 mol) at −78° C., and then the reaction mixture was stirred for 60 minutes at 0° C. The reaction mixture was cooled to −78° C., after which paraformaldehyde (13 g, 0.15 mol) was added to the reaction mixture. The reaction mixture was slowly raised to room temperature, and then the reaction mixture was stirred overnight at room temperature. To the reaction mixture were water, an ammonium chloride aqueous solution, and diethyl ether, and the organic layer was separated. The organic layer was washed first with a saturated sodium hydrogencarbonate aqueous solution and then with saturated aqueous sodium chloride. The organic layer was separated, and was concentrated under a reduced pressure. The residue was purified by neutral silica gel column chromatography (heptane:diethyl ether=4:1) to obtain the title compound (95 g, 80%).

$^1$H-NMR Spectrum (CDCl$_3$) δ (ppm): 0.88-0.94 (15H, m), 1.27-1.36 (6H, m), 1.49-1.55 (6H, m), 4.02 (2H, dd, J=1.8, 6.6 Hz).

Manufacturing Example 197-2-2

Tributyl-iodomethyl-tin

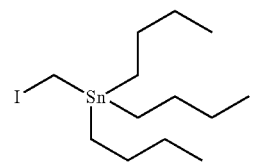

To a mixture of triphenylphosphine (70 g, 0.27 mol) and tetrahydrofuran (500 mL) was added dropwise a mixture of N-iodosuccinimide (60 g, 0.27 mol) and tetrahydrofuran (500 mL) at 0° C., and then the reaction mixture was stirred for 30 minutes at 0° C. To this mixture was added dropwise tributylstannyl-methanol (71 g, 0.22 mol) described in Manufacturing Example 197-2-1 at 0° C., and then the reaction mixture was stirred for 20 minutes at 0° C. The reaction mixture was stirred overnight at room temperature. Diethyl ether and water were added to the reaction mixture, and the organic layer was separated. The organic layer was washed first with a saturated sodium thiosulfate aqueous solution and then with saturated aqueous sodium chloride. The organic layer was separated, and was concentrated under a reduced pressure. Heptane (400 mL) was added to the residue and filtered. The solvent in the filtrate was evaporated under a reduced pressure, and the residue was purified by silica gel column chromatography (heptane) to obtain the title compound (90 g, 94%).

$^1$H-NMR Spectrum (CDCl$_3$) δ (ppm): 0.91 (9H, t, J=7.2 Hz), 0.96-1.00 (6H, m), 1.28-1.37 (6H, m), 1.49-1.56 (6H, m), 1.94 (2H, t, J=8.9 Hz).

Example 198

3-(1-(6-Benzyloxy-pyridin-3-ylmethyl)-1H-pyrazol-4-yl)-pyridin-2,6-diamine

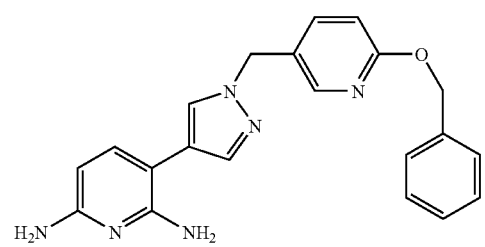

To an N,N-dimethylformamide (5.00 mL) solution of 3-(1H-pyrazol-4-yl)-pyridine-2,6-diamine (30.0 mg, 0.171 mmol) described in Manufacturing Example 36-1-2 was added sodium hydride (7.52 mg, 0.188 mmol, 60% in oil) on an ice bath (0° C.), which was stirred for 30 minutes at room temperature. Thereafter, 2-benzyloxy-5-chloromethyl-pyridine (59.9 mg, 0.257 mmol) described in Manufacturing Example 191-1-2 was added to the mixture, which was stirred for 30 minutes at room temperature. The reaction mixture was partitioned into ethyl acetate and water. The organic layer was washed with water and a saturated sodium chloride aqueous solution, and dried with anhydrous magnesium sulfate, and the solvent was evaporated under a reduced pressure. The residue was purified by NH silica gel column chromatography (ethyl acetate) to obtain the title compound (27.4 mg, 43.0%).

$^1$H-NMR Spectrum (DMSO-$d_6$) δ (ppm): 5.09 (2H, brs), 5.26 (2H, s), 5.34 (2H, s), 5.44 (2H, brs), 5.77 (1H, dd, J=2.8, 8.0 Hz), 6.86 (1H, dd, J=2.0, 8.8 Hz), 7.14-7.16 (1H, m), 7.29-7.44 (5H, m), 7.57 (1H, d, J=2.0 Hz), 7.68-7.71 (1H, m), 7.94 (1H, d, J=1.6 Hz), 8.17 (1H, s).

Example 199

3-(1-(4-Pyridin-2-ylmethoxy)-benzyl)-1H-pyrazol-4-yl)-pyridin-2,6-diamine

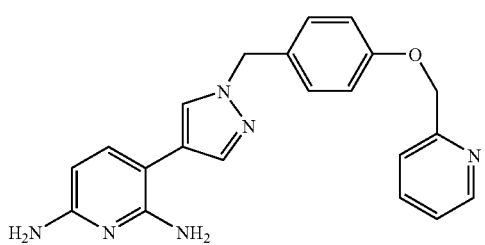

To an N,N-dimethylformamide (5.00 mL) solution of 3-(1H-pyrazol-4-yl)-pyridine-2,6-diamine (30.0 mg, 0.171 mmol) described in Manufacturing Example 36-1-2 was added sodium hydride (7.52 mg, 0.188 mmol, 60% in oil) on an ice bath (0° C.) under nitrogen atmosphere, which was stirred for 30 minutes at room temperature. Thereafter, 2-(4-chloromethyl-phenoxymethyl)-pyridine (59.9 mg, 0.257 mmol) described in Example 192 was added to the above mixture, where was stirred for 30 minutes at room temperature. The reaction mixture was partitioned into ethyl acetate and water at room temperature. The organic layer was washed with water and saturated aqueous sodium chloride and dried over anhydrous magnesium sulfate, and the solvent was evaporated under a reduced pressure. The residue was purified by NH silica gel column chromatography (ethyl acetate: heptane=2:1→ethyl acetate) to obtain the title compound (11.5 mg, 18.1%).

$^1$H-NMR Spectrum (DMSO-$d_6$) δ (ppm): 5.06 (2H, brs), 5.16 (2H, s), 5.21 (2H, s), 5.43 (2H, brs), 5.77 (1H, d, J=8.0 Hz), 6.99 (2H, d, J=8.8 Hz), 7.14 (1H, d, J=8.4 Hz), 7.25 (2H, d, J=8.8 Hz), 7.32-7.35 (1H, m), 7.49 (1H, d, J=7.6 Hz), 7.55 (1H, s), 7.80-7.84 (1H, m), 7.90 (1H, s), 8.56-8.57 (1H, m).

Example 200

3-(1-(6-Phenoxy-pyridin-3-ylmethyl)-1H-pyrazol-4-yl)-pyridin-2,6-diamine

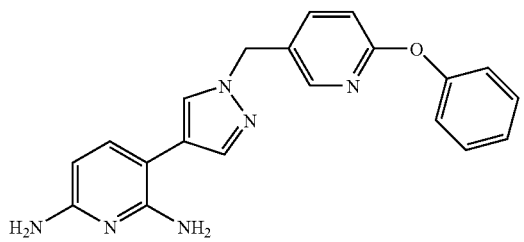

To an N,N-dimethylformamide (5.00 mL) solution of 3-(1H-pyrazol-4-yl)-pyridine-2,6-diamine (30.0 mg, 0.171 mmol) described in Manufacturing Example 36-1-2 was added sodium hydride (7.52 mg, 0.188 mmol, 60% in oil) on an ice bath (0° C.) under nitrogen atmosphere, which was stirred for 10 minutes at room temperature. Thereafter, 5-chloromethyl-2-phenoxy-pyridine (59.9 mg, 0.273 mmol) described in Manufacturing Example 193-1-2 was added to the above mixture, which was stirred for 30 minutes at room temperature. The reaction mixture was partitioned into ethyl acetate and water at room temperature. The organic layer was washed with water and saturated aqueous sodium chloride and dried over anhydrous magnesium sulfate, and the solvent was evaporated under a reduced pressure. The residue was purified by NH silica gel column chromatography (ethyl acetate) to obtain the title compound (15.4 mg, 25.2%).

$^1$H-NMR Spectrum (DMSO-$d_6$) δ (ppm): 5.09 (2H, brs), 5.29 (2H, s), 5.44 (2H, brs), 5.77 (1H, dd, J=0.8, 8.0 Hz), 7.01 (1H, d, J=8.4 Hz), 7.10-7.23 (4H, m), 7.41 (2H, t, J=7.6 Hz), 7.59 (1H, s), 7.79 (1H, dd, J=2.0, 8.4 Hz), 7.96 (1H, s), 8.14 (1H, d, J=2.8 Hz).

Example 201

3-(3-(4-Benzyloxy-benzyl)-isoxazol-5-yl)-pyridine

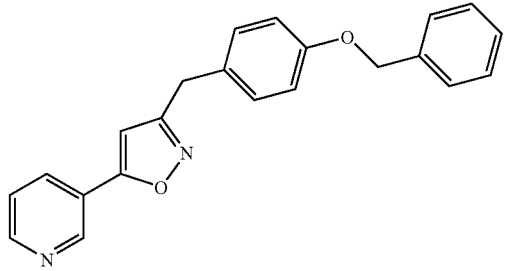

To a tetrahydrofuran (3 mL) solution of 3-ethynylpyridine (50 mg, 0.485 mmol) and (4-benzyloxy-phenyl)-acetohydroximoyl chloride (214 mg, 0.776 mmol) described in Manufacturing Example 1-1-3 was added triethylamine (270 μL, 1.94 mmol), which was stirred for 2.5 hours at room temperature. This mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:4 to 1:2) to obtain the title compound (80 mg, 48%).

¹H-NMR Spectrum (CDCl₃) δ (ppm): 4.02 (2H, s), 5.05 (2H, s), 5.37 (1H, s), 6.93-6.97 (2H, m), 7.19-7.22 (2H, m), 7.30-7.44 (6H, m), 8.04-8.06 (1H, m), 8.63-8.65 (1H, m), 8.95-8.96 (1H, m).

Example 202

3-(3-(4-(Pyridin-2-yloxymethyl)-benzyl)-isoxazol-5-yl)-pyridine

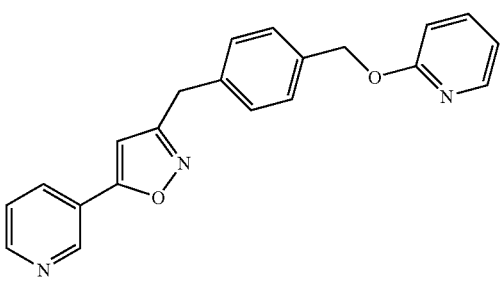

To a tetrahydrofuran (3 mL) solution of 3-ethynylpyridine (10 mg, 0.097 mmol) and (4-(pyridin-2-yloxymethyl)-phenyl)-acetohydroximoyl chloride (42.9 mg, 0.155 mmol) described in Manufacturing Example 2-1-5 was added triethylamine (54.1 μL, 0.388 mmol), which was stirred for 2.5 hours at room temperature. This mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:4 to 1:2, then 1:1) to obtain the title compound (8 mg, 24%).

¹H-NMR Spectrum (CDCl₃) δ (ppm): 4.09 (2H, s), 5.37 (2H, s), 6.38 (1H, s), 6.79-6.81 (1H, m), 6.87-6.90 (1H, m), 7.31 (2H, d, J=8.4 Hz), 7.37-7.40 (1H, m), 7.45 (2H, d, J=8.4 Hz), 7.56-7.61 (1H, m), 8.02-8.05 (1H, m), 8.16-8.18 (1H, m), 8.64-8.65 (1H, m), 8.956-8.959 (1H, m).

Example 203

3-(3-(4-(Pyridin-2-ylmethoxy)-benzyl)-isoxazol-5-yl)-pyridine

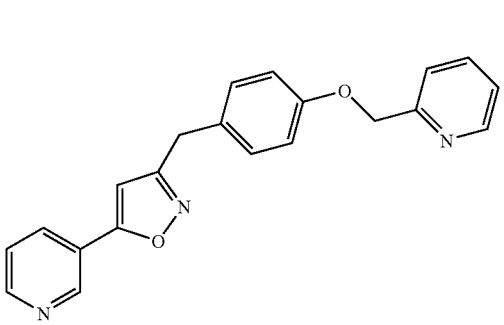

To a tetrahydrofuran (3 mL) solution of 3-ethynylpyridine (50 mg, 0.485 mmol) and (4-(pyridin-2-ylmethoxy)-phenyl)-acetohydroximoyl chloride (215 mg, 0.776 mmol) described in Manufacturing Example 203-1-4 was added triethylamine (270 μL, 1.94 mmol), which was stirred for 2.5 hours at room temperature. This mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:4 to 1:2, then 1:1) to obtain the title compound (71 mg, 43%).

¹H-NMR Spectrum (CDCl₃) δ (ppm): 4.02 (2H, s), 5.20 (2H, s), 6.37 (1H, s), 7.47 (2H, d, J=8.4 Hz), 7.20-7.24 (2H, m), 7.21 (1H, d, J=8.4 Hz), 7.37-7.40 (1H, m), 7.51-7.53 (1H, m), 7.69-7.73 (1H, m), 8.02-8.05 (1H, m), 8.59-8.60 (1H, m), 8.63-8.65 (1H, m), 8.95-8.96 (1H, m).

The starting material, (4-(pyridin-2-ylmethoxy)-phenyl)-acetohydroximoyl chloride, was synthesized as follows.

Manufacturing Example 203-1-1

4-(Pyridin-2-ylmethoxy)-benzaldehyde

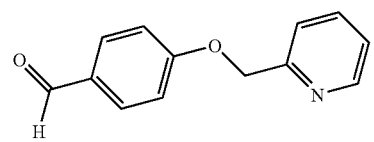

To an N,N-dimethylformamide (250 mL) solution of 4-hydroxybenzaldehyde (20 g, 164 mmol) and 2-picolyl chloride (27 g, 165 mmol) was added potassium carbonate (68 g, 492 mmol), which was stirred for 3 days at room temperature. This mixture was partitioned into ethyl acetate and water. The organic layer was separated, washed with water, dried over anhydrous magnesium sulfate, and filtered. The filtrate was concentrated under a reduced pressure to obtain the title compound (29 g, 83%). The title compound was not purified but used for the next reaction.

¹H-NMR Spectrum (DMSO-d₆) δ (ppm): 5.31 (2H, s), 7.21-7.25 (2H, m), 7.35-7.39 (1H, m), 7.53-7.55 (1H, m), 7.83-7.90 (3H, m), 8.59-8.61 (1H, m), 9.88 (1H, s).

Manufacturing Example 203-1-2

2-(4-((E)-Nitro-vinyl)-phenoxymethyl)-pyridine

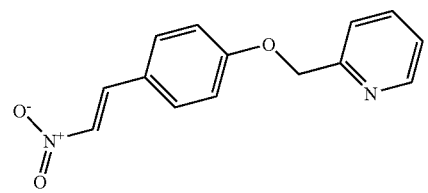

A mixture of 4-(pyridin-2-ylmethoxy)-benzaldehyde (29 g, 136 mmol) described in Manufacturing Example 203-1-1, nitromethane (36.6 mL, 680 mmol), ammonium acetate (21 g, 272 mmol), and acetic acid (300 mL) was stirred for 21 hours at 100° C. This mixture was cooled to room temperature and concentrated under a reduced pressure. The residue was partitioned into ethyl acetate and water. The organic layer was separated, washed with water and saturated aqueous sodium chloride, dried over anhydrous magnesium sulfate, and filtered. The filtrate was concentrated under a reduced pressure to obtain the title compound (33.9 g, 97%).

¹H-NMR Spectrum (CDCl₃) δ (ppm): 5.27 (2H, s), 7.04-7.06 (2H, m), 7.25-7.28 (1H, m), 7.49-7.54 (4H, m), 7.72-7.76 (1H, m), 7.96-7.99 (1H, m), 8.62-8.63 (1H, m).

Manufacturing Example 203-1-3

2-(4-(2-Nitro-ethyl)-phenoxymethyl)-pyridine

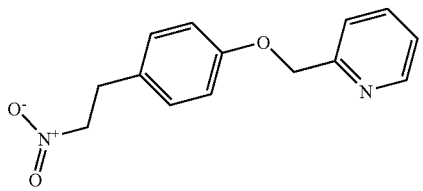

To a solution of 2-(4-((E)-nitro-vinyl)-phenoxymethyl)-pyridine (33.9 g, 132 mmol) described in Manufacturing Example 203-1-2 in acetic acid (34 mL) and dimethyl sulfoxide (576 mL) was added sodium borohydride (7.99 g, 211 mmol) at room temperature while cooling appropriately. This mixture was stirred for 5 hours at room temperature. This mixture was partitioned into ethyl acetate and water. The organic layer was separated, washed with water, dried over anhydrous magnesium sulfate, and filtered. The filtrate was concentrated under a reduced pressure, and the residue was recrystallized from heptane and ethyl acetate to obtain the title compound (6.81 g, 20%).

¹H-NMR Spectrum (CDCl₃) δ (ppm): 3.26-3.30 (2H, m), 4.57-4.61 (2H, m), 5.51 (2H, s), 6.97 (2H, d, J=8.8 Hz), 7.17 (2H, d, J=8.8 Hz), 7.41-7.44 (1H, m), 7.89-7.91 (1H, m), 7.96-8.00 (1H, m), 8.77-8.78 (1H, m).

Manufacturing Example 203-1-4

(4-(Pyridin-2-ylmethoxy)-phenyl)-acetohydroximoyl chloride

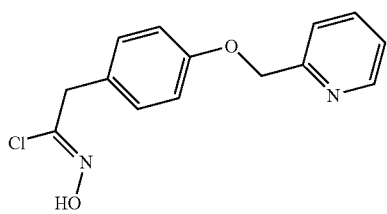

To a methanol (36 mL) solution of 2-(4-(2-nitro-ethyl)-phenoxymethyl)-pyridine (3 g, 11.6 mmol) described in Manufacturing Example 203-1-3 was added lithium methoxide (881 mg, 23.2 mmol), and this mixture was stirred at room temperature for 1 hour. The mixture was concentrated under a reduced pressure, water in the residue was azeotropically distilled with toluene, and that residue was diluted with methylene chloride (46 mL) and tetrahydrofuran (23 mL). The system was cooled to −78° C., after which titanium (IV) tetrachloride (4.08 mL, 37.1 mmol) was added dropwise to this suspension. The mixture was stirred for 1 hour at room temperature. This mixture was cooled to −78° C. and partitioned into ethyl acetate and water. The thin organic layer was separated, washed with saturated aqueous sodium chloride, dried over anhydrous magnesium sulfate, and filtered. The filtrate was concentrated under a reduced pressure to obtain the title compound (1.98 g, 61.7%).

This compound was used in the following reaction without any further purification.

Example 204

3-(3-(2-Fluoro-4-(pyridin-2-yloxymethyl)-benzyl)-isoxazol-5-yl)-pyridin-2-ylamine

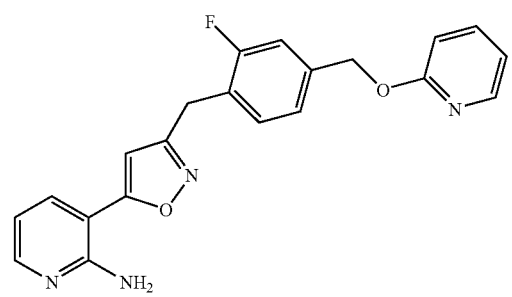

To a tetrahydrofuran (3 mL) solution of the 3-ethynyl-pyridin-2-ylamine (38.4 mg, 0.325 mmol) described in Manufacturing Example 1-2-3 and (2-fluoro-4-(pyridin-2-yloxymethyl)-phenyl)acetohydroximoyl chloride (150 mg, 0.509 mmol) described in Manufacturing Example 204-1-8 was added triethylamine (97.2 µL, 0.697 mmol), which was stirred for 2 hours at 60° C. The mixture was cooled to room temperature and partitioned into ethyl acetate and water. The organic layer was separated, washed with water, dried over anhydrous magnesium sulfate, and filtered. The filtrate was concentrated under a reduced pressure, and the residue was purified by NH silica gel column chromatography (ethyl acetate:heptane=1:4 to 1:2, then 1:1) to obtain the title compound (46 mg, 24%).

¹H-NMR Spectrum (CDCl₃) δ (ppm): 4.09 (2H, s), 5.37 (2H, s), 5.43 (2H, brs), 6.32 (1H, s), 6.70-6.73 (1H, m), 6.80-6.82 (1H, m), 6.88-6.92 (1H, m), 7.19-7.30 (3H, m), 7.58-7.62 (1H, m), 7.70-7.73 (1H, m), 8.13-8.18 (2H, m).

The starting material, (2-fluoro-4-(pyridin-2-yloxymethyl)-phenyl)acetohydroximoyl chloride, was synthesized as follows.

Manufacturing Example 204-1-1

2-(4-Bromo-2-fluoro-phenyl)-[1,3]dioxolane

A mixture of 4-bromo-2-fluorobenzaldehyde (10 g, 49.3 mmol), ethylene glycol (27.5 mL, 493 mmol), camphorsulfonic acid (115 mg, 0.493 mmol), and toluene (250 mL) was stirred for 5 hours under reflux. The mixture was cooled to room temperature and a saturated sodium hydrogencarbonate aqueous solution was added thereto. The organic layer was separated, washed with saturated aqueous sodium chloride, dried over anhydrous magnesium sulfate, and filtered. The filtrate was concentrated under a reduced pressure to obtain the title compound (12.5 g). The title compound was used in the following reaction without any further purification.

$^1$H-NMR Spectrum (CDCl$_3$) δ (ppm): 4.03-4.09 (2H, m), 4.10-4.16 (2H, m), 6.03 (1H, s), 7.25-7.28 (1H, m), 7.30-7.32 (1H, m), 7.40-7.44 (1H, m).

Manufacturing Example 204-1-2

4-[1,3]Dioxolan-2-yl-3-fluoro-benzaldehyde

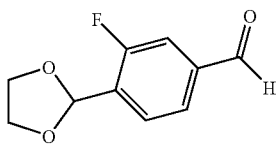

To a tetrahydrofuran (600 mL) solution of 2-(4-bromo-2-fluoro-phenyl)-[1,3]dioxolane (12.5 g, 50.7 mmol) described in Manufacturing Example 204-1-1 was added dropwise n-butyl lithium (28.5 mL, 2.67 M hexane solution, 76.1 mmol) over 15 minute. The system was stirred for 5 minutes at −78° C., after which a THF solution of N-formylmorpholine (5.61 mL, 55.8 mmol) was added to this reaction solution, which was stirred for another 2.5 hours at room temperature. Water and ethyl acetate were added to this mixture, which was partitioned. The organic layer was separated, washed with saturated aqueous sodium chloride, dried over anhydrous magnesium sulfate, and filtered. The filtrate was concentrated under a reduced pressure to obtain the title compound (9.99 g). The title compound was used in the following reaction without any further purification.

Manufacturing Example 204-1-3

(4-[1,3]Dioxolan-2-yl-3-fluoro-phenyl)-methanol

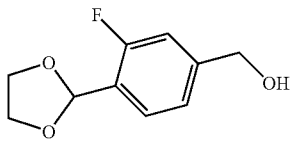

To a methanol solution (200 mL) of 4-[1,3]dioxolan-2-yl-3-fluoro-benzaldehyde (10 g, 50.9 mmol) described in Manufacturing Example 204-1-2 was added sodium borohydride (2.12 g, 56 mmol), which was stirred for 1 hour at room temperature. This mixture was partitioned into ethyl acetate and water. The organic layer was separated, washed with water, dried over anhydrous magnesium sulfate, and filtered. The filtrate was concentrated under a reduced pressure, and the residue was purified by NH silica gel column chromatography (ethyl acetate:heptane=1:1) to obtain the title compound (2.44 g, 24%).

$^1$H-NMR Spectrum (CDCl$_3$): δ (ppm): 3.80 (1H, brs), 4.03-4.17 (4H, m), 6.21 (2H, d, J=6.0 Hz), 6.08 (1H, s), 7.09-7.19 (1H, m), 7.38-7.54 (2H, m).

Manufacturing Example 204-1-4

2-(4-[1,3]Dioxolan-2-yl-3-fluoro-benzyloxy)-pyridine

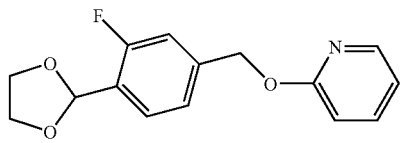

To an N,N-dimethylformamide solution (20 mL) of (4-[1,3]dioxolan-2-yl-3-fluoro-phenyl)-methanol (2.44 g, 12.3 mmol) described in Manufacturing Example 204-1-3 was added sodium hydride (537 mg, 14.8 mmol, 60% in oil), which was cooled to 0° C., after which 2-fluoropyridine (1.27 mL, 14.8 mmol) was added to this suspension, which was stirred for 2 hours at 60° C. The mixture was cooled to room temperature and partitioned into ethyl acetate and water. The organic layer was separated, washed with water, dried over anhydrous magnesium sulfate, and filtered. The filtrate was concentrated under a reduced pressure, and the residue was purified by silica gel column chromatography (ethyl acetate:heptane=1:4) to obtain the title compound (2.17 g, 64%).

$^1$H-NMR Spectrum (CDCl$_3$) δ (ppm): 4.05-4.17 (4H, m), 5.38 (2H, s), 6.09 (1H, s), 6.79-6.83 (1H, m), 6.88-6.91 (1H, m), 7.16-7.25 (2H, m), 7.50-7.54 (1H, m), 7.56-7.62 (1H, m), 8.14-8.16 (1H, m).

Manufacturing Example 204-1-5

2-Fluoro-4-(pyridin-2-yloxymethyl)-benzaldehyde

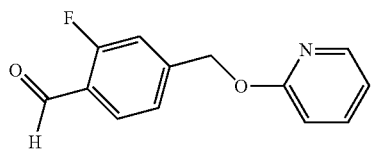

To a solution of 2-(4-[1,3]dioxolan-2-yl-3-fluoro-benzyloxy)-pyridine (2.17 g, 7.88 mmol) described in Manufacturing Example 204-1-4 in methanol (10 mL) and tetrahydrofuran (10 mL) was added 5 N hydrochloric acid (8.43 mL, 8.43 mmol). This solution was stirred for 15 minutes at room temperature. This mixture was cooled to 0° C. and neutralized with a saturated sodium hydrogencarbonate aqueous solution, after which it was extracted with ethyl acetate. The organic layer was separated, washed with water, dried over anhydrous magnesium sulfate, and filtered. The filtrate was concentrated under a reduced pressure to obtain the title compound (1.81 g). The title compound was used in the following reaction without any further purification.

$^1$H-NMR Spectrum (CDCl$_3$) δ (ppm): 5.46 (2H, s), 6.82-6.94 (3H, m), 7.29-7.34 (1H, m), 7.59-7.65 (1H, m), 7.85-7.89 (1H, m), 8.14-8.17 (1H, m), 10.35 (1H, s).

Manufacturing Example 204-1-6

2-(3-Fluoro-4-(E)-2-nitro-vinyl)-benzyloxy)-pyridine

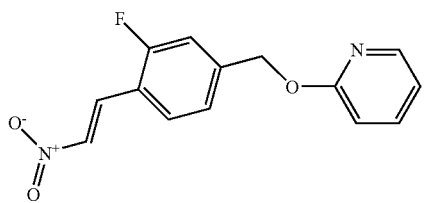

A mixture of 2-fluoro-4-(pyridin-2-yloxymethyl)-benzaldehyde (1.81 g 7.81 mmol) described in Manufacturing Example 204-1-5, nitromethane (2.12 mL, 39.1 mmol), ammonium acetate (1.2 g, 15.6 mmol), and acetic acid (20 mL) was stirred for 5 hours at 100° C. This mixture was cooled to room temperature and concentrated under a reduced pressure. The residue was partitioned into ethyl acetate and water. The organic layer was separated, washed with water, dried over anhydrous magnesium sulfate, and filtered. The residue was purified by silica gel column chromatography (ethyl acetate:heptane=1:4) to obtain the title compound (980 mg, 46%).

$^1$H-NMR Spectrum (CDCl$_3$) δ (ppm): 5.44 (2H, s), 6.84-6.87 (1H, s), 6.91-6.94 (1H, m), 7.24-7.32 (3H, m), 7.48-7.52 (1H, m), 7.61-7.65 (1H, m), 7.71-7.75 (1H, m), 8.14-8.16 (1H, m).

Manufacturing Example 204-1-7

2-(3-Fluoro-4-(2-nitro-ethyl)-benzyloxy)-pyridine

To a solution of 2-(3-fluoro-4-(E)-2-nitro-vinyl)-benzyloxy)-pyridine (980 mg, 3.57 mmol) described in Manufacturing Example 204-1-6 in acetic acid (1 mL) and dimethyl sulfoxide (17 mL) was added sodium borohydride (203 mg, 5.36 mmol) at room temperature while cooling appropriately. This mixture was stirred for 3 hours at room temperature. The mixture was partitioned into ethyl acetate and water. The organic layer was separated, washed with water, dried over anhydrous magnesium sulfate, and filtered. The filtrate was concentrated under a reduced pressure to obtain the title compound (960 mg).

$^1$H-NMR Spectrum (CDCl$_3$) δ (ppm): 3.34-3.39 (2H, m), 4.60-4.67 (2H, m), 5.36 (2H, s), 6.80-6.83 (1H, m), 6.89-6.92 (1H, m), 7.17-7.21 (3H, m), 7.58-7.62 (1H, m), 8.15-8.17 (1H, m).

Manufacturing Example 204-1-8

(2-Fluoro-4-(pyridin-2-yloxymethyl)-phenyl)acetohydroximoyl chloride

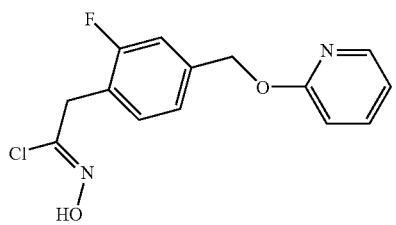

To a methanol (20 mL) solution of 2-(3-fluoro-4-(2-nitroethyl)-benzyloxy)-pyridine (960 mg, 3.47 mmol) described in Manufacturing Example 204-1-7 was added lithium methoxide (264 mg, 6.94 mmol), and this mixture was stirred at room temperature for 1 hour. The mixture was concentrated under a reduced pressure, water in the residue was azeotropically distilled with toluene, and that residue was diluted with methylene chloride (15 mL) and tetrahydrofuran (5 mL). The system was cooled to −78° C., after which titanium (IV) tetrachloride (1.22 mL, 11.1 mmol) was added dropwise to this suspension. The mixture was stirred for 2 hours at 0° C. This mixture was cooled to −78° C. and partitioned into ethyl acetate and water. The organic layer was separated, washed with saturated aqueous sodium chloride, dried over anhydrous magnesium sulfate, and filtered. The filtrate was concentrated under a reduced pressure to obtain the title compound (890 mg). The title compound was used in the following reaction without any further purification.

Example 205

3-(3-(4-Benzylsulfanyl-benzyl)-isoxazol-5-yl)-pyridin-2-ylamine

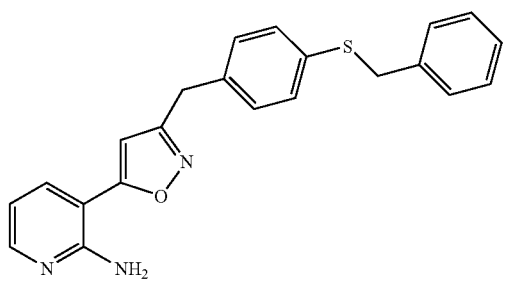

To a tetrahydrofuran (3 mL) solution of 3-ethynyl-pyridin-2-ylamine (50 mg, 0.423 mmol) described in Manufacturing Example 1-2-3 and (4-phenylsulfanylmethyl-phenyl)acetohydroximoyl chloride (197 mg, 0.677 mmol) described in Manufacturing Example 205-1-6 was added triethylamine (147 μL, 1.06 mmol), which was stirred for 18 hours at room temperature. This mixture was cooled to room temperature and partitioned into ethyl acetate and water. The organic layer was separated, washed with water, dried over anhydrous magnesium sulfate, and filtered. The filtrate was concentrated under a reduced pressure, and the residue was purified by NH silica gel column chromatography (ethyl acetate:heptane=1:4 to 1:2) to obtain the title compound (29 mg, 18%).

$^1$H-NMR Spectrum (CDCl$_3$) δ (ppm): 3.98 (2H, s), 4.11 (2H, s), 5.38 (2H, brs), 6.22 (1H, s), 6.70-6.73 (1H, m), 7.16-7.18 (2H, m), 7.22-7.31 (7H, m), 7.69-7.71 (1H, m), 8.14-8.15 (1H, m).

The starting material, (4-benzylphenylsulfanyl-phenyl)acetohydroximoyl chloride, was synthesized as follows.

Manufacturing Example 205-1-1

2-(4-Benzylsulfanyl-phenyl)-[1,3]dioxolane

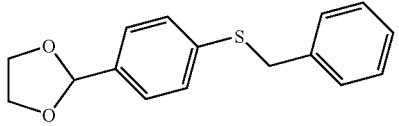

To a tetrahydrofuran (100 mL) solution of 2-(4-bromophenyl)-1,3-dioxane (5 g, 1.677 mmol) was added n-butyl lithium (14.9 mL, 2.64 M hexane solution, 39.2 mmol) at −78° C., which was stirred for 15 minutes. Benzyl disulfide (5.91 g, 24 mmol) was added dropwise to the reaction mixture at −78° C., which was stirred for 5 hours. The mixture was raised to 0° C. and partitioned into ethyl acetate and water. The organic layer was separated, washed with saturated aqueous sodium chloride, dried over anhydrous magnesium sulfate, and filtered. The filtrate was concentrated under a reduced pressure, and the residue was purified by silica gel column chromatography (ethyl acetate:heptane=1:4) to obtain the title compound (1.06 g, 18%).

$^1$H-NMR Spectrum (DMSO-d$_6$) δ (ppm): 3.90-4.04 (4H, m), 4.26 (2H, s), 5.67 (1H, s), 7.23-7.37 (9H, m).

Manufacturing Example 205-1-2

4-Benzylsulfanyl-benzaldehyde

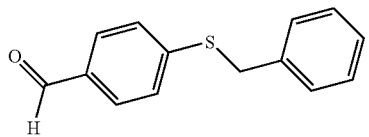

To a solution of 2-(4-benzylsulfanyl-phenyl)-[1,3]dioxolane (1.06 g, 3.89 mmol) described in Manufacturing Example 205-1-1 in methanol (5 mL) and tetrahydrofuran (5 mL) was added 1 N hydrochloric acid (4.16 mL), which was stirred for 30 minutes at room temperature. The mixture was cooled to 0° C. and neutralized with a saturated sodium hydrogencarbonate aqueous solution, and then extracted with ethyl acetate. The organic layer was separated, washed with water, dried over anhydrous magnesium sulfate, and filtered. The filtrate was concentrated under a reduced pressure to obtain the title compound (840 mg). The title compound was used in the following reaction without any further purification.

$^1$H-NMR Spectrum (DMSO-d$_6$) δ (ppm): 4.40 (2H, s), 7.26-7.28 (1H, m), 7.31-7.35 (2H, m), 7.43-7.45 (2H, m), 7.51-7.53 (2H, m), 7.79-7.81 (2H, m), 9.90 (1H, s).

Manufacturing Example 205-1-3

1-Benzylsulfanyl-4-((E)-2-nitro-vinyl)-benzene

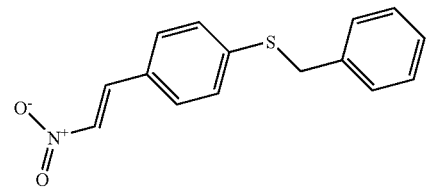

A mixture of 4-benzylsulfanyl-benzaldehyde (840 mg 3.68 mmol) described in Manufacturing Example 205-1-2, nitromethane (997 μL, 18.4 mmol), ammonium acetate (567 mg, 7.36 mmol), and acetic acid (10 mL) was stirred for 2 hours at 100° C. This mixture was cooled to room temperature and concentrated under reduced pressure. The residue was partitioned into ethyl acetate and water. The organic layer was separated, washed with water and saturated aqueous sodium chloride, dried over anhydrous magnesium sulfate, and filtered. The filtrate was concentrated under a reduced pressure to obtain the title compound (950 mg). The title compound was used in the following reaction without any further purification.

$^1$H-NMR Spectrum (DMSO-d$_6$) δ (ppm): 4.37 (2H, s), 7.23-7.34 (3H, m), 7.40-7.45 (4H, m), 7.76-7.81 (2H, m), 8.08 (1H, d, J=14 Hz), 8.20 (1H, d, J=14 Hz).

Manufacturing Example 205-1-4

1-Benzylsulfanyl-4-(2-nitro-ethyl)-benzene

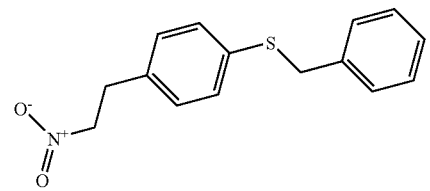

To a solution of 1-benzylsulfanyl-4-((E)-2-nitro-vinyl)-benzene (950 mg, 3.5 mmol) described in Manufacturing Example 205-1-3 in acetic acid (0.6 mL) and dimethyl sulfoxide (10 mL) was added sodium borohydride (212 mg, 5.6 mmol) while the internal temperature was held at 30° C. or lower, which was stirred for 30 minutes at room temperature. The mixture was cooled with ice water, water was added, which was stirred for another 30 minutes. This mixture was partitioned into ethyl acetate and water. The organic layer was separated, washed with water, dried over anhydrous magnesium sulfate, and filtered. The filtrate was concentrated under a reduced pressure to obtain the title compound (936 mg). The title compound was used in the following reaction without any further purification.

¹H-NMR Spectrum (DMSO-d₆) δ (ppm): 3.15-3.18 (2H, m), 4.21 (2H, s), 4.80-4.83 (2H, m), 7.18-7.35 (9H, m).

Manufacturing Example 205-1-5

(4-Benzylphenylsulfanyl-phenyl)acetohydroximoyl chloride

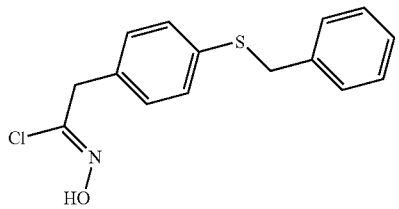

To a methanol solution (12 mL) of 1-benzylsulfanyl-4-(2-nitro-ethyl)-benzene (936 mg, 3.42 mmol) described in Manufacturing Example 205-1-4 was added lithium methoxide (260 mg, 6.84 mmol), which was stirred for 10 minutes at room temperature. The mixture was concentrated under a reduced pressure, water in the residue was azeotropically distilled with toluene, and that residue was diluted with methylene chloride (16 mL) and tetrahydrofuran (8 mL). The system was cooled to −78° C., after which titanium (IV) tetrachloride (825 µL, 7.52 mmol) was added dropwise to this suspension. The mixture was stirred for 1 hour at 0° C. This mixture was cooled to −78° C. and partitioned into ethyl acetate and water. The organic layer was separated, washed with saturated aqueous sodium chloride, dried over anhydrous magnesium sulfate, and filtered. The filtrate was concentrated under a reduced pressure to obtain the title compound (1.01 g). The title compound was used in the following reaction without any further purification.

¹H-NMR Spectrum (DMSO-d₆) δ (ppm): 3.77 (2H, s), 4.23 (2H, s), 7.16-7.38 (9H, m), 11.7 (1H, s).

Example 206

3-(3-(4-Phenylsulfanyl-benzyl)-isoxazol-5-yl)-pyridin-2-ylamine

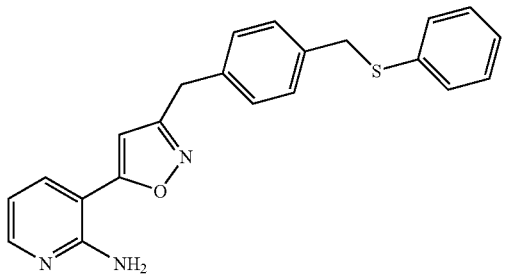

To a tetrahydrofuran (3 mL) solution of 3-ethynyl-pyridin-2-ylamine (50 mg, 0.423 mmol) described in Manufacturing Example 1-2-3 and (4-phenylsulfanylmethyl-phenyl)acetohydroximoyl chloride (197 mg, 0.677 mmol) described in Manufacturing Example 206-1-6 was added triethylamine (147 µL, 1.06 mmol), which was stirred for 18 hours at room temperature. The mixture was cooled to room temperature and partitioned into ethyl acetate and water. The organic layer was separated, washed with water, dried over anhydrous magnesium sulfate, and filtered. The filtrate was concentrated under a reduced pressure, and the residue was purified by NH silica gel column chromatography (ethyl acetate:heptane=1:4 to 1:2) to obtain the title compound (41 mg, 26%).

¹H-NMR Spectrum (CDCl₃) δ (ppm): 4.03 (2H, s), 4.11 (2H, s), 5.42 (2H, brs), 6.23 (1H, s), 6.69-6.73 (1H, m), 7.16-7.35 (9H, m), 7.69-7.71 (1H, m), 8.13-8.15 (1H, m).

The starting material, (4-phenylsulfanylmethyl-phenyl)acetohydroximoyl chloride, was synthesized as follows.

Manufacturing Example 206-1-1

4-Phenylsulfanylmethyl-benzoic acid

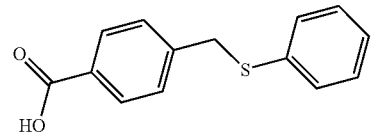

A mixture of 4-(bromomethyl)benzoic acid (10 g, 46.5 mmol), sodium thiophenoxide (6.15 g, 46.5 mmol), and ethanol (100 mL) was stirred for 1.5 hours under reflux. This mixture was cooled to room temperature and acidified with 1 N hydrochloric acid. The precipitate thus produced was collected, dissolved in ethyl acetate, and washed with water. The organic layer was concentrated under a reduced pressure to obtain the title compound (10 g). The title compound was used in the following reaction without any further purification.

¹H-NMR Spectrum (DMSO-d₆) δ (ppm): 4.31 (2H, s), 7.16-7.20 (1H, m), 7.26-7.34 (4H, m), 7.45-7.47 (2H, m), 7.84-7.86 (2H, m), 12.9 (1H, brs).

Manufacturing Example 206-1-2

(4-Phenylsulfanylmethyl-phenyl)-methanol

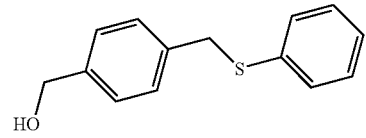

To a suspension of lithium aluminum hydride (1.95 g, 51.3 mmol) in tetrahydrofuran (50 mL) was added dropwise a tetrahydrofuran solution of 4-phenylsulfanylmethyl-benzoic acid (5 g, 20.5 mmol) described in Manufacturing Example 206-1-1, which was stirred for 30 minutes at room temperature. This mixture was cooled with ice water, and water was carefully added. The mixture was filtered through a Celite bed, and the filtrate was combined. The organic layer was separated, washed with water, dried over anhydrous magnesium sulfate, and filtered. The filtrate was concentrated under a reduced pressure to obtain the title compound (2.01 g). The title compound was used in the following reaction without any further purification.

$^1$H-NMR Spectrum (DMSO-d$_6$) δ (ppm): 4.22 (2H, s), 4.45 (2H, d, J=5.6 Hz), 5.13 (1H, t, J=5.6 Hz), 7.16-7.34 (9H, m).

Manufacturing Example 206-1-3

4-Phenylsulfanylmethyl-benzaldehyde

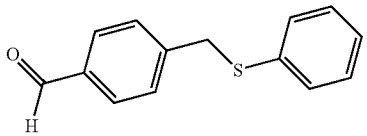

To a chloroform (10 mL) solution of (4-phenylsulfanylmethyl-phenyl)-methanol (1 g, 4.34 mmol) described in Manufacturing Example 206-1-2 was added manganese dioxide (3.77 g, 43.4 mmol), which was stirred for 15 hours at room temperature. The manganese dioxide was removed with a Celite bed, and the filtrate was concentrated under a reduced pressure to obtain the title compound (990 mg). The title compound was used in the following reaction without any further purification.

$^1$H-NMR Spectrum (DMSO-d$_6$) δ (ppm): 4.34 (2H, s), 7.16-7.20 (1H, m), 7.27-7.35 (4H, m), 7.56 (2H, d, J=8.0 Hz), 7.83 (2H, d, J=8.0 Hz), 9.95 (1H, s).

Manufacturing Example 206-1-4

1-((E)-2-Nitro-vinyl)-4-phenylsulfanylmethyl)-benzene

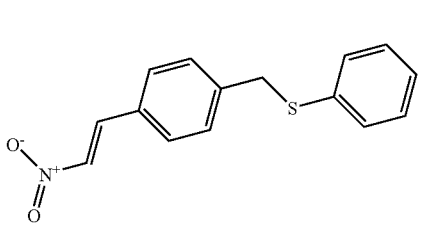

A mixture of 4-phenylsulfanylmethyl-benzaldehyde (990 mg, 4.34 mmol) described in Manufacturing Example 206-1-3, nitromethane (1.18 mL, 21.7 mmol), ammonium acetate (669 mg, 8.68 mmol), and acetic acid (5 mL) was stirred for 6 hours at 100° C. This mixture was cooled to room temperature and partitioned into ethyl acetate and water. The organic layer was separated, washed with water, dried over anhydrous magnesium sulfate, and filtered. The filtrate was concentrated under a reduced pressure to obtain the title compound (1.15 g). The title compound was used in the following reaction without any further purification.

$^1$H-NMR Spectrum (DMSO-d$_6$) δ (ppm): 4.29 (2H, s), 7.16-7.20 (1H, m), 7.27-7.35 (4H, m), 7.44 (2H, d, J=6.8 Hz), 7.77 (2H, d, J=6.8 Hz), 8.08 (1H, d, J=13.6 Hz), 8.18 (1H, d, J=13.6 Hz).

Manufacturing Example 206-1-5

1-(2-Nitro-ethyl)-4-phenylsulfanylmethyl-benzene

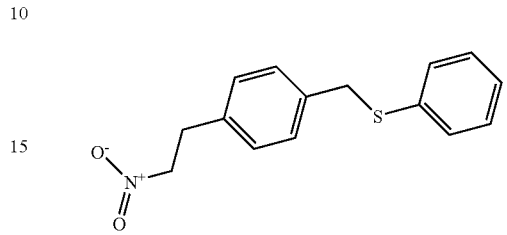

To a solution of 1-((E)-2-nitro-vinyl)-4-phenylsulfanylmethyl)-benzene (1.15 g, 4.24 mmol) described in Manufacturing Example 206-1-4 in acetic acid (0.6 mL) and dimethyl sulfoxide (10 mL) was added sodium borohydride (257 mg, 6.78 mmol), which was stirred for 30 minutes at room temperature. The mixture was cooled with ice water and partitioned into ethyl acetate and water. The organic layer was separated, washed with water, dried over anhydrous magnesium sulfate, and filtered. The filtrate was concentrated under a reduced pressure to obtain the title compound (1.15 g). The title compound was used in the following reaction without any further purification.

$^1$H-NMR Spectrum (DMSO-d$_6$) δ (ppm): 3.17-3.20 (2H, m), 4.21 (2H, s), 4.80-4.84 (2H, m), 7.15-7.20 (3H, m), 7.27-7.33 (6H, m).

Manufacturing Example 206-1-6

(4-Phenylsulfanylmethyl-phenyl)acetohydroximoyl chloride

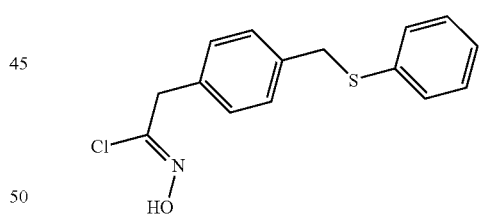

To a methanol solution (12 mL) of 1-(2-nitro-ethyl)-4-phenylsulfanylmethyl-benzene (1.1 g, 4.03 mmol) described in Manufacturing Example 206-1-5 was added lithium methoxide (306 mg, 8.06 mmol), which was stirred for 10 minutes at room temperature. The mixture was concentrated under a reduced pressure, water in the residue was azeotropically distilled with toluene, and that residue was diluted with methylene chloride (16 mL) and tetrahydrofuran (8 mL). The system was cooled to −78° C., after which titanium (IV) tetrachloride (972 μL, 8.87 mmol) was added dropwise to this suspension. The mixture was stirred for 1 hour at 0° C. This mixture was cooled to −78° C. and partitioned into ethyl acetate and water. The organic layer was separated, washed with saturated aqueous sodium chloride, dried over anhydrous magnesium sulfate, and filtered. The filtrate was concentrated under a reduced pressure to obtain the title compound (1.15 g). The title compound was used in the following reaction without any further purification.

¹H-NMR Spectrum (DMSO-d₆) δ (ppm): 3.78 (2H, s), 4.23 (2H, s), 7.15-7.19 (3H, m), 7.27-7.34 (6H, m), 11.7 (1H, s).

Example 207

3-(3-(4-bromo-benzyl)-isoxazol-5-yl)-pyridin-2-ylamine

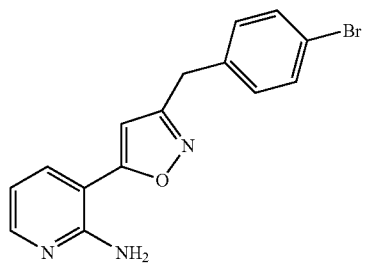

To a tetrahydrofuran (3 mL) solution of 3-ethynyl-pyridin-2-ylamine (50 mg, 0.423 mmol) described in Manufacturing Example 1-2-3 and 4-bromophenyl acetohydroximoyl chloride (168 mg, 0.677 mmol) described in Manufacturing Example 207-1-3 was added triethylamine (147 µL, 1.06 mmol), which was stirred for 15 hours at room temperature. The mixture was partitioned into ethyl acetate and water. The organic layer was separated, washed with water, dried over anhydrous magnesium sulfate, and filtered. The filtrate was concentrated under a reduced pressure, and the residue was purified by NH silica gel column chromatography (ethyl acetate:heptane=1:4 to 1:2) to obtain the title compound (33 mg, 24%).

¹H-NMR Spectrum (CDCl₃) δ (ppm): 4.02 (2H, s), 5.42 (2H, brs), 6.24 (1H, s), 6.70-6.74 (1H, m), 7.16-7.18 (2H, m), 7.44-7.48 (2H, m), 7.70-7.72 (1H, m), 8.14-8.16 (1H, m).

The starting material, 4-bromophenyl acetohydroximoyl chloride, was synthesized as follows.

Manufacturing Example 207-1-1

1-Bromo-4-((E)-2-nitro-vinyl)-benzene

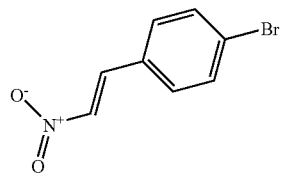

A mixture of 4-bromobenzaldehyde (16.8 g, 91 mmol), nitromethane (24.6 mL, 455 mmol), ammonium acetate (14 g, 182 mmol), and acetic acid (160 mL) was stirred for 4 hours at 100° C. This mixture was cooled to room temperature and poured into water. The precipitate thus produced was collected, washed with water, and dried under a reduced pressure to obtain the title compound (17.4 g). The title compound was used in the following reaction without any further purification.

¹H-NMR Spectrum (DMSO-d₆) δ (ppm): 7.71 (2H, d, J=8.4 Hz), 7.82 (2H, d, J=8.4 Hz), 8.13 (1H, d, J=13.6 Hz), 8.27 (1H, d, J=13.6 Hz).

Manufacturing Example 207-1-2

1-Bromo-4-(2-nitro-ethyl)-benzene

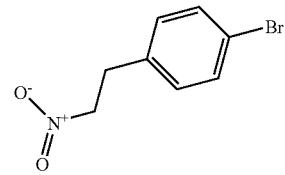

To a solution of 1-bromo-4-((E)-2-nitro-vinyl)-benzene (1 g, 4.37 mmol) described in Manufacturing Example 207-1-1 in acetic acid (0.6 mL) and dimethyl sulfoxide (10 mL) was added sodium borohydride (265 mg, 6.99 mmol), which was stirred for 30 minutes at room temperature. The mixture was cooled with ice water and partitioned into ethyl acetate and water. The organic layer was separated, washed with water, dried over anhydrous magnesium sulfate, and filtered. The filtrate was concentrated under a reduced pressure to obtain the title compound (948 mg). The title compound was used in the following reaction without any further purification.

¹H-NMR Spectrum (DMSO-d₆) δ (ppm): 3.20 (2H, t, J=6.8 Hz), 4.85 (2H, t, J=6.8 Hz), 7.25 (2H, d, J=8.2 Hz), 7.51 (2H, d, J=8.2 Hz).

Manufacturing Example 207-1-3

4-Bromophenyl acetohydroximoyl chloride

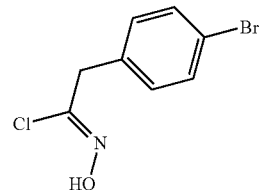

To a methanol solution (12 mL) of 1-bromo-4-(2-nitro-ethyl)-benzene (948 mg, 4.12 mmol) described in Manufacturing Example 207-1-2 was added lithium methoxide (313 mg, 8.24 mmol), which was stirred for 10 minutes at room temperature. The mixture was concentrated under a reduced pressure, water in the residue was azeotropically distilled with toluene, and that residue was diluted with methylene chloride (16 mL) and tetrahydrofuran (8 mL). The system was cooled to −78° C., after which titanium (IV) tetrachloride (994 µL, 9.06 mmol) was added dropwise to this suspension. The mixture was stirred for 1 hour at 0° C. This mixture was cooled to −78° C. and partitioned into ethyl acetate and water. The organic layer was separated, washed with saturated aqueous sodium chloride, dried over anhydrous magnesium sulfate, and filtered. The filtrate was concentrated under a reduced pressure to obtain the title compound (990 mg). The title compound was used in the following reaction without any further purification.

¹H-NMR Spectrum (DMSO-d₆) δ (ppm): 3.82 (2H, s), 7.23 (2H, d, J=8.4 Hz), 7.54 (2H, d, J=8.4 Hz), 11.8 (1H, s).

Example 208

3-(3-(5-(4-Fluoro-benzyl)-furan-2-ylmethyl)-isoxazol-5-yl)-pyridin-2-ylamine

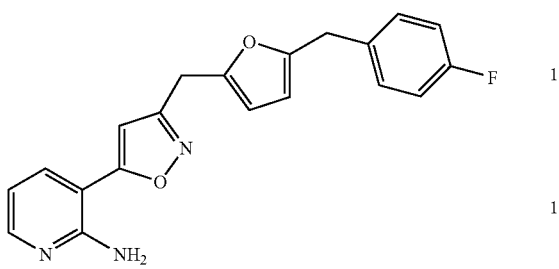

To a tetrahydrofuran (3 mL) solution of 3-ethynyl-pyridin-2-ylamine (50 mg, 0.423 mmol) described in Manufacturing Example 1-2-3 and (5-(4-fluorobenzyl)-furan-2-yl)acetohydroximoyl chloride (181 mg, 0.677 mmol) described in Manufacturing Example 208-1-5 was added triethylamine (147 μL, 1.06 mmol), which was stirred for 19 hours at room temperature. The mixture was partitioned into ethyl acetate and water. The organic layer was separated, washed with water, dried over anhydrous magnesium sulfate, and filtered. The filtrate was concentrated under a reduced pressure, and the residue was purified by NH silica gel column chromatography (ethyl acetate:heptane=1:4 to 1:2) to obtain the title compound (9 mg, 6%).

$^1$H-NMR Spectrum (CDCl$_3$) δ (ppm): 3.91 (2H, s), 4.04 (2H, s), 5.39 (2H, brs), 5.93 (1H, d, J=3.0 Hz), 6.07 (1H, d, J=3.0 Hz), 6.30 (1H, s), 6.72-6.75 (1H, m), 6.96-7.01 (2H, m), 7.17-7.21 (2H, m), 7.66-7.68 (1H, m), 8.15-8.17 (1H, m).

The starting material, (5-(4-fluorobenzyl)-furan-2-yl)acetohydroximoyl chloride, was synthesized as follows.

Manufacturing Example 208-1-1

2-(5-(4-Fluoro-benzyl)-furan-2-yl)-[1,3]dioxolane

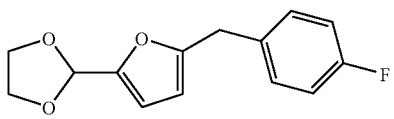

To a tetrahydrofuran (50 mL) solution of 2-(1,3-dioxolan-2-yl-furan (5 g, 35.7 mmol) was added n-butyl lithium (15.6 mL, 2.64 M hexane solution, 41.1 mmol) at −78° C., which was stirred for 1 hour at that temperature. A tetrahydrofuran solution of 4-fluorobenzyl bromide (6.9 g, 36.5 mmol) was added dropwise to this mixture, which was stirred for another hour at −78° C. The mixture was raised to room temperature and partitioned into ethyl acetate and a saturated ammonium chloride aqueous solution. The organic layer was separated, washed with saturated aqueous sodium chloride, dried over anhydrous magnesium sulfate, and filtered. The filtrate was concentrated under a reduced pressure, and the residue was purified by silica gel column chromatography (ethyl acetate:heptane=1:10 to 1:3) to obtain the title compound (4.51 g, 51%).

$^1$H-NMR Spectrum (DMSO-d$_6$) δ (ppm): 3.86-3.90 (2H, m), 3.96-4.00 (4H, m), 5.78 (1H, s), 6.07 (1H, d, J=3.0 Hz), 6.42 (1H, d, J=3.0 Hz), 7.12-7.16 (2H, m), 7.25-7.29 (2H, m).

Example 208-1-2

5-(4-Fluoro-benzyl)-furan-2-carbaldehyde

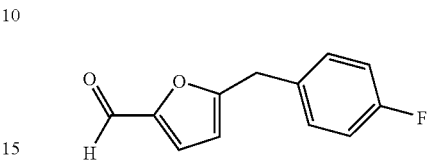

To a methanol (45 mL) solution of 2-(5-(4-fluoro-benzyl)-furan-2-yl)-[1,3]dioxolane (4.51 g, 18.2 mmol) described in Manufacturing Example 208-1-1 was added a solution (45 mL) of citric acid (12.2 g, 63.7 mmol), which was vigorously stirred for 1 hour at room temperature. This mixture was partitioned into ethyl acetate and water. The organic layer was separated, washed with a saturated sodium hydrogencarbonate aqueous solution, dried over anhydrous magnesium sulfate, and filtered. The filtrate was concentrated under a reduced pressure to obtain the title compound (4.51 g, 51%). The title compound was used in the following reaction without any further purification.

$^1$H-NMR Spectrum (DMSO-d$_6$) δ (ppm): 4.11 (2H, s), 6.47-6.48 (1H, m), 7.15-7.19 (2H, m), 7.30-7.34 (2H, m), 7.47-7.48 (1H, m), 9.49 (1H, s).

Manufacturing Example 208-1-3

2-(4-Fluoro-benzyl)-5-((E)-2-nitro-vinyl)-furan

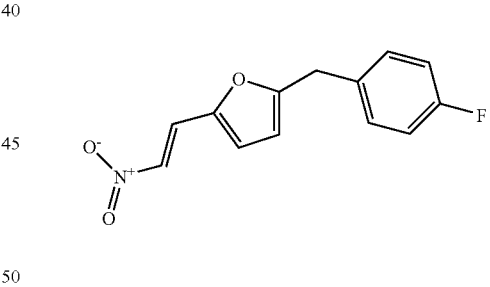

A mixture of 5-(4-fluoro-benzyl)-furan-2-carbaldehyde (1 g, 4.89 mmol) described in Manufacturing Example 208-1-2, nitromethane (1.32 mL, 24.5 mmol), ammonium acetate (754 mg, 9.78 mmol), and acetic acid (10 mL) was stirred for 3 hours at 100° C. This mixture was cooled to room temperature and partitioned into ethyl acetate and water. The organic layer was separated, washed with water, dried over anhydrous magnesium sulfate, and filtered. The filtrate was concentrated under a reduced pressure to obtain the title compound (1.21 g). The title compound was used in the following reaction without any further purification.

$^1$H-NMR Spectrum (DMSO-d$_6$) δ (ppm): 4.08 (2H, s), 6.42 (1H, d, J=3.4 Hz), 7.08-7.19 (2H, m), 7.22 (1H, d, J=3.4 Hz), 7.29-7.37 (2H, m), 7.64 (1H, d, J=13.2 Hz), 7.96 (1H, d, J=13.2 Hz).

Manufacturing Example 208-1-4

2-(4-Fluoro-benzyl)-5-(2-nitro-ethyl)-furan

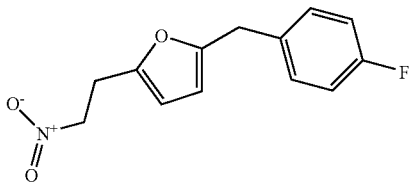

To a solution of 2-(4-fluoro-benzyl)-5-((E)-2-nitro-vinyl)-furan (1.21 g, 4.89 mmol) described in Manufacturing Example 208-1-3 in acetic acid (0.6 mL) and dimethyl sulfoxide (10 mL) was added sodium borohydride (296 mg, 7.82 mmol), which was stirred for 30 minutes at room temperature. The mixture was cooled with ice water and partitioned into ethyl acetate and water. The organic layer was separated, washed with water, dried over anhydrous magnesium sulfate, and filtered. The filtrate was concentrated under a reduced pressure to obtain the title compound (1.14 g). The title compound was used in the following reaction without any further purification.

$^1$H-NMR Spectrum (DMSO-d$_6$) δ (ppm): 3.20-3.24 (2H, m), 3.91 (2H, s), 4.77-4.80 (2H, m), 6.00 (1H, d, J=3.0 Hz), 6.10 (1H, d, J=3.0 Hz), 7.08-7.15 (2H, m), 7.23-7.28 (2H, m).

Manufacturing Example 208-1-5

(5-(4-Fluoro-benzyl)-furan-2-yl)acetohydroximoyl chloride

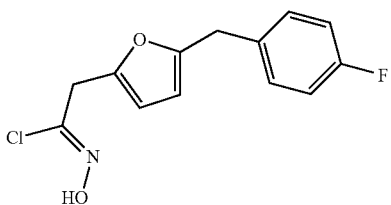

To a methanol solution (12 mL) of 2-(4-fluoro-benzyl)-5-(2-nitro-ethyl)-furan (1.14 g, 4.57 mmol) described in Manufacturing Example 208-1-4 was added lithium methoxide (347 mg, 9.14 mmol), which was stirred for 10 minutes at room temperature. The mixture was concentrated under a reduced pressure, water in the residue was azeotropically distilled with toluene, and that residue was diluted with methylene chloride (16 mL) and tetrahydrofuran (8 mL). The system was cooled to −78° C., after which titanium (IV) tetrachloride (1.1 mL, 10.1 mmol) was added dropwise to this suspension. The mixture was stirred for 1 hour at 0° C. This mixture was cooled to −78° C. and partitioned into ethyl acetate and water. The organic layer was separated, washed with saturated aqueous sodium chloride, dried over anhydrous magnesium sulfate, and filtered. The filtrate was concentrated under a reduced pressure to obtain the title compound (940 mg). The title compound was used in the following reaction without any further purification.

$^1$H-NMR Spectrum (DMSO-d$_6$) δ (ppm): 3.82 (2H, s), 3.93 (2H, s), 6.03 (1H, d, J=3.0 Hz), 6.20 (1H, d, J=3.0 Hz), 7.11-7.15 (2H, m), 7.23-7.27 (2H, m), 11.8 (1H, s).

Example 209

3-(3-(4-(Pyridin-2-yloxy)-benzyl)-isoxazol-5-yl)-pyridin-2-ylamine

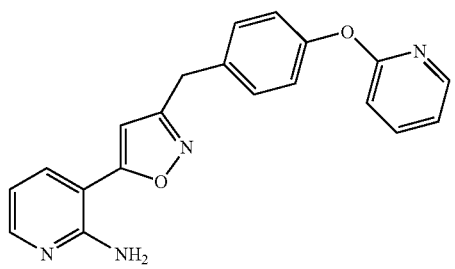

To a tetrahydrofuran (5 mL) solution of 3-ethynyl-pyridin-2-ylamine (45 mg, 0.38 mmol) described in Manufacturing Example 1-2-3 and (4-(pyridin-2-yloxy)benzene)-acetohydroximoyl chloride (200 mg, 0.76 mmol) described in Manufacturing Example 209-1-4 was added triethylamine (139 mg, 1.4 mmol), which was stirred for 10 minutes at 60° C. The reaction solution was cooled to room temperature, NH silica gel was added, and the solvent was evaporated under a reduced pressure. The crude product that had adsorbed to the NH silica gel was purified by NH silica gel column chromatography (heptane:ethyl acetate=2:1, 1:1) to obtain the title compound (40 mg, 30%).

$^1$H-NMR Spectrum (DMSO-d$_6$) δ (ppm): 4.05 (2H, s), 6.28 (2H, brs), 6.68-6.72 (1H, m), 6.87 (1H, s), 7.00-7.03 (1H, m), 7.06-7.14 (3H, m), 7.37 (2H, d, J=8.4 Hz), 7.81-87 (1H, m), 7.87-7.91 (1H, m), 8.08-8.11 (1H, m), 8.11-8.14 (1H, m).

The starting material, (4-(pyridin-2-yloxy)benzene)-acetohydroximoyl chloride, was synthesized as follows.

Manufacturing Example 209-1-1

4-(Pyridin-2-yloxy)-benzaldehyde

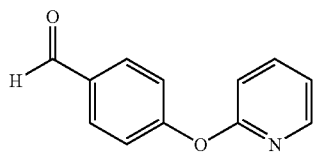

To an N,N-dimethylformamide solution (100 mL) of 4-hydroxybenzaldehyde (10 g, 82 mmol) and 2-fluoropyridine (8.0 g, 82 mmol) was added sodium hydride (3.3 g, 82 mmol, 60% in oil), which was stirred for 30 minutes at 120° C., then for 45 minutes at 140° C., and then for 2 hours at 160° C. The mixture was cooled to room temperature and partitioned into ethyl acetate and water. The organic layer was separated, washed with water (three times), and filtered. The filtrate was concentrated under a reduced pressure, and the residue was purified by silica gel column chromatography (heptane:ethyl acetate=4:1) to obtain the title compound (9.3 g, 57%).

¹H-NMR Spectrum (DMSO-d₆) δ (ppm): 7.15-7.20 (1H, m), 7.20-7.25 (1H, m), 7.33 (2H, d, J=8.0 Hz), 7.40-8.00 (3H, m), 8.20-8.24 (1H, m), 9.98 (1H, s).

Manufacturing Example 209-1-2

2-(4-((E)-2-Nitro-vinyl)-phenoxy)-pyridine

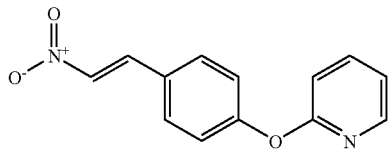

A mixture of 4-(pyridin-2-yloxy)-benzaldehyde (9.3 g, 47 mmol) described in Manufacturing Example 209-1-1, nitromethane (14 g, 230 mmol), ammonium acetate (11 g, 140 mmol), and acetic acid (50 mL) was stirred for 1 hour and 30 minutes at 100° C. This mixture was cooled to room temperature, and water was added to precipitate a solid. The solid was filtered to obtain the title compound (9.9 g, 87%).

¹H-NMR Spectrum (DMSO-d₆) δ (ppm): 7.11-7.14 (1H, m), 7.18-7.25 (3H, m), 7.89-7.94 (3H, m), 8.13-8.24 (3H, m).

Manufacturing Example 209-1-3

2-(4-(2-Nitro-ethyl)-phenoxy)-pyridine

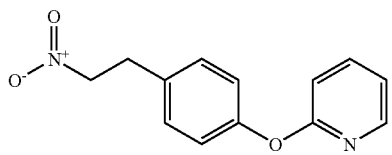

To a solution of 2-(4-((E)-2-nitro-vinyl)-phenoxy)-pyridine (9.9 g, 41 mmol) described in Manufacturing Example 209-1-2, acetic acid (2.5 g) and dimethyl sulfoxide (60 mL) was added sodium borohydride (770 mg, 20 mmol) while the temperature was held at 30° C. or lower, which was stirred for 15 minutes at room temperature. This reaction solution was partitioned into ethyl acetate and water while the temperature was held at 30° C. or lower. The organic layer was separated and concentrated under reduced pressure. The residue was purified by NH silica gel column chromatography (heptane:ethyl acetate=3:1) to obtain the title compound (4.5 g, 45%).

¹H-NMR Spectrum (DMSO-d₆) δ (ppm): 3.24 (2H, t, J=7.2 Hz), 4.87 (2H, t, J=7.2 Hz), 6.99-7.20 (1H, m), 7.07 (2H, d, J=8.0 Hz), 7.09-7.14 (1H, m), 7.31 (2H, d, J=8.0 Hz), 7.81-7.86 (1H, m), 8.12-8.16 (1H, m).

Manufacturing Example 209-1-4

(4-(Pyridin-2-yloxy)benzene)-acetohydroximoyl chloride

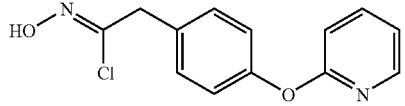

To a methanol solution (30 mL) of 2-(4-(2-nitro-ethyl)-phenoxy)-pyridine (2.0 g, 8.2 mmol) described in Manufacturing Example 209-1-3 was added lithium methoxide (470 mg, 12 mmol), and this mixture was concentrated under a reduced pressure. Toluene was added to the residue, and the solvent was evaporated under a reduced pressure. To a solution of this residue in methylene chloride (40 mL) and tetrahydrofuran (20 mL) was added titanium (IV) tetrachloride (2.3 mL, 21 mmol) while stirring at −76° C. This suspension was stirred for 15 minutes at 0° C., and then for another 20 minutes at room temperature. The mixture was poured into ice water and stirred for 30 minutes. Ethyl acetate was added, and the organic layer was separated, washed with aqueous sodium chloride (one time), dried over anhydrous magnesium sulfate, and filtered. The filtrate was concentrated under a reduced pressure to obtain the title compound (2.1 g, 98%).

¹H-NMR Spectrum (DMSO-d₆) δ (ppm): 3.84 (2H, s), 7.01-7.05 (1H, m), 7.07-7.15 (3H, m), 7.29 (2H, d, J=8.0 Hz), 7.82-7.88 (1H, m), 8.13-8.16 (1H, m), 11.75 (1H, s).

Example 210

3-(3-(6-Benzyl-pyridin-3-ylmethyl)-isoxazol-5-yl)-pyridin-2-ylamine

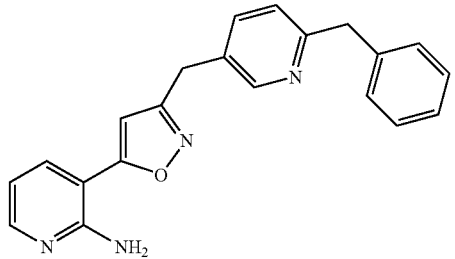

A mixture of 3-ethynyl-pyridin-2-ylamine (30 mg, 0.25 mmol) described in Manufacturing Example 1-2-3, 2-(6-benzyl-pyridin-3-yl)-acetohydroximoyl chloride (88 mg, 0.34 mmol) described in Manufacturing Example 210-1-7, triethylamine (77 mg, 0.76 mmol), and tetrahydrofuran (5 mL) was stirred for 25 minutes at 50° C. This reaction solution was partitioned into ethyl acetate and water. The organic layer was separated and concentrated under a reduced pressure. The residue was purified by NH silica gel column chromatography (heptane:ethyl acetate=2:1, 1:1, ethyl acetate) to obtain the title compound (4.6 mg, 5.3%).

¹H-NMR Spectrum (DMSO-d₆) δ (ppm): 4.03 (2H, s), 4.06 (2H, s), 6.26 (2H, brs), 6.69 (1H, dd, J=4.8, 7.6 Hz), 6.84

(1H, s), 7.15-7.22 (1H, m), 7.22-7.30 (5H, m), 7.65 (1H, dd, J=2.0, 8.0 Hz), 7.86 (1H, dd, J=2.0, 8.0 Hz), 8.08 (1H, dd, J=2.4, 4.8 Hz), 8.48 (1H, d, J=2.4 Hz).

The starting material, (6-benzyl-pyridin-3-yl)-acetohydroximoyl chloride, was synthesized as follows.

Manufacturing Example 210-1-1

6-Bromo-pyridine-3-carbaldehyde

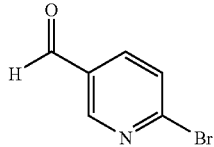

To a diethyl ether (500 mL) solution of 2,5-dibromopyridine (25 g, 110 mmol) was added dropwise n-butyl lithium (2.67 M n-hexane solution, 45 mL, 120 mmol) at −76° C., which was stirred for 25 minutes. To this solution was added dropwise N,N-dimethylformamide (9.0 mL, 120 mmol) at −76° C. Upon completion of this addition, the reaction solution was gradually cooled to room temperature. This mixture was partitioned into ethyl acetate and water. The organic layer was separated and concentrated under a reduced pressure. The residue was purified by silica gel column chromatography (heptane:ethyl acetate=8:1) to obtain the title compound (8.0 g, 41%).

$^1$H-NMR Spectrum (DMSO-$d_6$) δ (ppm): 7.89-7.92 (1H, m), 8.15-8.19 (1H, m), 8.89-8.92 (1H, m), 10.09 (1H, s).

Manufacturing Example 210-1-2

2-Bromo-5-[1,3]dioxolan-2-yl-pyridine

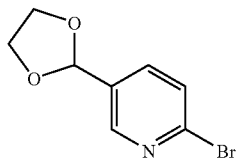

A mixture of 6-bromo-pyridine-3-carbaldehyde (8.0 g, 43 mmol) described in Manufacturing Example 210-1-1, ethylene glycol (5.3 g, 86 mmol), p-toluenesulfonic acid (820 mg, 4.3 mmol), and toluene (110 mL) was stirred for 40 minutes under reflux. (The water produced in this reaction was removed with a Dean-Stark trap.) The reaction solution was concentrated under a reduced pressure, and the residue was partitioned into ethyl acetate and water. The organic layer was separated and passed through a glass filter provided with NH silica gel (eluted with ethyl acetate). The eluate was concentrated under a reduced pressure, and the residue was purified by silica gel column chromatography (heptane:ethyl acetate=8:1) to obtain the title compound (5.8 g, 59%).

$^1$H-NMR Spectrum (DMSO-$d_6$) δ (ppm): 3.93-4.11 (4H, m), 5.84 (1H, s), 7.68-7.72 (1H, m), 7.77-7.82 (1H, m), 8.44-8.47 (1H, m).

Manufacturing Example 210-1-3

2-Benzyl-5-[1,3]dioxolan-2-yl-pyridine

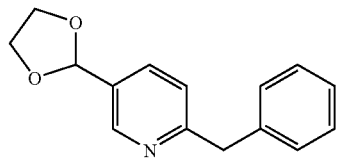

To a suspension of zinc (5.0 g, 77 mmol, highly reactive Rieke metal, 100 mL tetrahydrofuran suspension) and tetrahydrofuran (300 mL) was added dropwise benzyl bromide (7.9 mL, 66 mmol) at 0° C., which was stirred for 4 hours at the same temperature. To this suspension were added bis(triphenylphosphine)nickel (II) chloride (5.8 g, 8.8 mmol) and 2-bromo-5-[1,3]dioxolan-2-yl-pyridine (11 g, 49 mmol) described in Manufacturing Example 210-1-2, which was stirred for another 2 hours at room temperature. The reaction solution was partitioned into ethyl acetate and an ammonium chloride aqueous solution. The organic layer was separated and concentrated under a reduced pressure. The residue was purified by silica gel column chromatography (heptane:ethyl acetate=2:1, 1:1) to obtain the title compound (7.3 g, 62%).

$^1$H-NMR Spectrum (DMSO-$d_6$) δ (ppm): 3.92-4.06 (4H, m), 4.10 (2H, s), 5.78 (1H, s), 7.16-7.22 (1H, m), 7.25-7.32 (5H, m), 7.74 (1H, dd, J=2.0, 8.0 Hz), 8.55 (1H, d, J=2.0 Hz).

Manufacturing Example 210-1-4

6-Benzyl-pyridine-3-carbaldehyde

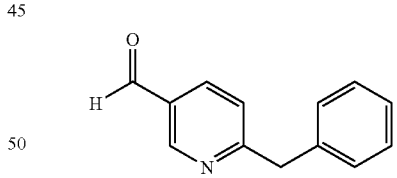

2-Benzyl-5-[1,3]dioxolan-2-yl-pyridine (7.3 g, 30 mmol) described in Manufacturing Example 210-1-3 and 2 N hydrochloric acid (100 mL) were stirred for 55 minutes at 100° C. The reaction solution was cooled to room temperature and partitioned into ethyl acetate and a 5 N sodium hydroxide solution (40 mL). The organic layer was separated, dried over anhydrous magnesium sulfate, and filtered.

The filtrate was concentrated under a reduced pressure to obtain the title compound (4.7 g, 79%).

$^1$H-NMR Spectrum (DMSO-$d_6$) δ (ppm): 4.20 (2H, s), 7.18-7.25 (1H, m), 7.26-7.32 (4H, m), 7.50 (1H, d, J=8.0 Hz), 8.16 (1H, dd, J=2.0, 8.0 Hz), 8.97-9.01 (1H, m), 10.06 (1H, s).

Manufacturing Example 210-1-5

2-Benzyl-5-((E)-2-nitro-vinyl)-pyridine

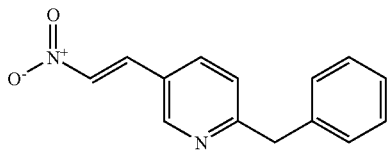

A mixture of 6-benzyl-pyridine-3-carbaldehyde (4.7 g, 24 mmol) described in Manufacturing Example 210-1-4, nitromethane (7.3 g, 120 mmol), ammonium acetate (5.6 g, 72 mmol), and acetic acid (40 mL) was stirred for 90 minutes at 100° C. The reaction solution was partitioned into ethyl acetate and water. The organic layer was washed with saturated aqueous sodium bicarbonate and concentrated under a reduced pressure. The residue was purified by silica gel column chromatography (heptane:ethyl acetate=2:1) to obtain the title compound (1.2 g, 21%).

$^1$H-NMR Spectrum (DMSO-$d_6$) δ (ppm): 4.11 (2H, s), 7.14-7.21 (1H, m), 7.23-7.29 (4H, m), 7.38 (1H, d, J=8.0 Hz), 8.12 (1H, d, J=13.6 Hz), 8.18 (1H, dd, J=2.0, 8.0 Hz), 8.26 (1H, d, J=13.6 Hz), 8.87 (1H, d, J=2.0 Hz).

Manufacturing Example 210-1-6

2-Benzyl-5-(2-nitro-ethyl)-pyridine

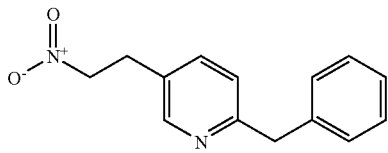

To a mixture of 2-benzyl-5-((E)-2-nitro-vinyl)-pyridine (1.2 g, 5.0 mmol) described in Manufacturing Example 210-1-5, acetic acid (300 mg, 5.0 mmol), and dimethyl sulfoxide (10 mL) was added sodium borohydride (94 mg, 2.5 mmol), which was stirred for 10 minutes at room temperature. The reaction solution was partitioned into ethyl acetate and water. The organic layer was separated and passed through a glass filter provided with NH silica gel (eluted with ethyl acetate). The eluate was concentrated under reduced pressure, and the residue was purified by silica gel column chromatography (heptane:ethyl acetate=2:1) to obtain the title compound (260 mg, 22%).

$^1$H-NMR Spectrum (DMSO-$d_6$) δ (ppm): 3.19 (2H, t, J=6.8 Hz), 4.04 (2H, s), 4.86 (2H, t, J=6.8 Hz), 7.16-7.30 (6H, m), 7.62 (1H, dd, J=2.4, 8.0 Hz), 8.39 (1H, d, J=2.4 Hz).

Manufacturing Example 210-1-7

(6-Benzyl-pyridin-3-yl)-acetohydroximoyl chloride

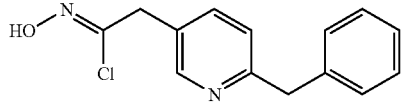

To 2-benzyl-5-(2-nitro-ethyl)-pyridine (260 mg, 1.1 mmol) described in Manufacturing Example 210-1-6 and methanol (5 mL) was added lithium methoxide (81 mg, 2.1 mmol), which was concentrated under a reduced pressure. Titanium (IV) tetrachloride (0.38 mL, 3.4 mmol) was added dropwise at −76° C. to a suspension of the residue in methylene chloride (5 mL) and tetrahydrofuran (2.5 mL), which was stirred for 20 minutes at room temperature. This reaction solution was added to ice water and extracted with ethyl acetate. The aqueous layer was extracted with ethyl acetate again (four times). The organic layers were combined, washed with aqueous sodium chloride (one time), dried over anhydrous magnesium sulfate, and filtered. The filtrate was concentrated under a reduced pressure, and tetrahydrofuran was added to the residue. The insolubles thus produced were filtered out. The filtrate was concentrated under a reduced pressure to obtain the title compound (180 mg, 63%).

$^1$H-NMR Spectrum (DMSO-$d_6$) δ (ppm): 3.83 (2H, s), 4.07 (2H, s), 7.17-7.22 (1H, m), 7.25-7.30 (5H, m), 7.60 (1H, dd, J=2.0, 8.0 Hz), 8.39 (1H, d, J=2.0 Hz), 11.77 (1H, s).

Example 211

3-(3-(2-Fluoro-4-(pyridin-2-yloxymethyl)-benzyl)-isoxazol-5-yl)-pyridin-2,6-diamine

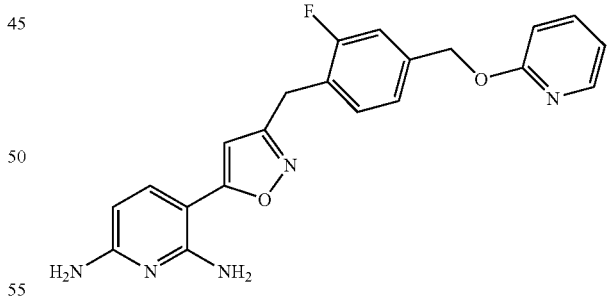

To a tetrahydrofuran (3 mL) solution of 3-ethynyl-pyridine-2,6-diamine (43.2 mg, 0.325 mmol) described in Manufacturing Example 13-1-3 and (2-fluoro-4-(pyridin-2-yloxymethyl)-phenyl)acetohydroximoyl chloride (150 mg, 0.509 mmol) described in Manufacturing Example 204-1-8 was added triethylamine (97.2 µL, 0.697 mmol), which was stirred for 2 hours at room temperature. The mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:1, then ethyl acetate) to obtain the title compound (73 mg, 37%).

$^1$H-NMR Spectrum (CDCl$_3$) δ (ppm): 4.05 (2H, s), 4.49 (2H, brs), 5.26 (2H, brs), 5.37 (2H, s), 5.91-5.94 (1H, m), 6.06 (1H, s), 6.81-6.83 (1H, m), 6.89-6.92 (1H, m), 7.18-7.29 (3H, m), 7.48-7.51 (1H, m), 7.58-7.62 (1H, m), 8.16-8.18 (1H, m).

Example 212

3-(4-(5-(2,6-Diamino-pyridin-3-yl)-isoxazol-3-ylmethyl)-phenoxymethyl)-benzonitrile

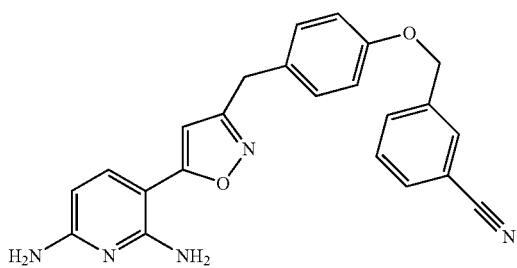

To a methanol (6.3 mL) solution of 4-(5-(2,6-diamino-pyridin-3-yl)-isoxazol-3-ylmethyl)-phenol (100 mg, 0.36 mmol) described in Manufacturing Example 18-1-1 was added a 2 N sodium hydroxide aqueous solution (180 μL, 0.36 mmol). This mixture was concentrated under a reduced pressure. N,N-dimethylformamide (1.3 mL) and 3-bromomethyl-benzonitrile (58 mg, 0.29 mmol) were added to the residue, which was stirred for 15 minutes at 60° C. This reaction solution was partitioned into ethyl acetate and water. The organic layer was separated and concentrated under reduced pressure. The residue was purified by NH silica gel column chromatography (heptane:ethyl acetate=1:2, then ethyl acetate) to obtain the title compound (24 mg, 17%).

$^1$H-NMR Spectrum (DMSO-d$_6$) δ (ppm): 3.88 (2H, s), 5.14 (2H, s), 5.79 (2H, brs), 5.82 (1H, d, J=8.4 Hz), 6.11 (2H, brs), 6.34 (1H, s), 6.98 (2H, d, J=8.4 Hz), 7.23 (2H, d, J=8.4 Hz), 7.50 (1H, d, J=8.4 Hz), 7.61 (1H, dd, J=8.0, 8.0 Hz), 7.76-7.82 (2H, m), 7.91 (1H, s).

Example 213

3-(4-(5-(2,6-Diamino-pyridin-3-yl)-isoxazol-3-ylmethyl)-phenoxymethyl)-benzoic acid methyl ester

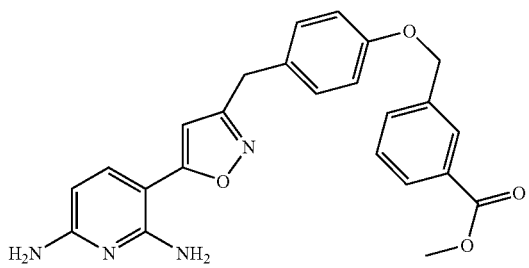

The title compound (48 mg, 16%) was obtained according to the methods similar to those of Example 212, using 4-(5-(2,6-diamino-pyridin-3-yl)-isoxazol-3-ylmethyl)-phenol (200 mg, 0.71 mmol) described in Manufacturing Example 18-1-1 and 3-bromomethyl-benzoic acid methyl ester (160 mg, 0.71 mmol).

$^1$H-NMR Spectrum (DMSO-d$_6$) δ (ppm): 3.86 (3H, s), 3.88 (2H, s), 5.17 (2H, s), 5.79 (2H, brs), 5.82 (1H, d, J=8.4 Hz), 6.11 (2H, brs), 6.34 (1H, s), 6.97 (2H, d, J=8.4 Hz), 7.22 (2H, d, J=8.4 Hz), 7.50 (1H, d, J=8.4 Hz), 7.55 (1H, dd, J=8.0, 8.0 Hz), 7.71 (1H, d, J=8.0 Hz), 7.91 (1H, d, J=8.0 Hz), 8.03 (1H, s).

Example 214

3-(3-(4-(3-Ethynyl-benzyloxy)-benzyl)-isoxazol-5-yl)-pyridin-2,6-diamine

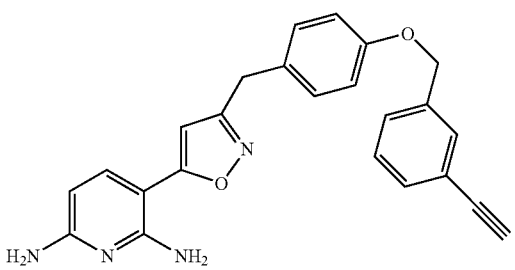

To a tetrahydrofuran (10 mL) solution of 4-(5-(2,6-di-amino-pyridin-3-yl)-isoxazol-3-ylmethyl)-phenol (150 mg, 0.53 mmol) described in Manufacturing Example 18-1-1, (3-ethynyl-phenyl)-methanol (91 mg, 0.69 mmol) described in Manufacturing Example 214-1-2, and triphenylphosphine (180 mg, 0.69 mmol) was added diethyl azodicarboxylate (300 mg, 0.69 mmol, 40% toluene solution), which was stirred for 30 minutes at room temperature. NH silica gel was added to the reaction solution, and the solvent was evaporated under a reduced pressure. The crude product that had adsorbed to the NH silica gel was purified by NH silica gel column chromatography (heptane:ethyl acetate=2:1, then 1:1, then ethyl acetate) to obtain the title compound (110 mg, 51%).

$^1$H-NMR Spectrum (DMSO-d$_6$) δ (ppm): 3.88 (2H, s), 4.20 (1H, s), 5.09 (2H, s), 5.79 (2H, brs), 5.82 (1H, d, J=8.4 Hz), 6.10 (2H, brs), 6.34 (1H, s), 6.96 (2H, d, J=8.8 Hz), 7.22 (2H, d, J=8.8 Hz), 7.38-7.54 (5H, m).

The starting material, (3-ethynyl-phenyl)-methanol, was synthesized as follows.

Manufacturing Example 214-1-1

1-Bromo-3-methoxymethoxymethyl-benzene

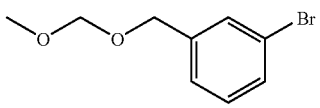

To a tetrahydrofuran (100 mL) solution of 3-bromobenzyl alcohol (10 g, 54 mmol) was added sodium hydride (2.3 g, 98 mmol, 60% in oil) at room temperature. Then, chloromethyl methyl ether (5.2 g, 64 mmol) was added to this suspension, which was stirred for 15 minutes at 60° C. This mixture was partitioned into ethyl acetate and water. The organic layer was separated and concentrated under a reduced pressure. The residue was purified by silica gel column chromatography (heptane:ethyl acetate=8:1) to obtain the title compound (10 g, 83%).

$^1$H-NMR Spectrum (DMSO-d$_6$) δ (ppm): 3.30 (3H, s), 4.53 (2H, s), 4.66 (2H, s), 7.30-7.38 (2H, m), 7.47-7.51 (1H, m), 7.54 (1H, m).

Manufacturing Example 214-1-2

(3-Ethynyl-phenyl)-methanol

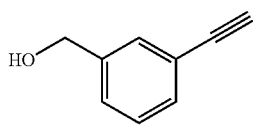

To a mixture of 1-bromo-3-methoxymethoxymethyl-benzene (3.0 g, 13 mmol) described in Manufacturing Example 214-1-1, trimethylsilylacetylene (2.6 g, 26 mmol), N,N-diisopropylethylamine (3.4 g, 26 mmol), copper (I) iodide (500 mg, 2.6 mmol), and 1-methyl-2-pyrrolidone (30 mL) was added tetrakis(triphenylphosphine)palladium (0) (1.5 g, 1.3 mmol), which was stirred for 15 minutes at 60° C. This mixture was partitioned into ethyl acetate and water. The organic layer was separated and concentrated under a reduced pressure. The residue was purified by silica gel column chromatography (heptane:ethyl acetate=8:1) to obtain a mixture of (3-methoxymethoxymethyl-phenylethynyl)-trimethyl-silane and 1-bromo-3-methoxymethoxymethyl-benzene (3.0 g of mixture, including approximately 30% (3-methoxymethoxymethyl-phenylethynyl)-trimethyl-silane). Tetrabutylammonium fluoride (2 mL, 1 M tetrahydrofuran solution) was added to a tetrahydrofuran (20 mL) solution of this mixture, which was stirred for 15 minutes at room temperature. The reaction solution was partitioned into ethyl acetate and water. The organic layer was separated and concentrated under a reduced pressure. The residue was purified by silica gel column chromatography (heptane:ethyl acetate=20:1) to obtain 1-ethynyl-3-methoxymethoxymethyl-benzene (470 mg). To a methanol (10 mL) solution of this 1-ethynyl-3-methoxymethoxymethyl-benzene (470 mg, 2.6 mmol) was added 5 N hydrochloric acid, which was stirred for 25 minutes at 70° C. The reaction solution was partitioned into ethyl acetate and water. The organic layer was separated and concentrated under a reduced pressure to obtain the title compound (350 mg, 20%).

$^1$H-NMR Spectrum (DMSO-d$_6$) δ (ppm): 4.15 (1H, s), 4.49 (2H, d, J=6.0 Hz), 5.25 (1H, t, J=6.0 Hz), 7.31-7.35 (3H, m), 7.40-7.42 (1H, m).

Example 215

3-(3-(4-(6-Chloro-pyrazin-2-yloxy)-benzyl)-isoxazol-5-yl)-pyridin-2,6-diamine

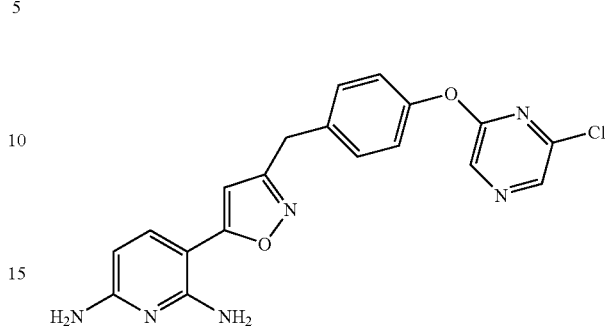

To a methanol (1.5 mL) solution of 4-(5-(2,6-diamino-pyridin-3-yl)-isoxazol-3-ylmethyl)-phenol (50 mg, 0.18 mmol) described in Manufacturing Example 18-1-1 was added a 2 N sodium hydroxide solution (89 µL), which was concentrated under a reduced pressure. 2,6-Dichloropyrazine (28 mg, 0.19 mmol) and N,N-dimethylformamide (0.75 mL) were added to the residue, which was stirred for 10 minutes at 100° C. The reaction solution was partitioned into ethyl acetate and water. The organic layer was separated and concentrated under a reduced pressure. The residue was purified by NH silica gel column chromatography (heptane:ethyl acetate=1:1, then ethyl acetate) to obtain the title compound (47 mg, 67%).

$^1$H-NMR Spectrum (DMSO-d$_6$) δ (ppm): 4.01 (2H, s), 5.82 (2H, brs), 5.83 (1H, d, J=8.4 Hz), 6.12 (2H, brs), 6.44 (1H, s), 7.21 (2H, d, J=8.4 Hz), 7.40 (2H, d, J=8.4 Hz), 7.53 (1H, d, J=8.4 Hz), 8.50 (1H, s), 8.53 (1H, s).

Example 216

3-(3-(4-Benzylsulfanyl-benzyl)-isoxazol-5-yl)-pyridin-2,6-diamine

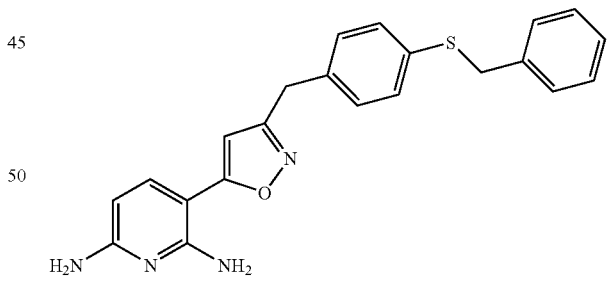

To a tetrahydrofuran (3 mL) solution of 3-ethynyl-pyridine-2,6-diamine (50 mg, 0.376 mmol) described in Manufacturing Example 13-1-3 and (4-benzylphenylsulfanyl-phenyl)acetohydroximoyl chloride (176 mg, 0.602 mmol) described in Manufacturing Example 205-1-5 was added triethylamine (131 µL, 0.94 mmol), which was stirred for 2 hours at room temperature. This mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:1, then ethyl acetate) to obtain the title compound (80 mg, 55%).

$^1$H-NMR Spectrum (CDCl$_3$) δ (ppm): 3.97 (2H, s), 4.10 (2H, s), 4.47 (2H, brs), 5.25 (2H, brs), 5.92 (1H, d, J=8.2 Hz), 5.96 (1H, s), 7.17 (2H, d, J=8.8 Hz), 7.23-7.29 (7H, m), 7.47 (1H, d, J=8.2 Hz).

Example 217

3-(3-(4-Phenylsulfanylmethyl-benzyl)-isoxazol-5-yl)-pyridin-2,6-diamine

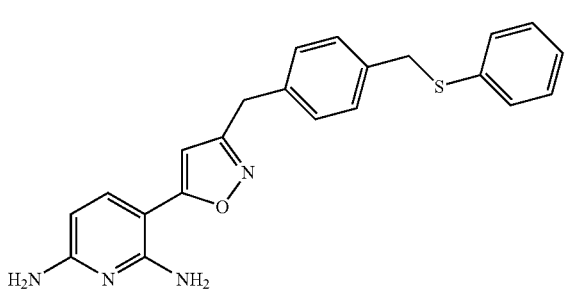

To a tetrahydrofuran (3 mL) solution of 3-ethynyl-pyridine-2,6-diamine (50 mg, 0.376 mmol) described in Manufacturing Example 13-1-3 and (4-phenylsulfanylmethyl-phenyl)acetohydroximoyl chloride (176 mg, 0.602 mmol) described in Manufacturing Example 206-1-6 was added triethylamine (131 μL, 0.94 mmol), which was stirred for 2 hours at room temperature. This mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:1, then ethyl acetate) to obtain the title compound (98 mg, 67%).

$^1$H-NMR Spectrum (CDCl$_3$) δ (ppm): 3.98 (2H, s), 4.11 (2H, s), 4.46 (2H, brs), 5.25 (2H, brs), 5.92 (1H, d, J=8.4 Hz), 5.97 (1H, s), 7.18-7.32 (9H, m), 7.47 (1H, d, J=8.4 Hz).

Example 218

3-(3-(4-(3-Methyl-2-but-2-enyloxy)-benzyl)-isoxazol-5-yl)-pyridin-2,6-diamine

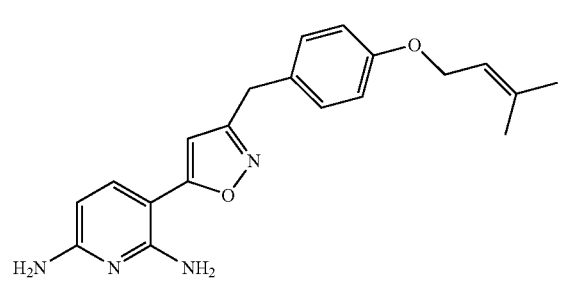

The title compound (15 mg, 23%) was obtained according to the methods similar to those of Example 212, using 4-(5-(2,6-diamino-pyridin-3-yl)-isoxazol-3-ylmethyl)-phenol (50 mg, 0.18 mmol) described in Manufacturing Example 18-1-1 and 1-bromo-3-methyl-but-2-ene (32 mg, 0.21 mmol).

$^1$H-NMR Spectrum (DMSO-d$_6$) δ (ppm): 1.69 (3H, s), 1.73 (3H, s), 3.87 (2H, s), 4.48 (2H, d, J=6.4 Hz), 5.41 (1H, t, J=6.4 Hz), 5.79 (2H, brs), 5.82 (1H, d, J=8.0 Hz), 6.10 (2H, brs), 6.34 (1H, s), 6.86 (2H, d, J=8.4 Hz), 7.19 (2H, d, J=8.4 Hz), 7.50 (1H, d, J=8.0 Hz).

Example 219

3-(3-(4-Prop-2-ynyloxy-benzyl)-isoxazol-5-yl)-pyridine-2,6-diamine

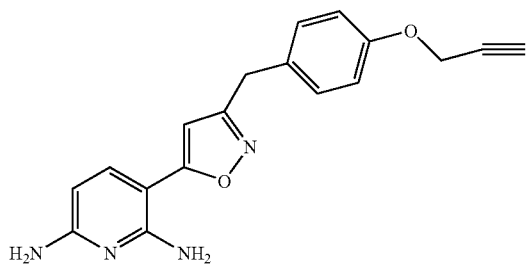

The title compound (38 mg, 66%) was obtained according to the methods similar to those of Example 212, using 4-(5-(2,6-diamino-pyridin-3-yl)-isoxazol-3-ylmethyl)-phenol (50 mg, 0.18 mmol) and propargyl bromide (32 mg, 0.27 mmol).

$^1$H-NMR Spectrum (DMSO-d$_6$) δ (ppm): 3.54 (1H, t, J=2.0 Hz), 3.89 (2H, s), 4.76 (2H, d, J=2.0 Hz), 5.79 (2H, brs), 5.82 (1H, d, J=8.4 Hz), 6.10 (2H, brs), 6.35 (1H, s), 6.93 (2H, d, J=8.8 Hz), 7.23 (2H, d, J=8.8 Hz), 7.51 (1H, d, J=8.4 Hz).

Example 220

3-(3-(4-Bromo-benzyl)-isoxazol-5-yl)-pyridine-2,6-diamine

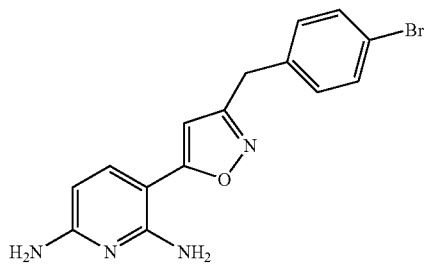

To a tetrahydrofuran (3 mL) solution of 3-ethynyl-pyridine-2,6-diamine (50 mg, 0.376 mmol) described in Manufacturing Example 13-1-3 and 4-bromophenyl acetohydroximoyl chloride (150 mg, 0.602 mmol) described in Manufacturing Example 207-1-3 was added triethylamine (131 μL, 0.94 mmol), which was stirred for 2 hours at room temperature. This mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:1, then ethyl acetate) to obtain the title compound (85 mg, 66%).

¹H-NMR Spectrum (CDCl₃) δ (ppm): 3.97 (2H, s), 4.48 (2H, brs), 5.26 (2H, brs), 5.92 (1H, d, J=8.4 Hz), 5.97 (1H, s), 7.15-7.13 (2H, m), 7.44-7.46 (2H, m), 7.48 (1H, d, J=8.4 Hz).

Example 221

3-(3-(5-(4-Fluoro-benzyl)-furan-2-ylmethyl)-isoxazol-5-yl)-pyridin-2,6-diamine

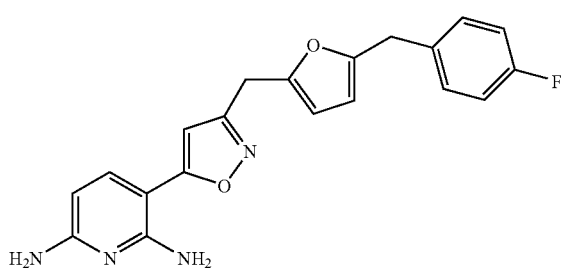

To a tetrahydrofuran (3 mL) solution of 3-ethynyl-pyridin-2,6-diamine (50 mg, 0.376 mmol) described in Manufacturing Example 13-1-3 and (5-(4-fluorobenzyl)-furan-2-yl)acetohydroximoyl chloride (161 mg, 0.602 mmol) described in Manufacturing Example 208-1-5 was added triethylamine (131 μL, 0.94 mmol), which was stirred for 19 hours at room temperature. This mixture was partitioned into ethyl acetate and water. The organic layer was separated, washed with water and saturated aqueous sodium chloride, dried over anhydrous magnesium sulfate, and filtered. The filtrate was concentrated under a reduced pressure, and the residue was purified by NH silica gel column chromatography (ethyl acetate:heptane=1:1, then ethyl acetate) to obtain the title compound (45 mg, 33%).

¹H-NMR Spectrum (CDCl₃) δ (ppm): 3.91 (2H, s), 3.99 (2H, s), 4.49 (2H, brs), 5.25 (2H, brs), 5.92 (1H, d, J=2.8 Hz), 5.95 (1H, d, J=8.4 Hz), 6.04 (1H, s), 6.06 (1H, d, J=2.8 Hz), 6.96-7.01 (2H, m), 7.17-7.21 (2H, m), 7.45 (1H, d, J=8.4 Hz).

Example 222

3-(3-(4-(Pyridin-2-yloxy)-benzyl)-isoxazol-5-yl)-pyridin-2,6-diamine

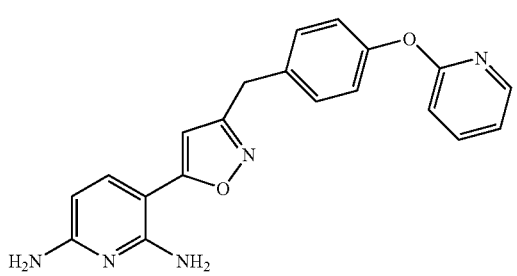

To a tetrahydrofuran (15 mL) solution of 3-ethynyl-pyridin-2,6-diamine (45 mg, 0.34 mmol) described in Manufacturing Example 13-1-3 and (4-(pyridin-2-yloxy)benzene)-acetohydroximoyl chloride (300 mg, 1.1 mmol) described in Manufacturing Example 209-1-4 was added triethylamine (120 mg, 1.1 mmol), which was stirred for 10 minutes at 60° C. The reaction solution was cooled to room temperature, NH silica gel was added, and the solvent was evaporated under a reduced pressure. The crude product that had adsorbed to the NH silica gel was purified by NH silica gel column chromatography (heptane:ethyl acetate=1:1, then ethyl acetate) to obtain the title compound (57 mg, 14%).

¹H-NMR Spectrum (DMSO-d₆) δ (ppm): 3.97 (2H, s), 5.82 (2H, brs), 5.84 (1H, d, J=8.0 Hz), 6.11 (2H, brs), 6.42 (1H, s), 6.99-7.03 (1H, m), 7.05-7.13 (3H, m), 7.34 (2H, d, J=8.0 Hz), 7.53 (1H, d, J=8.0 Hz), 7.81-7.86 (1H, m), 8.12-8.14 (1H, m).

Example 223

3-(3-(6-Benzyl-pyridin-3-ylmethyl)-isoxazol-5-yl)-pyridin-2,6-diamine

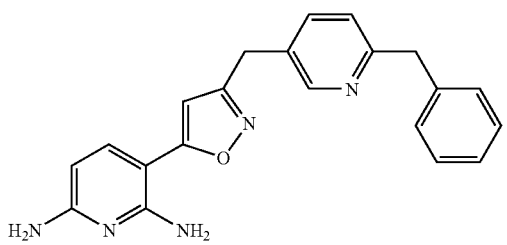

To a tetrahydrofuran (5 mL) solution of 3-ethynyl-pyridin-2,6-diamine (20 mg, 0.15 mmol) described in Manufacturing Example 13-1-3 and 2-(6-benzyl-pyridin-3-yl)-acetohydroximoyl chloride (79 mg, 0.30 mmol) described in Manufacturing Example 210-1-7 was added triethylamine (46 mg, 0.45 mmol), which was stirred for 30 minutes at 50° C. The reaction solution was cooled to room temperature and partitioned into ethyl acetate and water. The organic layer was separated and concentrated under a reduced pressure. The residue was purified by NH silica gel column chromatography (ethyl acetate, then ethyl acetate:methanol=20:1) to obtain the title compound (43 mg, 80%).

¹H-NMR Spectrum (DMSO-d₆) δ (ppm): 3.95 (2H, s), 4.05 (2H, s), 5.80 (2H, brs), 5.82 (1H, d, J=8.8 Hz), 6.11 (2H, brs), 6.40 (1H, s), 7.15-7.30 (6H, m), 7.50 (1H, d, J=8.8 Hz), 7.62 (1H, dd, J=2.0, 8.0 Hz), 8.46 (1H, d, J=2.0 Hz).

Example 224

3-(3-(6-Benzyloxy-pyridin-3-ylmethyl)-isoxazol-5-yl)-N⁶-methyl-pyridin-2,6-diamine

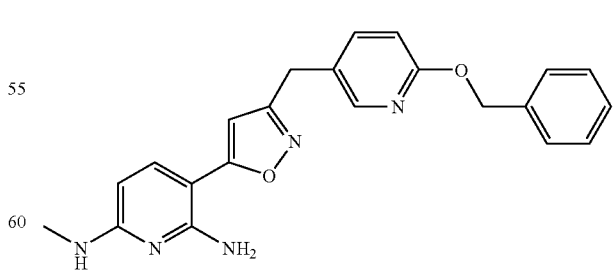

To a mixture of 3-(3-(6-benzyloxy-pyridin-3-ylmethyl)-isoxazol-5-yl)-pyridine-2,6-diamine (50 mg, 0.13 mmol) described in Example 25 and N,N-dimethylformamide (0.5 mL) were added a formaldehyde aqueous solution (14 mg, 0.17 mmol, content: 37%), α-picoline-borane (17 mg, 0.16 mmol), and acetic acid (50 μL) at room temperature, which was stirred overnight at the same temperature. A saturated sodium hydrogencarbonate aqueous solution was added to the reaction mixture, which was extracted with ethyl acetate. The organic layer was washed with saturated aqueous sodium chloride and dried over anhydrous magnesium sulfate, after which the organic layer was concentrated under a reduced pressure. The residue thus obtained was purified by reverse-phase high performance liquid chromatography (using an acetonitrile-water mobile phase containing 0.1% trifluoroacetic acid) to obtain a crude product, and then purified by silica gel thin-layer chromatography (diethyl ether:hexane=2:1) to obtain the title compound (2.3 mg, 4.4%).

1H-NMR Spectrum (DMSO-d6) δ (ppm): 2.76 (3H, d, J=4.2 Hz), 3.91 (2H, s), 5.33 (2H, s), 5.83 (1H, d, J=8.4 Hz), 5.87 (2H, br s), 6.40 (1H, s), 6.68 (1H, br s), 6.85 (1H, d, J=8.6 Hz), 7.31-7.33 (1H, m), 7.35-7.39 (2H, m), 7.42-7.44 (2H, m), 7.52 (1H, d, J=8.6 Hz), 7.66 (1H, dd, J=2.1, 8.3 Hz), 8.14 (1H, d, J=2.6 Hz).

Example 225

2-(6-Amino-5-(3-(6-benzyloxy-pyridin-3-ylmethyl)-isoxazol-5-yl)-pyridin-2-ylamino)-ethanol

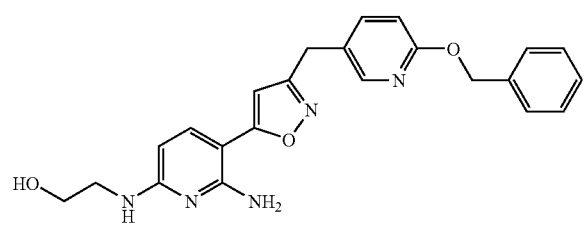

To a mixture of 3-(3-(6-benzyloxy-pyridin-3-ylmethyl)-isoxazol-5-yl)-pyridin-2,6-diamine (40 mg, 0.11 mmol) described in Example 25 and N,N-dimethylformamide (0.5 mL) were 2-hydroxyacetaldehyde (7.7 mg, 0.13 mmol), α-picoline-borane (14 mg, 0.13 mmol), and acetic acid (40 μL) at room temperature, which was stirred for 100 minutes at the same temperature. A saturated sodium hydrogencarbonate aqueous solution was added to the reaction mixture, which was extracted with ethyl acetate. The organic layer was washed with saturated aqueous sodium chloride and dried over anhydrous magnesium sulfate, after which the organic layer was concentrated under a reduced pressure. The residue thus obtained was purified by reverse-phase high performance liquid chromatography (using an acetonitrile-water mobile phase containing 0.1% trifluoroacetic acid) to obtain a crude product, and then purified by NH silica gel column chromatography (ethyl acetate:methanol=50:1) to obtain the title compound (4.5 mg, 10%).

1H-NMR Spectrum (DMSO-d6) δ (ppm): 3.31-3.34 (2H, m), 3.48-3.51 (2H, m), 3.91 (2H, s), 5.33 (2H, s), 5.86 (2H, brs), 5.89 (1H, d, J=8.6 Hz), 6.39 (1H, s), 6.72 (1H, br s), 6.85 (1H, d, J=8.4 Hz), 7.29-7.33 (1H, m), 7.35-7.39 (2H, m), 7.42-7.44 (2H, m), 7.50 (1H, d, J=8.6 Hz), 7.66 (1H, dd, J=2.6, 8.6 Hz), 8.14 (1H, d, J=2.0 Hz).

Example 226

N-(6-Amino-5-(3-(6-benzyloxy-pyridin-3-ylmethyl)-isoxazol-5-yl)-pyridin-2-yl)-2-methoxy-acetamide

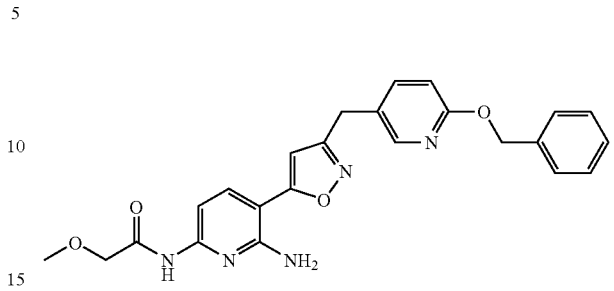

To a mixture of 3-(3-(6-benzyloxy-pyridin-3-ylmethyl)-isoxazol-5-yl)-pyridine-2,6-diamine (40 mg, 0.11 mmol) described in Example 25 and dichloromethane (1 mL) were added triethylamine (22 μL, 0.16 mmol) and methoxyacetyl chloride (15 mg, 0.14 mmol) at room temperature, which was stirred for 2 hours at the same temperature. The solids that precipitated in the reaction mixture were filtered out. Tetrahydrofuran was added to the solid thus obtained, and this mixture was filtered. The filtrate was concentrated under a reduced pressure to obtain the title compound (3.4 mg, 7%).

$^1$H-NMR Spectrum (DMSO-d$_6$) δ (ppm): 3.37 (3H, m), 3.98 (2H, s), 4.05 (2H, s), 5.33 (2H, s), 6.23 (2H, br s), 6.73 (1H, s), 6.86 (1H, d, J=8.4 Hz), 7.29-7.33 (1H, m), 7.35-7.44 (5H, m), 7.68 (1H, dd, J=2.6, 8.4 Hz), 7.91 (1H, d, J=8.4 Hz), 8.16 (1H, d, J=2.4 Hz), 9.50 (1H, br s).

Example 227

(6-Amino-5-(3-(6-benzyloxy-pyridin-3-ylmethyl)-isoxazol-5-yl)-pyridin-2-ylamino)-acetic acid ethyl ester

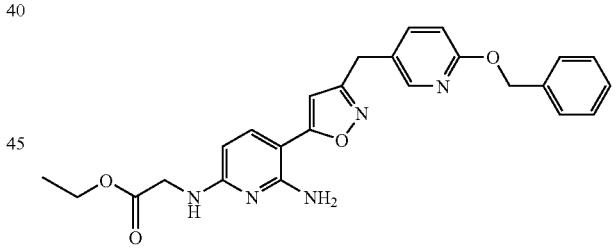

To a mixture of 3-(3-(6-benzyloxy-pyridin-3-ylmethyl)-isoxazol-5-yl)-pyridin-2,6-diamine (40 mg, 0.11 mmol) described in Example 25 and N,N-dimethylformamide (0.5 mL) were added glyoxylic acid ethyl ester polymer foam (16 mg, 0.16 mmol), α-picoline-borane (14 mg, 0.13 mmol), and acetic acid (40 μL), which was stirred overnight at the same temperature. A saturated sodium hydrogencarbonate aqueous solution was added to the reaction mixture, which was extracted with ethyl acetate. The organic layer was washed with saturated aqueous sodium chloride and dried over anhydrous magnesium sulfate, after which the organic layer was concentrated under a reduced pressure. The residue thus obtained was purified by reverse-phase high performance liquid chromatography (using an acetonitrile-water mobile phase containing 0.1% trifluoroacetic acid) to obtain the title compound (4.9 mg, 8%) as a trifluoroacetic acid salt.

MS m/e (ESI) 460.51 (MH$^+$)

Example 228

(3-(3-(4-Benzyloxy-benzyl)-isoxazol-5-yl)-pyridin-2-yl)-dimethyl-amine

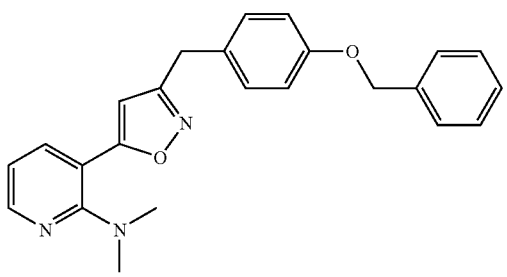

To a mixture of 3-(3-(4-benzyloxy-benzyl)-isoxazol-5-yl)-pyridin-2-ylamine (50 mg, 0.14 mmol) described in Example 1 and N,N-dimethylformamide (0.5 mL) were added a formaldehyde aqueous solution (34 mg, 0.42 mmol, content: 37%), α-picoline-borane (37 mg, 0.35 mmol), and acetic acid (50 μL), which was stirred overnight at the same temperature. Trifluoroacetic acid (50 μL) was added to the reaction mixture, which was stirred for 30 minutes at room temperature. The solvent was evaporated under a reduced pressure, and the residue thus obtained was purified by reverse-phase high performance liquid chromatography (using an acetonitrile-water mobile phase containing 0.1% trifluoroacetic acid) to obtain the title compound (15 mg, 21%) as a trifluoroacetate.

MS m/e (ESI) 386.30 (MH$^+$)

The various acetohydroximoyl chloride intermediates can be manufactured by the Manufacturing Examples described above, and can also be manufactured by the following alternative methods. For instance, set out below are alternative methods for manufacturing 4-benzyloxy-phenyl-acetoxyhydroximoyl chloride described in [Manufacturing Example 1-1-3], 4-(pyridin-2-yloxymethyl)-phenyl-acetohydroximoyl chloride described in [Manufacturing Example 2-1-5], (2-benzyloxy-pyridin-5-yl)-acetohydroximoyl chloride described in [Manufacturing Example 12-1-5] and (2-phenoxy-pyridin-5-yl)-acetohydroxymoyl chloride described in [Manufacturing Example 40-1-4].

Alternative method to the method described in [Manufacturing Example 1-1-3] for manufacturing 4-benzyloxy phenyl acetoxyhydroximoyl chloride

Manufacturing Example 229-1-1

1-Benzyloxy-4-((E)-2-nitro-vinyl)-benzene

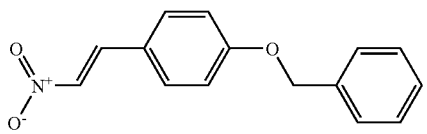

To a mixture of 4-benzyloxy benzaldehyde (50 g, 0.24 mol) and acetic acid (200 mL) were added nitromethane (64 mL, 1.2 mol) and ammonium acetate (36 g, 0.47 mol), which was stirred for 90 minutes at 100° C. The reaction mixture was cooled to room temperature, and water (1 L) was added at the same temperature. The deposited solids were filtered to obtain the title compound (60 g).

Manufacturing Example 229-1-2

1-Benzyloxy-4-(2-nitro-ethyl)-benzene

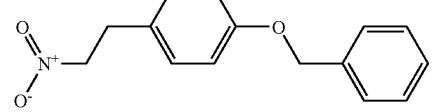

While cooling using a water bath, to a mixture of 1-benzyloxy-4-((E)-2-nitro-vinyl)-benzene described in Manufacturing Example 229-1-1 (60 g, 0.23 mol), acetic acid (27 mL) and dimethyl sulfoxide (400 mL) was added sodium borohydrate (8.9 g, 0.23 mol), which was stirred for 20 minutes at room temperature. Water (2.5 L) was added dropwise to the reaction mixture, and the deposited solids were filtered. Diethyl ether (300 mL) was added to the obtained solids to dissolve the title compound, and separation into filtrate and solids was carried out by filtration. The filtrate was concentrated under a reduced pressure to obtain the title compound (39 g). On the other hand, diethyl ether (300 mL) was added to the previously separated solid to dissolve the title compound, and separation into filtrate and solids was carried out by filtration. The filtrate was concentrated under a reduced pressure to obtain the title compound (12 g). This was combined with the previously obtained solids to obtain the title compound (51 g) as a crude product.

Manufacturing Example 229-1-3

4-Benzyloxy-phenyl-acetohydroximoyl chloride

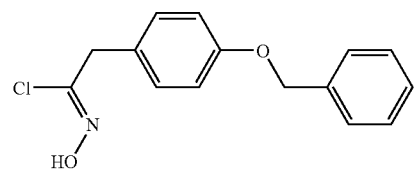

To a mixture of 1-benzyloxy-4-(2-nitro-ethyl)-benzene described in Manufacturing Example 229-1-2 (39 g, 0.15 mol), tetrahydrofuran (350 mL) and dichloromethane (350 mL) was added n-butyl lithium (63 mL, 2.6 M n-hexane solution, 0.17 mol) at −78° C., which was stirred for 20 minutes at the same temperature. To the reaction mixture was added titanium (IV) chloride (25 mL, 0.23 mol) at the same temperature, and the mixture was warmed gradually to 10° C. After cooling the reaction mixture to 0° C., water (500 mL) and ethyl acetate (700 mL) were added, and the reaction mixture was warmed to room temperature. This organic layer was separated, washed with water (500 mL) and saturated sodium chloride water, dried over anhydrous magnesium sulfate, and then filtered. The filtrate was concentrated under a reduced pressure. This residue was filtered with neutral silica gel (ethyl acetate:heptane=1:1), and this filtrate was concentrated under a reduced pressure. The obtained residue was washed with diethyl ether-heptane (1:10) to obtain the title compound (33 g, 78%).

Alternative method to the method described in [Manufacturing Example 2-1-5] for manufacturing 4-(pyridin-2-yloxymethyl)-phenyl-acetohydroximoyl chloride Manufacturing Example 230-1-1

2-(4-Bromo-benzyloxy)-pyridine

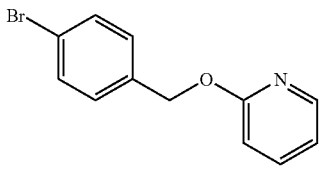

To a solution of 4-bromobenzyl alcohol (25 g, 130 mmol) in N,N-dimethyl formamide (125 mL) was added potassium tert-butoxide (15.8 g, 141 mmol) at room temperature, which was stirred at 54° C. for 10 minutes. To this reaction solution was added 2-fluoropyridine (15 mL, 154 mmol) at from 40° C. to 58° C., which was further stirred for 30 minutes at 65° C. The reaction solution was allowed to room temperature, water and ethyl acetate were added, and liquid separation was carried out. The aqueous layer was further extracted with ethyl acetate (twice). The ethyl acetate layers were combined, washed with water (3 times) and sodium chloride water (once), dried over anhydrous magnesium sulfate, and then filtered. The filtrate was concentrated under a reduced pressure. Diethyl ether was added to the residue, which was concentrated under a reduced pressure to obtain the title compound (34 g) as a crude product.

$^1$H-NMR Spectrum (CDCl$_3$) δ (ppm): 5.33 (2H, s), 6.87-6.70 (1H, m), 6.98-7.02 (1H, m), 7.38-7.44 (2H, m), 7.55-7.60 (2H, m), 7.71-7.76 (1H, m), 8.15-8.18 (1H, m).

Manufacturing Example 230-1-2

4-(Pyridin-2-yloxymethyl)-benzaldehyde

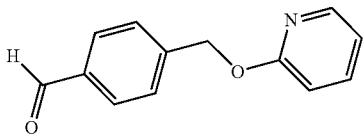

To a solution of 2-(4-bromo-benzyloxy)-pyridine described in Manufacturing Example 230-1-1 (34 g, 128 mmol) in tetrahydrofuran (120 mL) was added dropwise n-butyl lithium (50 mL, 2.6 M hexane solution, 134 mmol) at −78° C. After stirring for 30 minutes, N,N-dimethyl formamide (10 mL, 134 mmol) was added dropwise to this reaction solution at −78° C., which was stirred at room temperature. Water and ethyl acetate were added to the reaction solution, and liquid separation was carried out. The ethyl acetate layer was washed with water (twice) and sodium chloride water (once). The aqueous layers were combined and extracted with ethyl acetate. The obtained ethyl acetate layer was washed with water (twice) and aqueous sodium chloride (once). The previously obtained ethyl acetate layer and the ethyl acetate layer obtained this time were combined, dried over anhydrous magnesium sulfate, and then filtered. This filtrate was concentrated under a reduced pressure to obtain the title compound (26.8 g) as a crude product.

Manufacturing Example 230-1-3

2-(4-((E)-2-Nitro-vinyl)-benzyloxy)-pyridine

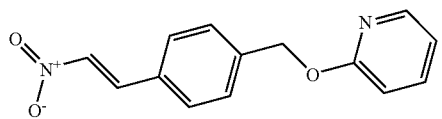

A mixture of 4-(pyridin-2-yloxymethyl)-benzaldehyde described in Manufacturing Example 230-1-2 (26.8 g, 126 mmol), nitromethane (34 mL, 630 mmol), ammonium acetate (19 g, 252 mmol) and acetic acid (90 mL) was stirred for 1 hour and 30 minutes at 100° C. Ethyl acetate and water were added to the reaction solution, and liquid separation was carried out. This organic layer was separated, washed with water (5 times) and saturated aqueous sodium bicarbonate solution (once), dried over anhydrous magnesium sulfate, and then filtered. The filtrate was concentrated under a reduced pressure to obtain the title compound (31 g) as a crude product.

Manufacturing Example 230-1-4

2-(4-(2-Nitro-ethyl)-benzyloxy)-pyridine

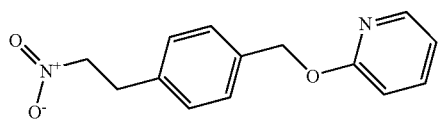

To a solution of 2-(4-((E)-2-nitro-vinyl)-benzyloxy)-pyridine described in Manufacturing Example 230-1-3 (30.8 g, 120 mmol) and acetic acid (7.4 mL) in dimethyl sulfoxide (150 mL) was added sodium borohydrate (2.45 g, 64.8 mmol) at 30° C. or below. The reaction solution was stirred for 40 minutes at room temperature. Water, ethyl acetate and diethyl ether were added to the reaction solution at 30° C. or below, which was partitioned into aqueous and organic layers. The aqueous layer was extracted with ethyl acetate. The previously obtained organic layer and the ethyl acetate layer were combined, washed with water (3 times) and aqueous sodium chloride (once), dried over anhydrous magnesium sulfate, and then filtered. The filtrate was concentrated under a reduced pressure. The residue was purified by NH silica gel column chromatography (ethyl acetate:heptane=1:4) to obtain the title compound (15.2 g, 49%).

Manufacturing Example 230-1-5

4-(pyridin-2-yloxymethyl)-phenyl-acetohydroximoyl chloride

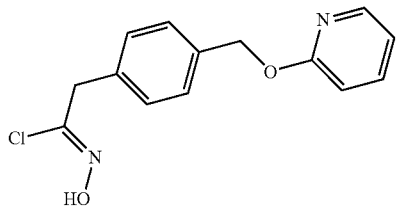

To a solution of 2-(4-(2-nitro-ethyl)-benzyloxy)-pyridine described in Manufacturing Example 230-1-4 (15.2 g, 59 mmol) in methanol (80 mL) was added lithium methoxide (4.49 g, 118 mmol), which was stirred for 3 minutes. The reaction solution was concentrated under a reduced pressure. Toluene was added to the residue, and this solvent was concentrated under a reduced pressure. The solution of the obtained residue in methylene chloride (100 mL) and tetrahydrofuran (50 mL) was cooled to −66° C., and titanium (IV) chloride (20.8 mL, 189 mmol) was added while stirring. The reaction solution was stirred for 10 minutes at 0° C., then stirred for 30 minutes at room temperature. The reaction solution was poured into ice water, and stirred for 30 minutes at room temperature. Ethyl acetate and diethyl ether were added to the reaction solution, and liquid separation was carried out. The organic layer was washed with water (3 times) and aqueous sodium chloride (once). The aqueous layers were combined and extracted with ethyl acetate (twice). The ethyl acetate layers were combined and washed with water (3 times) and aqueous sodium chloride (once). The previous organic layer and the ethyl acetate layer were combined, dried over anhydrous magnesium sulfate and sodium sulfate, and filtered. The filtrate was concentrated under a reduced pressure to obtain the title compound (11.5 g) as a crude product.

Alternative method to the method described in [Manufacturing Example 12-1-5] for manufacturing (2-benzyloxy-pyridine-5-yl)-acetohydroximoyl chloride Manufacturing Example 231-1-1

2-Benzyloxy-5-bromo pyridine

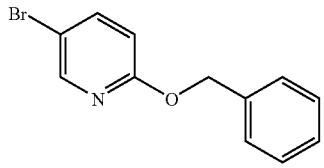

To a solution of phenyl-methanol (2.7 g, 25.0 mmol) in N,N-dimethylformamide (25 mL) was added sodium hydride (1.0 g, 25.0 mmol) on an ice bath (0° C.) under nitrogen atmosphere, which was stirred for 30 minutes at room temperature. Thereafter, 2,5-dibromopyridine (3.0 g, 12.7 mmol) was added on the ice bath (0° C.), which was stirred for 10 minutes at 60° C. This reaction was repeated 16 times. These reaction mixtures were combined and partitioned into water and ethyl acetate on the ice bath (0° C.). This organic layer was separated, washed with water and saturated aqueous sodium chloride, dried over anhydrous magnesium sulfate, and then filtered. The filtrate was concentrated under a reduced pressure. The residue was purified by silica gel column chromatography (ethyl acetate:heptane=1:10) to obtain the title compound (53.0 g, 99%).

Manufacturing Example 231-1-2

6-Benzyloxy-pyridine-3-carbaldehyde

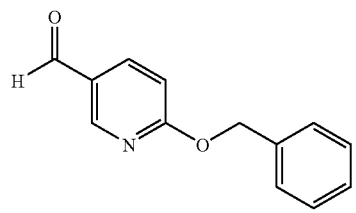

To a solution of 2-benzyloxy-5-bromopyridine described in Manufacturing Example 231-1-1 (53.0 g, 201 mmol) in diethyl ether (500 mL) was added n-butyl lithium (82.8 mL, 2.67 M n-hexane solution, 221 mmol) was added dropwise on a dry ice-ethanol bath (−78° C.) under nitrogen atmosphere, which was stirred for 30 minutes at −78° C. While cooling at the same temperature, N,N-dimethylformamide (17.6 g, 241 mmol) was added to this reaction mixture, which was stirred for 30 minutes. Water and ethyl acetate were added to the reaction mixture, which was stirred for 10 minutes at room temperature, the organic layer was then separated. The organic layer was washed with water and saturated aqueous sodium chloride, dried over anhydrous magnesium sulfate, and then filtered. The filtrate was concentrated under a reduced pressure. The residue was purified by NH silica gel column chromatography (ethyl acetate:heptane=1:5 then 1:4) to obtain the title compound (36.8 g, 86%).

Manufacturing Example 231-1-3

2-Benzyloxy-5-((E)-2-nitro-vinyl)-pyridine

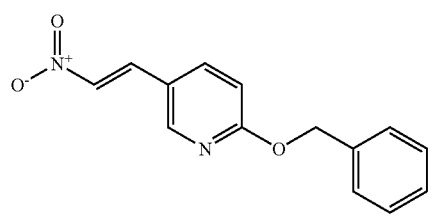

To a solution of 6-benzyloxy-pyridine-3-carbaldehyde described in Manufacturing Example 231-1-2 (36.8 g, 173 mmol) in acetic acid (100 mL) were added nitromethane (52.8 g, 865 mmol) and ammonium acetate (26.7 g, 346 mmol) under nitrogen atmosphere at room temperature, which was stirred for 2.5 hours at 100° C. The reaction mixture was partitioned into water and ethyl acetate. The organic layer was washed with water and saturated aqueous sodium chloride, dried over anhydrous magnesium sulfate, and then filtered. The filtrate was concentrated under a reduced pressure to obtain the title compound (44.0 g) as a crude product.

Manufacturing Example 231-1-4

2-Benzyloxy-5-(2-nitro-ethyl)pyridine

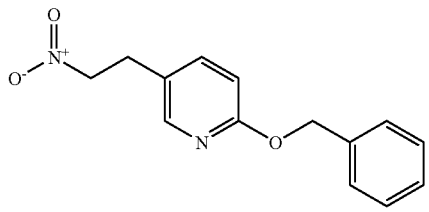

To a solution of 2-benzyloxy-5-((E)-2-nitro-vinyl)-pyridine described in Manufacturing Example 231-1-3 (44.0 g, 172 mmol) and acetic acid (44.0 mL) in dimethyl sulfoxide (200 mL) was added sodium borohydrate (11.0 g, 275 mmol) at room temperature while cooling appropriately under nitrogen atmosphere, which was stirred for 30 minutes. Water was added to this reaction solution at room temperature while cooling appropriately, which was then partitioned into water and ethyl acetate. The organic layer was separated, washed with water and saturated aqueous sodium chloride, dried over anhydrous magnesium sulfate, and then filtered. The filtrate was concentrated under a reduced pressure. The residue was purified by NH silica gel column chromatography (ethyl acetate:heptane=1:4) to obtain the title compound (18.1 g, 40.7%).

Manufacturing Example 231-1-5

(2-Benzyloxy-pyridine-5-yl)-acetohydroximoyl chloride

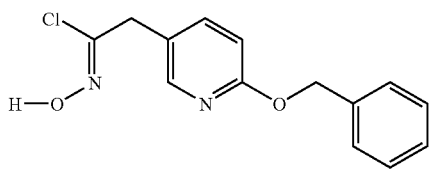

To a solution of 2-methyl-6-(4-(2-nitro-ethyl)-benzyloxy) pyridine described in Manufacturing Example 231-1-4 (11.0 g, 42.6 mmol) in methanol (30 mL) was added lithium methoxide (3.24 g, 85.2 mmol) under nitrogen atmosphere, which was stirred for 30 minutes at room temperature. The reaction mixture was concentrated under a reduced pressure. Anhydrous methylene chloride (40 mL) and anhydrous tetrahydrofuran (40 mL) were added to the residue. While cooling on a dry ice-ethanol bath (−78° C.), titanium (IV) chloride (15.0 mL, 136 mmol) was added dropwise to the reaction mixture, which was stirred for 40 minutes at room temperature. Water, ethyl acetate then tetrahydrofuran were added to the reaction mixture on an ice bath (0° C.), and then the organic layer was separated. The organic layer was washed with water and saturated aqueous sodium chloride, dried over anhydrous magnesium sulfate, and then filtered. The filtrate was concentrated under a reduced pressure to obtain the title compound (11.2 g) as a crude product.

Alternative method to the method described in [Manufacturing Example 40-1-4] for manufacturing (2-phenoxy-pyridin-5-yl)-acetohydroximoyl chloride

Manufacturing Example 232-1-1

5-Bromo-2-phenoxy-pyridine

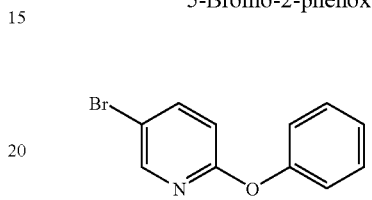

A mixture of 2,5-dibromo pyridine (25 g, 106 mmol), phenol (10.5 g, 111 mmol), potassium tert-butoxide (12.5 g, 111 mmol) and dimethyl sulfoxide (250 mL) was stirred for 4 hours at 160° C. This mixture was cooled to room temperature, and partitioned into ethyl acetate and water. The organic layer was separated, washed with water, dried with anhydrous magnesium sulfate, and then filtered. The filtrate was concentrated under a reduced pressure, and the residue was purified by silica gel column chromatography (heptane:ethyl acetate=10:1) to obtain the title compound (18.7 g, 70%).

Manufacturing Example 232-1-2

6-Phenoxy-pyridine-3-carbaldehyde

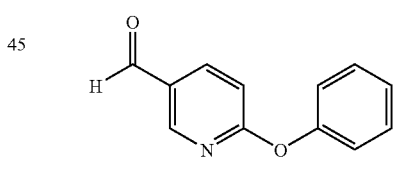

To a solution of 5-bromo-2-phenoxy-pyridine described in Manufacturing Example 231-1-1 (18.7 g, 74.6 mmol) in tetrahydrofuran (360 mL) was added n-butyl lithium (31.1 mL, 2.64 M hexane solution, 82.1 mmol) under nitrogen atmosphere at −78° C., which was stirred for 30 minutes at −78° C. To this reaction solution was added N,N-dimethylformamide (7.46 mL, 97 mmol) at −78° C., which was stirred for 1 hour at this temperature. The reaction solution was partitioned into ethyl acetate and water. The organic layer was separated, washed with saturated aqueous sodium chloride, dried over anhydrous magnesium sulfate, and then filtered. The filtrate was concentrated under a reduced pressure. The residue was purified by silica gel column chromatography (heptane:ethyl acetate=5:1) to obtain the title compound (4.75 g, 32%).

Manufacturing Example 232-1-3

5-((E)-2-Nitro-vinyl)-2-phenoxy-pyridine

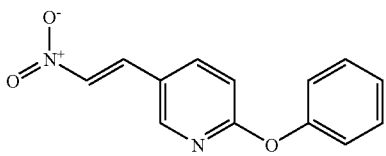

A mixture of 6-phenoxy-pyridine-3-carbaldehyde described in Manufacturing Example 232-1-2 (4.75 g, 23.8 mmol), nitromethane (6.45 mL, 119 mmol), ammonium acetate (3.67 g, 47.6 mmol) and acetic acid (20 mL) was stirred for 3 hours at 100° C. This mixture was cooled to room temperature, and partitioned into ethyl acetate and water. The organic layer was separated, washed with water, dried over anhydrous magnesium sulfate, and then filtered. The filtrate was concentrated under a reduced pressure to obtain the title compound (5.97 g) as a crude product.

Manufacturing Example 232-1-4

5-(2-Nitro-ethyl)-2-phenoxy-pyridine

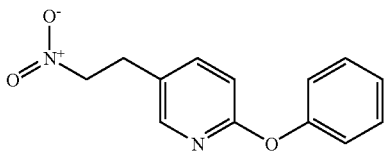

To a solution of 5-((E)-2-nitro-vinyl)-2-phenoxy-pyridine described in Manufacturing Example 232-1-3 (5.97 g, 24.6 mmol) and acetic acid (3.2 mL) in dimethyl sulfoxide (52 mL) was added sodium borohydrate (1.4 g, 36.9 mmol), at room temperature while cooling appropriately. This mixture was stirred for 30 minutes at room temperature. This mixture was cooled appropriately, then, water was added, which was stirred for 30 minutes at room temperature. This mixture was liquid-separated, and the organic layer was separated. The organic layer was washed with water, dried over anhydrous magnesium sulfate, and then filtered. The filtrate was concentrated under a reduced pressure to obtain the title compound (5.72 g) as a crude product.

Manufacturing Example 232-1-5

(2-Phenoxy-pyridine-5-yl)-acetohydroximoyl chloride

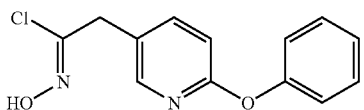

To a solution of 5-(2-nitro-ethyl)-2-phenoxy-pyridine described in Manufacturing Example 232-1-4 (5.72 g, 23.4 mmol) in methanol (68 mL) was added lithium methoxide (1.78 g, 46.8 mmol), which was stirred for 5 minutes. This reaction solution was concentrated under a reduced pressure, methylene chloride (91 mL) and tetrahydrofuran (45 mL) were added to the obtained residue. This mixture was cooled to −78° C., then, titanium tetrachloride (15.7 mL, 74.9 mmol) was added dropwise, which was further stirred for 1 hour at 0° C. This mixture was cooled to −78° C., water was added, which was stirred for 30 minutes at room temperature. This mixture was partitioned into water and ethyl acetate. The organic layer was separated, washed with water, dried over anhydrous magnesium sulfate, and then filtered. The filtrate was concentrated under a reduced pressure to obtain the title compound (4.72 g) as a crude product.

The compounds (I) of the present invention or salts thereof exhibits excellent inhibition activity on the GPI-anchored protein transport process based on the inhibition of fungal GPI biosynthesis, anti-*Candida* activity and anti-*Aspergillus* activity, and are also superior in terms of its physical properties, safety and metabolic stability, making it extremely useful as a preventive or therapeutic agent for fungal infections.

Pharmacological Test Examples

In order to demonstrate the usefulness of the compounds (I) of the present invention, the antifungal activity of the compounds (I) of the present invention was measured by measuring 1; anti-*Candida* and anti-*Aspergillus* activity and 2; activity in the experimental systemic candidal infection model in mice.

1. Anti-*Candida* Activity and Anti-*Aspergillus* Activity (1) Preparation of Fungal Suspension For the *C. albicans* CAF2-1 strain, a fungal suspension from a standing culture for 48 hours at 30° C. in a Sabouraud dextrose liquid culture medium (SDB) was diluted with RPMI1640 medium to adjust a fungal suspension of $1.2 \times 10^3$ cells/mL. For the *A. fumigatus* Tsukuba strain, −80° C. stored strain was diluted with RPMI1640 medium to adjust to a fungal suspension of $4.5 \times 10^3$ cells/mL.

(2) Preparation of an Agent Dilution Plate

Using a U-bottomed 96 well plate, 8 samples/plate (A to H) of sample dilution solutions were prepared. On the $2^{nd}$ to $12^{th}$ rows were dispensed 10 μL of dimethyl sulfoxide solution. Weighted sample was dissolved in dimethyl sulfoxide to prepare a 2.5 mg/mL solution, 20 μL of this solution was added to the first row of the prepared plate, and 12 steps of two-fold step dilutions (10 μL of solution+10 μL of dimethyl sulfoxide solution) were performed on the plate. This sample dilution solution was dispensed in the amount of 1 μL to a flat-bottomed 96 well plate for MIC measurement to prepare a sample dilution plate.

(3) Inoculation of Fungal Suspension and Culture

The fungal suspension prepared in (1) was used in the amount of 99 μL/well to inoculate the flat-bottomed 96 well plate containing 1 μL/well of the test compound dilution prepared in (2), and a standing culture was carried out aerobically for 42-48 hours at 35° C.

(4) MIC Measurement

The minimum concentration that clearly inhibited fungal growth as compared to the control by visual inspection was determined as the minimum inhibitory concentration (MIC).

The following representative compounds prepared in the examples were measured for anti-*Candida* activity and anti-*Aspergillus* activity by the measurement method described in 1. As a result, as shown in Tables 1 to 6, it was found that the compounds according to the present invention clearly had anti-*Candida* and anti-*Aspergillus* activity.

TABLE 1

| Ex. No. | Anti-Candida Activity (µg/mL) | Anti-Aspergillus Activity (µg/mL) |
| --- | --- | --- |
| 1 | 0.20 | 0.20 |
| 2 | 0.05 | 0.20 |
| 3 | 0.10 | 0.78 |
| 4 | 0.20 | 0.39 |
| 5 | 0.39 | 0.39 |
| 6 | 0.39 | 0.39 |
| 7 | 1.56 | 0.20 |
| 8 | 1.56 | 0.78 |
| 9 | 0.20 | 0.39 |
| 10 | 0.39 | 0.78 |
| 11 | 0.10 | 0.39 |
| 12 | 0.10 | 0.10 |
| 13 | 0.20 | 0.10 |
| 14 | 0.39 | 0.39 |
| 15 | 0.20 | 0.39 |
| 16 | 0.39 | 0.39 |
| 17 | 0.78 | 0.20 |
| 18 | 1.56 | 0.78 |
| 19 | 0.78 | 0.39 |
| 20 | 0.78 | 0.20 |
| 21 | 1.56 | 0.78 |
| 22 | 0.20 | 0.39 |
| 23 | 0.78 | 1.56 |
| 24 | 0.39 | 0.78 |
| 25 | 0.20 | 0.20 |
| 26 | 0.78 | 0.78 |
| 27 | 0.20 | 0.39 |
| 28 | >25 | 0.39 |
| 29 | 0.39 | 0.20 |
| 30 | 0.10 | 0.20 |
| 31 | 0.20 | 0.39 |
| 32 | 0.20 | 0.78 |
| 33 | 0.39 | 0.78 |
| 34 | 0.78 | 0.39 |
| 35 | 0.20 | 1.56 |
| 36 | 0.39 | 0.78 |
| 37 | 0.39 | 1.56 |
| 38 | 0.78 | 1.56 |
| 39 | 3.13 | 3.13 |
| 40 | 0.39 | 0.39 |

TABLE 2

| Ex. No. | Anti-Candida Activity (µg/mL) | Anti-Aspergillus Activity (µg/mL) |
| --- | --- | --- |
| 41 | 0.39 | 0.20 |
| 42 | 0.78 | 1.56 |
| 43 | 0.20 | 0.39 |
| 44 | 1.56 | 1.56 |
| 45 | 0.39 | 0.20 |
| 46 | 0.05 | 0.20 |
| 47 | 0.20 | 0.39 |
| 48 | 0.39 | 0.20 |
| 49 | 0.05 | 0.39 |
| 50 | 0.78 | 1.56 |
| 51 | 0.10 | 0.39 |
| 52 | 0.39 | 0.39 |
| 53 | 0.20 | 0.20 |
| 54 | 0.10 | 0.39 |
| 55 | 0.05 | 0.10 |
| 56 | 1.56 | >25 |
| 57 | 0.05 | 0.20 |
| 58 | 0.78 | 0.10 |
| 59 | 0.39 | 0.39 |
| 60 | 0.20 | 1.56 |
| 61 | 0.20 | 0.39 |
| 62 | 0.20 | 0.20 |
| 63 | 0.78 | 0.78 |
| 64 | 0.20 | 0.78 |
| 65 | 0.39 | 0.78 |

TABLE 2-continued

| Ex. No. | Anti-Candida Activity (µg/mL) | Anti-Aspergillus Activity (µg/mL) |
| --- | --- | --- |
| 66 | 0.10 | 0.78 |
| 67 | 1.56 | 0.78 |
| 68 | 0.10 | 0.39 |
| 69 | 0.10 | 0.20 |
| 70 | 1.56 | 0.39 |
| 71 | 0.20 | 0.39 |
| 72 | 6.25 | 12.5 |
| 73 | 0.10 | 0.39 |
| 74 | 0.10 | 0.20 |
| 75 | 0.78 | 0.20 |
| 76 | 1.56 | 1.56 |
| 77 | 0.20 | 0.39 |
| 78 | 0.78 | 1.56 |
| 79 | 1.56 | 6.25 |
| 80 | 0.20 | 0.78 |

TABLE 3

| Ex. No. | Anti-Candida Activity (µg/mL) | Anti-Aspergillus Activity (µg/mL) |
| --- | --- | --- |
| 81 | 0.20 | 0.39 |
| 82 | 0.20 | 0.39 |
| 83 | 0.20 | 0.20 |
| 84 | 3.13 | >25 |
| 85 | 1.56 | 3.13 |
| 86 | 0.05 | 0.20 |
| 87 | 0.20 | 0.78 |
| 88 | 0.20 | 0.20 |
| 89 | 0.39 | 0.20 |
| 90 | 1.56 | 0.39 |
| 91 | 0.20 | 0.10 |
| 92 | 0.39 | 0.39 |
| 93 | 0.20 | 1.56 |
| 94 | 0.78 | 0.39 |
| 95 | 0.39 | 1.56 |
| 96 | 3.13 | 0.78 |
| 97 | 0.39 | 0.20 |
| 98 | 0.39 | 0.39 |
| 99 | 3.13 | 0.78 |
| 100 | 3.13 | 6.25 |
| 101 | 1.56 | 1.56 |
| 102 | 0.20 | 0.39 |
| 103 | 1.56 | 0.78 |
| 104 | 0.78 | 0.78 |
| 105 | 0.20 | 0.20 |
| 106 | 0.78 | 0.20 |
| 107 | 0.78 | 0.78 |
| 108 | 1.56 | 3.13 |
| 109 | 0.39 | 0.78 |
| 110 | 0.78 | 0.78 |
| 111 | 0.39 | 0.78 |
| 112 | 0.78 | 0.39 |
| 113 | 0.10 | 0.20 |
| 114 | 6.25 | 6.25 |
| 115 | 0.10 | 0.20 |
| 116 | 0.78 | 0.20 |
| 117 | 1.56 | 0.78 |
| 118 | 0.78 | 3.13 |
| 119 | 0.39 | 0.78 |
| 120 | 0.39 | 0.20 |

TABLE 4

| Ex. No. | Anti-Candida Activity (µg/mL) | Anti-Aspergillus Activity (µg/mL) |
| --- | --- | --- |
| 121 | 0.39 | 0.78 |
| 122 | 1.56 | 0.78 |
| 123 | 0.20 | 0.39 |
| 124 | 0.20 | 0.39 |

TABLE 4-continued

| Ex. No. | Anti-Candida Activity (μg/mL) | Anti-Aspergillus Activity (μg/mL) |
|---|---|---|
| 125 | 0.10 | 0.39 |
| 126 | 1.56 | 0.39 |
| 127 | 0.78 | 1.56 |
| 128 | 0.20 | 0.39 |
| 129 | 0.20 | 0.20 |
| 130 | 1.56 | 0.20 |
| 131 | 0.20 | 0.20 |
| 132 | 3.13 | 3.13 |
| 133 | 0.20 | 0.39 |
| 134 | 0.39 | 0.78 |
| 135 | 0.78 | 0.39 |
| 136 | 0.20 | 0.20 |
| 137 | 0.78 | 1.56 |
| 138 | 0.78 | 0.78 |
| 139 | 1.56 | >25 |
| 140 | 0.20 | 0.78 |
| 141 | 0.39 | 0.20 |
| 142 | 0.39 | 0.39 |
| 143 | 0.39 | 0.78 |
| 144 | 0.39 | 0.20 |
| 145 | 6.25 | 12.5 |
| 146 | 6.25 | >25 |
| 147 | 1.56 | 1.56 |
| 148 | 0.20 | 0.20 |
| 149 | 6.25 | 1.56 |
| 150 | 0.39 | 0.78 |
| 151 | 0.78 | 0.39 |
| 152 | 0.78 | 0.39 |
| 153 | 1.56 | 0.39 |
| 154 | 0.78 | 1.56 |
| 155 | 0.10 | 0.10 |
| 156 | 0.20 | 0.20 |
| 157 | 3.13 | 0.78 |
| 158 | 1.56 | 3.13 |
| 159 | 0.78 | 3.13 |
| 160 | 0.39 | 0.78 |

TABLE 5

| Ex. No. | Anti-Candida Activity (μg/mL) | Anti-Aspergillus Activity (μg/mL) |
|---|---|---|
| 161 | 0.39 | 0.39 |
| 162 | 0.78 | 0.39 |
| 163 | 3.13 | 1.56 |
| 164 | 6.25 | 6.25 |
| 165 | 0.78 | 1.56 |
| 166 | 0.39 | 0.78 |
| 167 | 1.56 | 0.78 |
| 168 | 0.78 | 0.78 |
| 169 | 0.39 | 0.39 |
| 170 | 0.78 | 0.39 |
| 171 | 0.20 | 0.39 |
| 172 | 6.25 | 12.5 |
| 173 | 1.56 | 0.78 |
| 174 | 6.25 | 1.56 |
| 175 | 0.78 | 1.56 |
| 176 | 0.20 | 0.20 |
| 177 | 0.39 | 0.78 |
| 178 | 0.39 | 0.20 |
| 179 | 0.78 | 0.39 |
| 180 | 0.39 | 1.56 |
| 181 | 1.56 | 0.39 |
| 182 | >25 | 0.20 |
| 183 | 0.20 | 0.78 |
| 184 | >25 | 0.39 |
| 185 | 0.78 | 0.78 |
| 186 | 3.13 | 0.78 |
| 187 | 1.56 | 0.78 |
| 188 | 1.56 | 0.78 |
| 189 | 0.05 | 0.20 |
| 190 | 0.78 | 0.78 |
| 191 | 0.20 | 0.39 |

TABLE 5-continued

| Ex. No. | Anti-Candida Activity (μg/mL) | Anti-Aspergillus Activity (μg/mL) |
|---|---|---|
| 192 | 0.39 | 1.56 |
| 193 | 0.78 | 0.78 |
| 194 | 1.56 | 3.13 |
| 195 | 0.39 | 0.78 |
| 196 | 6.25 | 6.25 |
| 197 | 3.13 | 1.56 |
| 198 | 0.78 | 1.56 |
| 199 | 3.13 | 6.25 |
| 200 | 3.13 | 3.13 |

TABLE 6

| Ex. No. | Anti-Candida Activity (μg/mL) | Anti-Aspergillus Activity (μg/mL) |
|---|---|---|
| 201 | 0.78 | 0.39 |
| 202 | 0.05 | 0.20 |
| 203 | 0.20 | 1.56 |
| 204 | 0.20 | 0.39 |
| 205 | 0.39 | 0.78 |
| 206 | 0.10 | 0.39 |
| 207 | 25 | 6.25 |
| 208 | 6.25 | 0.78 |
| 209 | 0.20 | 0.39 |
| 210 | 0.10 | 0.20 |
| 211 | 0.39 | 0.39 |
| 212 | 0.78 | 0.78 |
| 213 | 6.25 | 1.56 |
| 214 | 0.39 | 0.39 |
| 215 | 0.39 | 0.78 |
| 216 | 0.39 | 0.39 |
| 217 | 0.10 | 0.20 |
| 218 | 0.20 | 0.10 |
| 219 | 3.13 | 3.13 |
| 220 | 6.25 | 6.25 |
| 221 | 1.56 | 0.39 |
| 222 | 0.39 | 0.39 |
| 223 | 0.39 | 0.39 |
| 224 | 0.39 | 0.20 |
| 225 | 0.78 | 3.13 |
| 226 | 0.39 | 0.39 |
| 227 | 1.56 | 1.56 |
| 228 | 0.78 | 0.78 |

2. Experimental Systemic Candidal Infection Model in Mice (1) Preparation of Fungal Inoculant A standing culture of *C. albicans* E81022 strain was carried out for 48 hours at 30° C. in sabouraud dextrose agar medium (SDA), the recovered fungal cells were suspended in sterilized physiological saline. By counting the fungal number on cytometry plate, the suspension was diluted to $2 \times 10^7$ cells/mL with sterilized physiological saline to serve fungal inoculum.

(2) Infection

The fungal inoculum was used in the amounts of 0.2 mL to inoculate 4.5 to 5.5 week-old female ICR mice in the tail vein ($4 \times 10^6$ cells/mouse).

(3) Treatment

From 0.5 to 1 hour after fungal inoculation, 0.2 mL of agent solution (dissolved or suspended in sterilized physiological saline containing 6.5% dimethyl sulfoxide and 3.5% Tween 80) was administered into the stomach using a peroral probe, 3 times every 4 hours. The agent concentration was 2.5 mg/kg or 10 mg/kg, and the number of animals in one group was 5 animals.

(4) Determination of Effects

The protective effect was determined by observing life/death until 14 days after infection and calculating the mean survival days.

As a result, as shown in Tables 7 and 8, mice administered with the compounds of the present invention survived for a long time as compared to the untreated group, and the compounds according to the present invention have been also found to demonstrate anti-*Candida* activity in vivo.

TABLE 7

| Example Nos. | Mean Survival Days | | |
|---|---|---|---|
| | Non-Adminstered Group (control) | 2.5 mg/kg | 10 mg/kg |
| 1 | 4.0 | 12.2 | 14.0 |
| 2 | 4.0 | 13.2 | 14.0 |
| 9 | 3.4 | 12.8 | 14.0 |
| 11 | 2.6 | 8.2 | 13.6 |
| 12 | 2.6 | 10.8 | 14.0 |
| 13 | 6.0 | 13.8 | 14.0 |
| 14 | 4.0 | 13.4 | 14.0 |
| 15 | 2.6 | 10.8 | 12.6 |
| 16 | 4.0 | 4.8 | 12.8 |
| 17 | 4.0 | 8.2 | 13.0 |
| 24 | 2.6 | 7.4 | 14.0 |
| 25 | 2.6 | 12.2 | — |
| 27 | 2.6 | 3.0 | 10.0 |
| 29 | 3.2 | — | 11.4 |
| 30 | 6.0 | 13.0 | — |
| 31 | 6.0 | — | 13.0 |
| 32 | 6.0 | 10.2 | 12.2 |
| 33 | 6.0 | 2.4 | 8.4 |
| 36 | 6.0 | 9.4 | 14.0 |
| 37 | 6.0 | 5.4 | 14.0 |
| 38 | 6.0 | 4.8 | 10.0 |
| 40 | 4.0 | 11.6 | 14.0 |
| 41 | 4.0 | 11.4 | 11.8 |

TABLE 8

| Example Nos. | Mean Survival Days | | |
|---|---|---|---|
| | Non-Adminstered Group (control) | 2.5 mg/kg | 10 mg/kg |
| 43 | 3.2 | 10.6 | 14.0 |
| 45 | 3.2 | 10.6 | 10.8 |
| 51 | 4.0 | 13.5 | 14.0 |
| 52 | 4.0 | 10.6 | 13.4 |
| 54 | 2.8 | 13.0 | 13.6 |
| 55 | 2.8 | 13.8 | 14.0 |
| 58 | 2.8 | 3.8 | 12.0 |
| 62 | 1.4 | 10.2 | — |
| 73 | 2.2 | 4.4 | 12.6 |
| 102 | 3.2 | 13.2 | 13.0 |
| 104 | 3.2 | 8.2 | 13.2 |
| 105 | 3.2 | 5.4 | 12.8 |
| 109 | 2.8 | 11.0 | 11.8 |
| 110 | 2.8 | 12.0 | — |
| 111 | 2.8 | 13.6 | — |
| 112 | 4.0 | — | 12.2 |
| 113 | 2.8 | 13.0 | 14.0 |
| 115 | 2.8 | 10.8 | 13.2 |
| 116 | 2.8 | 4.6 | 12.6 |
| 120 | 2.8 | 3.2 | 13.4 |
| 131 | 1.4 | 12.6 | 12.8 |
| 133 | 2.2 | 7.0 | 13.4 |
| 135 | 2.2 | 11.0 | 13.4 |
| 151 | 2.4 | 7.0 | 14.0 |
| 155 | 2.4 | 10.4 | 13.0 |
| 166 | 2.8 | 3.4 | 12.4 |
| 171 | 2.8 | 8.4 | 12.6 |
| 176 | 4.2 | 12.6 | 13.4 |

TABLE 8-continued

| Example Nos. | Mean Survival Days | | |
|---|---|---|---|
| | Non-Adminstered Group (control) | 2.5 mg/kg | 10 mg/kg |
| 192 | 1.0 | 3.2 | 9.4 |
| 202 | 1.0 | 2.4 | 10.0 |

What is claimed is:

1. A compound represented by the following formula (I), or a salt thereof:

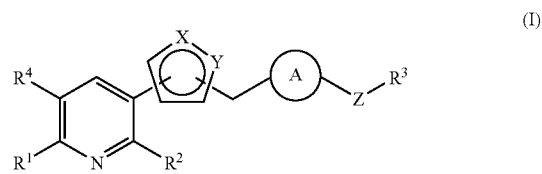

(I)

wherein $R^1$ represents a hydrogen atom, a halogen atom, an amino group, $R^{11}$—NH— (wherein $R^{11}$ represents a $C_{1-6}$ alkyl group, a hydroxy $C_{1-6}$ alkyl group, a $C_{1-6}$ alkoxy $C_{1-6}$ alkyl group, or a $C_{1-6}$ alkoxycarbonyl $C_{1-6}$ alkyl group), $R^{12}$—(CO)—NH— (wherein $R^{12}$ represents a $C_{1-6}$ alkyl group or a $C_{1-6}$ alkoxy $C_{1-6}$ alkyl group), a $C_{1-6}$ alkyl group, a hydroxy $C_{1-6}$ alkyl group, a cyano $C_{1-6}$ alkyl group, a $C_{1-6}$ alkoxy group or a $C_{1-6}$ alkoxy $C_{1-6}$ alkyl group;

$R^2$ represents a hydrogen atom, a $C_{1-6}$ alkyl group, an amino group or a di $C_{1-6}$ alkylamino group;

X is an oxygen atom;

Y is a nitrogen atom;

ring A represents a benzene ring which may have 1 or 2 halogen atoms, or 1 or 2 $C_{1-6}$ alkyl groups;

Z represents a single bond, a methylene group, an ethylene group, an oxygen atom, a sulfur atom, —CH$_2$O—, —OCH$_2$—, —NH—, —CH$_2$NH—, —NHCH$_2$—, —CH$_2$S—, or —SCH$_2$—;

$R^3$ represents a pyridine ring which may have 1 or 2 substituents selected from substituent group α: and substituent group α represents the group consisting of a halogen atom, a cyano group, a $C_{1-6}$ alkyl group, a $C_{1-6}$ alkoxy group, a $C_{1-6}$ alkoxycarbonyl group, a $C_{3-8}$ cycloalkyl group, a $C_{2-6}$ alkenyl group and a $C_{2-6}$ alkynyl group $R^4$ represents a hydrogen atom or a halogen atom;

excluding compounds where all of $R^1$, $R^2$, and $R^4$ represent the hydrogen atom at the same time when Z represents the single bond or $R^3$ represents the hydrogen atom.

2. The compound according to Claim 1 or a salt thereof, wherein a partial structure represented by formula (II):

(II)

in a compound represented by the formula (I):

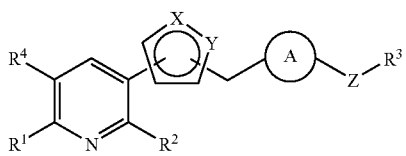

is a partial structure of:

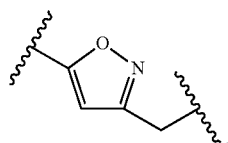

3. The compound according to Claim 1 or a salt thereof, wherein $R^2$ represents an amino group.

4. The compound according to Claim 3 or a salt thereof, wherein $R^1$ represents a hydrogen atom, an amino group or a $C_{1-6}$ alkoxy $C_{1-6}$ alkyl group.

5. The compound according to Claim 1 or a salt thereof, wherein $R^1$ represents an amino group and $R^2$ represents a hydrogen atom.

6. The compound according to Claim 1 or a salt thereof, wherein Z represents an oxygen atom, —CH$_2$O— or —OCH$_2$—.

7. A pharmaceutical composition comprising:
a compound according to Claim 1 or a salt thereof; and
a pharmaceutically acceptable carrier.

8. A method for treating a fungal infection comprising: administering a pharmacologically effective dose of a compound according to Claim 1 or a salt thereof, to a patient in need thereof.

9. A compound, or a pharmaceutically salt thereof, selected from the group consisting of:
3-(3-(4-(pyridin-2-yloxymethyl)-benzyl-isoxazol-5-yl)-pyridin-2-ylamine;
3-(3-(4-(pyridin-2-ylmethoxy)-benzyl)-isoxazol-5-yl)-pyridin-2-ylamine;
3-(3-(4-pyridin-2-yloxymethyl)-benzyl)-isoxazol-5-yl)-pyridine-2,6-diamine;
3-(3-(4-(5-fluoro-pyridin-2-ylmethoxy)-benzyl)-isoxazol-5-yl)-pyridin-2-ylamine;
3-(3-(4-(6-fluoro-pyridin-2-ylmethoxy)-benzyl)-isoxazol-5-yl)-pyridin-2-ylamine;
3-(3-(4-(4-chloro-pyridin-2-ylmethoxy)-benzyl)-isoxazol-5-yl)-pyridin-2-ylamine;
3-(3-(4-(4-methyl-pyridin-2-yloxymethyl)-benzyl)-isoxazol-5-yl)-pyridin-2,6-diamine;
3-(3-(4-(6-Fluoro-pyridin-2-yloxymethyl)-benzyl)-isoxazol-5-yl)-pyridin-2,6-diamine;
5-(3-(4-pyridin-2-yloxymethyl)-benzyl)-isoxazol-5-yl)-pyridin-2-ylamine,
3-(3-(4-(6-methyl-pyridin-2-yloxymethyl)-benzyl)-isoxazol-5-yl)-pyridin-2,6-diamine,
3-(3-(4-(pyridin-2-ylmethoxy)-benzyl)-isoxazol-5-yl)-pyridin-2,6-diamine,
3-(3-(4-(4-methyl-pyridin-2-ylmethoxy)-benzyl)-isoxazol-5-yl)-pyridin-2,6-diamine,
3-(3-(4-(4-methyl-pyridin-2-yloxymethyl)-benzyl)-isoxazol-5-yl)-pyridin-2-ylamine,
3-(3-(4-(6-fluoro-pyridin-2-yloxymethyl)-benzyl)-isoxazol-5-yl)-pyridin-2-ylamine, and
3-(3-(4-(6-fluoro-pyridin-2-ylmethoxy)-benzyl)-isoxazol-5-yl)-pyridin-2,6-diamine.

10. A compound of 3-(3-(4-(Pyridin-2-yloxymethyl)-benzyl)-isoxazol-5-yl)-pyridin-2-ylamine, represented by:

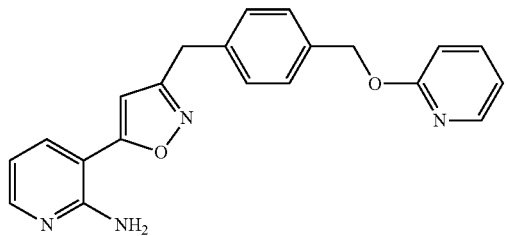

or a pharmaceutically acceptable salt thereof.

11. A compound of 3-(3-(4-(Pyridin-2-ylmethoxy)-benzyl)-isoxazol-5-yl)-pyridin-2-ylamine, represented by:

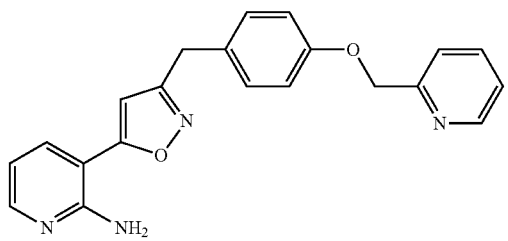

or a pharmaceutically acceptable salt thereof.

12. A compound of 3-(3-(4-Pyridin-2-yloxymethyl)-benzyl)-isoxazol-5-yl)-pyridine-2,6-diamine, represented by:

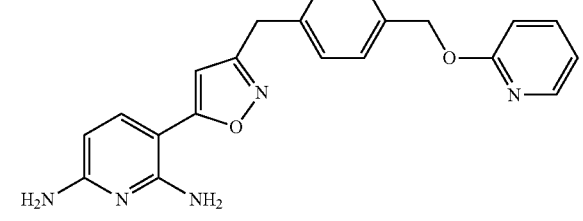

or a pharmaceutically acceptable salt thereof.

13. A compound of 3-(3-(4-(6-methyl-pyridin-2-yloxymethyl)-benzyl)-isoxazol-5-yl)-pyridin-2,6-diamine, represented by:

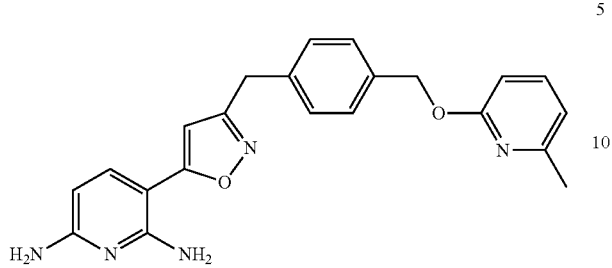

or a pharmaceutically acceptable salt thereof.

14. A compound of 3-(3-(4-(pyridin-2-ylmethoxy)-benzyl)-isoxazol-5-yl)-pyridin-2,6-diamine, represented by:

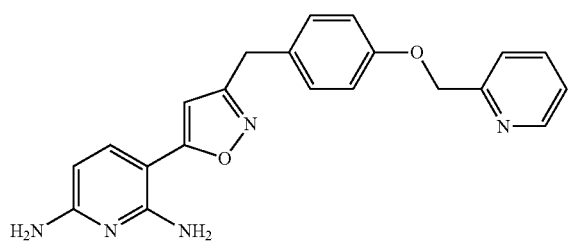

or a pharmaceutically acceptable salt thereof.

15. A compound of 3-(3-(4-(4-methyl-pyridin-2-ylmethoxy)-benzyl)-isoxazol-5-yl)-pyridin-2,6-diamine, represented by:

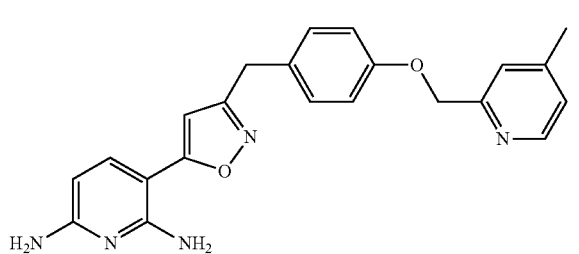

or a pharmaceutically acceptable salt thereof.

16. A compound of 3-(3-(4-(4-methyl-pyridin-2-yloxymethyl)-benzyl)-isoxazol-5-yl)-pyridin-2-ylamine, represented by:

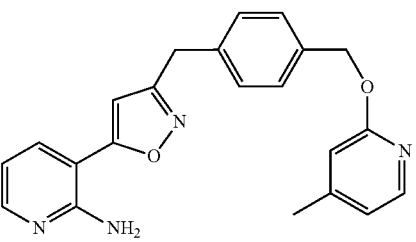

or a pharmaceutically acceptable salt thereof.

17. A compound of 3-(3-(4-(6-fluoro-pyridin-2-yloxymethyl)-benzyl)-isoxazol-5-yl)-pyridin-2-ylamine, represented by:

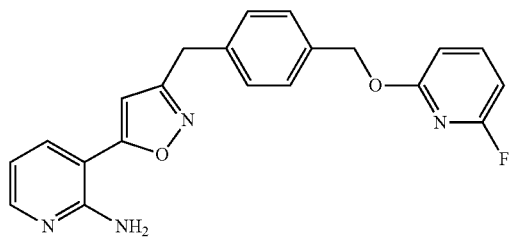

or a pharmaceutically acceptable salt thereof.

18. A compound of 3-(3-(4-(6-fluoro-pyridin-2-ylmethoxy)-benzyl)-isoxazol-5-yl)-pyridin-2,6-diamine, represented by:

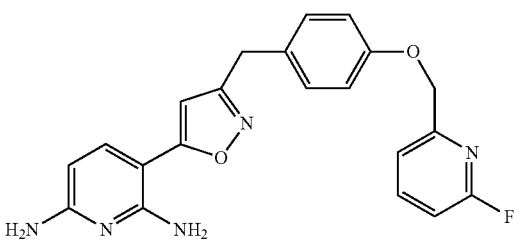

or a pharmaceutically acceptable salt thereof.

\* \* \* \* \*